United States Patent
Kim et al.

(10) Patent No.: US 11,856,844 B2
(45) Date of Patent: Dec. 26, 2023

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Dongjun Kim, Suwon-si (KR); Minji Kim, Hwaseong-si (KR); Eunjae Jeong, Hwaseong-si (KR); Sohee Jo, Seoul (KR); Sanghyun Han, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 535 days.

(21) Appl. No.: 17/080,732

(22) Filed: Oct. 26, 2020

(65) Prior Publication Data

US 2021/0159420 A1    May 27, 2021

(30) Foreign Application Priority Data

Nov. 21, 2019 (KR) .................. 10-2019-0150292

(51) Int. Cl.
| | |
|---|---|
| *C07D 333/76* | (2006.01) |
| *H10K 85/60* | (2023.01) |
| *C07D 307/91* | (2006.01) |
| *C07D 209/86* | (2006.01) |

(Continued)

(52) U.S. Cl.
CPC ......... *H10K 85/636* (2023.02); *C07D 209/86* (2013.01); *C07D 307/91* (2013.01); *C07D 333/76* (2013.01); *H10K 85/633* (2023.02); *H10K 50/15* (2023.02); *H10K 50/17* (2023.02);

(Continued)

(58) Field of Classification Search
None
See application file for complete search history.

(56) References Cited

U.S. PATENT DOCUMENTS

2011/0147717 A1* 6/2011 LeCloux ............. H10K 85/633
                                                    564/429
2016/0293843 A1* 10/2016 Itoi ..................... H10K 85/615

(Continued)

FOREIGN PATENT DOCUMENTS

| KR | 10-2016-0118123 A | 10/2016 | |
|---|---|---|---|
| KR | 10-1994448 B1 | 6/2019 | |
| WO | WO-2020073605 A1 * | 4/2020 | ........... C07D 209/80 |

*Primary Examiner* — Robert S Loewe
(74) *Attorney, Agent, or Firm* — Lewis Roca Rothgerber Christie LLP

(57) ABSTRACT

An organic electroluminescence device of an embodiment of the present disclosure includes a first electrode, a second electrode facing the first electrode, and a plurality of organic layers disposed between the first electrode and the second electrode, wherein at least one organic layer of the plurality of organic layers includes an amine compound containing a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one amine group, which is substituted to the fluorene group; wherein all the carbons of the aryl group are substituted with deuterium, and the organic electroluminescence device exhibits high efficiency and a long service life.

20 Claims, 2 Drawing Sheets

(51) Int. Cl.
　　　*H10K 50/15*　　　(2023.01)
　　　*H10K 50/17*　　　(2023.01)
(52) U.S. Cl.
　　　CPC ..... *H10K 85/6572* (2023.02); *H10K 85/6574* (2023.02); *H10K 85/6576* (2023.02)

(56) References Cited

U.S. PATENT DOCUMENTS

2018/0114906 A1* 4/2018 Itoi .................. H10K 85/615
2023/0025656 A1* 1/2023 Liu .................. C07D 405/12

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2019-0150292, filed on Nov. 21, 2019, the entire content of which is hereby incorporated by reference.

BACKGROUND

One or more aspects of embodiments of the present disclosure relate to an organic electroluminescence device and an amine compound used therein.

Organic electroluminescence displays are being actively developed as image display devices. An organic electroluminescence display is a so-called self-luminescent displays in which holes and electrons respectively injected from a first electrode and a second electrode recombine in an emission layer, and a luminescent material including an organic compound in the emission layer emits light to implement display.

In the application of an organic electroluminescence device to a display device, there is a demand for an organic electroluminescence device having a low driving voltage, high luminous efficiency, and/or a long service life (life span), and materials capable of stably attaining such characteristics in an organic electroluminescence device are demanded.

Amine compounds are being developed as hole transport region materials, and an amine compound providing high efficiency and/or a long service life to an organic electroluminescence device is demanded.

SUMMARY

One or more aspects of embodiments of the present disclosure are directed toward an organic electroluminescence device having an increased or improved luminous efficiency and/or service life (life span).

One or more aspects of embodiments of the present disclosure are directed toward an amine compound that can provide increased or improved luminous efficiency and/or device service life (life span) when applied to a luminescence device.

One or more example embodiments of the present disclosure provide an organic electroluminescence device including a first electrode, a second electrode facing the first electrode, and a plurality of organic layers disposed between the first electrode and the second electrode, wherein at least one organic layer of the plurality of organic layers includes an amine compound containing a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one amine group, which is substituted to the fluorene group; wherein all the carbons of the aryl group are substituted with deuterium (e.g., the aryl group is a deuterated aryl group).

In an embodiment, the heteroaryl group may be a substituted or unsubstituted dibenzofuranyl group, a substituted or unsubstituted dibenzothiophene group, or a substituted or unsubstituted carbazole group.

In embodiment, the organic layers may include a hole transport region, an emission layer, and an electron transport region, and the hole transport region may include the amine compound.

In an embodiment, the hole transport region may include a hole transport layer and a hole injection layer, and the hole transport layer or the hole injection layer may include the amine compound.

In an embodiment, the amine compound may be represented by Formula 1:

Formula 1

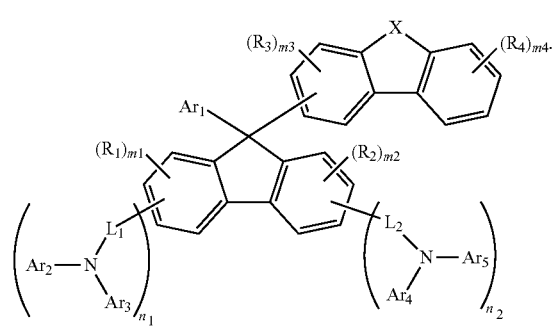

In Formula 1, X may be O, S, or $NAr_6$; $L_1$ and $L_2$ may each independently be a direct linkage, a substituted or unsubstituted arylene group having 6 to 60 ring-forming carbon atoms, or a substituted or unsubstituted heteroarylene group having 2 to 60 ring-forming carbon atoms; $R_1$ to $R_4$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring; $m_1$, $m_2$, and $m_4$ may each independently be an integer of 0 to 4; $m_3$ may be an integer of 0 to 3; $Ar_1$ may be a phenyl group substituted with deuterium, a naphthyl group substituted with deuterium, or a biphenyl group substituted with deuterium; $Ar_2$ to $Ar_6$ may each independently be a substituted or unsubstituted aryl group having 6 to 60 ring-forming carbon atoms, or a substituted or unsubstituted heteroaryl group having 3 to 60 ring-forming carbon atoms; $n_1$ and $n_2$ may each independently be 0 or 1, and at least one of $n_1$ and $n_2$ may be 1.

In an embodiment, $Ar_1$ may be represented by at least one of Formula $t_1$ to Formula $t_5$:

Formula $t_1$

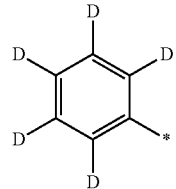

Formula t₂
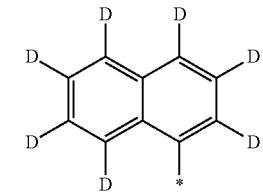

Formula t₃
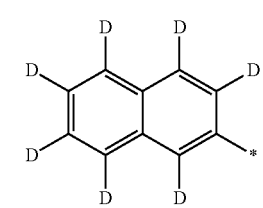

Formula t₄

Formula t₅
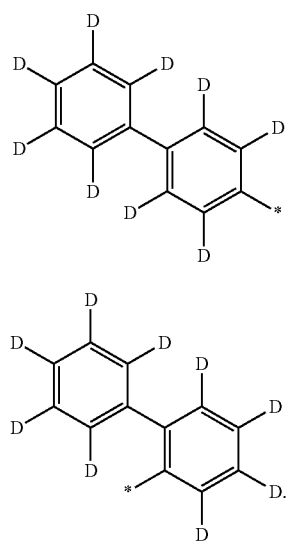

In an embodiment, the amine compound represented by Formula 1 may represented by at least one of Formula 1-1 to Formula 1-3:

Formula 1-1

Formula 1-2

Formula 1-3

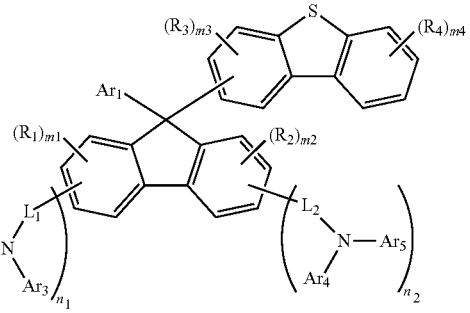

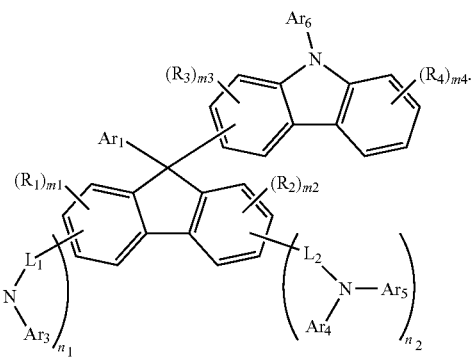

In Formula 1-1 to Formula 1-3, $L_1$, $L_2$, $R_1$ to $R_4$, $m_1$ to $m_4$, $Ar_1$ to $Ar_6$, $n_1$ and $n_2$ may each independently be the same as defined in Formula 1.

In an embodiment, the amine compound represented by Formula 1 may be represented by at least one of Formula 2-1 to Formula 2-5:

Formula 2-1

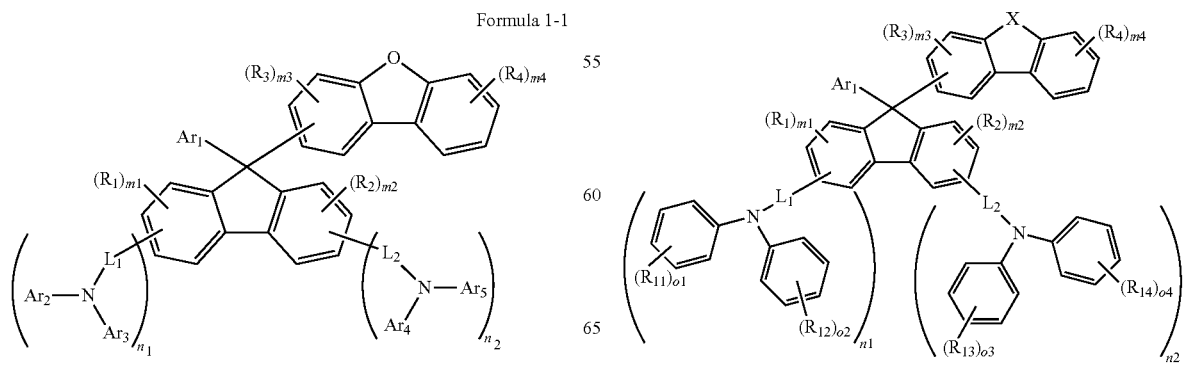

-continued

Formula 2-2
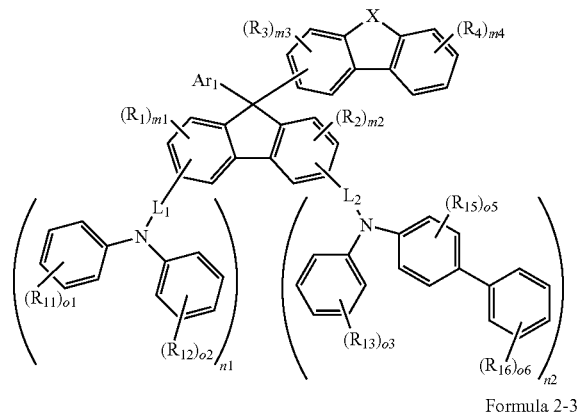

Formula 2-3
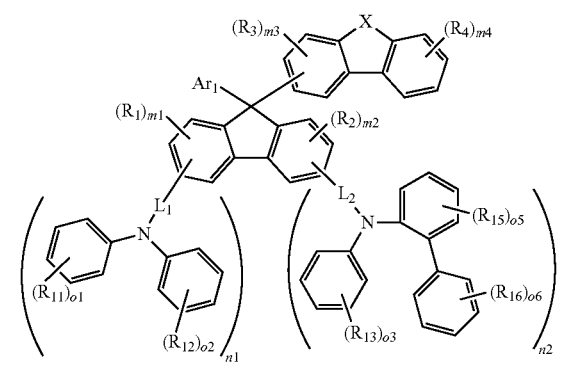

Formula 2-4
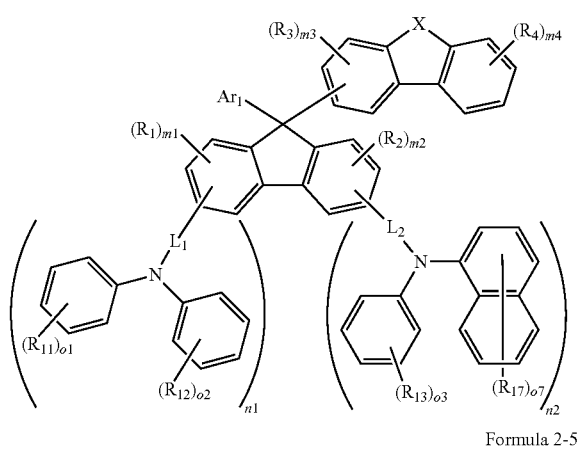

Formula 2-5
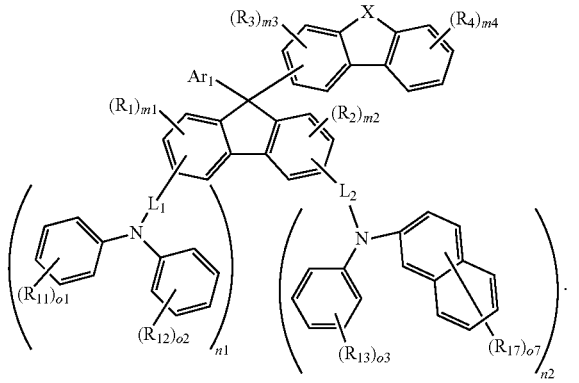

In Formula 2-1 to Formula 2-5, $R_{11}$ to $R_{17}$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring; $o_1$ to $o_4$ and $o_6$ may be each independently an integer of 0 to 5; $o_5$ may be an integer of 0 to 4; $o_7$ may be an integer of 0 to 7; and X, $R_1$ to $R_4$, $L_1$, $L_2$, $n_1$, $n_2$, $m_1$ to $m_4$, and $Ar_1$ may each independently be the same as defined in Formula 1.

In an embodiment, the amine compound represented by Formula 1 may be represented by Formula 3-1:

Formula 3-1
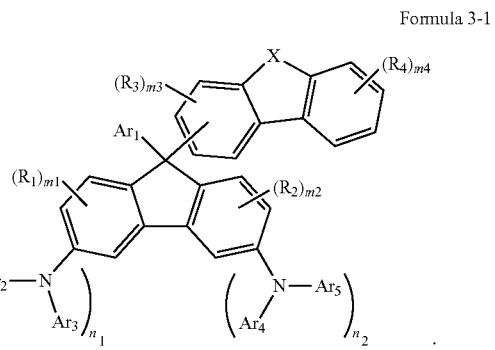

In Formula 3-1, X, $Ar_1$ to $Ar_5$, $R_1$ to $R_4$, $n_1$, $n_2$, and $m_1$ to $m_4$ may each independently be the same as defined in Formula 1.

In an embodiment, X may be $NAr_6$, and $Ar_6$ may be a substituted or unsubstituted phenyl group.

In an embodiment, the amine compound represented by Formula 1 may be represented by at least one of Formula 4-1 or Formula 4-2:

Formula 4-1
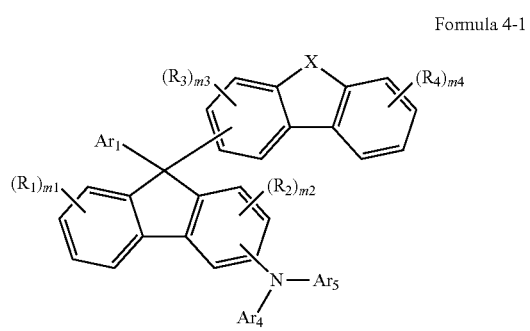

Formula 4-2
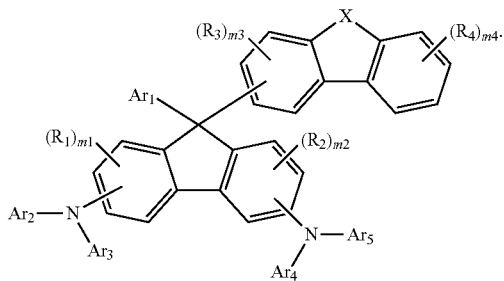

In Formula 4-1 and Formula 4-2, X, $Ar_1$ to $Ar_5$, $R_1$ to $R_4$, $m_1$ to $m_4$ may each independently be the same as defined in Formula 1.
In an embodiment, the amine compound represented by the Formula 1 may include at least one of the compounds represented by Compound Group 1:
Compound Group 1
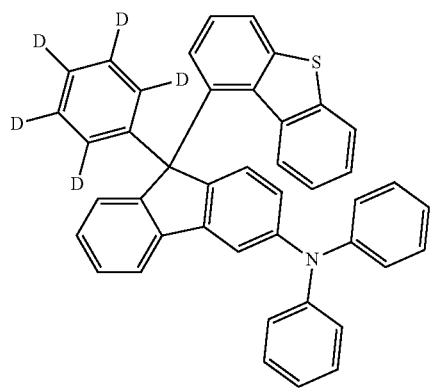
1
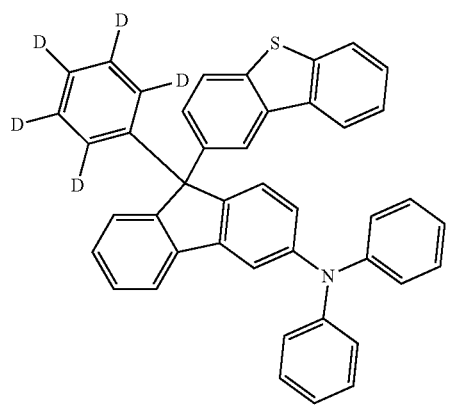
2
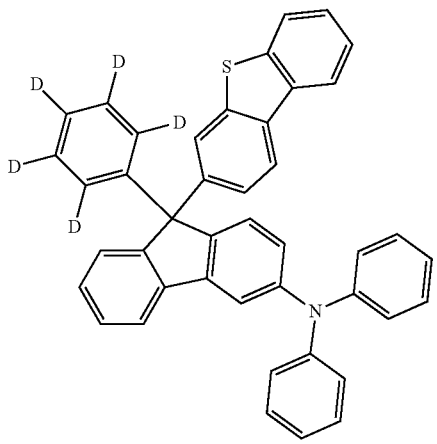
3
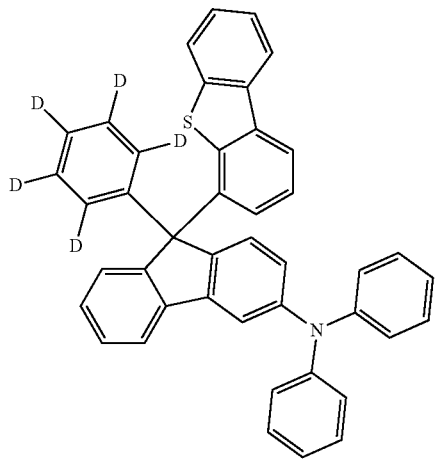
4
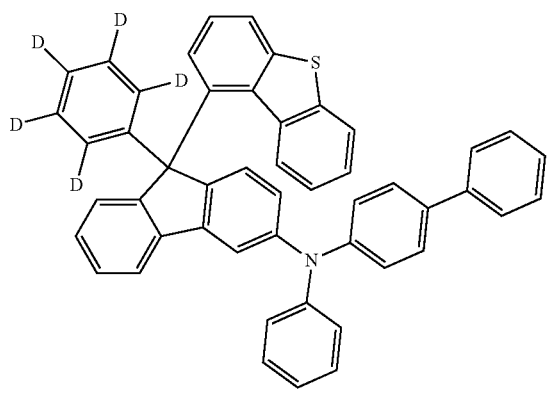
5
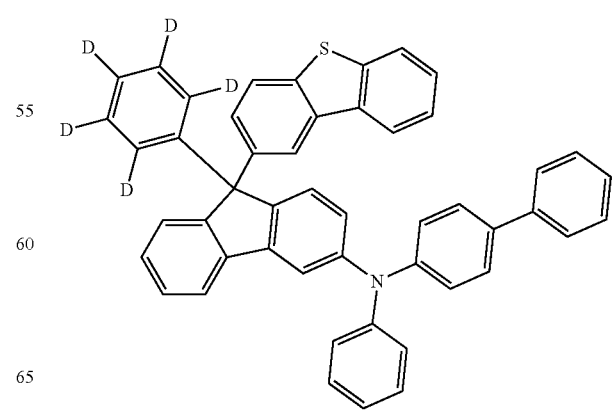
6

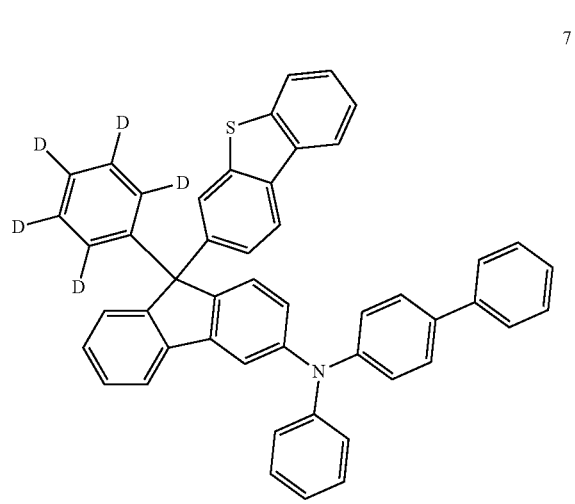
7
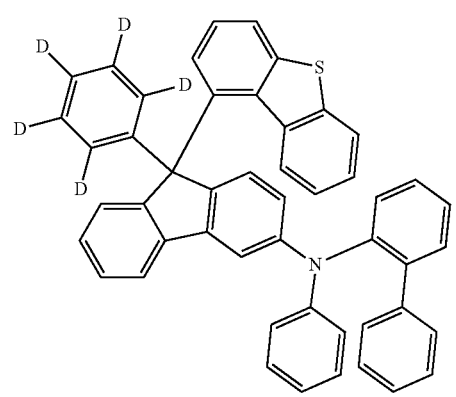
8
9
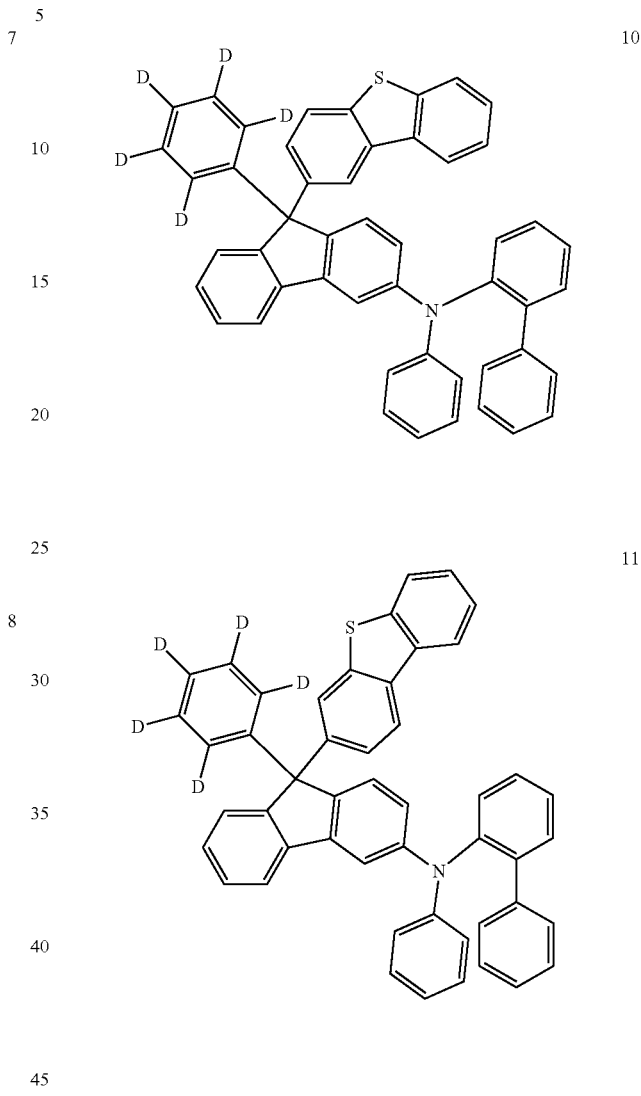
10
11
12

13
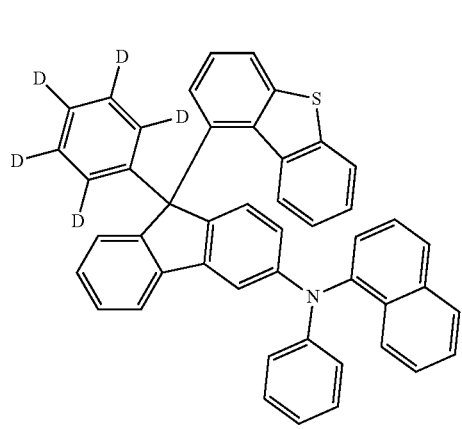
14
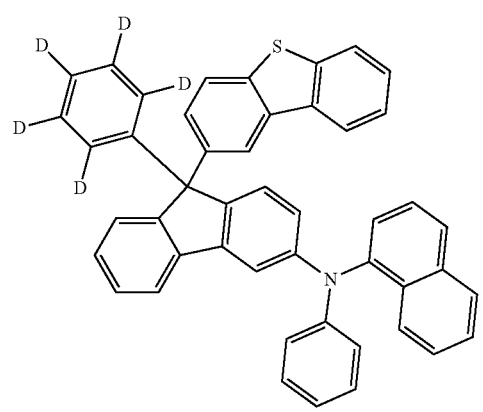
15
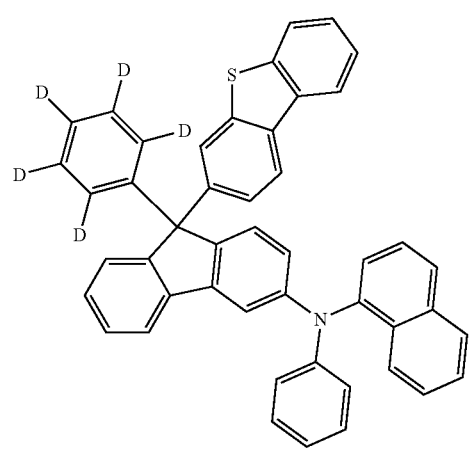
16
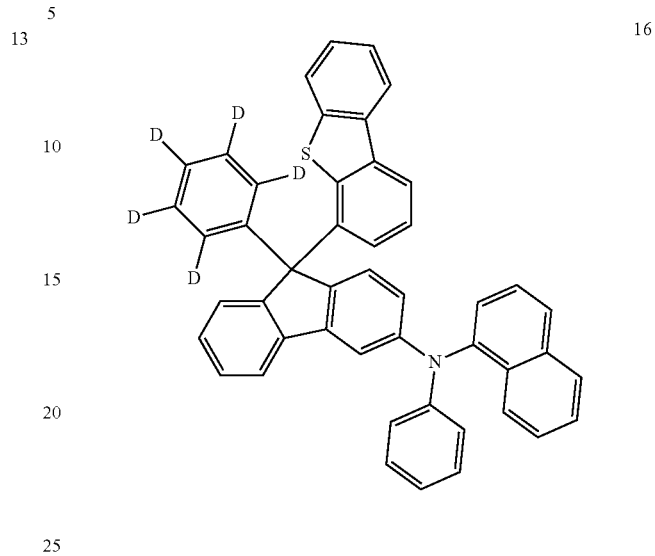
17
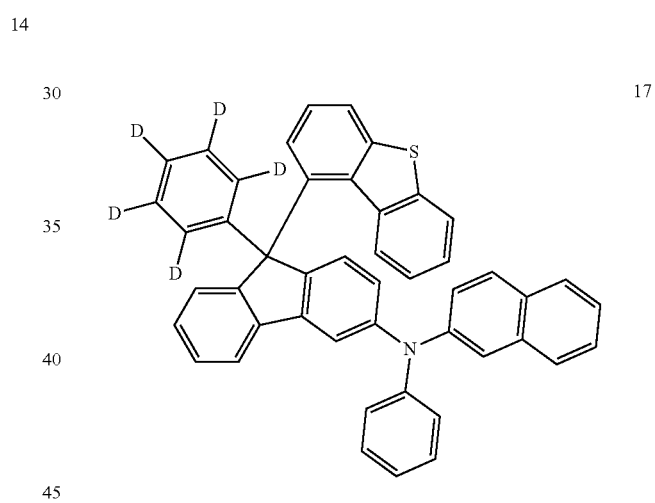
18
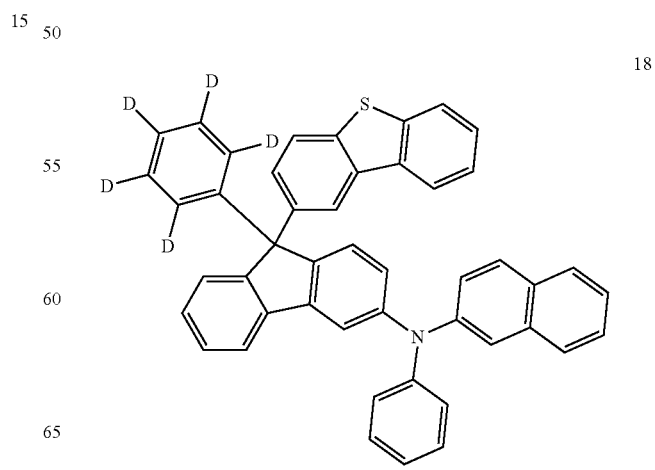

19
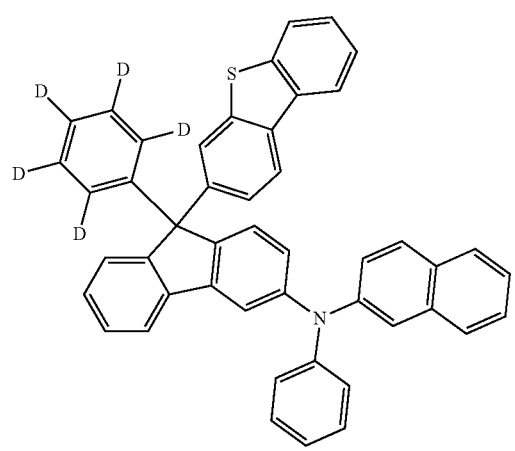
20
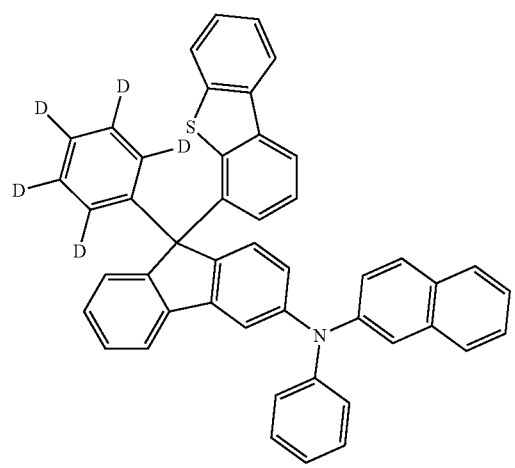
21
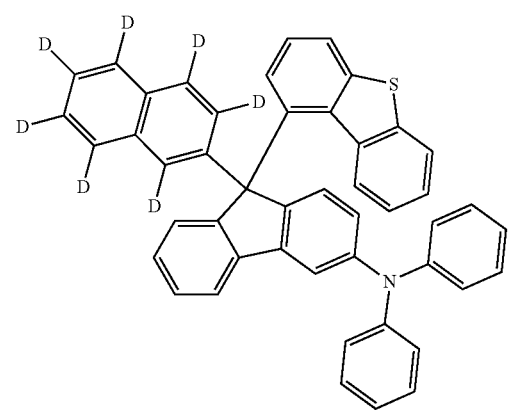
22
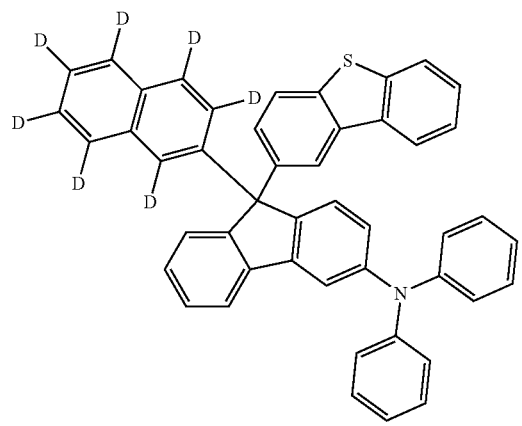
23
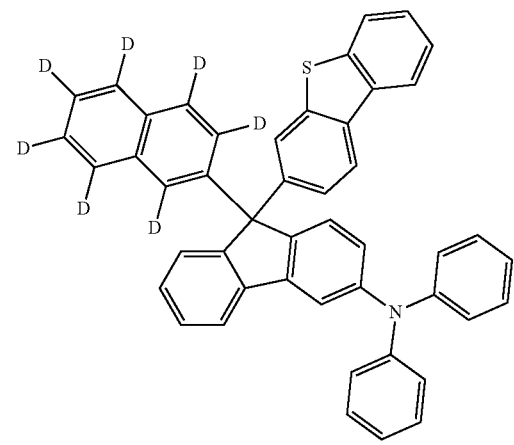
24
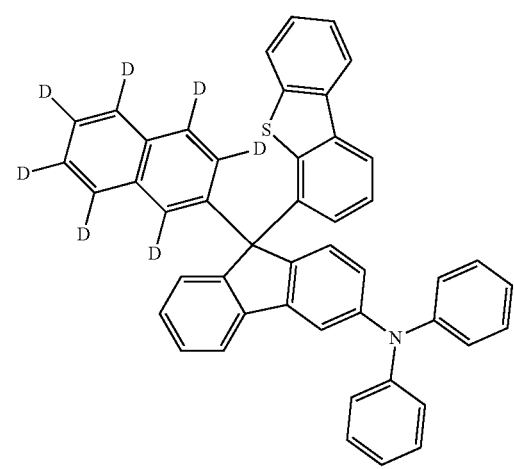

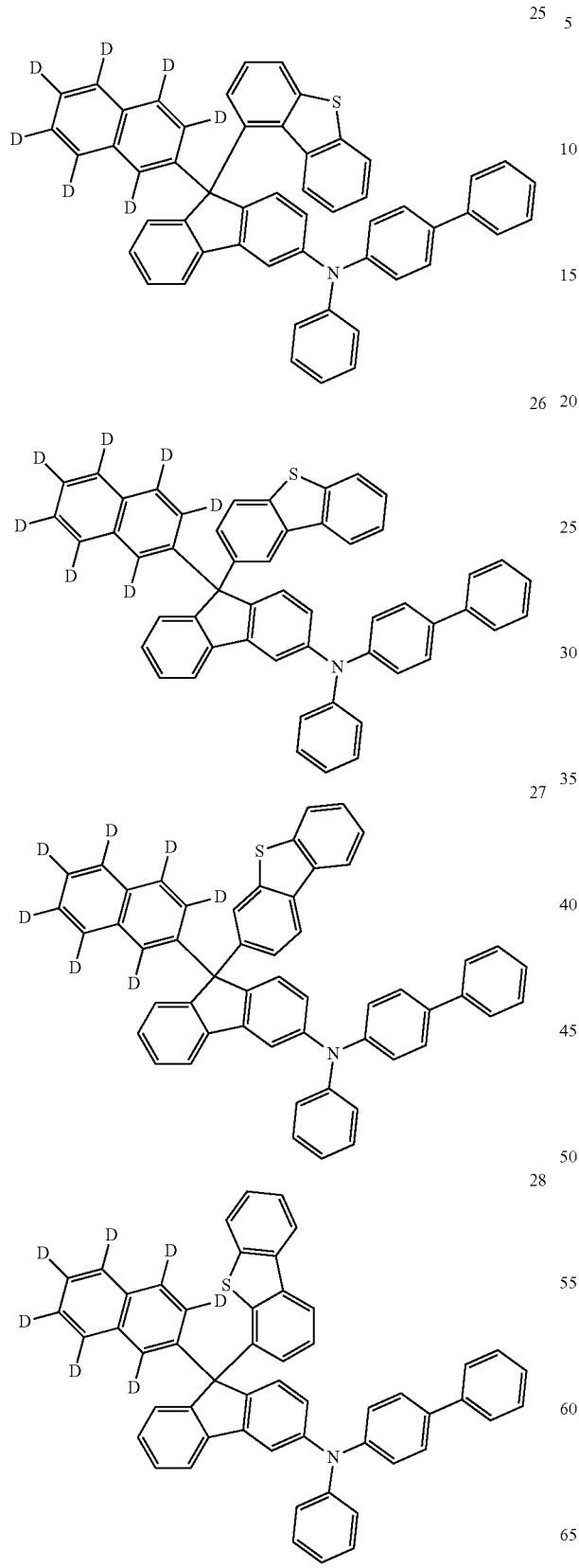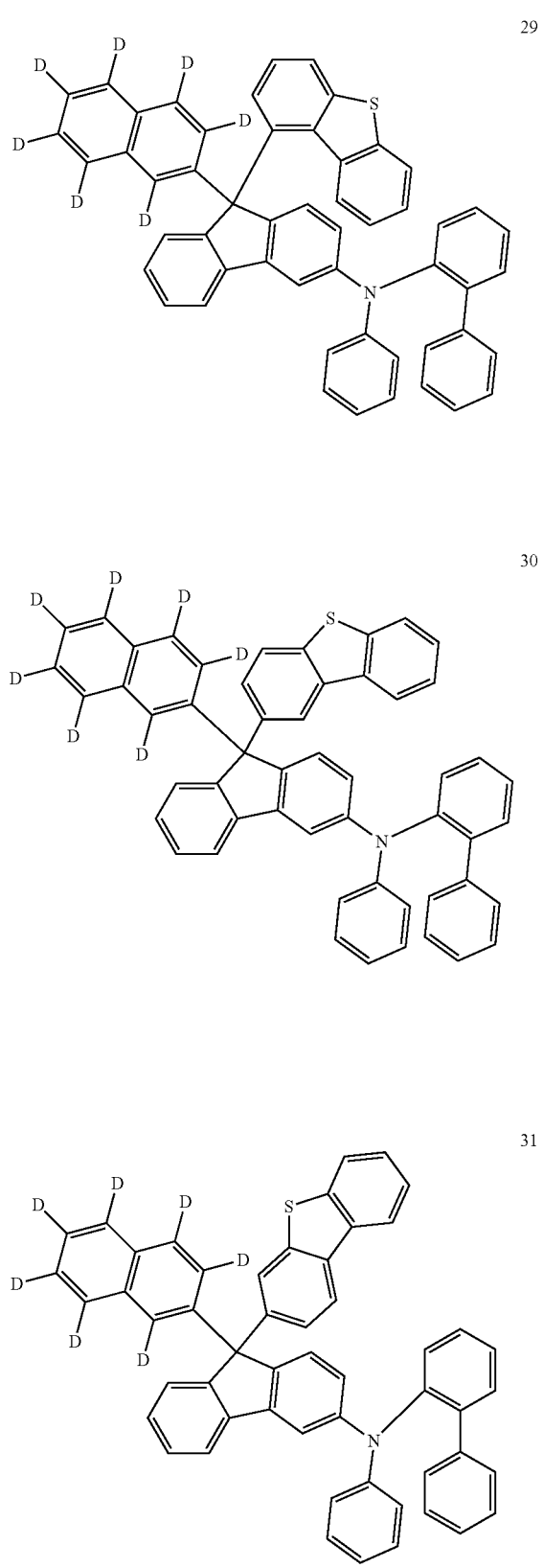

32
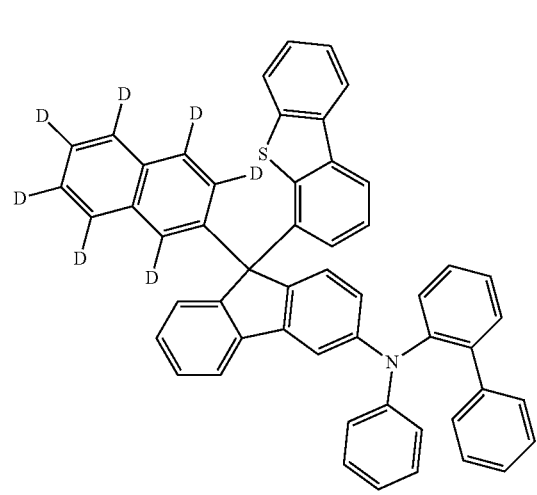
33
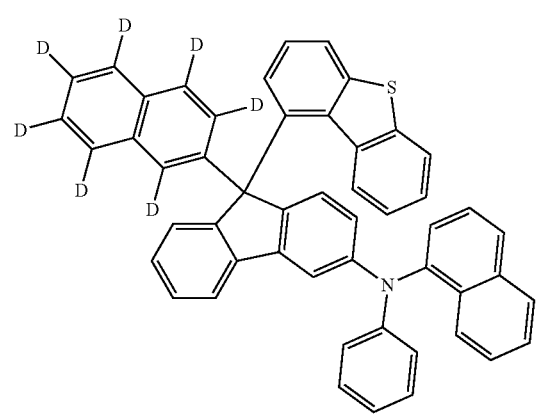
34
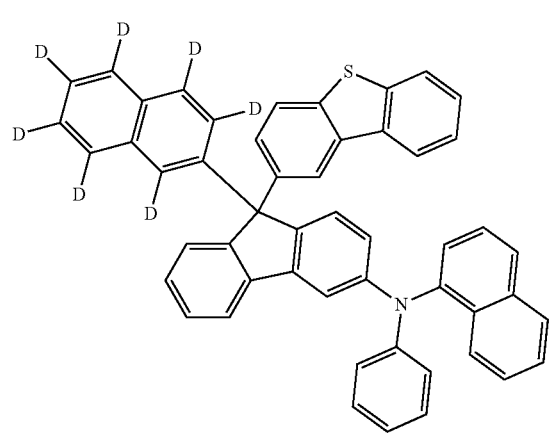
35
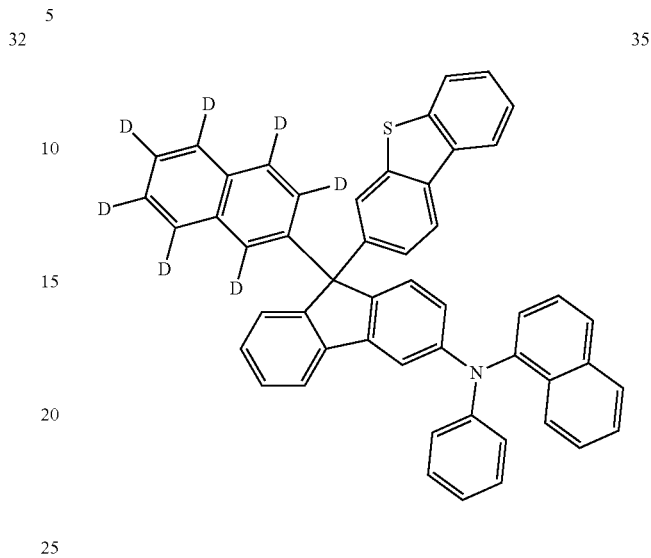
36
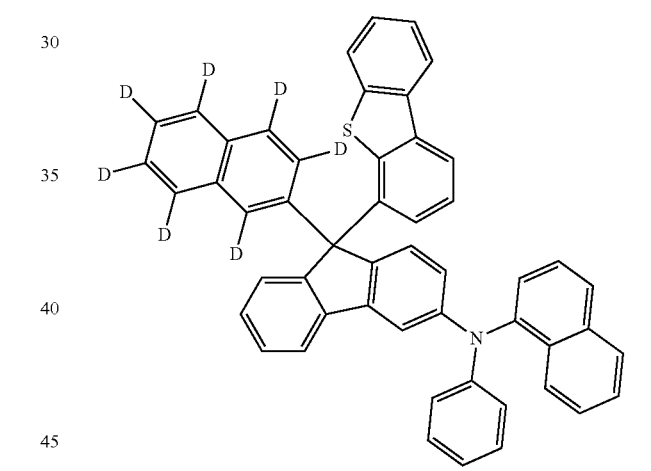
37
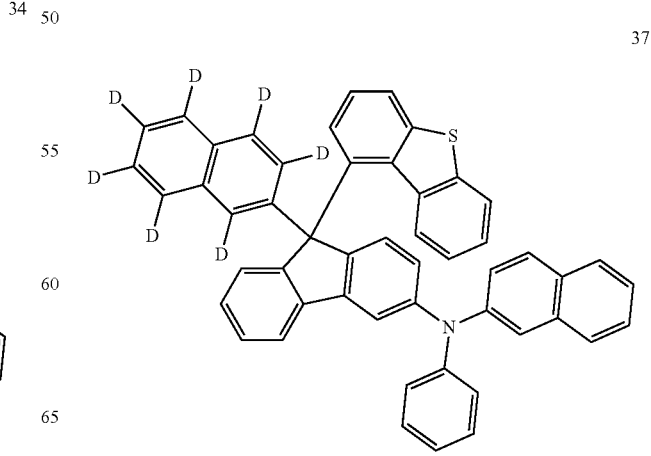

38
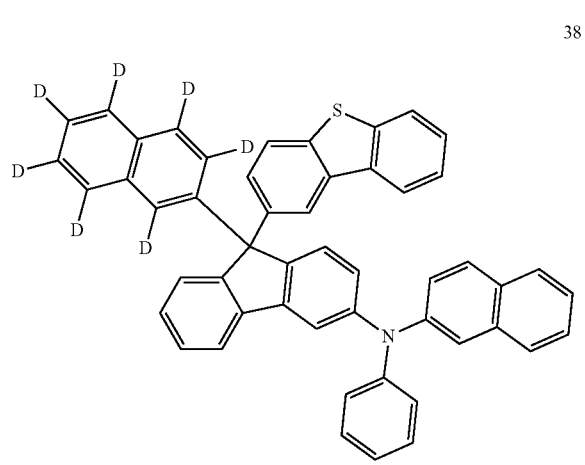
39
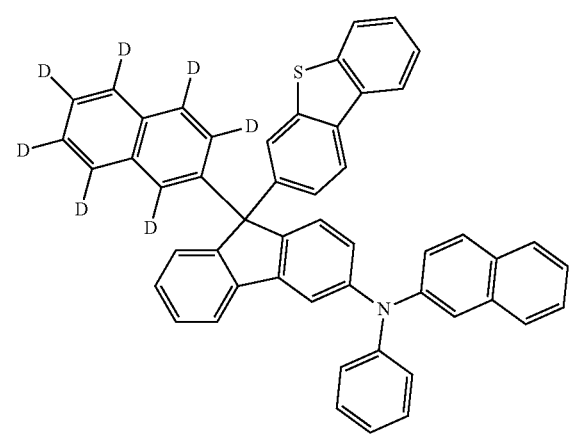
40
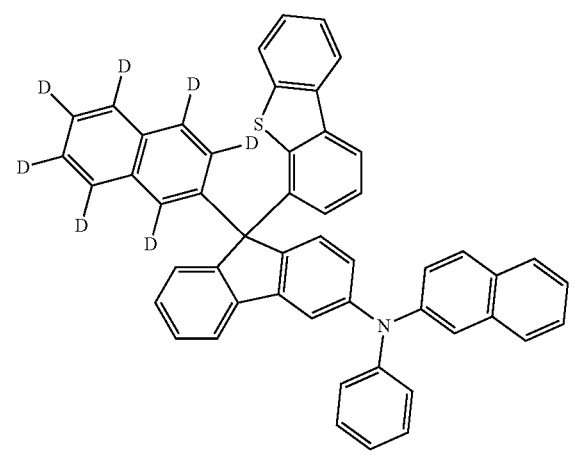
41
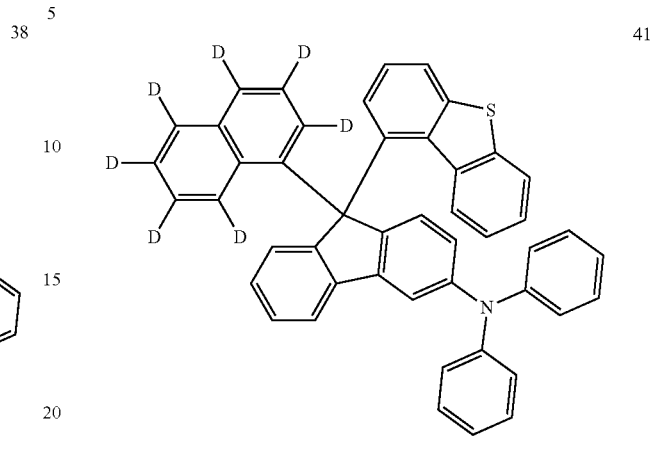
42
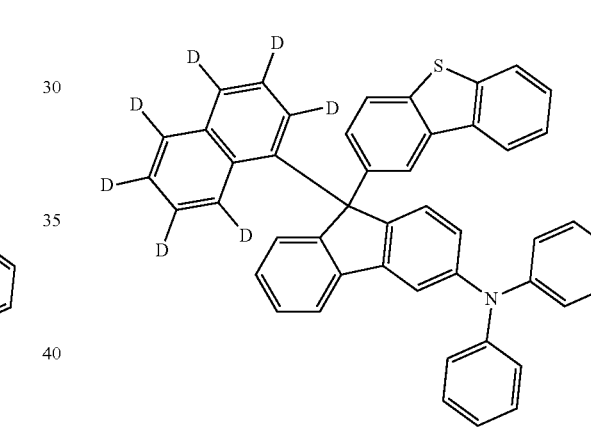
43
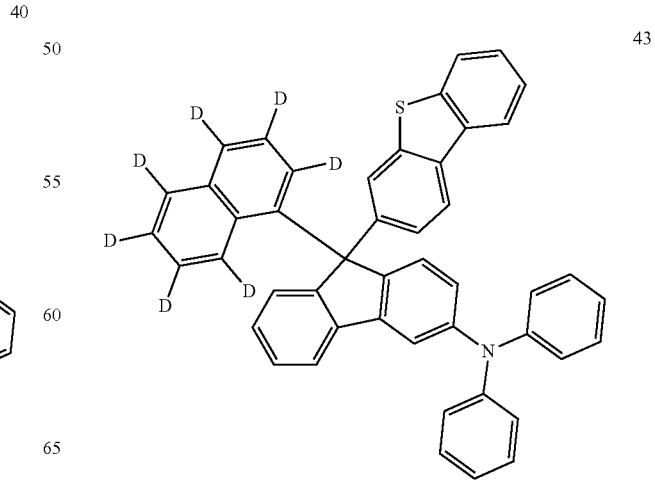

44
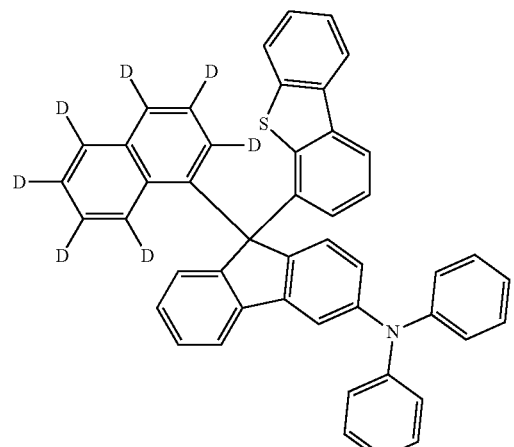
45
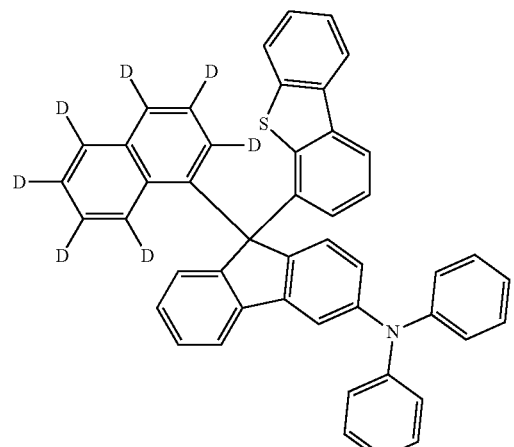
46
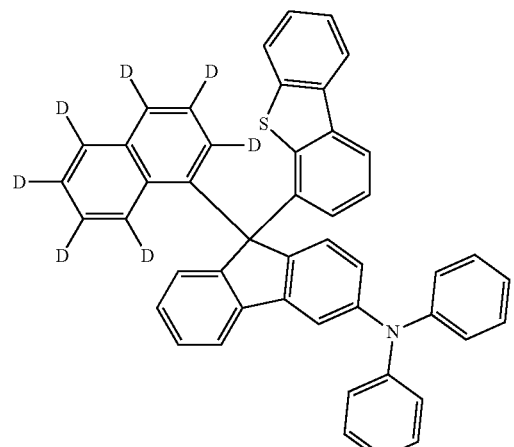
47
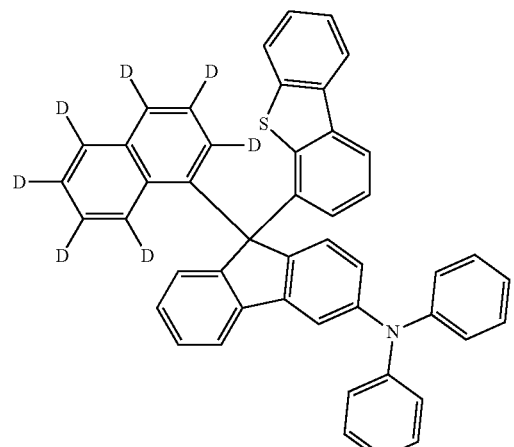
48
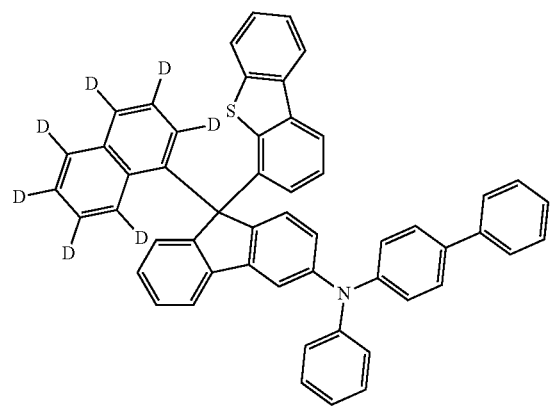
49
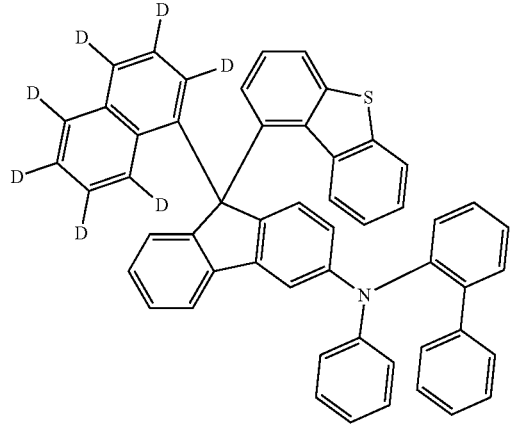
50
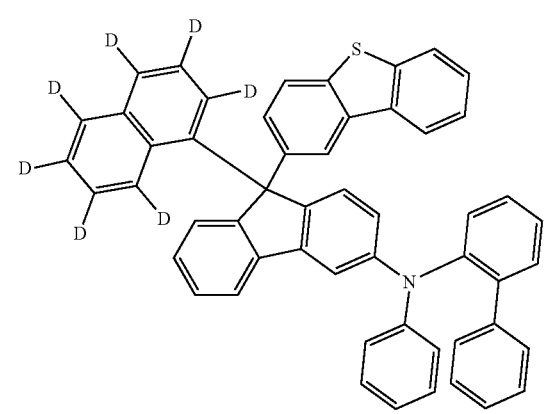

51
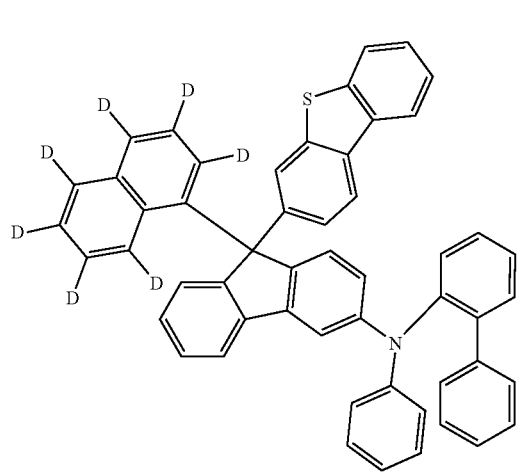
52
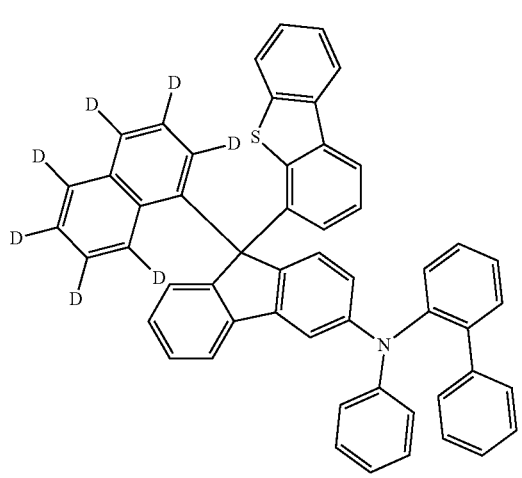
53
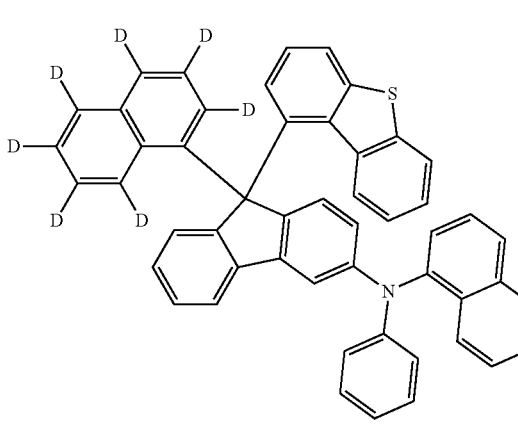
54
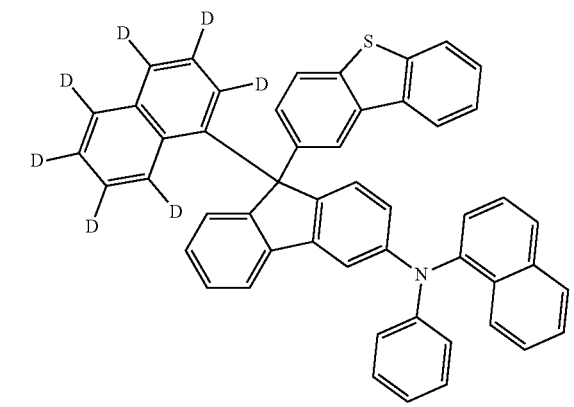
55
56

57
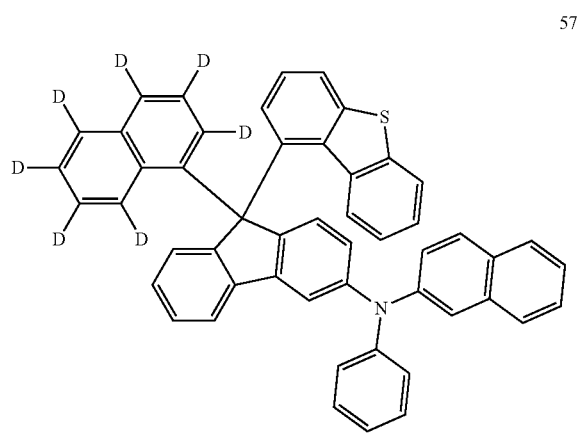
58
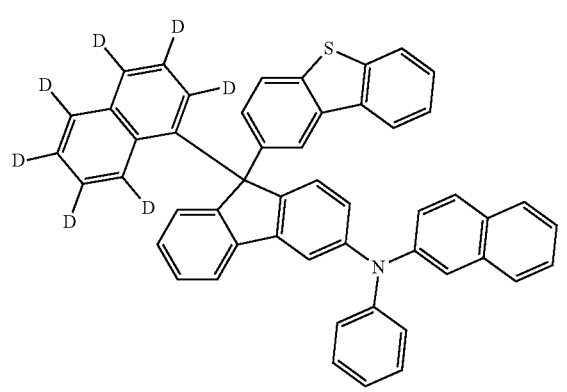
59
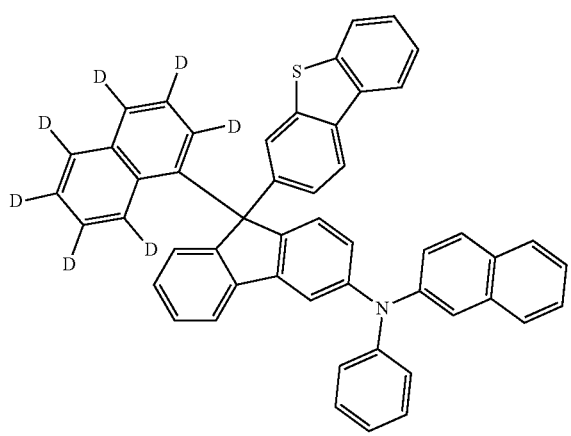
60
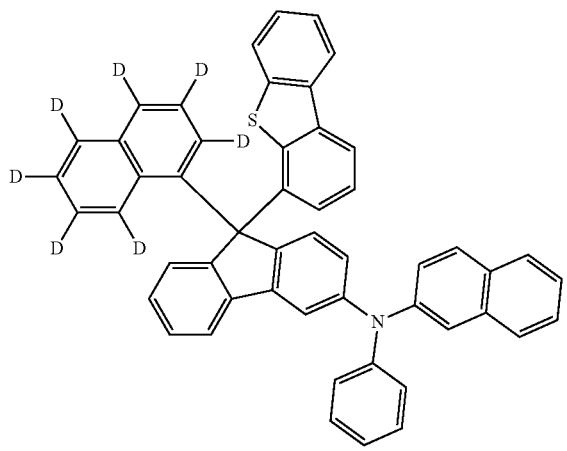
61
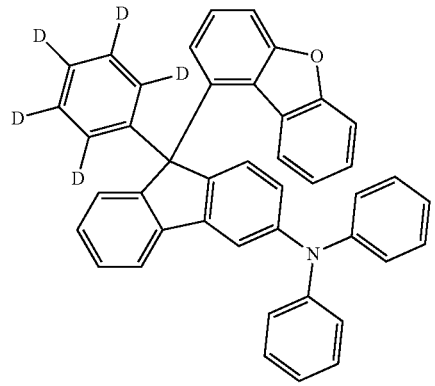
62
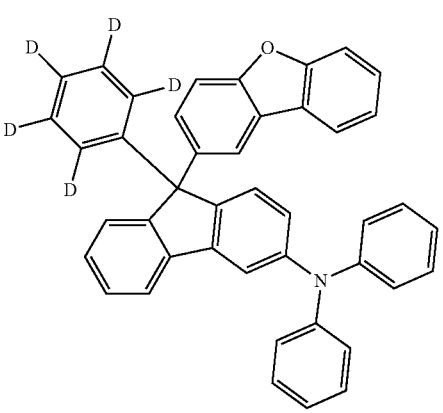

63
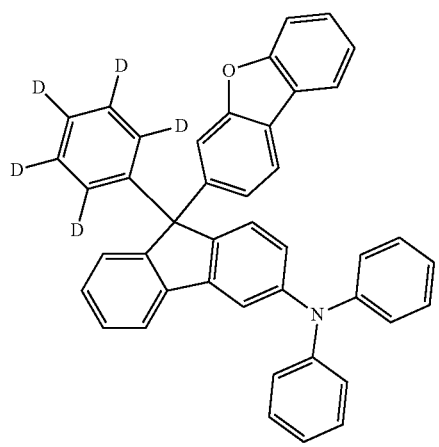
64
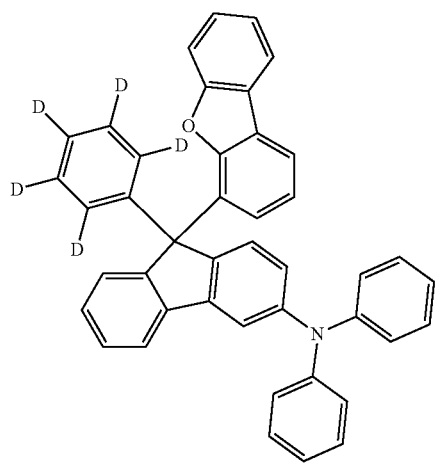
65
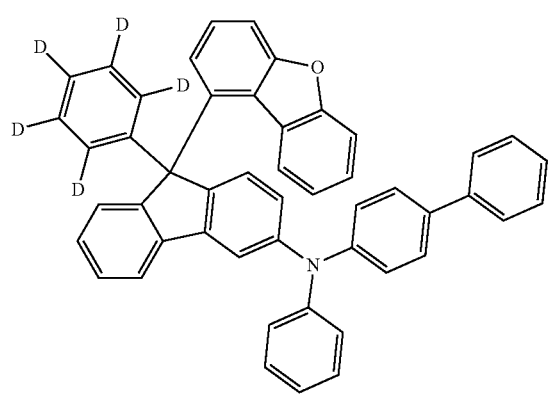
66
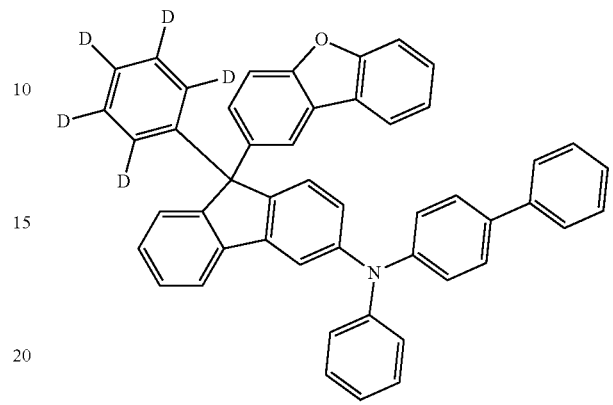
67
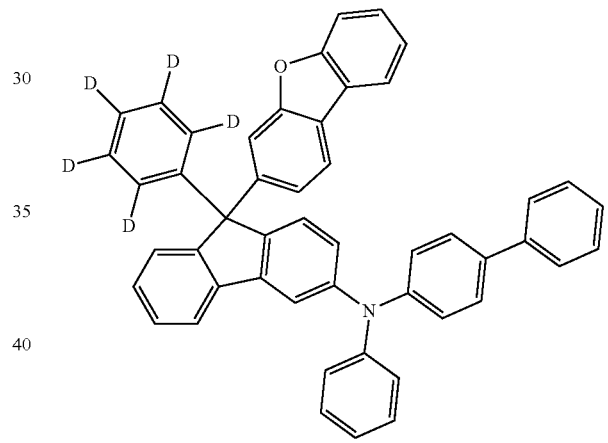
68
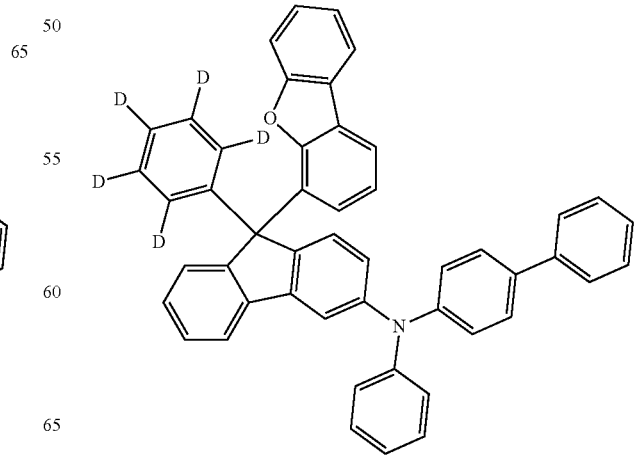

69
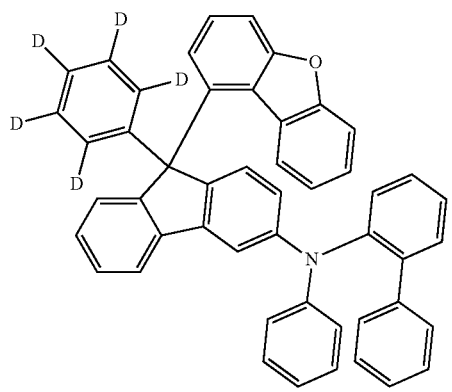
70
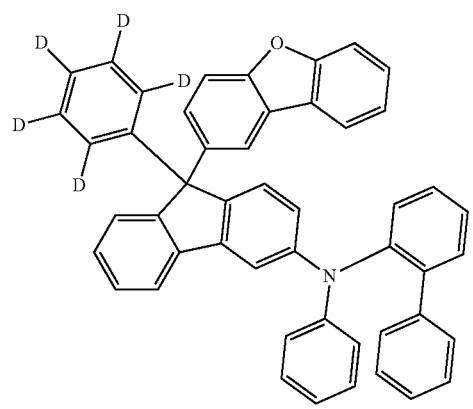
71
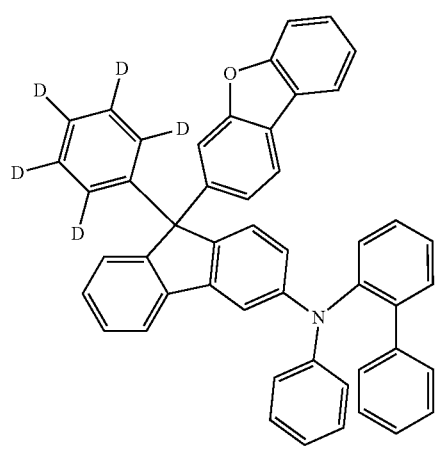
72
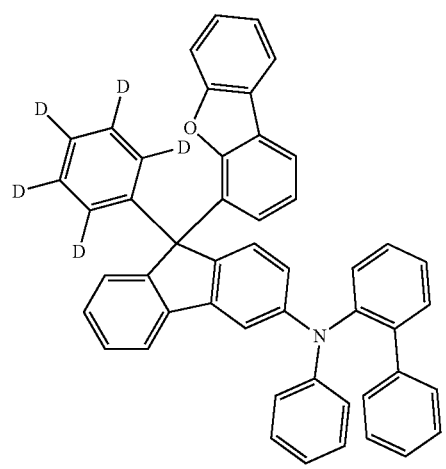
73
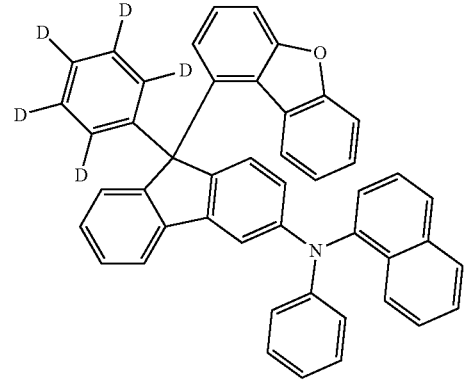
74
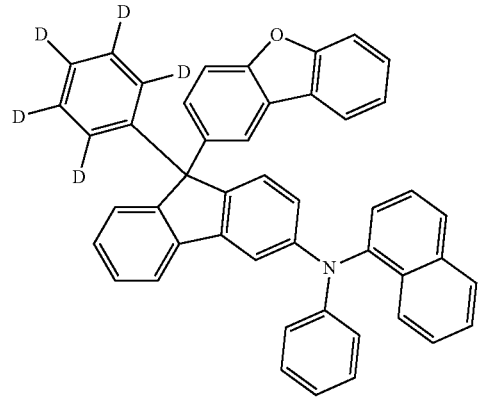

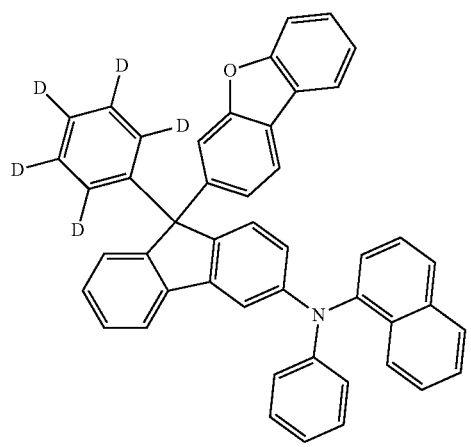
75
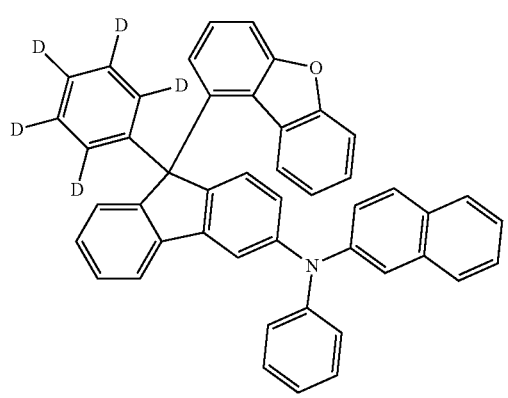
76
77
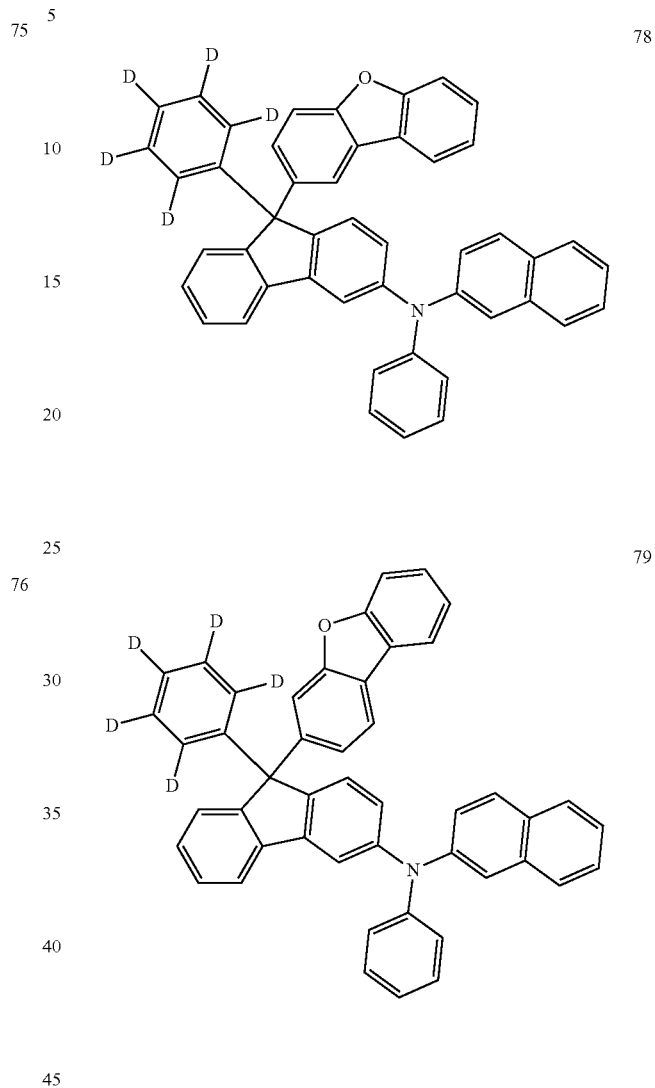
78
79
80

81
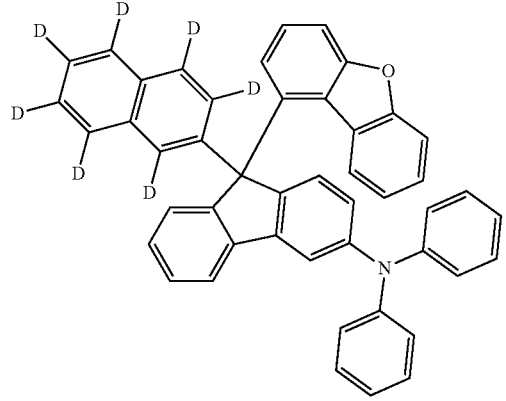
82
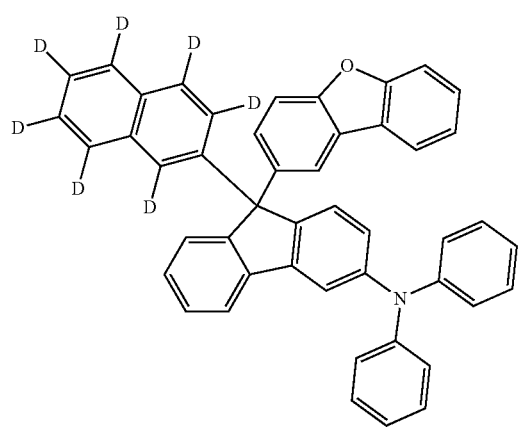
83
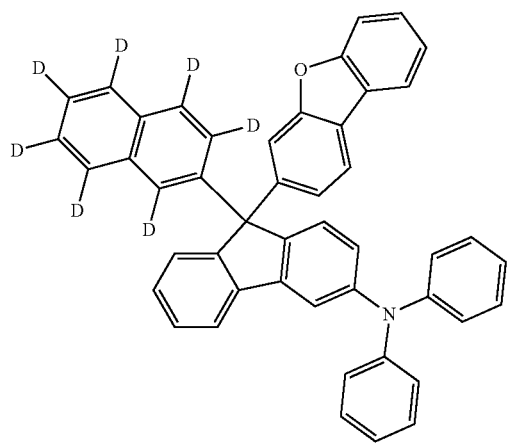
84
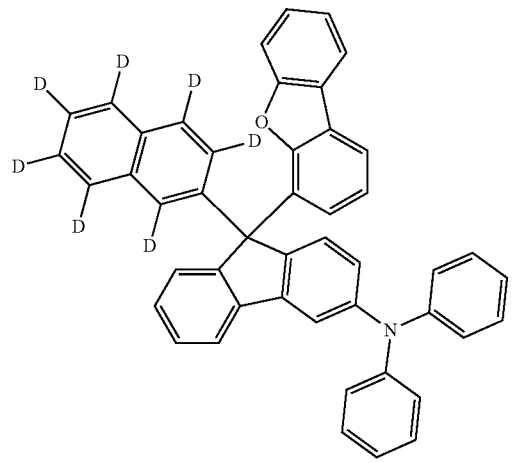
85
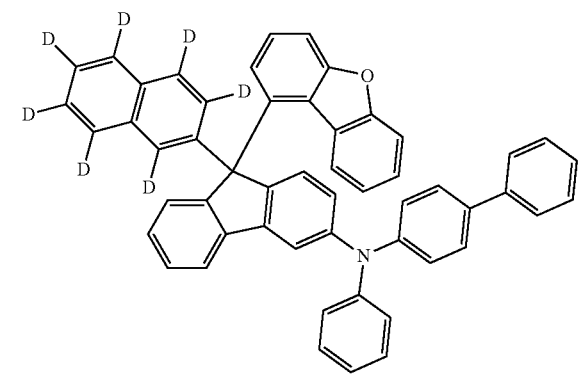
86
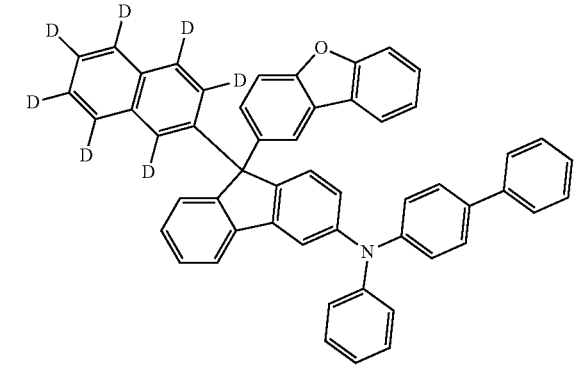
87
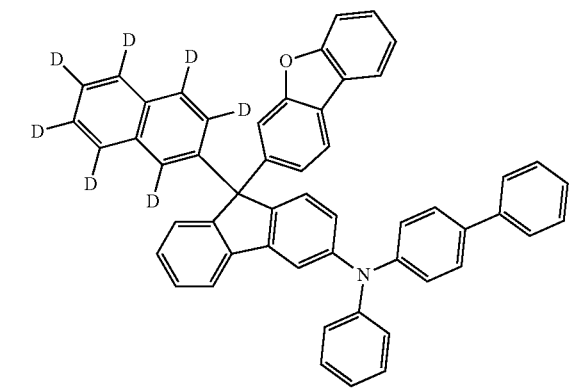

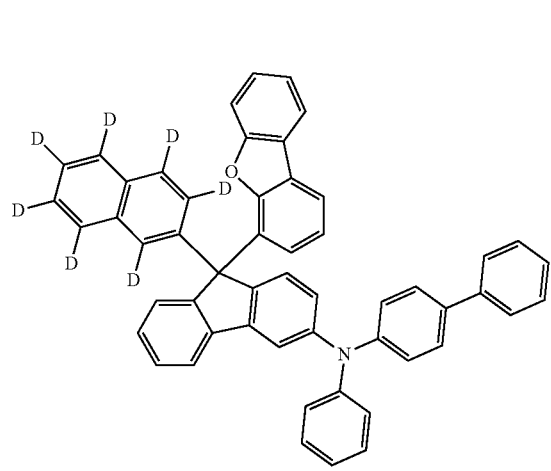
88
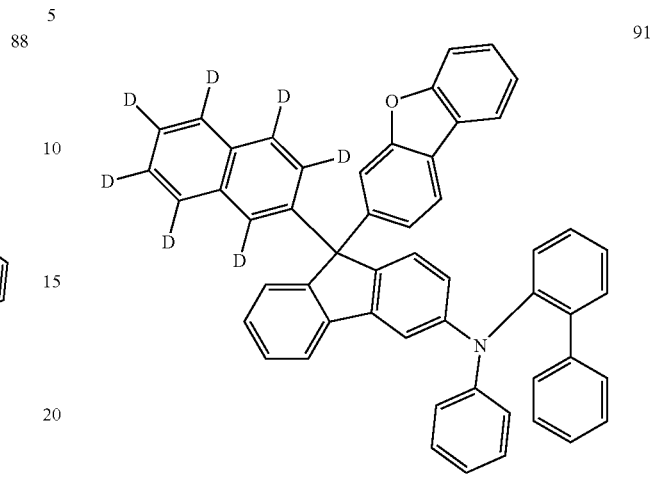
91
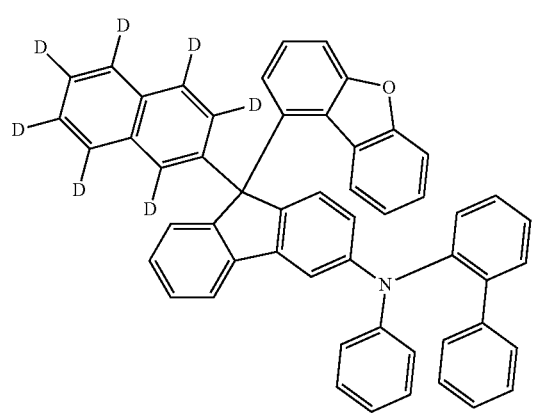
89
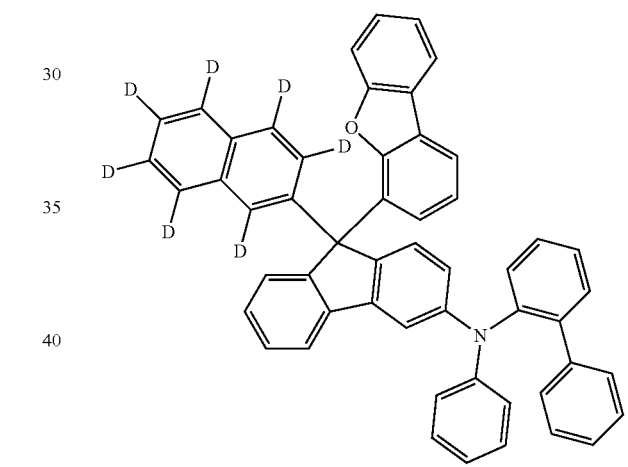
92
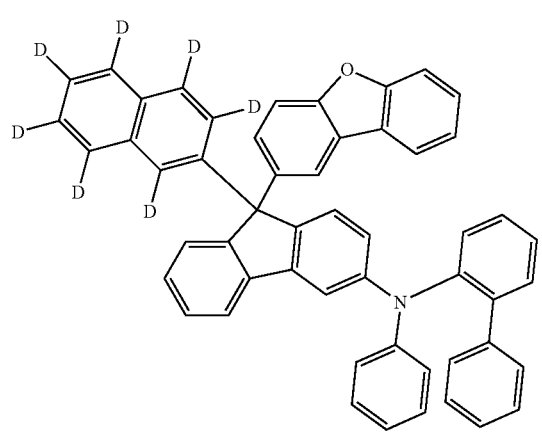
90
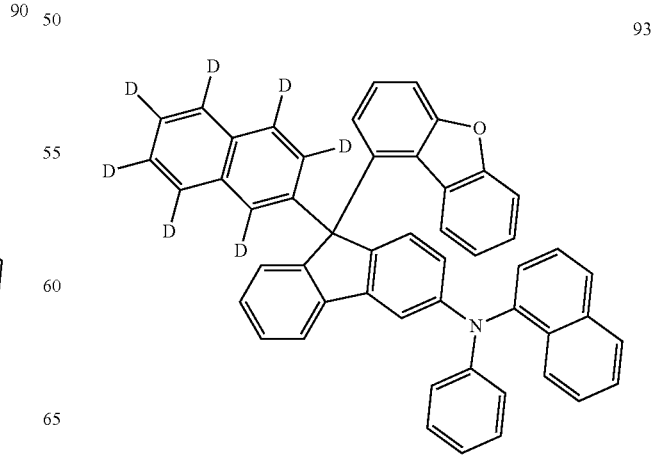
93

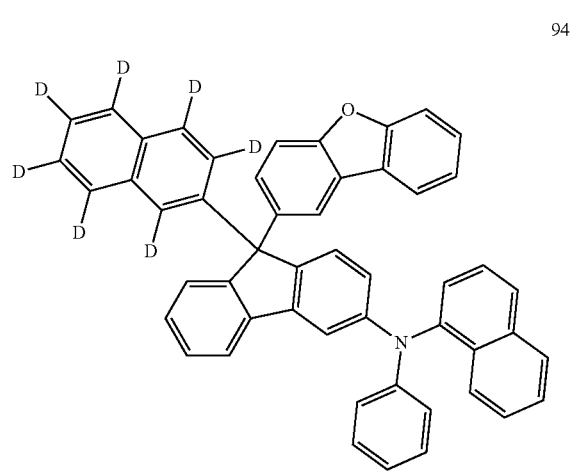
94
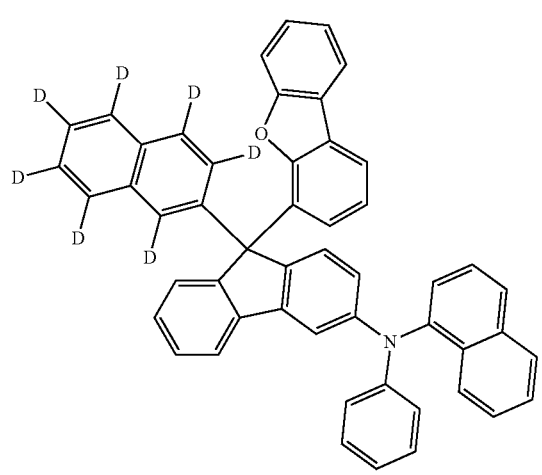
95
96
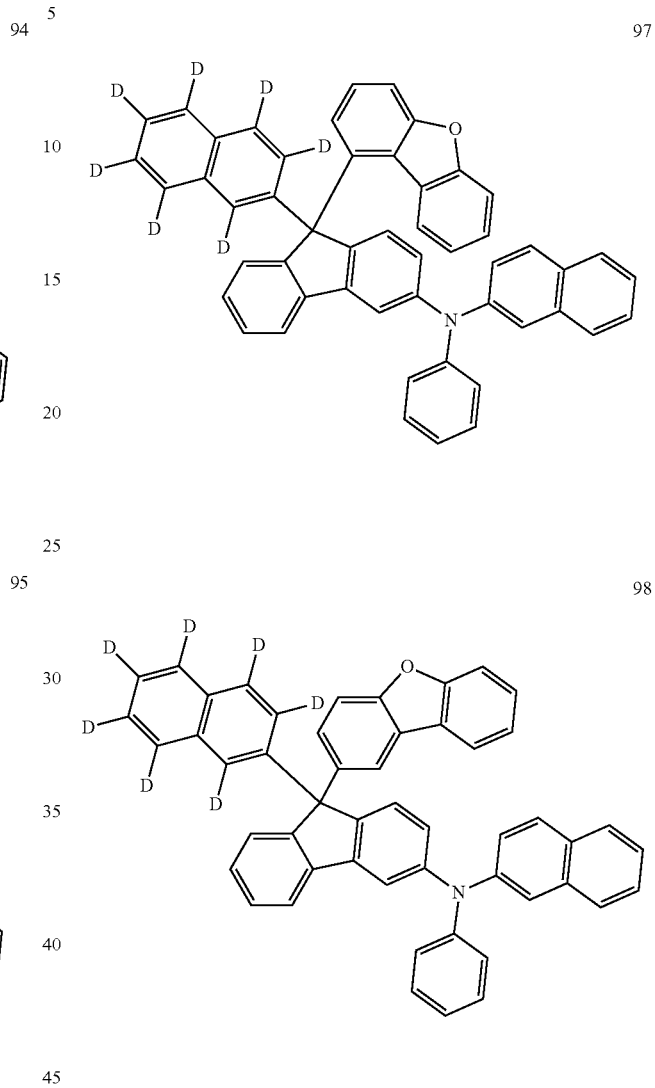
97
98
99

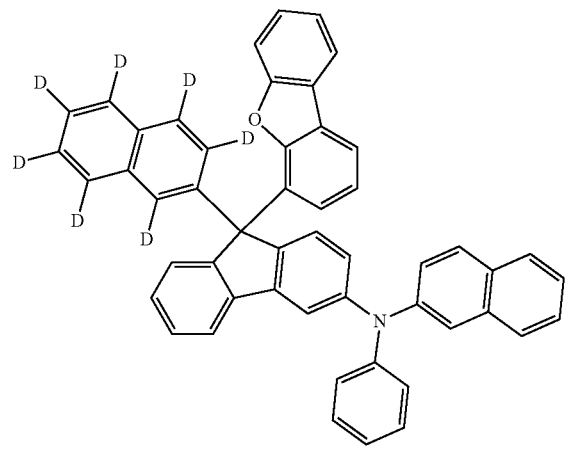
100
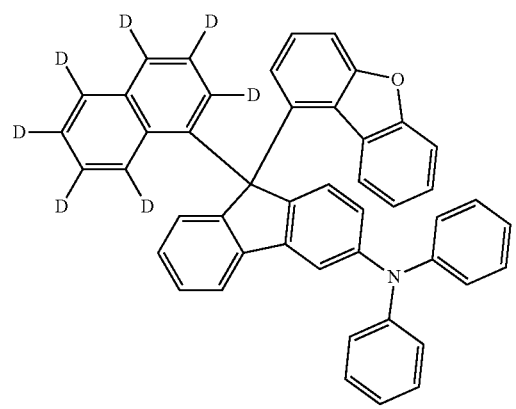
101
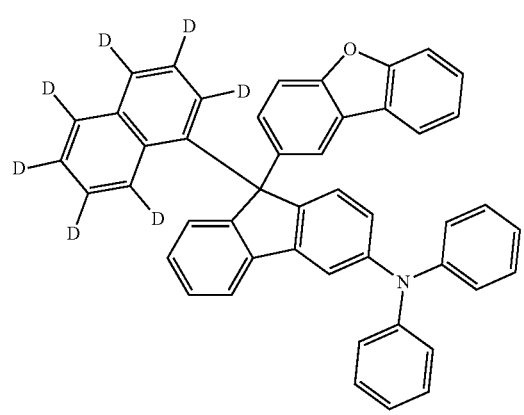
102
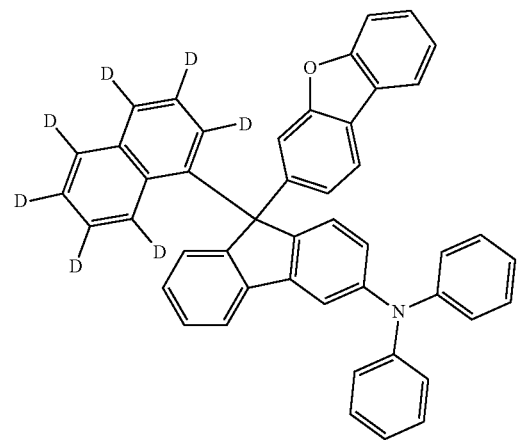
103
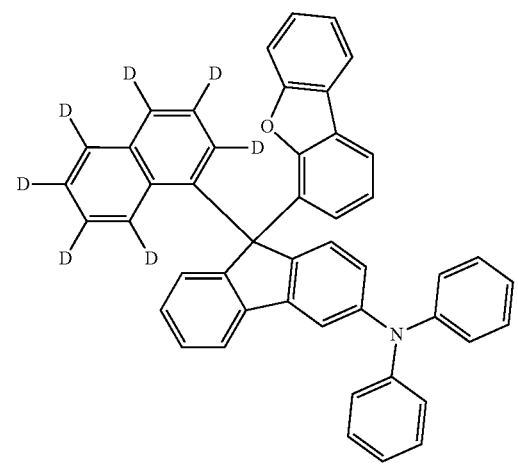
104
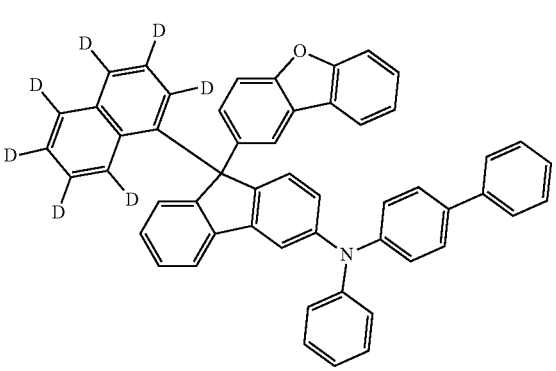
105
106

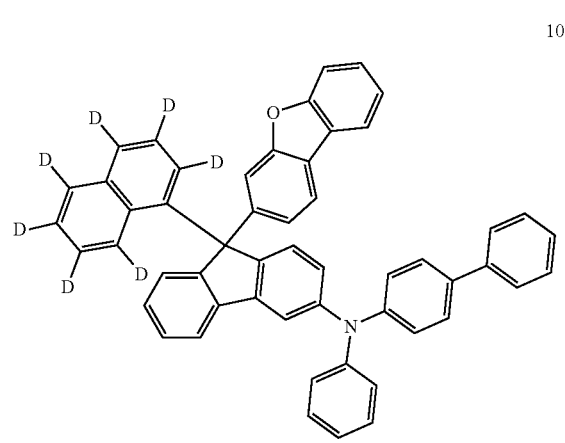
107
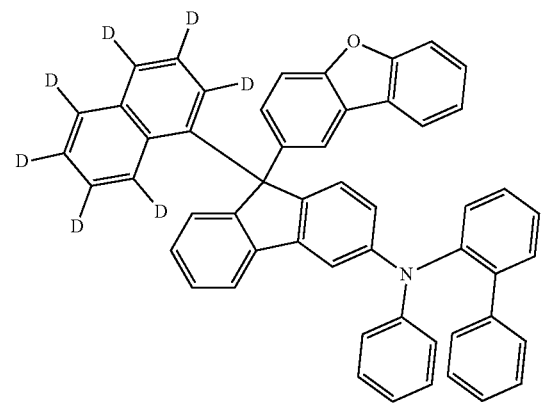
110
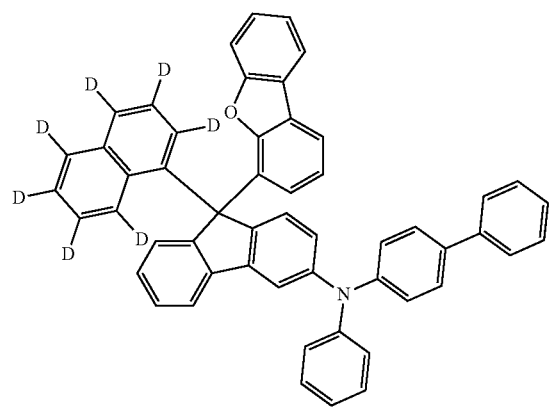
108
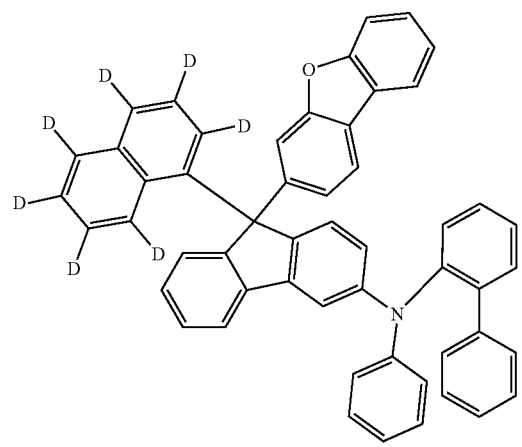
111
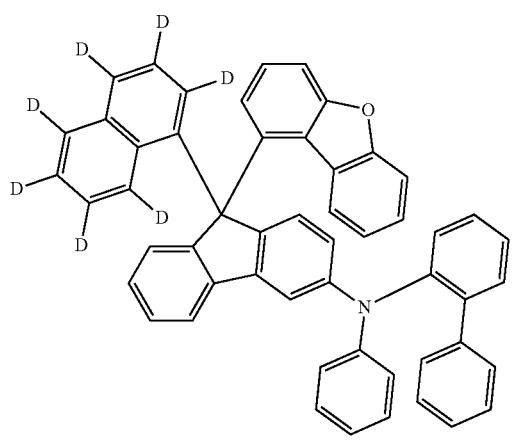
109
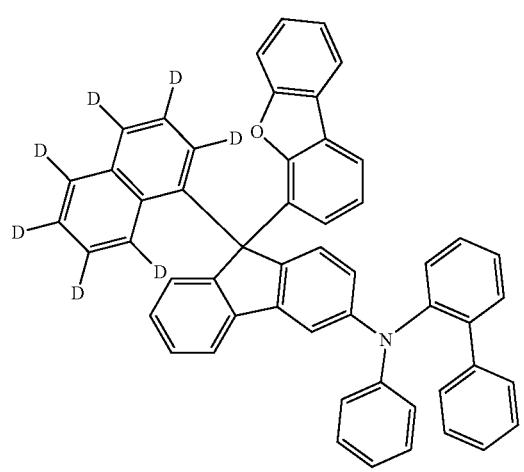
112

113 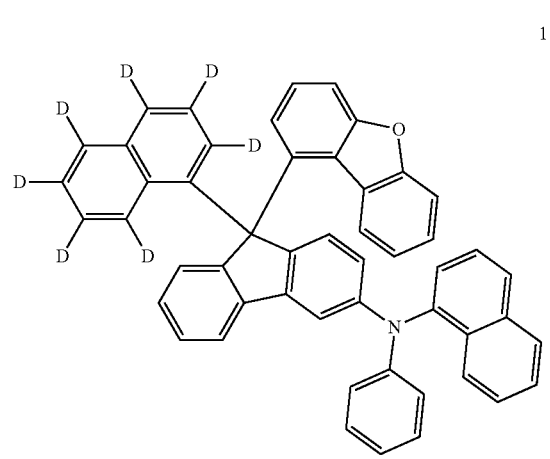
114 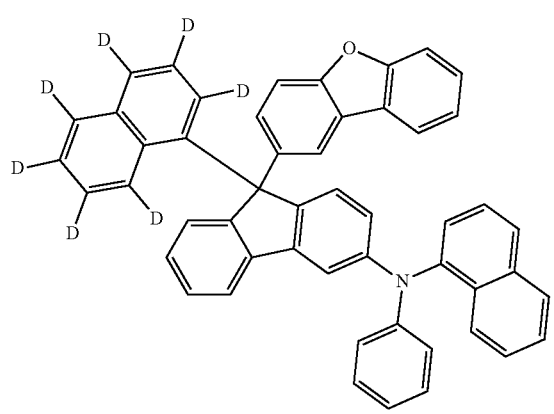
115 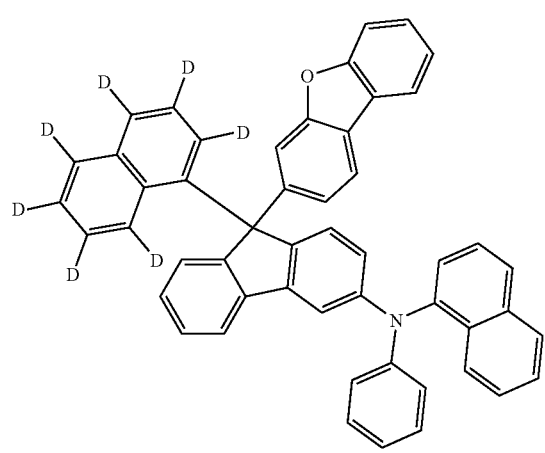
116 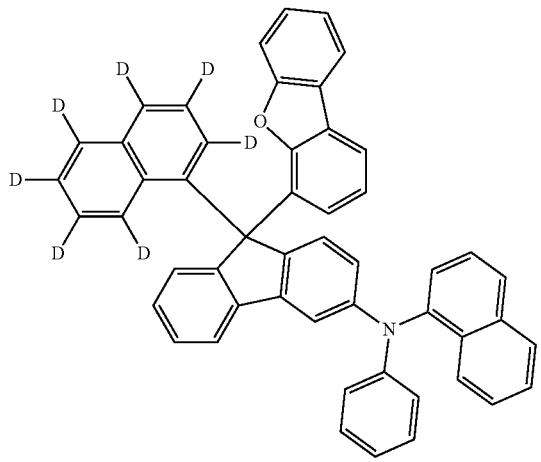
117
118 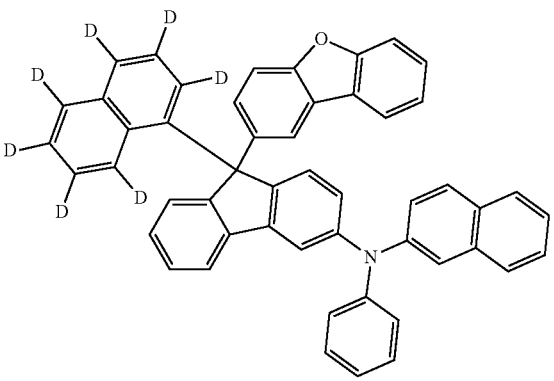

119
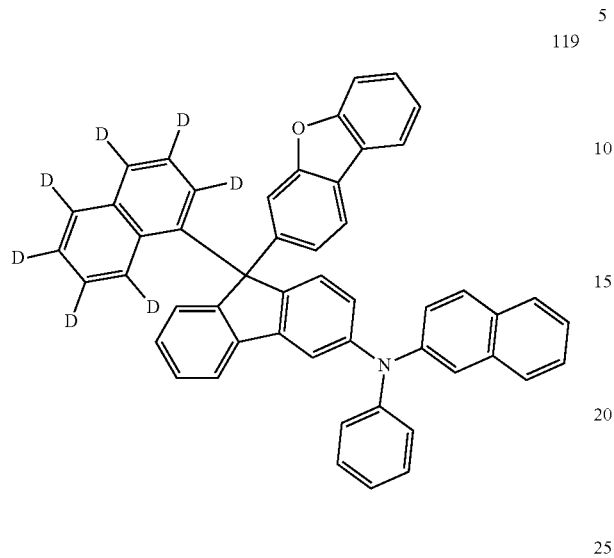
122
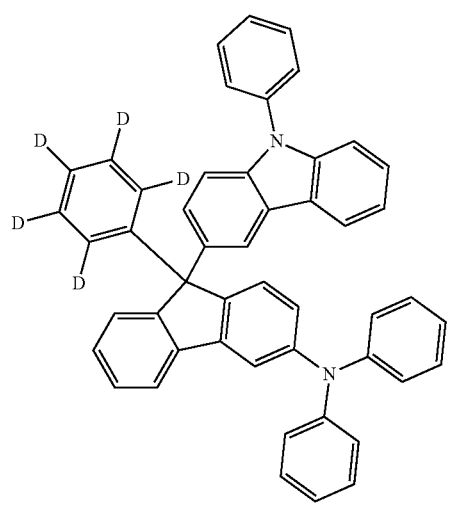
120
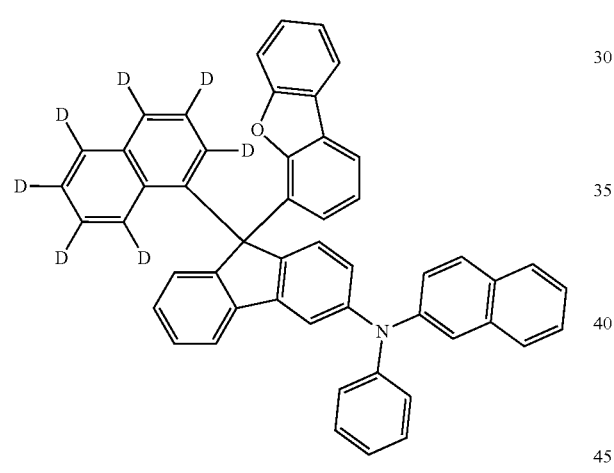
123
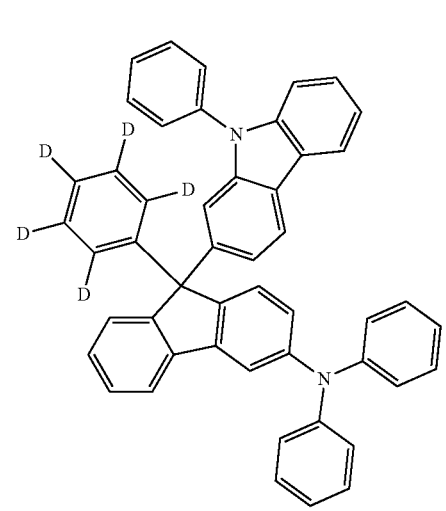
121
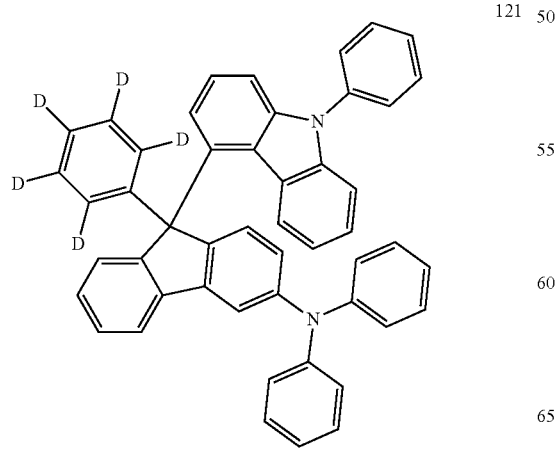
124
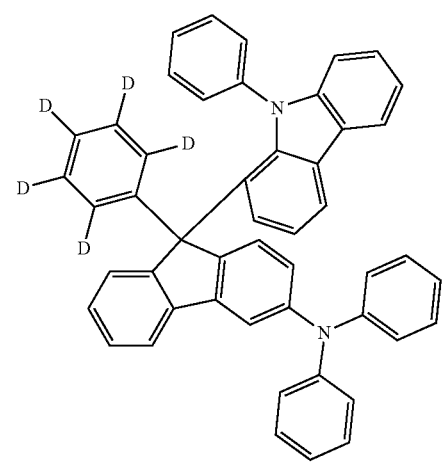

125
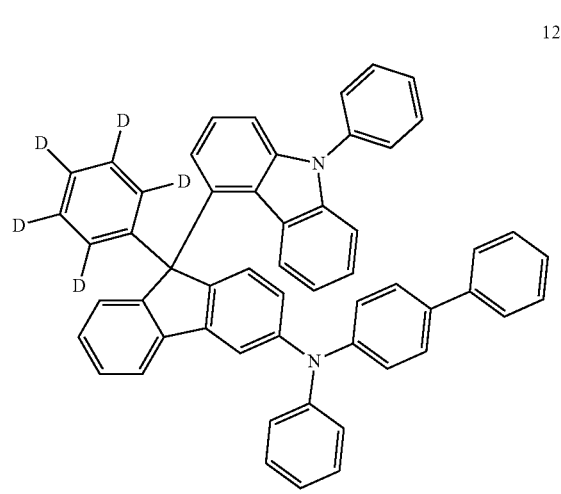
126
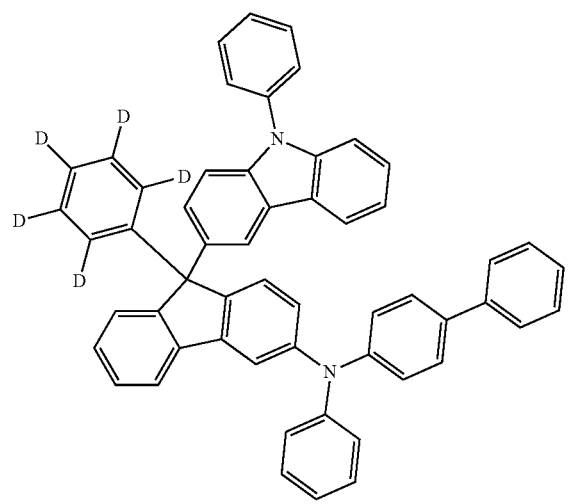
127
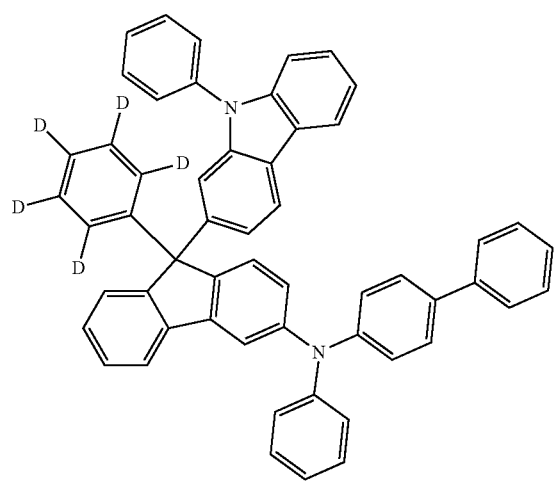
128
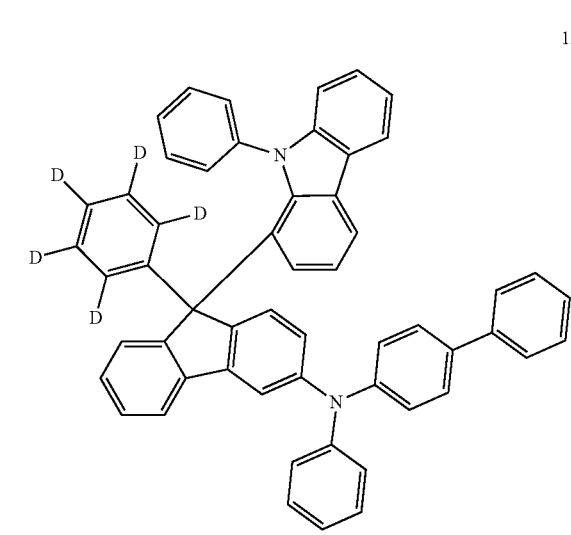
129
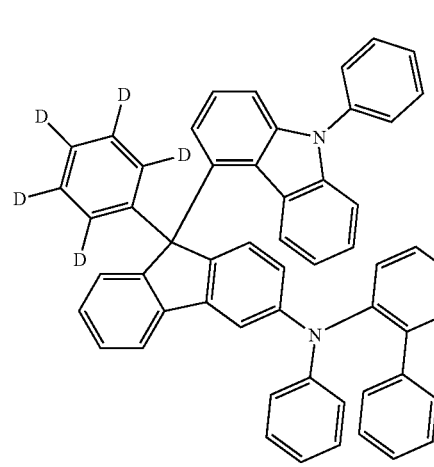
130
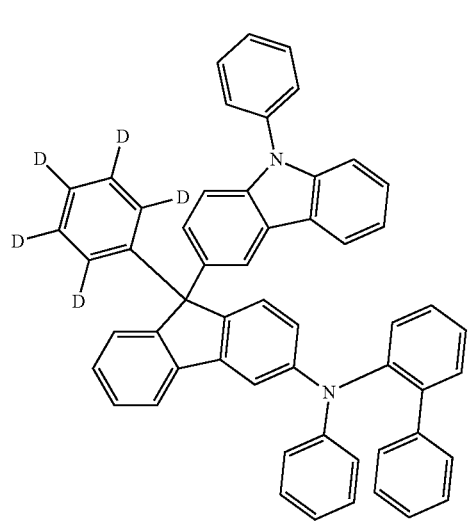

131
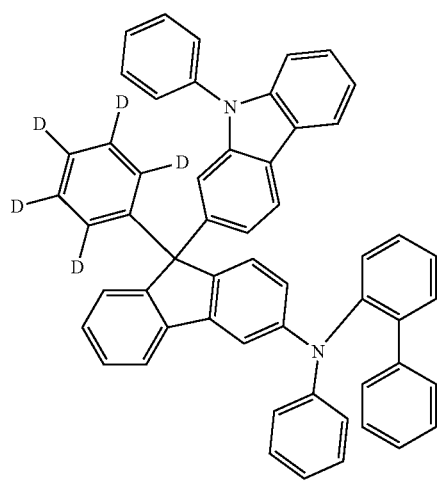
132
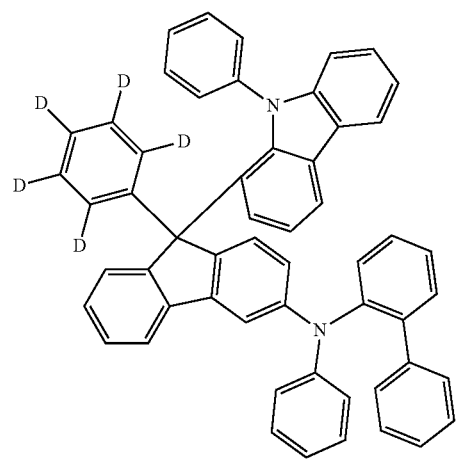
133
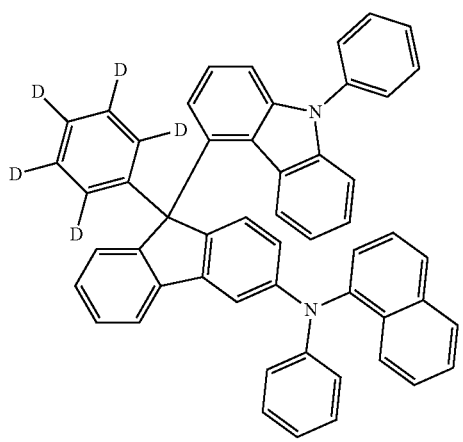
134
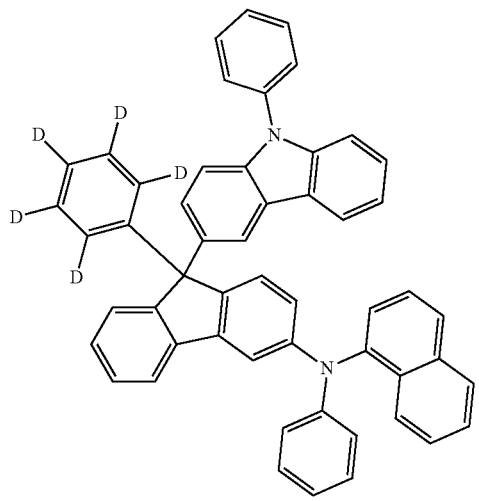
135
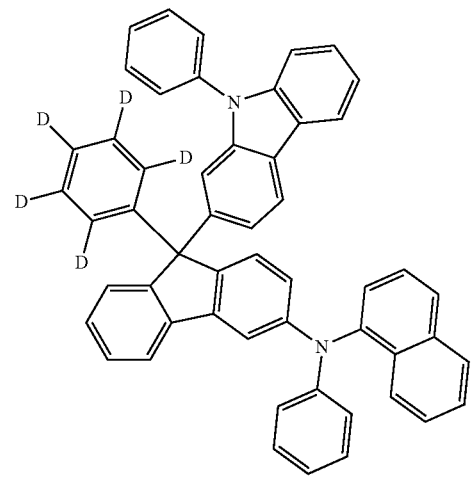
136
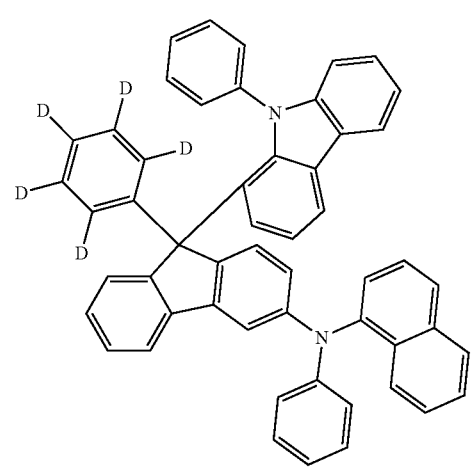

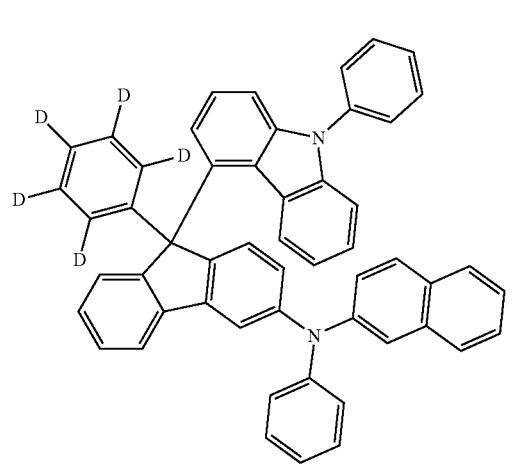
137
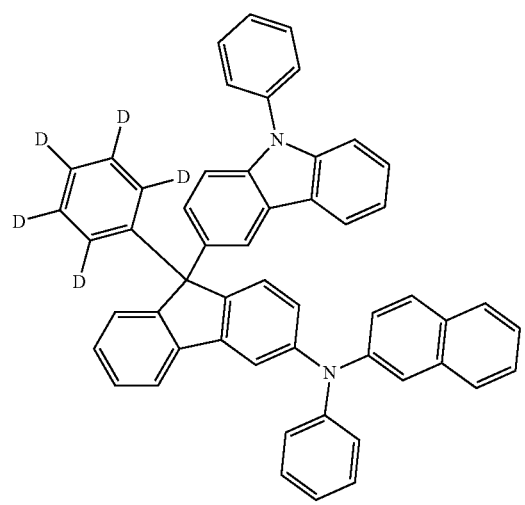
138
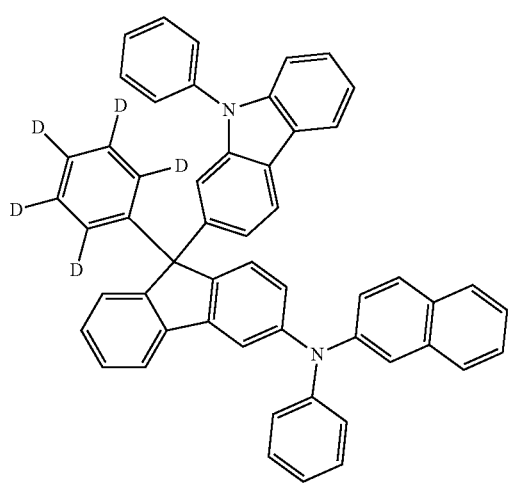
139
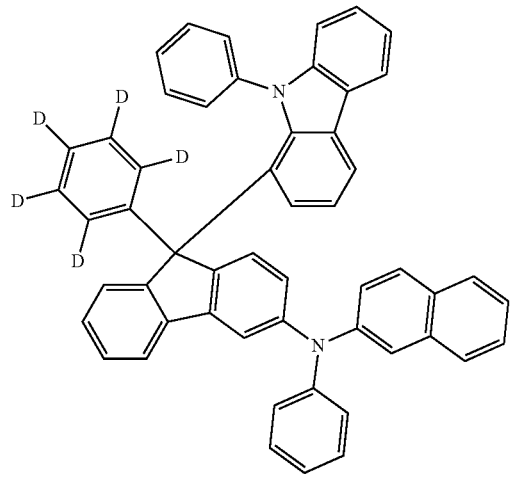
140
141
142

143
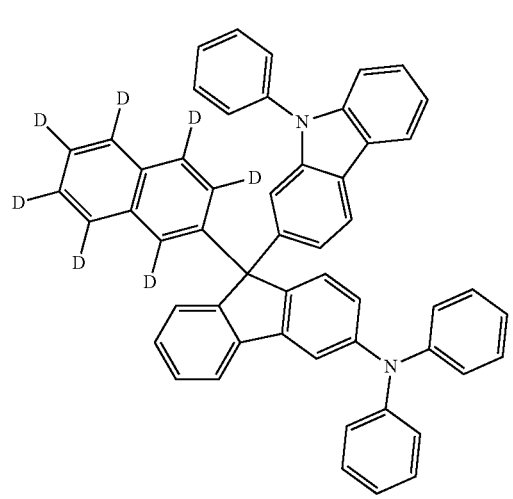
144
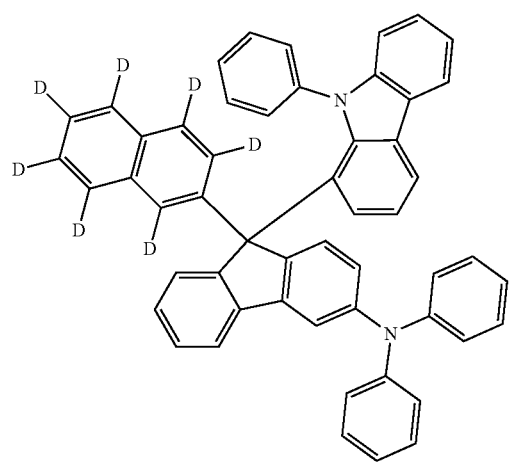
145
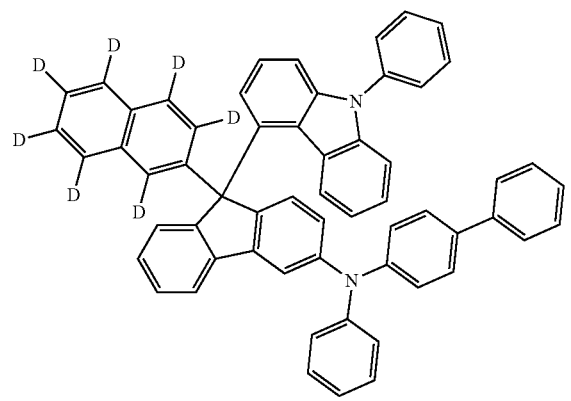
146
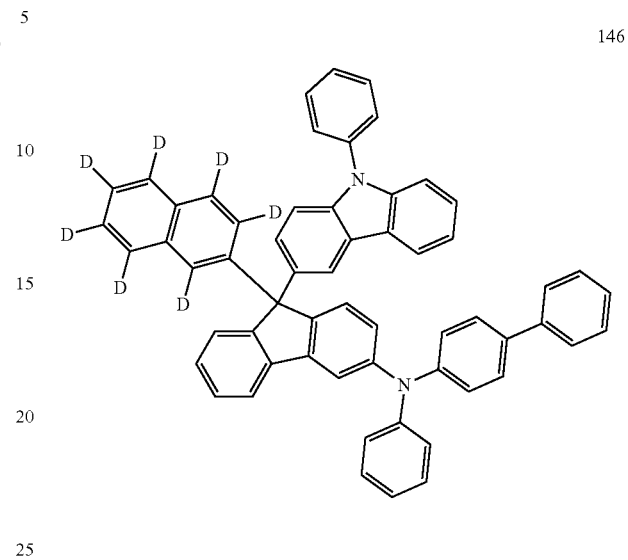
147
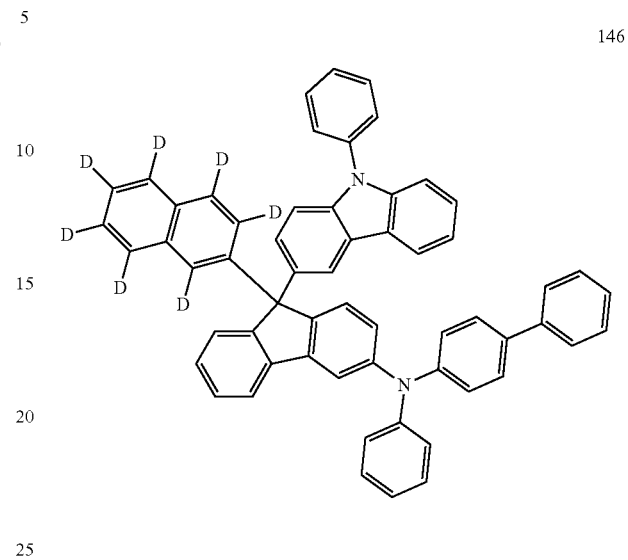
148
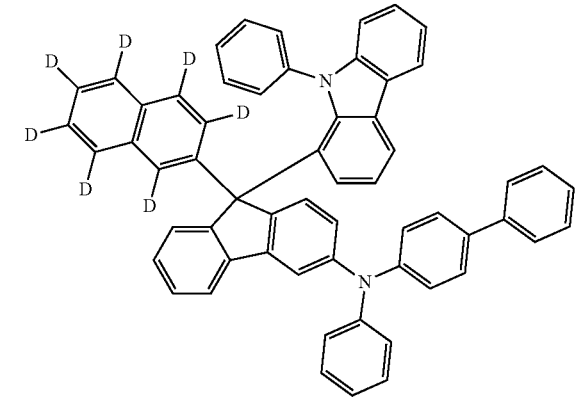

149
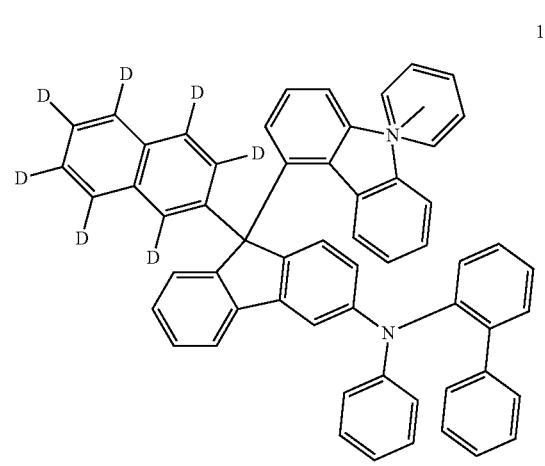
150
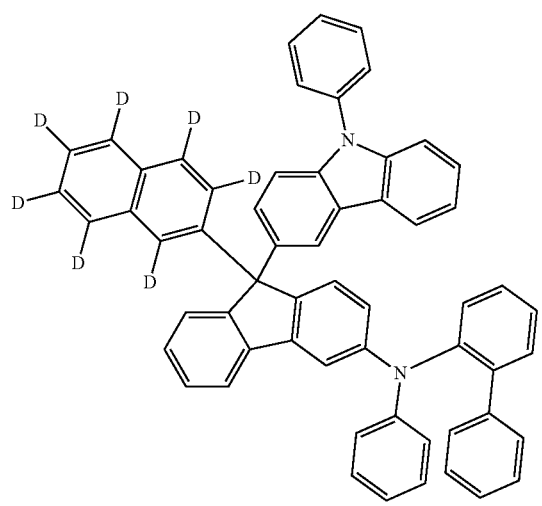
151
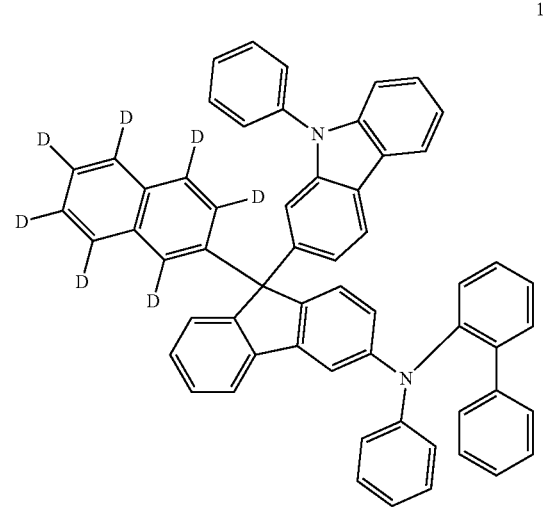
152
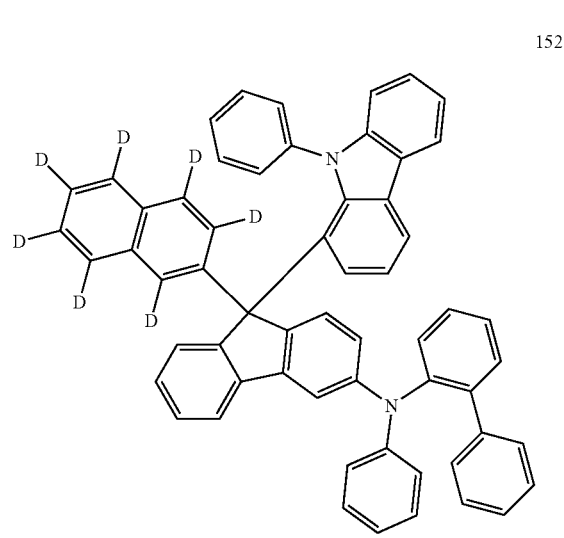
153
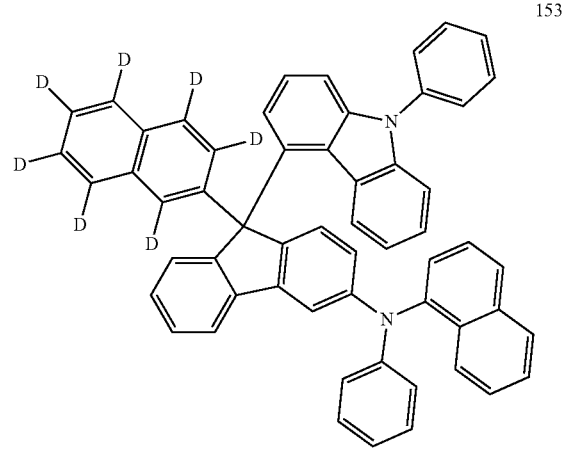
154
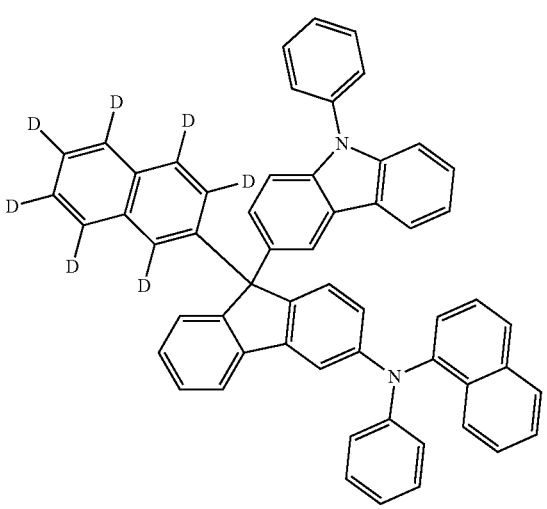

155 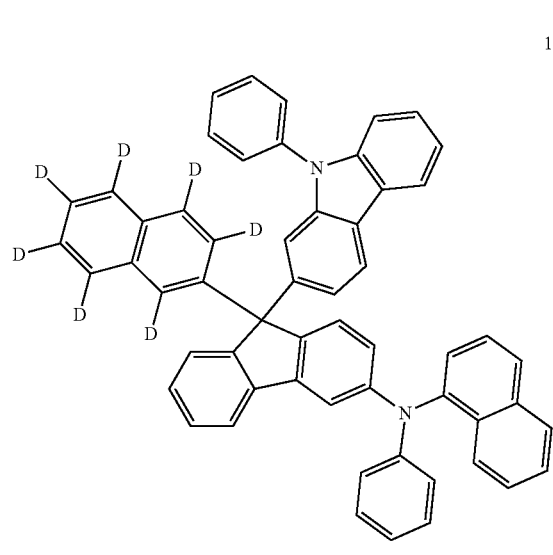
156 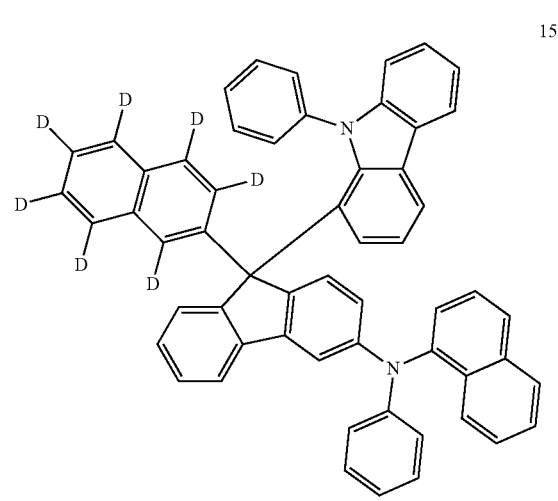
157 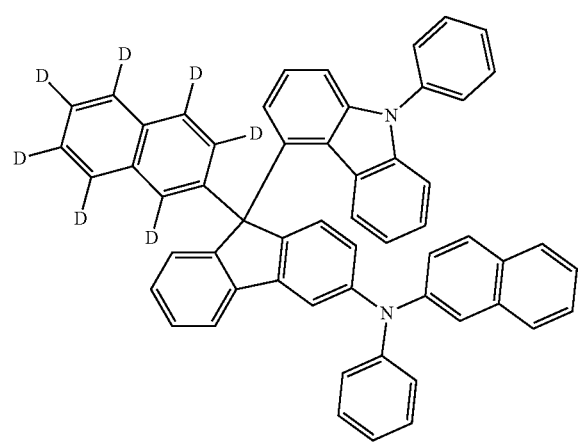
158 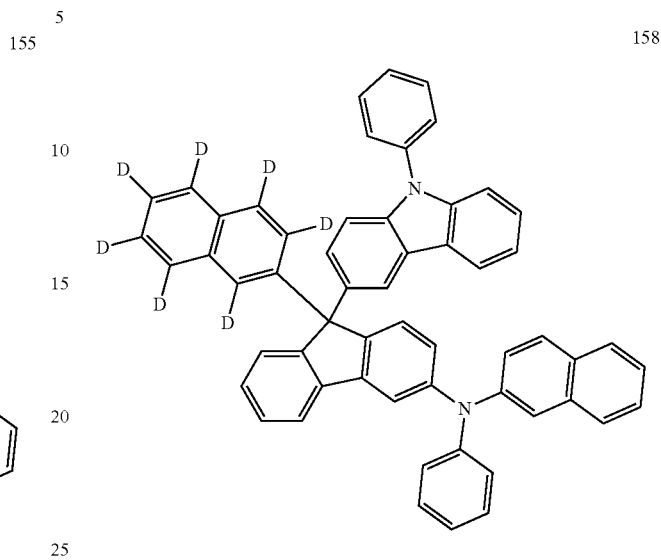
159 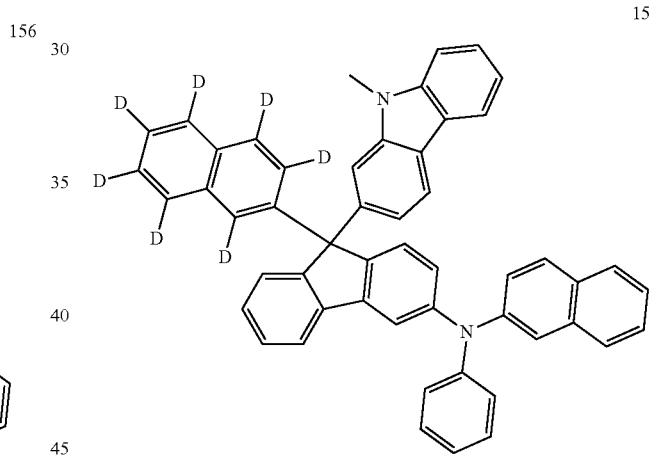
160 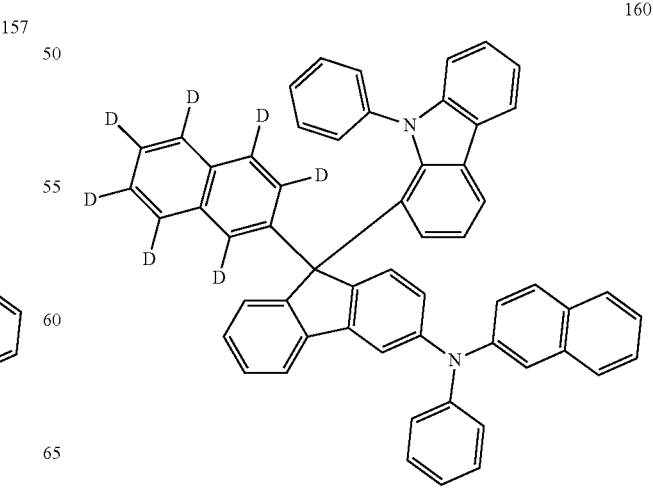

161
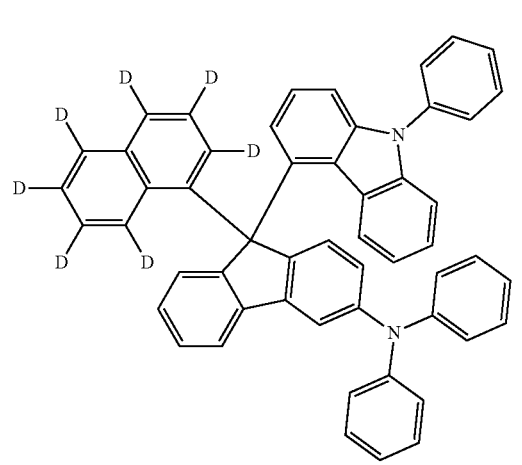
162
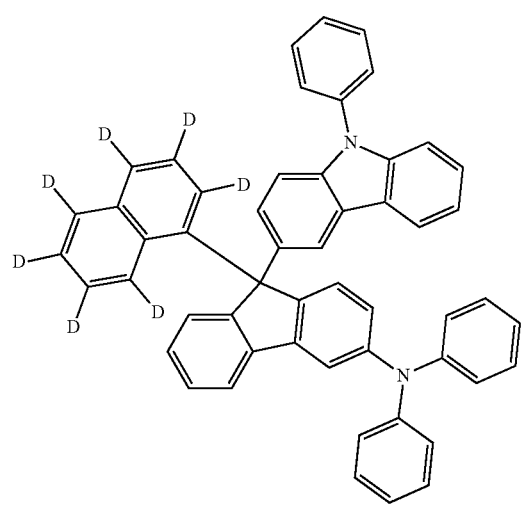
163
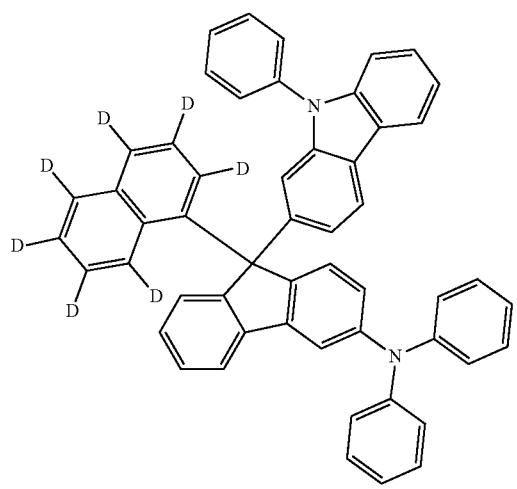
164
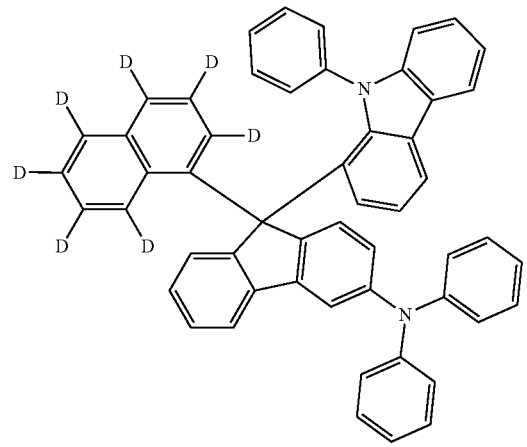
165
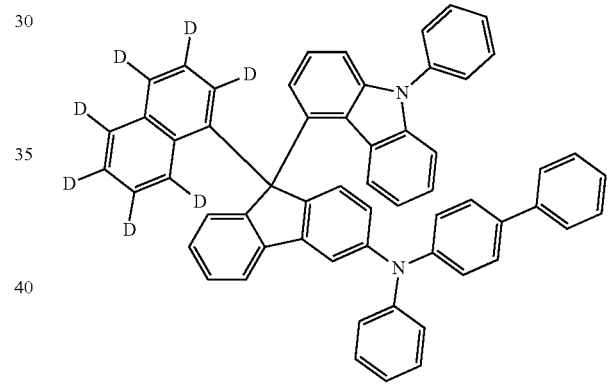
166
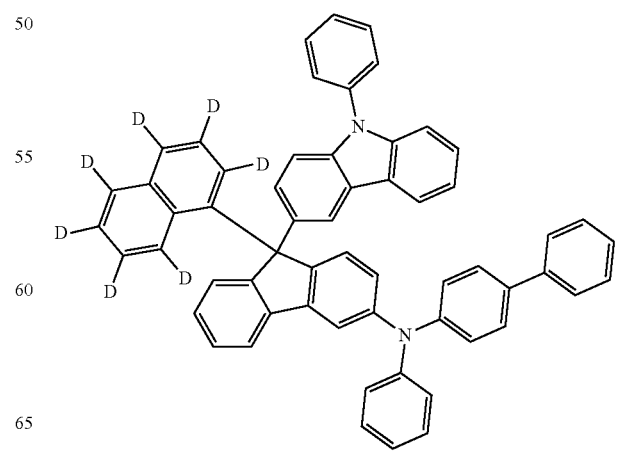

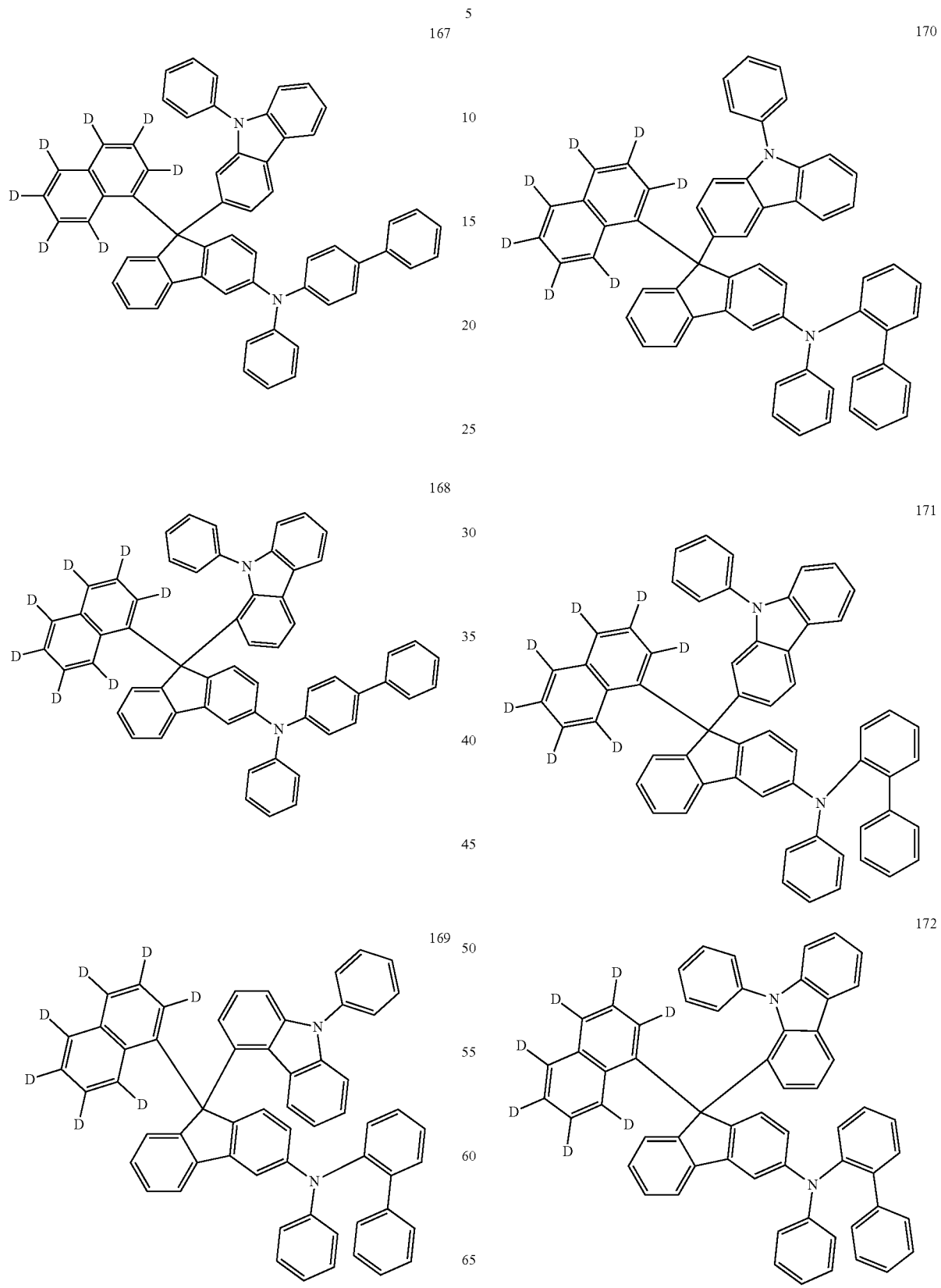

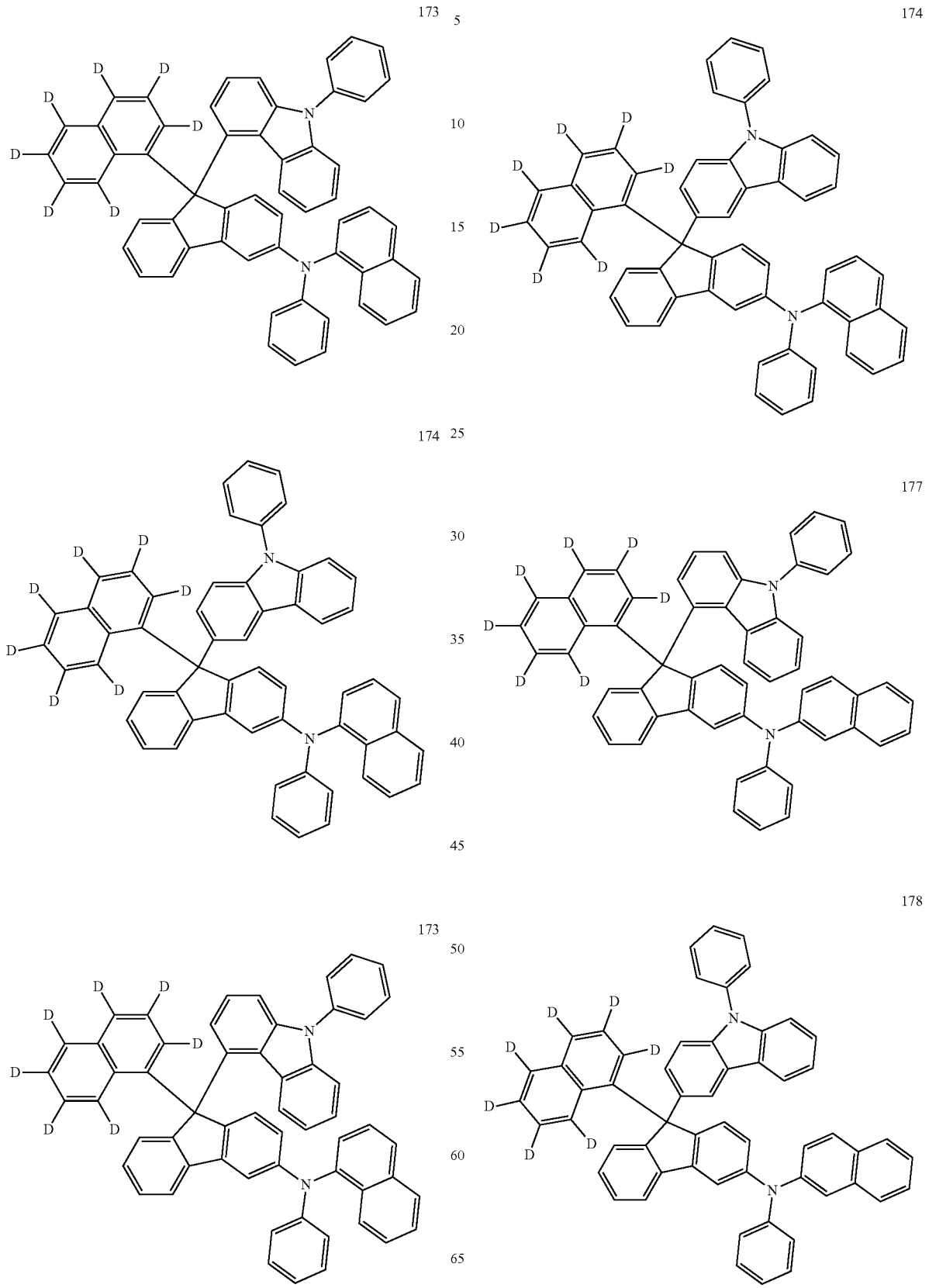

179
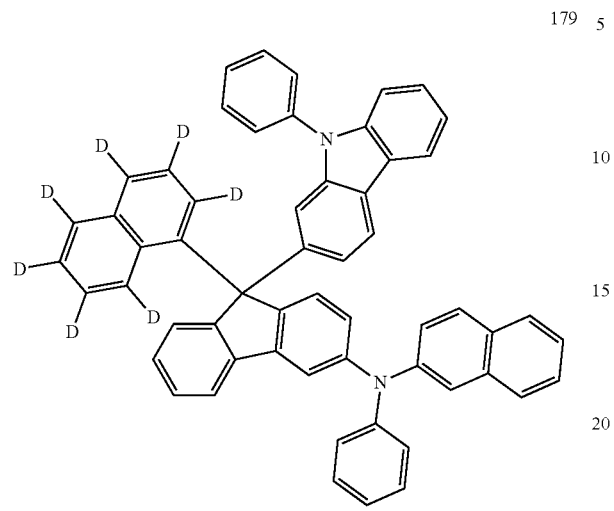
180
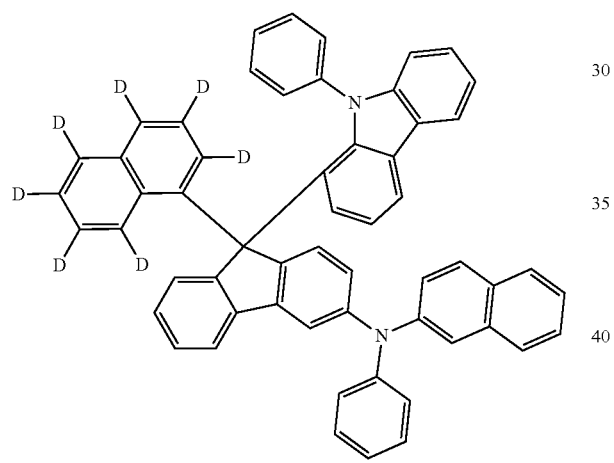
181
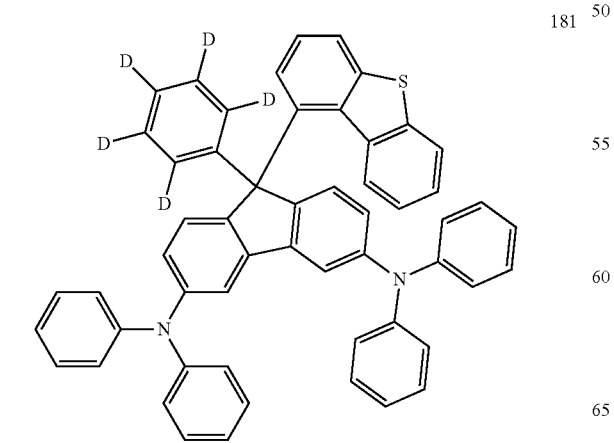
182
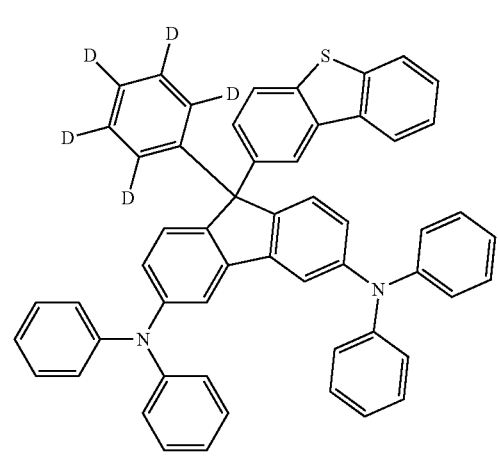
183
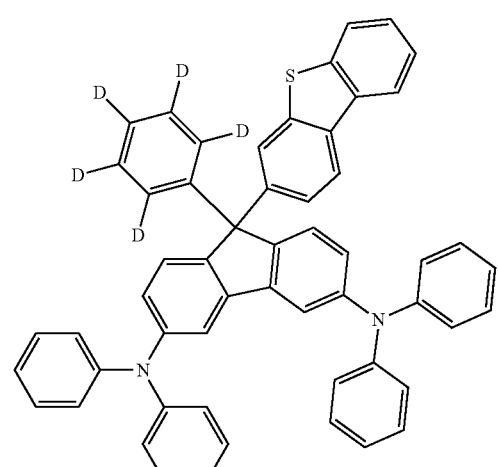
184
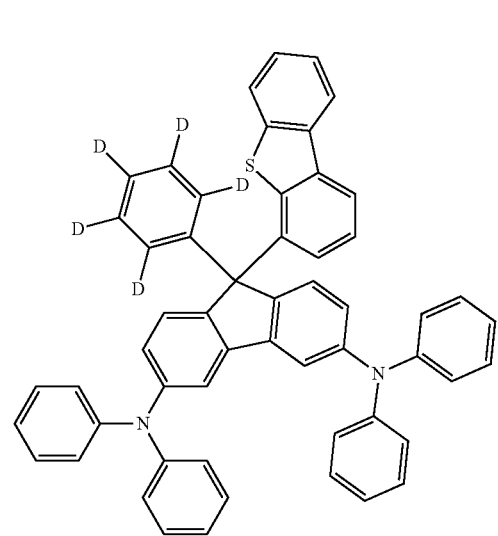

185
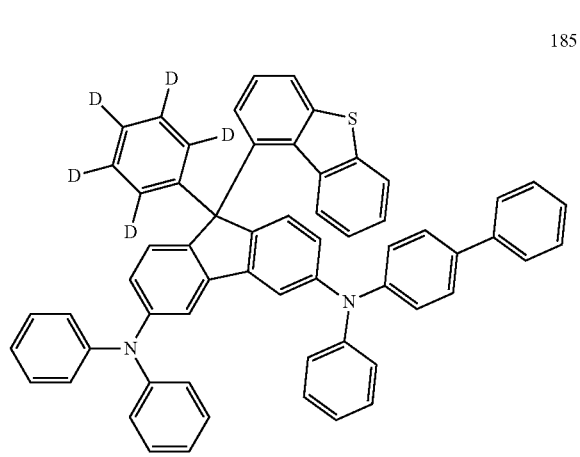
186
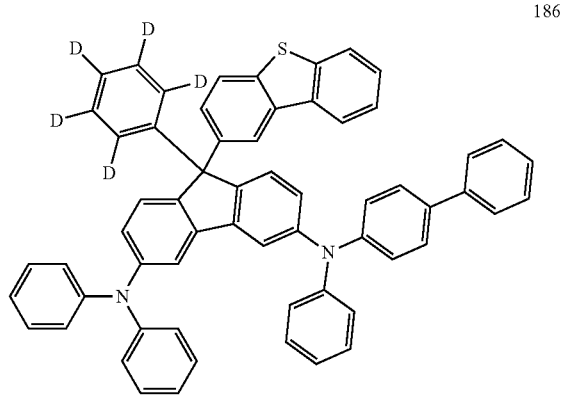
187
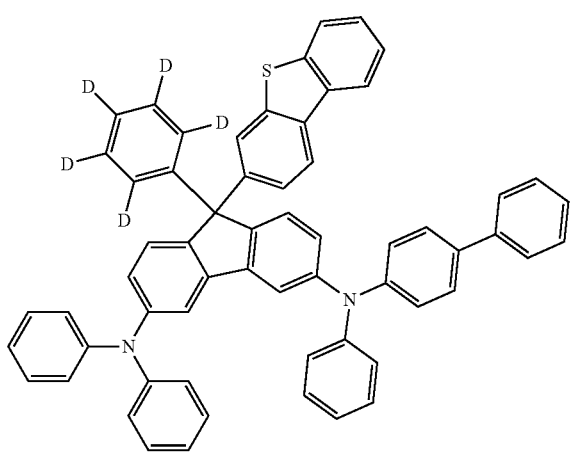
188
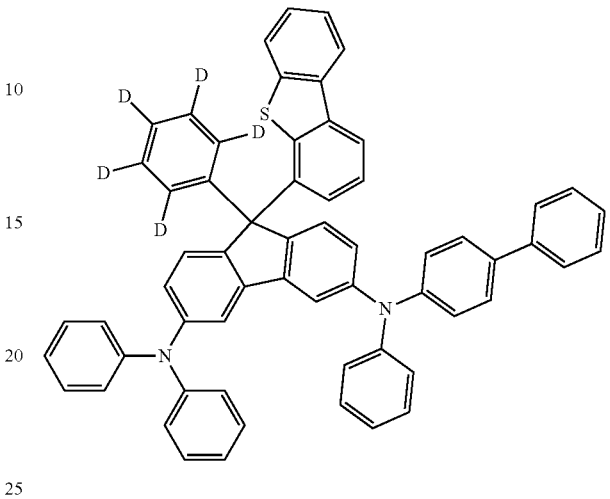
189
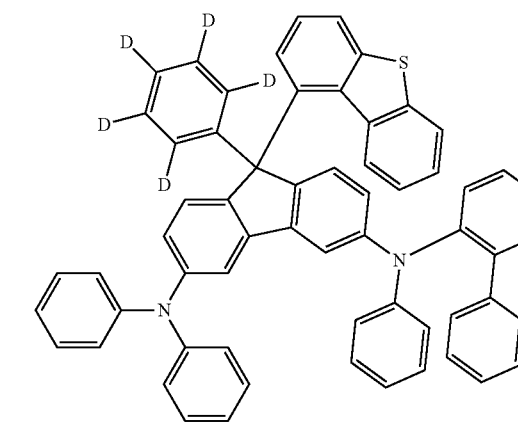
190
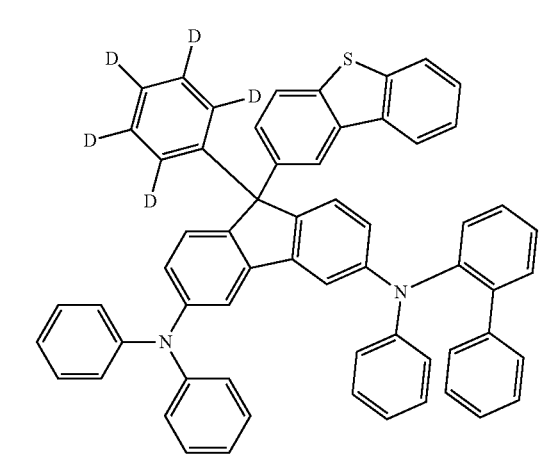

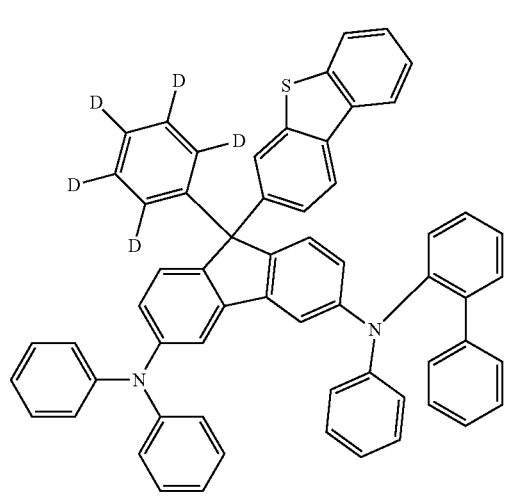
191
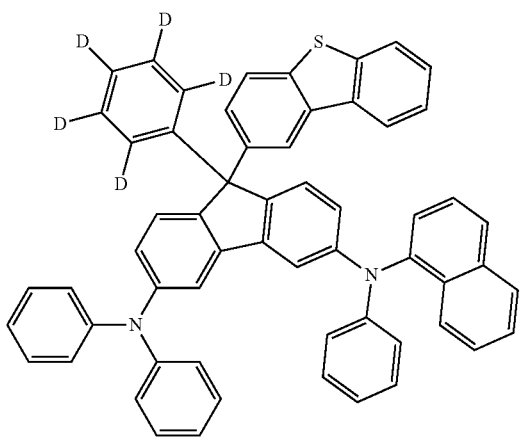
194
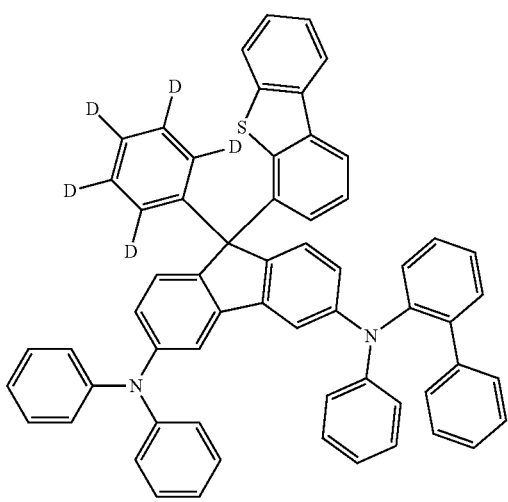
192
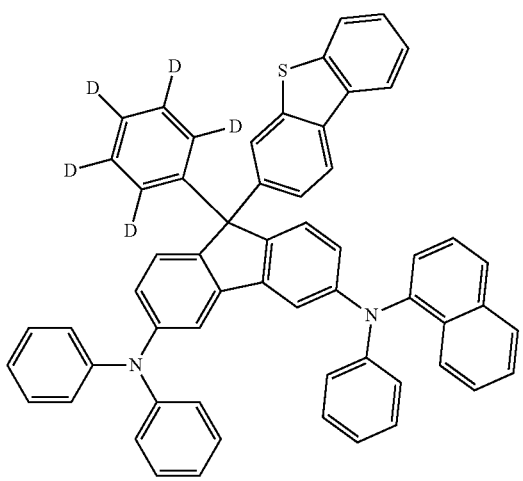
195
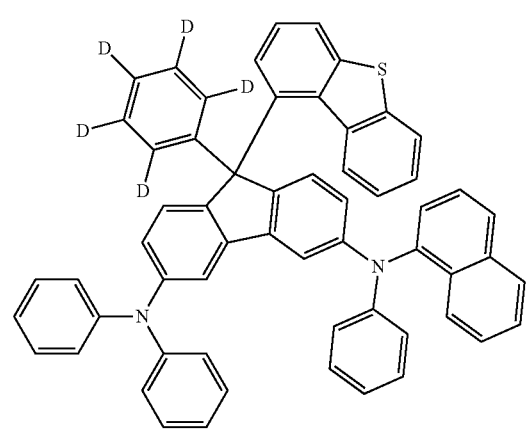
193
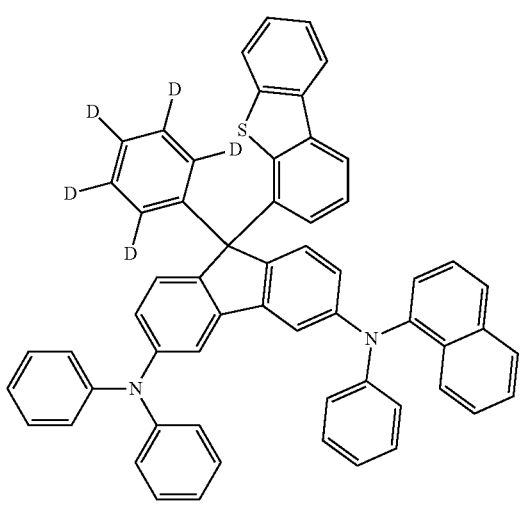
196

197
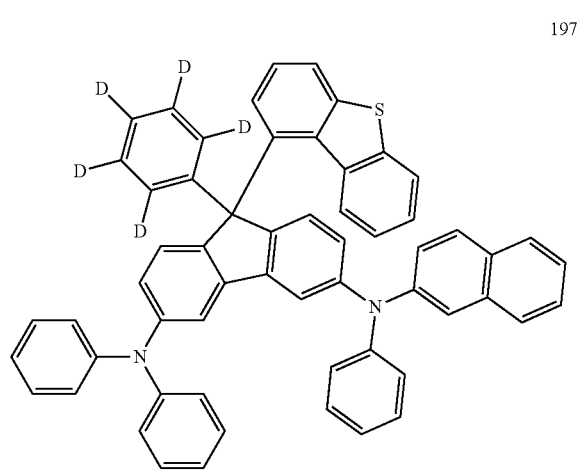
198
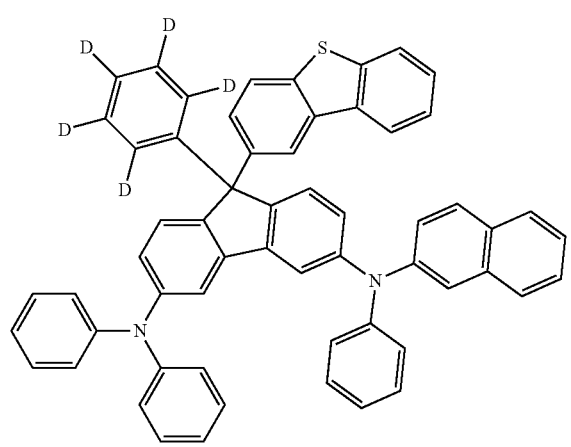
199
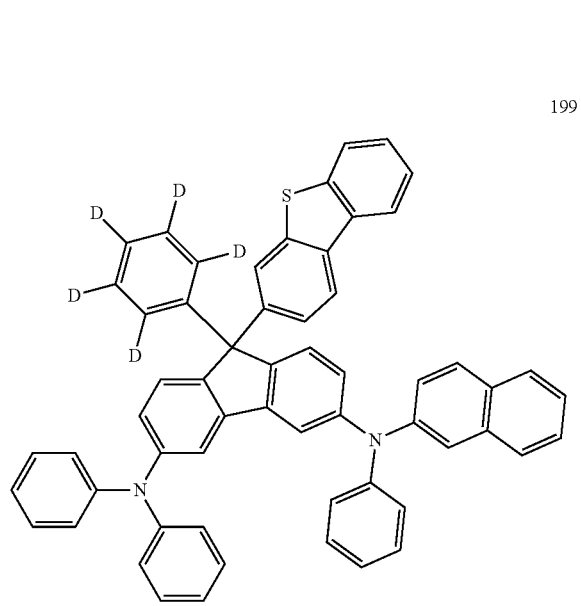
200
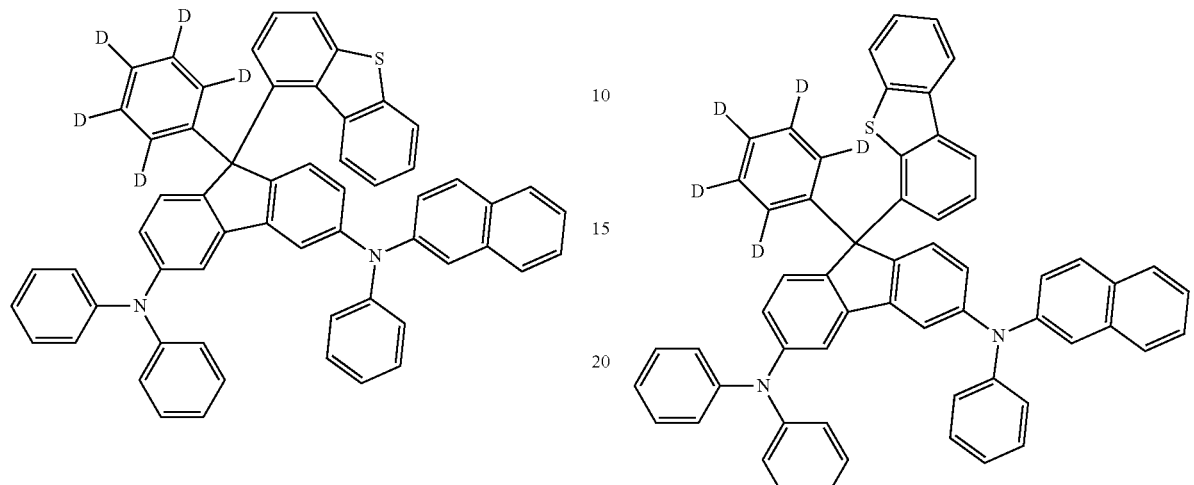
201
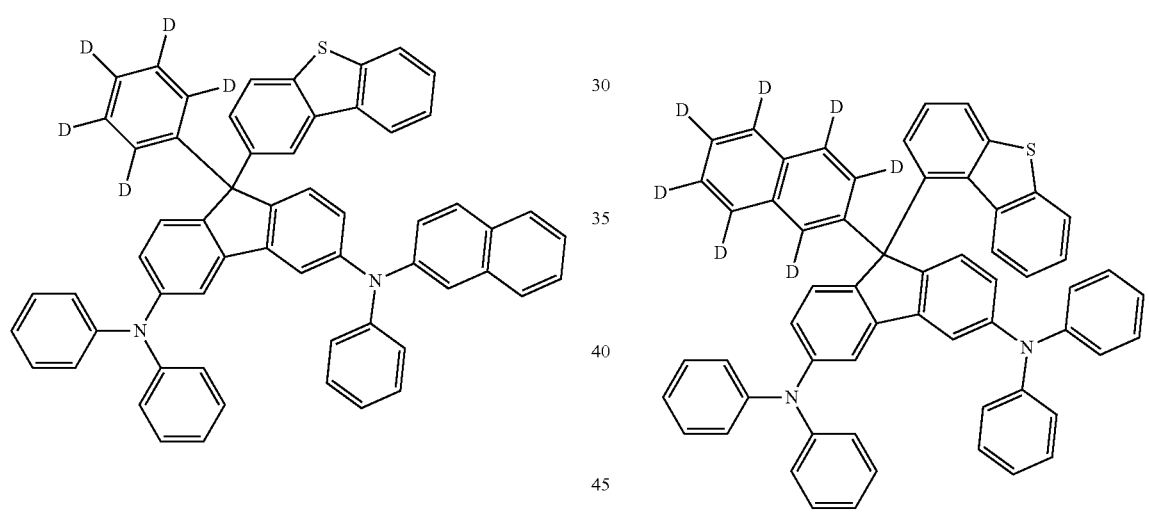
202
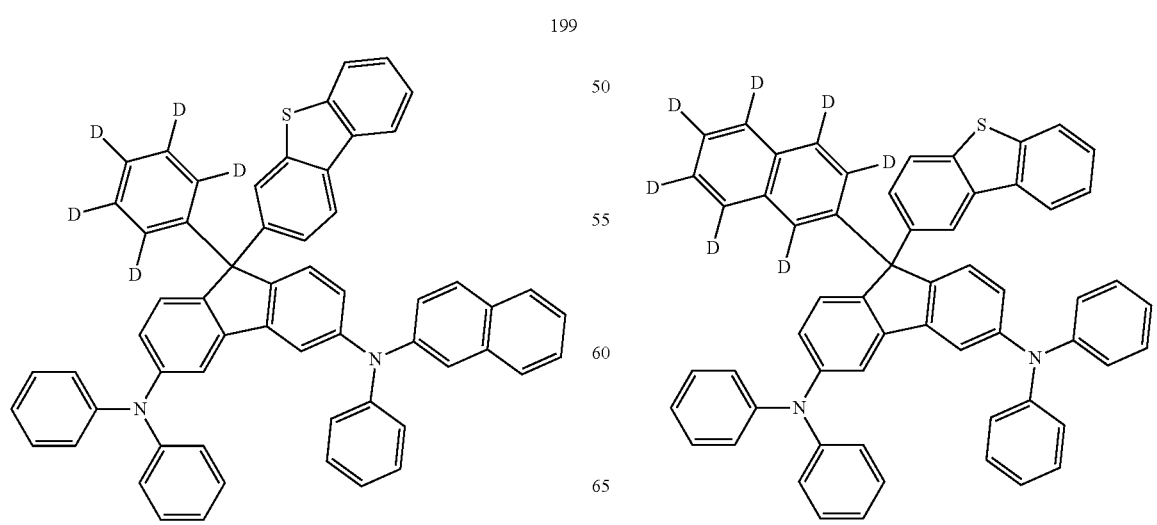

203
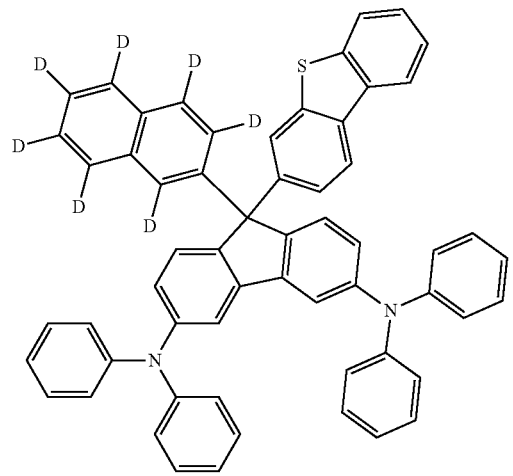
204
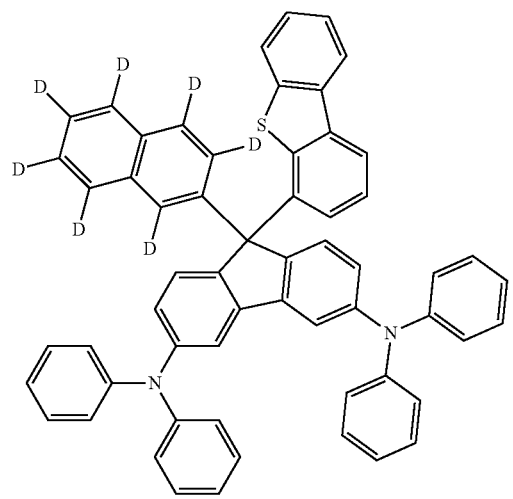
205
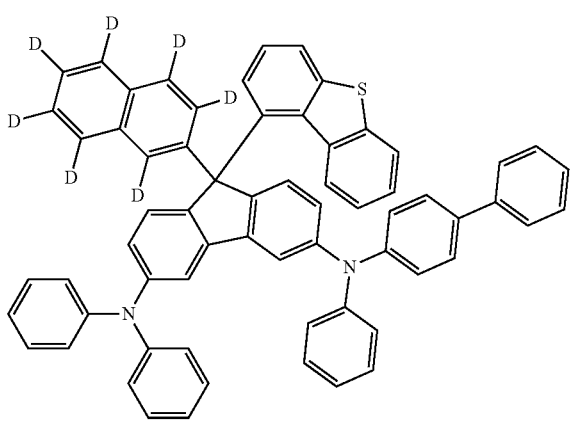
206
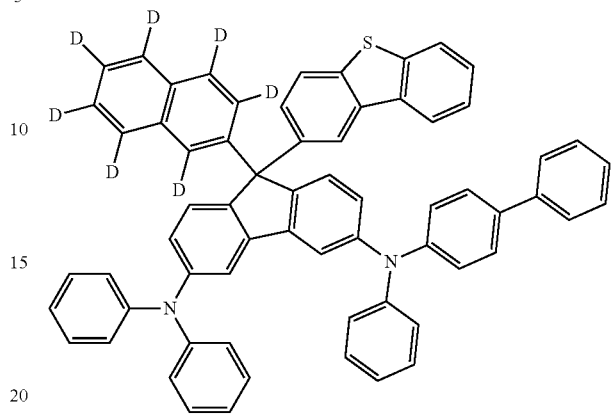
207
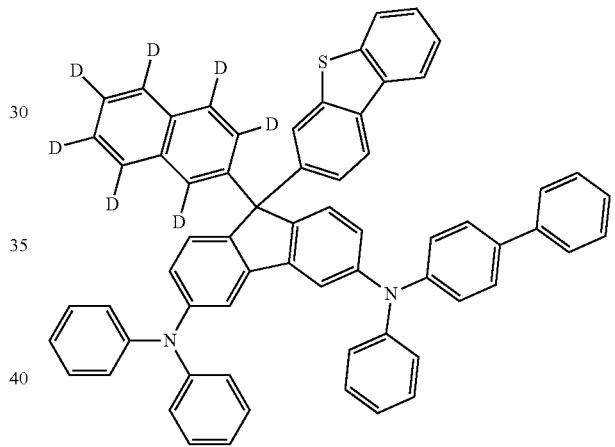
208
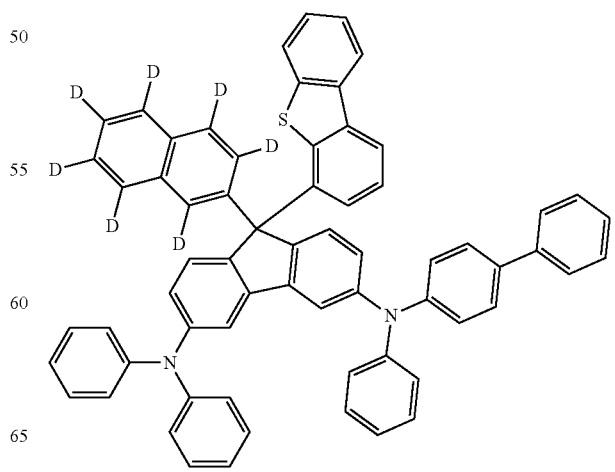

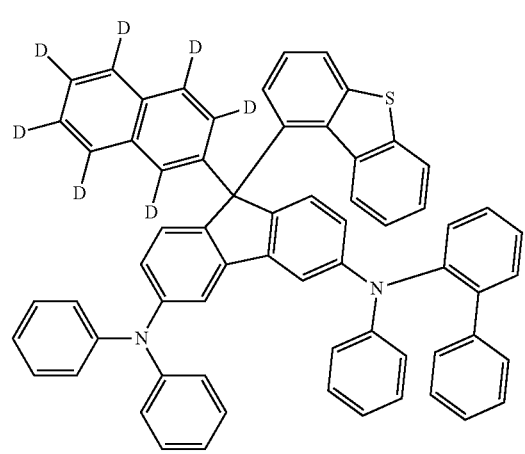
209
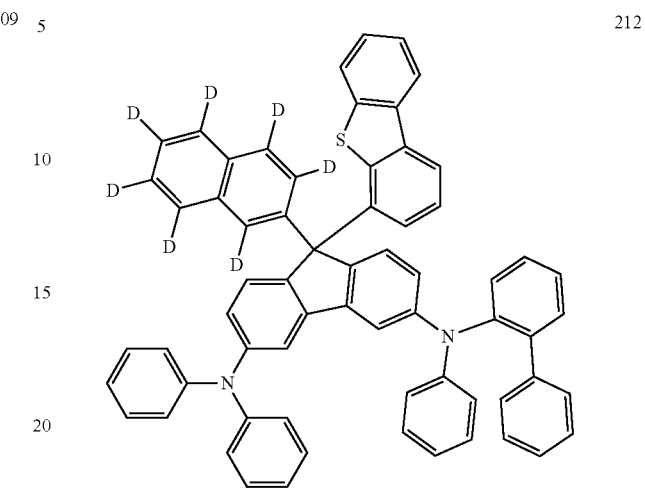
212
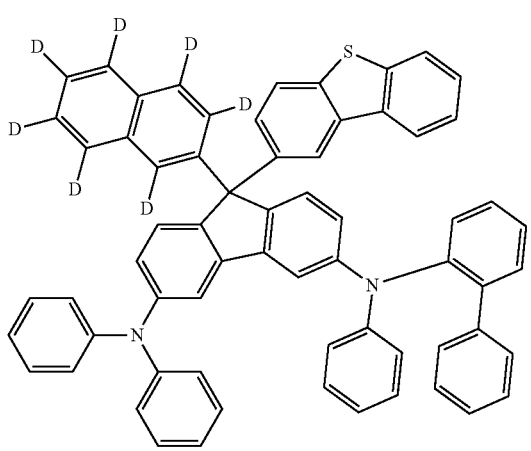
210
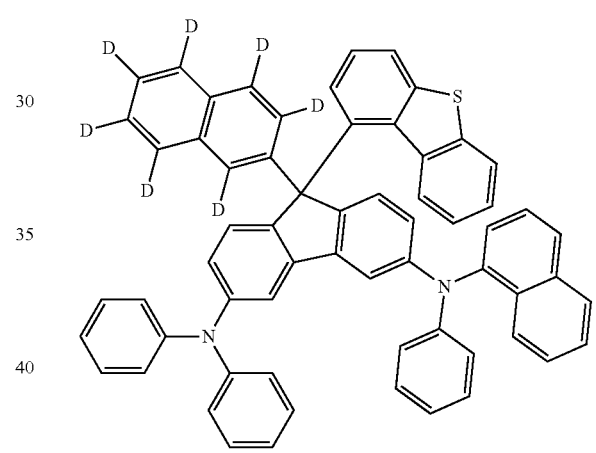
213
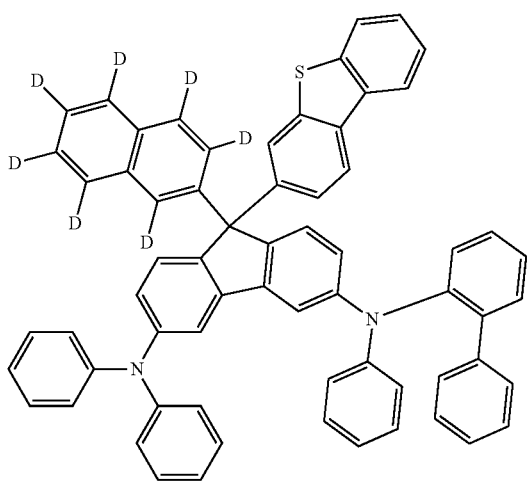
211
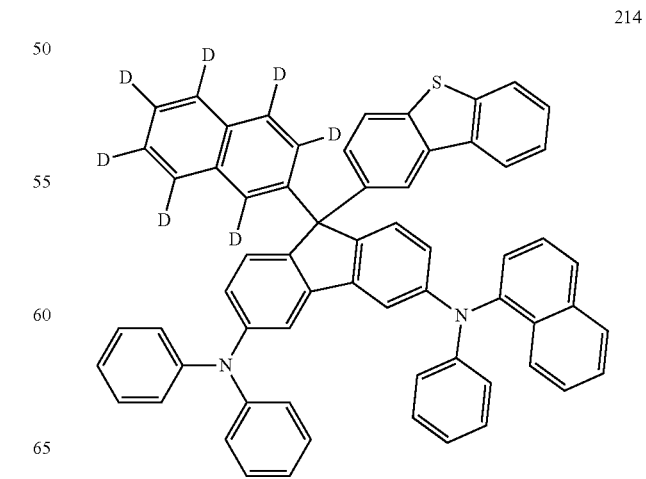
214

215
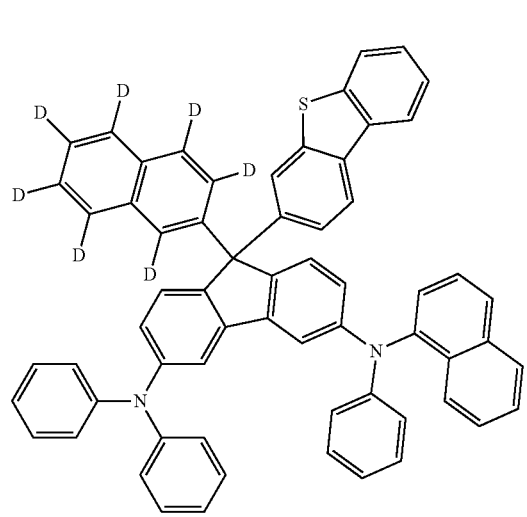
216
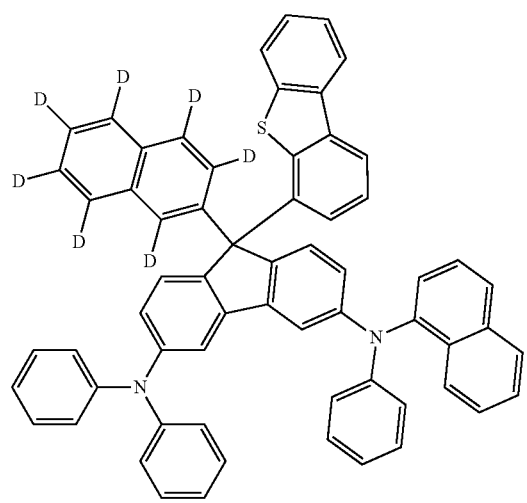
217
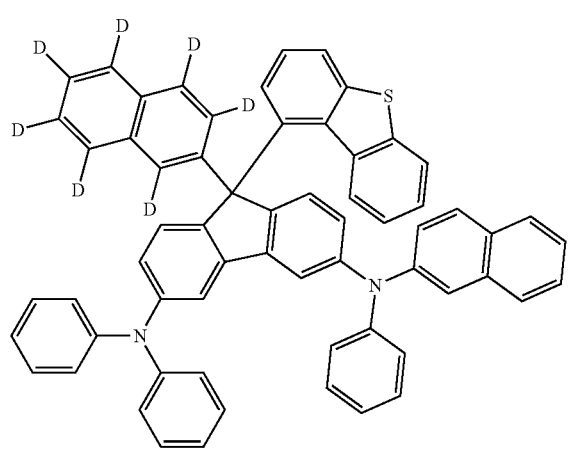
218
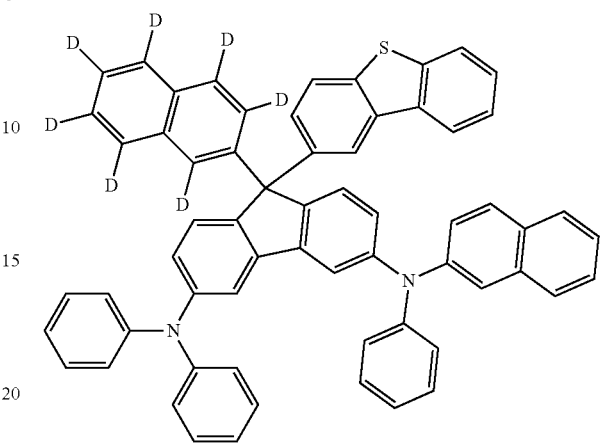
219
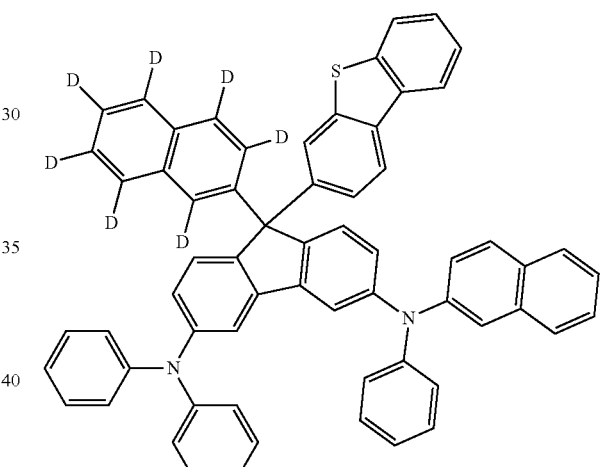
220
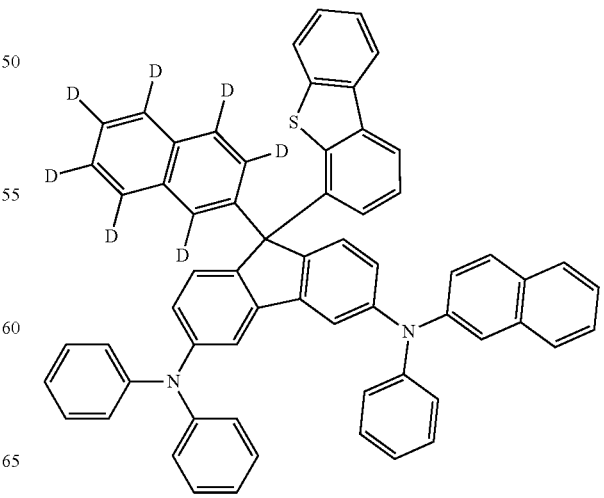

221
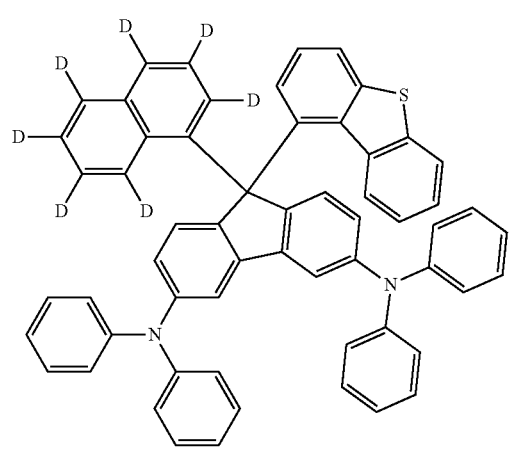
222
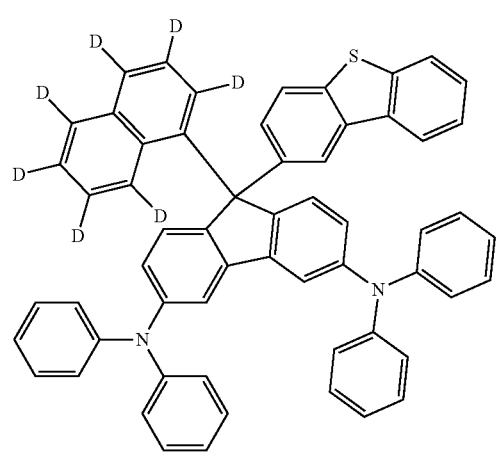
223
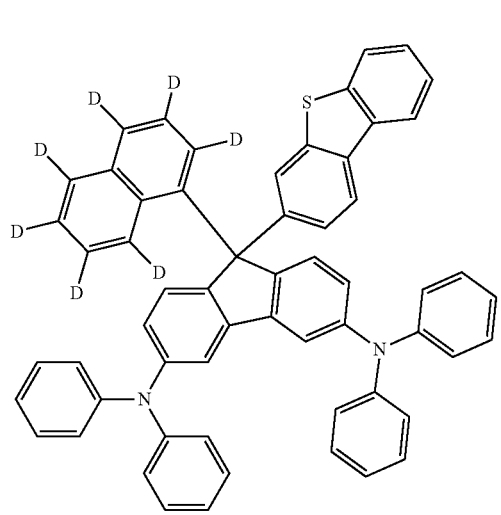
224
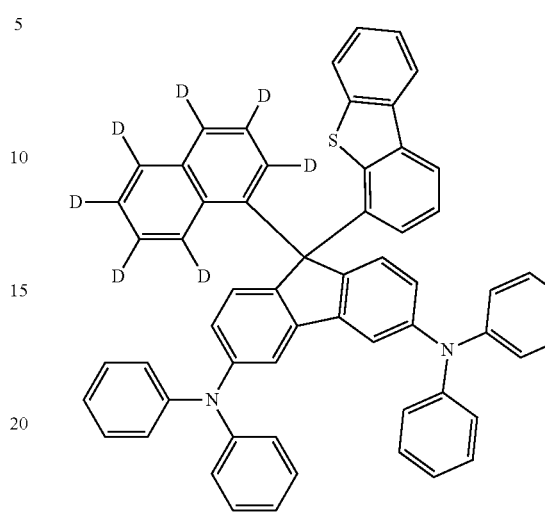
225
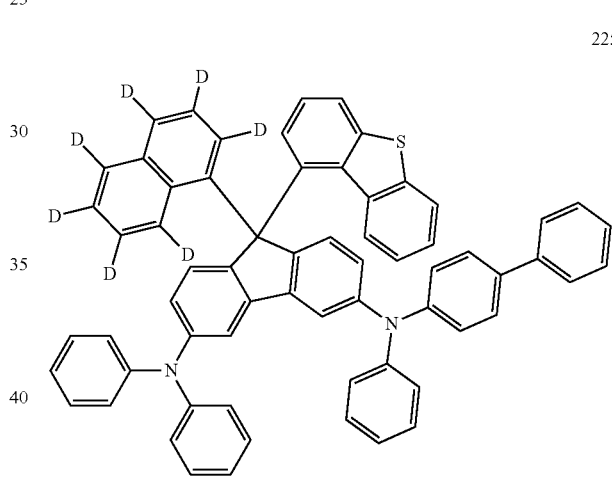
226
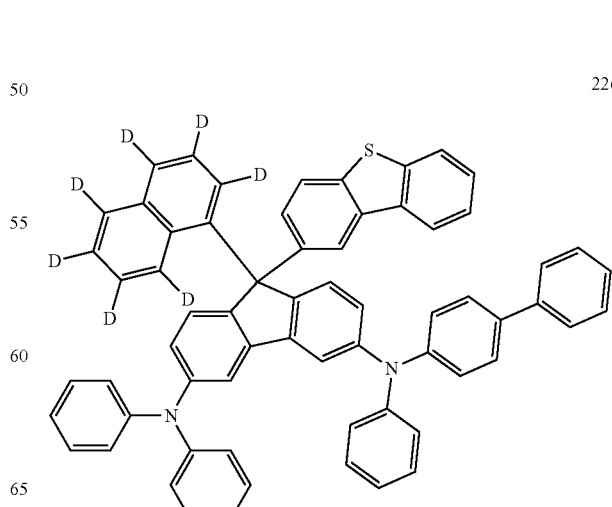

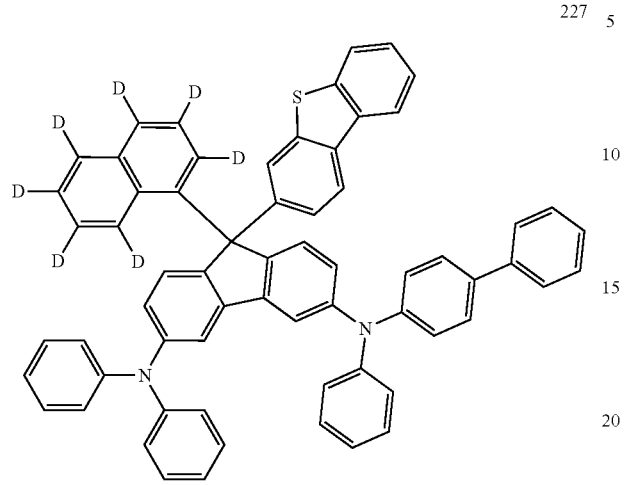
227
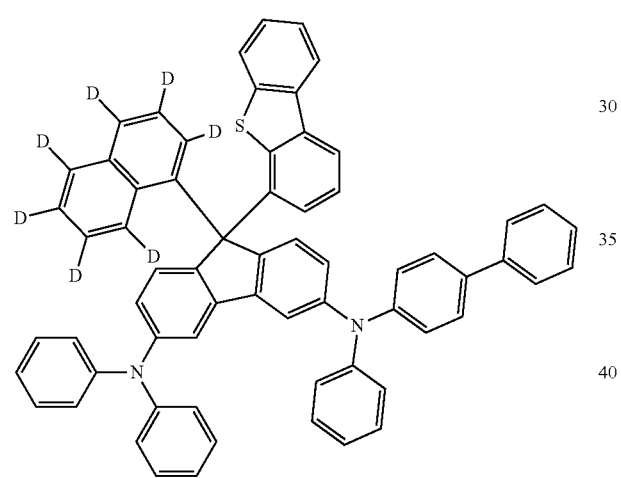
228
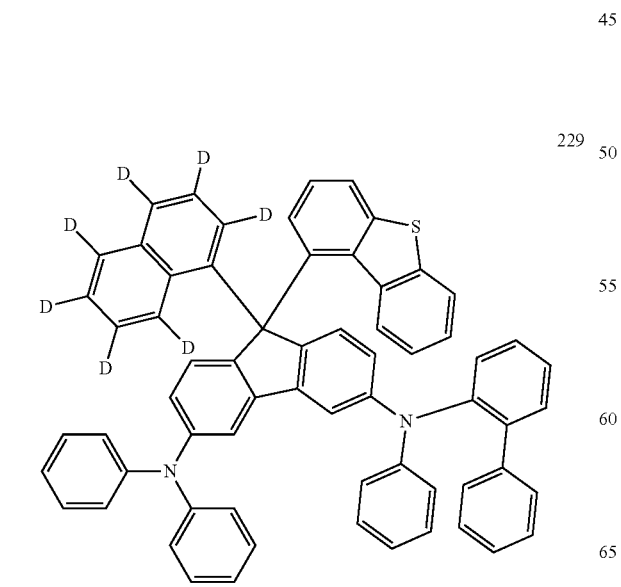
229
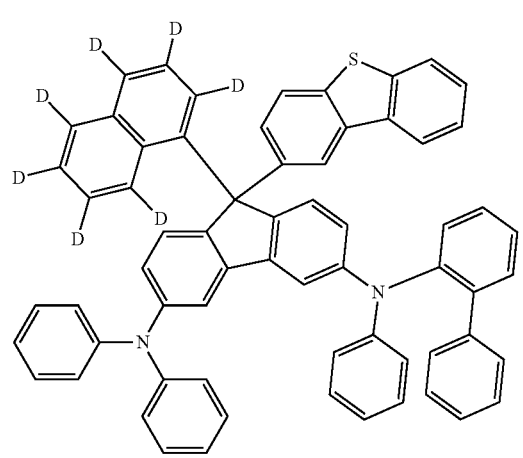
230
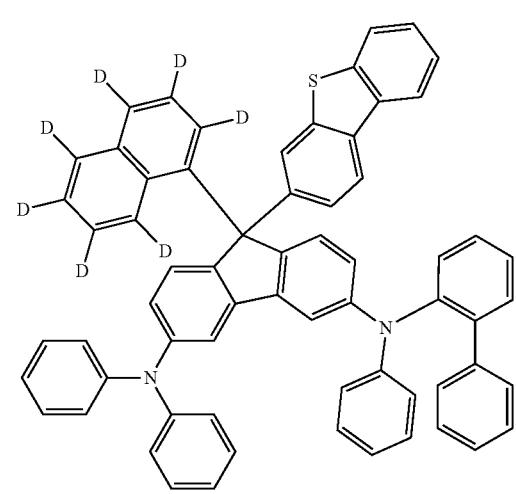
231
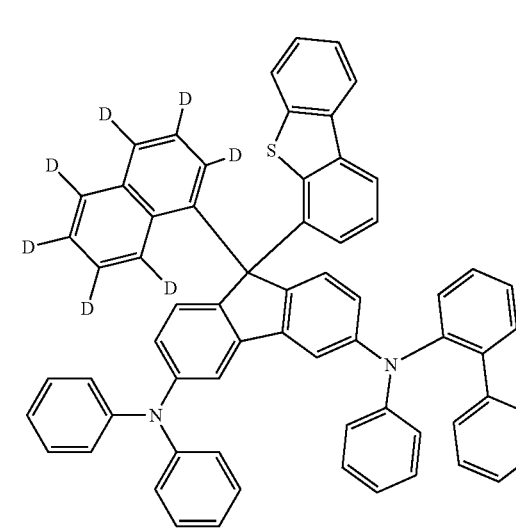
232

233
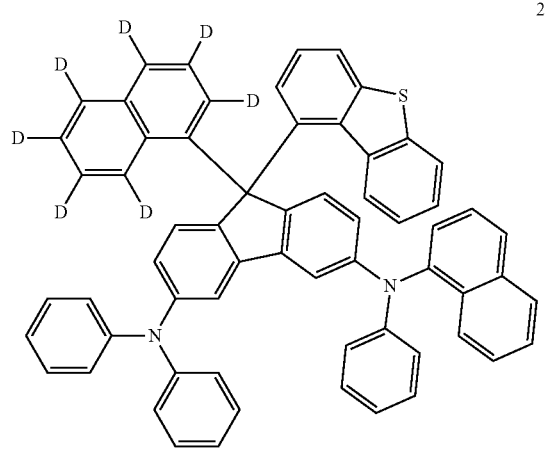
234
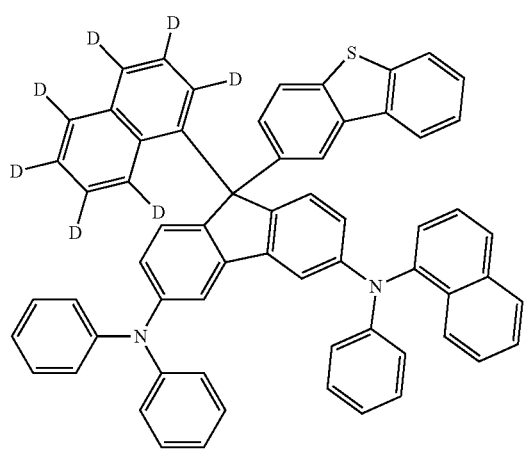
235
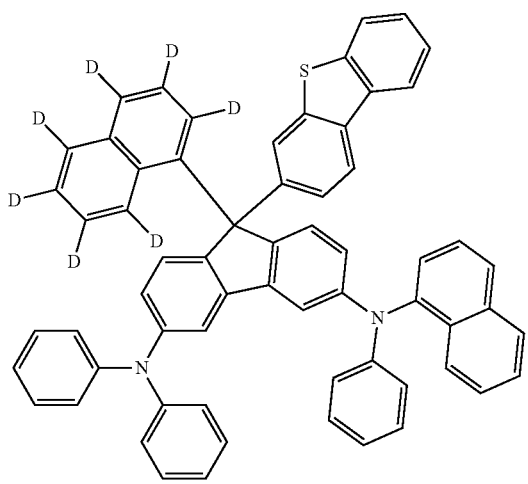
236
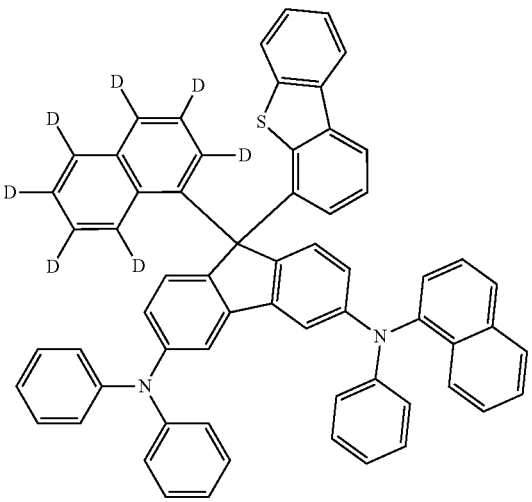
237
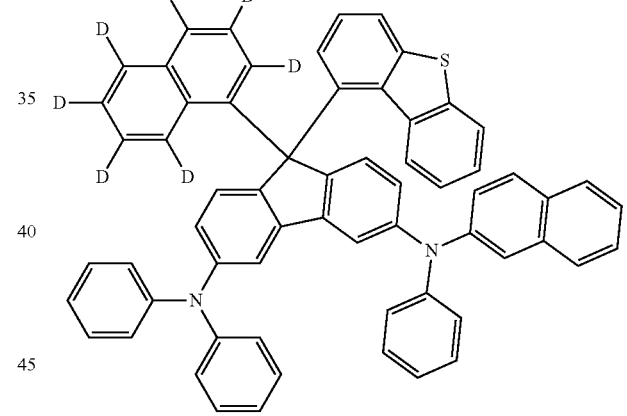
238
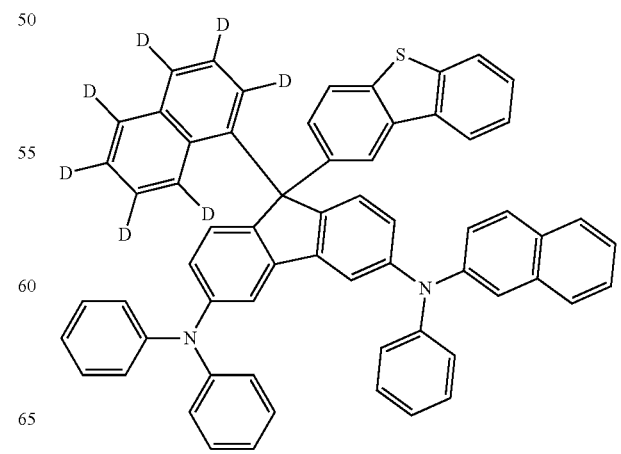

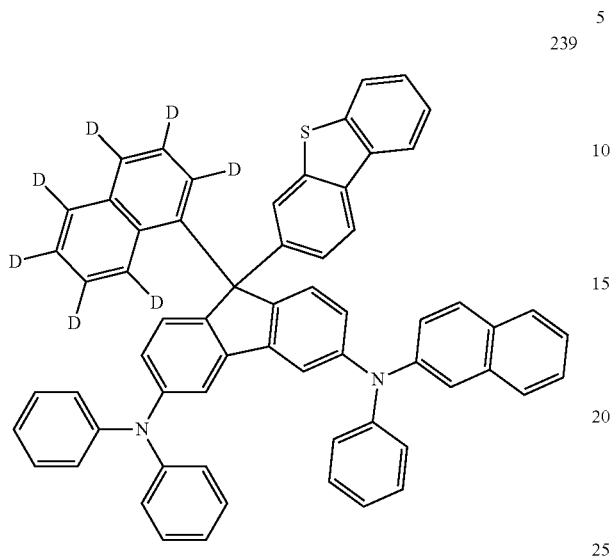
239
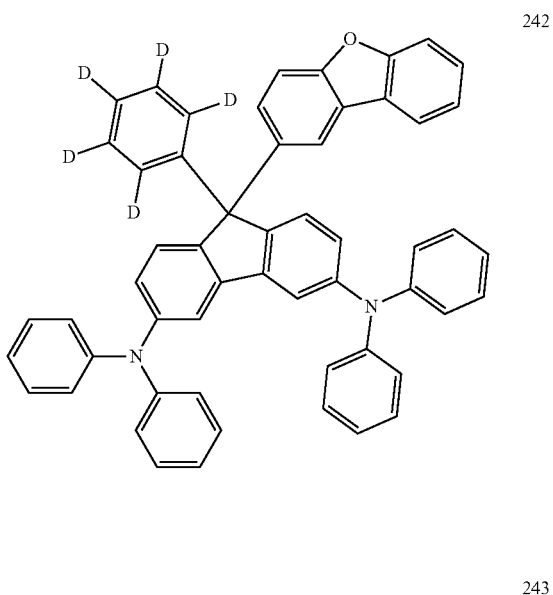
242
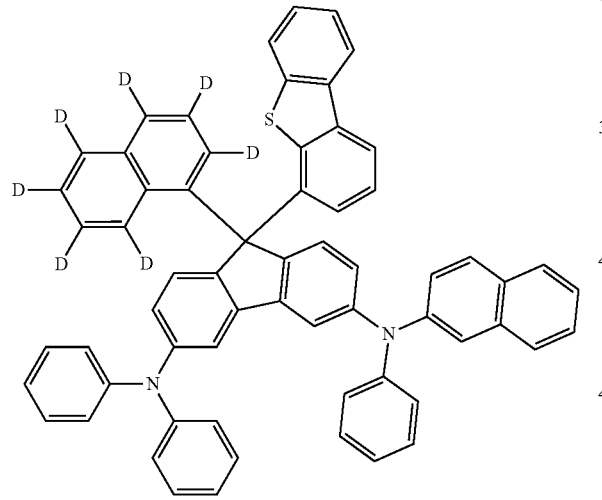
240
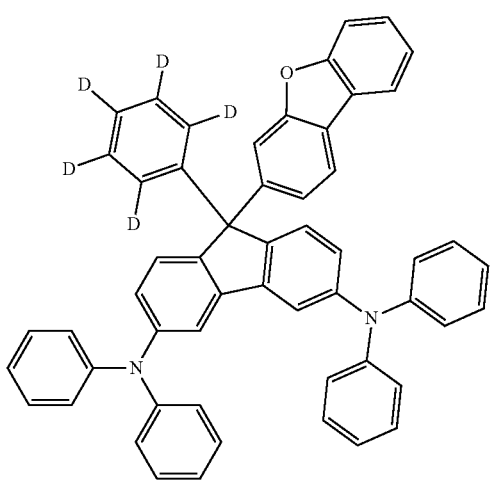
243
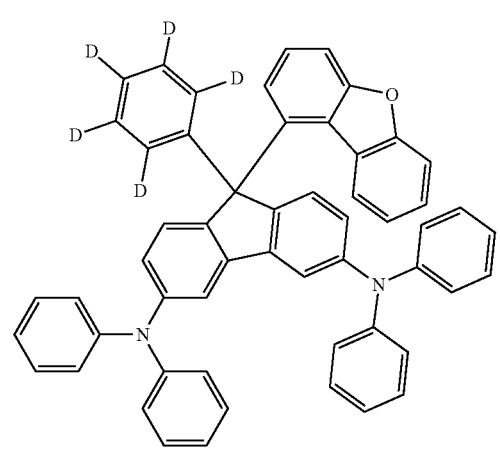
241
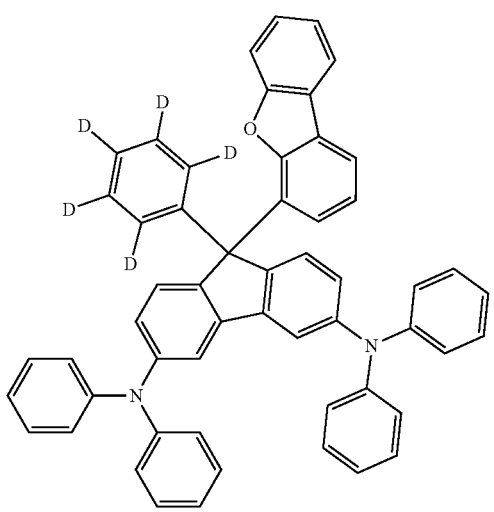
244

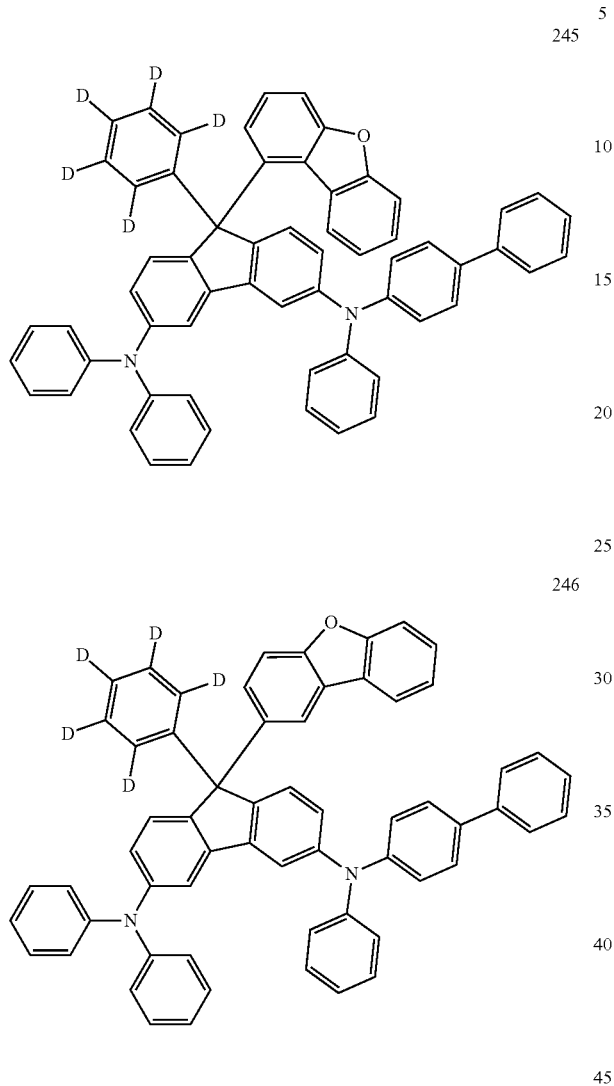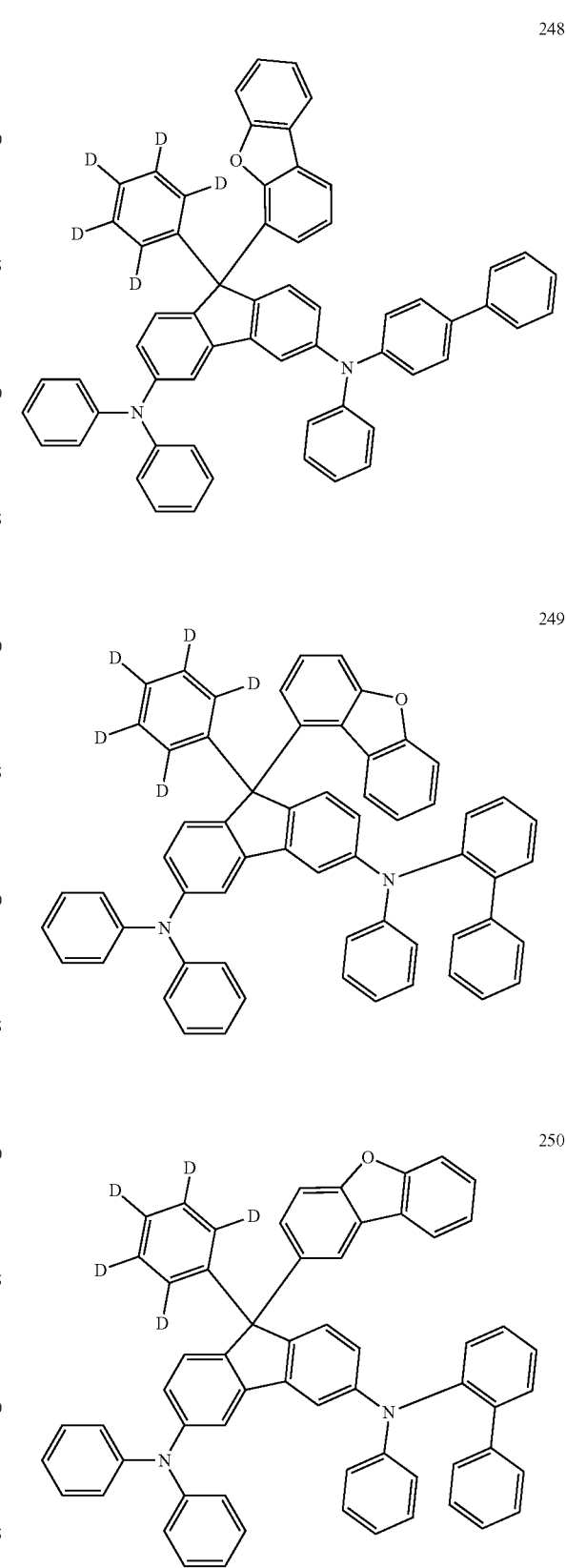

89
-continued
251
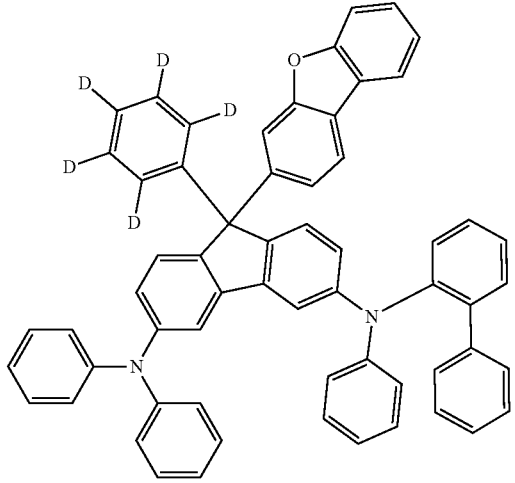
252
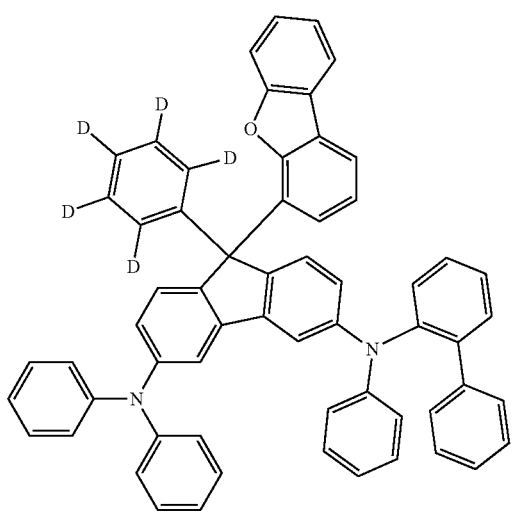
253
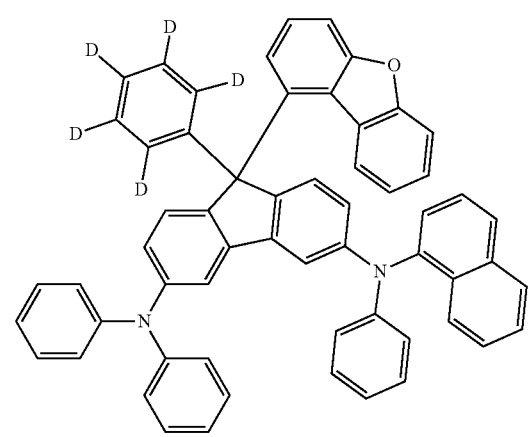
90
-continued
254
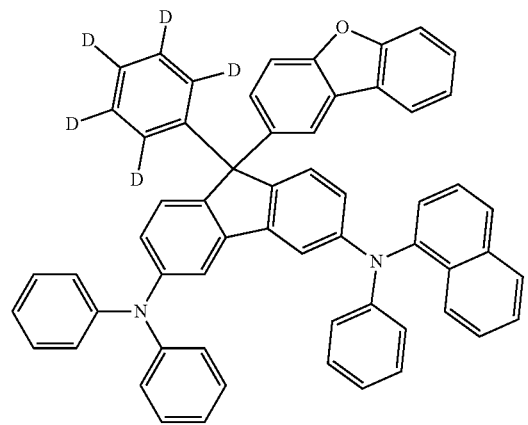
255
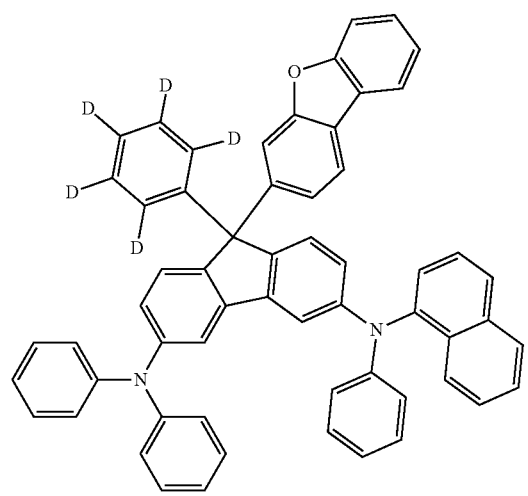
256
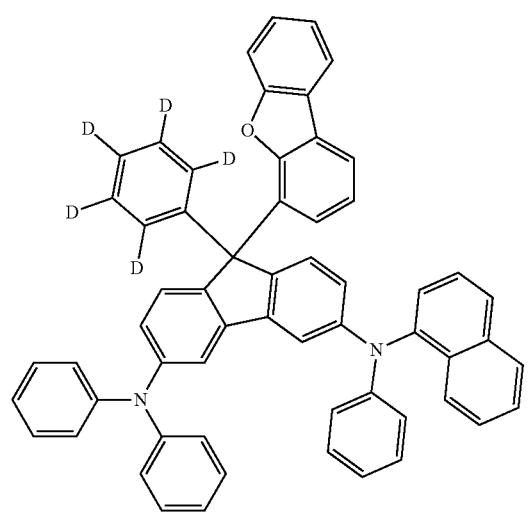

91
-continued
257
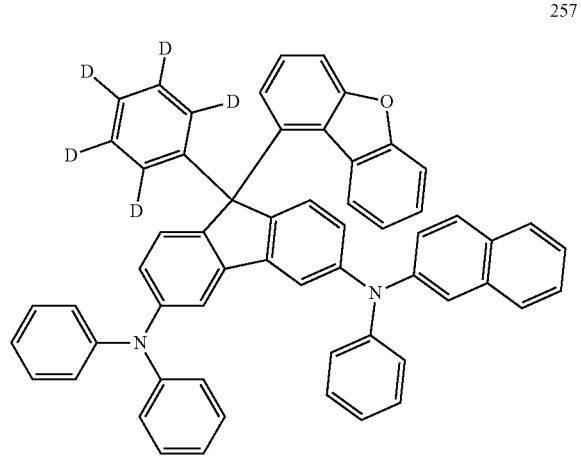
258
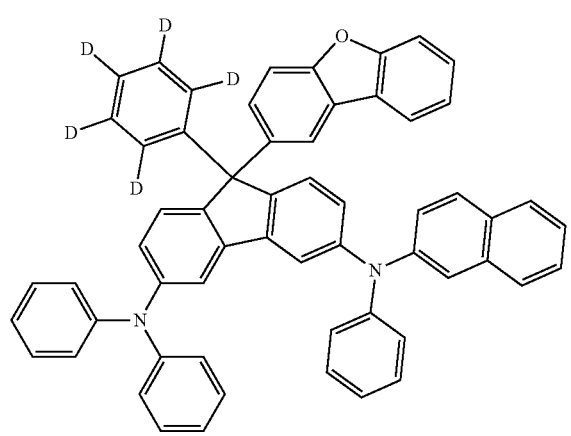
259
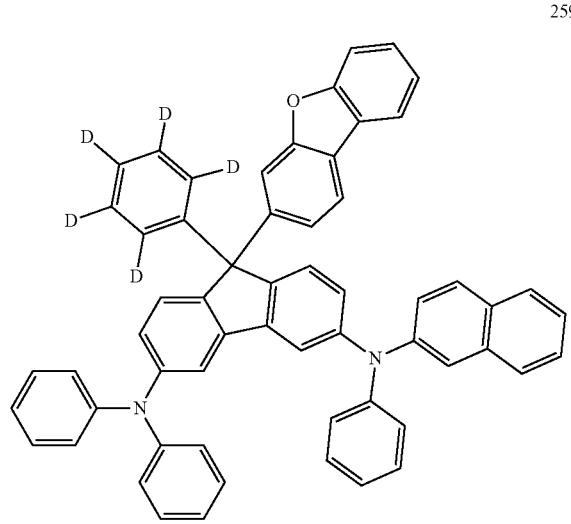
92
-continued
260
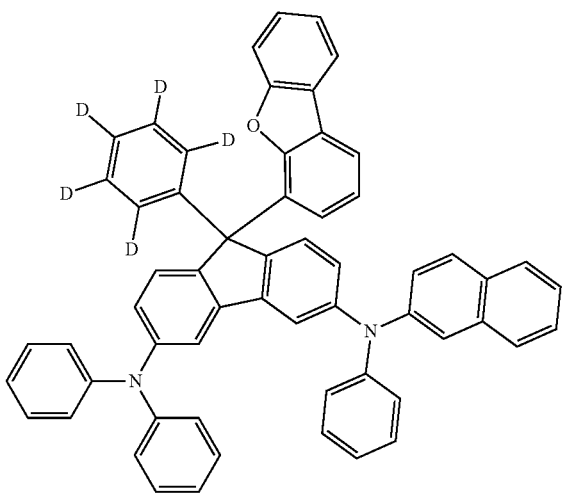
261
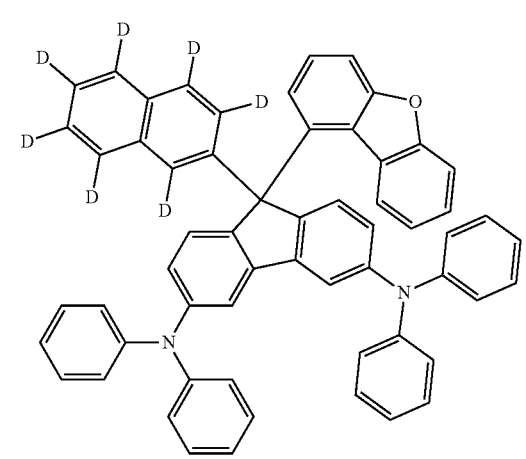
262
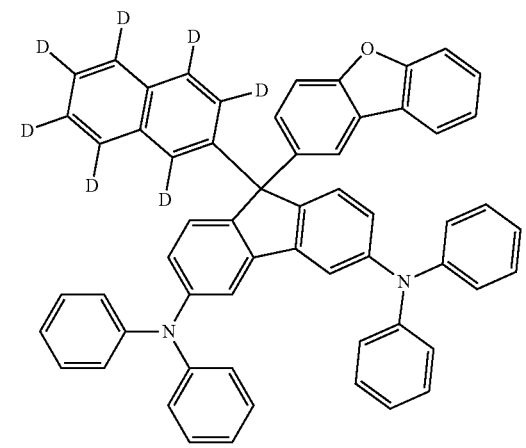

263
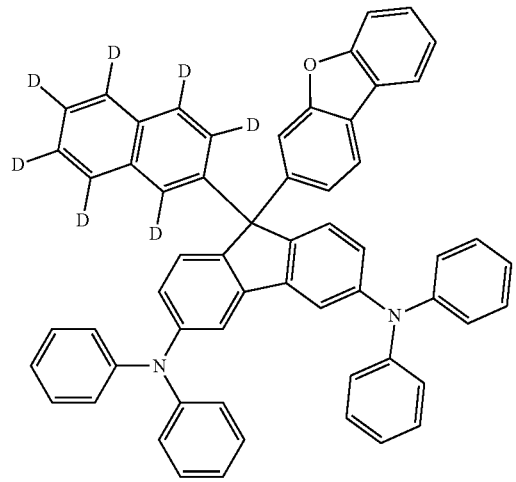
264
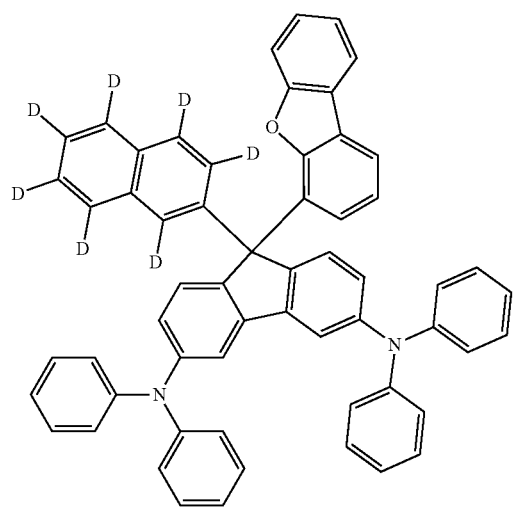
265
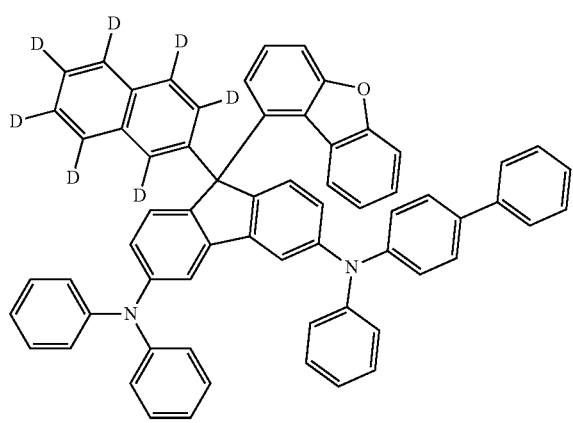
266
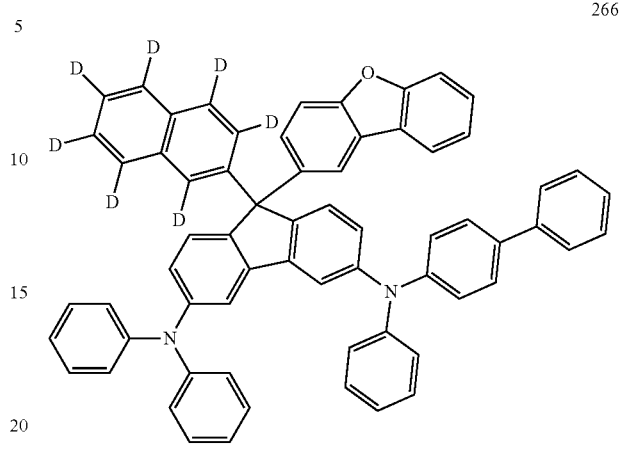
267
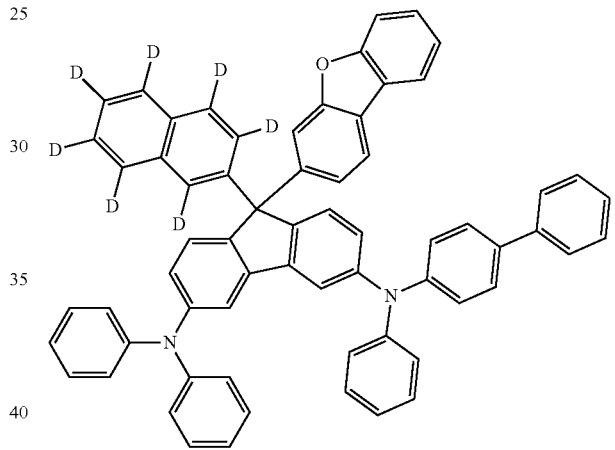
268
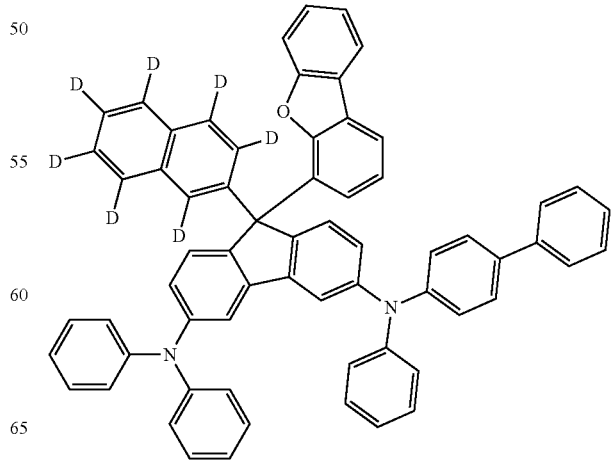

269
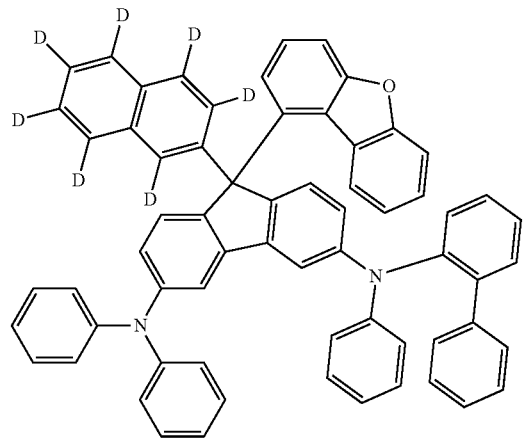
270
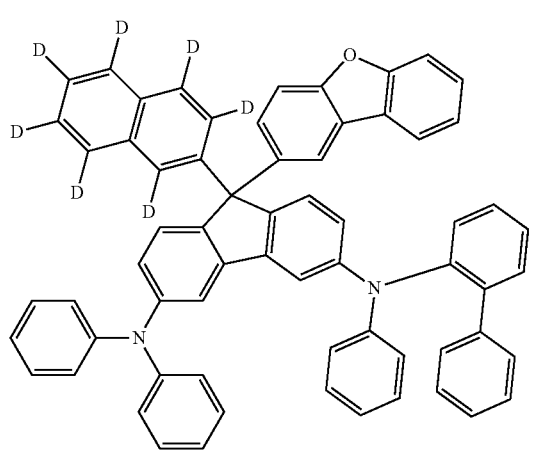
271
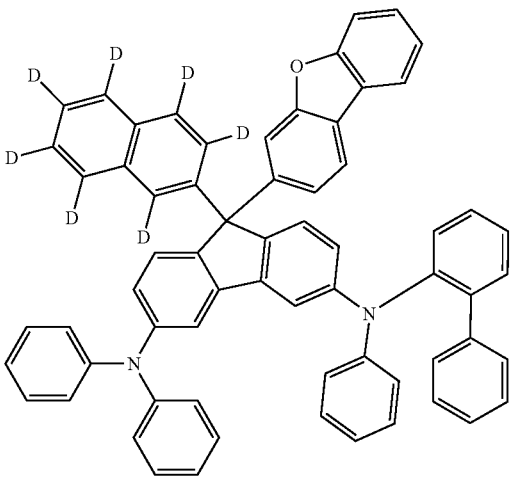
272
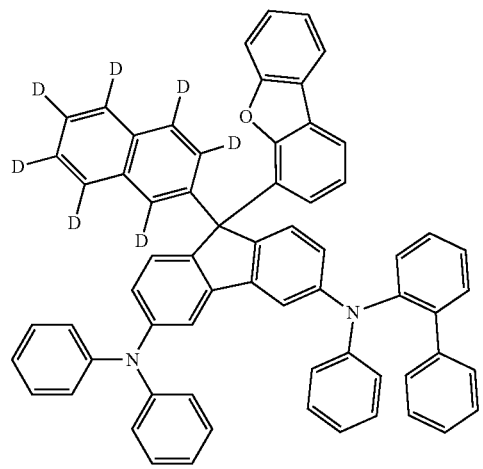
273
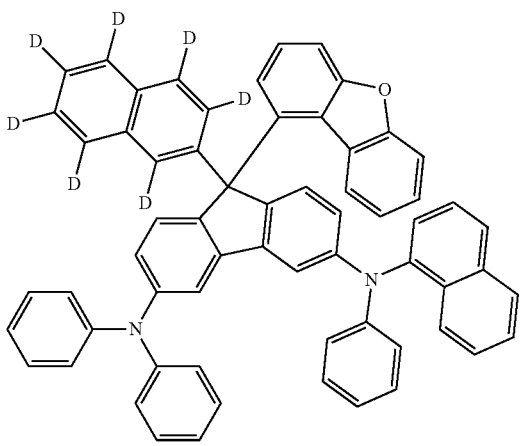
274
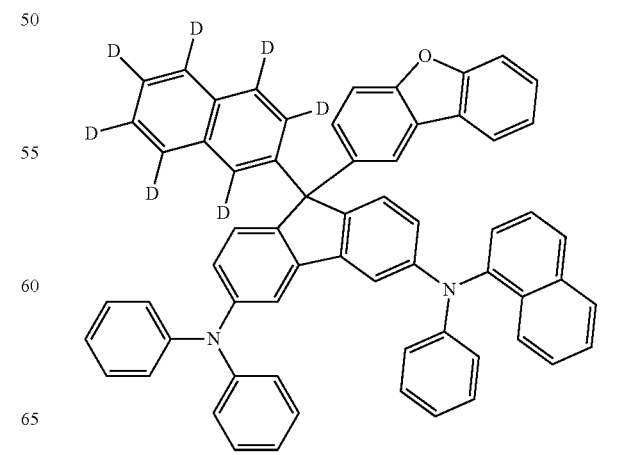

275 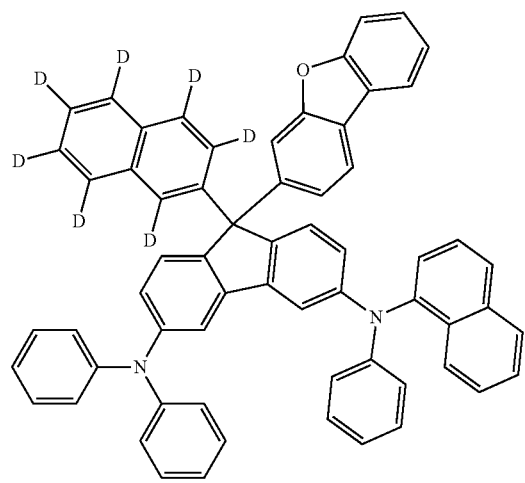
276 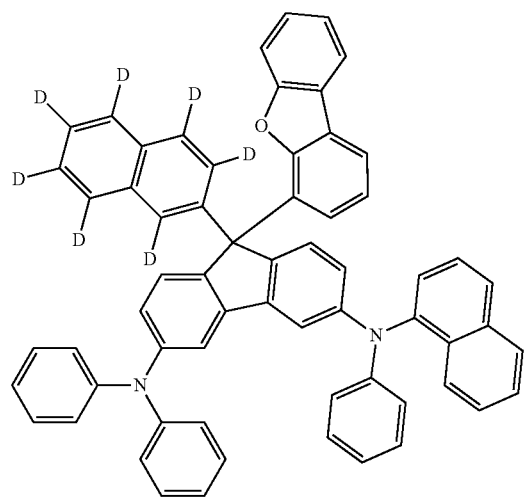
277 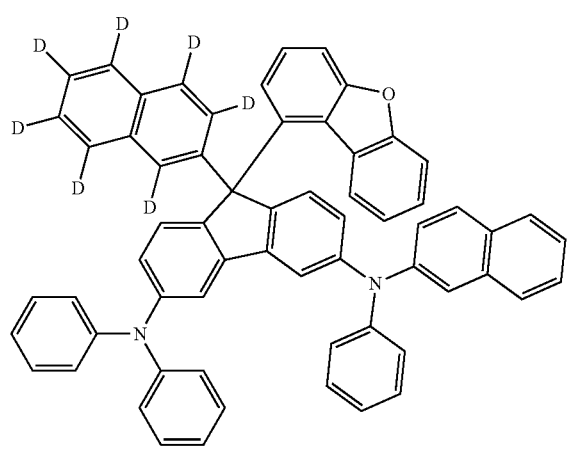
278 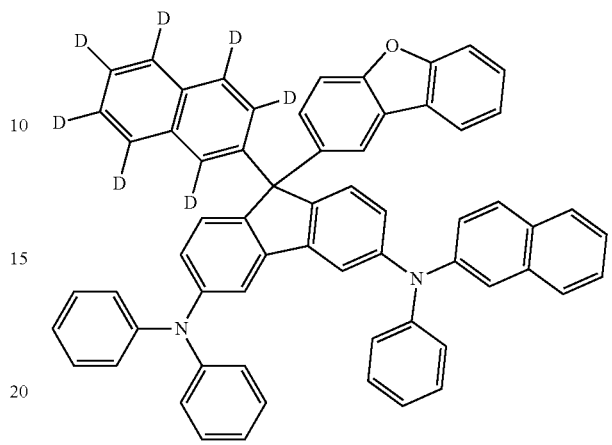
279 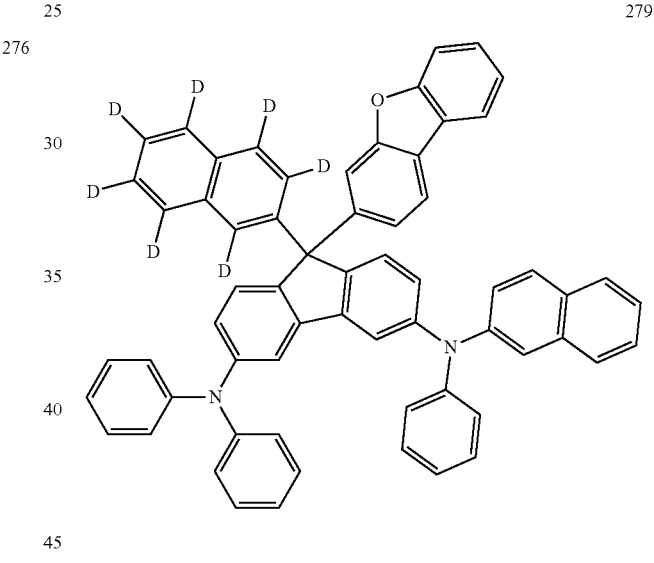
280 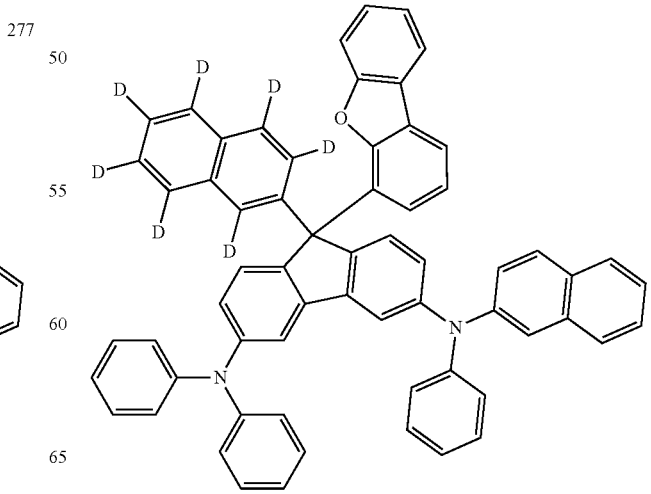

281
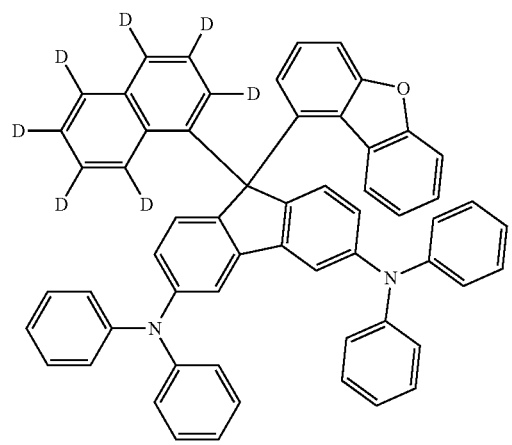
282
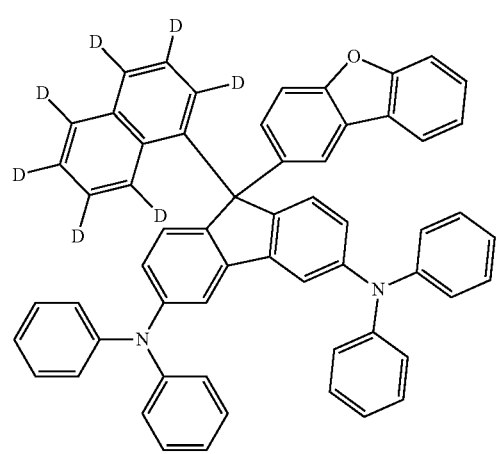
283
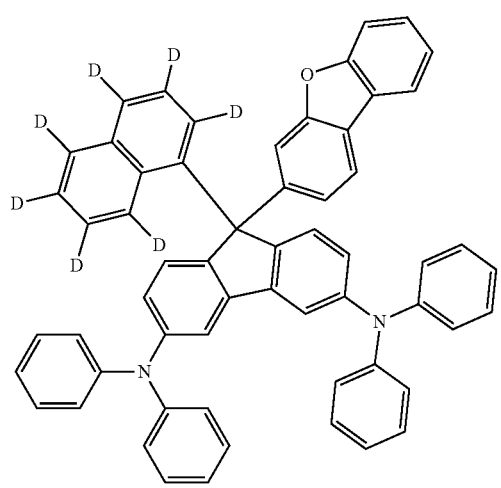
284
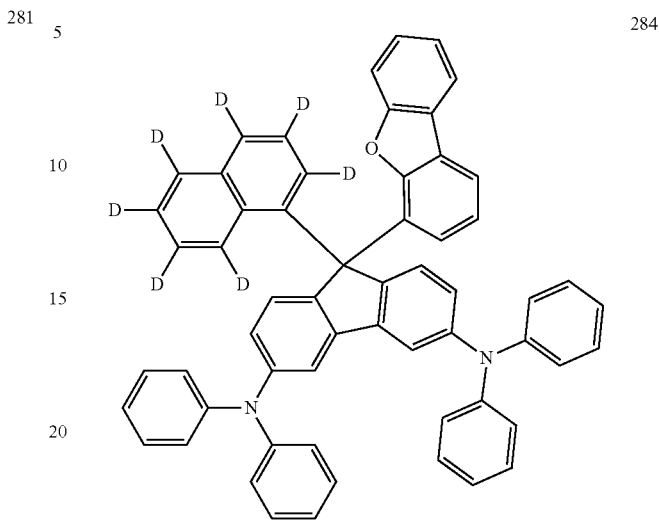
285
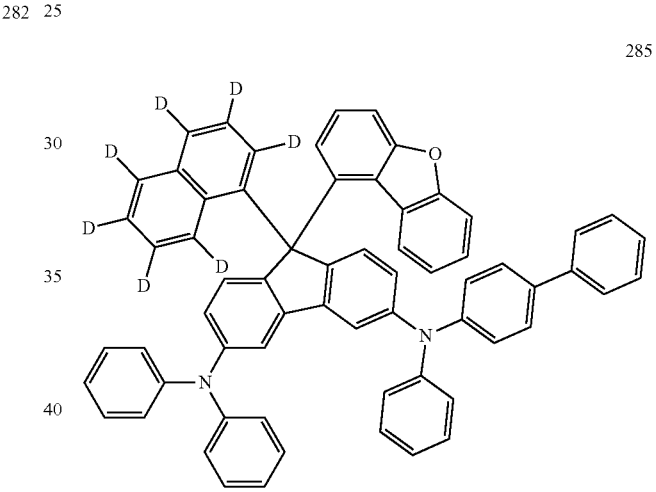
286
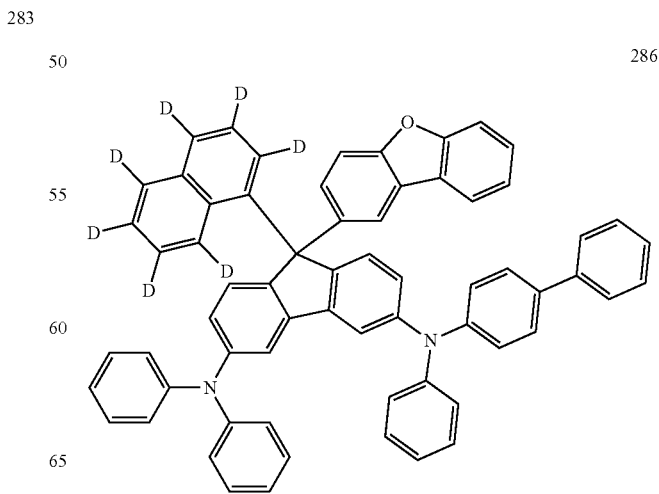

101
-continued
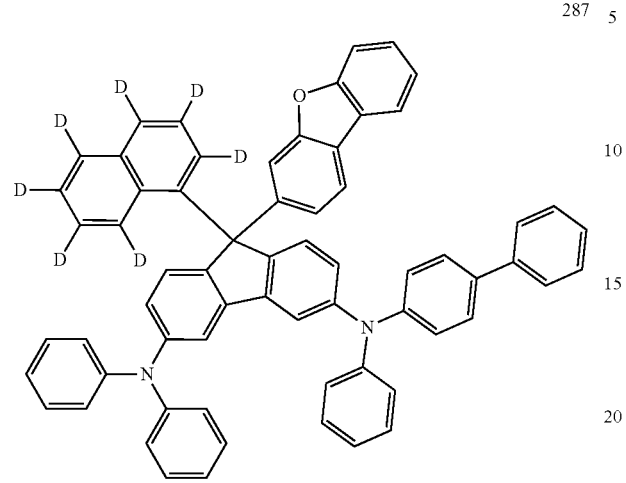
287
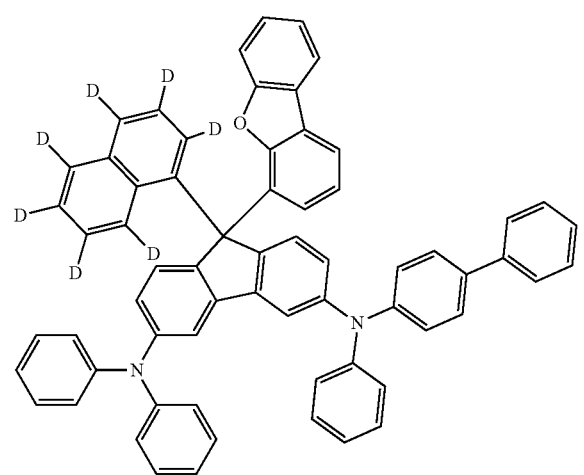
288
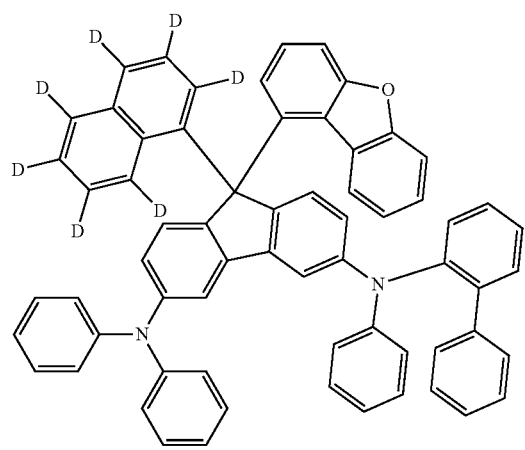
289
102
-continued
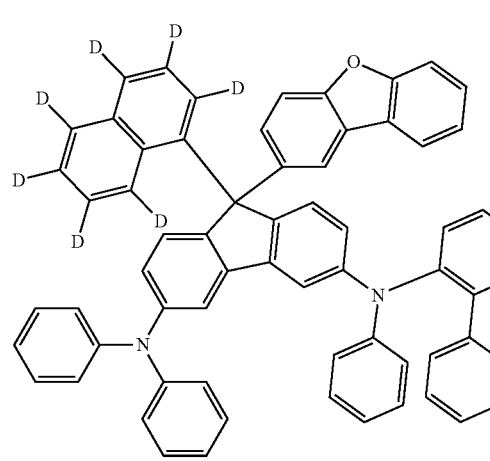
290
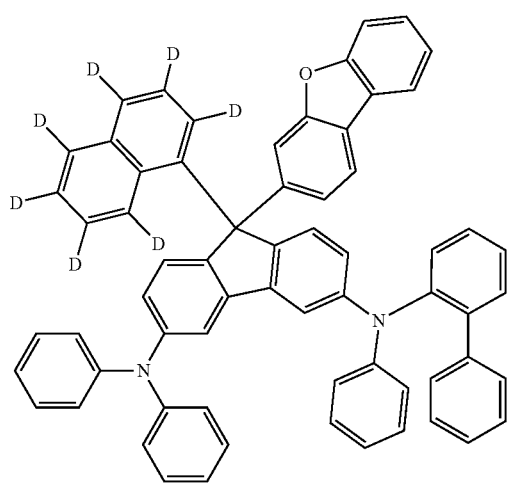
291
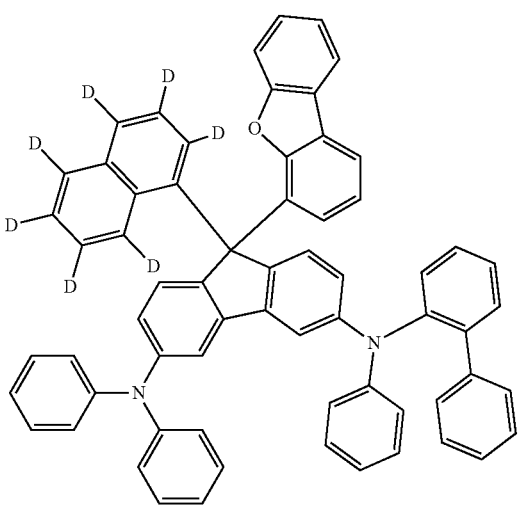
292

103
-continued
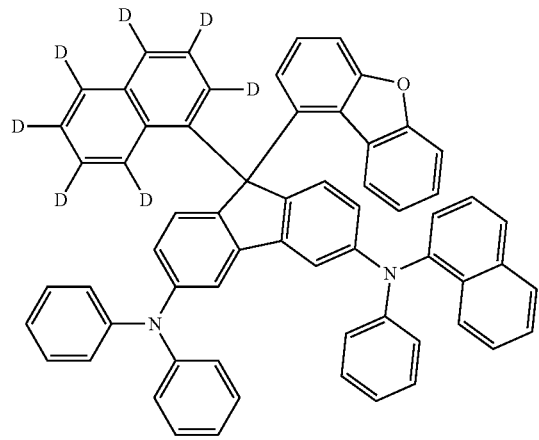
293
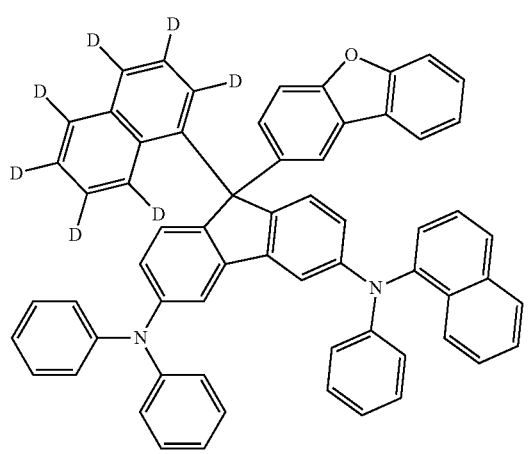
294
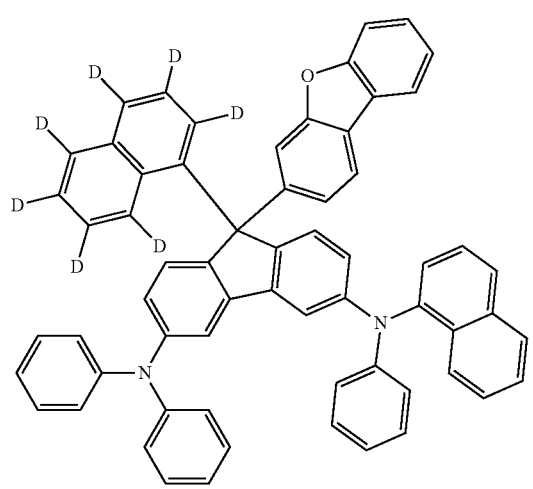
295
104
-continued
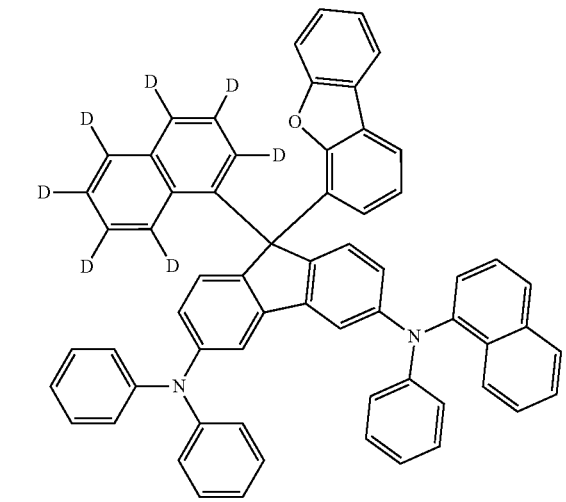
296
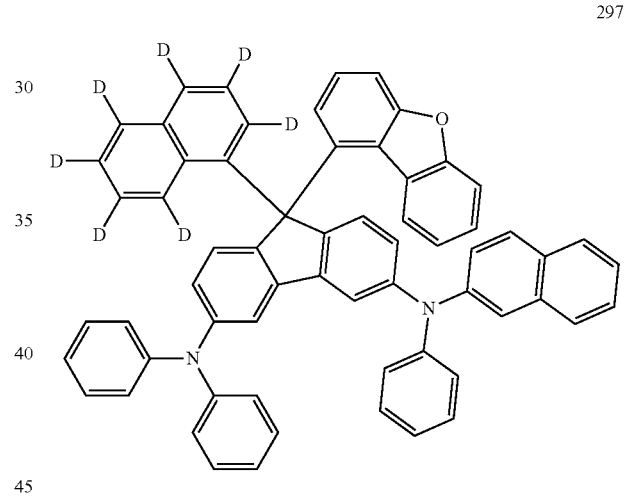
297
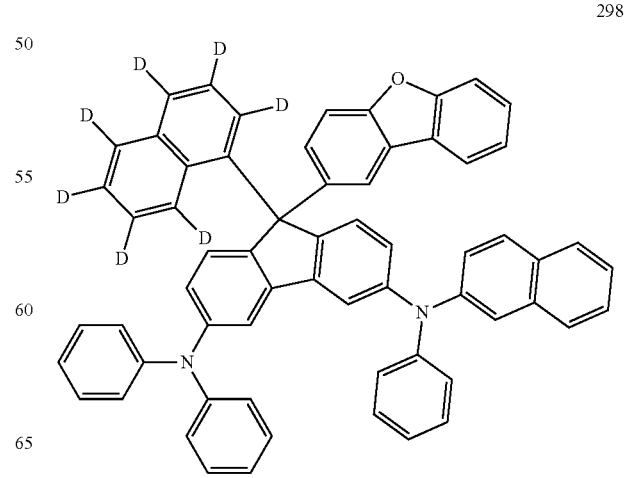
298

299
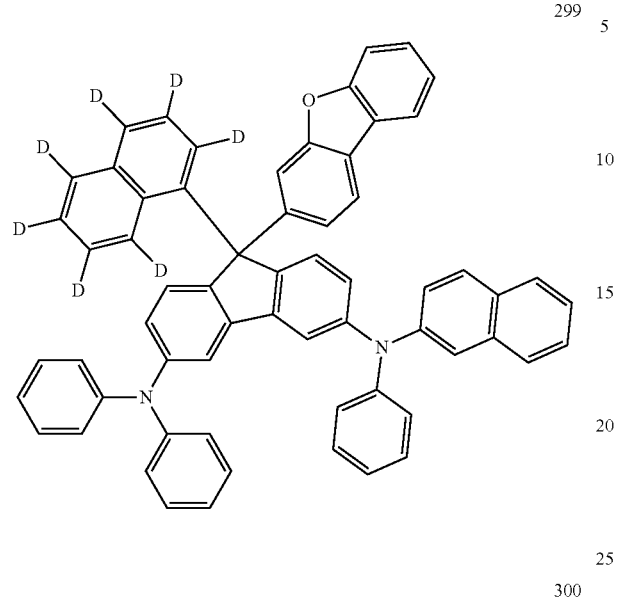
300

301
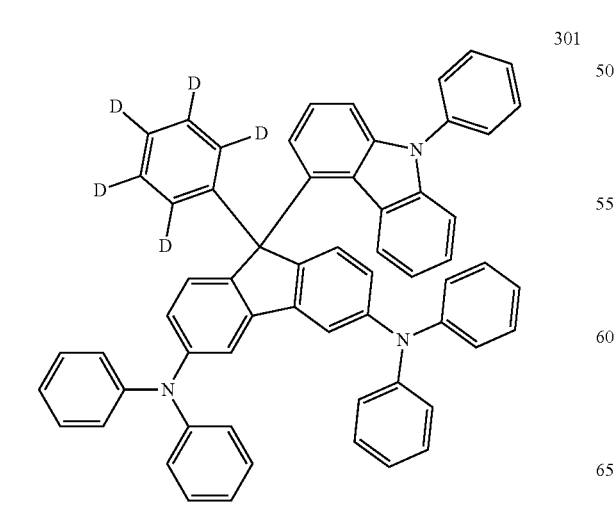
302
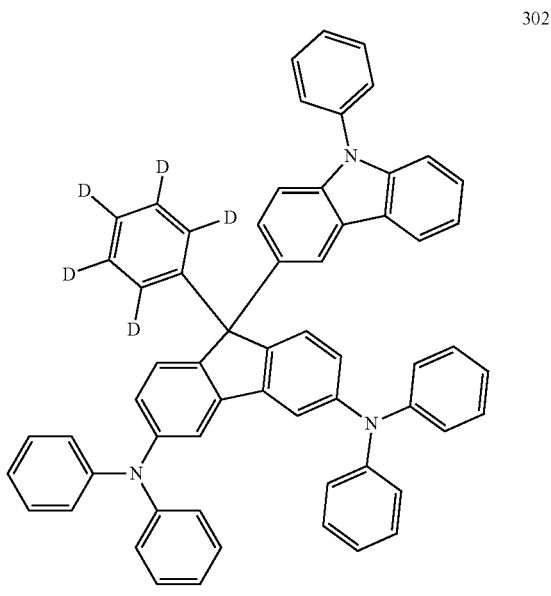
303
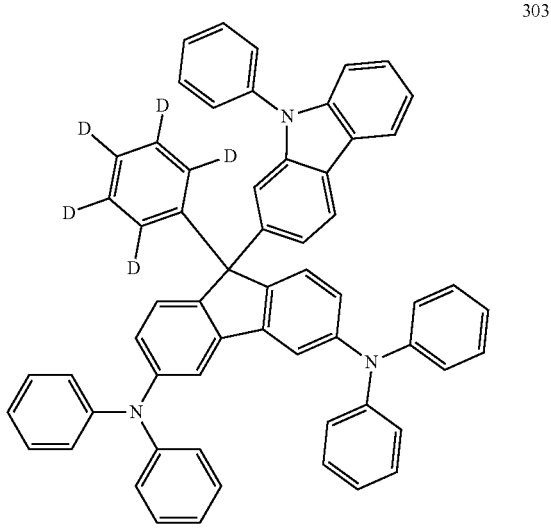
304

305
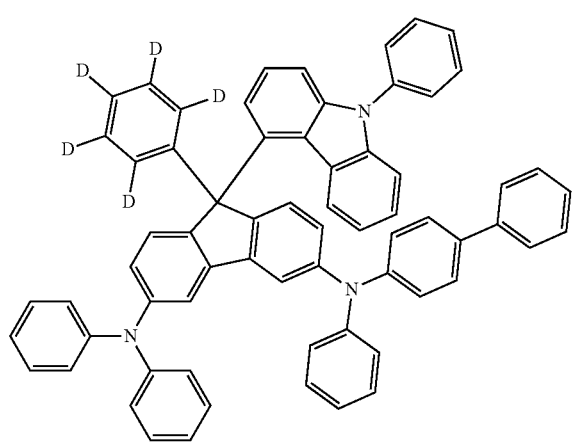
306
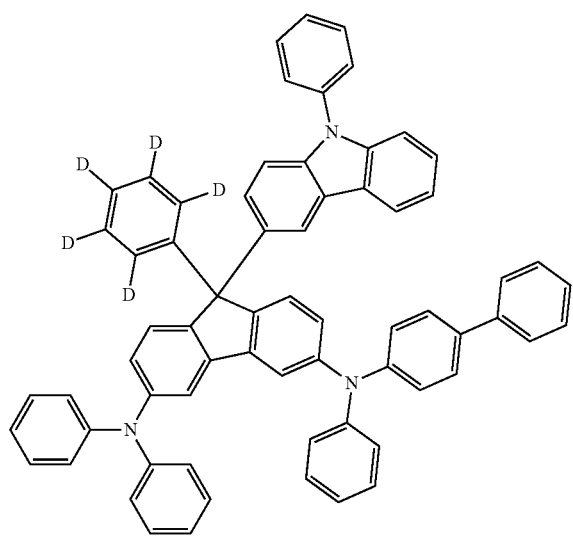
307
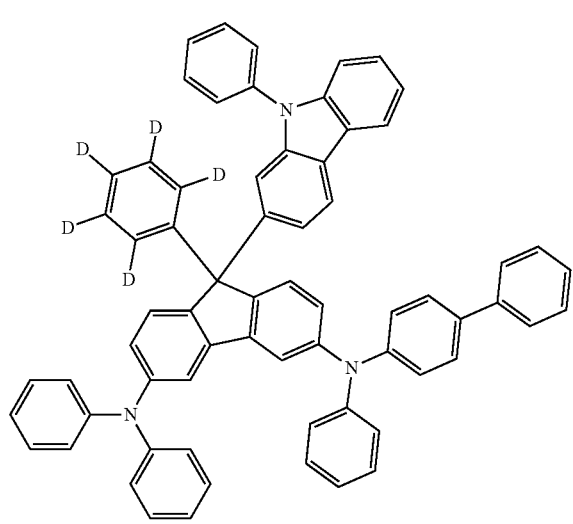
308
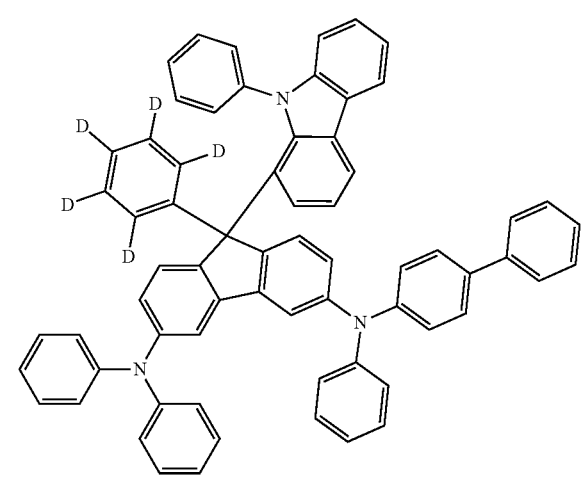
309
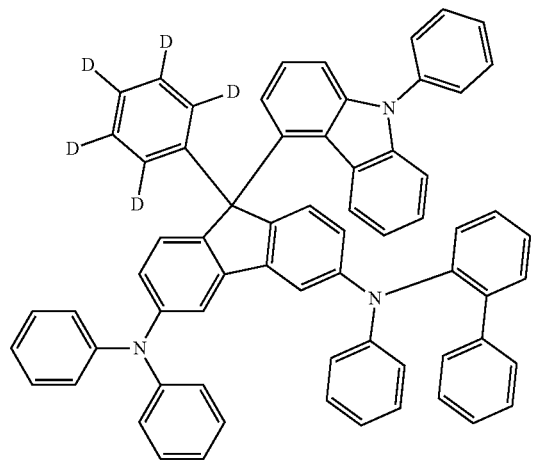
310
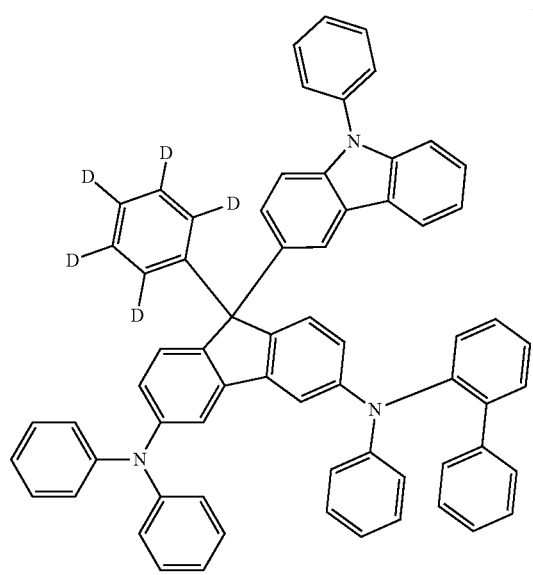

311
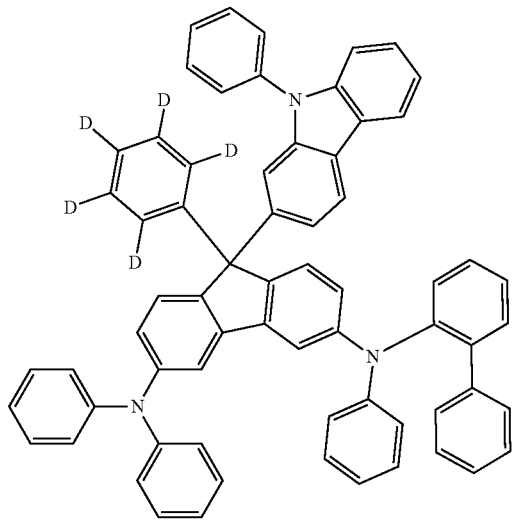
312
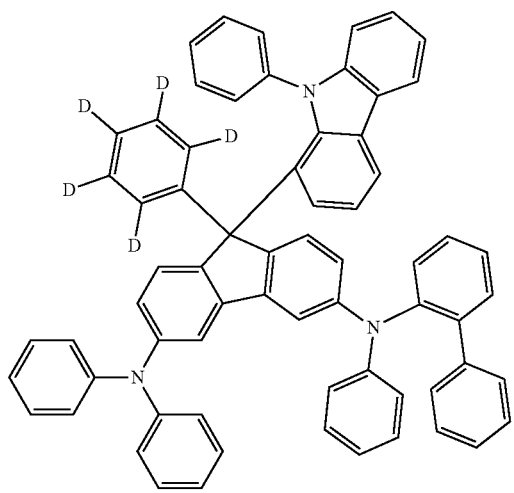
313
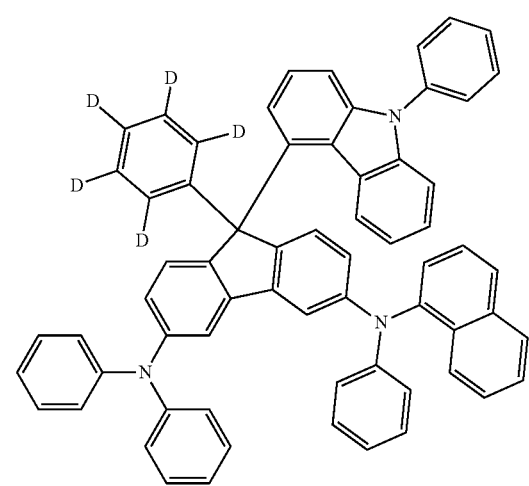
314
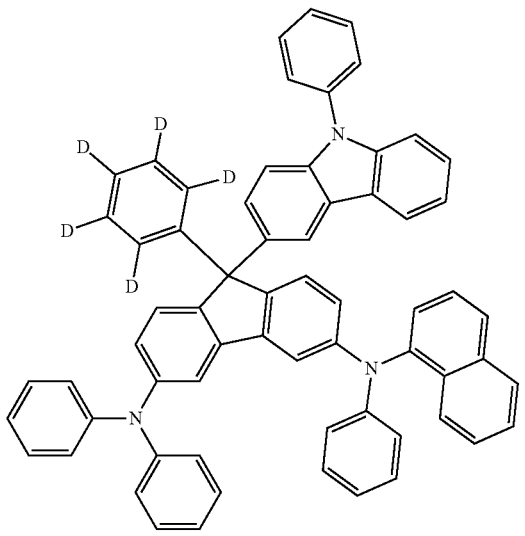
315
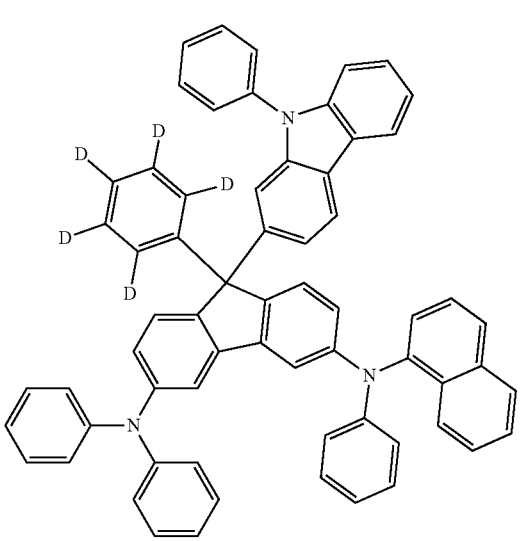
316
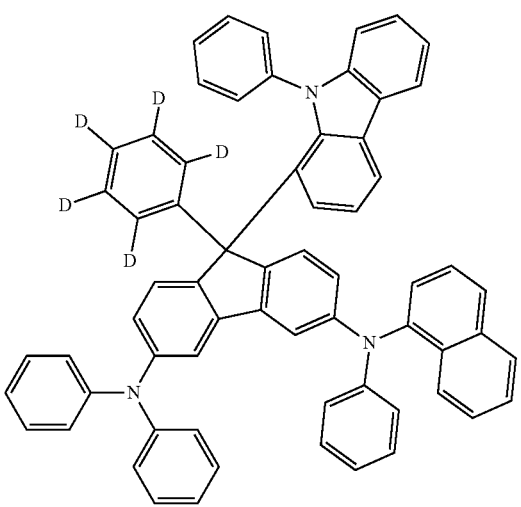

111
-continued
317
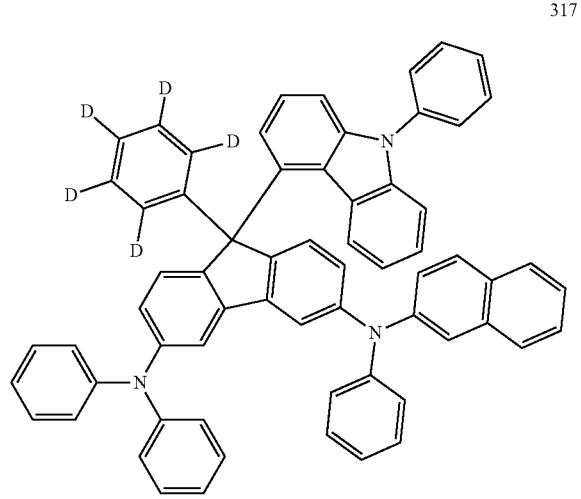
318
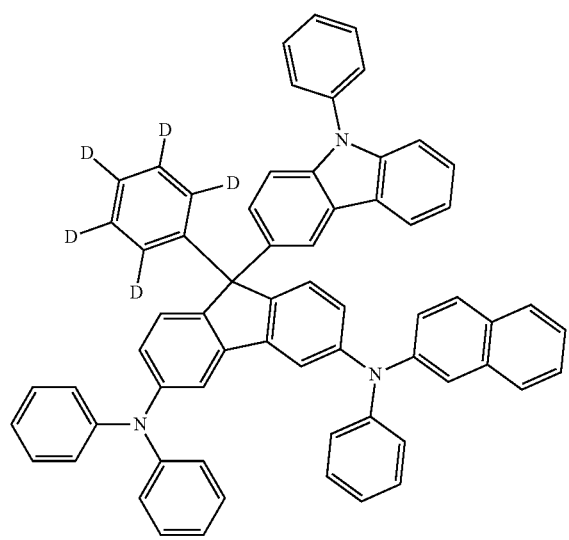
319
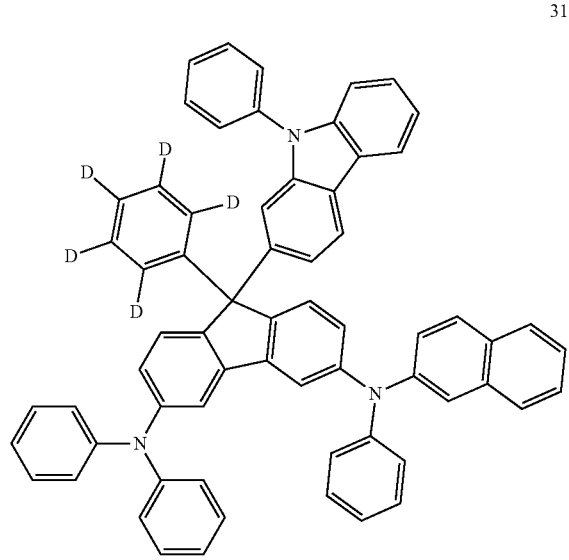
112
-continued
320
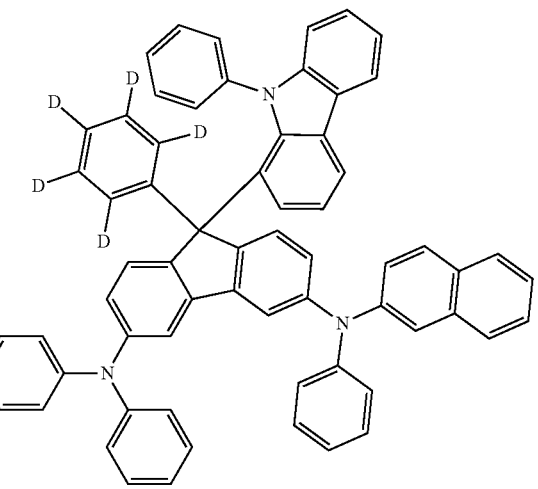
321
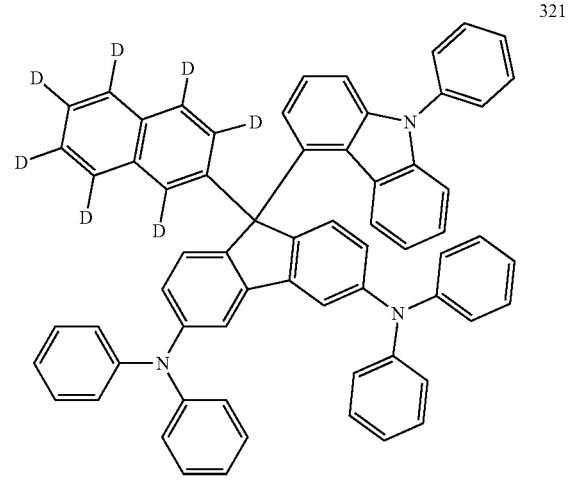
322
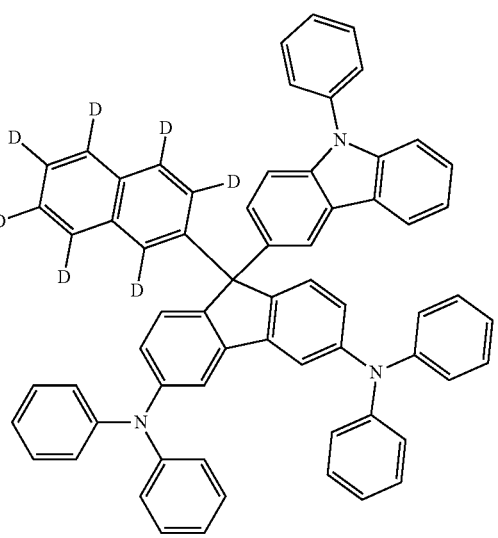

323
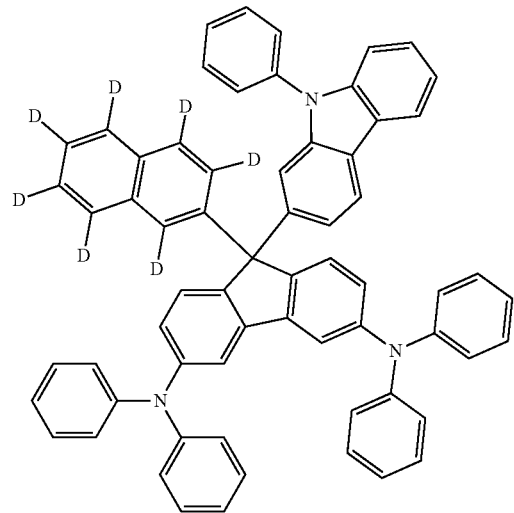
324
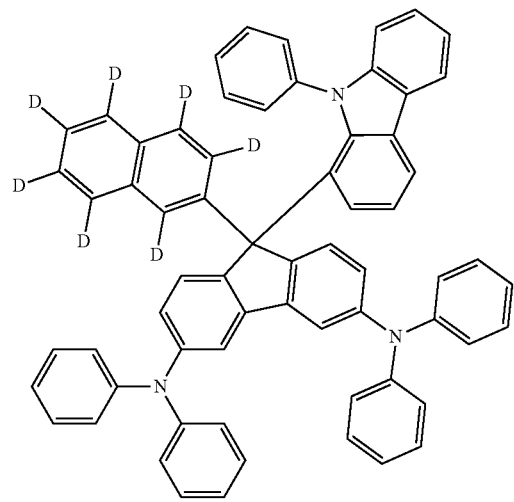
325
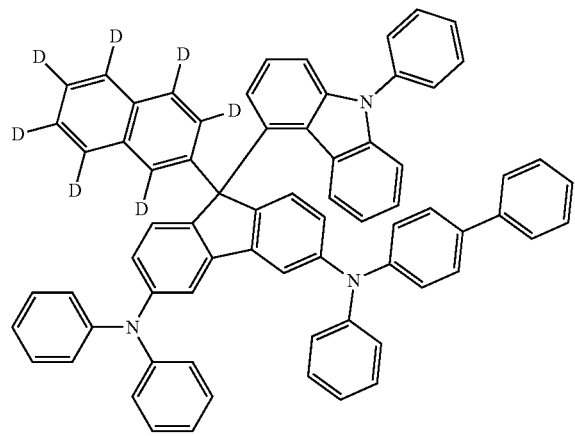
326
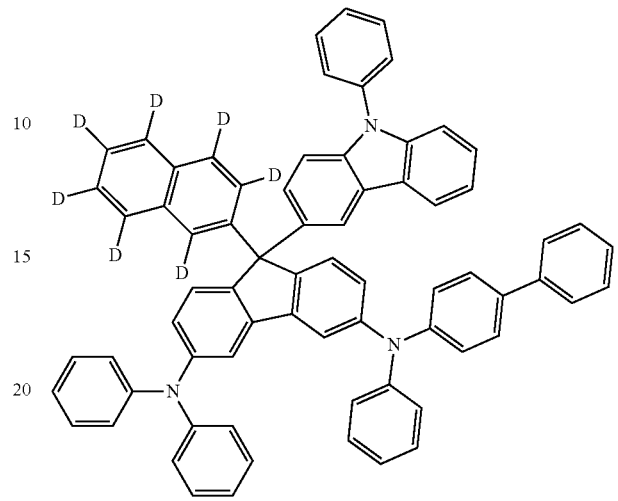
327
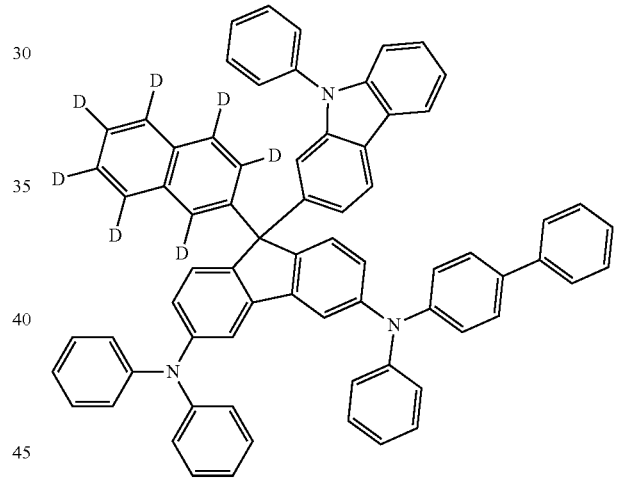
328
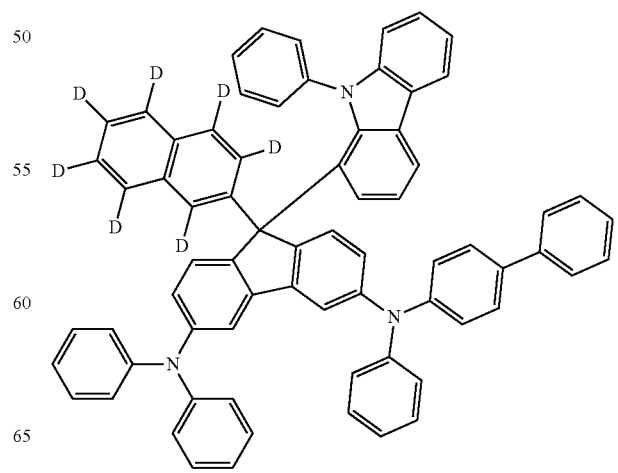

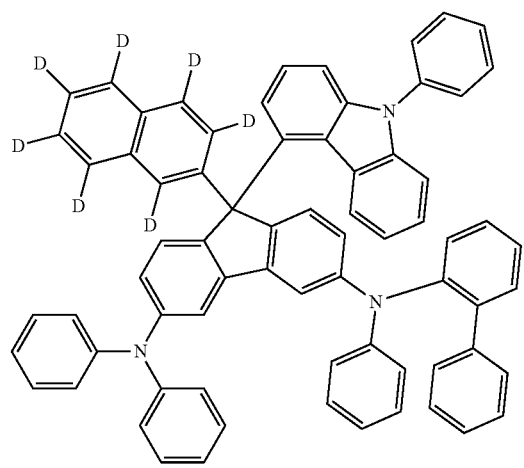
329
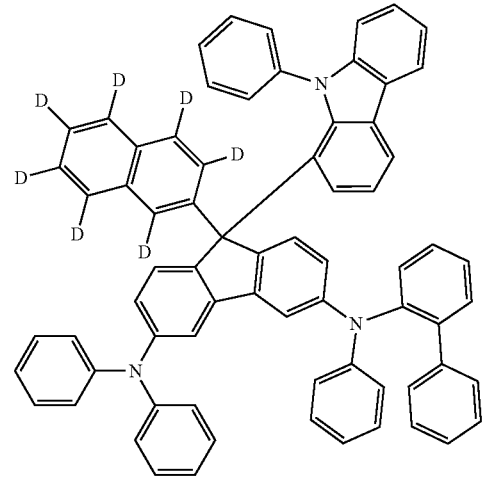
332
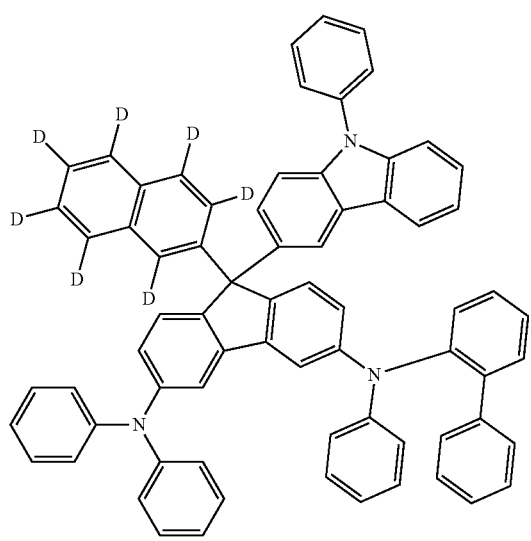
330
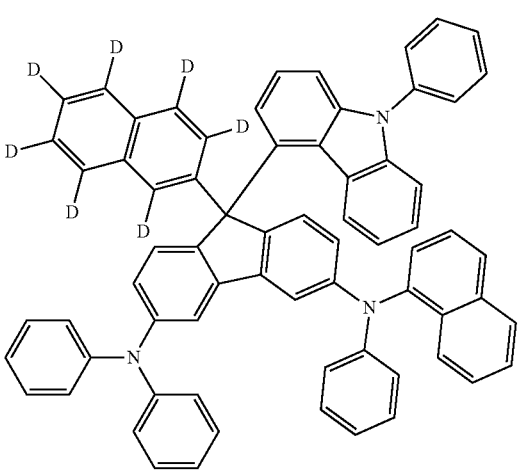
333
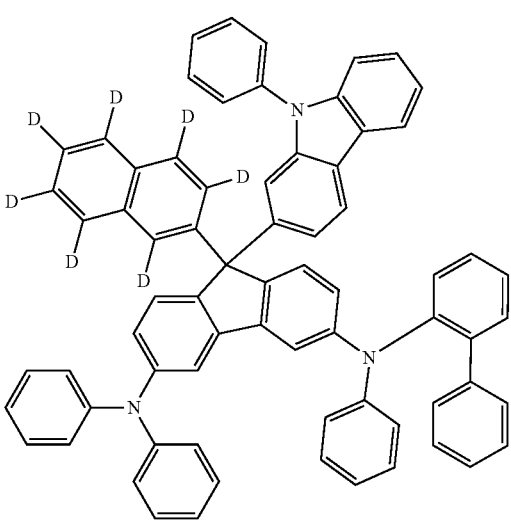
331
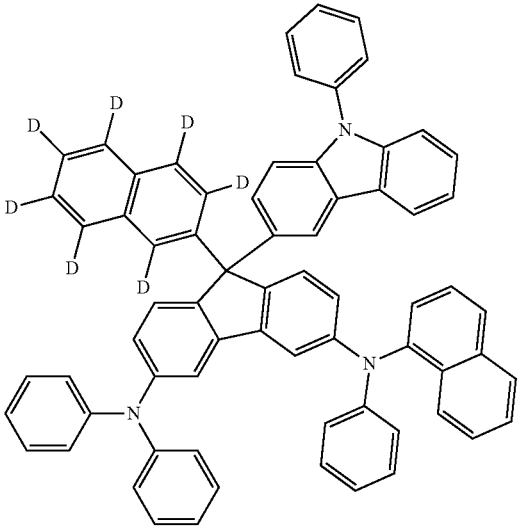
334

335
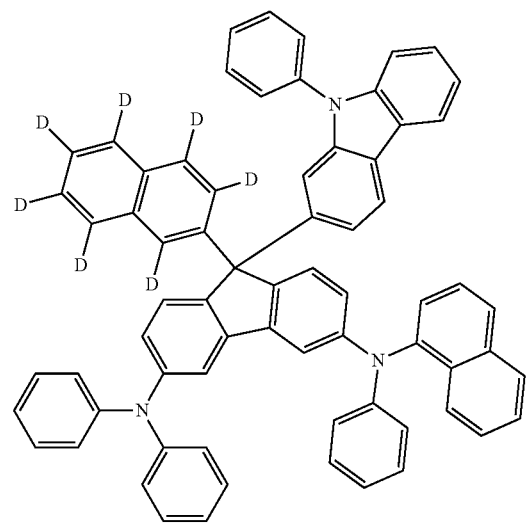
336
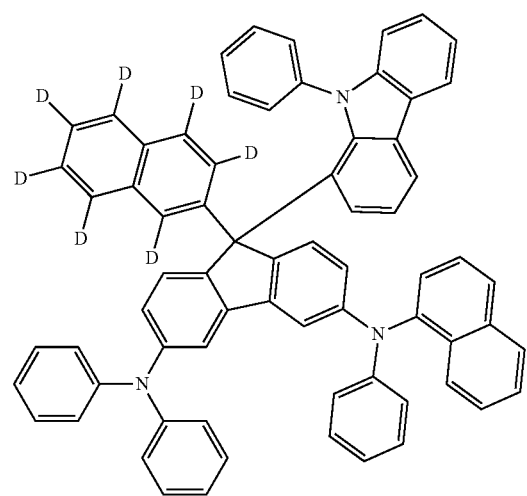
339
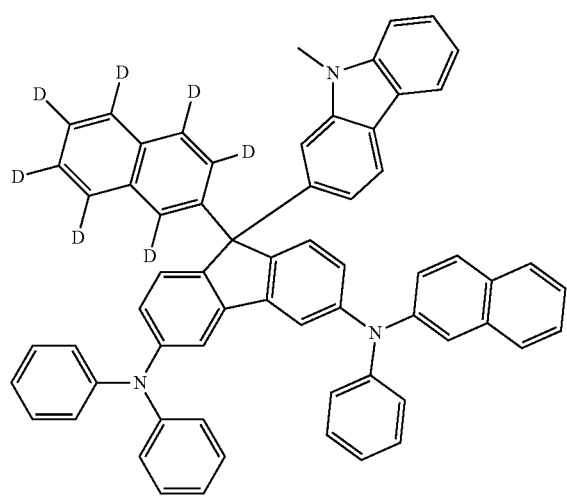
340
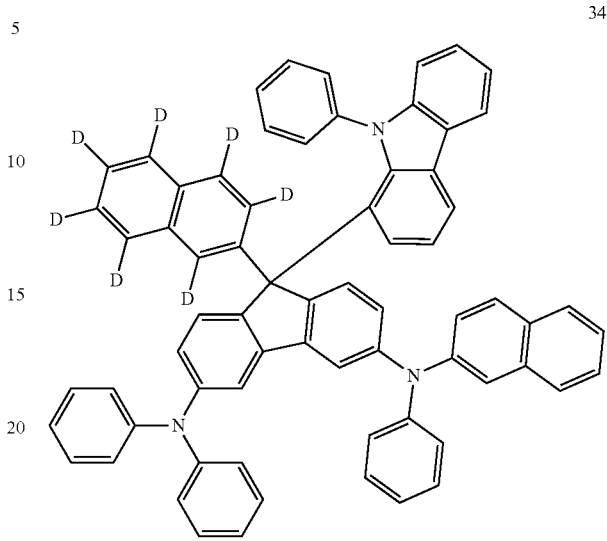
341
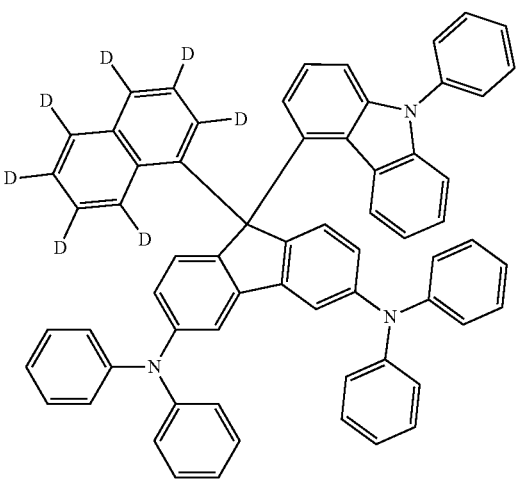
342
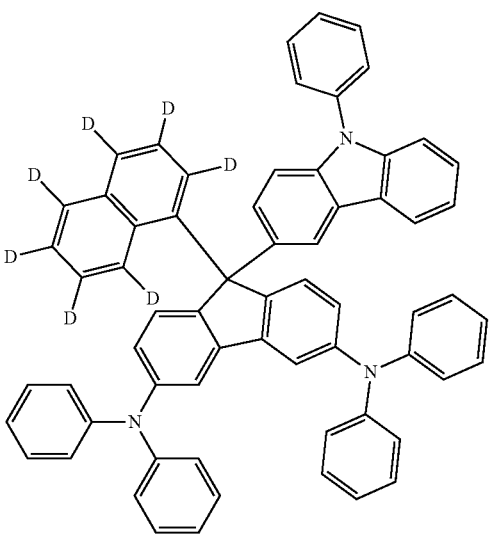

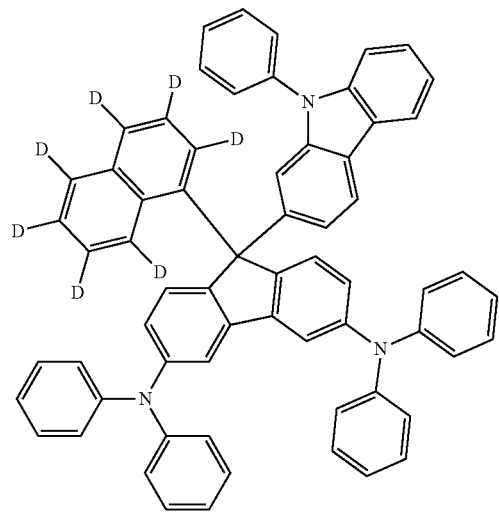
343
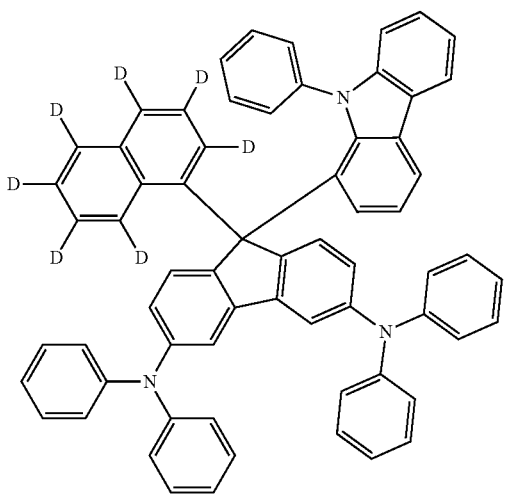
344
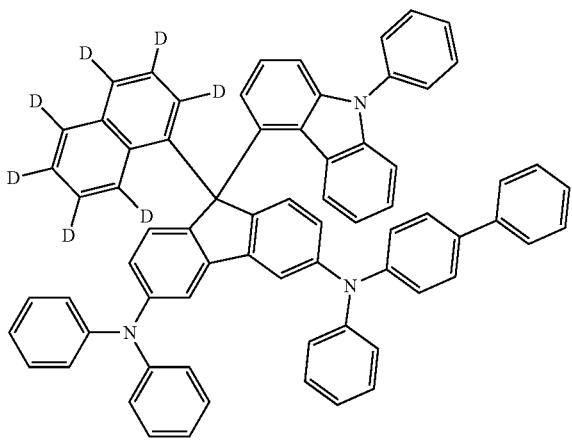
345
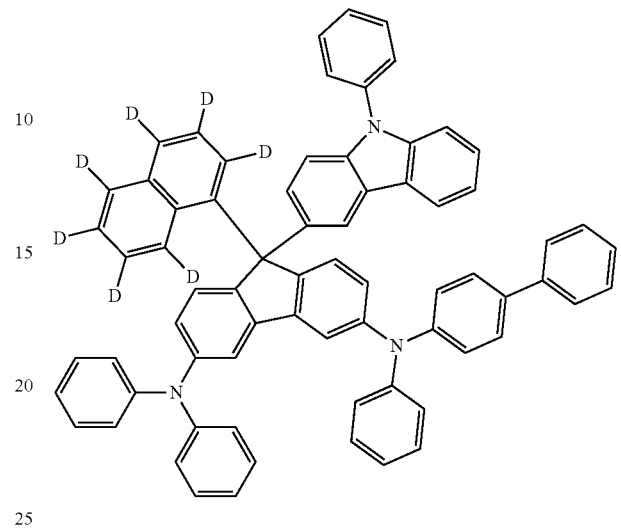
346
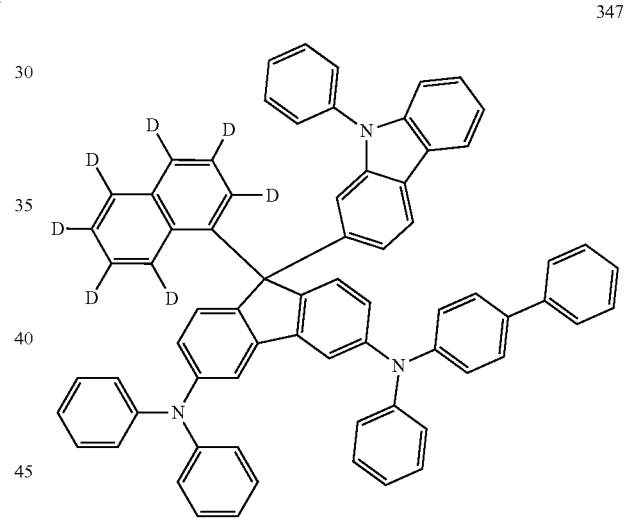
347
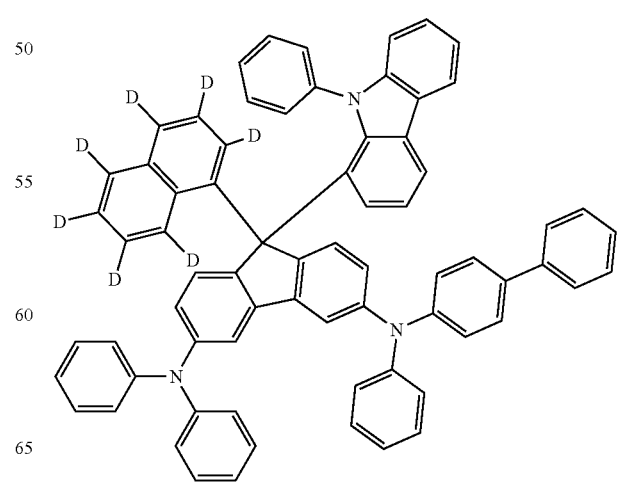
348

349
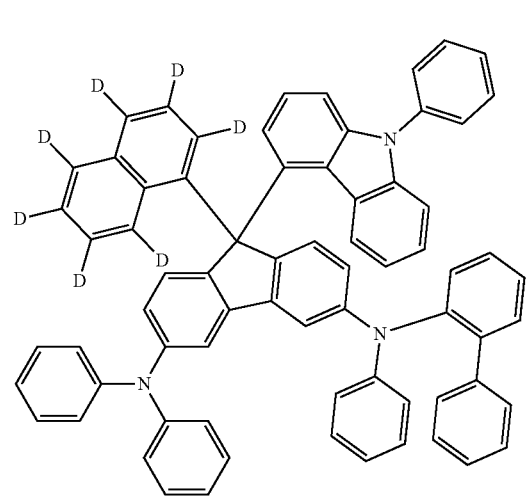
350
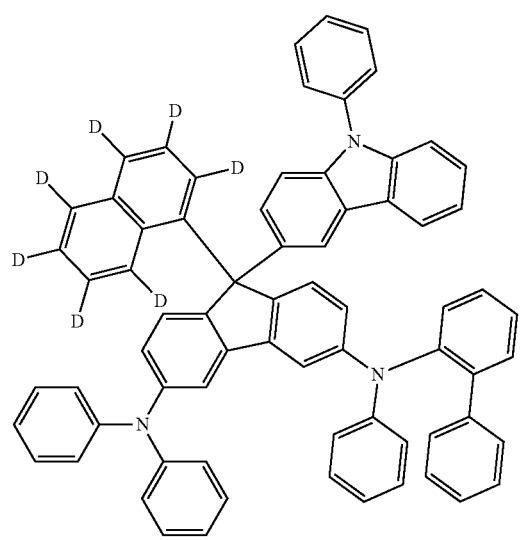
351
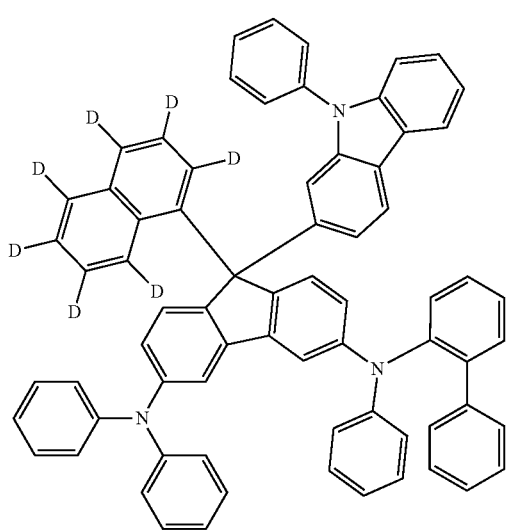
352
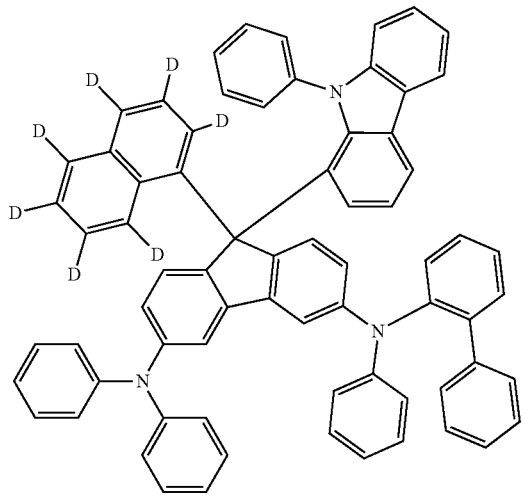
353
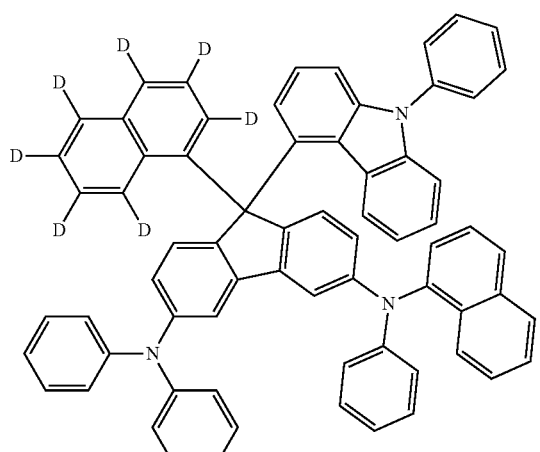
354
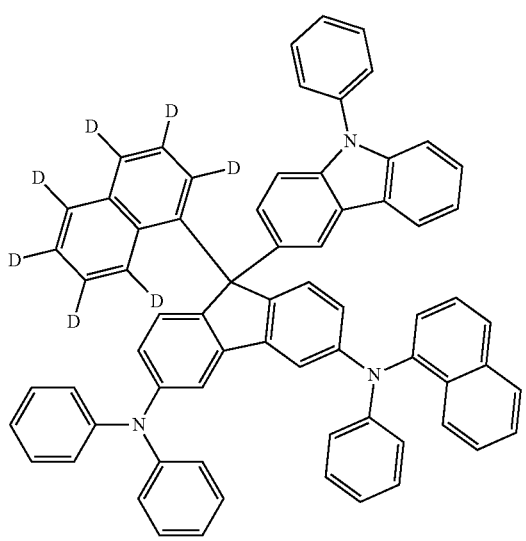

355
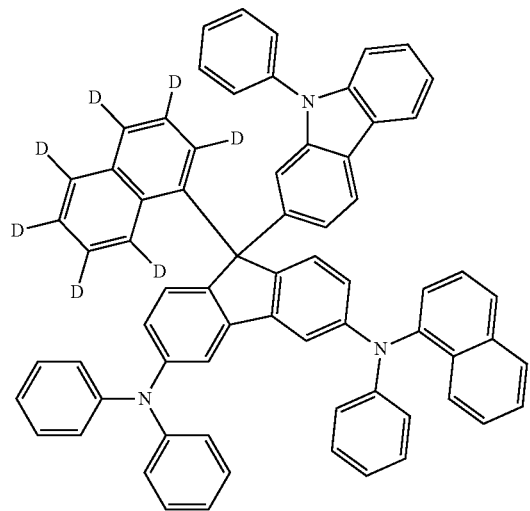
356
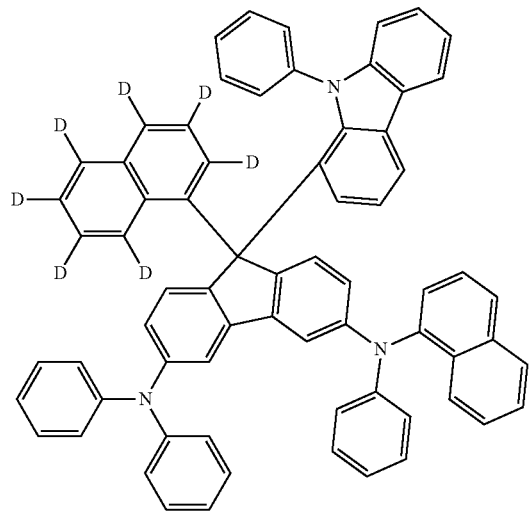
357
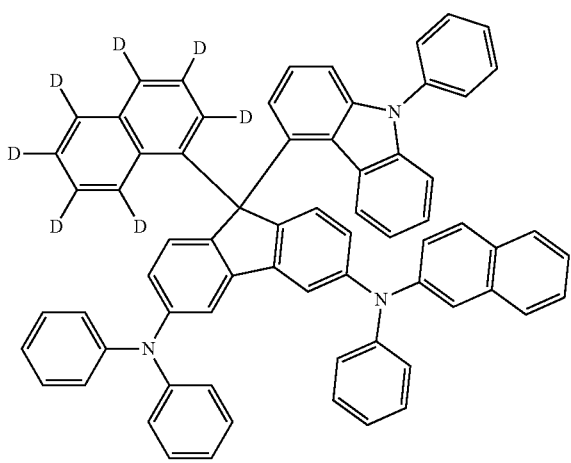
358
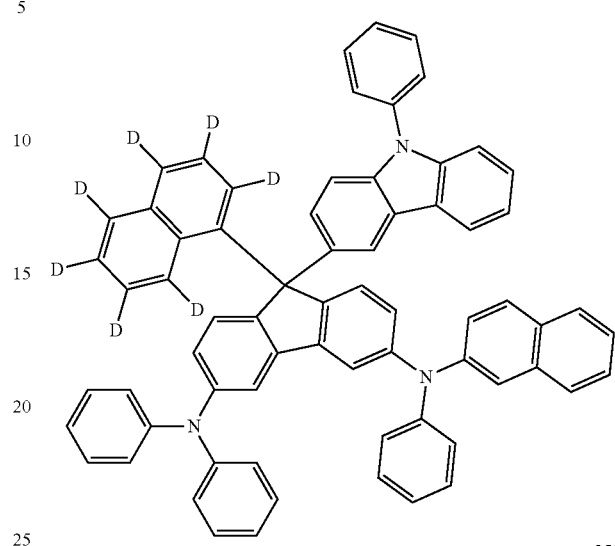
359
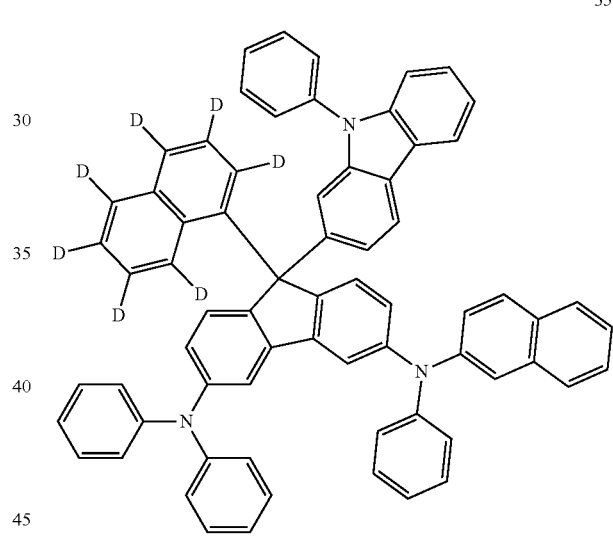
360
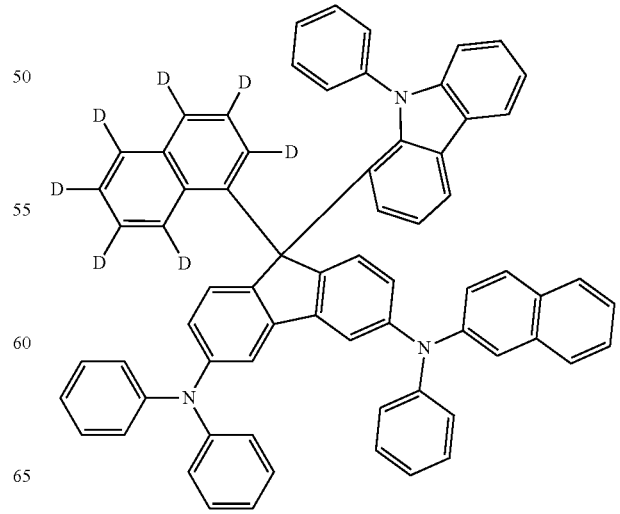

125
-continued

175

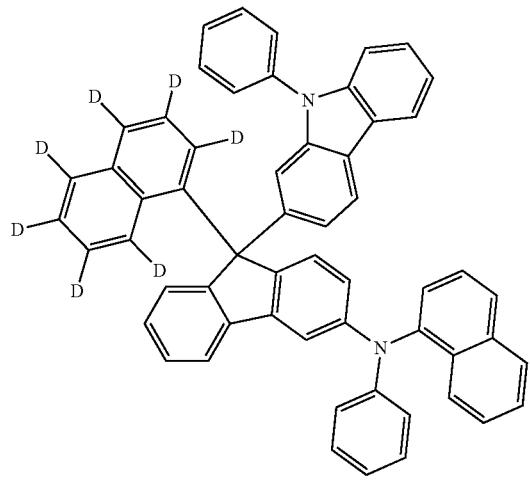

176

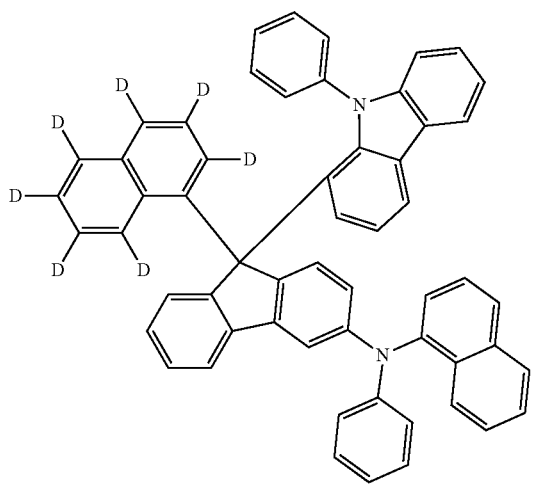

337

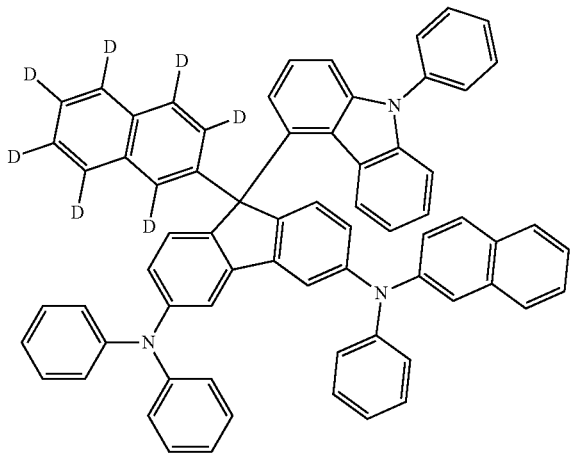

126
-continued

338

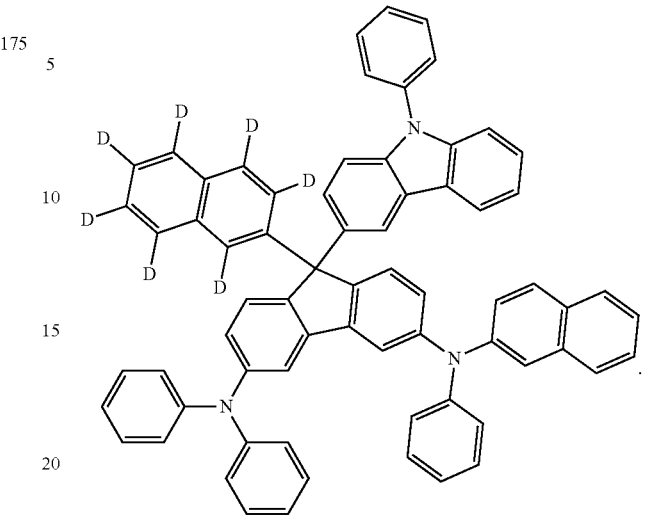

BRIEF DESCRIPTION OF THE DRAWINGS

The accompanying drawings are included to provide further understanding of the present disclosure, and are incorporated in and constitute a part of this specification. The drawings illustrate example embodiments of the present disclosure and, together with the description, serve to explain principles of the present disclosure.

In the drawings.

DETAILED DESCRIPTION

Figure 1:
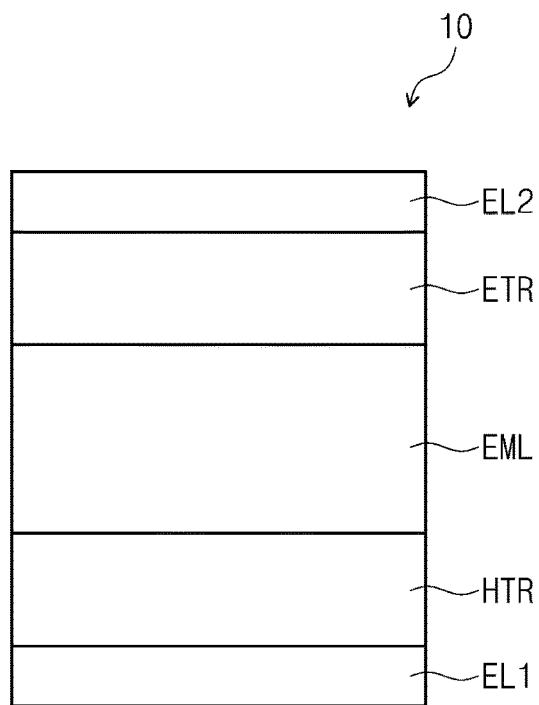
FIG. 1 is a schematic cross-sectional view illustrating an organic electroluminescence device according to an embodiment of the present disclosure.

The present disclosure may have various modifications and may be embodied in different forms, and example embodiments will be explained in detail with reference to the accompanying drawings. The present disclosure may, however, be embodied in different forms, and should not be construed as being limited to the embodiments set forth herein. Rather, any and all modifications, equivalents, and/or substituents that are in the spirit and technical scope of the present disclosure are included in the present disclosure.

In the accompanying drawings, like reference numbers refer to like elements, and duplicative descriptions thereof may not be provided. The dimensions of each structure may be exaggerated for clarity. It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present disclosure. The terms of a singular form may include plural forms unless the context clearly indicates otherwise.

As used herein, the singular forms "a," "an," and "the" are intended to include the plural forms as well, unless the context clearly indicates otherwise.

In the present application, it will be understood that the meaning of "includes," "including," "comprises," "comprising," and/or "have" specifies the presence of a feature, a fixed number, a step, a process, an element, a component, or a combination thereof disclosed in the specification, but does not exclude the possibility of presence or addition of one or more other features, fixed numbers, steps, processes, elements, components, or combinations thereof.

In the present application, when a layer, a film, a region, or a plate is referred to as being "above" or "in a upper portion of" another layer, film, region, or plate, it can be not only directly on the layer, film, region, or plate, but intervening layers, films, regions, or plates may also be present. When a layer, a film, a region, or a plate is referred to as being "under" or "in a lower portion of" another layer, film, region, or plate, it can be not only directly under the layer, film, region, or plate, but intervening layers, films, regions, or plates may also be present. In addition, it will be understood that when a layer, a film, a region, or a plate is referred to as being 'on' another layer, film, region, or plate, it can be not only disposed on the layer, film, region, or plate, but also disposed under the layer, film, region, or plate.

As used herein, expressions such as "at least one of," "one of," and "selected from," when preceding a list of elements, modify the entire list of elements and do not modify the individual elements of the list.

As used herein, the term "and/or" includes any and all combinations of one or more of the associated listed items. Further, the use of "may" when describing embodiments of the present disclosure refers to "one or more embodiments of the present disclosure".

In an embodiment of the description, the term "substituted or unsubstituted" may refer to a state of being unsubstituted, or being substituted or with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. Each of these example substituents may be further substituted or unsubstituted. For example, a biphenyl group may be interpreted as a named aryl group, and/or as a phenyl group substituted with a phenyl group.

In the description, the phrase "bonded to an adjacent group to form a ring" refers to a state of being bonded to an adjacent group to form a substituted or unsubstituted hydrocarbon ring, or a substituted or unsubstituted heterocycle. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each independently be monocyclic or polycyclic. In addition, the rings formed by being bonded to each other may be connected to another ring to form a spiro structure.

In the description, the term "an adjacent group" may refer to a substituent on the same atom or point, a substituent on an atom that is directly connected to the base atom or point, or a substituent sterically positioned (e.g., within intramolecular bonding distance) to the corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other.

In the description, non-limiting examples of the halogen atom include a fluorine atom, a chlorine atom, a bromine atom, and an iodine atom.

In the description, the term "alkyl group" may refer to a linear, branched or cyclic alkyl group. The number of carbons in the alkyl group may be 1 to 50, 1 to 30, 1 to 20, 1 to 10, or 1 to 6. Non-limiting examples of the alkyl group include a methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

In the description, the term "hydrocarbon ring" may refer to any functional group or substituent derived from an aliphatic hydrocarbon ring. The hydrocarbon ring group may be a saturated hydrocarbon ring group having 5 to 20 ring-forming carbon atoms.

In the description, the term "aryl group" may refer to any functional group or substituent derived from an aromatic hydrocarbon ring. The aryl group may be a monocyclic aryl group or a polycyclic aryl group. The number of ring-forming carbon atoms in the aryl group may be 6 to 60, 6 to 30, 6 to 20, or 6 to 15. Non-limiting examples of the aryl group include phenyl, naphthyl, fluorene, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the description, the fluorene group may be substituted, and two substituents (e.g., at the 9H position) may be connected to each other to form a spiro structure. Non-limiting examples of the substituted fluorene group are as follows. However, embodiments of the present disclosure are not limited thereto.

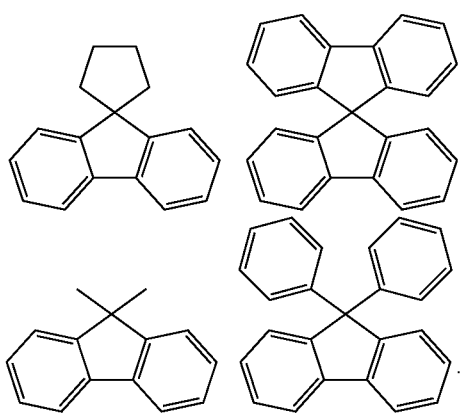

In the description, the term "heterocyclic group" may refer to any functional group or substituent derived from a ring including at least one of boron (B), oxygen (O), sulfur (S), nitrogen (N), phosphorus (P), silicon (Si), or selenium (Se) as a heteroatom. The heterocyclic group may be an aliphatic heterocyclic group or an aromatic heterocyclic group. The aromatic heterocyclic group may be a heteroaryl group. The aliphatic heterocycle and the aromatic heterocycle may each independently be monocyclic or polycyclic.

When the heterocyclic group contains two or more hetero atoms, the two or more hetero atoms may be the same as or different from each other. The heterocyclic group may be a monocyclic heterocyclic group or a polycyclic heterocyclic group, and in some embodiments may be a heteroaryl group. The number of ring-forming carbon atoms in the heterocyclic group may be 2 to 60, 2 to 30, 2 to 20, or 2 to 10.

The number of carbons for forming a ring of the aliphatic heterocyclic group may be 2 to 30, 2 to 20, or 2 to 10. Non-limiting examples of the aliphatic heterocyclic group include an oxirane group, thiirane group, pyrrolidine group, piperidine group, tetrahydrofuran group, tetrahydrothiophene group, thiane group, tetrahydropyran group, 1,4-dioxane group, etc.

When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Non-limiting examples of the heteroaryl group include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazolyl, phthalazinyl, pyrido pyrimidyl, pyrido pyrazinyl, pyrazino pyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothiophenyl, dibenzothiophenyl, thienothiophenyl, benzofuranyl, phenanthrolinyl, thiazolyl, isoxazolyl, oxadiazolyl, thiadiazolyl, phenothiazolyl, phenothiazinyl, dibenzosilolyl, dibenzofuranyl, etc.

In the description, the above description of the aryl group may be applied to an arylene group, except that the arylene group is a divalent group. The above description of the heteroaryl group may be applied to a heteroarylene group, except that the heteroarylene group is a divalent group.

In the description, the number of carbon atoms in an amino group is not specifically limited, but may be 1 to 30.

The term "amino group" may refer to an alkyl amino group, an aryl amino group, or a heteroaryl amino group. Non-limiting examples of the amino group include a methylamino group, a dimethylamino group, a phenylamino group, a diphenylamino group, a naphthylamino group, a 9-methyl-anthracenylamino group, a triphenylamino group, etc.

In the description, the alkenyl group may be linear or branched. The number of carbon atoms is not specifically limited, and may be 2 to 30, 2 to 20, or 2 to 10. Non-limiting examples of the alkenyl group include a vinyl group, a 1-butenyl group, a 1-pentenyl group, a 1,3-butadienyl aryl group, a styrenyl group, a styryl vinyl group, etc.

In the description, the number of carbon atoms in the amine group is not specifically limited, but may be 1 to 30. The amine group may be an alkyl amine group or an aryl amine group. Non-limiting examples of the amine group include, but are not limited to, a methylamine group, dimethylamine group, phenylamine group, diphenylamine group, naphthylamine group, 9-methyl-anthracenylamine group, triphenylamine group, etc.

In the description, the alkyl group in the alkylamine group may be the same as the alkyl group generally described above.

In the description, the aryl group in the arylamine group may be the same as the aryl group generally described above.

In the description, the term "direct linkage" may refer to a single bond.

In the description, "—•" refers to a point of connection (e.g., a bond).

Hereinafter, an organic electroluminescence device according to an embodiment of the present disclosure and an amine compound included therein will be explained with reference to the drawings.

Figure 2:
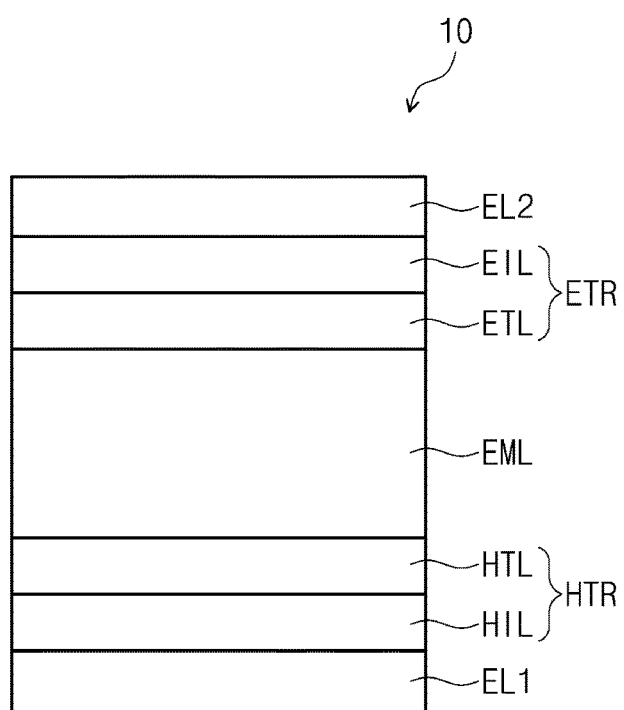
FIG. 2 is a schematic cross-sectional view illustrating an organic electroluminescence device according to an embodiment of the present disclosure.
Figure 3:
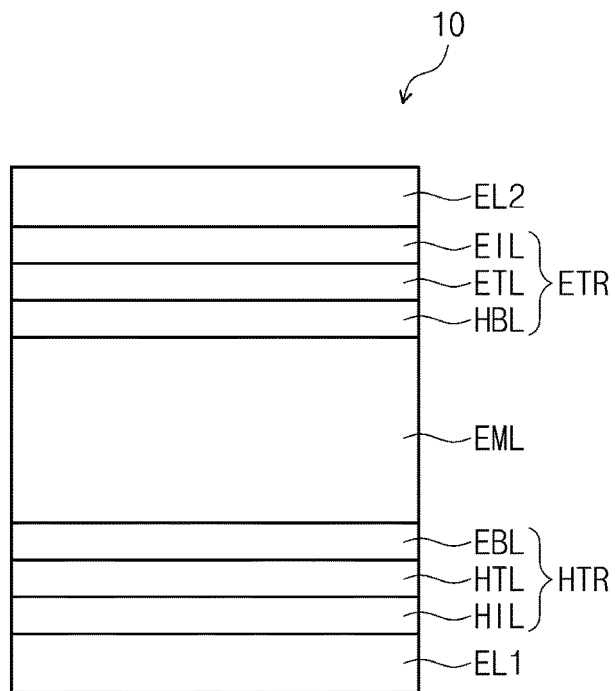
FIG. 3 is a schematic cross-sectional view illustrating an organic electroluminescence device according to an embodiment of the present disclosure.
Figure 4:
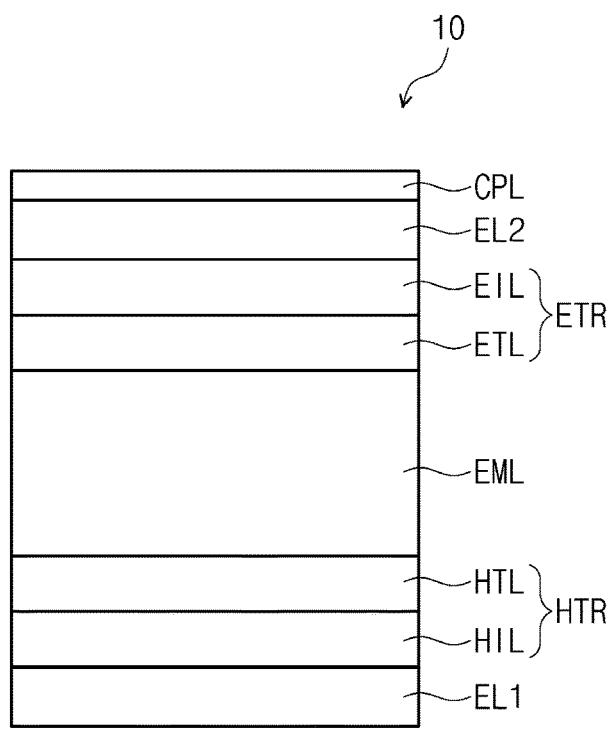
FIG. 4 is a schematic cross-sectional view illustrating an organic electroluminescence device according to an embodiment of the present disclosure.

FIGS. 1 to 4 are schematic cross-sectional views illustrating an organic electroluminescence device according to an embodiment of the present disclosure. Referring to FIGS. 1 to 4, in an organic electroluminescence device 10 according to an embodiment, a first electrode EU and a second electrode EL2 are disposed to face each other and an emission layer EML is disposed between the first electrode EL1 and the second electrode EL2.

in some embodiments, the organic electroluminescence device 10 of an embodiment may further include a plurality of functional layers between the first electrode EL1 and the second electrode EL2 in addition to the emission layer EML. The plurality of functional layers may include a hole transport region HTR and an electron transport region ETR. For example, the organic electroluminescence device 10 according to an embodiment may include the first electrode EL1, the hole transport region HTR, the emission layer EML, the electron transport region ETR, and the second electrode EL2, which are sequentially stacked. In some embodiments, the organic electroluminescence device 10 of an embodiment may include a capping layer CPL disposed on the second electrode EL2.

The organic electroluminescence device 10 of an embodiment may include a compound of an embodiment, which will be described later, in the hole transfer region HTR disposed between the first electrode EL1 and the second electrode EL2. However, embodiments are not limited thereto, and the organic electroluminescence device 10 of an embodiment may include a compound according to an embodiment not only in the hole transport region HTR but also in the emission layer EML or electron transport region ETR, which are among the plurality of functional layers disposed between the first electrode EL1 and the second electrode EL2, or in the capping layer CPL disposed on the second electrode EL2.

The first electrode EL1 may have conductivity (e.g., may be conductive). The first electrode EL1 may be formed of a metal alloy and/or a conductive compound. The first electrode EL1 may be an anode. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may include a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or any mixture thereof (e.g., a mixture of Ag and Mg). In some embodiments, the first electrode EL1 may have a multilayer structure including a reflective layer and/or a transflective layer formed of the above-described materials, and a transparent conductive layer formed of ITO, IZO, ZnO, ITZO, etc. For example, the first electrode EL1 may have a three-layer structure of ITO/Ag/ITO, but embodiments of the present disclosure are not limited thereto. The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be, for example, about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of a hole injection layer HIL or a hole transport layer HTL, or a single layer structure formed of a hole injection material and a hole transport material. In some embodiments, the hole transport region HTR may have a single layer structure formed of a plurality of different materials, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, which may be sequentially laminated on the first electrode EL1, but embodiments are not limited thereto.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR may include the amine compound of an embodiment. For example, the hole injection layer HIL and/or the hole transport layer HTL may include the amine compound of an embodiment.

The amine compound of an embodiment contains (includes) a fluorene group, an aryl group having 6 to 60 ring-forming carbon atoms that is substituted to the fluorene group, a heteroaryl group having 2 to 60 ring-forming carbon atoms that is substituted to the fluorene group, and at least one amine group that is substituted to the fluorene group. For example, the amine compound may have a structure in which the above-mentioned substituents are substituted to a core including the fluorene group.

In an embodiment, the amine compound may include an aryl group, a heteroaryl group, and at least one amine group as substituents of the fluorene group. The aryl group and the heteroaryl group may each be connected to the 9-position carbon of the fluorene group. The aryl group substituted at the 9-position carbon of the fluorene group may be an aryl group in which all the carbons of the aryl group are substituted with deuterium (e.g., may be a deuterated aryl group). For example, the aryl group substituted at the 9-position carbon of the fluorene group may be a phenyl group that is substituted with deuterium, a naphthyl group that is substituted with deuterium, or a biphenyl group that is substituted with deuterium. The heteroaryl group substituted at the 9-position carbon of the fluorene group may be a dibenzoheterole group. For example, the heteroaryl group substituted to the 9-position carbon of the fluorene group may be a fused polycyclic heteroaryl group in which three rings are fused. In some embodiments, the heteroaryl group substituted at the 9-position carbon of the fluorene group may be a substituted or unsubstituted dibenzothiophene group, a substituted or unsubstituted dibenzofuran group, or a substituted or unsubstituted carbazole group.

At least one amine group may be connected to at least one carbon among positions 1 through 8 of the fluorene group. In an embodiment, the amine group may be a tertiary amine. The fluorene group may be connected to the nitrogen atom of the amine group, and the nitrogen atom may include two substituents that are each independently a substituted or unsubstituted aryl group having 6 to 60 ring-forming carbon atoms, or a substituted or unsubstituted heteroaryl group having 3 to 60 ring-forming carbon atoms. In some embodiments, the amine group nitrogen atom substituents may each independently be an unsubstituted phenyl group, an unsubstituted biphenyl group, or an unsubstituted naphthyl group.

An amine compound according to an embodiment may be represented Formula 1:

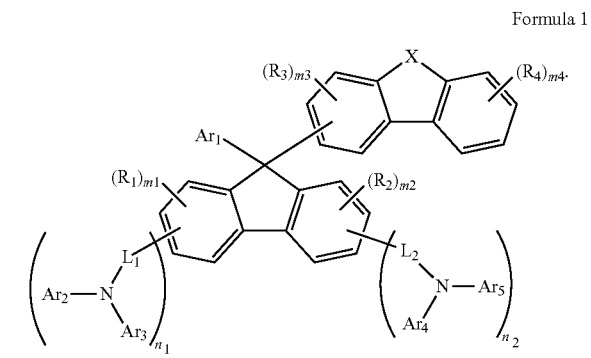

Formula 1

In Formula 1, X may be O, S, or $NAr_6$. For example, the heteroaryl group may be a substituted or unsubstituted dibenzofuran group, a substituted or unsubstituted dibenzothiophene group, or a substituted or unsubstituted carbazole group.

L₁ and L₂ may each independently be a direct linkage, a substituted or unsubstituted arylene group having 6 to 60 ring-forming carbon atoms, or a substituted or unsubstituted heteroarylene group having 2 to 60 ring-forming carbon atoms. For example, L₁ and L₂ may be a direct linkage.

$n_1$ and $n_2$ may each independently be 0 or 1, and at least one of $n_1$ or $n_2$ may be 1. For example, the amine compound of an embodiment may include one or two substituted amine groups.

$R_1$ to $R_4$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring. For example, $R_1$ to $R_4$ may each independently be a hydrogen atom.

$m_1$, $m_2$, and $m_4$ may each independently be an integer of 0 to 4, and $m_3$ may be an integer of 0 to 3. For example, $m_1$ to $m_4$ may each be 0.

$Ar_1$ may be a phenyl group substituted with deuterium, a naphthyl group substituted with deuterium, or a biphenyl group substituted with deuterium. For example, An may be represented by at least one of Formula $t_1$ to Formula $t_5$:

Formula t₁

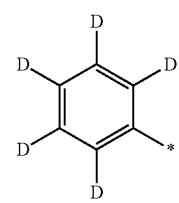

Formula t₂

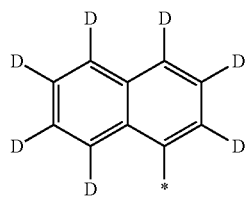

Formula t₃

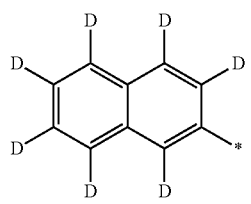

Formula t₄

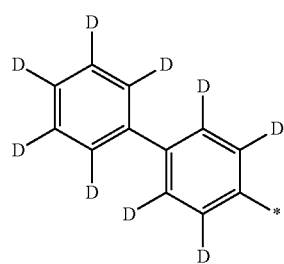

Formula t₅

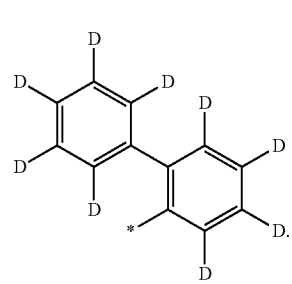

$Ar_2$ to $Ar_6$ may each independently be a substituted or unsubstituted aryl group having 6 to 60 ring-forming carbon atoms, or a substituted or unsubstituted heteroaryl group having 3 to 60 ring-forming carbon atoms. For example, $Ar_2$ to $Ar_4$ and $Ar_6$ may each be an unsubstituted phenyl group. $Ar_5$ may each be an unsubstituted phenyl group, an unsubstituted biphenyl group, or an unsubstituted naphthyl group. However, embodiments are not limited thereto.

In an embodiment, the amine compound represented by Formula 1 may be represented by at least one of Formula 1-1 to Formula 1-3:

Formula 1-1

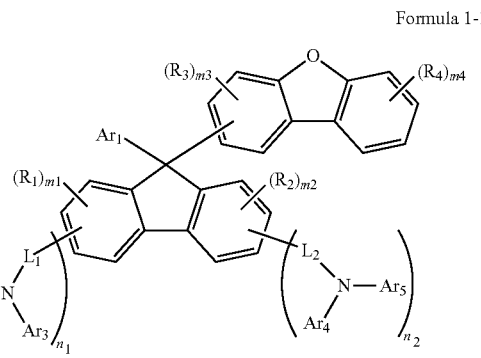

Formula 1-2

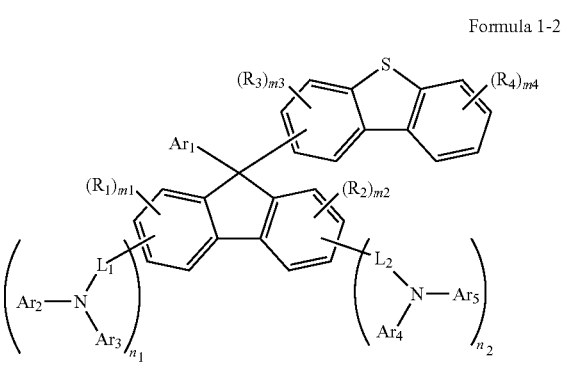

Formula 1-3

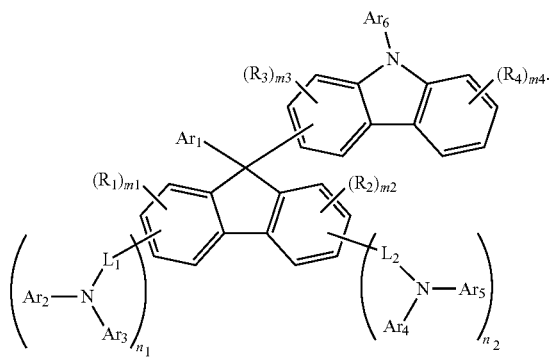

Formula 2-3

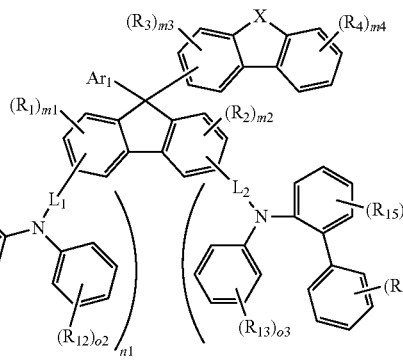

Formula 1-1 to Formula 1-3 are embodiments of Formula 1 in which X is specified. For example, Formula 1-1 to Formula 1-3 are formulae in which X is specified as O, S, and NAr₆, respectively. For example, Formula 1-1 includes a dibenzofuran group in the amine compound. Formula 1-2 includes a dibenzothiophene group in the amine compound. Formula 1-3 includes a carbazole group in the amine compound.

In Formula 1-1 to Formula 1-3, $L_1$, $L_2$, $R_1$ to $R_4$, $m_1$ to $m_4$, $Ar_1$ to $Ar_6$, $n_1$ and $n_2$ may each independently be the same as defined in Formula 1.

In an embodiment, the amine compound represented by Formula 1 may be represented by at least one of Formula 2-1 to Formula 2-5:

Formula 2-4

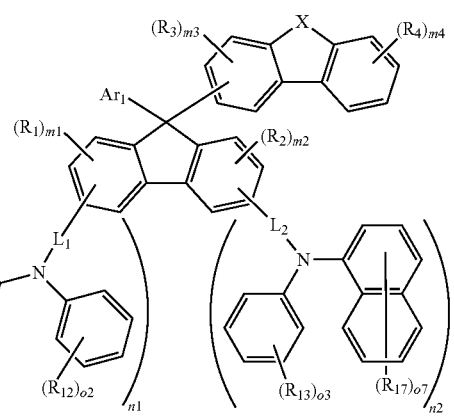

Formula 2-1

Formula 2-5

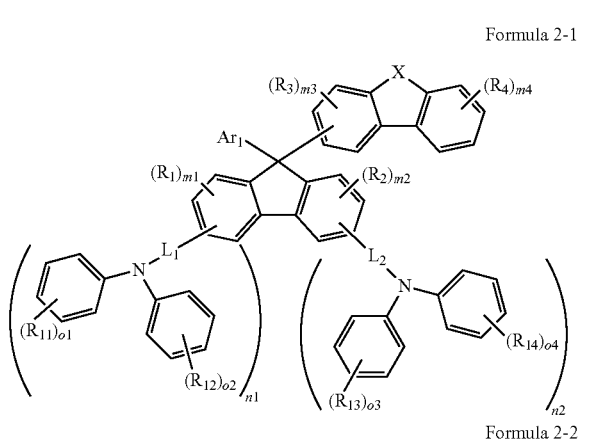

Formula 2-2

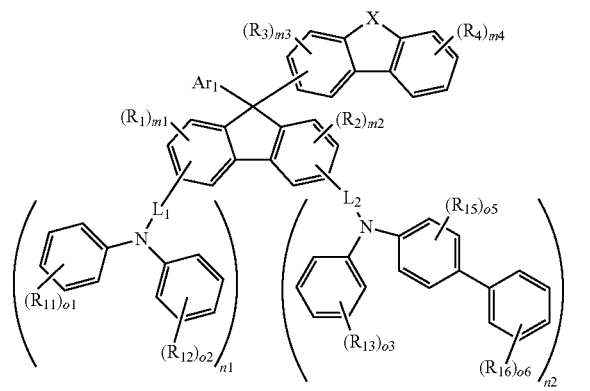

Formula 2-1 to Formula 2-5 are embodiments of Formula 1 in which $Ar_2$ to $Ar_5$ are specified. For example, in Formula 2-1, $Ar_2$ to $Ar_5$ are each independently a phenyl group. In Formula 2-2 and Formula 2-3, $Ar_2$ to $Ar_4$ are each independently a phenyl group and $Ar_5$ is as a biphenyl group. In Formula 2-2 and Formula 2-3, $Ar_5$ is a biphenyl group in which the nitrogen atom of the amine is connected to the para-position and ortho-position, respectively, with respect to the single bond connecting the two phenyl groups of the biphenyl group. In Formula 2-4 and Formula 2-5, $Ar_2$ to $Ar_4$ are each independently a phenyl group, and $Ar_5$ is a naphthyl group.

In Formula 2-1 to Formula 2-5, $R_{11}$ to $R_{17}$ may each independently be a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or may be bonded to an adjacent group to form a ring. For example, $R_{11}$ to $R_{17}$ may each be hydrogen atoms. However, embodiments are not limited thereto.

$o_1$ to $o_4$ and $o_6$ may each independently be an integer of 0 to 5. $o_5$ may be an integer of 0 to 4. $o_7$ may be an integer of 0 to 7. For example, $o_1$ to $o_7$ may be 0. However, embodiments are not limited thereto.

In Formula 2-1 to Formula 2-5, X, $R_1$ to $R_4$, $L_1$, $L_2$, $n_1$, $n_2$, $m_1$ to $m_4$ and $Ar_1$ may each independently be the same as defined in Formula 1.

In an embodiment, the amine compound represented by Formula 1 may be represented by Formula 3-1:

Formula 3-1

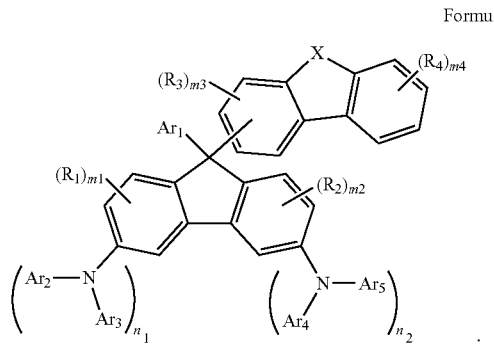

Formula 3-1 is a formula in which the amine groups are substituted to the fluorene group at specified positions. In Formula 3-1, the two amine groups may be respectively connected to the 3-position carbon and 6-position carbons. However, embodiments are not limited thereto.

In Formula 3-1, X, $Ar_1$ to $Ar_5$, $R_1$ to $R_4$, $n_1$, $n_2$, and $m_1$ to $m_4$ may each independently be the same as defined in Formula 1.

In an embodiment, the amine compound represented by Formula 1 may be represented by at least one of Formula 4-1 and Formula 4-2:

Formula 4-1

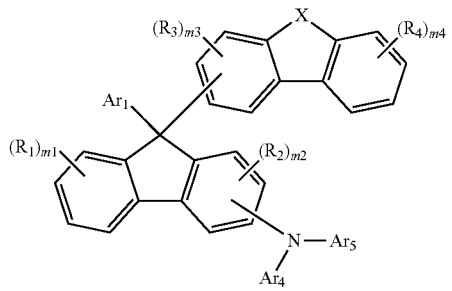

Formula 4-2

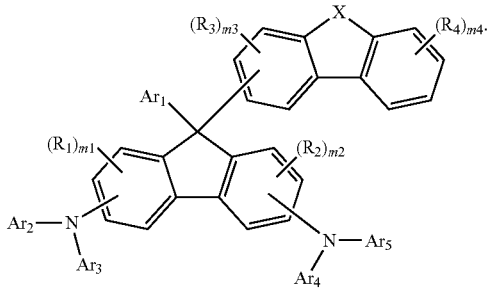

Formula 4-1 is an embodiment of Formula 1 in which $n_1$ is 0, and $n_2$ is 1. The amine compound represented by Formula 4-1 may include one amine group substituted to the fluorene group.

Formula 4-2 is an embodiment of Formula 1 in which $n_1$ and $n_2$ are each 1. The amine compound represented by Formula 4-2 may include two amine groups substituted to the fluorene group.

In Formula 4-1 and Formula 4-2, X, $Ar_1$ to $Ar_5$, $R_1$ to $R_4$, and $m_1$ to $m_4$ may each independently be the same as defined in Formula 1.

In an embodiment, the amine compound represented by Formula 1 may include at least one of the compounds represented by Compound Group 1:

Compound Group 1

Compound Group 1

1

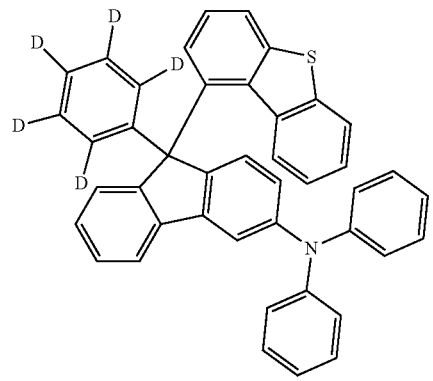

2

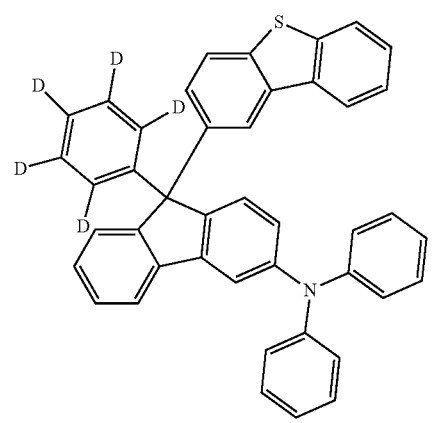

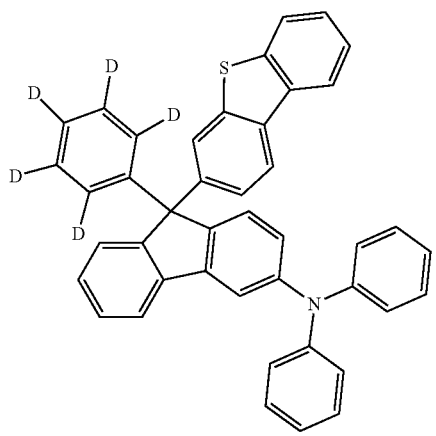
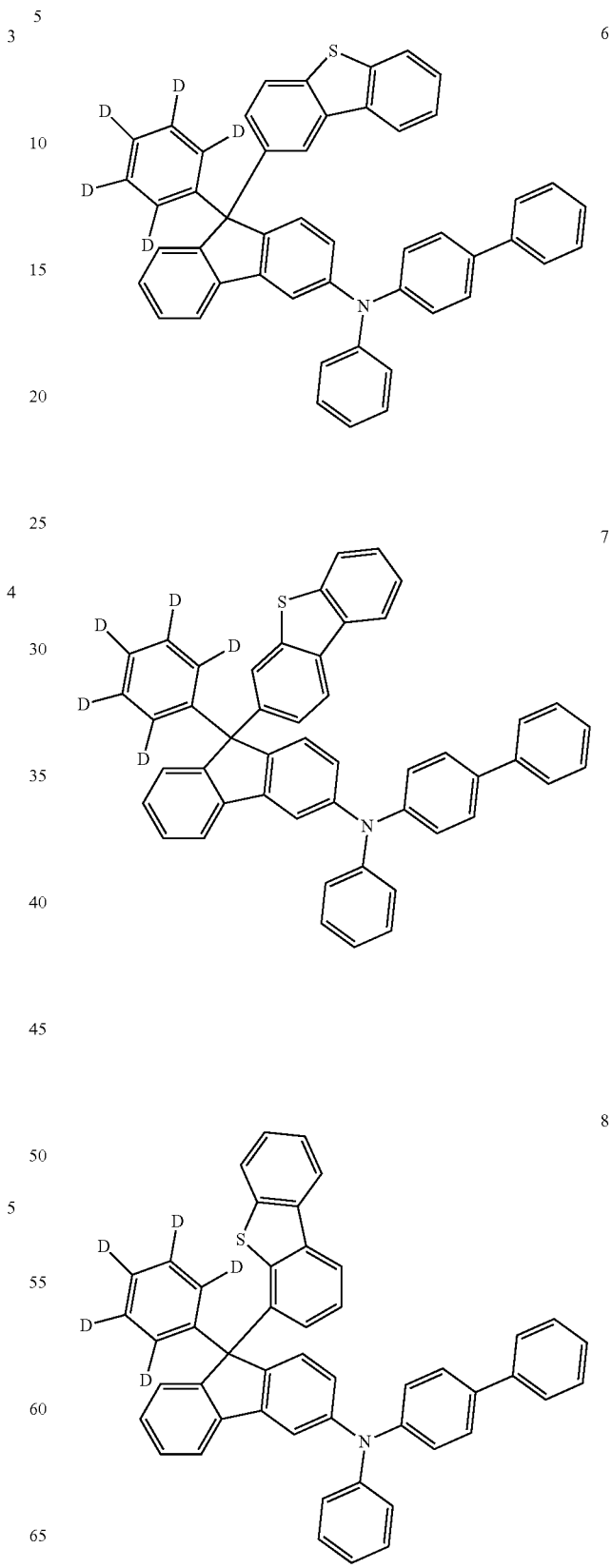

9
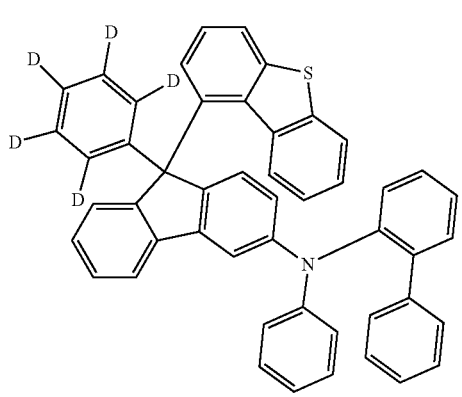
10
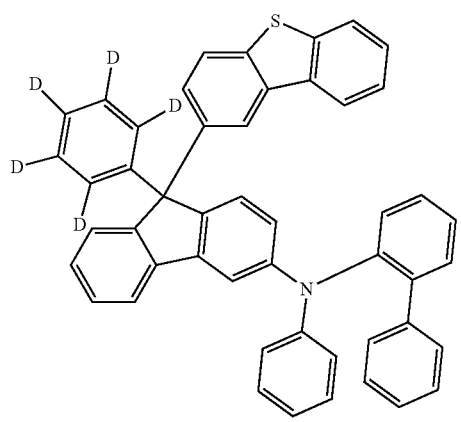
11
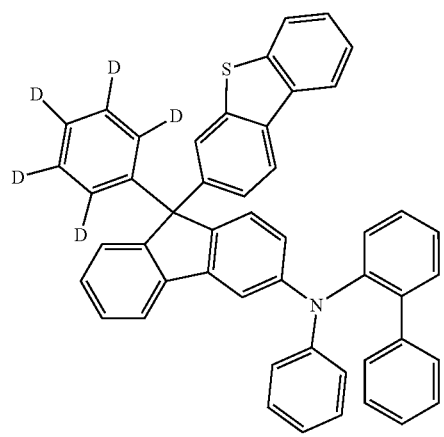
12
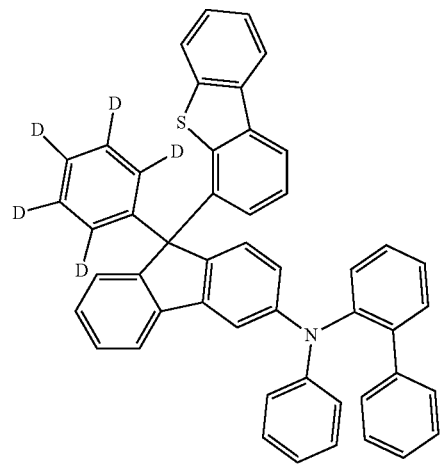
13
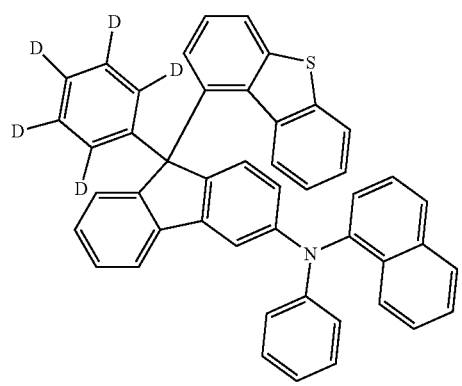
14
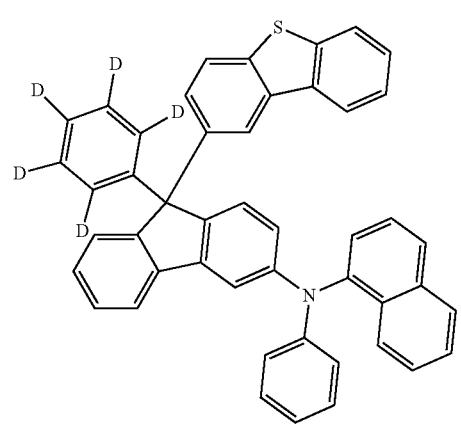

15
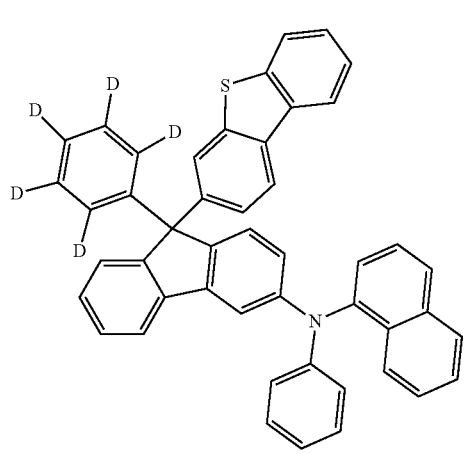
16
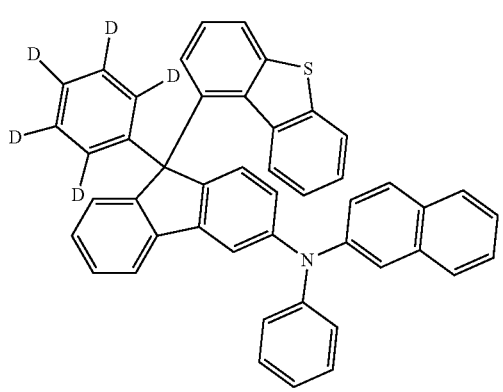
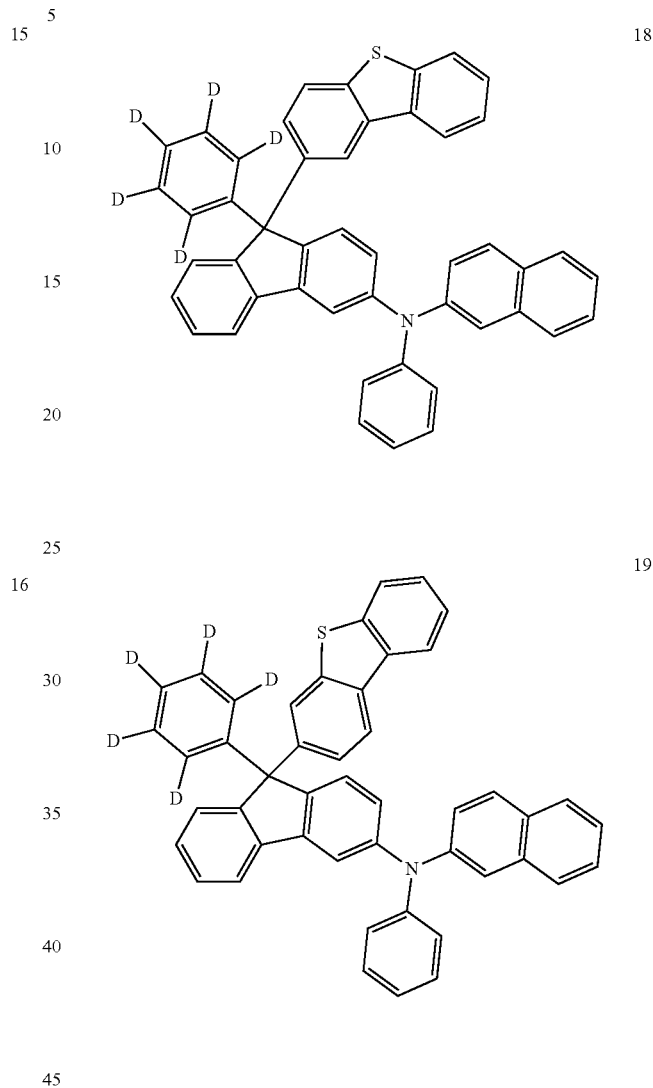
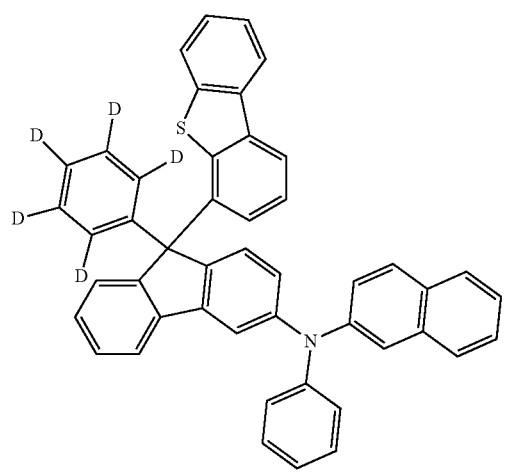

21
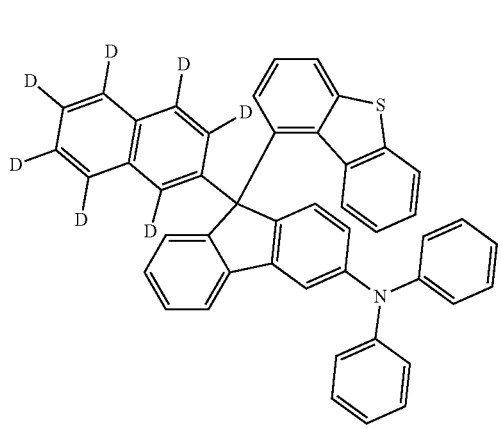
22
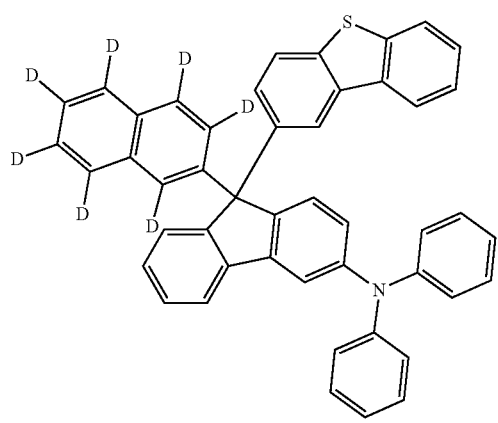
23
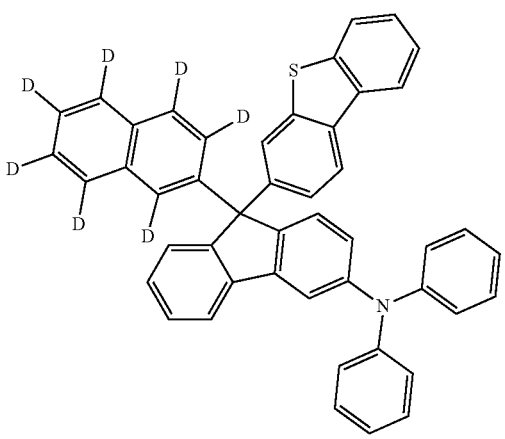
24
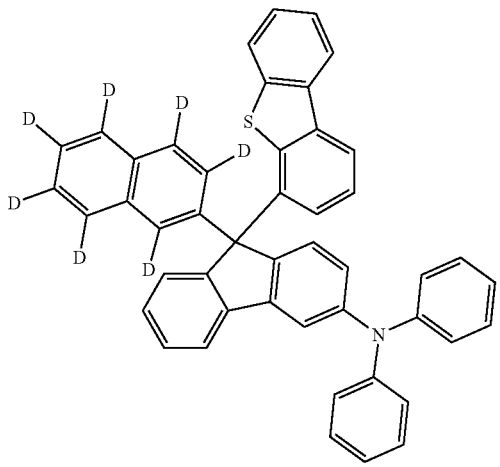
25
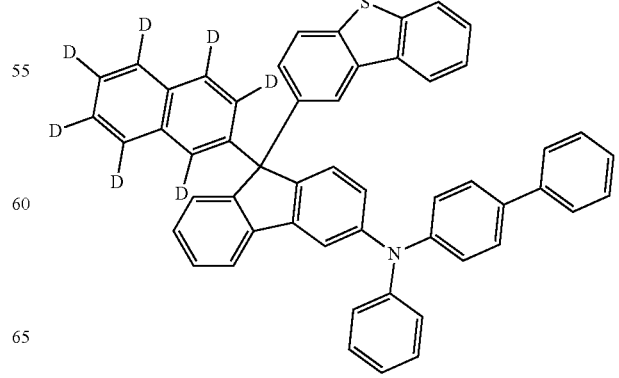
26

27
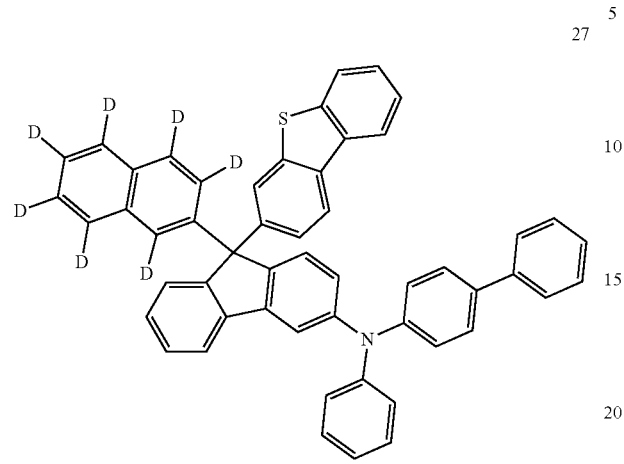
30
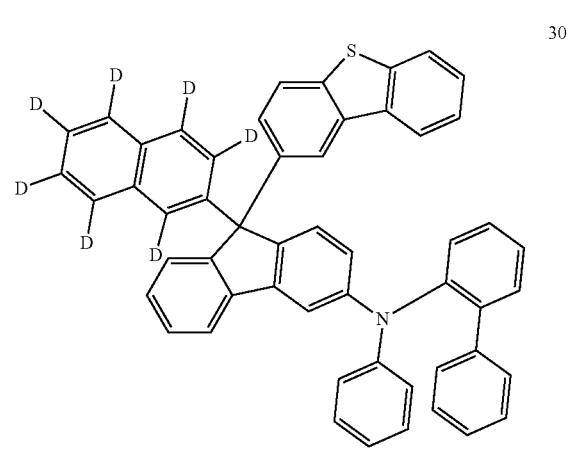
28
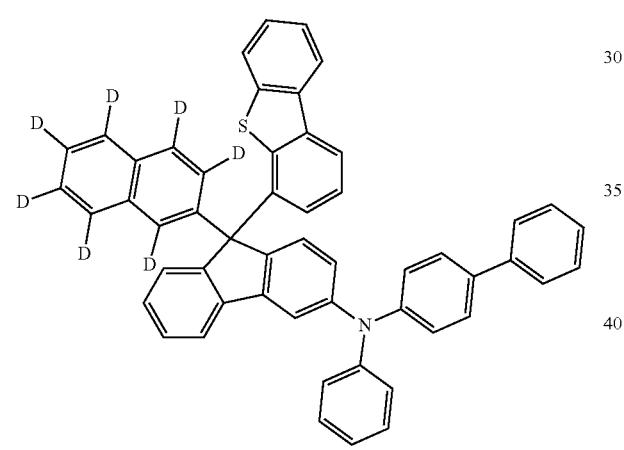
31
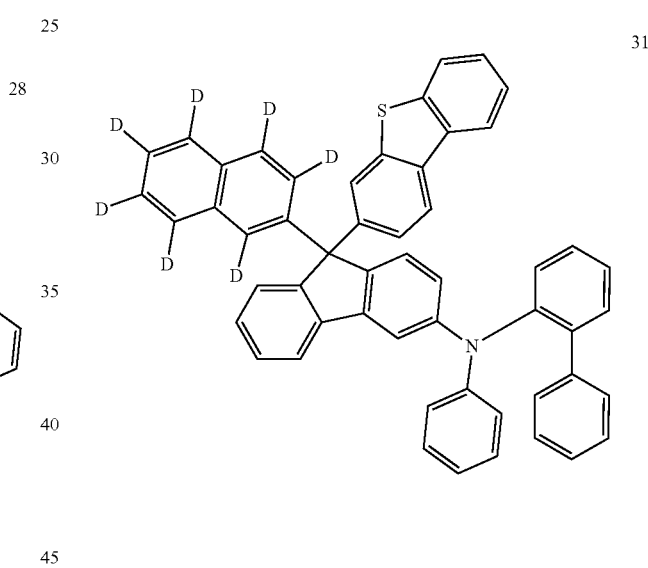
29
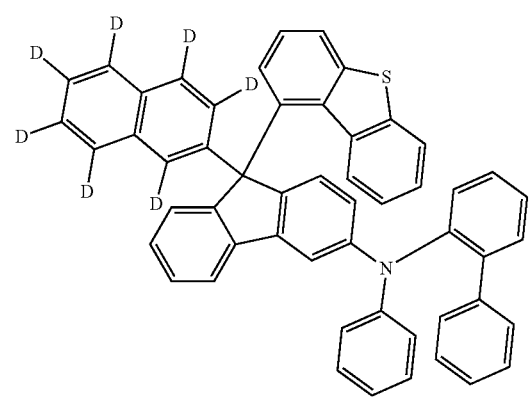
32
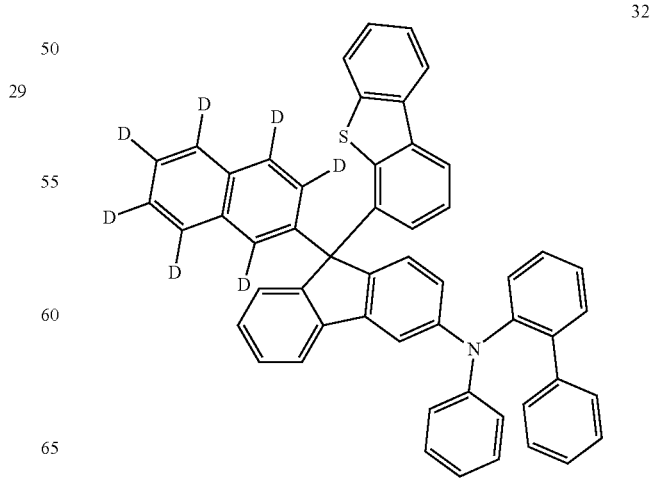

149
-continued
150
-continued
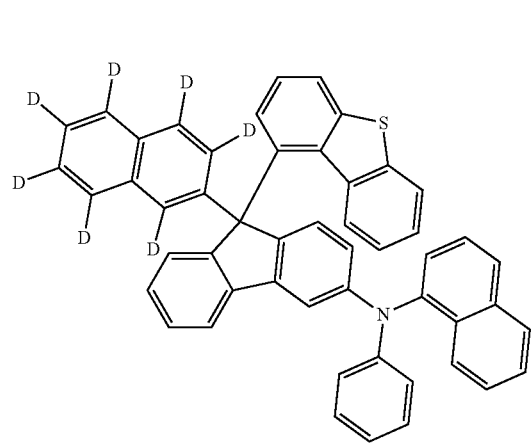
33
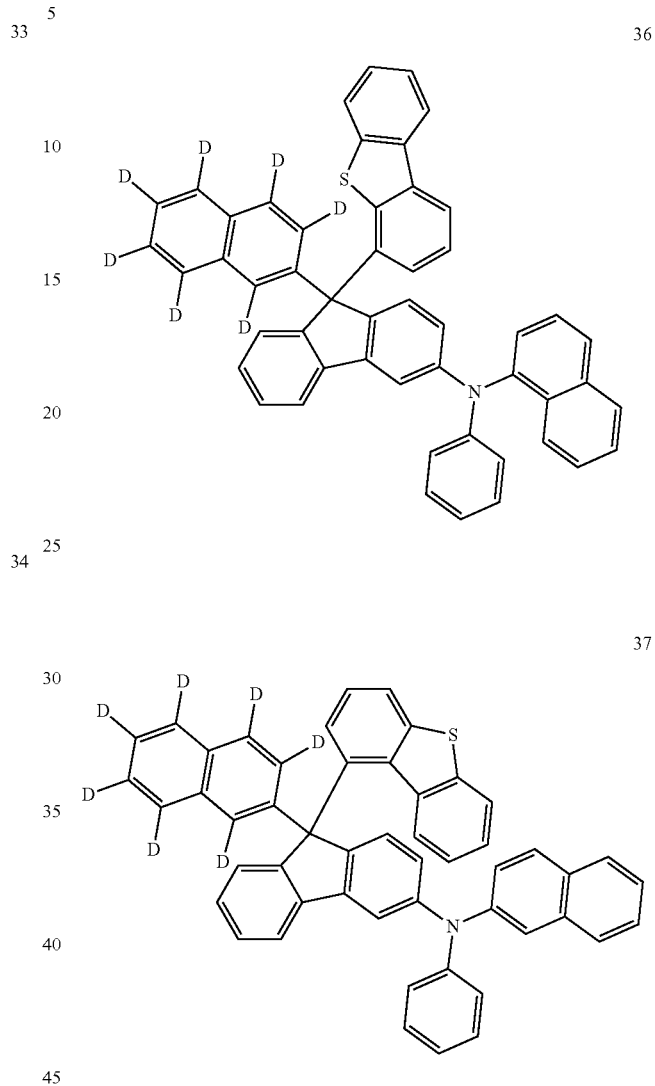
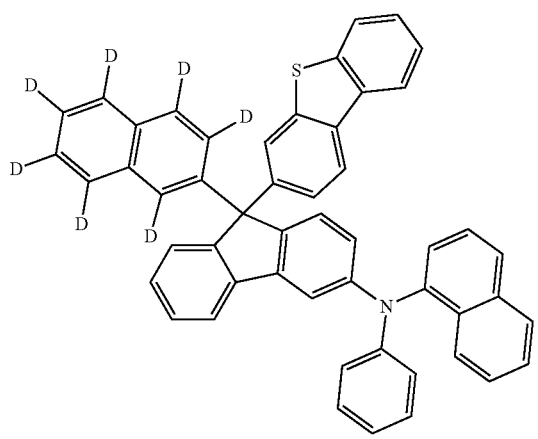
35

151
-continued
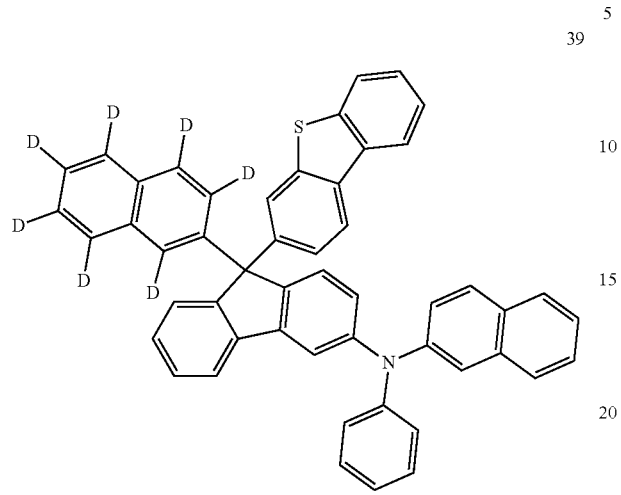
39
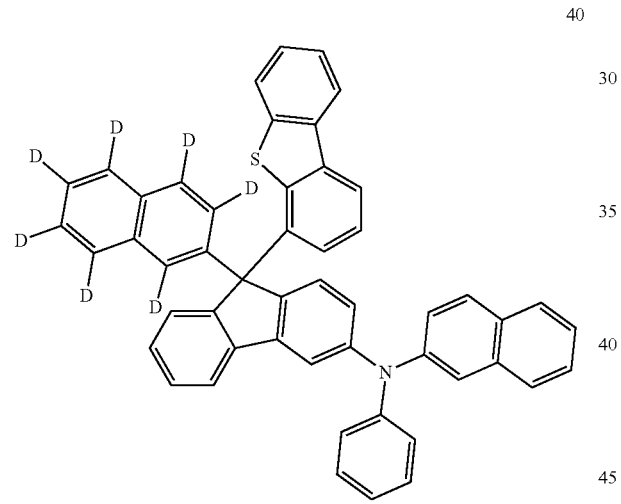
40
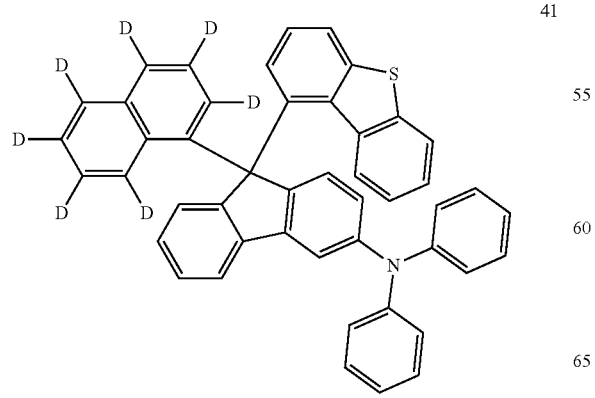
41
152
-continued
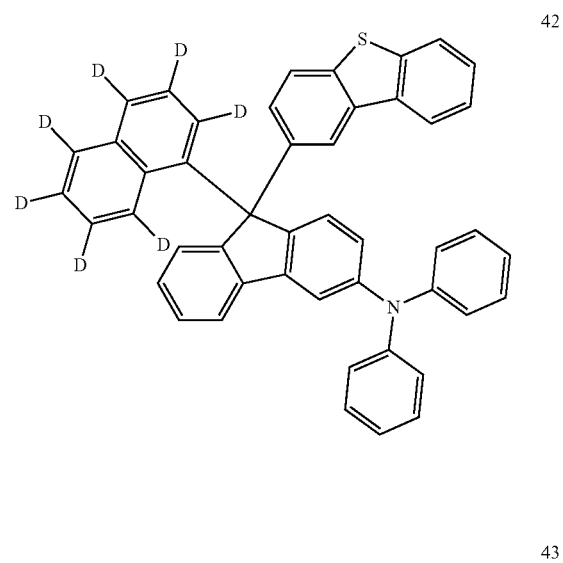
42
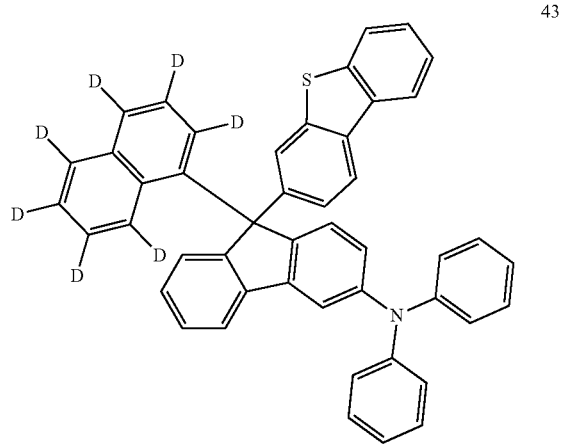
43
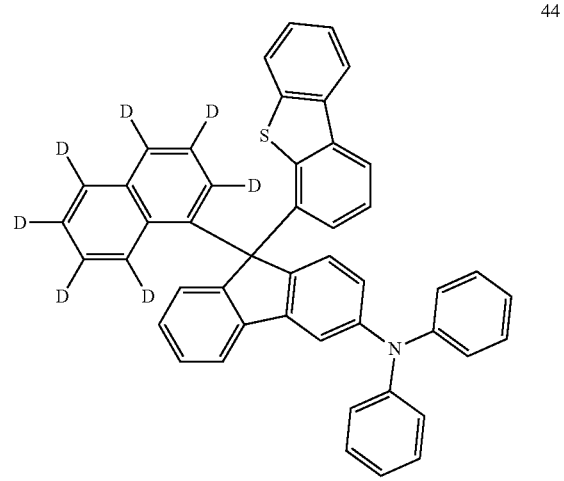
44

45
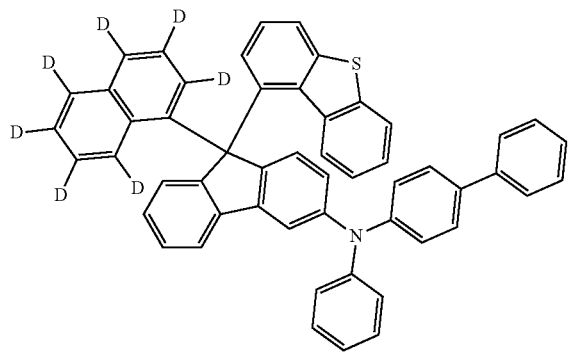
46
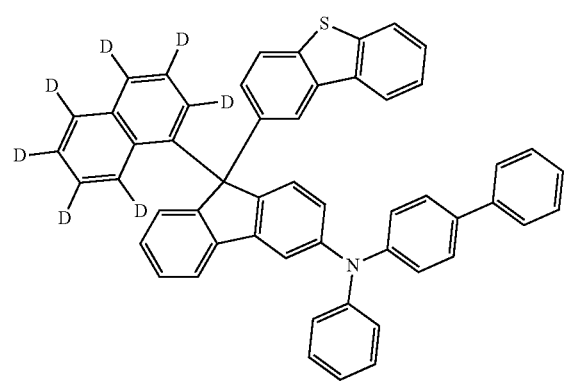
47
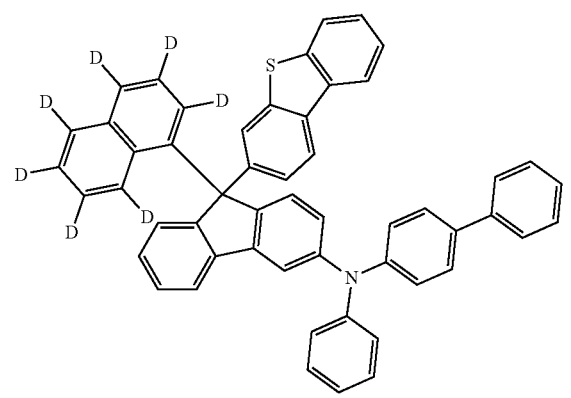
48
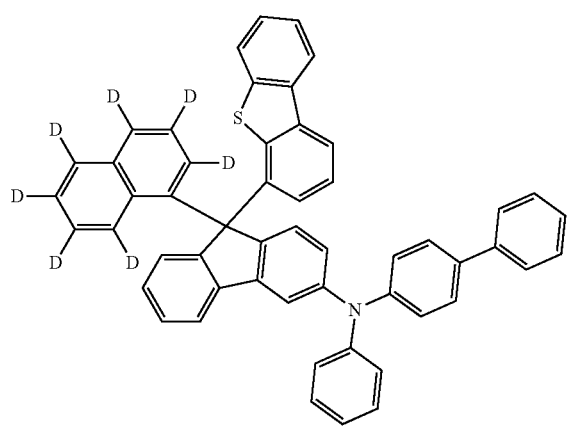
49
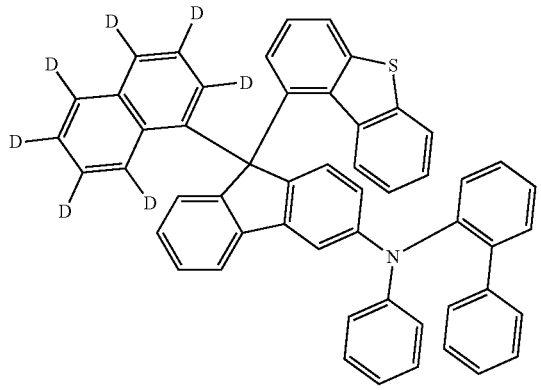
50
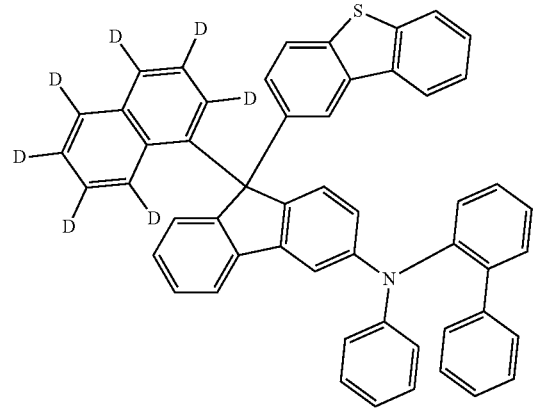
51
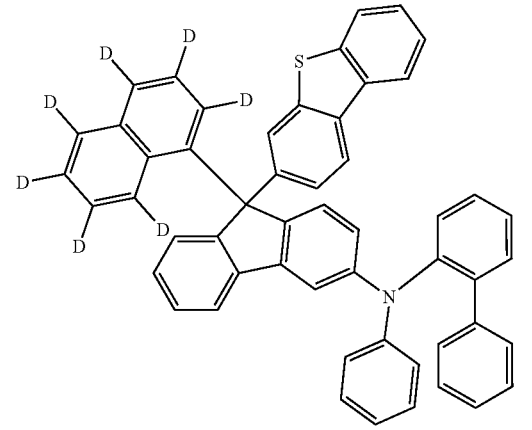

52
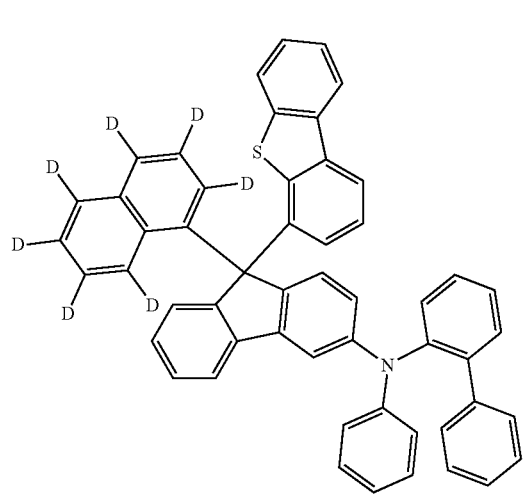
53
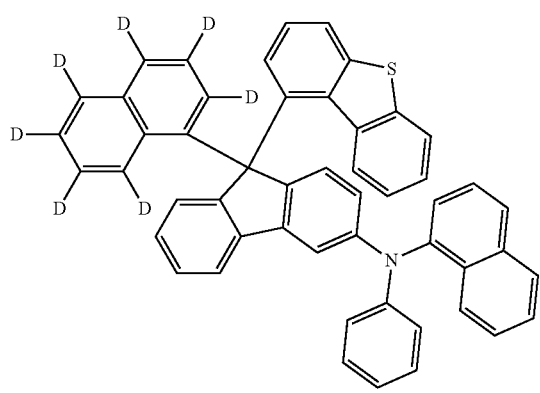
54
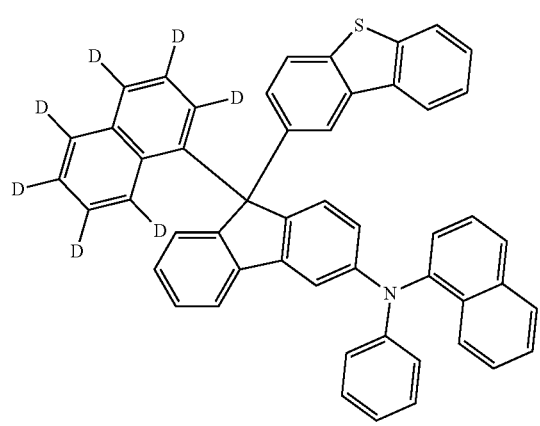
55
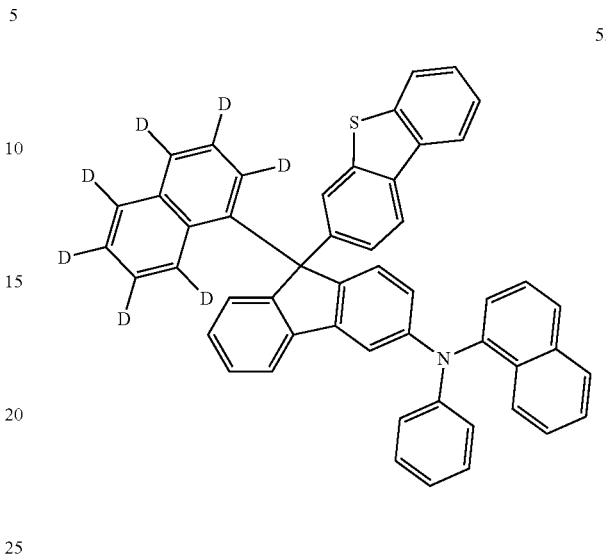
56
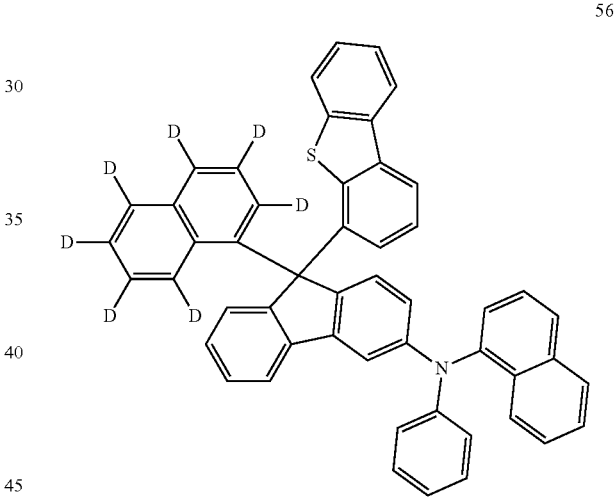
57
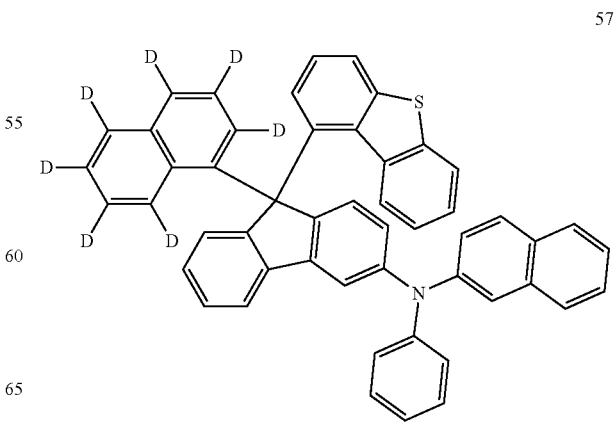

58
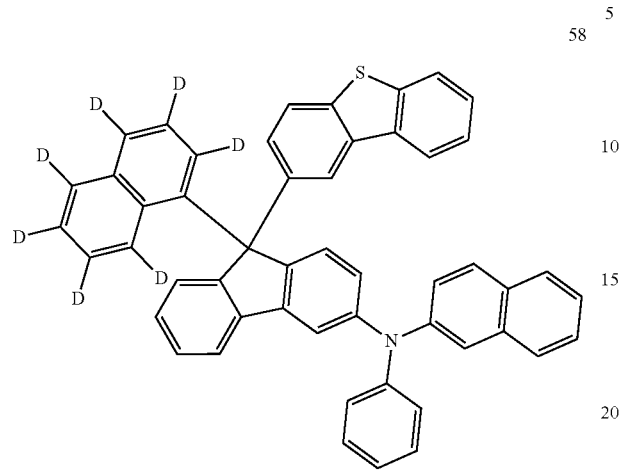
59
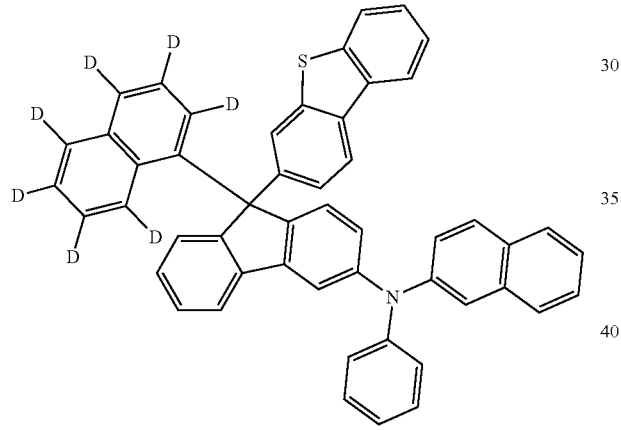
60
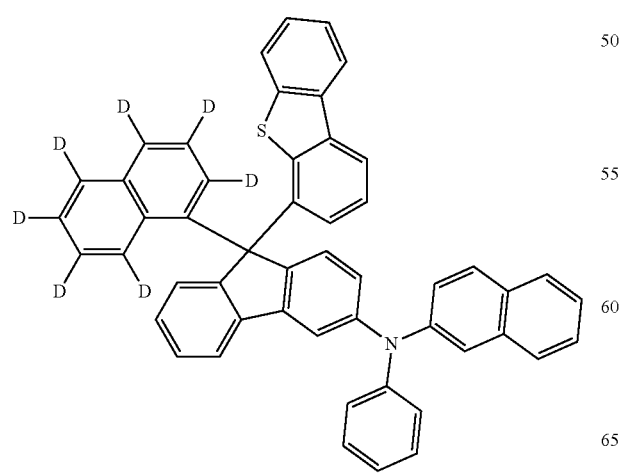
61
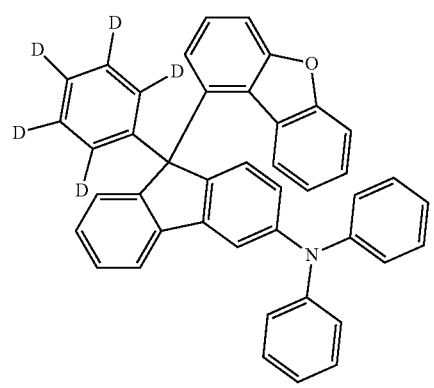
62
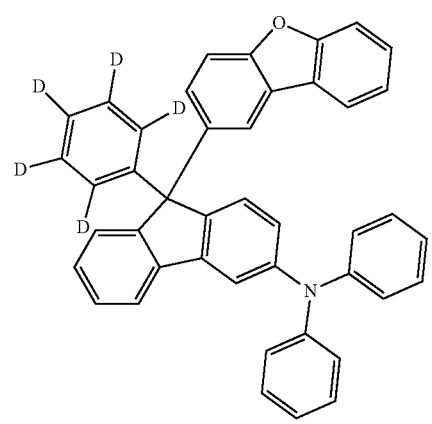
63
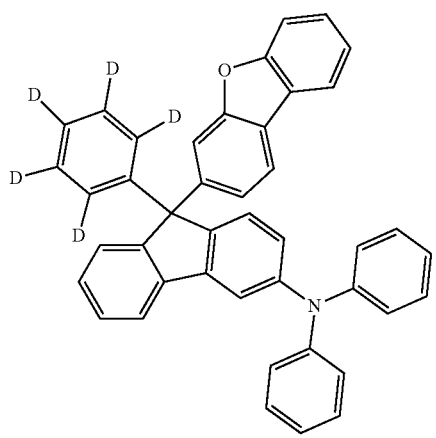

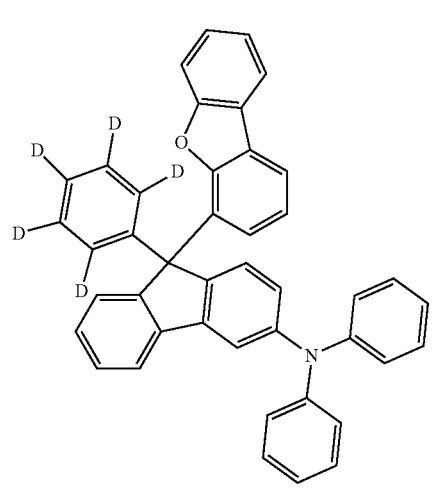
64
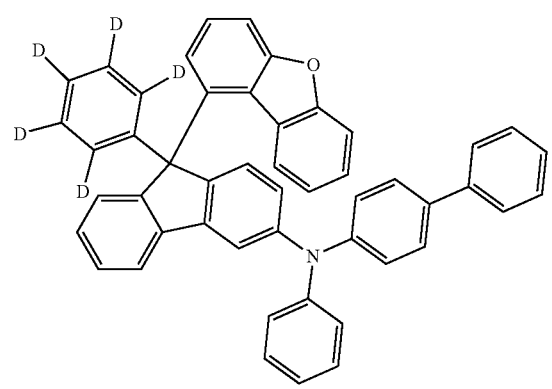
65
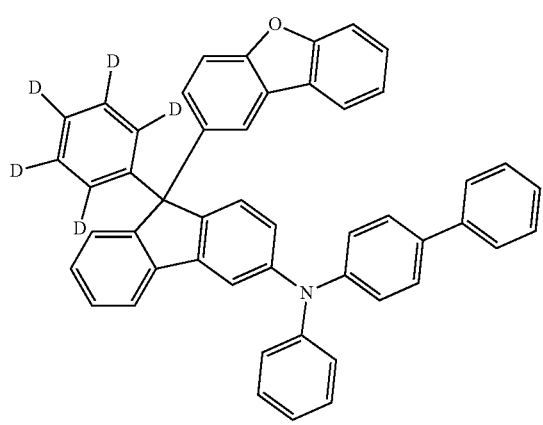
66
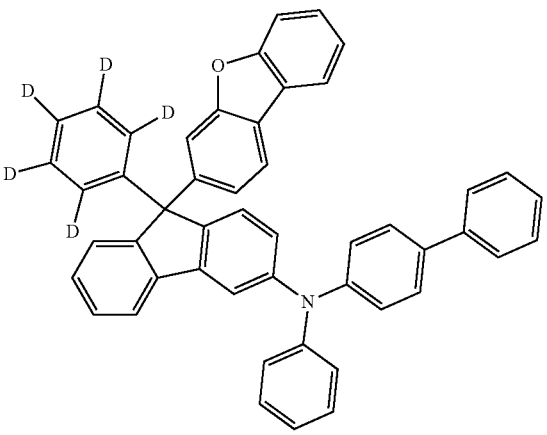
67
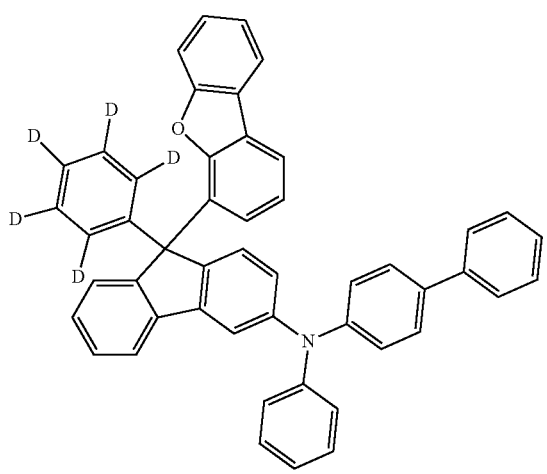
68
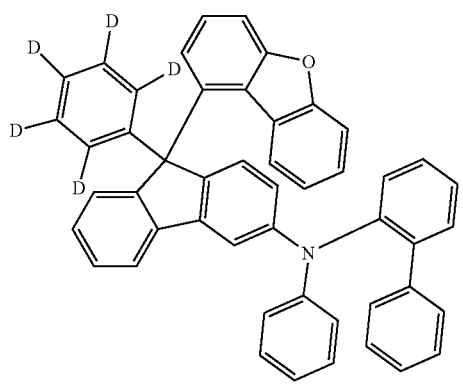
69

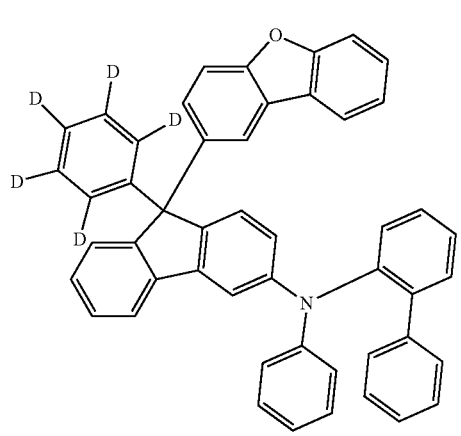
70
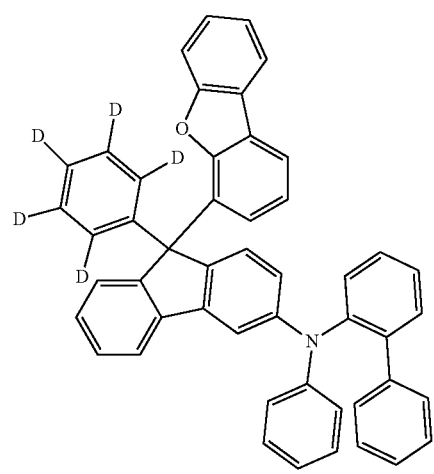
71
72
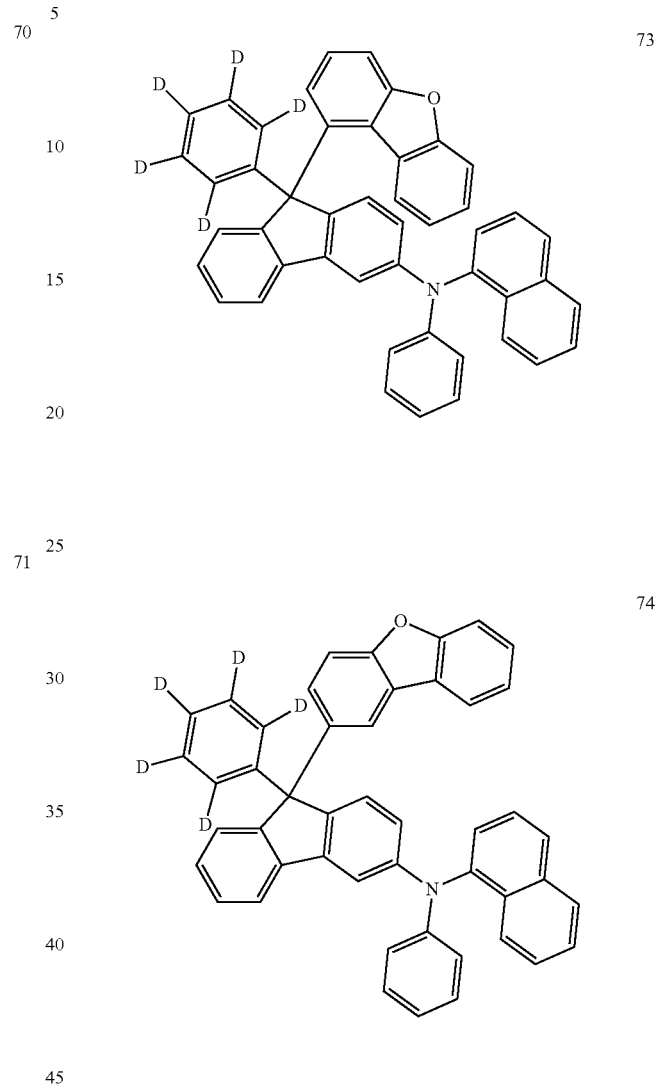
73
74
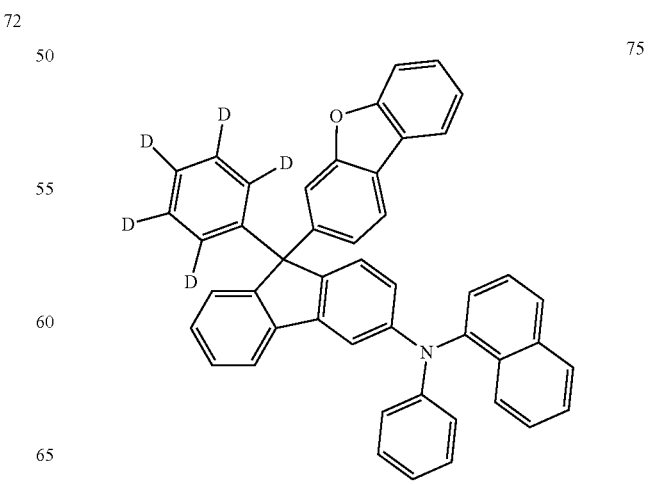
75

76
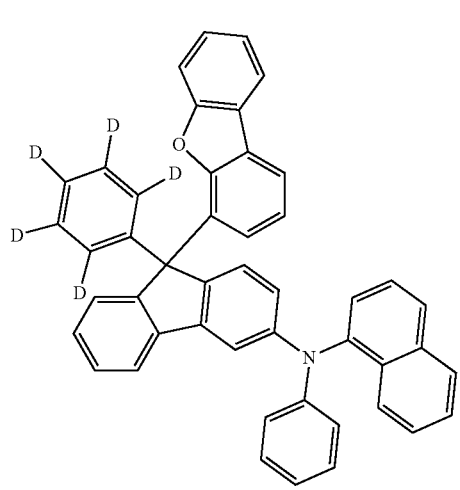
77
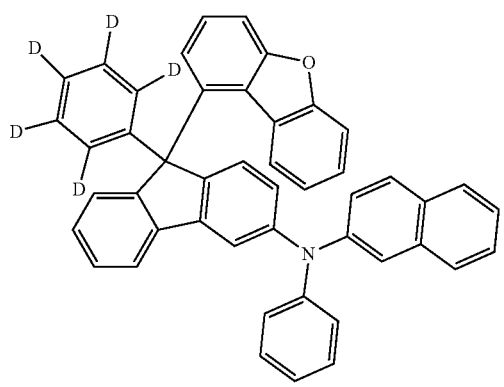
78
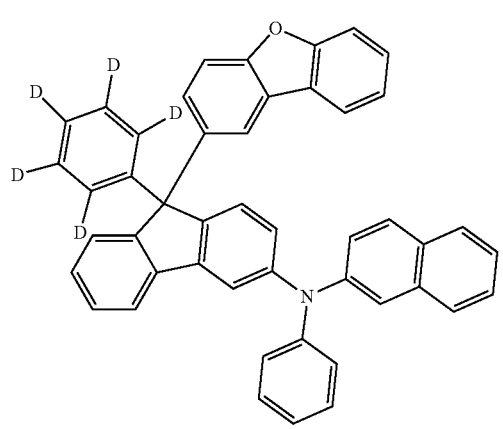
79
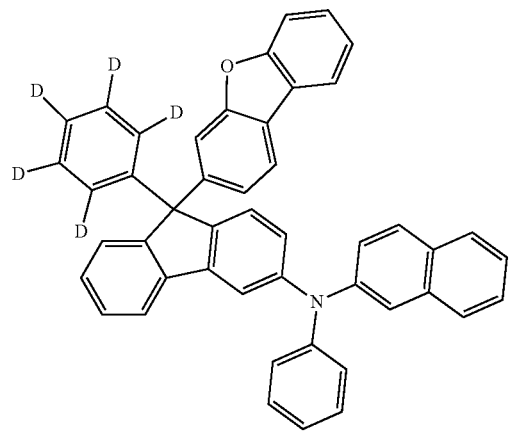
80
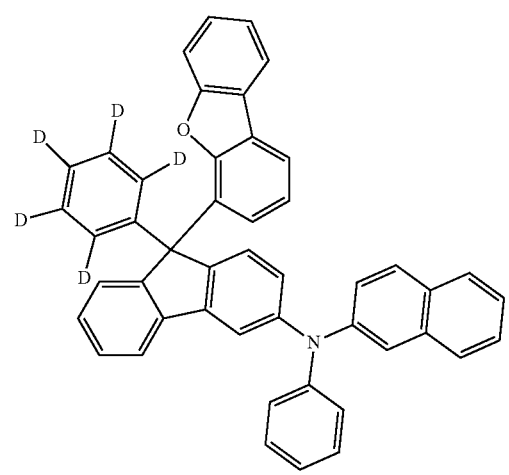
81
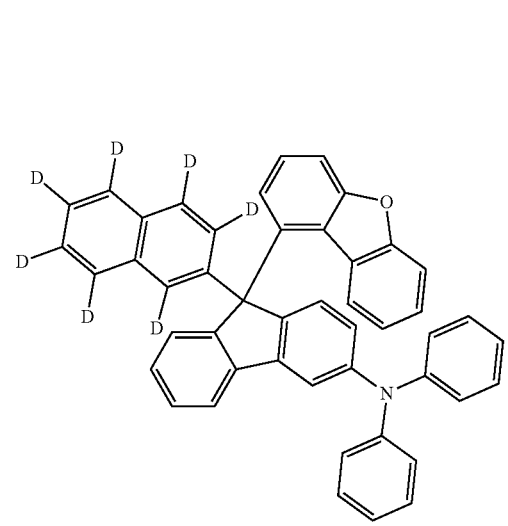

| 82 | 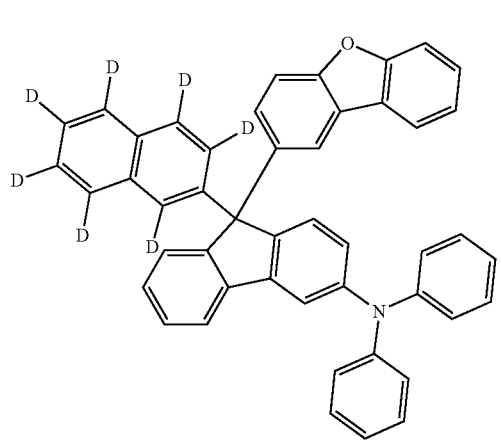 | 85 | 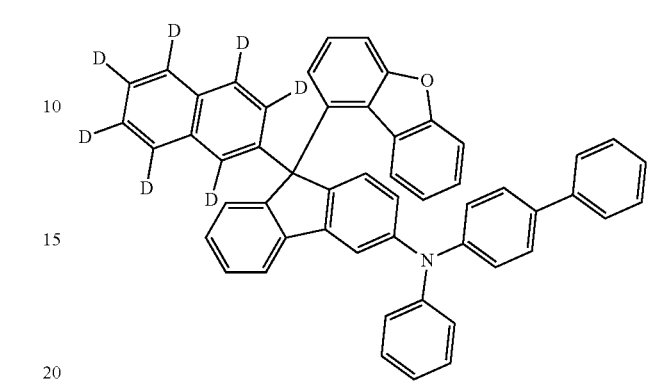 |
| 83 | 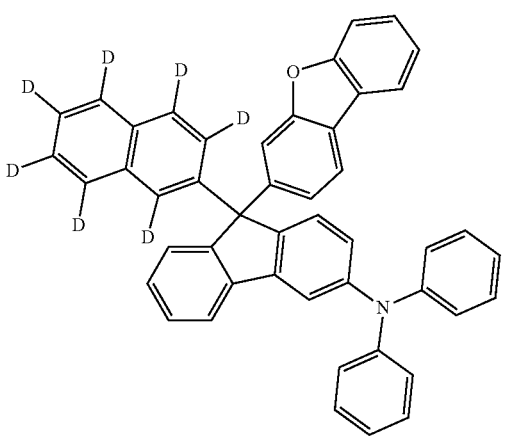 | 86 | 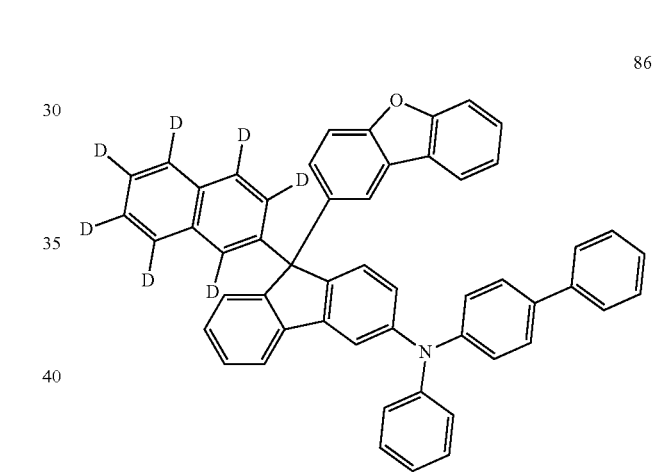 |
| 84 | 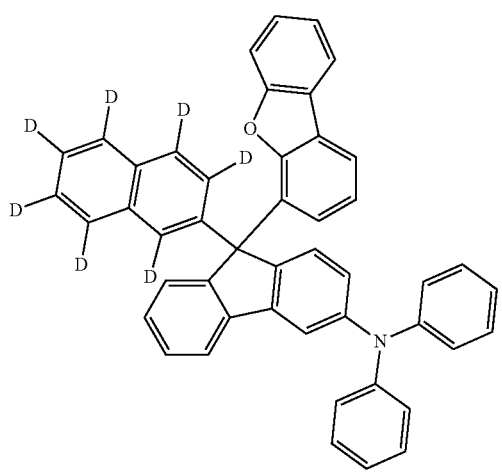 | 87 | 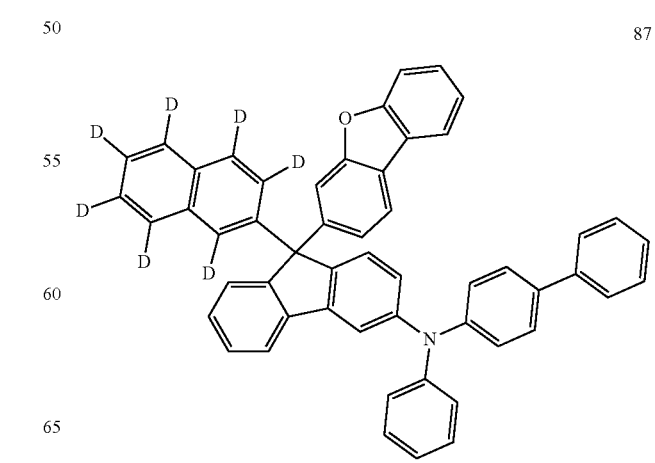 |

88
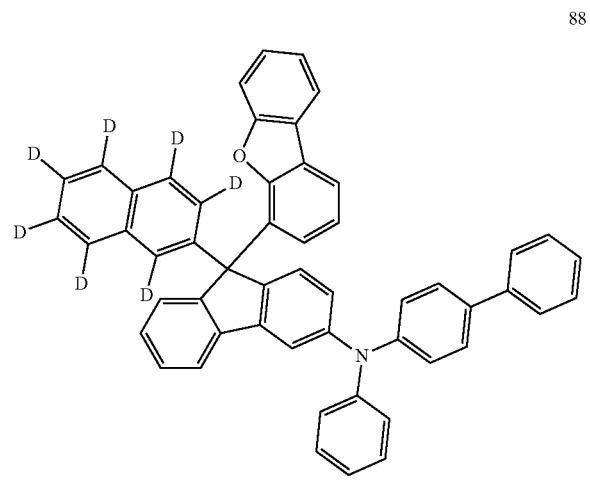
89
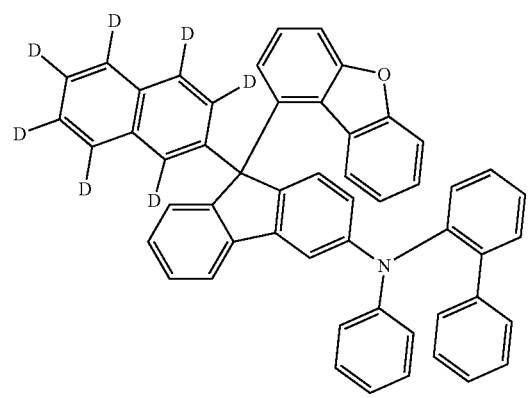
90
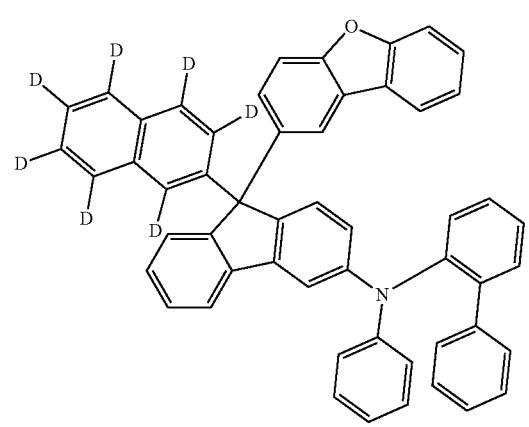
91
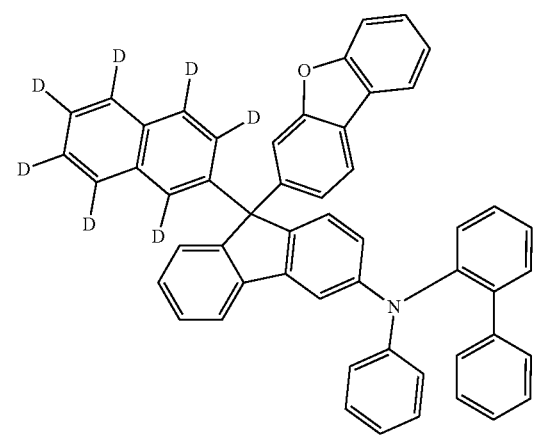
92
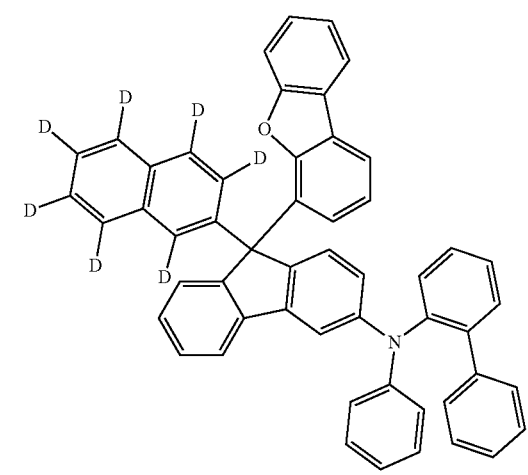
93
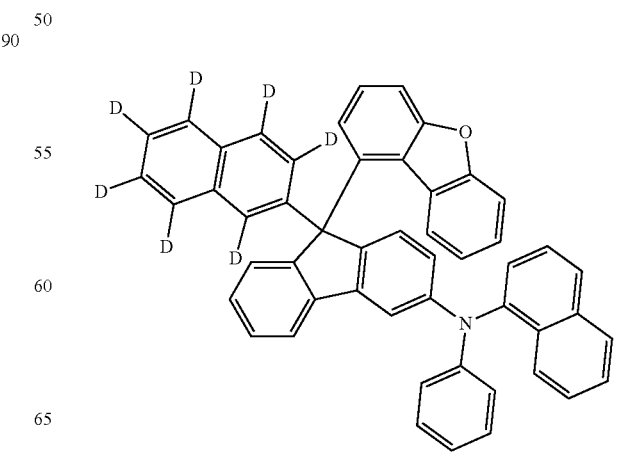

94
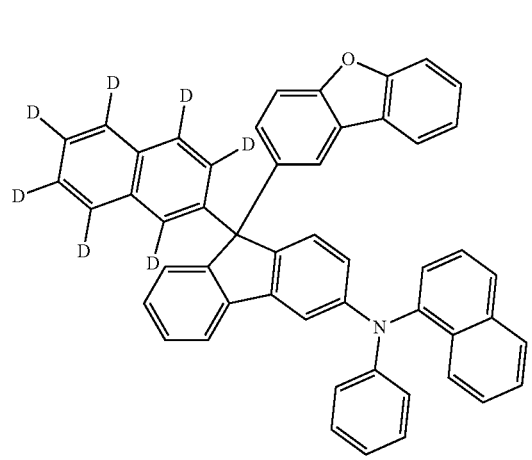
95
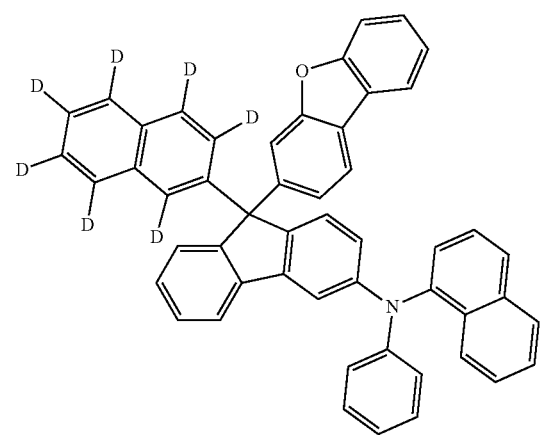
96
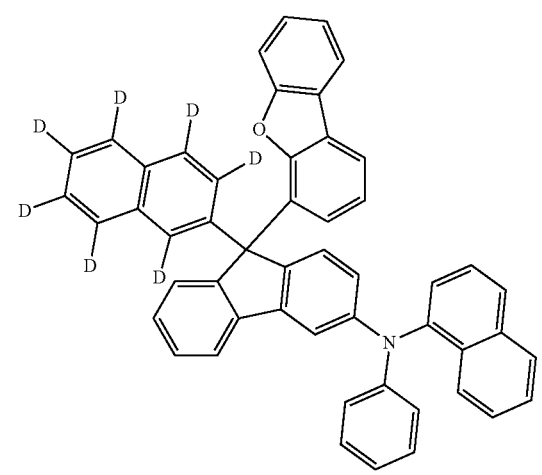
97
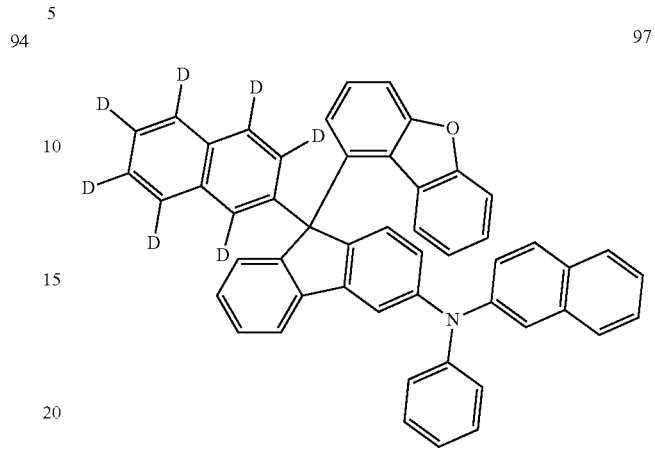
98
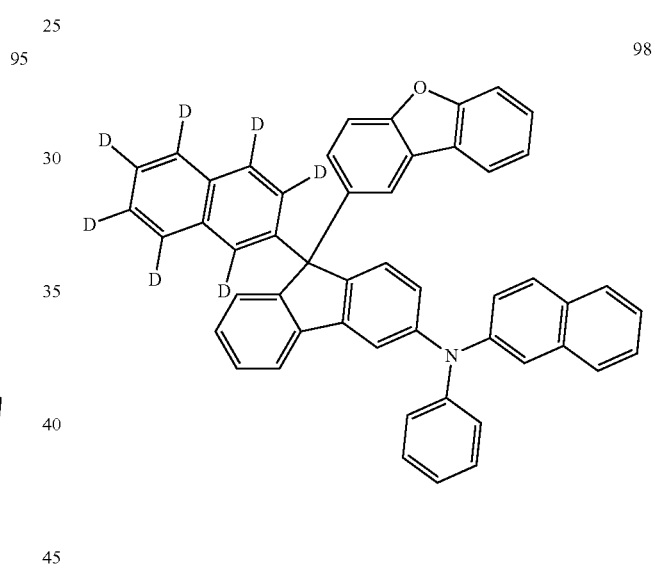
99
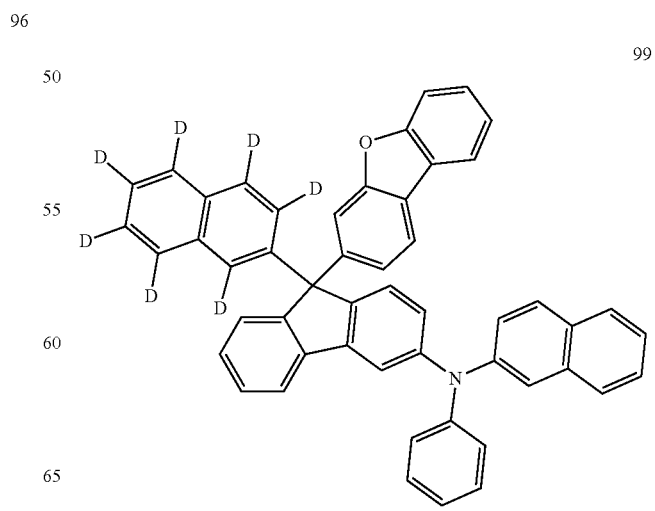

100
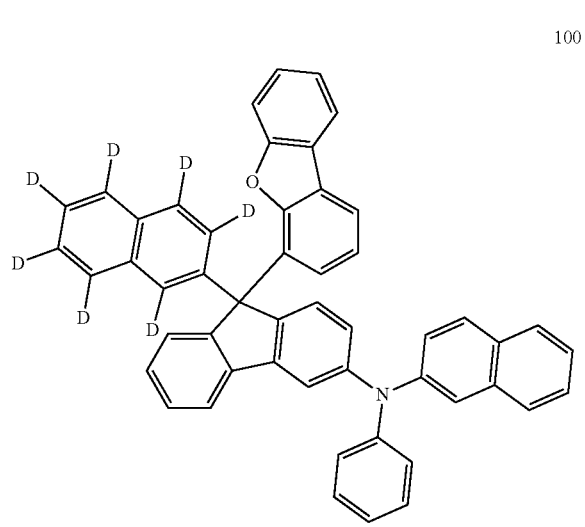
101
103
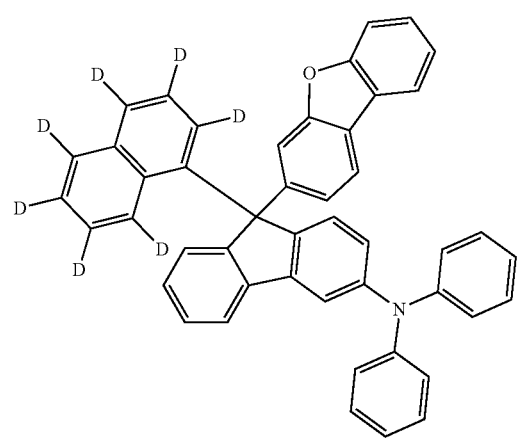
104
102
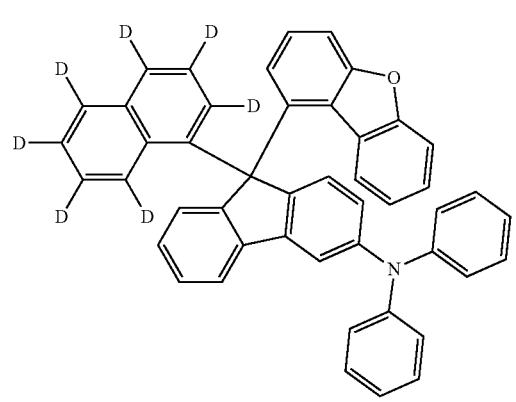
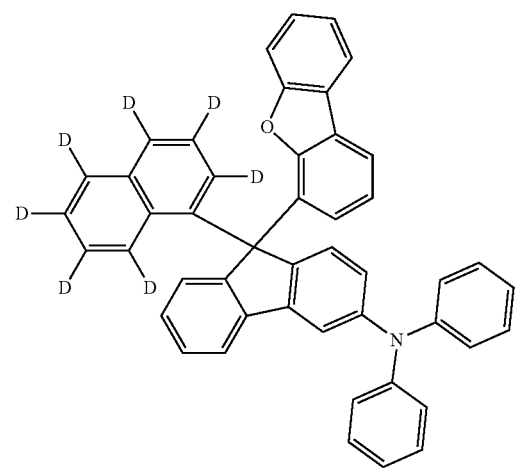
105
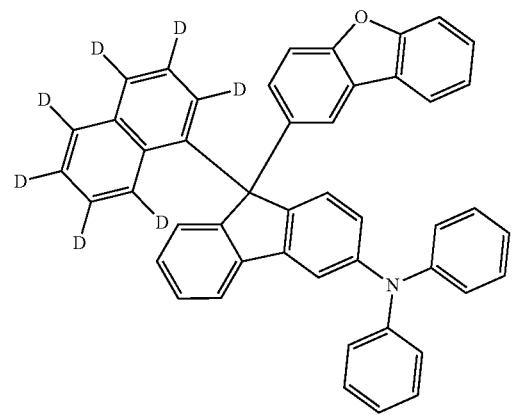
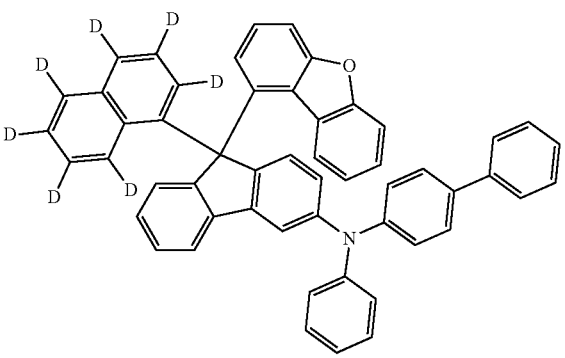

106
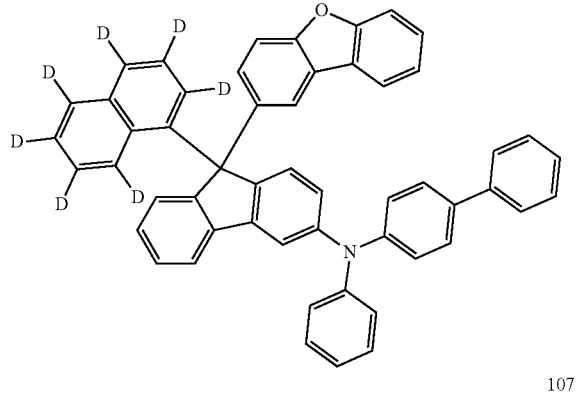
107
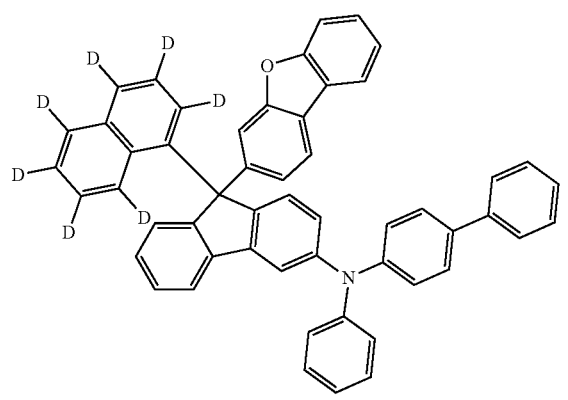
108
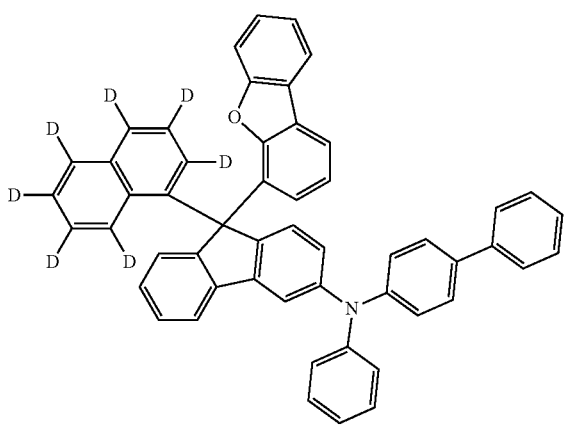
109
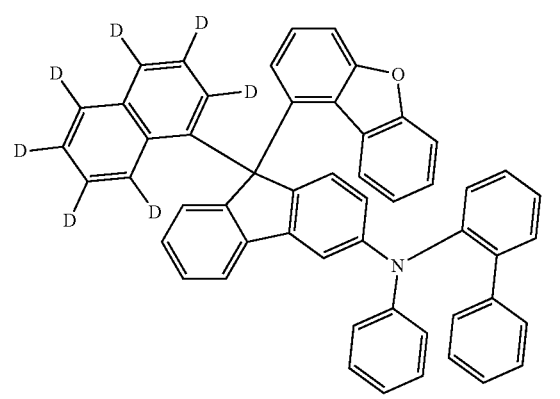
110
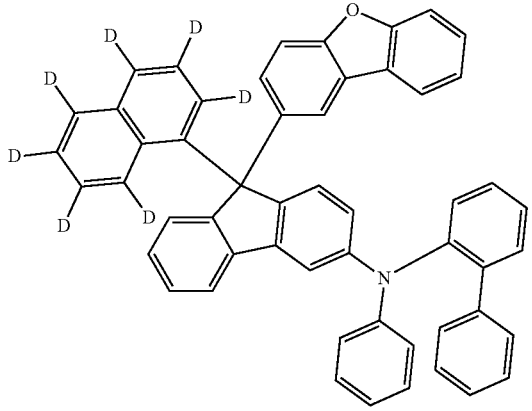
111
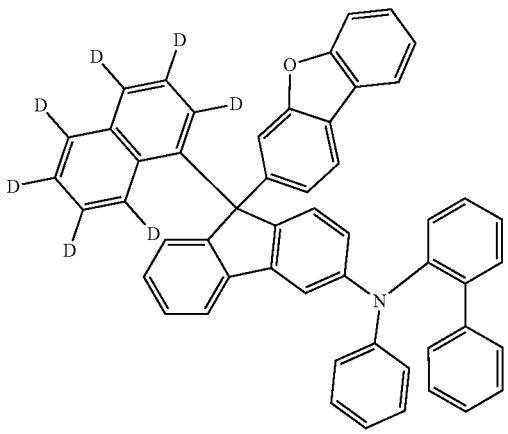
112
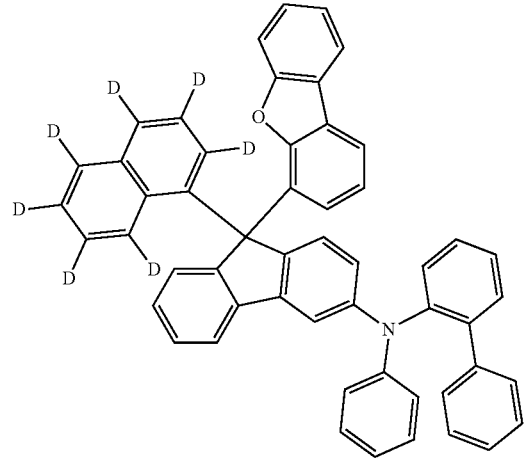

-continued
113
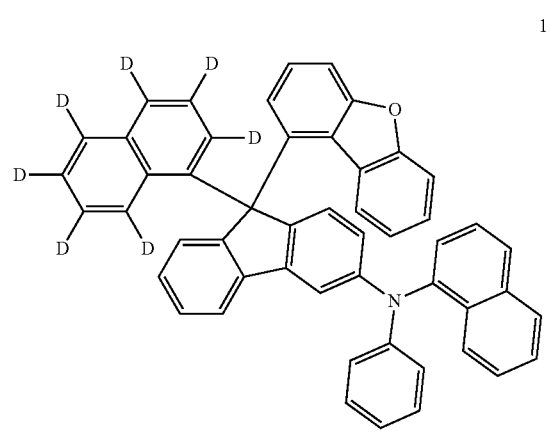
114
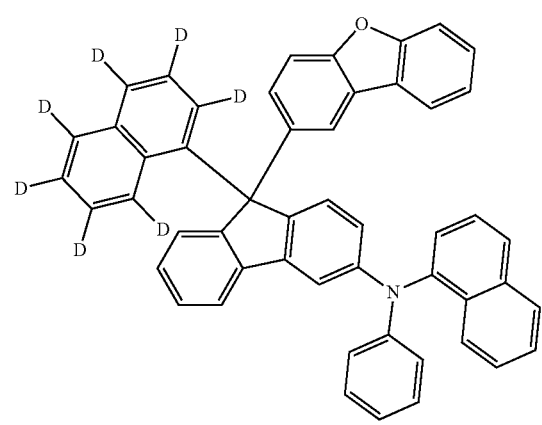
115
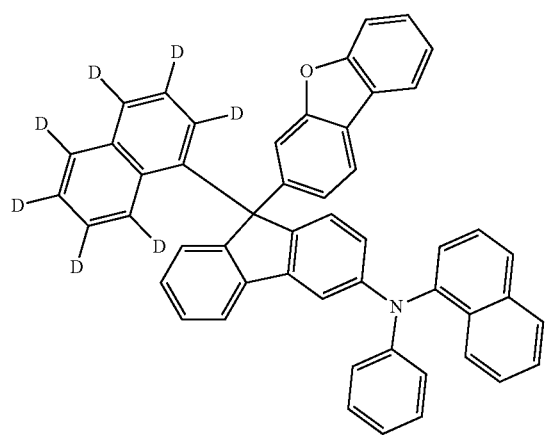
-continued
116
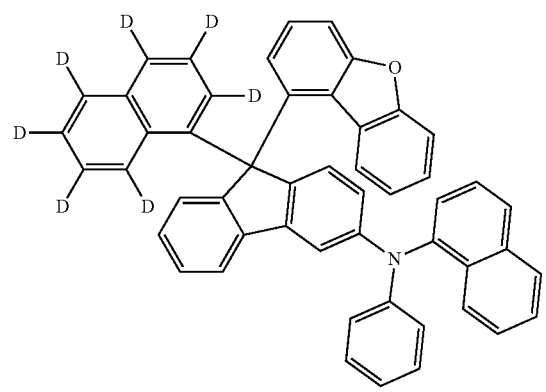
117
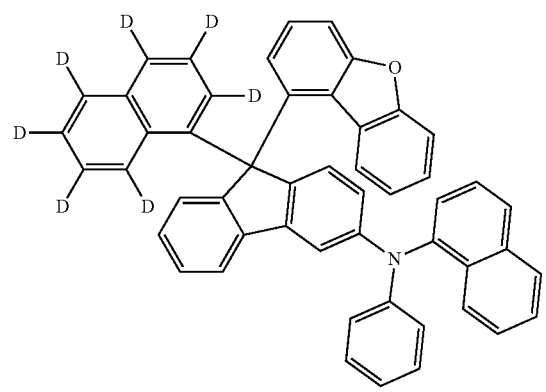
118

119
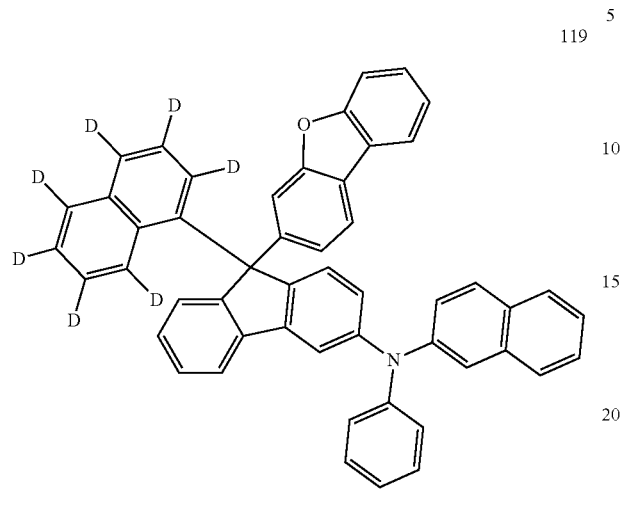
120
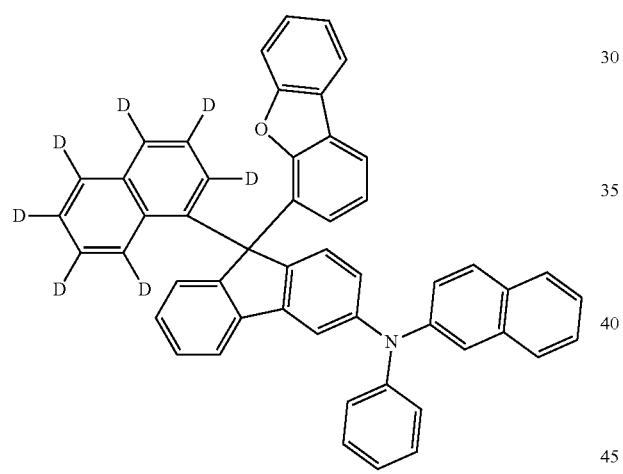
121
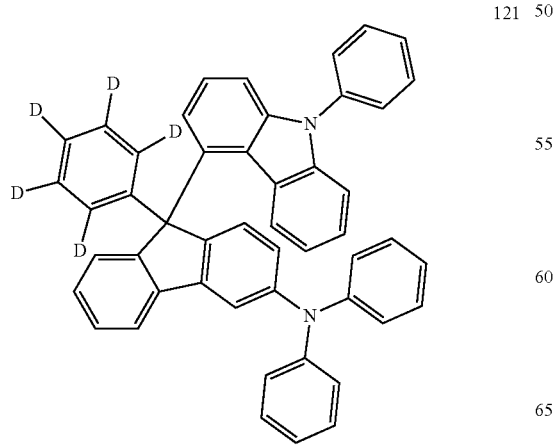
122
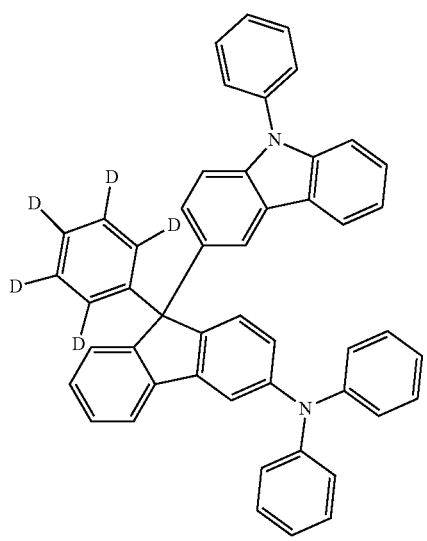
123
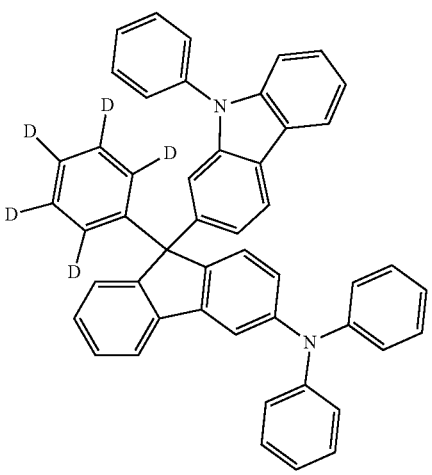
124
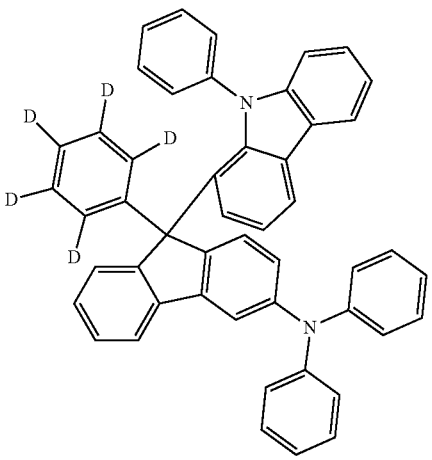

125 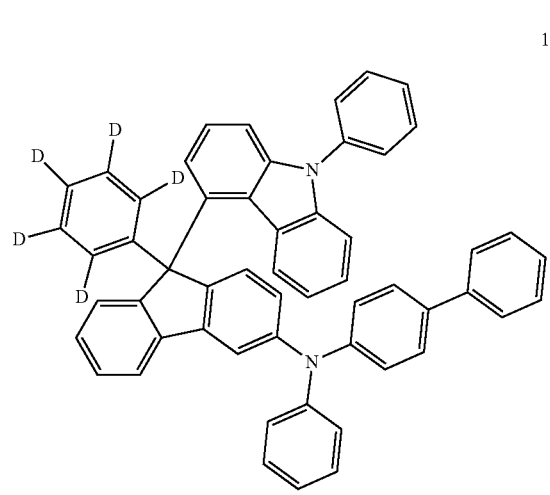
126 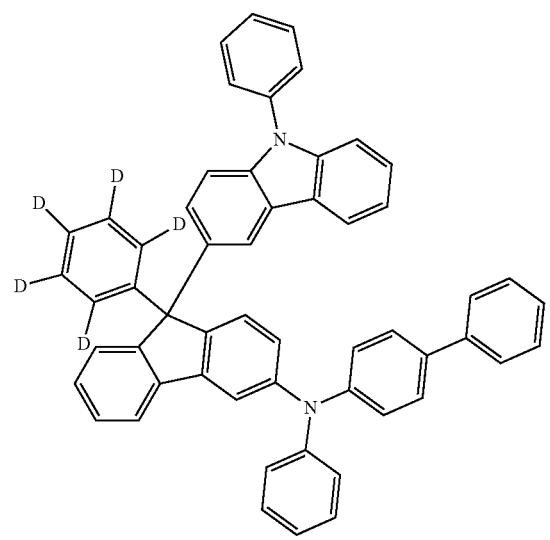
127 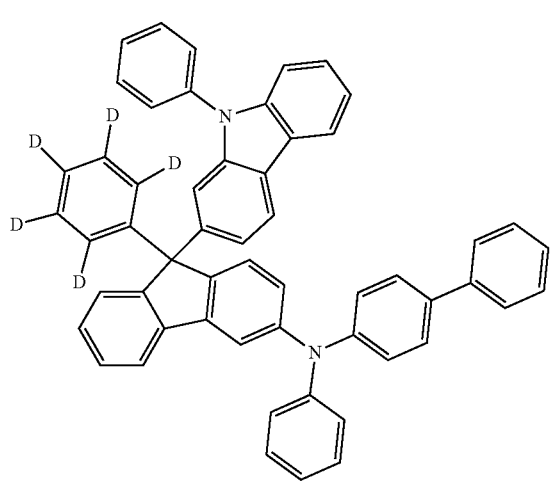
128 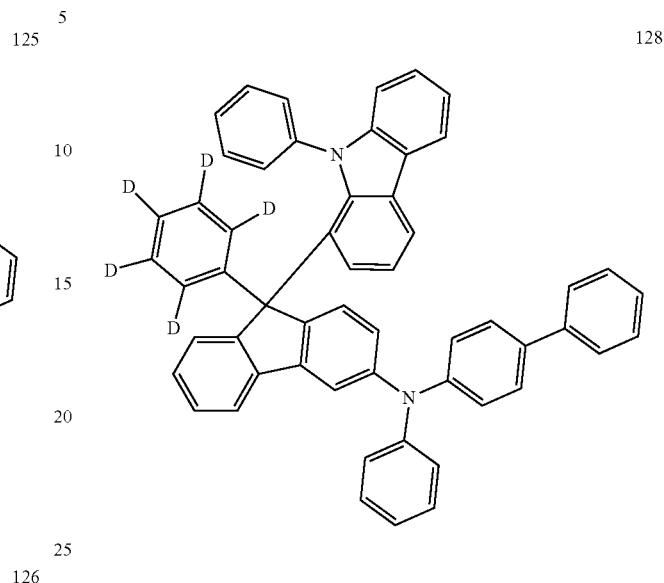
129 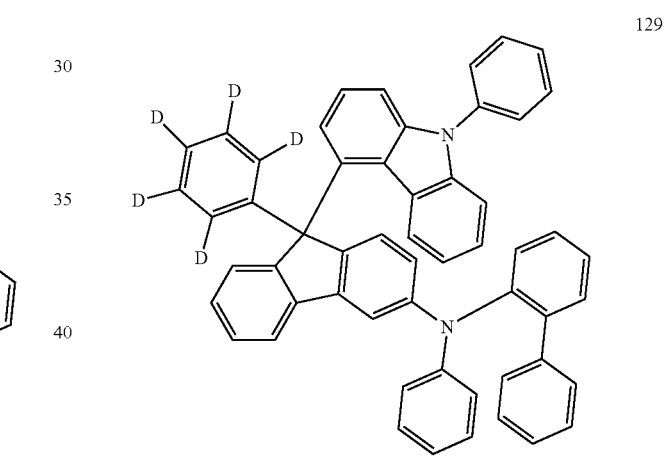
130 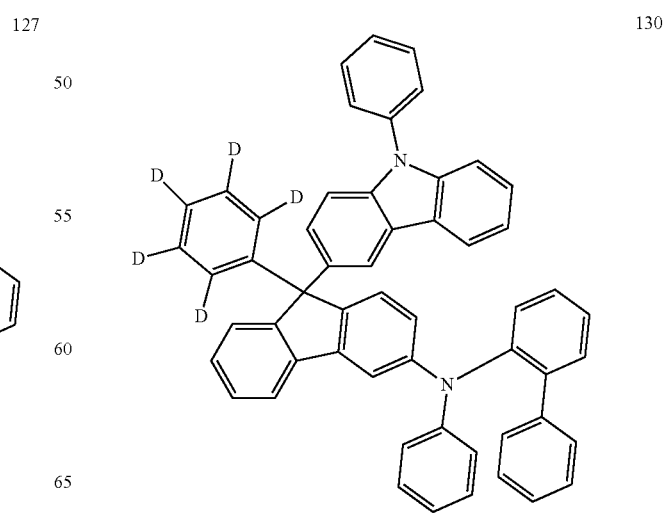

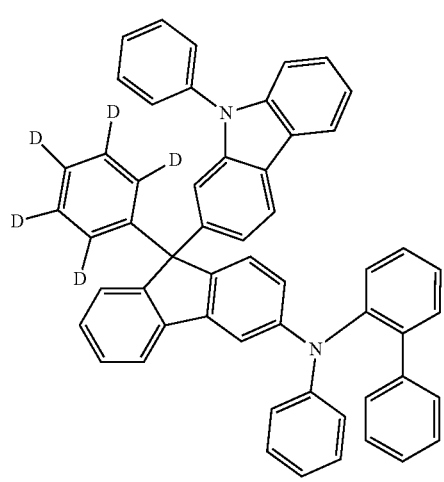
131
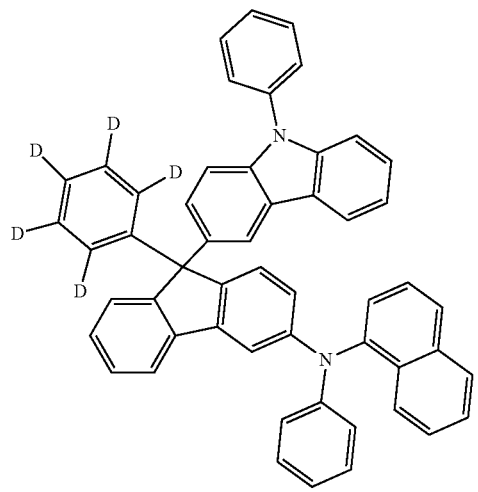
134
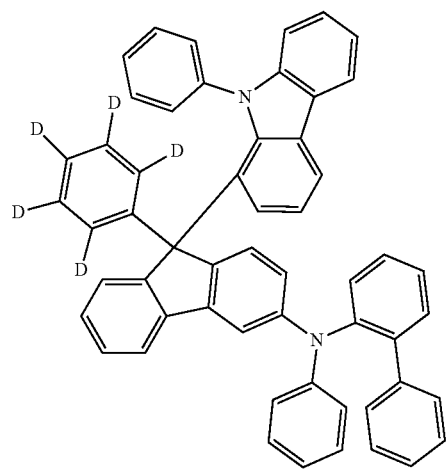
132
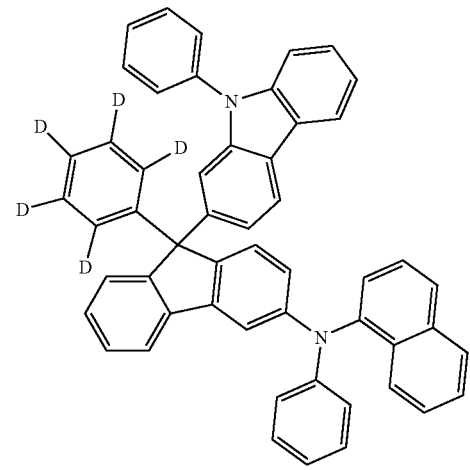
135
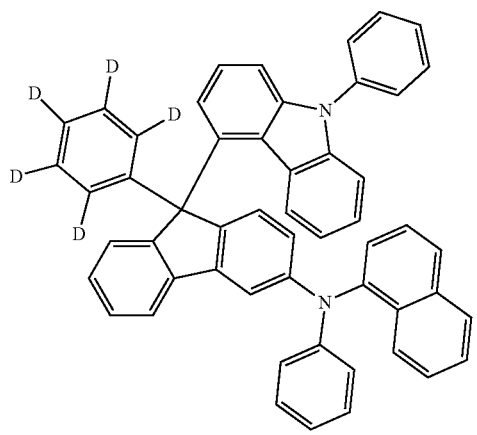
133
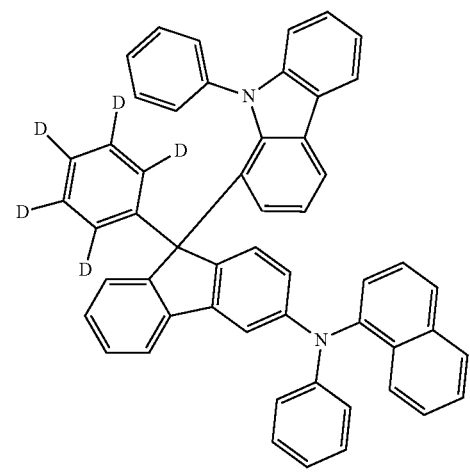
136

137
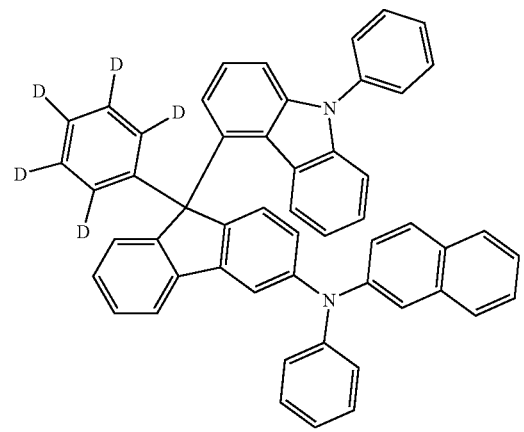
138
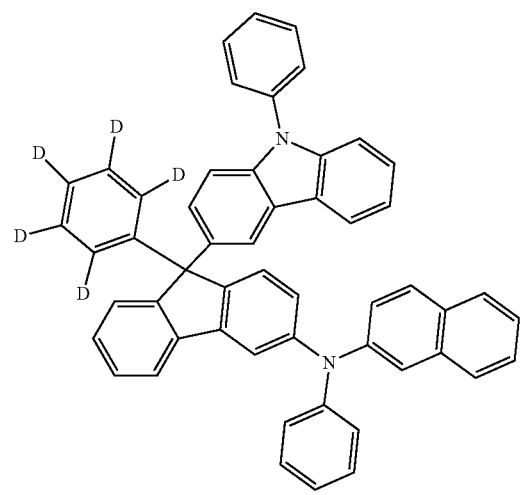
139
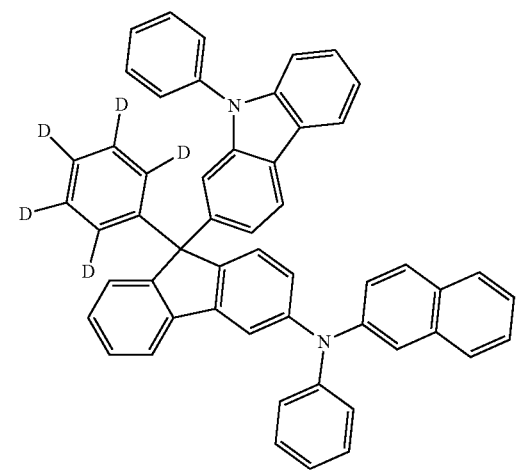
140
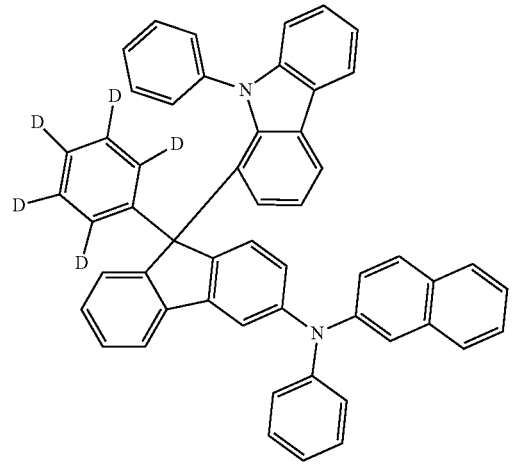
141
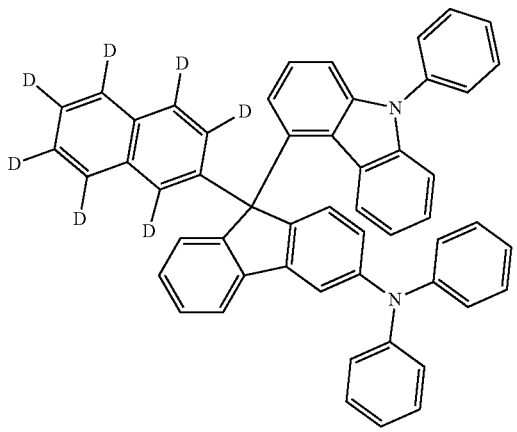
142
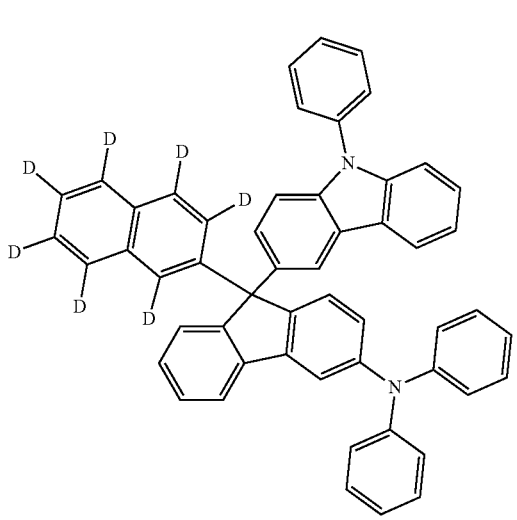

143
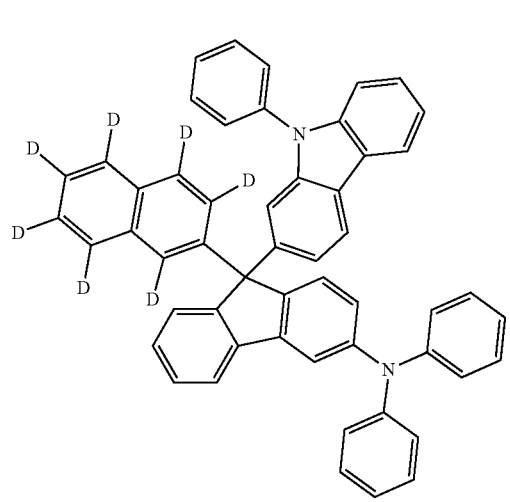
144
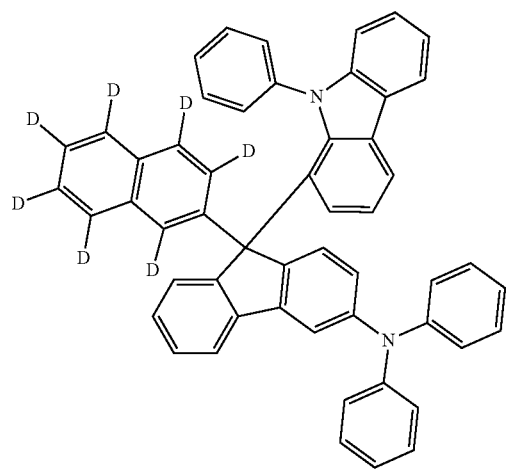
145
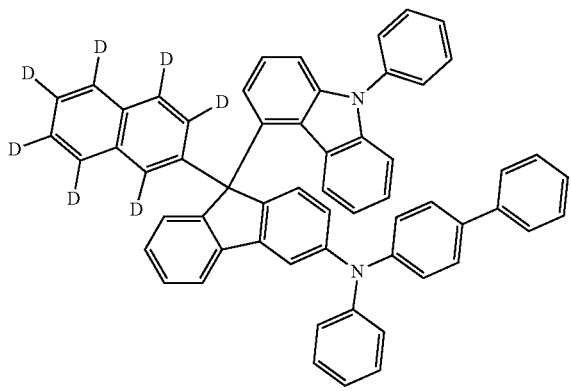
146
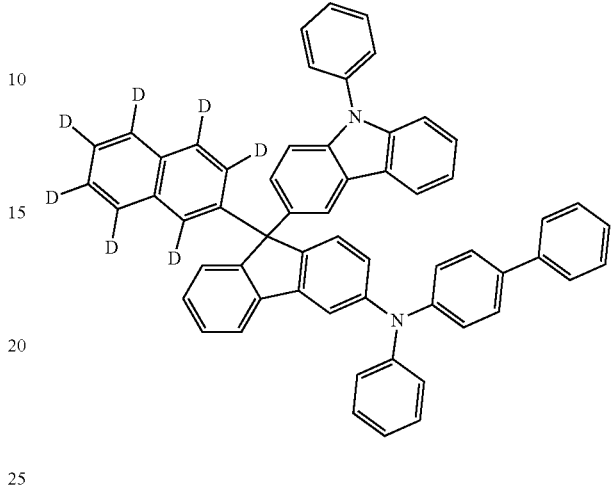
147
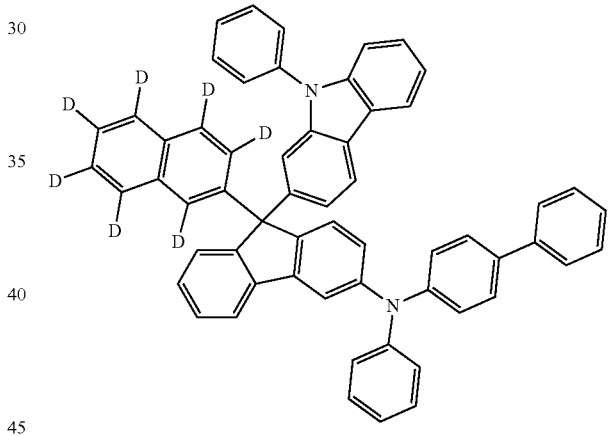
148
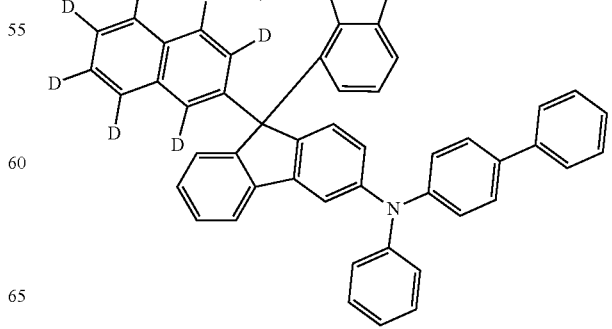

149
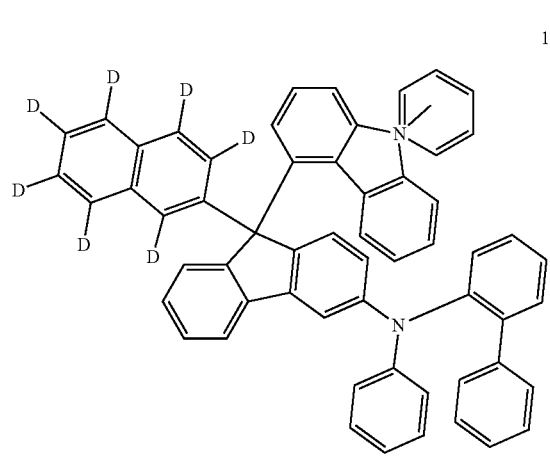
150
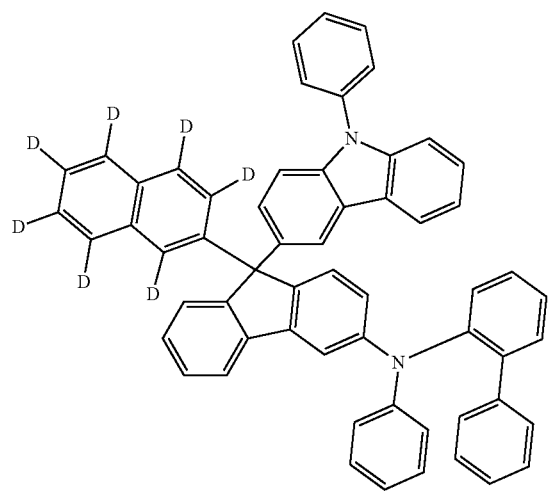
151
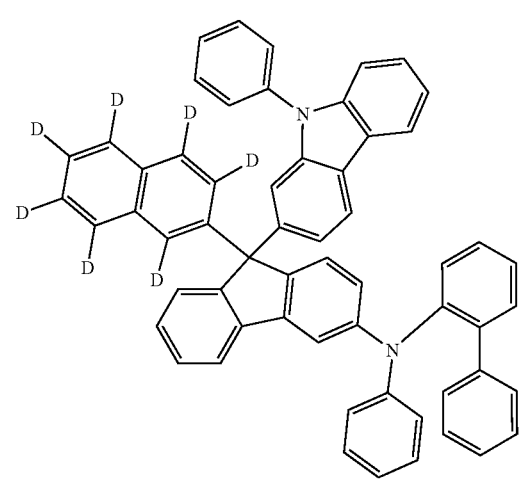
152
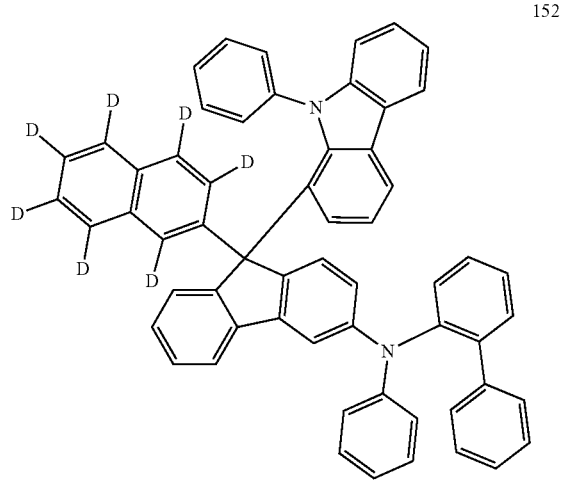
153
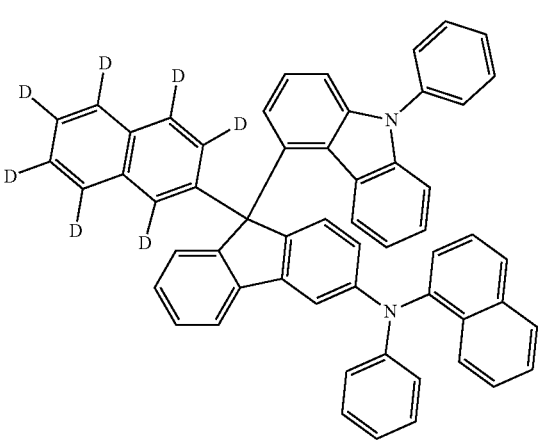
154
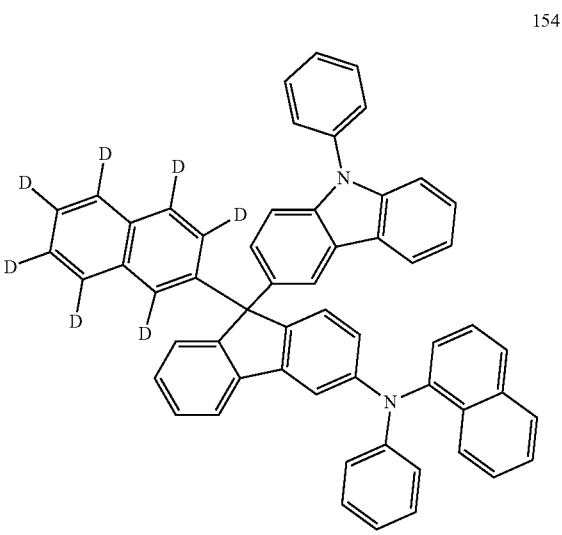

155
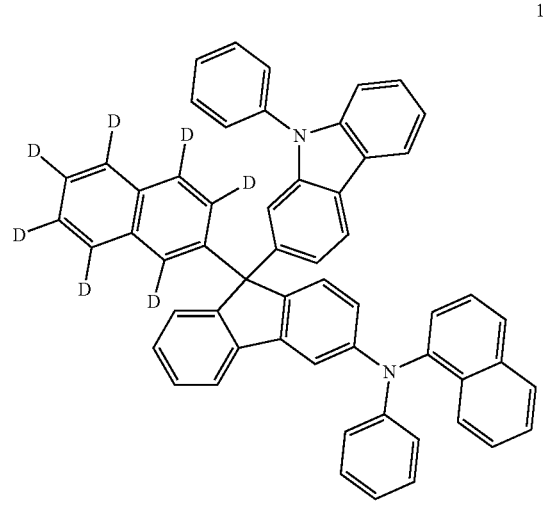
156
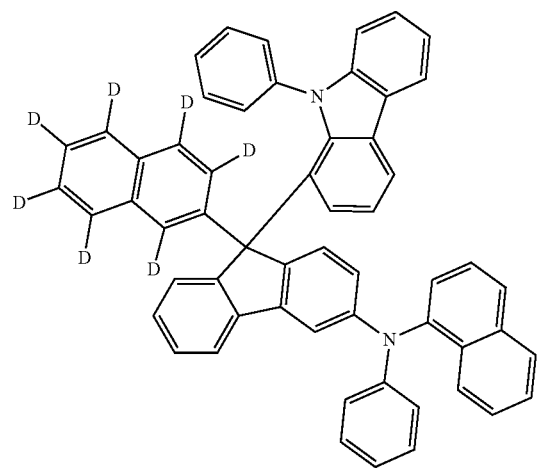
157
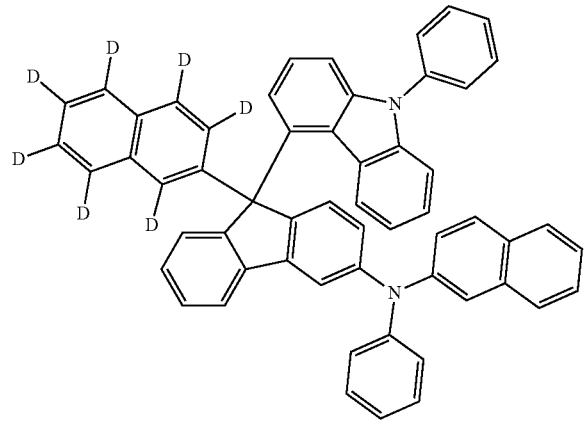
158
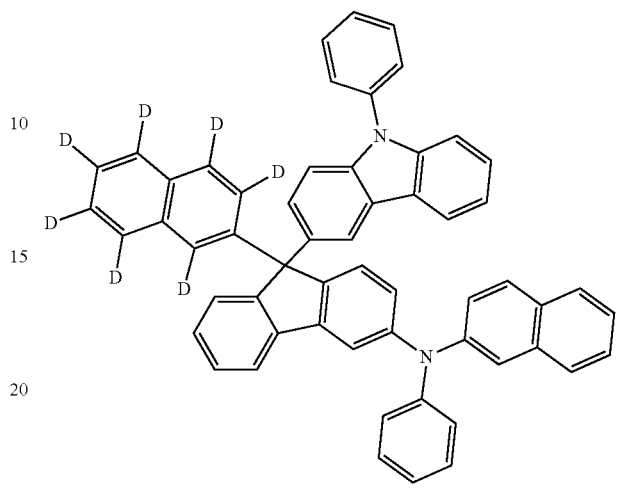
159
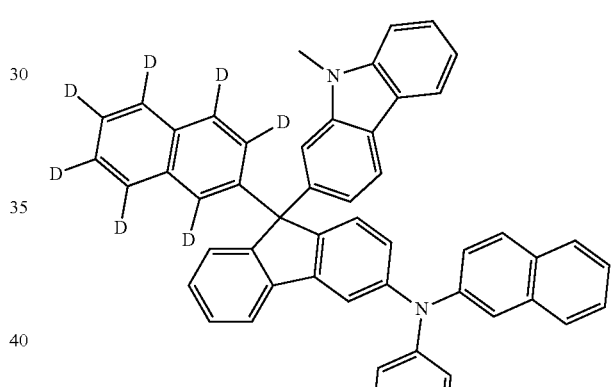
160
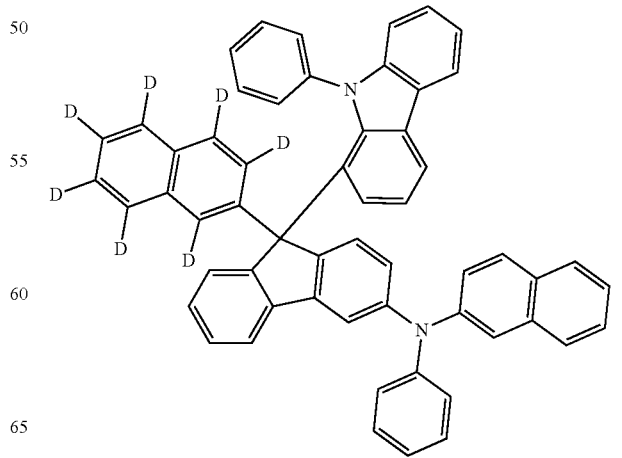

191
-continued
161
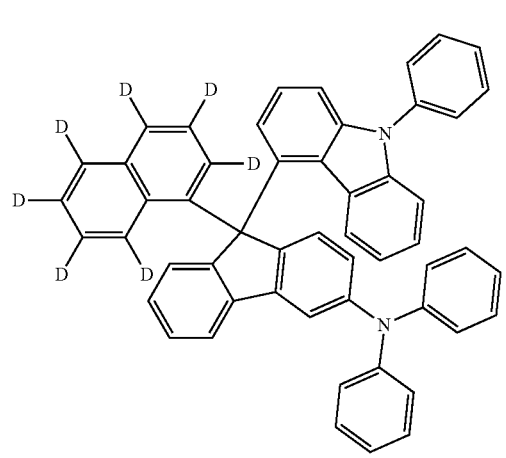
162
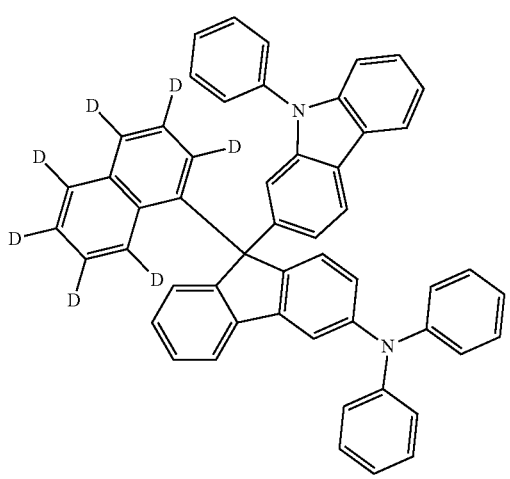
163
192
-continued
164
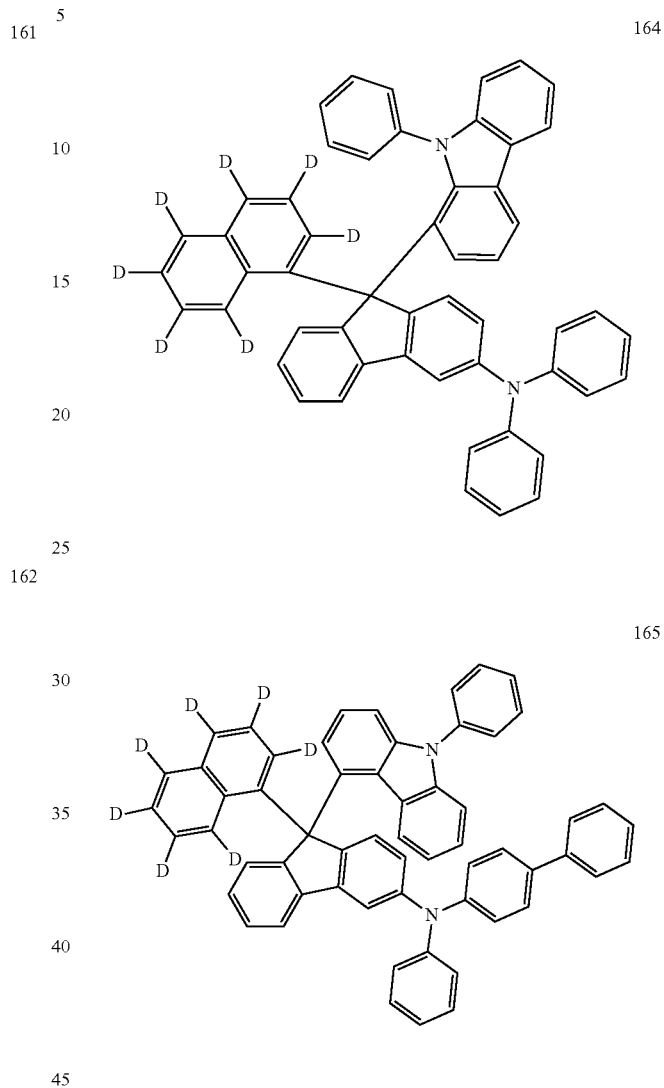
165
166

167 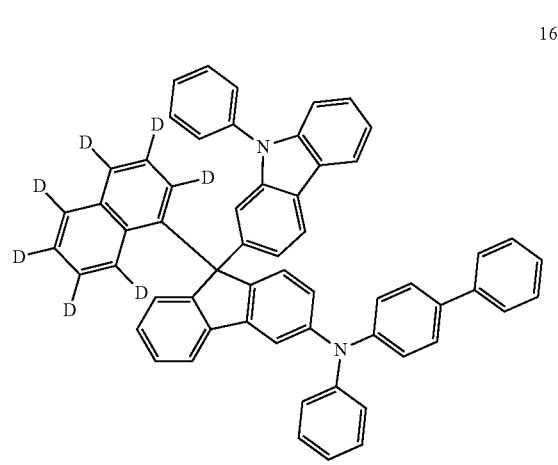
168 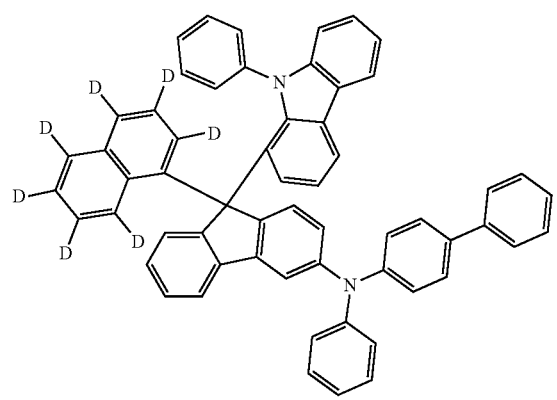
169 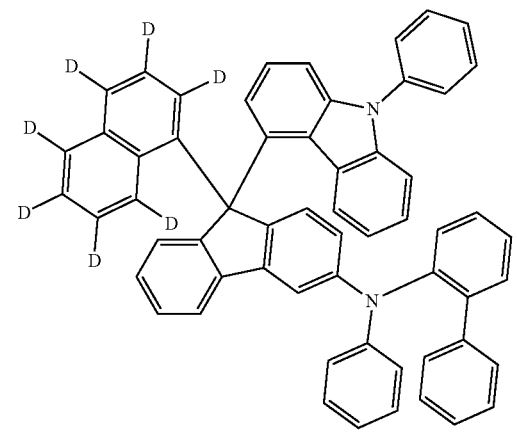
170 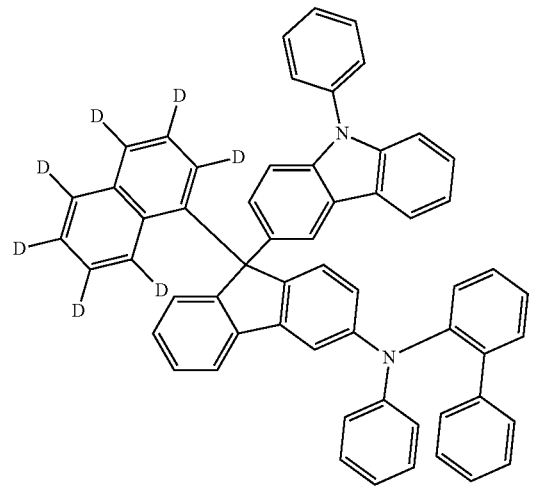
171 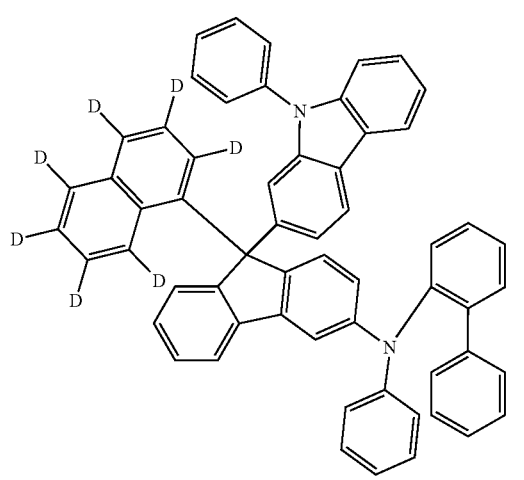
172 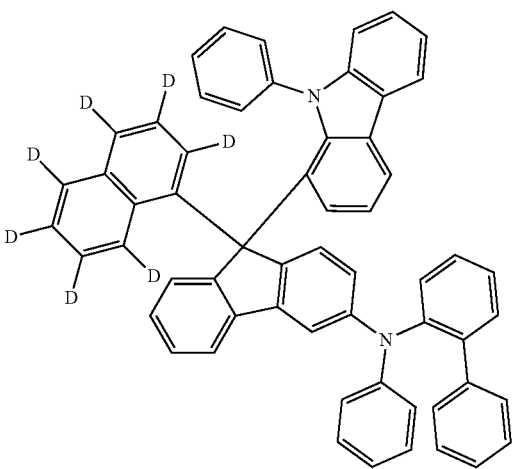

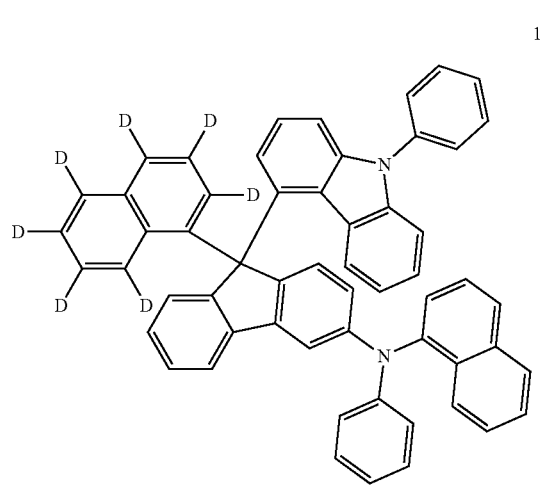
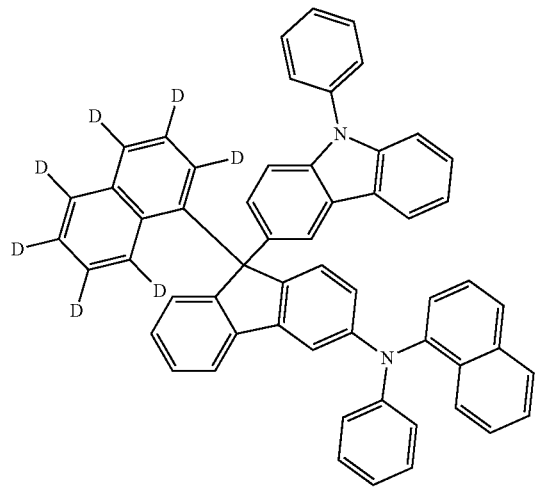
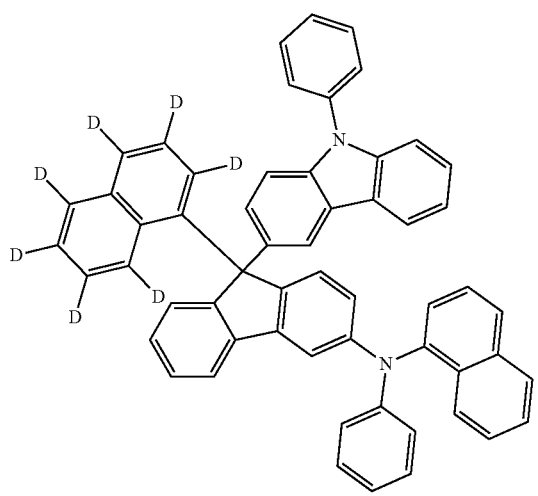
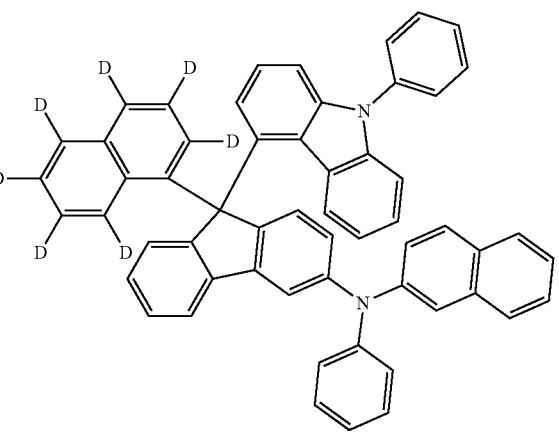
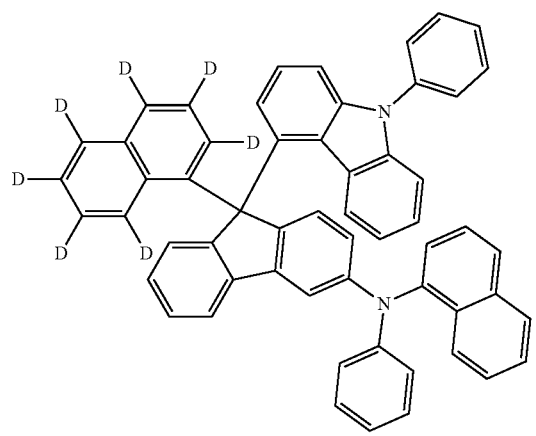
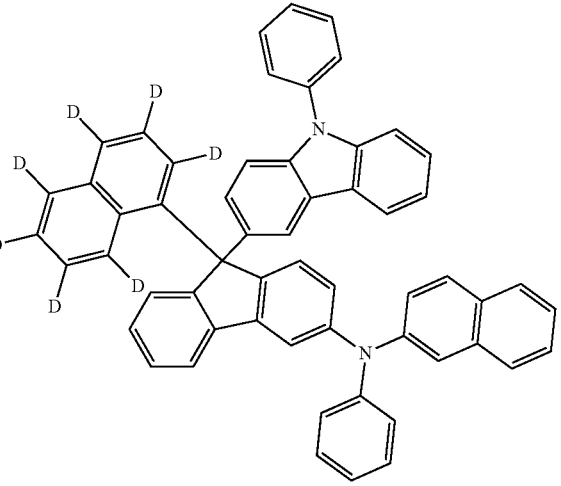

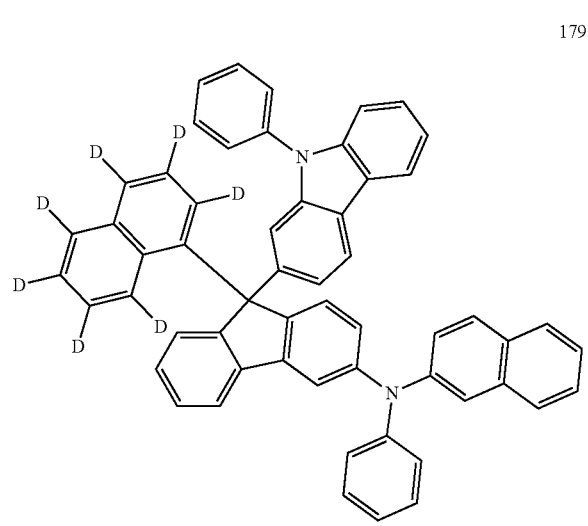
179
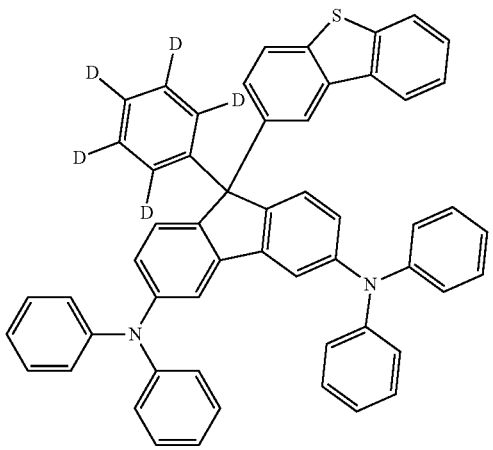
182
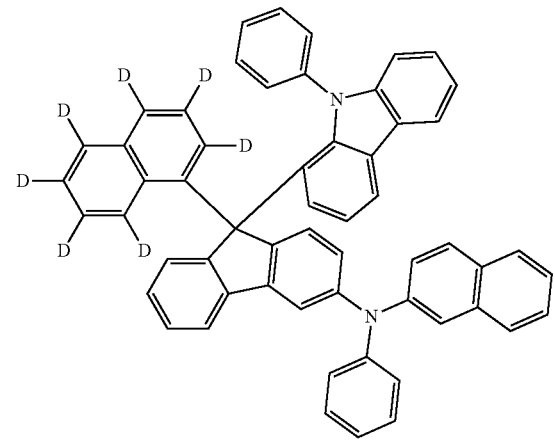
180
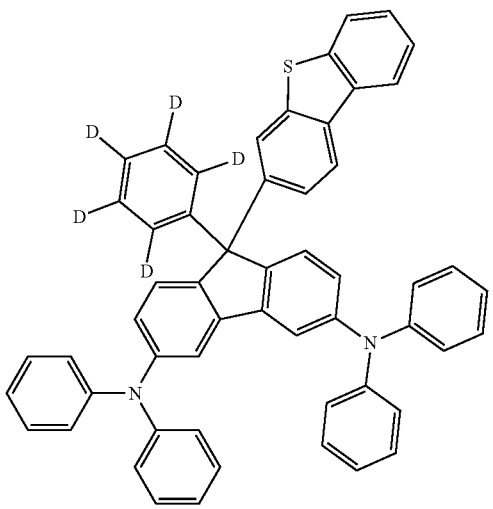
183
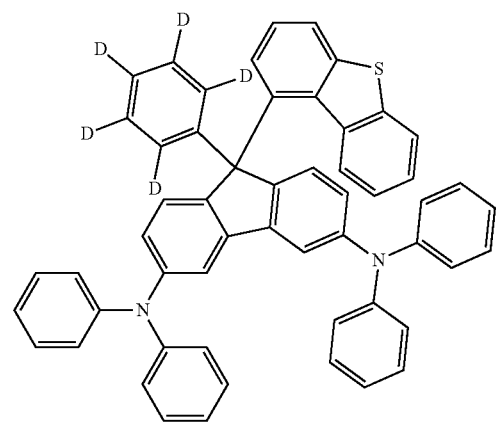
181
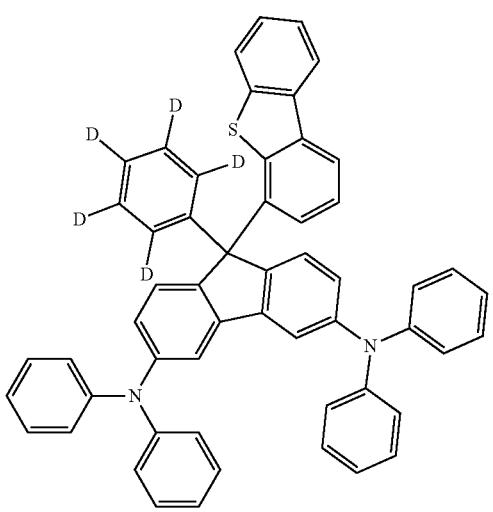
184

185
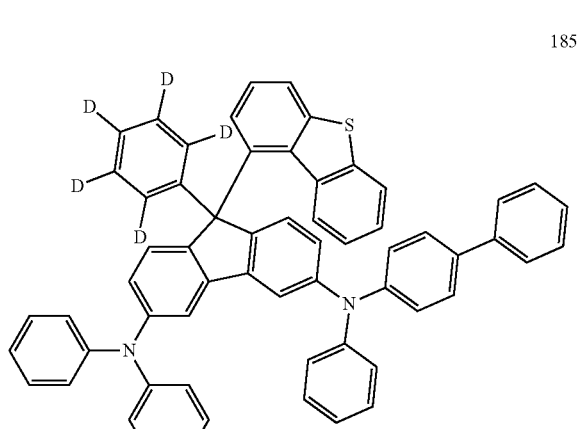
186
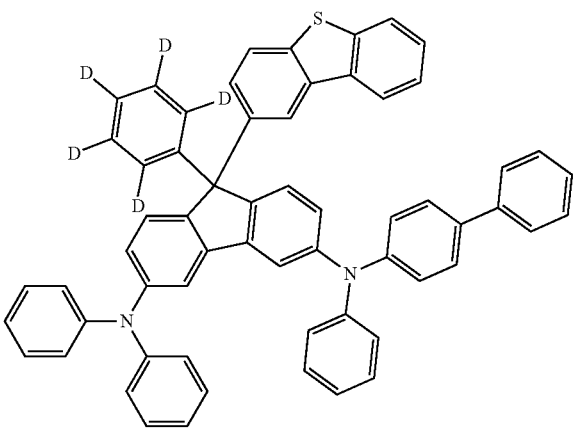
187
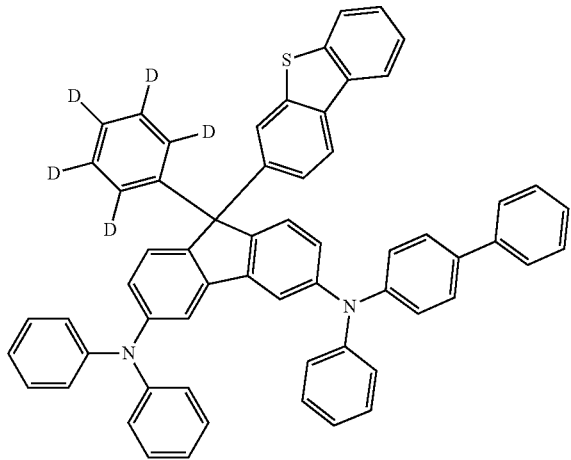
188
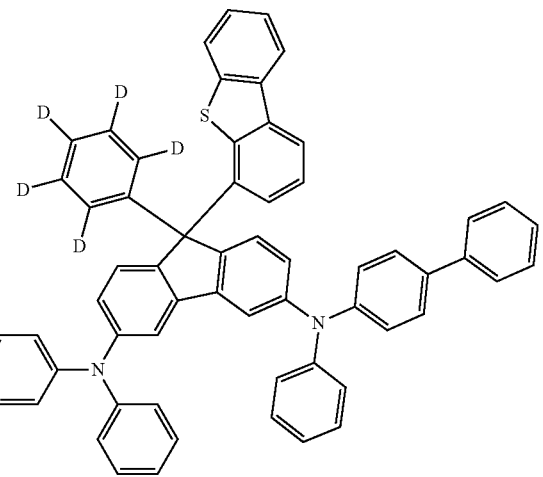
189
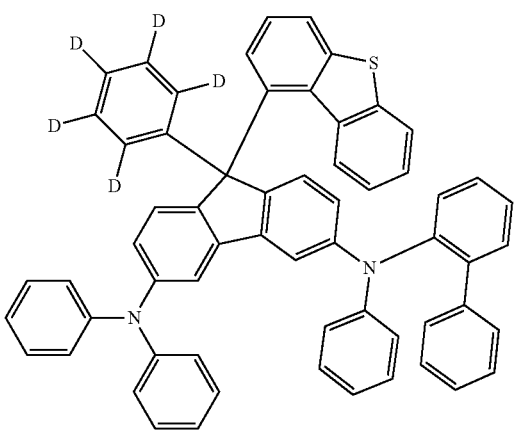
190
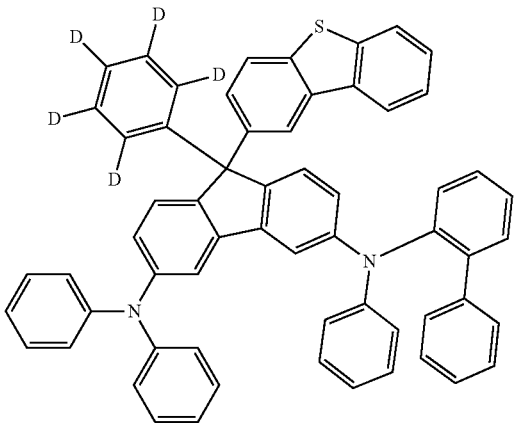

-continued
191
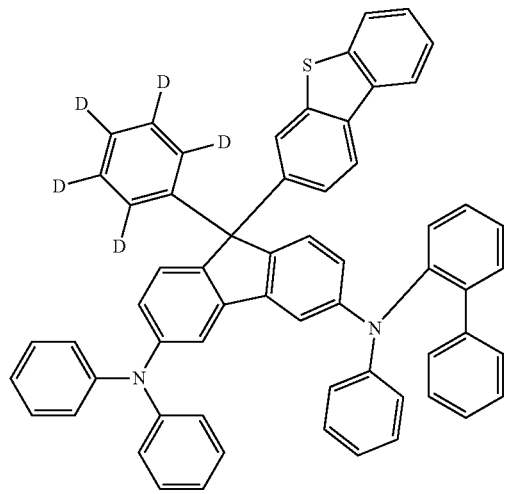
192
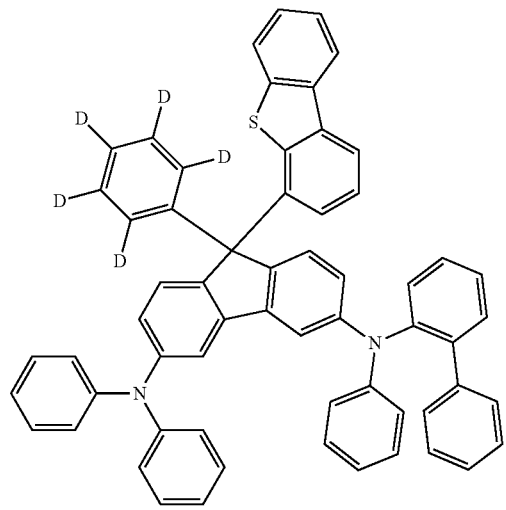
193
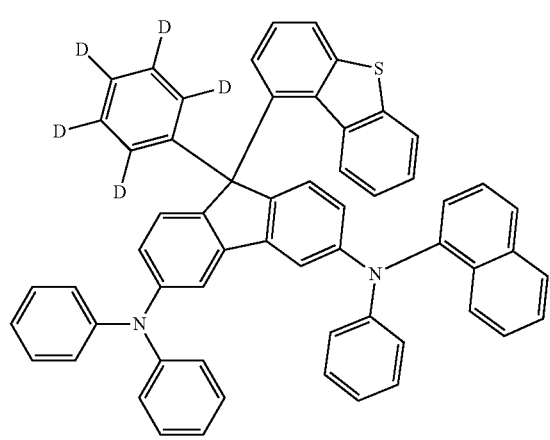
-continued
194
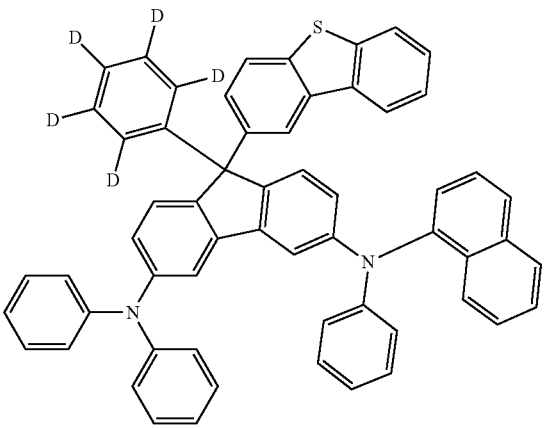
195
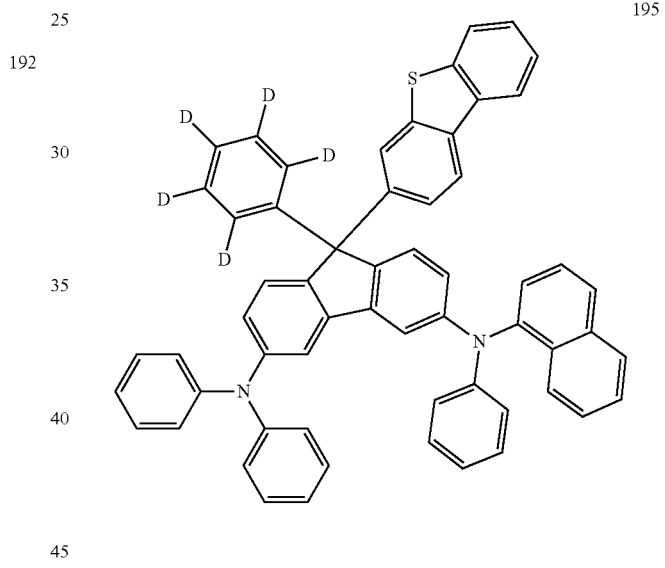
196
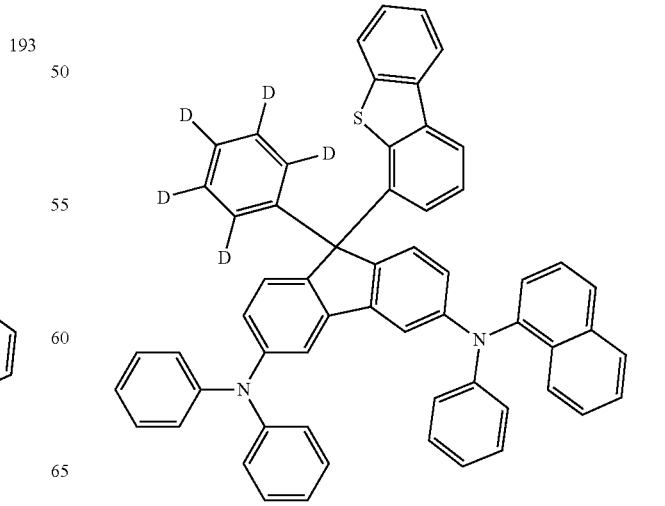

197
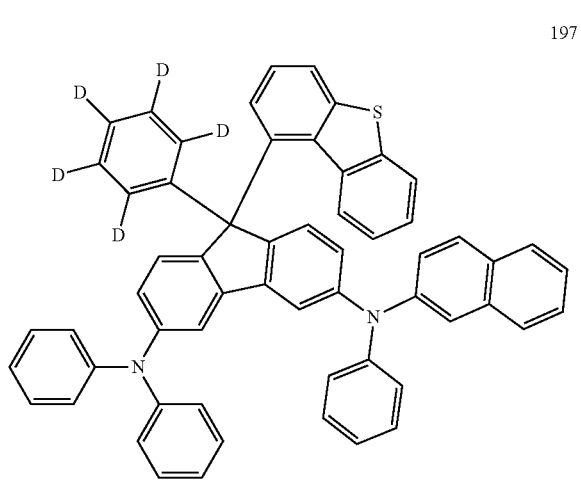
198
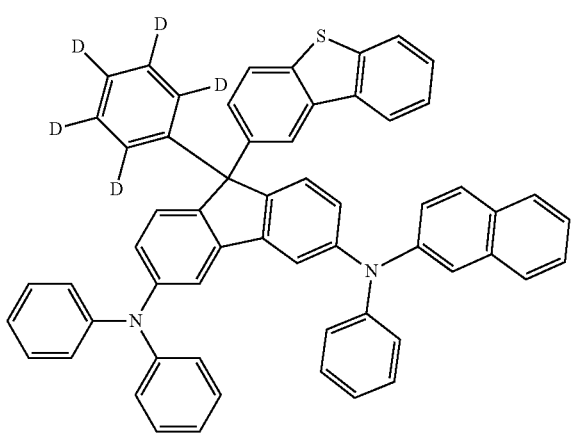
199
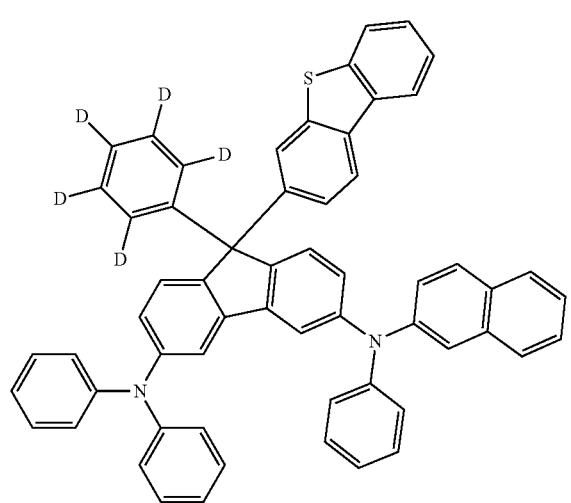
200
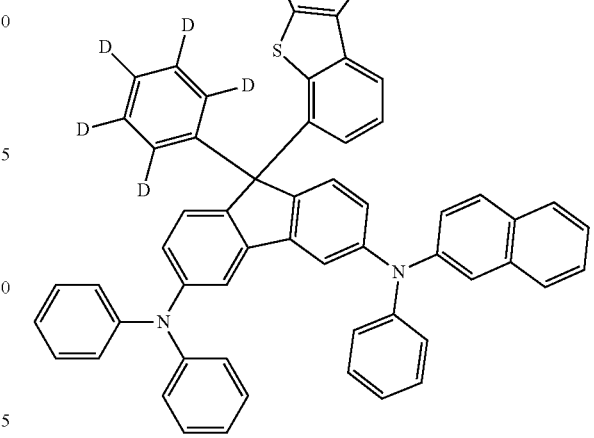
201
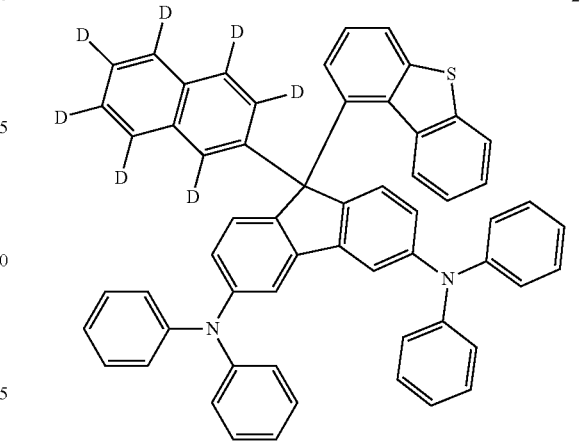
202
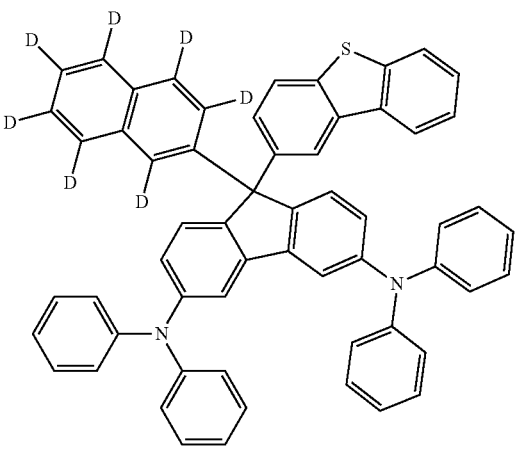

205
-continued
203
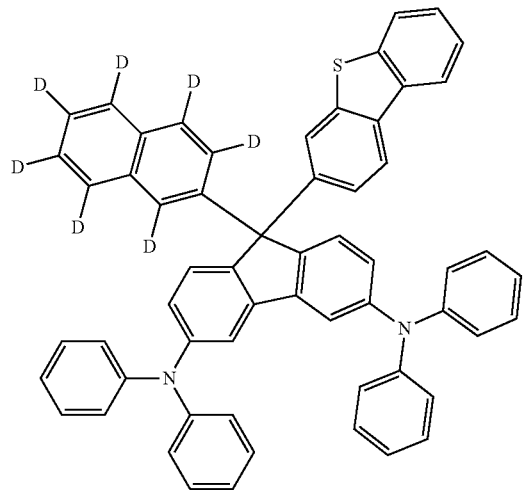
204
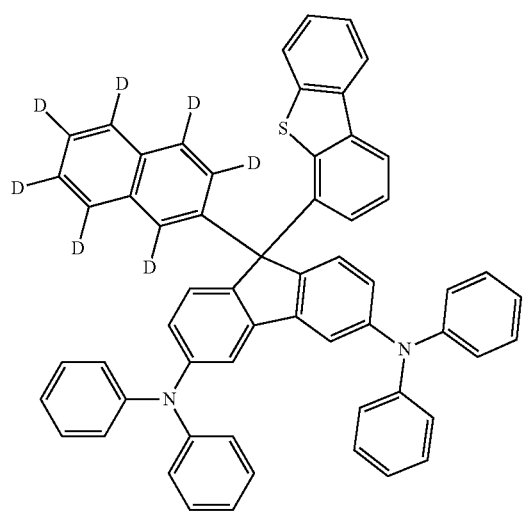
205
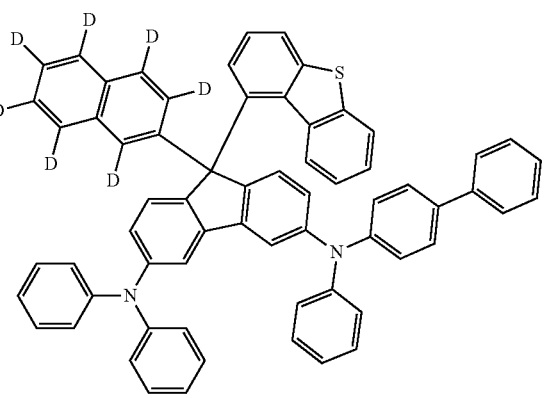
206
-continued
206
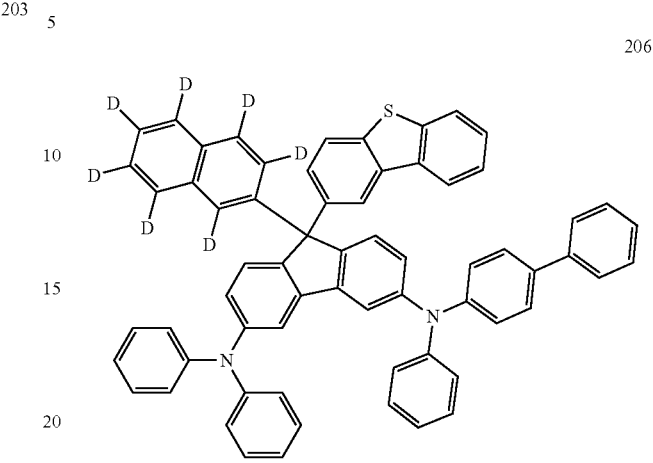
207
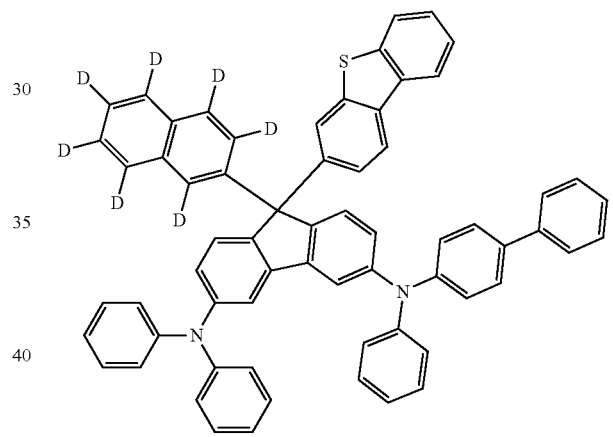
208
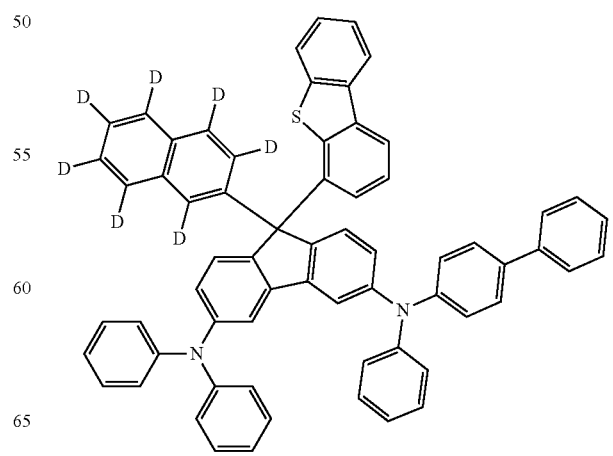

207
-continued
209
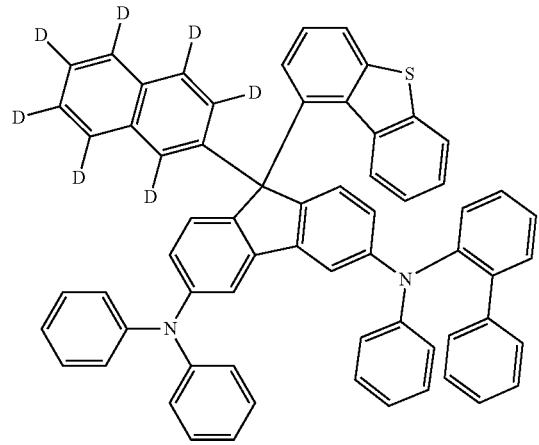
210
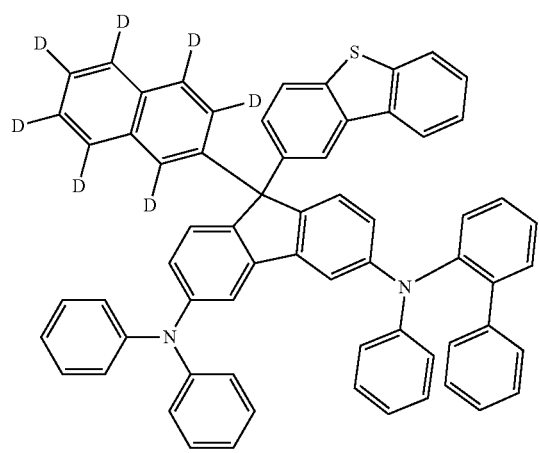
211
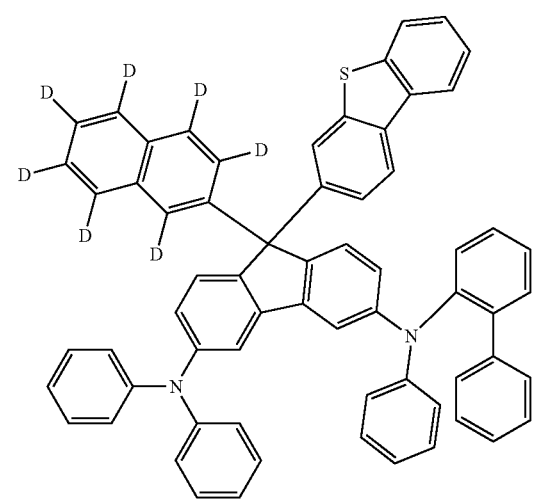
208
-continued
212
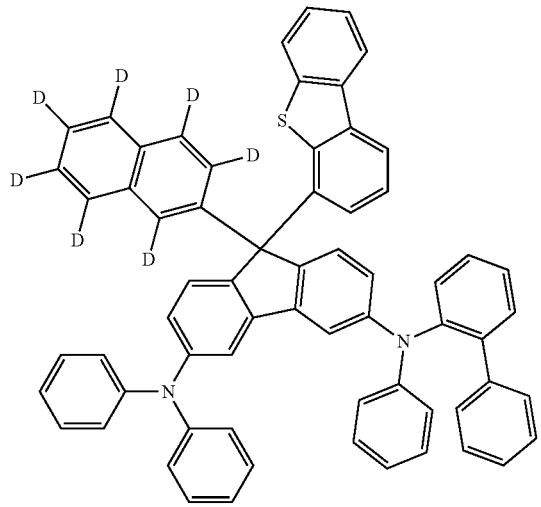
213
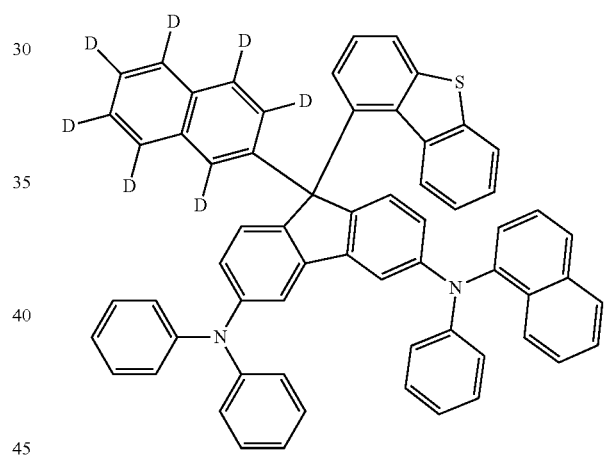
214
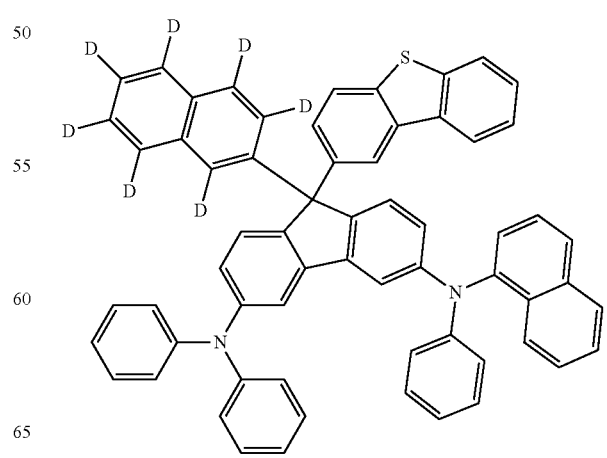

-continued
215
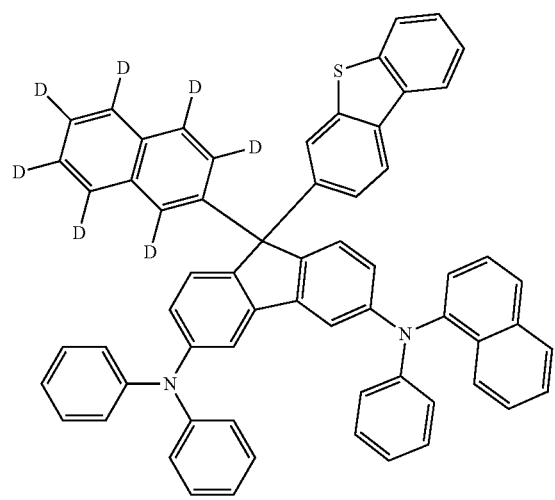
216
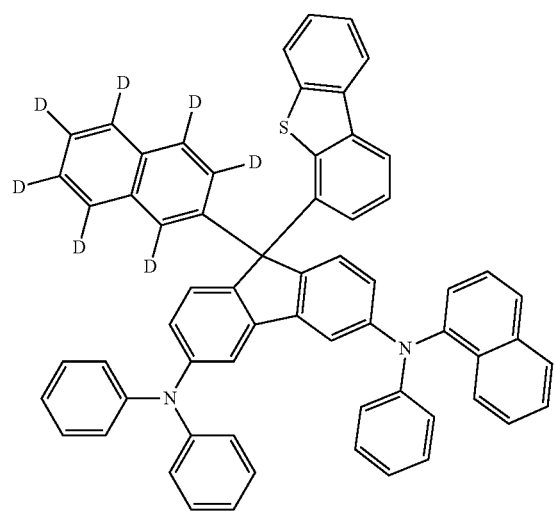
217
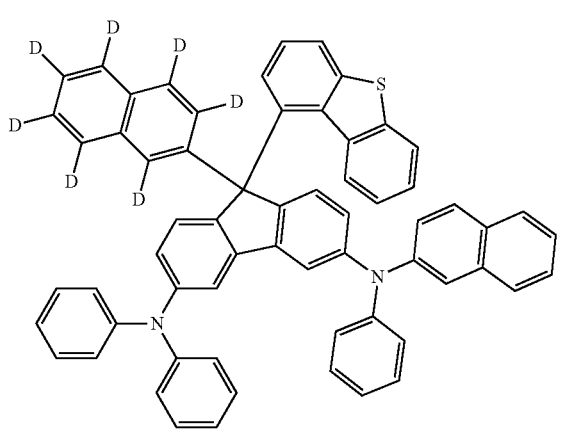
-continued
218
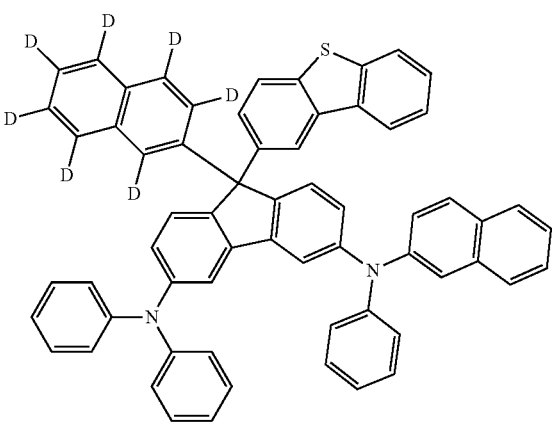
219
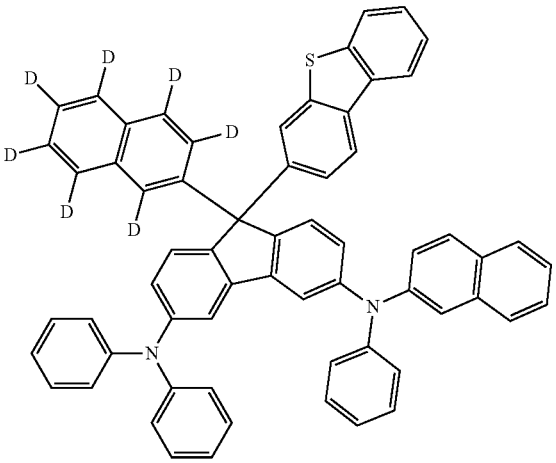
220
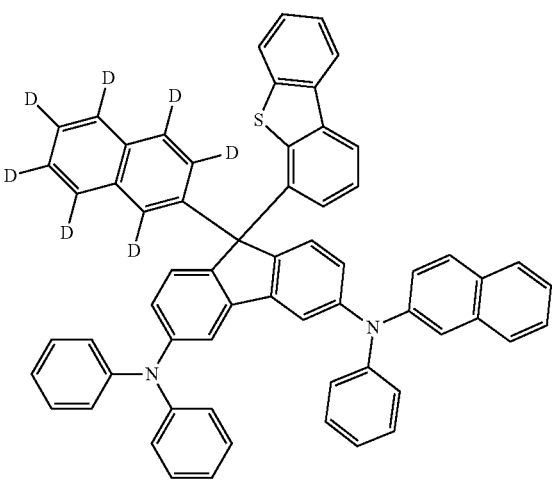

211
-continued
221
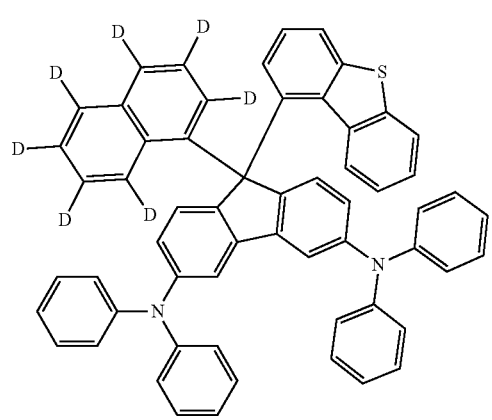
222
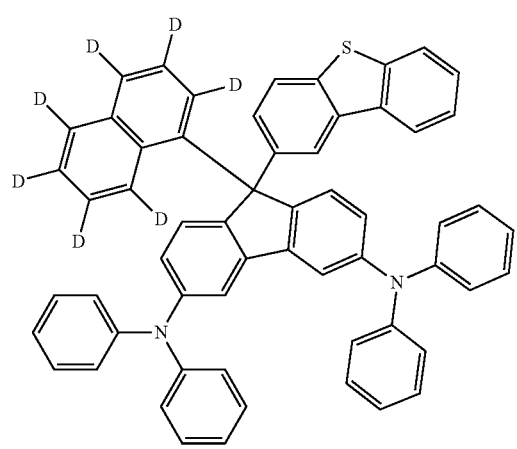
223
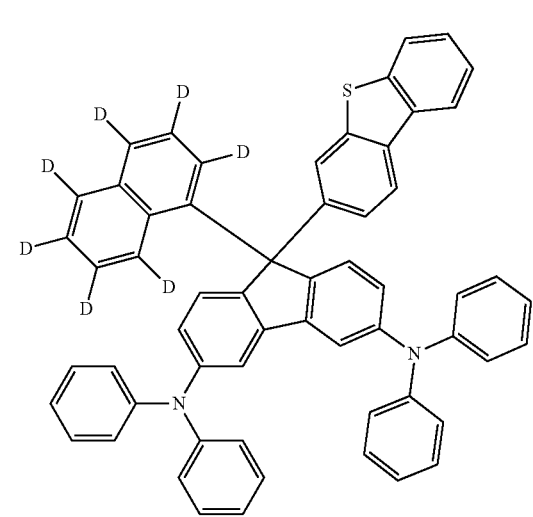
212
-continued
224
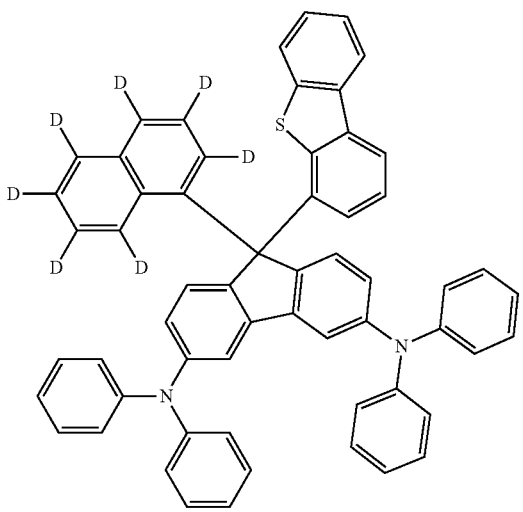
225
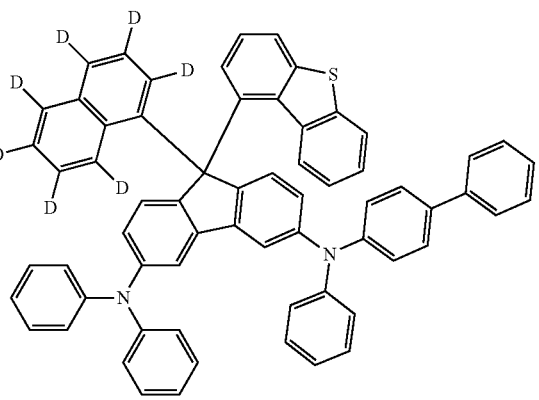
226
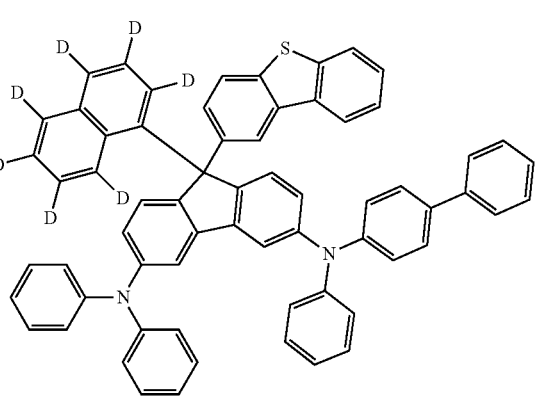

227
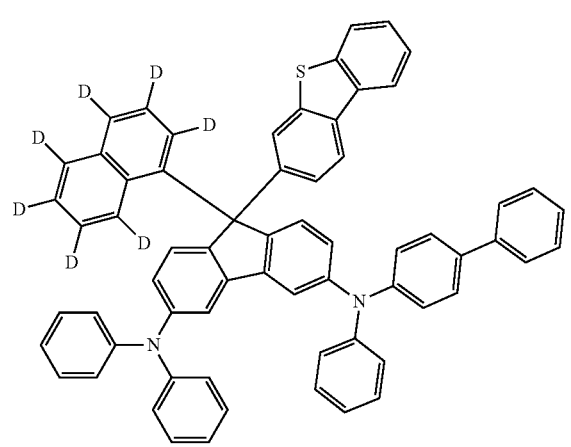
228
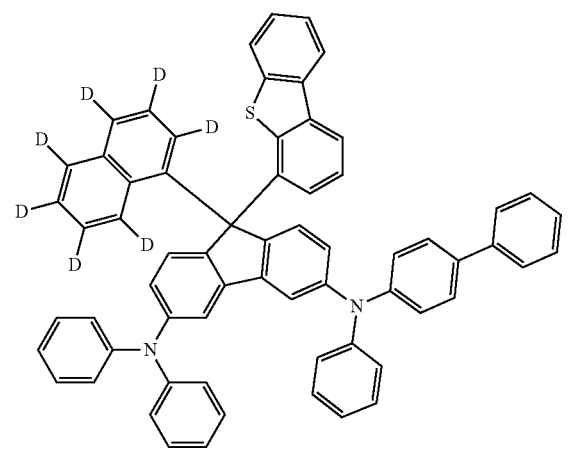
229
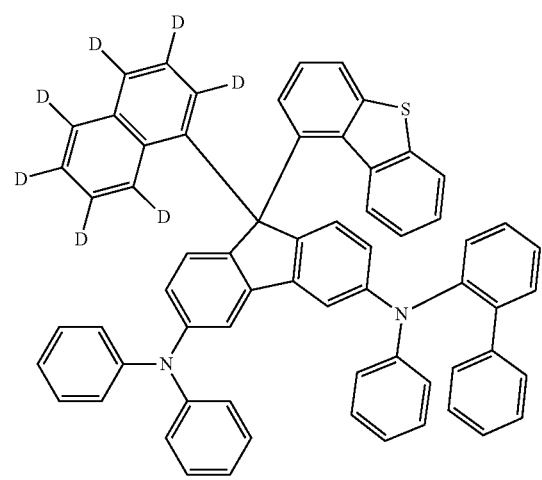
230
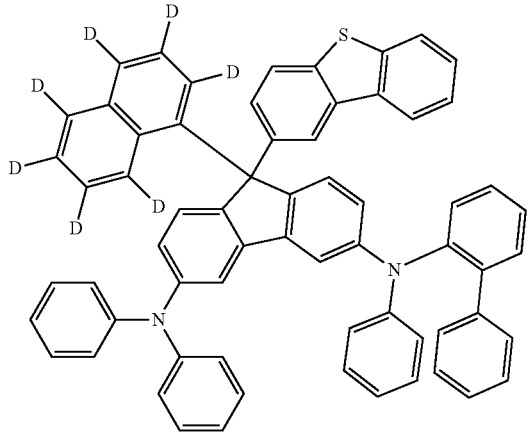
231
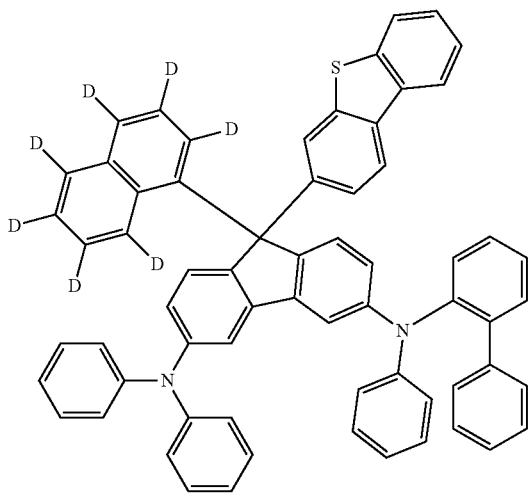
232
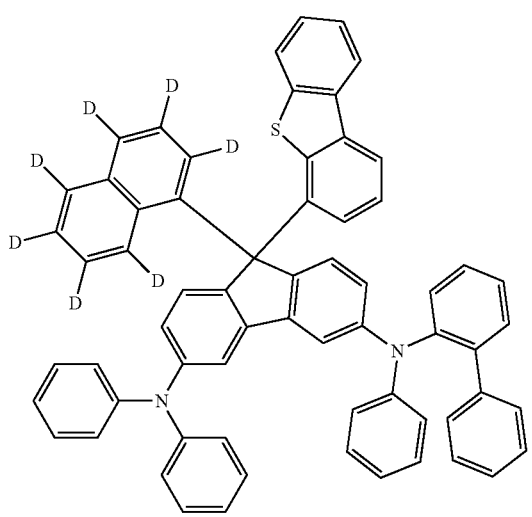

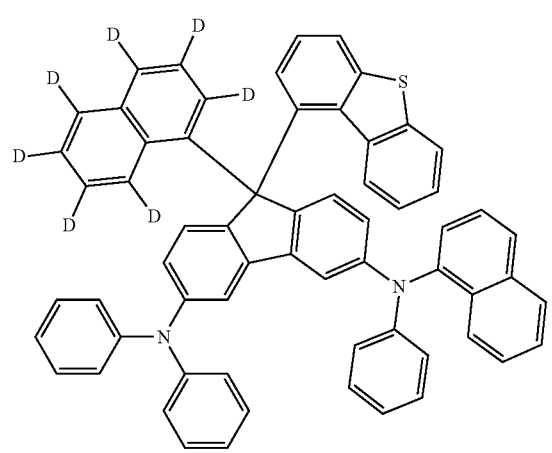
233
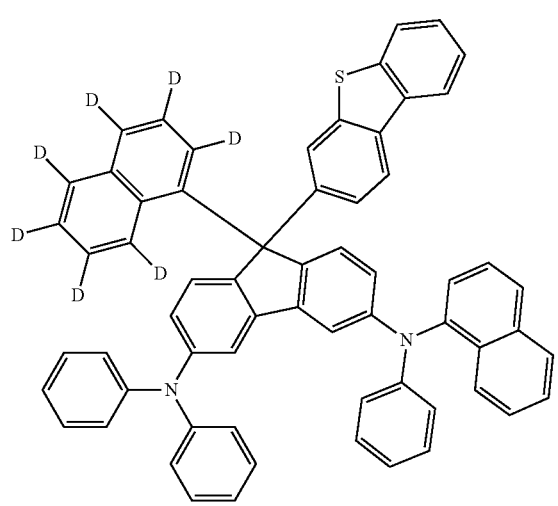
234
235
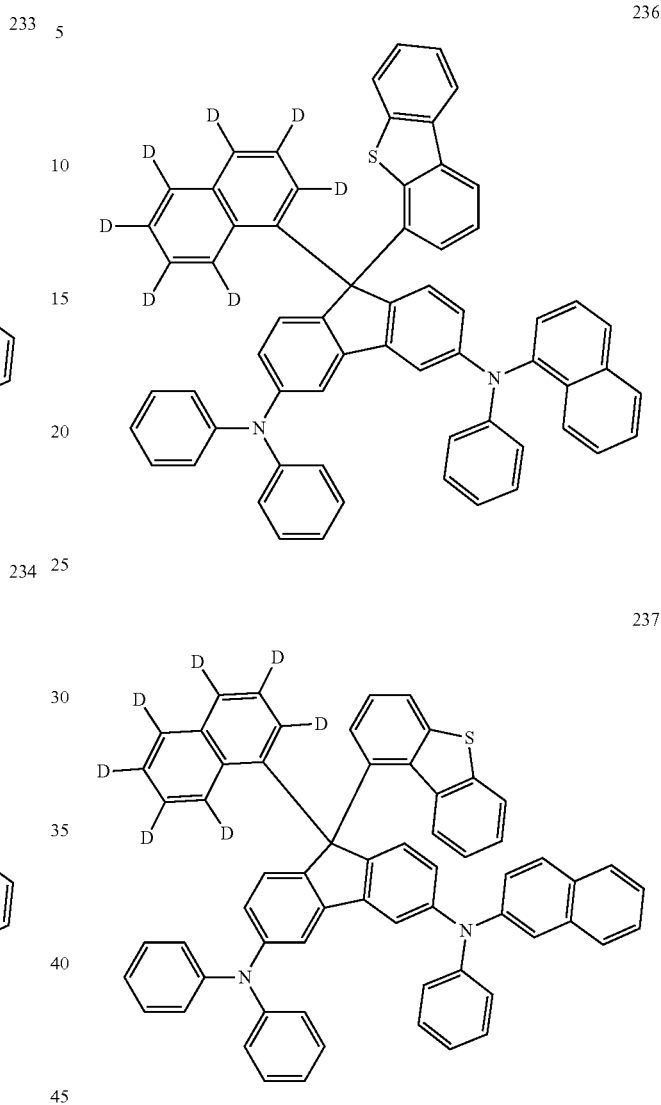
236
237
238

239
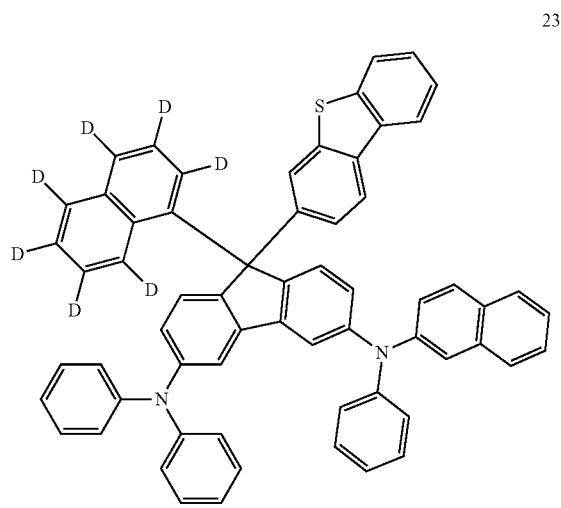
240
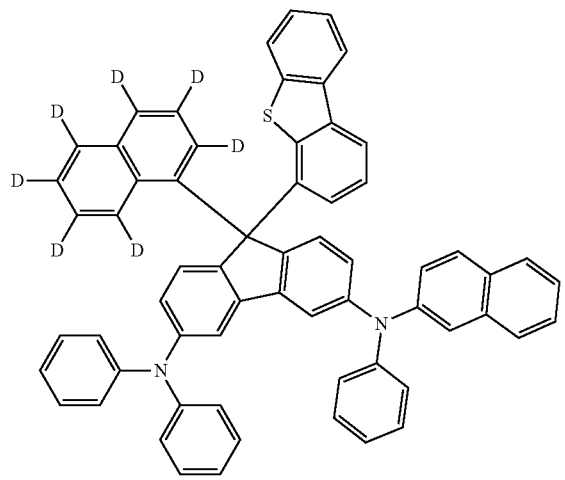
241
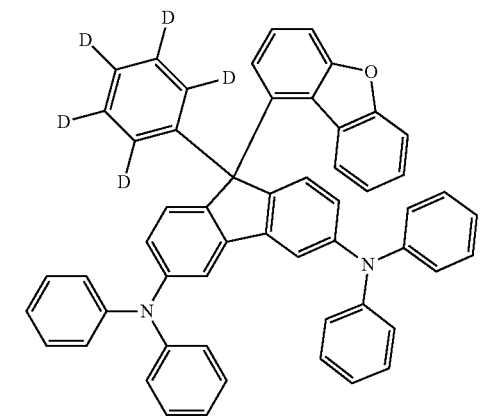
242
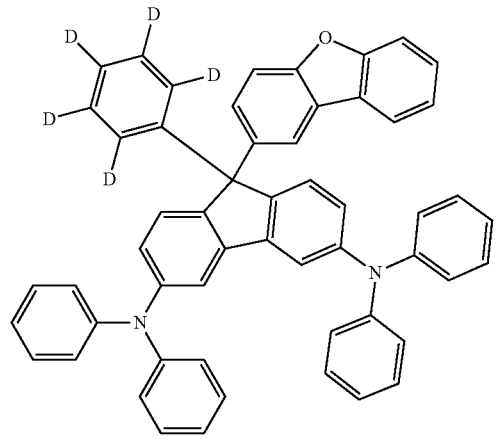
243
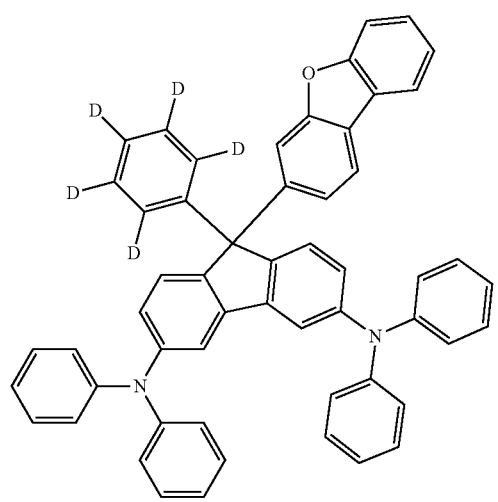
244
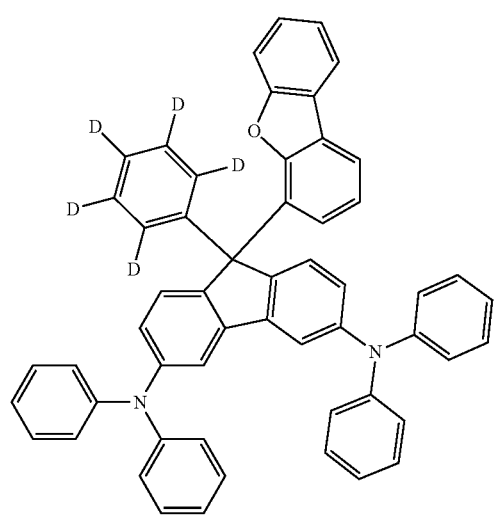

245
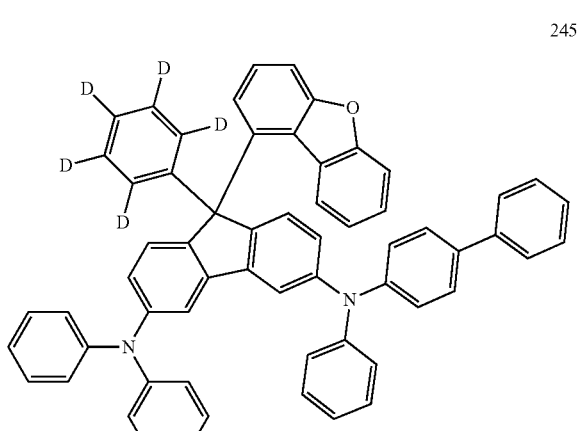
246
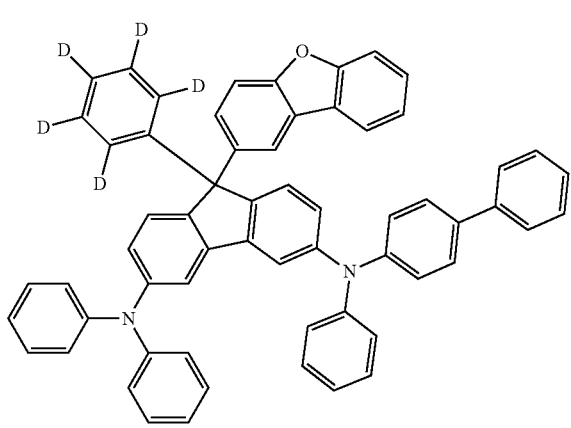
247
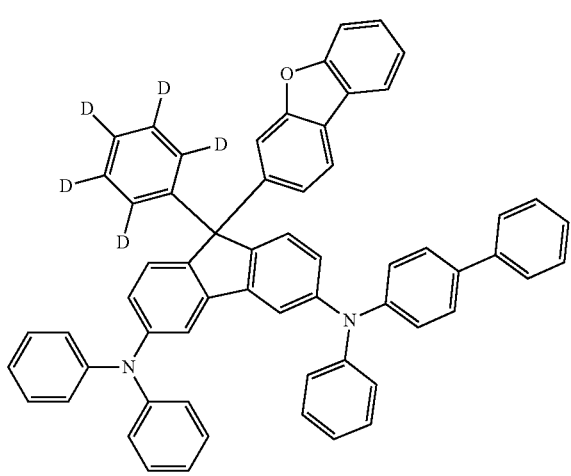
248
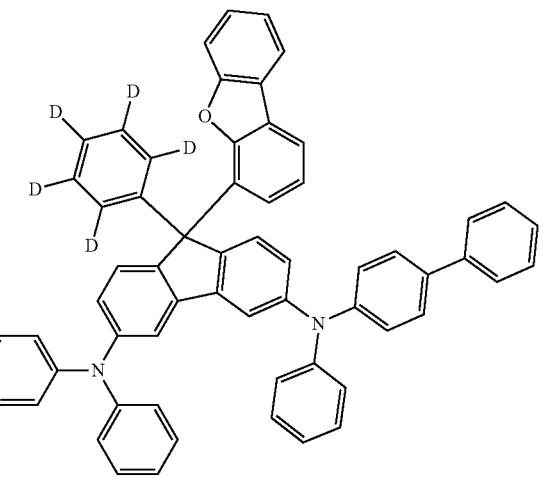
249
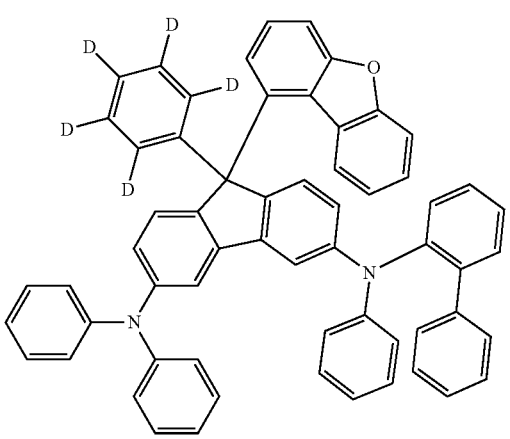
250
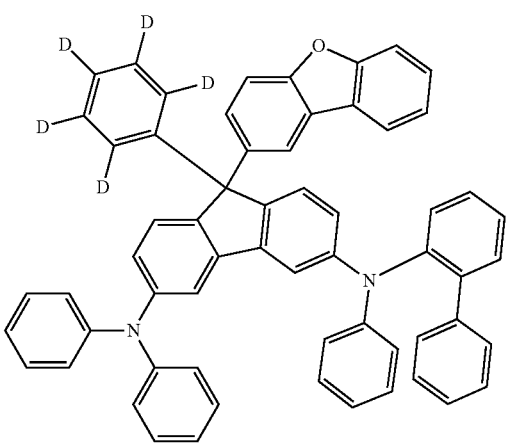

221
-continued
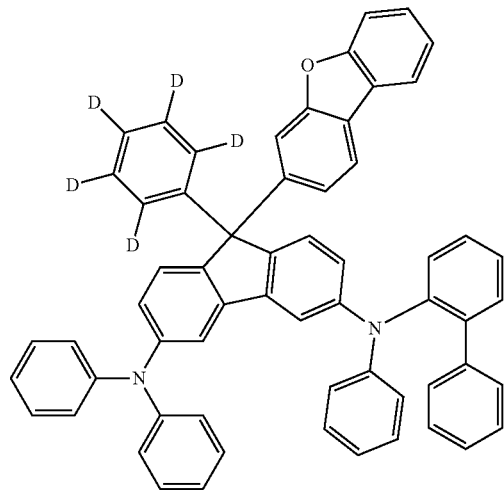
251
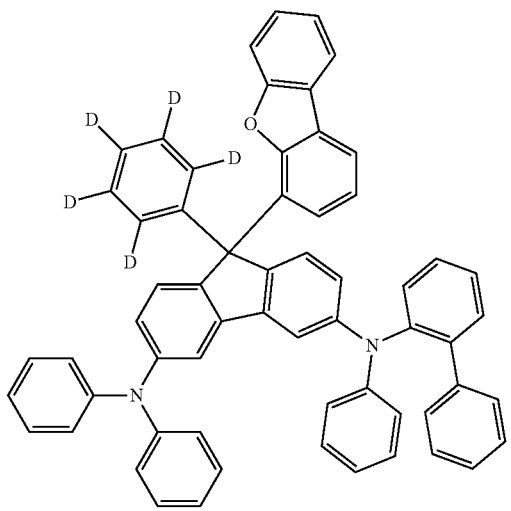
252
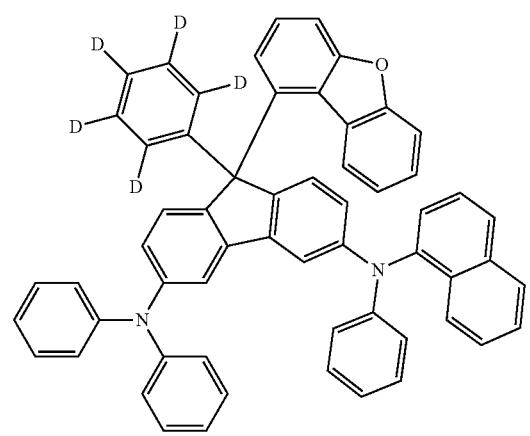
253
222
-continued
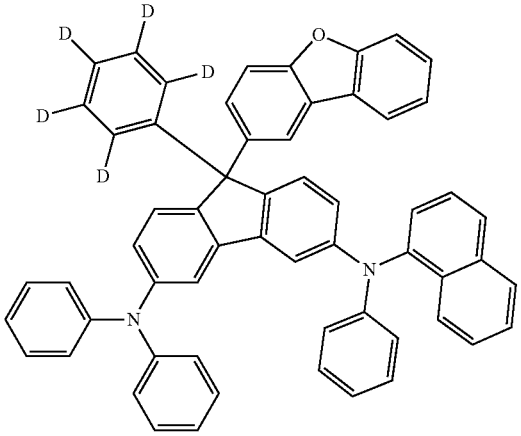
254
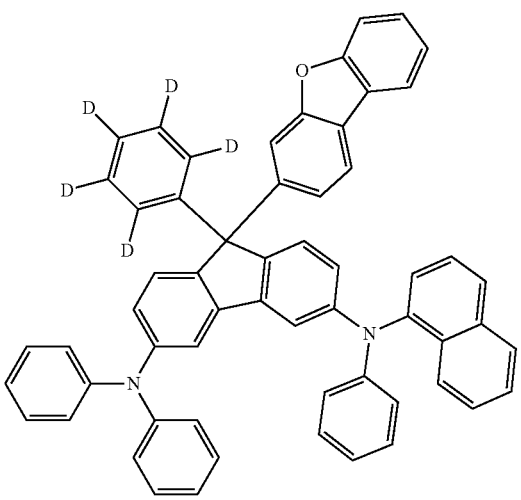
255
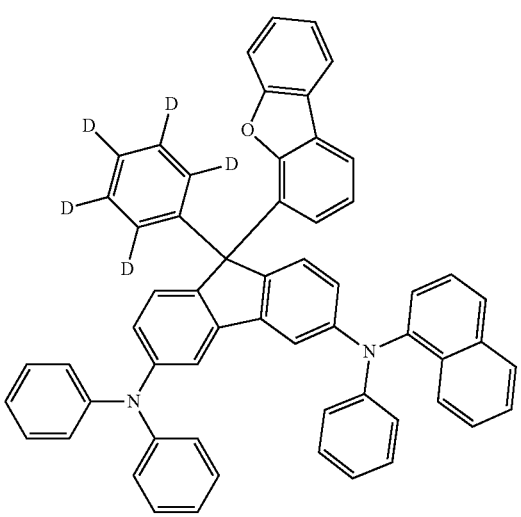
256

257
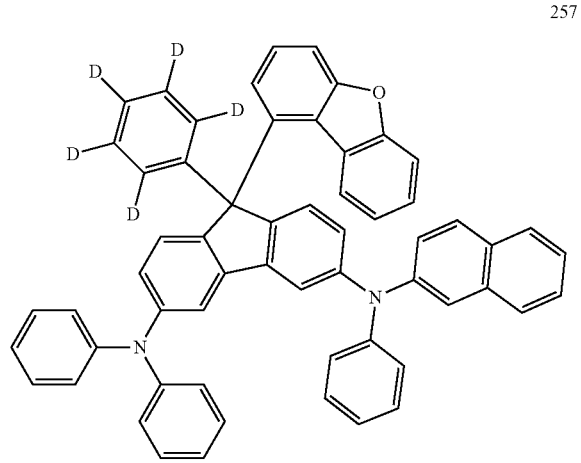
258
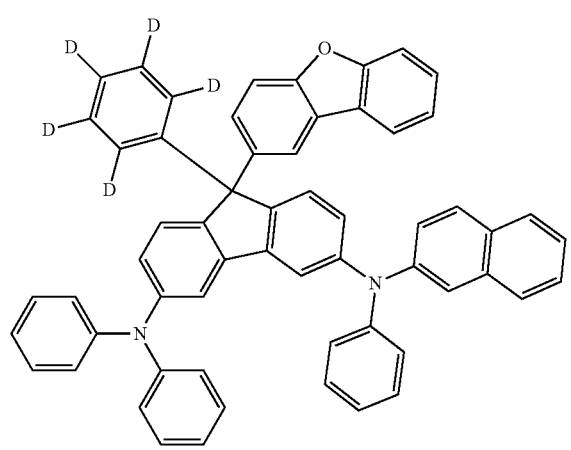
259
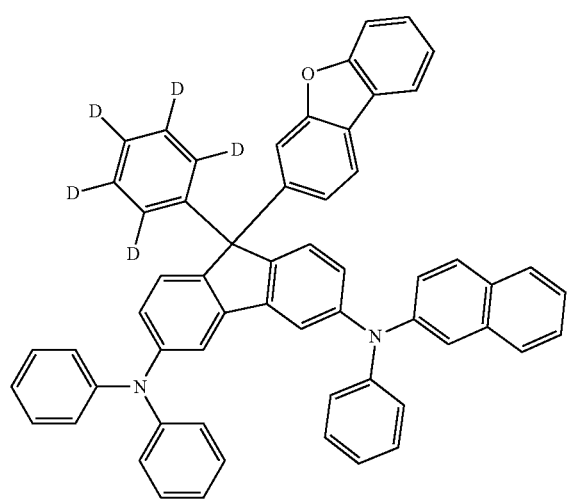
260
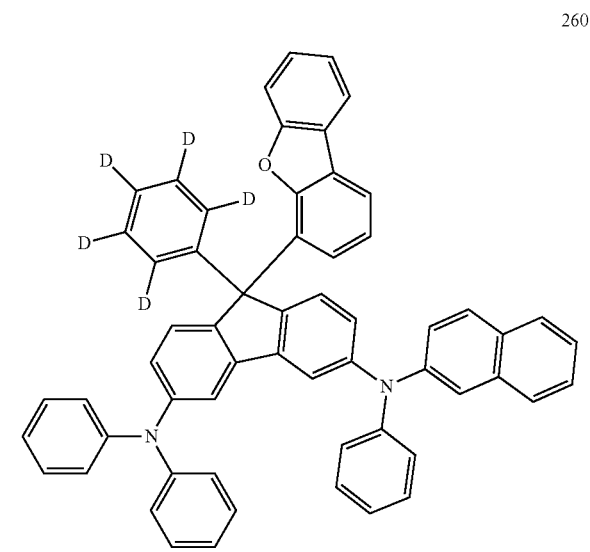
261
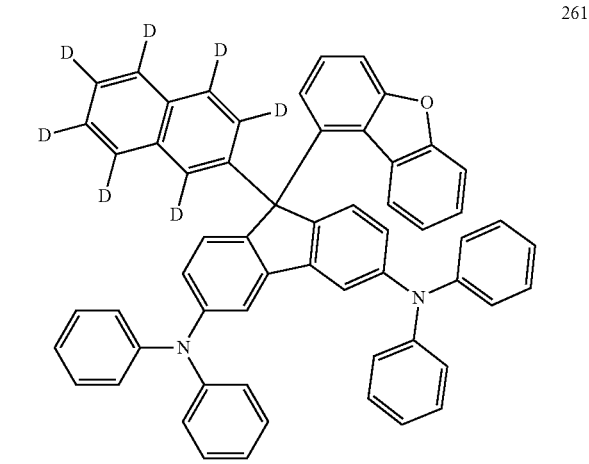
262
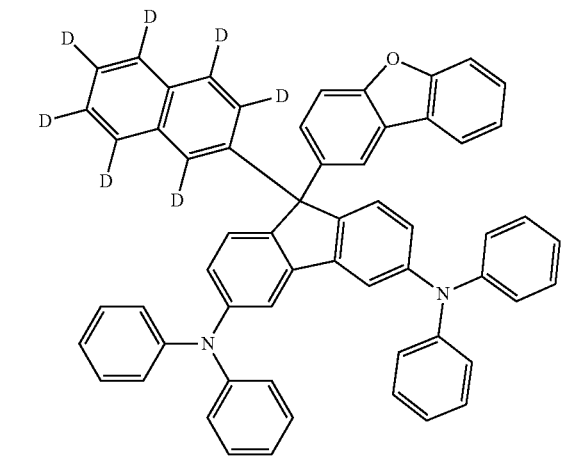

225
-continued
226
-continued
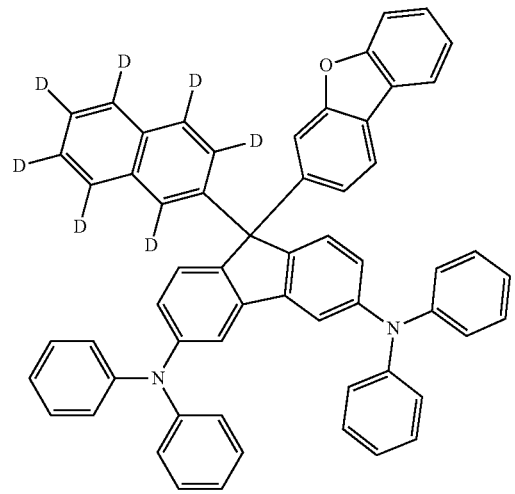
263
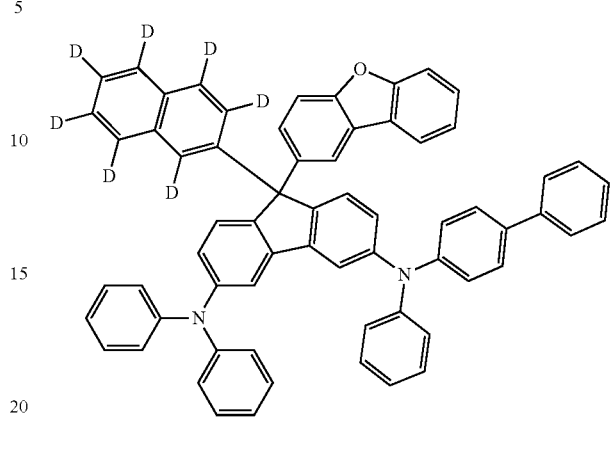
266
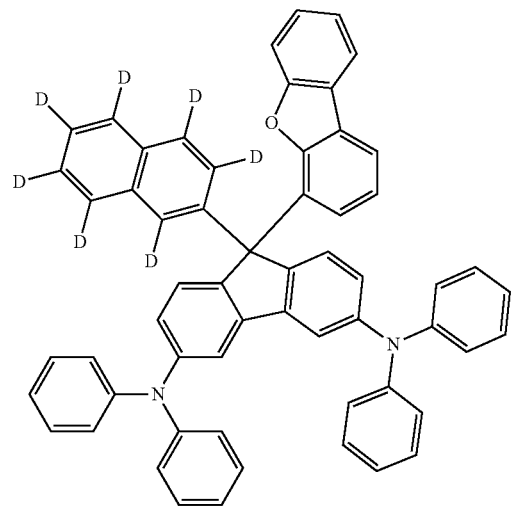
264
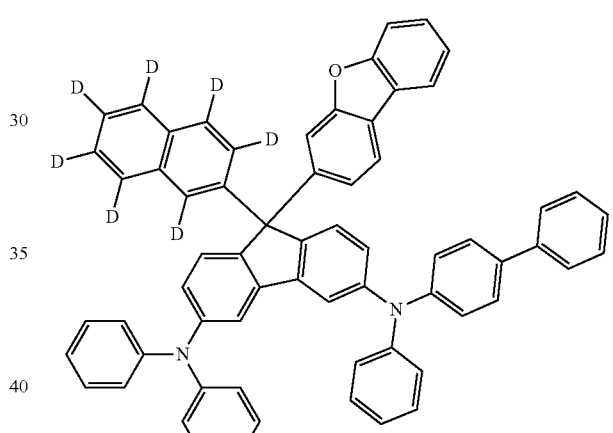
267
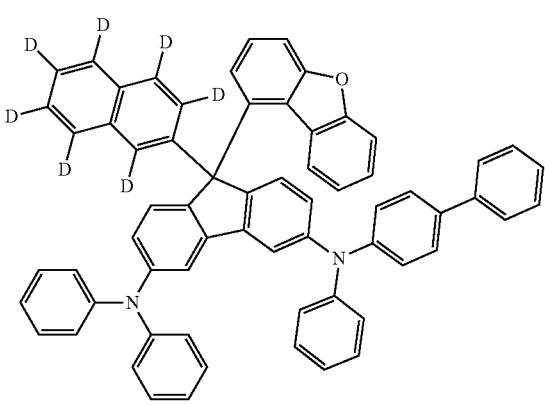
265
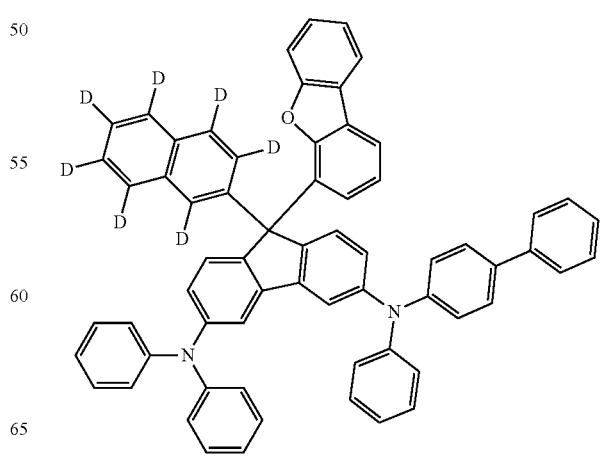
268

269 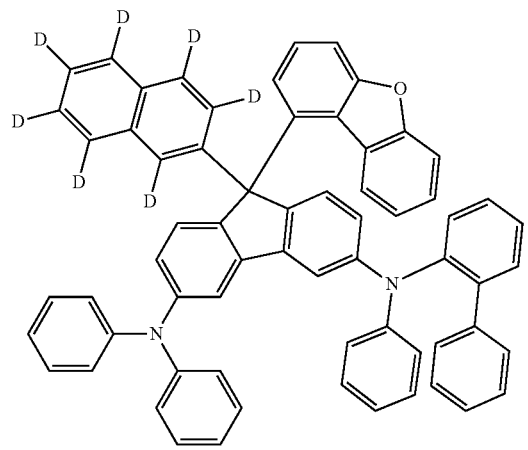
270 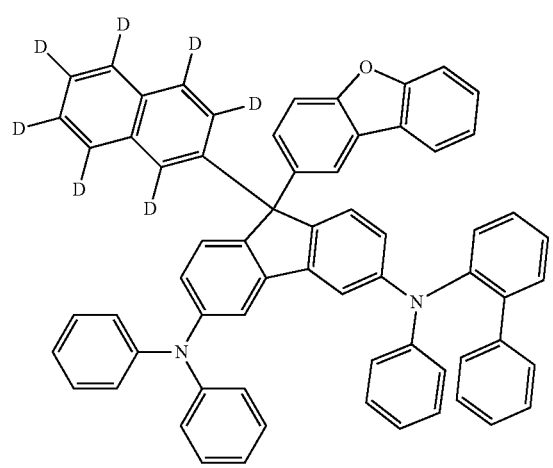
271 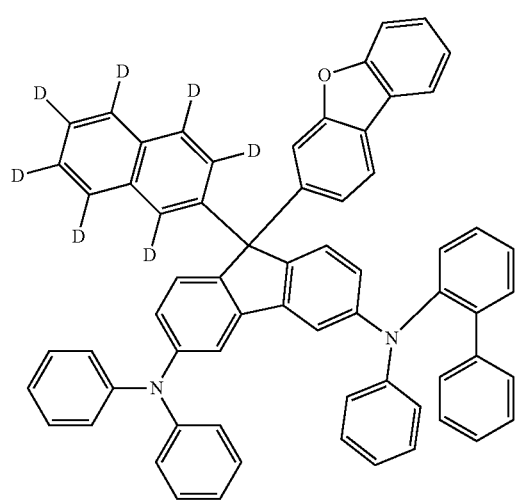
272 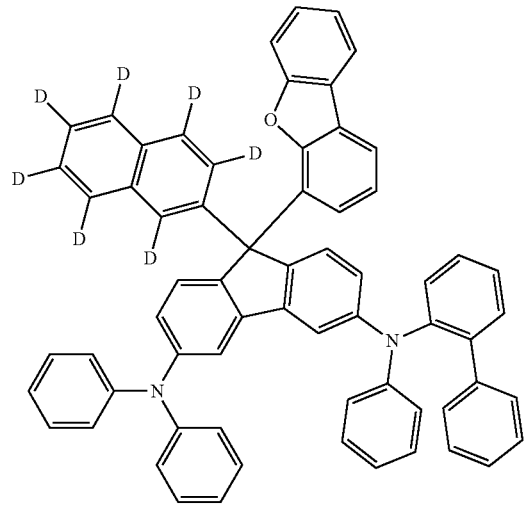
273 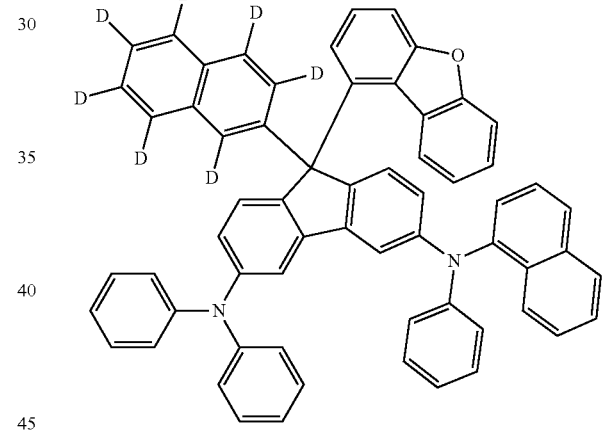
274 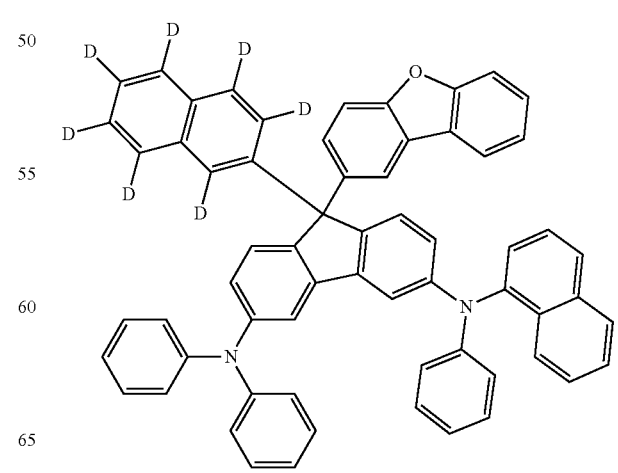

229
-continued
275
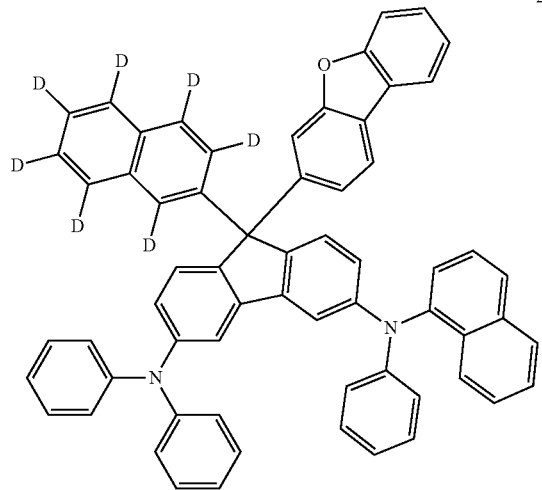
276
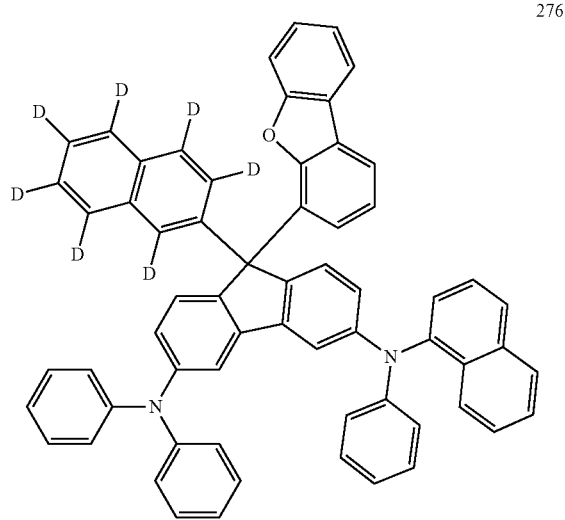
277
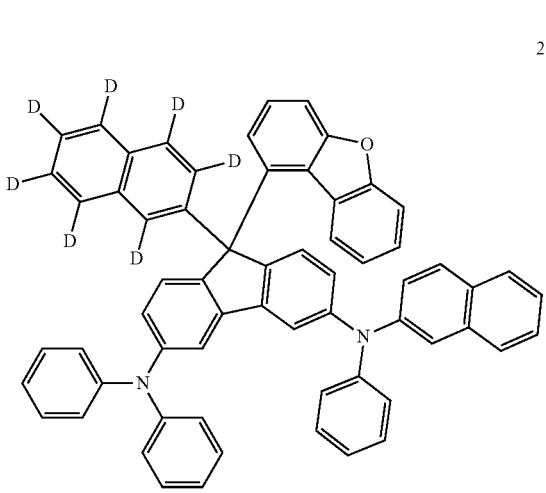
230
-continued
278
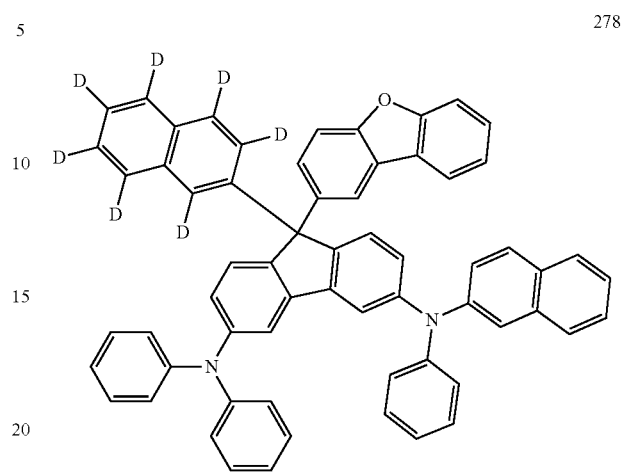
279
280
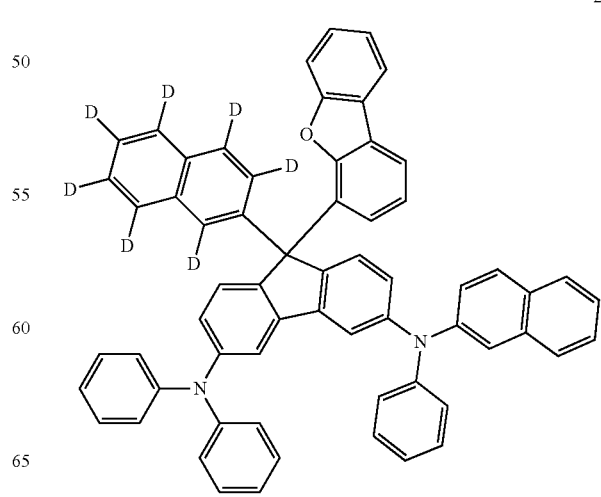

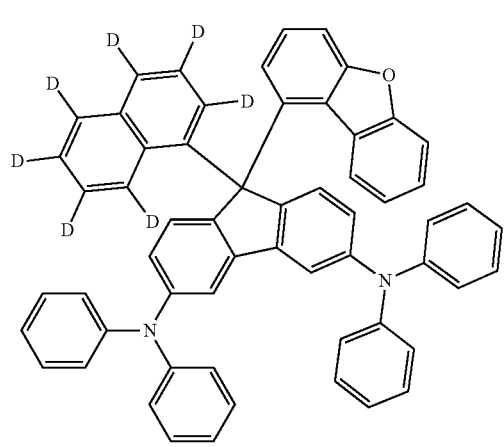
281
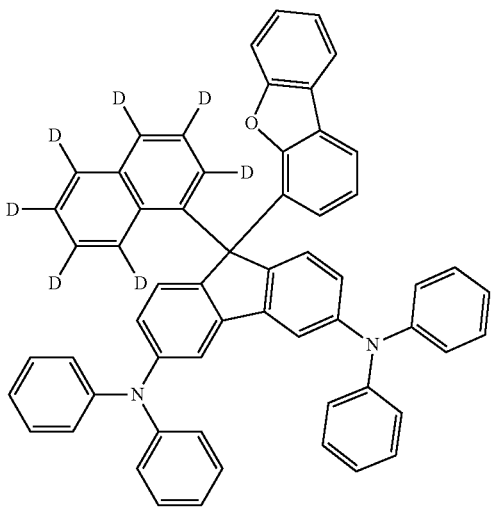
284
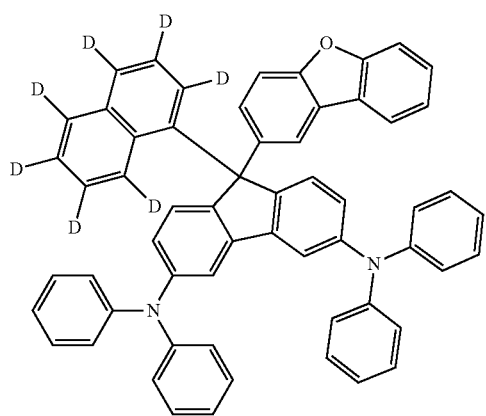
282
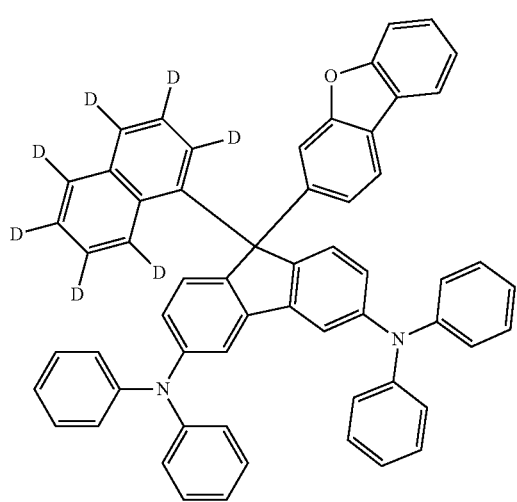
283
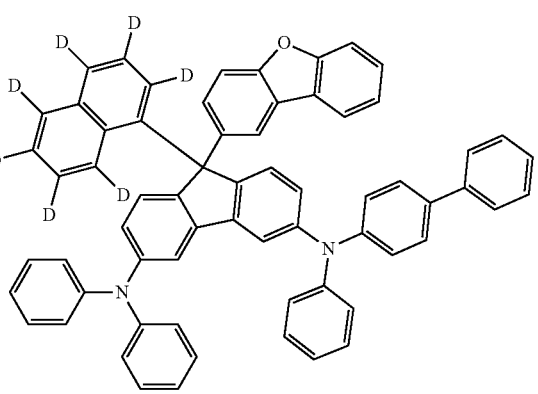
285
286

287
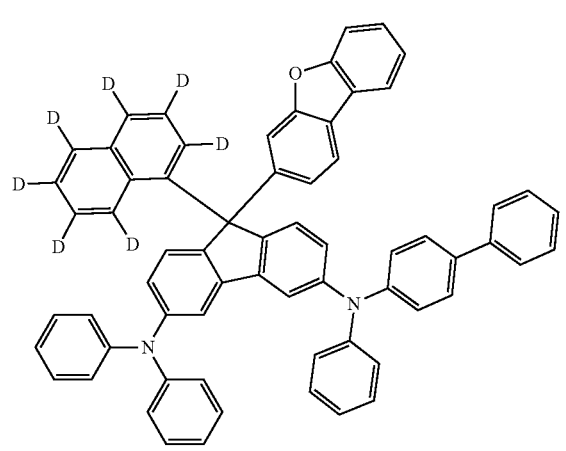
288
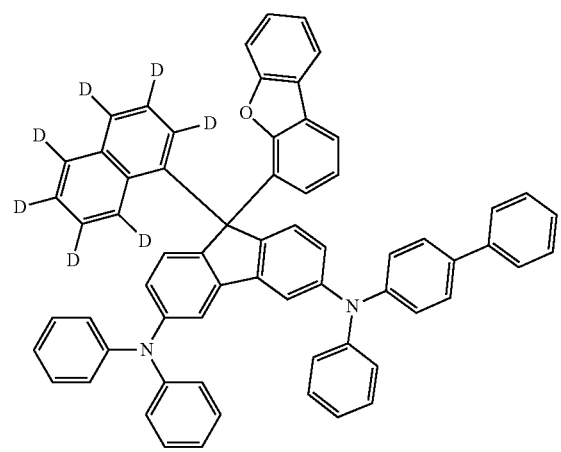
289
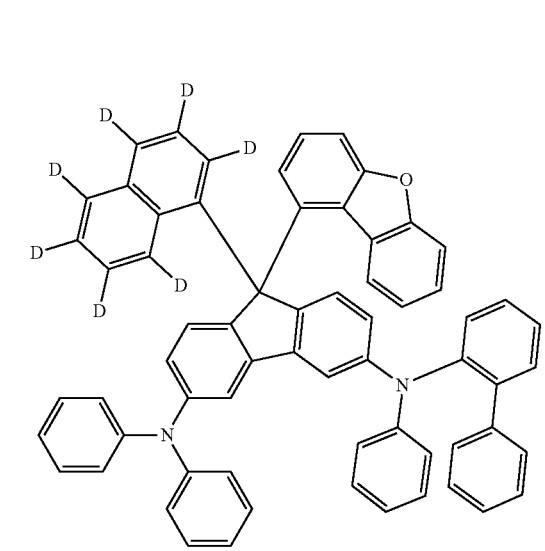
290
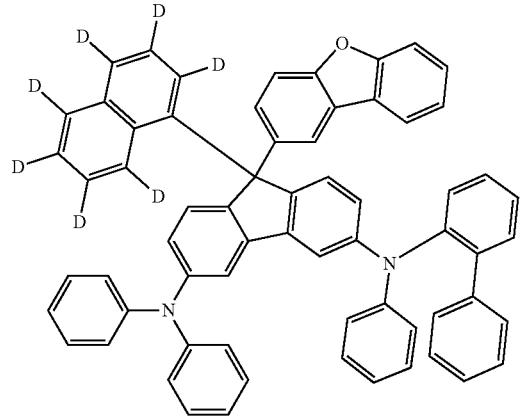
291
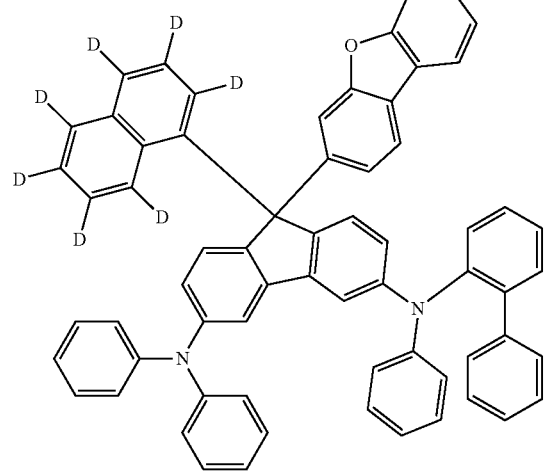
292
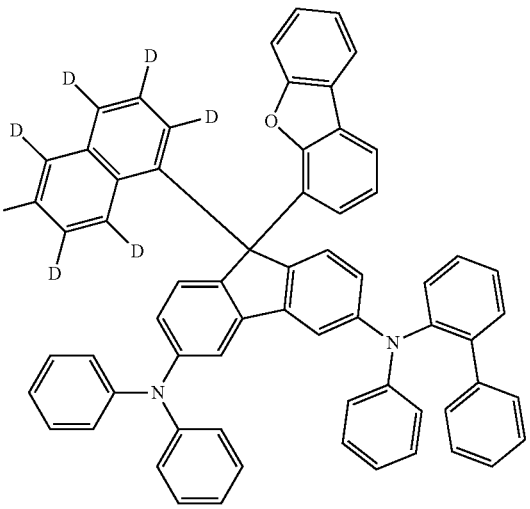

293
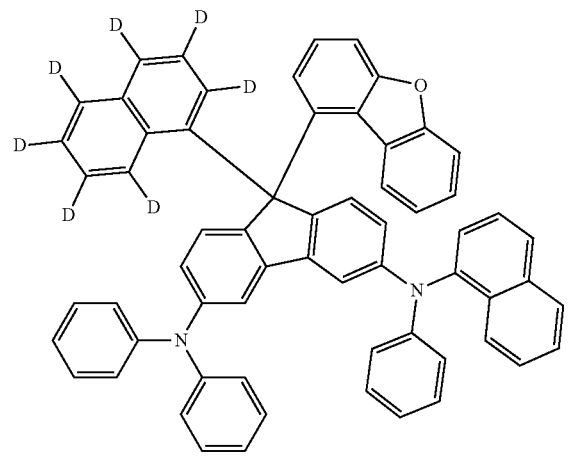
294
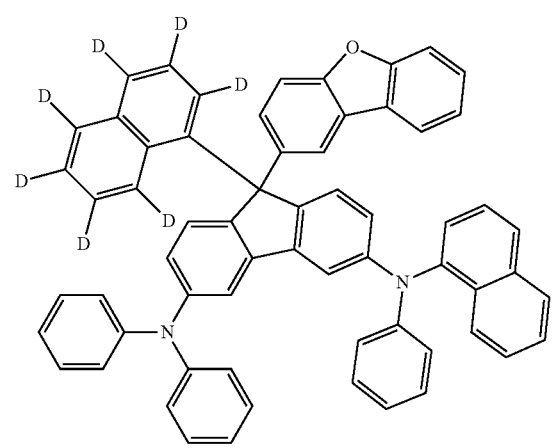
295
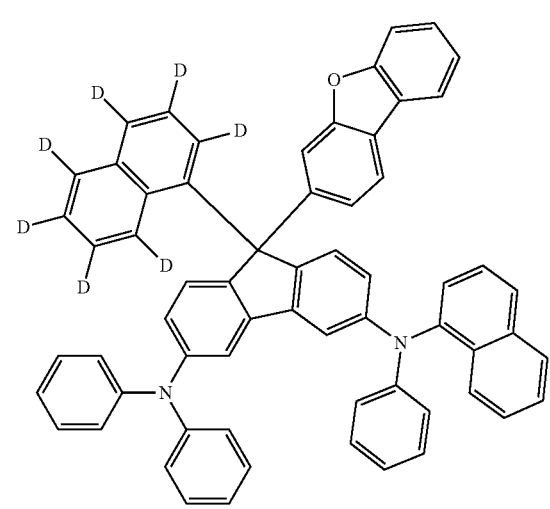
296
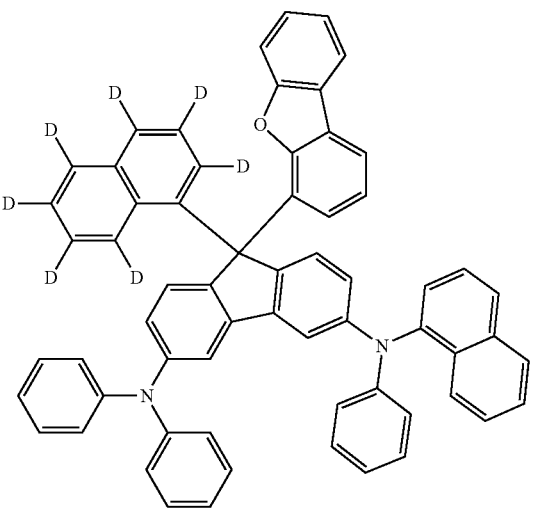
297
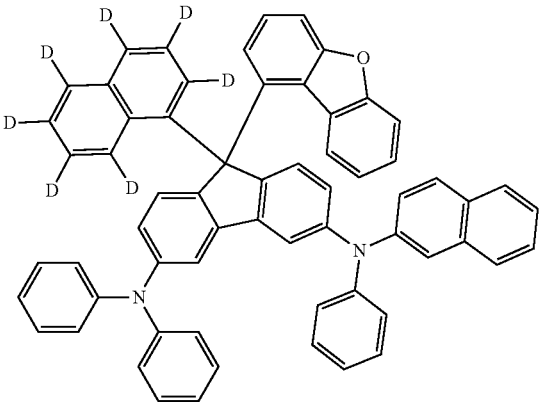
298
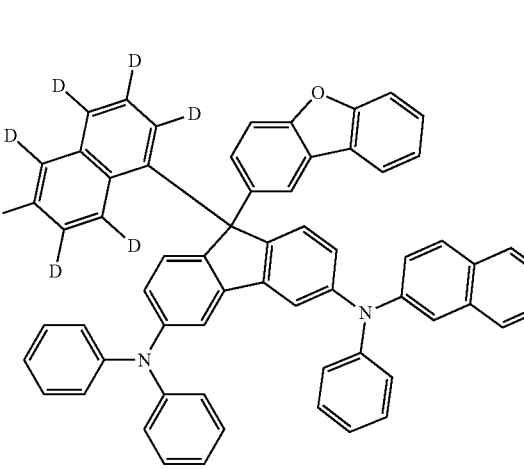

299
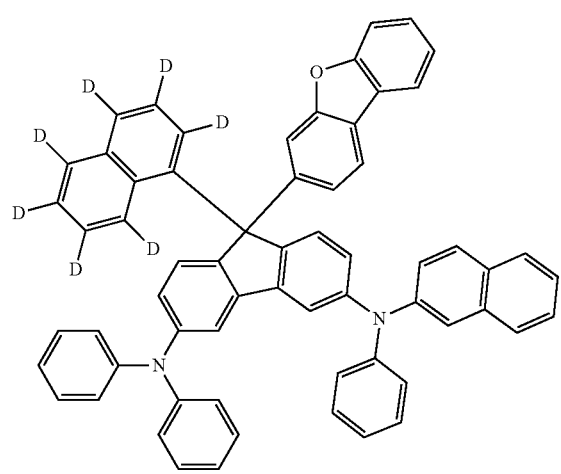
300
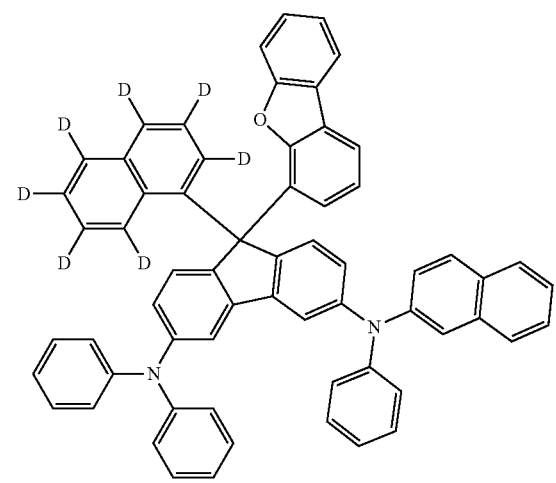
301
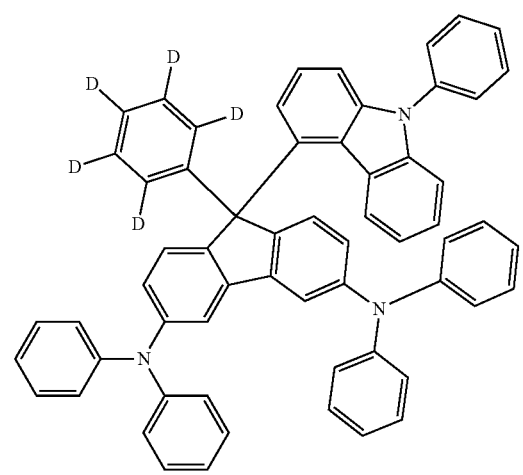
302
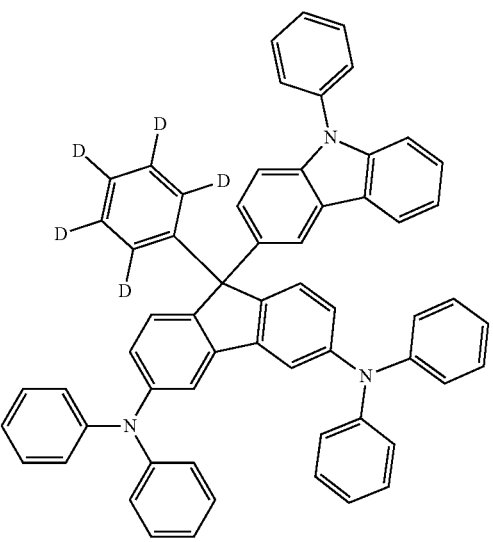
303
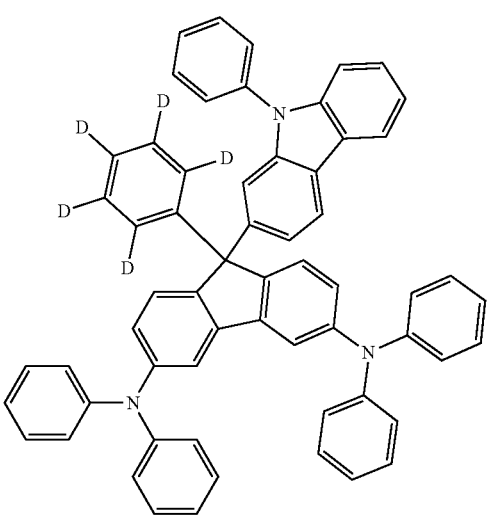
304
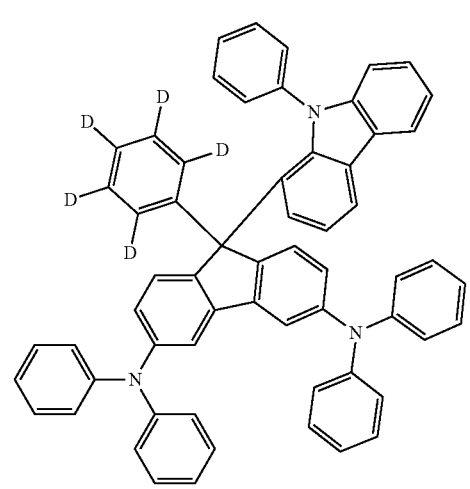

239
-continued
305
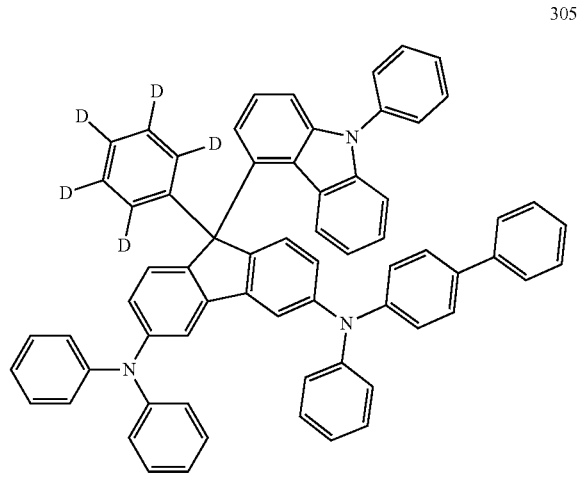
306
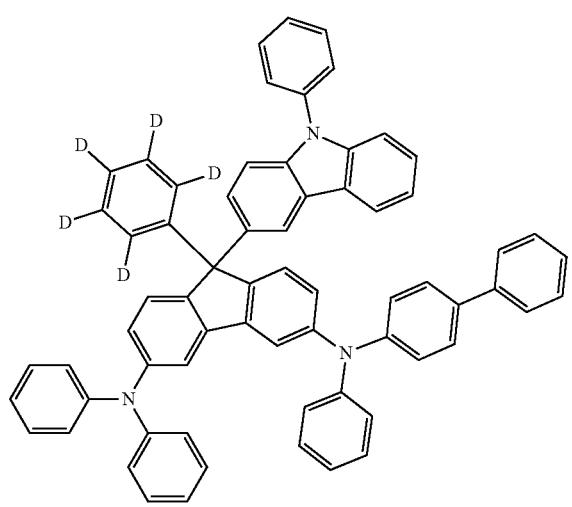
307
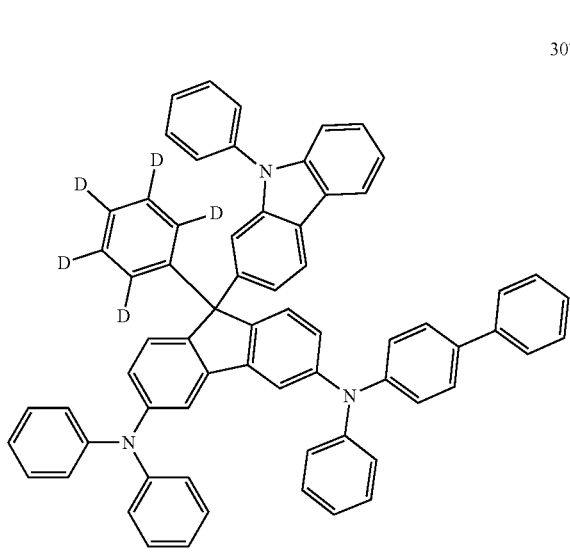
240
-continued
308
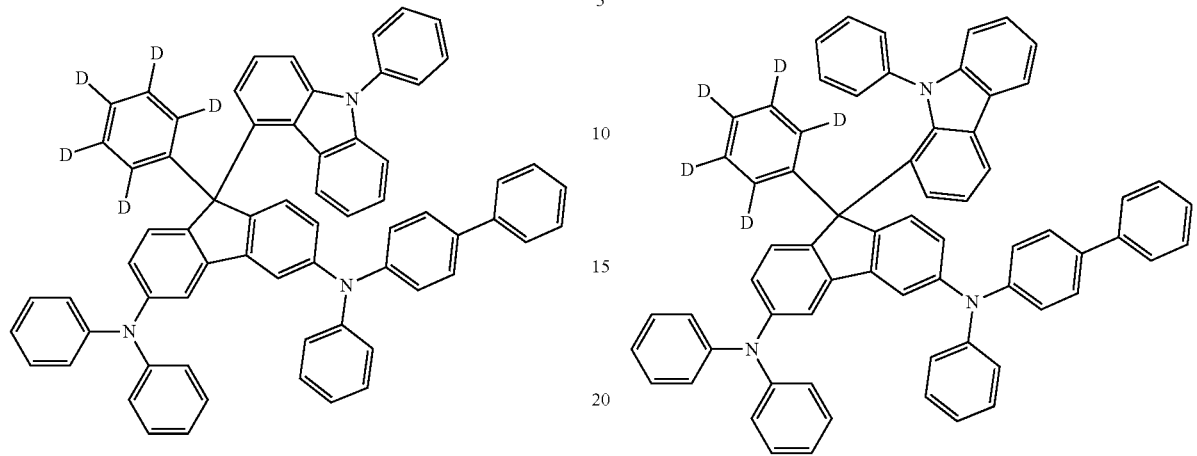
309
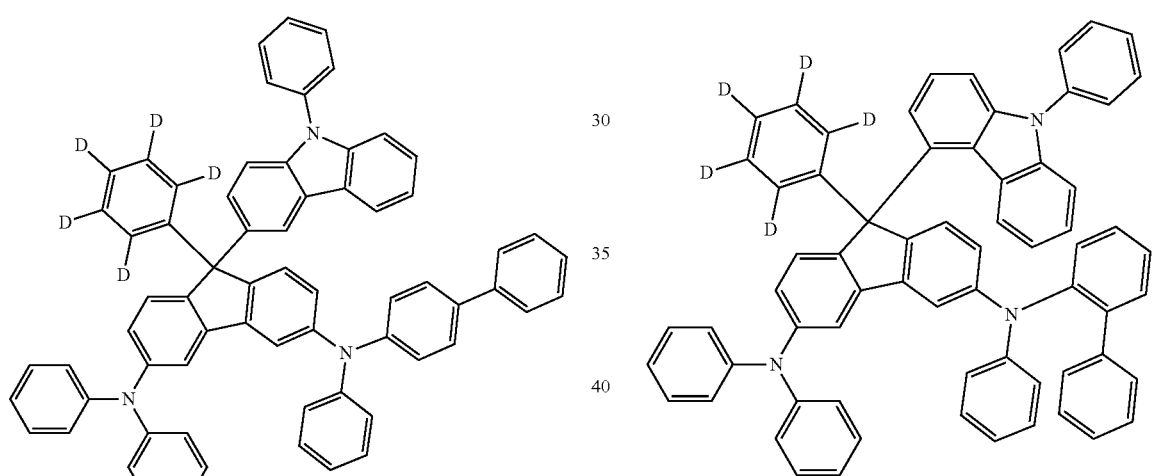
310
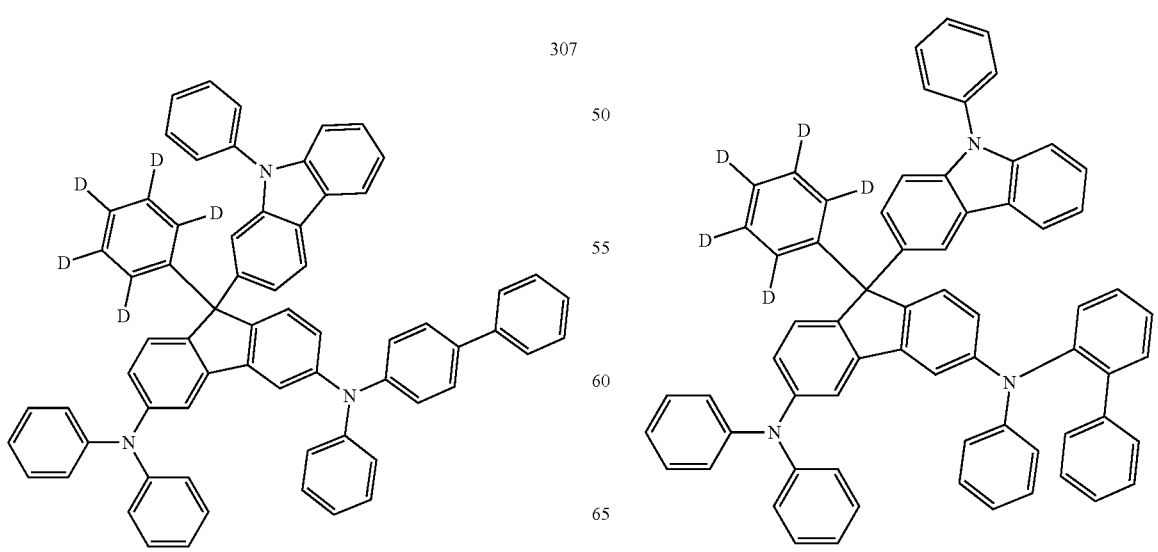

241
-continued
311
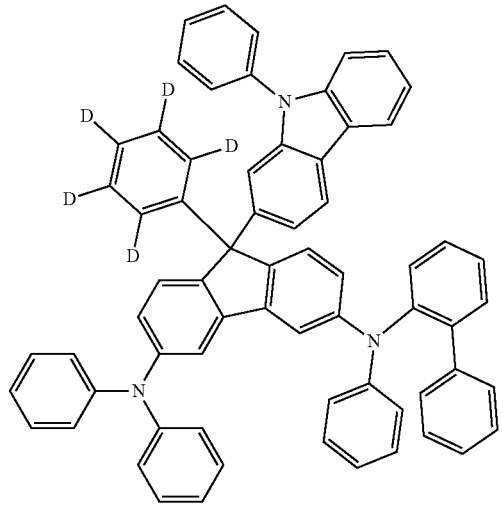
312
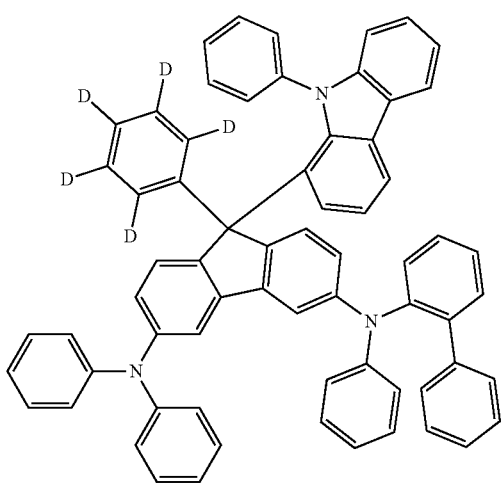
313
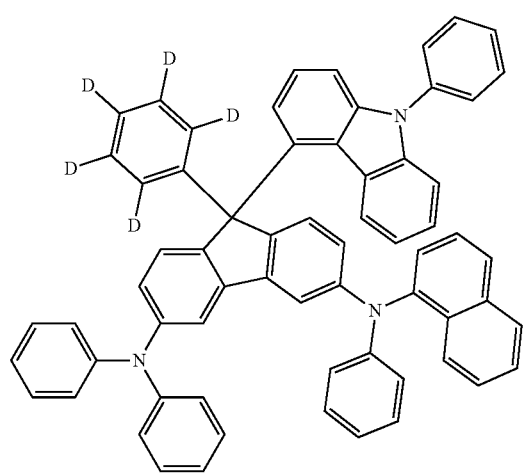
242
-continued
314
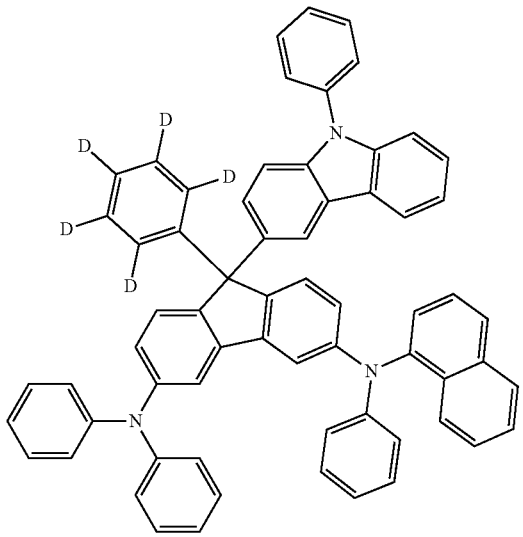
315
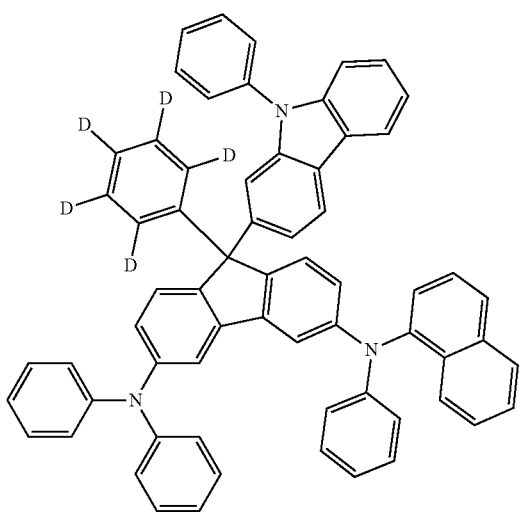
316
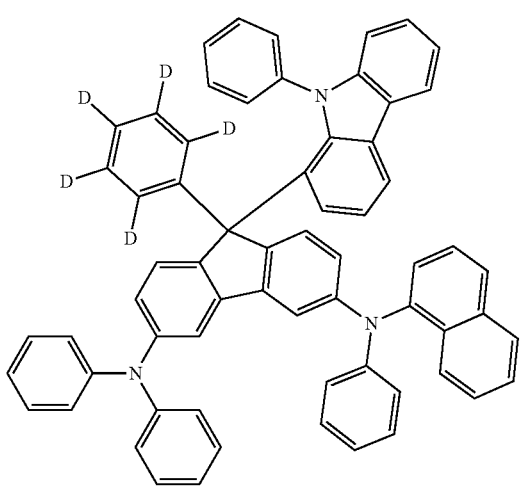

317
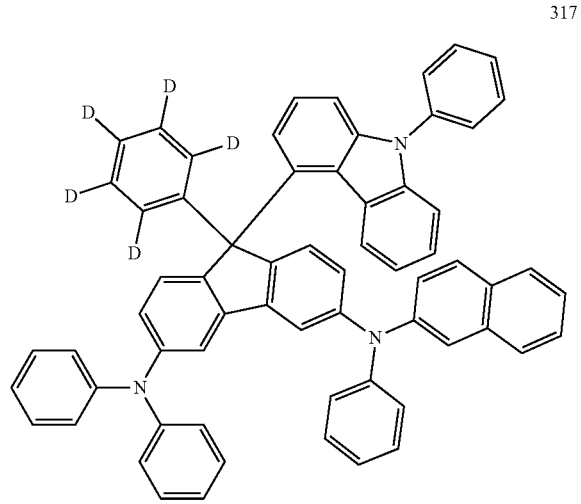
318
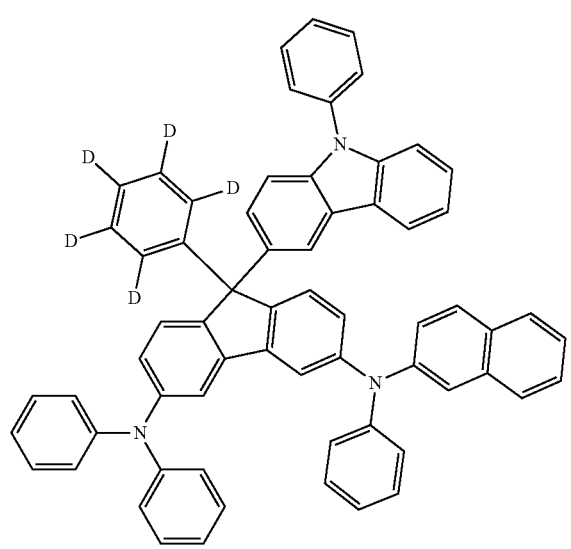
319
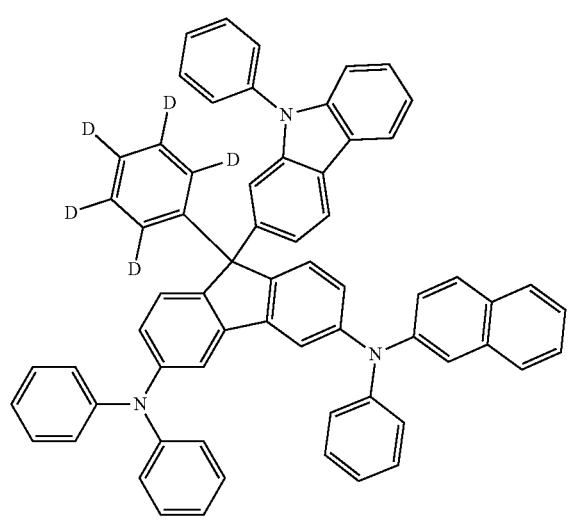
320
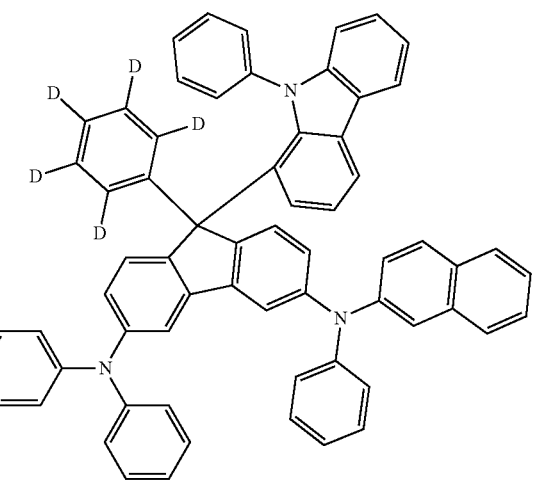
321
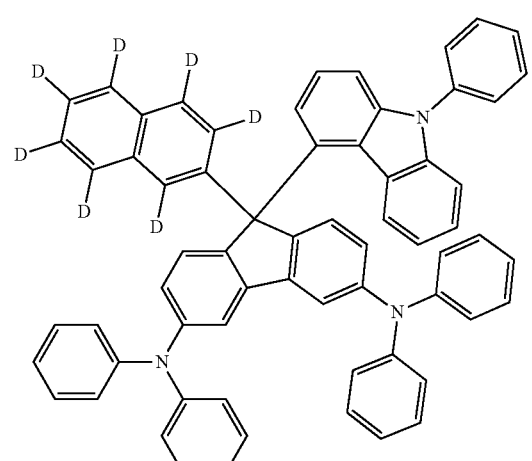
322
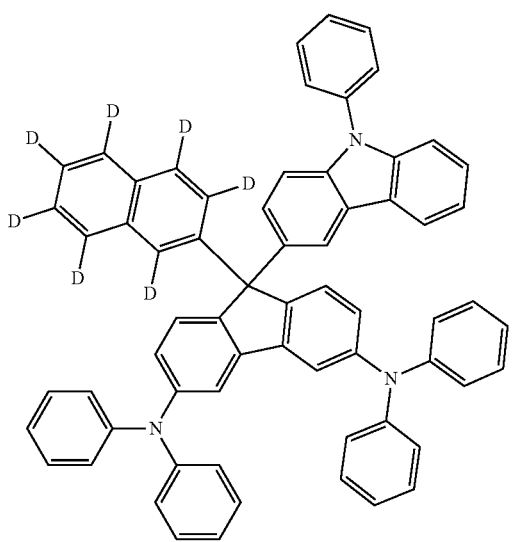

323
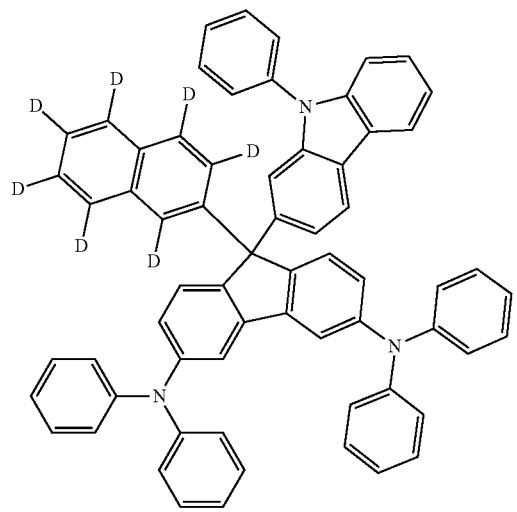
324
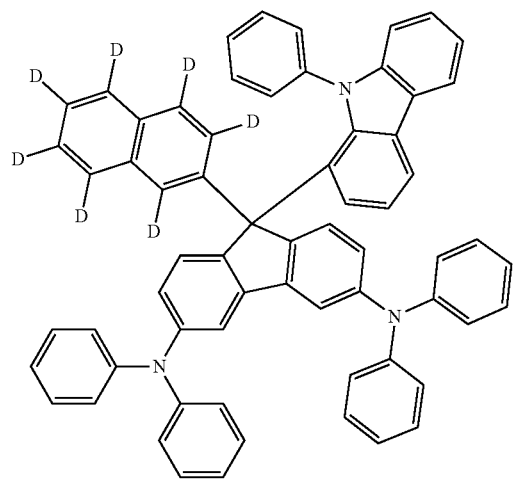
325
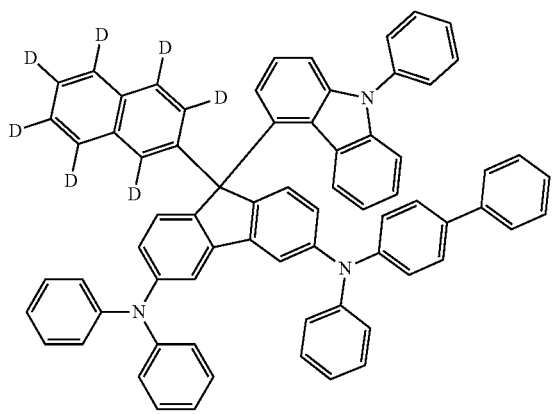
326
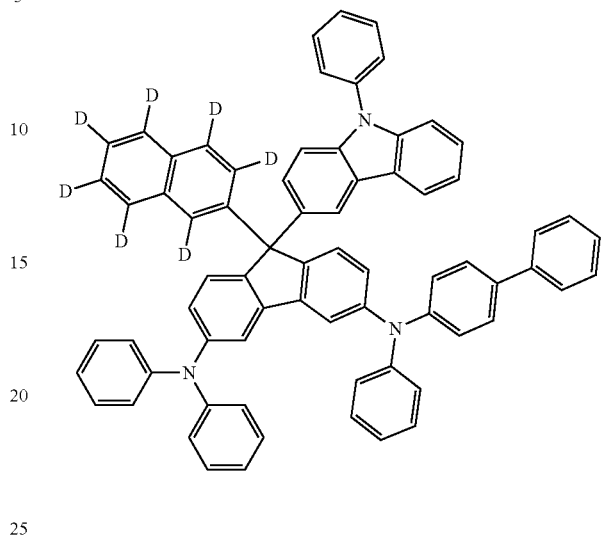
327
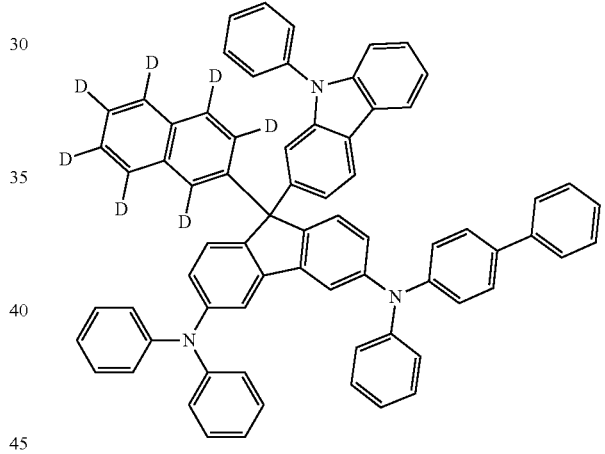
328
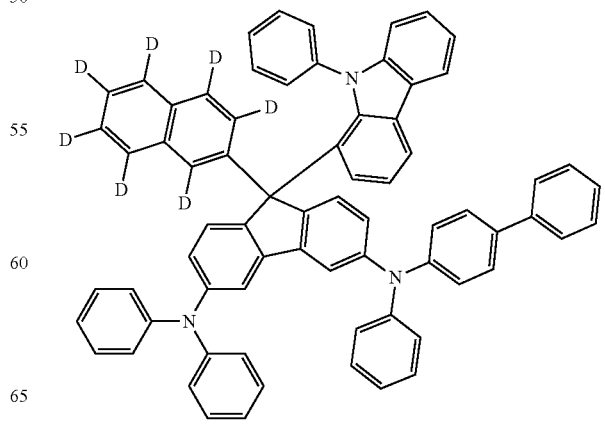

329
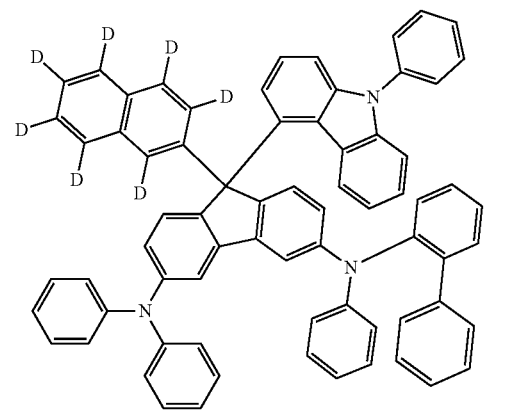
330
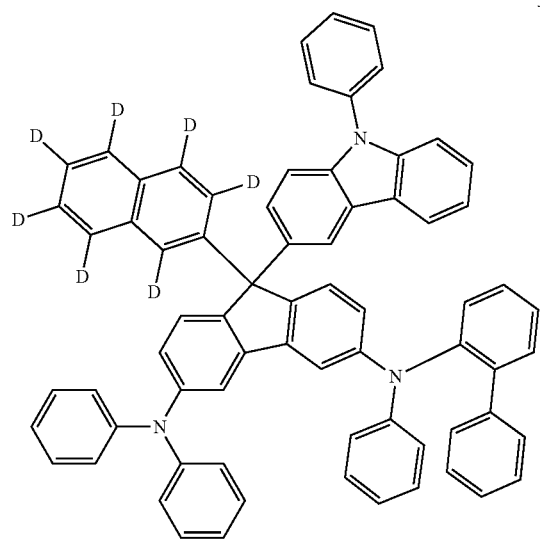
331
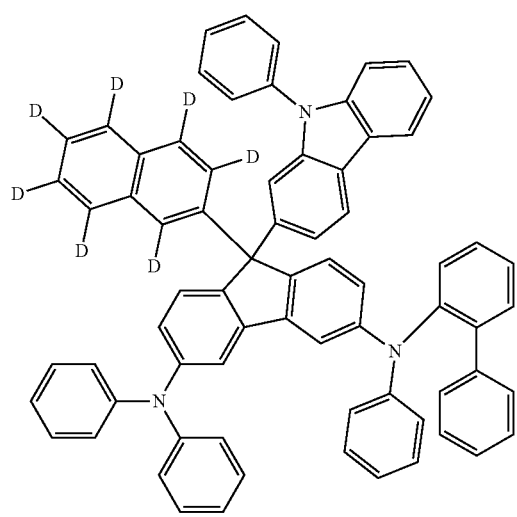
332
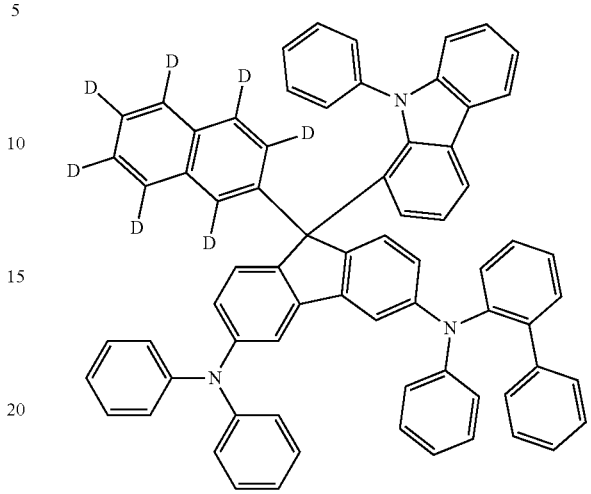
333
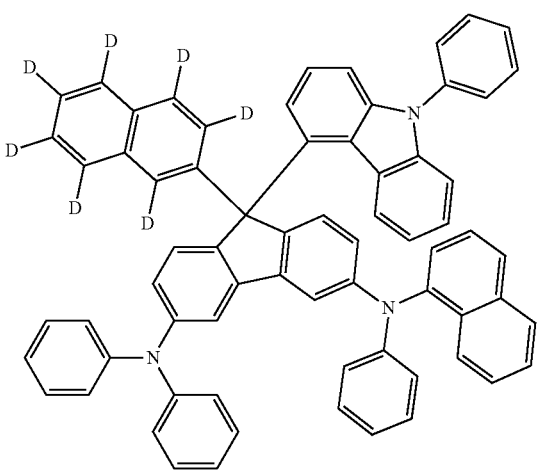
334
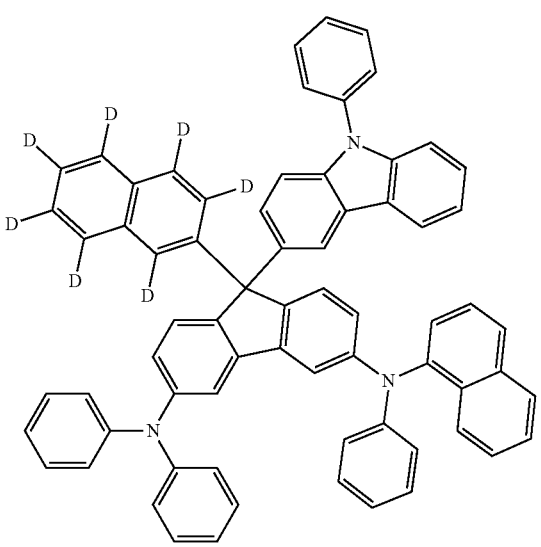

249
-continued
335
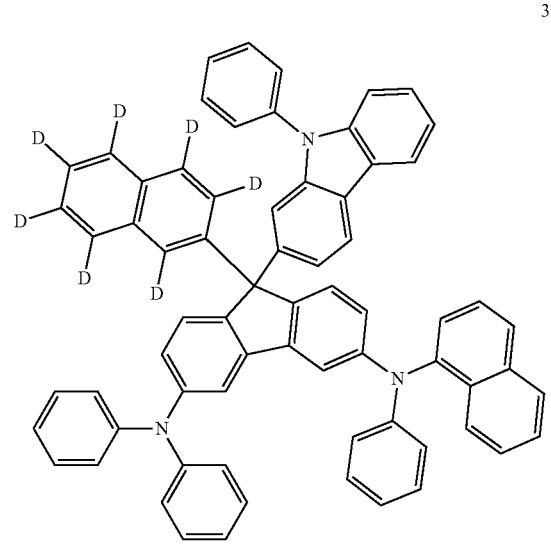
336
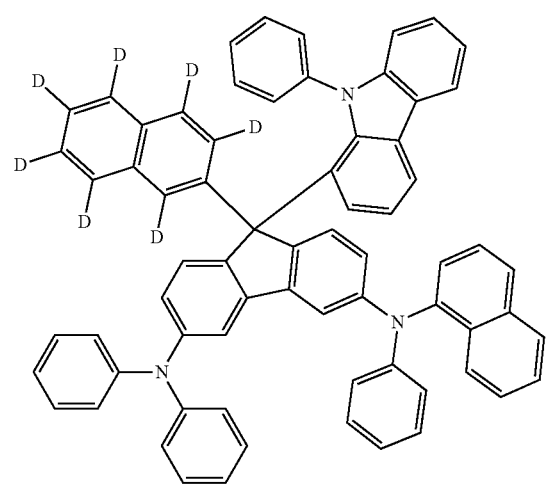
339
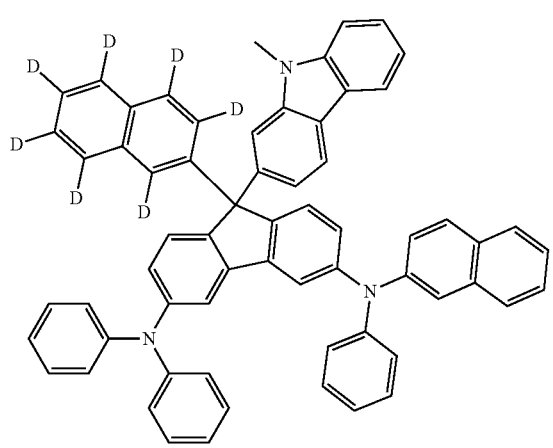
250
-continued
340
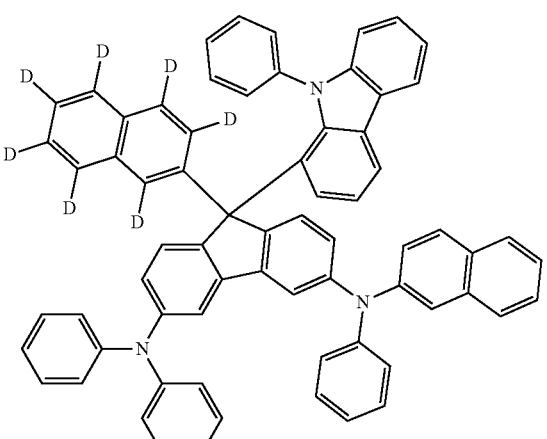
341
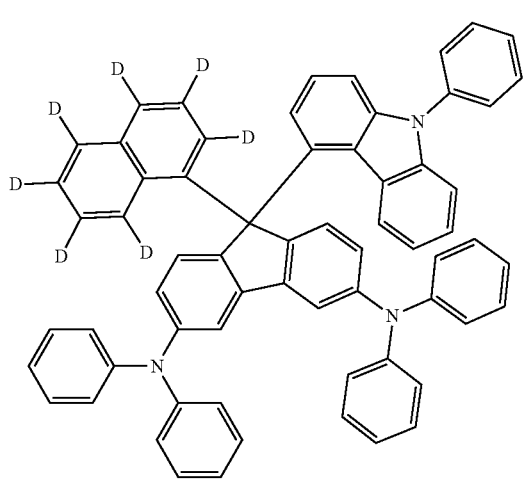
342
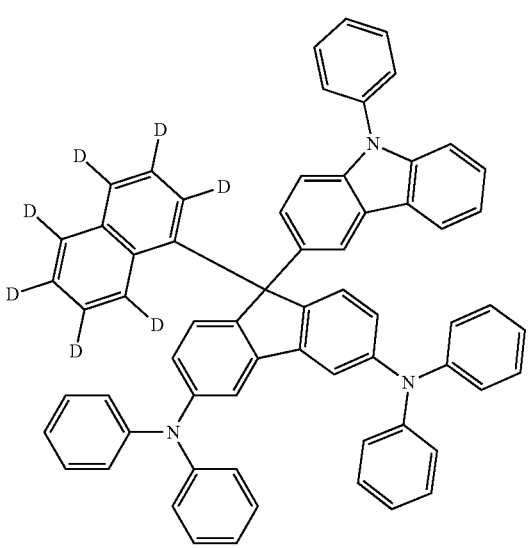

251
-continued
343
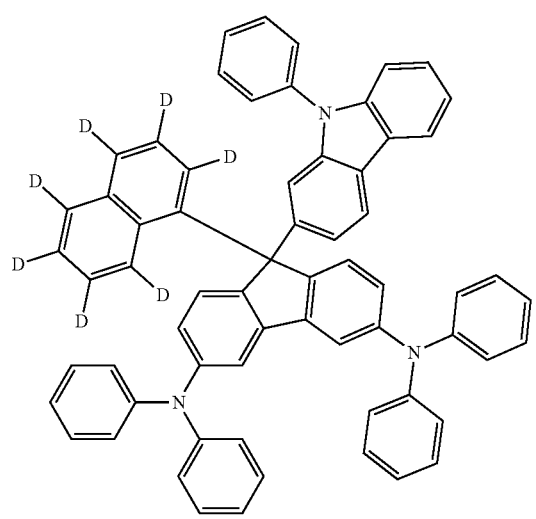
344
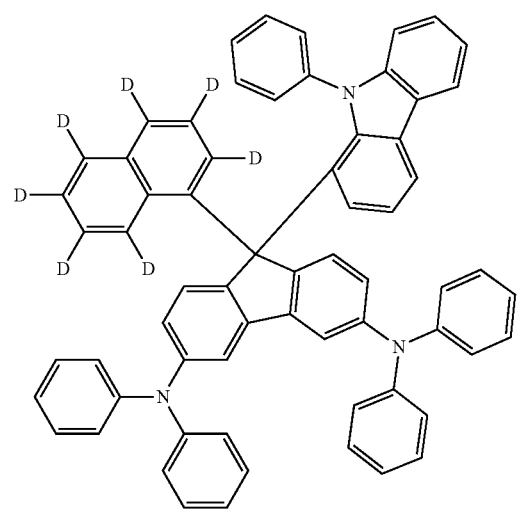
345
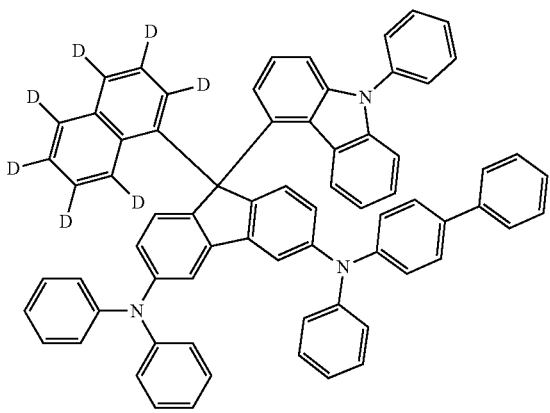
252
-continued
346
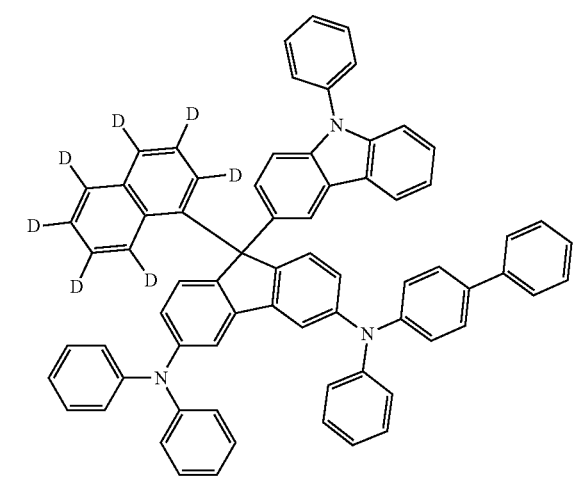
347
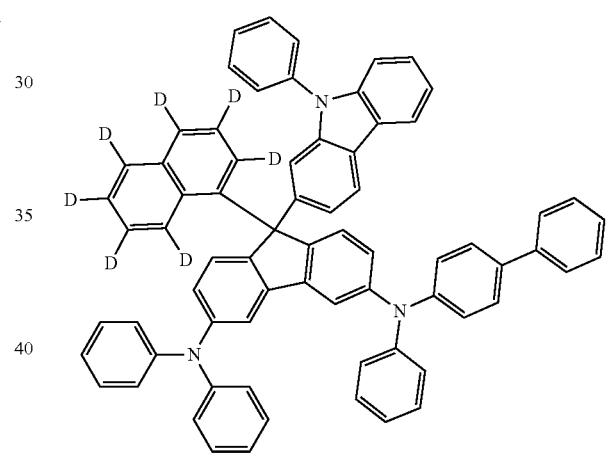
348
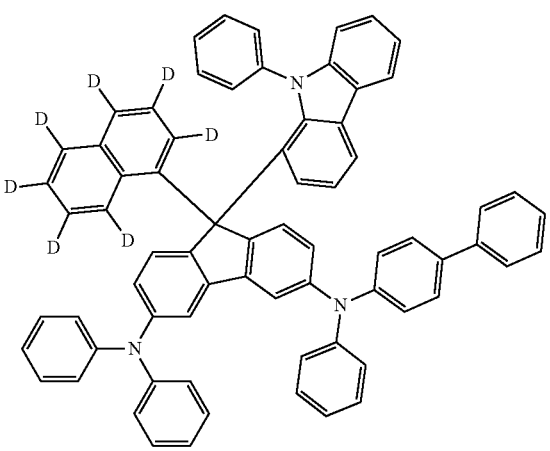

253
-continued
349
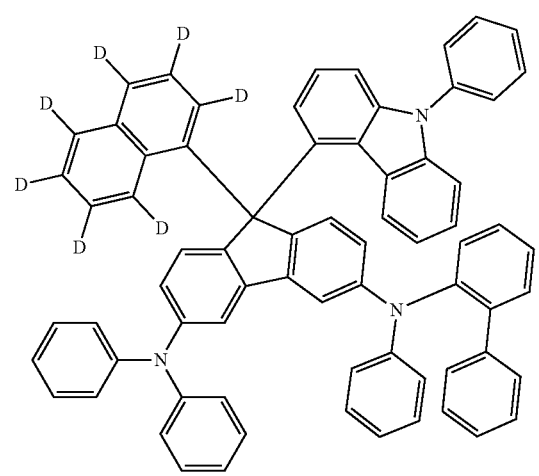
350
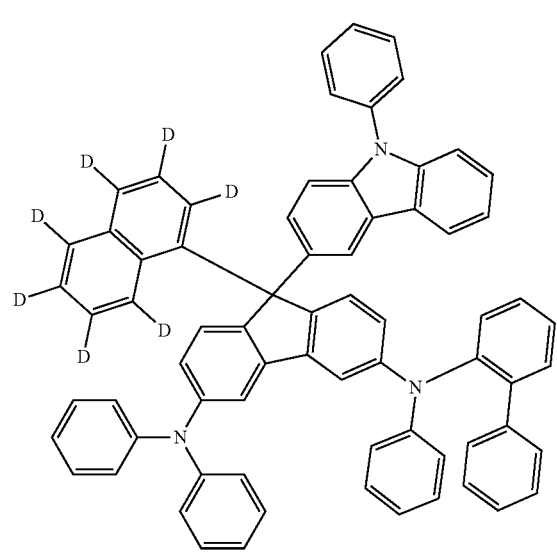
351
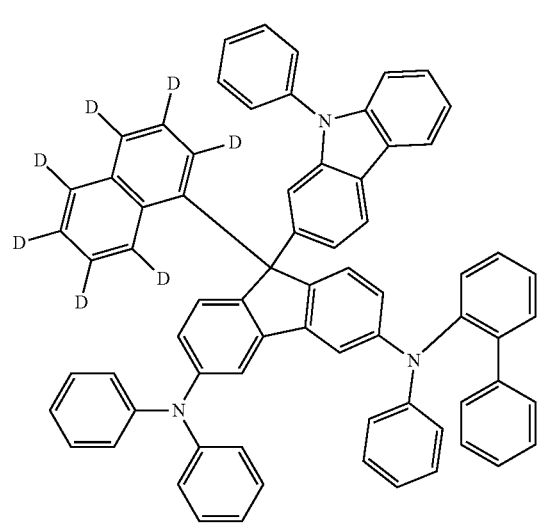
254
-continued
352
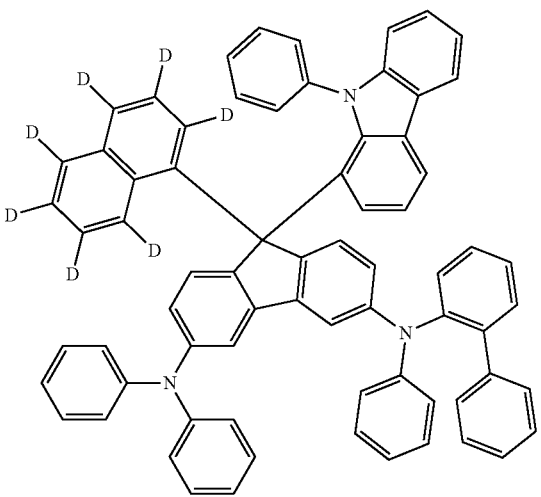
353
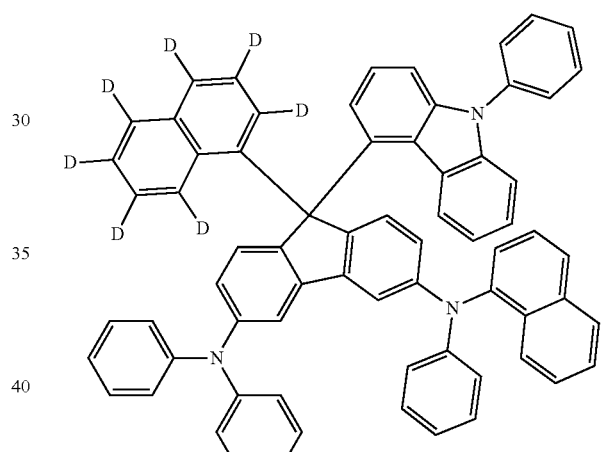
354
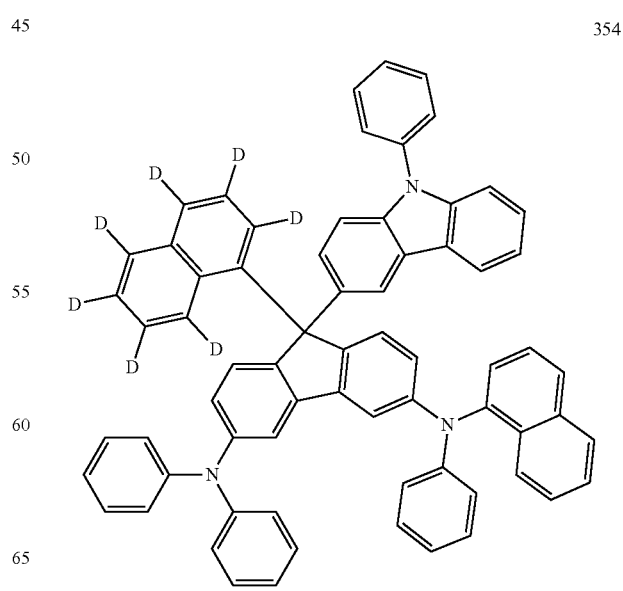

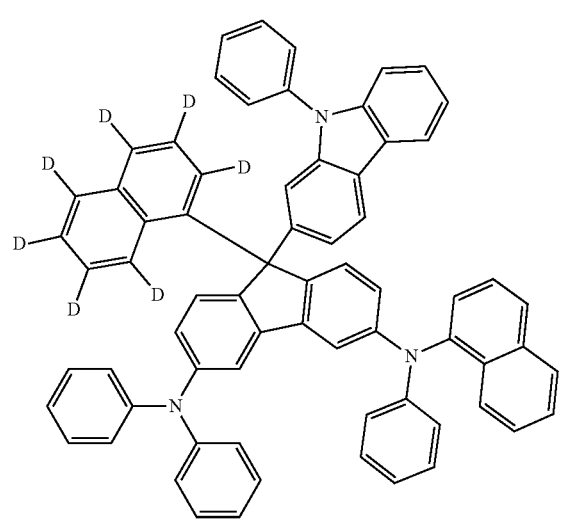
355
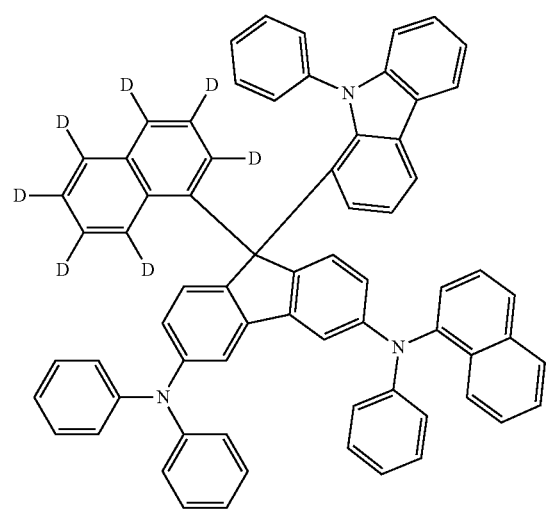
356
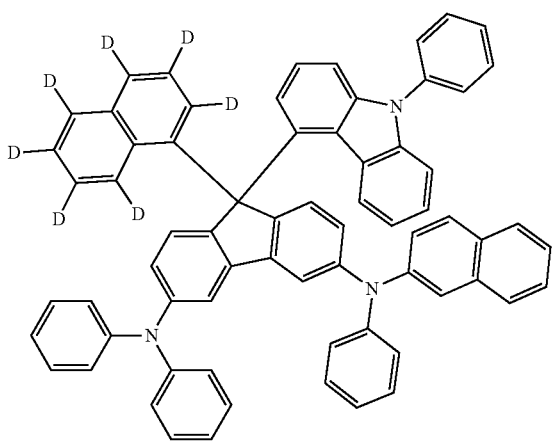
357
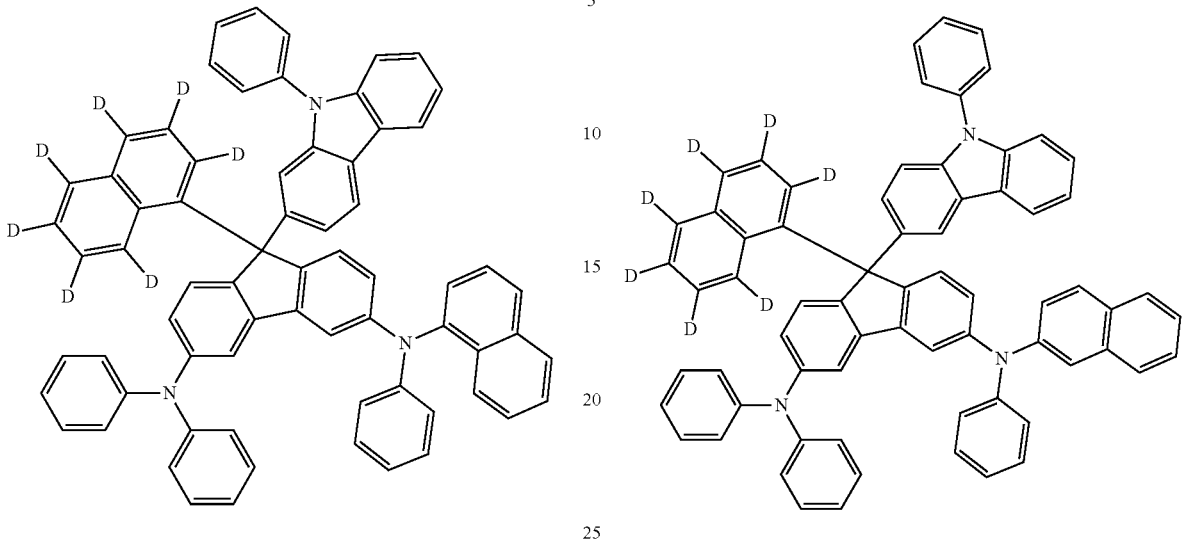
358
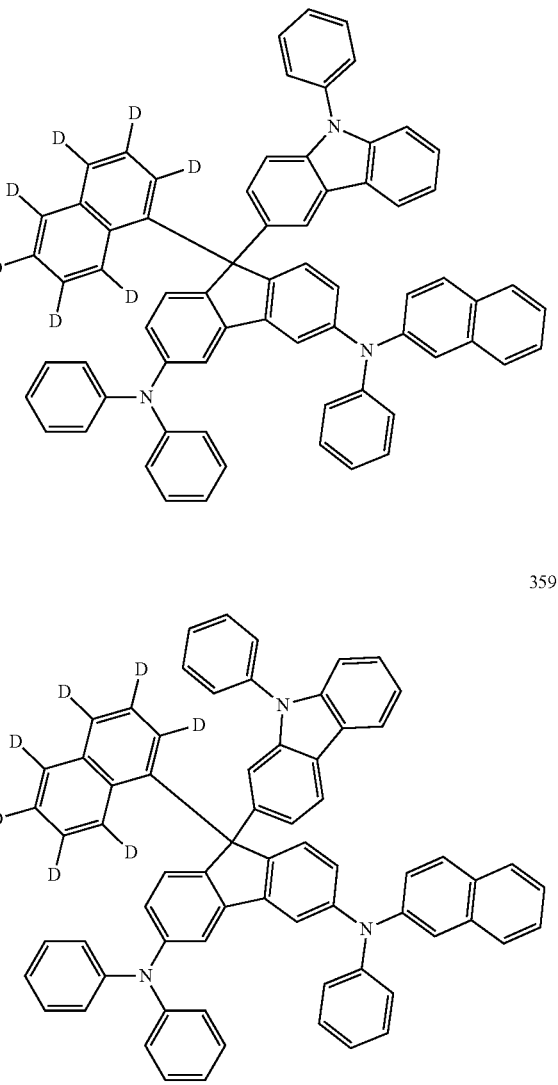
359
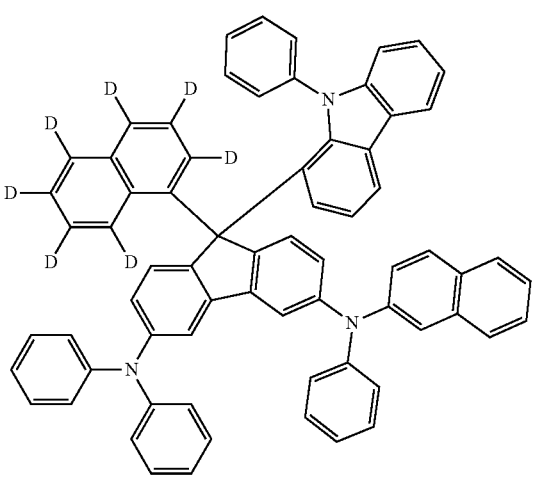
360

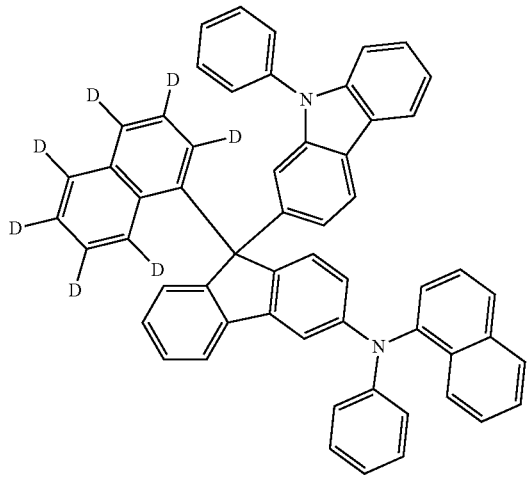

175

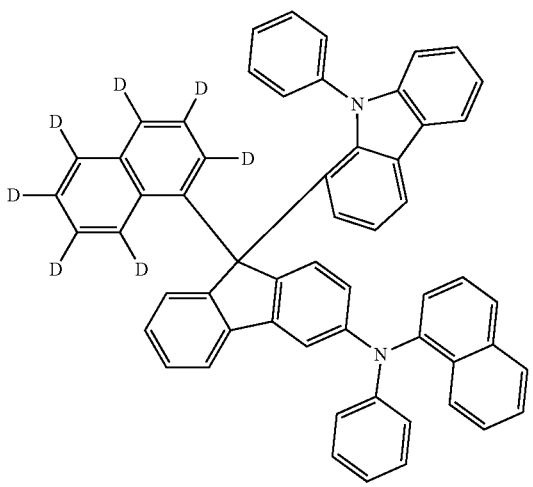

176

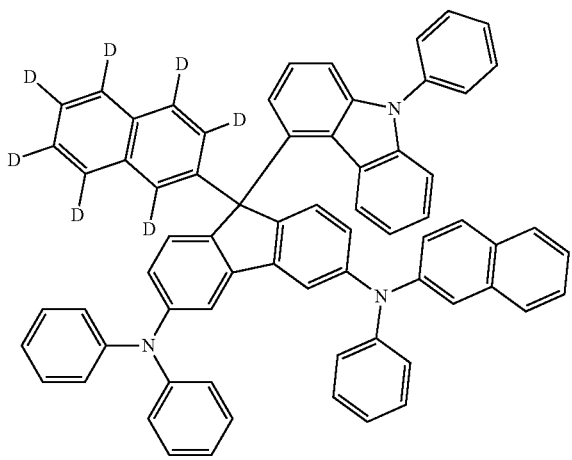

337

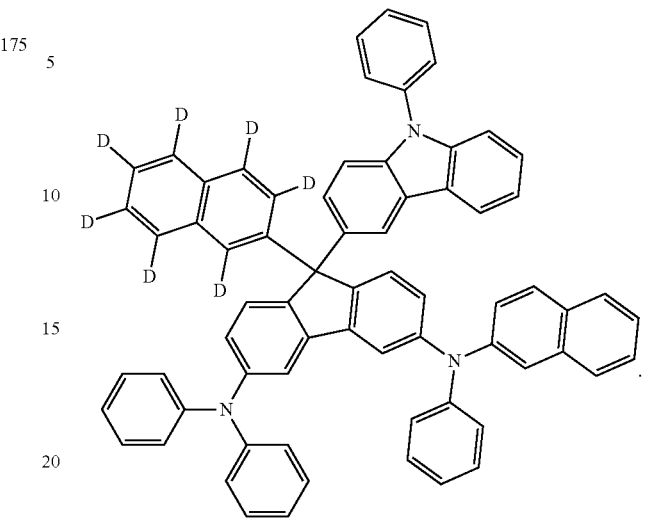

338

In the organic electroluminescence device 10 of an embodiment illustrated in FIGS. 1 to 4, the hole transport region HTR may include an amine compound represented by Formula 1. For example, the hole transport layer HTL and/or the hole injection layer HIL may include the amine compound represented by Formula 1 as a material. However, embodiments are not limited thereto.

The hole transport region HTR may include one or two or more of the amine compounds represented by Compound Group 1 as described above. The hole transport region HTR may further include any suitable material in the art, in addition to the above-described amine compounds.

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl)-N-phenylamino)-triphenylamine (2-TNATA), poly(3,4-ethylene dioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrene sulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives (such as N-phenyl carbazole and/or polyvinyl carbazole), fluorene derivatives, N,N'-bis(3-methylphenyl)-N,N'-diphenyl-[1,1-biphenyl]-4,4'-diamine (TPD), triphenylamine derivatives (such as 4,4',4"-tris(N-carbazolyl)triphenylamine (TCTA)), N,N'-di(naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-Bis(N-carbazolyl)benzene (mCP), etc.

The thickness of the hole transport region HTR may be about 100 Å to about 10,000 Å, for example, about 100 Å to about 5,000 Å. The thickness of the hole injection layer HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without a substantial increase in driving voltage.

The hole transport region HTR may further include, in addition to the above-described materials, a charge generating material to increase conductivity. The charge generating material may be dispersed substantially uniformly or non-uniformly in the hole transport region HTR. The charge generating material may be, for example, a p-dopant. The p-dopant may be a quinone derivative, metal oxide, and/or cyano group-containing compound, but is not limited thereto. Non-limiting examples of the p-dopant include, but are not limited to, quinone derivatives (such as tetracyanoquinodimethane (TCNQ) and/or 2,3,5,6-tetrafluoro-tetracyanoquinodimethane (F4-TCNQ)), and metal oxides (such as tungsten oxides and/or molybdenum oxides).

The hole transport region HTR may further include at least one of a hole buffer layer or an electron blocking layer EBL, in addition to the hole injection layer HIL and the hole transport layer HTL. The hole buffer layer may compensate for a resonance distance of the wavelength of light emitted from an emission layer EML to increase light emission efficiency. Materials included in the hole transport region HTR may also be included in the hole buffer layer. The electron blocking layer EBL may prevent or reduce electrons from being injected from the electron transport region ETR to the hole transport region HTR.

The emission layer EML is provided on the hole transport region HTR. The thickness of the emission layer EML may be, for example, about 100 Å to about 1000 Å, or about 100 Å to about 300 Å. The emission layer EML may have a single layer formed of a single material, a single layer formed of a plurality of different materials, or a multilayer structure having a plurality of layers formed of a plurality of different materials.

In the organic electroluminescence device 10 of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include anthracene derivatives and/or pyrene derivatives.

The emission layer EML may include anthracene derivatives represented by Formula A:

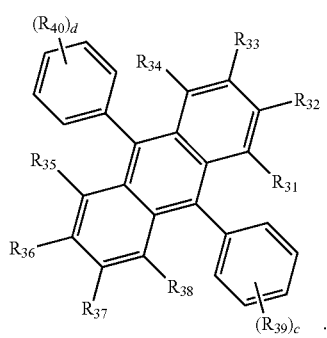

Formula A

In Formula A, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In some embodiments, $R_{31}$ to $R_{40}$ may be bonded to an adjacent group to form a saturated hydrocarbon ring or an unsaturated hydrocarbon ring.

In Formula A, c and d may each independently be an integer of 0 to 5.

Formula A may be represented by at least one of Compound 4-1 to Compound 4-6:

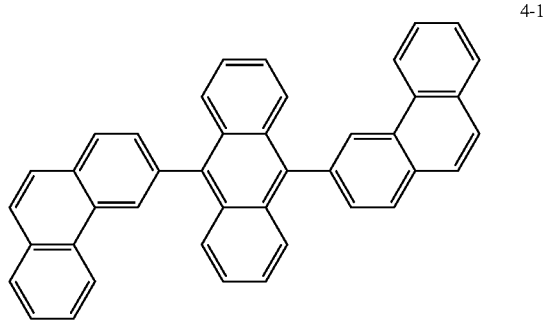

4-1

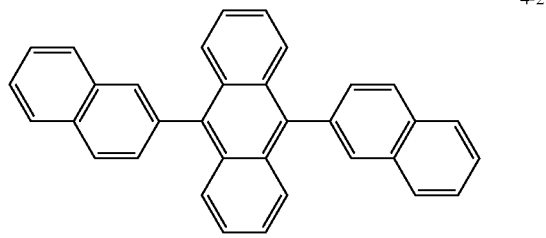

4-2

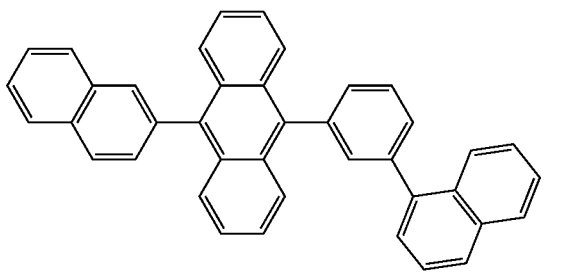

4-3

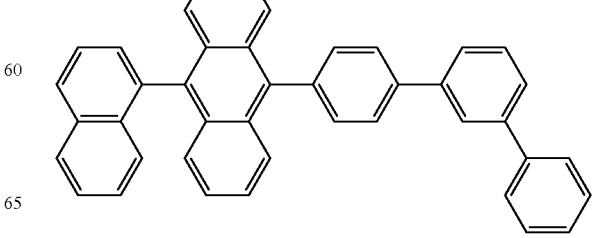

4-4

-continued

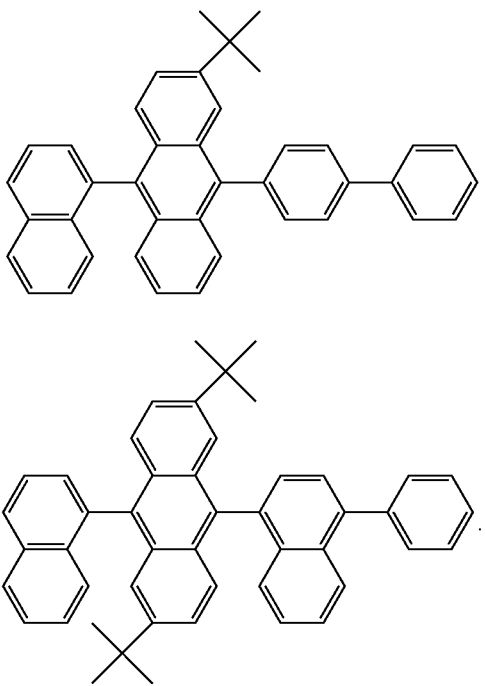

4-5

4-6

The emission layer EML may further include any suitable material in the art as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-Bis(diphenylphosphoryl)dibenzo[b,d]furan (PPF), 4,4',4"-tris(carbazol-9-yl)-triphenylamine (TcTa), or 1,3,5-tris(1-phenyl-1H-benzo[d]imidazole-2-yl)benzene (TPBi). However, embodiments are not limited thereto, and for example, tris(8-hydroxyquinolino)aluminum ($Alq_3$), 4,4'-bis(N-carbazolyl)-1,1'-biphenyl (CBP), poly(n-vinylcarbazole (PVK), 9,10-di(naphthalene-2-yl)anthracene (ADN), 4,4',4"-tris(carbazol-9-yl)-triphenylamine (TcTa), 1,3,5-tris(N-phenylbenzimidazol-2-Abenzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be used as a host material.

In an embodiment, the emission layer EML may include, as a dopant material, styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), 4,4'-bis[2-(4-(N,N-diphenylamino)phenyl)vinyl]biphenyl (DPAVBi) etc.

The emission layer EML may include any suitable phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), and/or thulium (Tm) may be used as a phosphorescence dopant. For example, iridium(III) bis(4,6-difluorophenylpyridinato-N,C2') (Flrpic), bis(2,4-difluorophenylpyridinato) (Fir6), and/or platinum octaethyl porphyrin (PtOEP) may be used as a phosphorescence dopant. However, embodiments are not limited thereto.

The emission layer EML may further include any suitable phosphorescence host material, for example, bis(4-(9H-carbazol-9-yl)phenyl)diphenylsilane (BCPDS).

When the emission layer EML is to emit red light, the emission layer EML may further include, for example, a fluorescent material (such as tris(dibenzoylmethanato) phenanthroline europium ($PBD:Eu(DBM)_3(Phen)$) and/or perylene). When the emission layer EML is to emit red light, a dopant included in the emission layer EML may be, for example, a metal complex or organometallic compound (such as bis(1-phenylisoquinoline) acetylacetonate iridium (PIQIr(acac)), bis(1-phenylquinoline) acetylacetonate iridium (PQIr(acac)), tris(1-phenylquinoline) iridium (PQIr), and/or octaethylporphyrin platinum (PtOEP)), rubrene and derivatives thereof, and/or 4-dicyanomethylene-2-(p-dimethylaminostyryl)-6-methyl-4H-pyran (DCM) and derivatives thereof.

When the emission layer EML is to emit green light, the emission layer EML may further include, for example, a fluorescent material (such as tris(8-hydroxyquinolino) aluminum ($Alq_3$)). When the emission layer EML is to emit green light, a dopant included in the emission layer EML may be, for example, a metal complex or organometallic compound (such as fac-tris(2-phenylpyridine) iridium (Ir$(ppy)_3$)), and/or coumarins and derivatives thereof.

When the emission layer EML is to emit blue light, the emission layer EML may further include, for example, a fluorescent material including any one selected from the group consisting of spiro-DPVBi, spiro-6P, distyryl-benzene (DSB), distyryl-arylene (DSA), polyfluorene (PFO)-based polymer, and poly(p-phenylene vinylene) (PPV)-based polymer. When the light emitting layer EML is to emit blue light, a dopant included in the emission layer EML may be selected from a metal complex or organometallic compound (such as $(4,6-F2ppy)_2Irpic$), perylene and derivatives thereof, etc.

In the organic electroluminescence device 10 of an embodiment illustrated in FIGS. 1 to 4, the electron transport region ETR is provided on the emission layer EML. The electron transport region ETR may include at least one of a hole blocking layer HBL, an electron transport layer ETL, or an electron injection layer EIL, but embodiments are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, or may have a single layer structure formed of an electron injection material and an electron transport material. In some embodiments, the electron transport region ETR may have a single layer structure formed of a plurality of different materials, or may have a structure in which an electron transport layer ETL/electron injection layer EIL and a hole blocking layer HBL/electron transport layer ETL/electron injection layer EIL are stacked in order from the emission layer EML, but is not limited thereto. The thickness of the electron transport region ETR may be, for example, about 1000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, a laser induced thermal imaging (LITI) method, etc.)

When the electron transport region ETR includes an electron transport layer ETL, the electron transport region ETR may include an anthracene-based compound. However, embodiments are not limited thereto, and the electron transport region may include, for example, tris(8-hydroxyquinolinato)aluminum (Alq$_3$), 1,3,5-tri[(3-pyridyl)-phen-3-yl]benzene, 2,4,6-tris(3-(pyridin-3-yl)biphenyl-3-yl)-1,3,5-triazine, 2-(4-(N-phenylbenzimidazolyl-1-yl phenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate) (Bebq2), 9,10-di(naphthalene-2-yl)anthracene (ADN), 1,3-Bis[3,5-di(pyridin-3-yl)phenyl]benzene (BmPyPhB), or a mixture thereof. The thickness of the electron transport layers ETL may be about 100 Å to about 1,000 Å, for example, about 150 Å to about 500 Å. When the thickness of the electron transport layers ETL satisfies the above-described range, satisfactory electron transport characteristics may be obtained without a substantial increase in driving voltage.

When the electron transport region ETR includes the electron injection layer EIL, the electron transport region ETR may be formed using a metal halide (such as LiF, NaCl, CsF, RbCl, RbI, and/or CuI), a lanthanide metal (such as Yb), a metal oxide (such as Li$_2$O and/or BaO), or lithium quinolate (Liq), etc., but embodiments of the present disclosure are not limited thereto. The electron injection layer EIL may also be formed of a mixture of an electron transport material and an insulating organo-metal salt. The organometal salt may be a material having an energy band gap of about 4 eV or more. In some embodiments, the organo-metal salt may include, for example, metal acetates, metal benzoates, metal acetoacetates, metal acetylacetonates and/or metal stearates. The thickness of the electron injection layers EIL may be about 1 Å to about 100 Å, and about 3 Å to about 90 Å. When the thickness of the electron injection layers EIL satisfies the above-described range, satisfactory electron injection properties may be obtained without a substantial increase in driving voltage.

The electron transport region ETR may include a hole blocking layer HBL as described above. The hole blocking layer HBL may include, for example, at least one of 2,9-dimethyl-4,7-diphenyl-1,10-phenanthroline (BCP) or 4,7-diphenyl-1,10-phenanthroline (Bphen), but is not limited thereto.

The second electrode EL2 is provided on the electron transport region ETR. The second electrode EL2 may be a common electrode and/or a negative electrode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, L$_1$, Ca, LiF/Ca, LiF/Al, Mo, Ti, a compound thereof, or a mixture thereof (for example, a mixture of Ag and Mg). In some embodiments, the first electrode EL1 may have a multilayer structure including a reflective layer or a transflective layer formed of the above-described materials, and a transparent conductive layer formed of ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, a capping layer CPL may be further disposed on the second electrode EL2 of the organic electroluminescence device 10 according to an embodiment. The capping layer CPL may include, for example, α-NPD, NPB, TPD, m-MTDATA, Alq$_3$, CuPc, N4,N4, N4',N4'-tetra(biphenyl-4-yl) biphenyl-4,4'-diamine (TPD15), 4,4',4"-tris(carbazol sol-9-yl) triphenylamine (TCTA), etc.

The amine compound of an embodiment described above may be included in one or more organic layers, as well as in the hole transport region HTR as a material for the organic electroluminescence device 10. The organic electroluminescence device 10 of an embodiment of the present disclosure may also include the above-described amine compound in at least one organic layer disposed between the first electrode EL1 and the second electrode EL2, or the capping layer CPL disposed on the second electrode EL2.

Hereinafter, with reference to Examples and Comparative Examples, an amine compound according to an embodiment of this present disclosure and an organic electroluminescence device of an embodiment will be described in more detail. The Examples below are provided only for the understanding of this present disclosure, and the scope of the present disclosure is not limited thereto.

Synthesis of Amine Compound

An amine compound according to an embodiment of the present disclosure may be synthesized, for example, as follows. However, a synthetic method of the amine compound according to an embodiment of the present disclosure is not limited thereto.

1. Synthesis of Compound 4

Reaction Formula 1

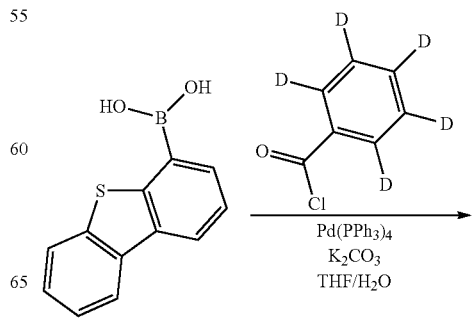

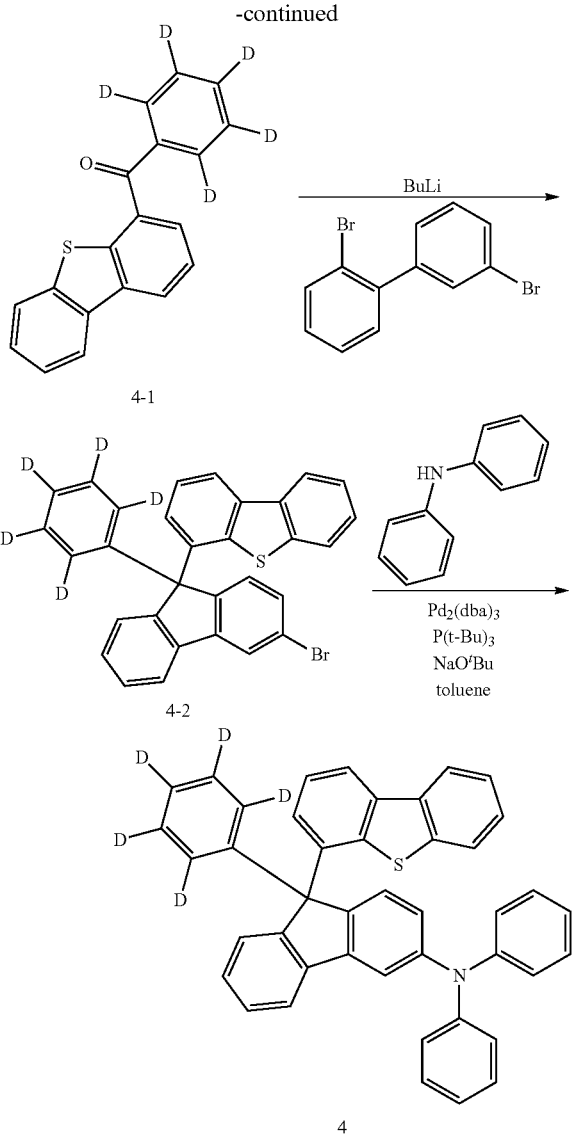

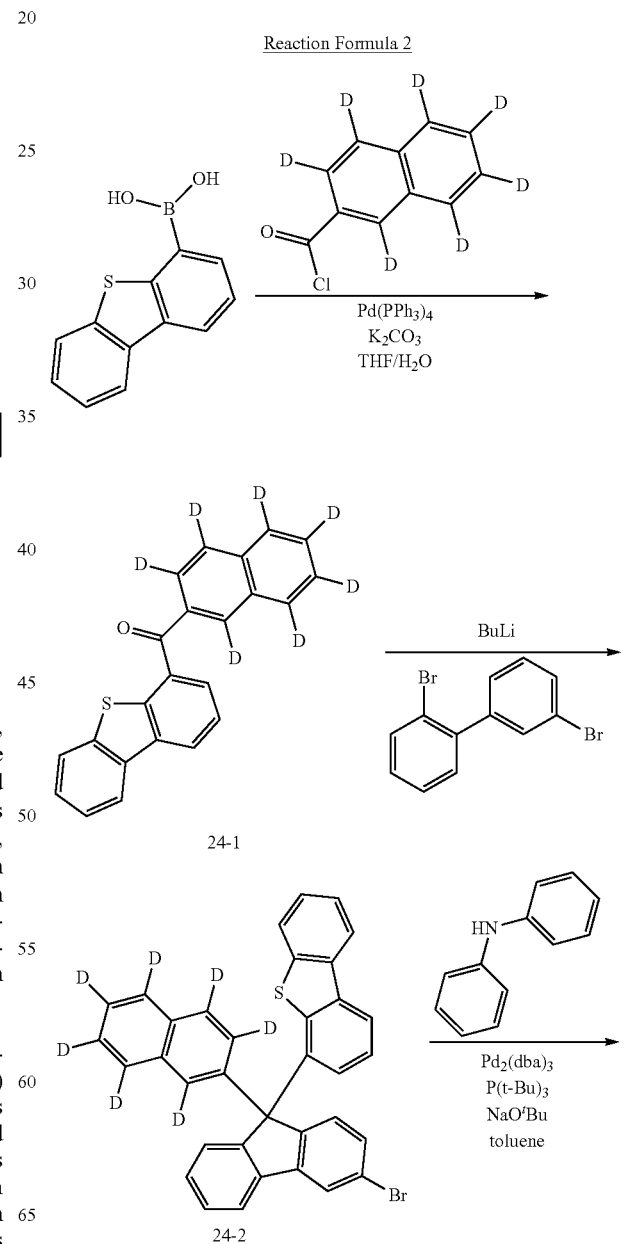

1-1. Synthesis of Intermediate Compound 4-1

Dibenzo[b,d]thiophen-4-ylboronic acid (2.28 g), Pd(PPh$_3$)$_4$ (0.56 g), K$_2$CO$_3$ (3.45 g), and benzoyl-d$^5$ chloride (1.88 g) were dissolved in THF/H$_2$O (100 mL/25 mL), and then stirred at 80° C. for 12 hours. This reaction solution was cooled to room temperature and then quenched with water, followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4-1 (1.85 g, yield: 63%).

1-2. Synthesis of Intermediate Compound 4-2

Compound 2,3'-dibromo-1,1'-biphenyl (3.12 g) was dissolved in THF (50 mL), and then 2.5 M n-BuLi (4.8 mL) was added dropwise at −78° C. Compound 4-1 (2.93 g) was dissolved in THF (50 mL), and then the mixture was added dropwise to the prepared solution. The resultant mixture was stirred at −78° C. for 1 hour, and then stirred at room temperature for 2 hours. The reaction was quenched with water followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4-2 (4.07 g, yield: 60%).

1-3. Synthesis of Compound 4

Compound 4-2 (5.08 g), diphenylamine (1.69 g), Pd$_2$(dba)$_3$ (0.46 g), P(t-Bu)$_3$ (0.21 g), and NaOtBu (2.44 g) were dissolved in toluene (50 mL), and then stirred at 80° C. for 1 hour. This reaction solution was cooled to room temperature and then quenched with water, followed by extracting an organic layer three times with ethyl ether. The separated organic layer was dried with anhydrous magnesium sulfate and distilled at reduced pressure to obtain residues. The obtained residues were separated and purified by column chromatography to obtain Compound 4 (4.24 g, yield: 71%).

2. Synthesis of Compound 24

Reaction Formula 2

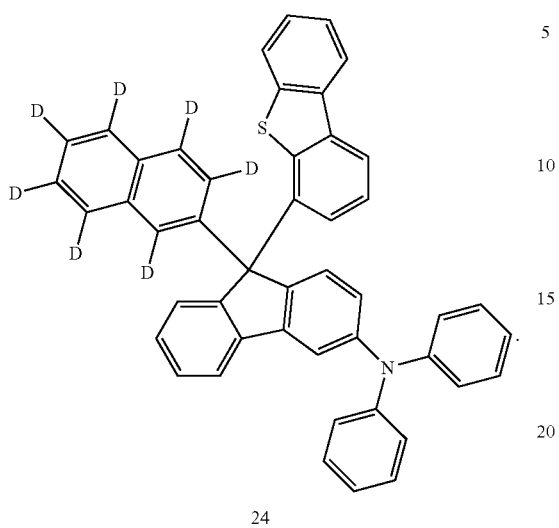

24

Compound 24 was obtained by performing substantially the same method as the synthetic method of Compound 4, except that 2-naphthoyl-d$^7$ chloride (1.97 g) was used instead of benzoyl-d$^5$ chloride (4.98 g, yield: 77%).

3. Synthesis of Compound 64

Reaction Formula 3

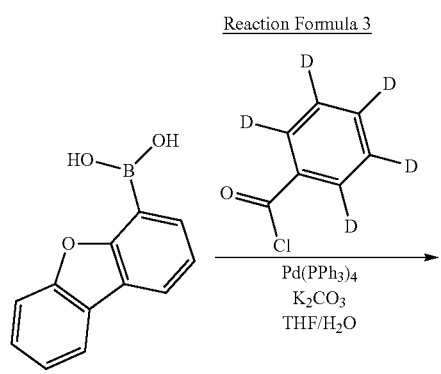

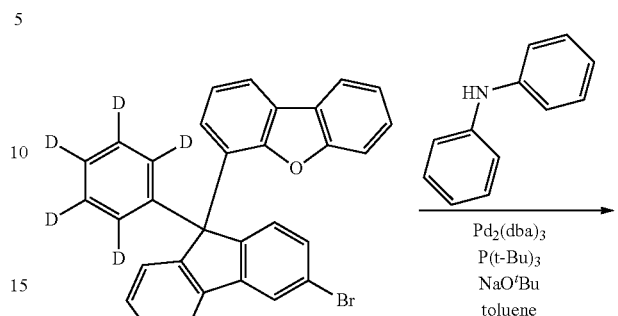

64-2

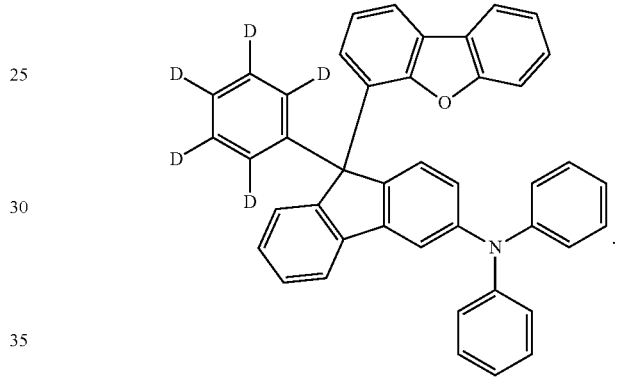

64

Compound 64 was obtained by performing substantially the same method as the synthetic method of Compound 4, except that dibenzo[b,d]furan-4-ylboronic acid (2.12 g) was used instead of dibenzo[b,d]thiophen-4-ylboronic acid (4.06 g, yield: 70%).

4. Synthesis of Compound 84

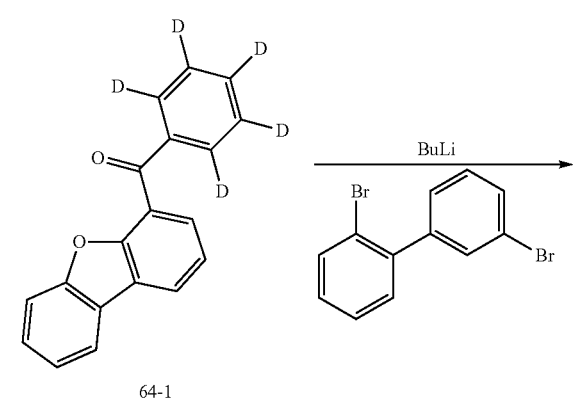

64-1

Reaction Formula 4

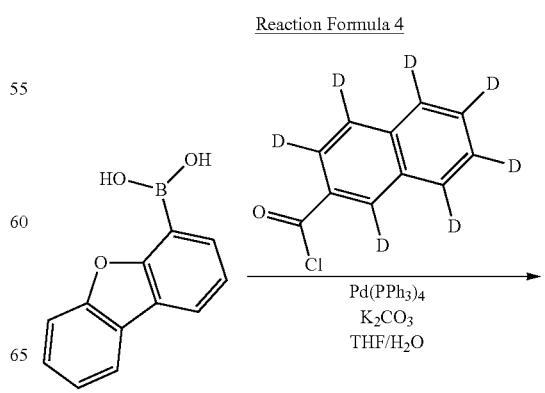

5. Synthesis of Compound 124

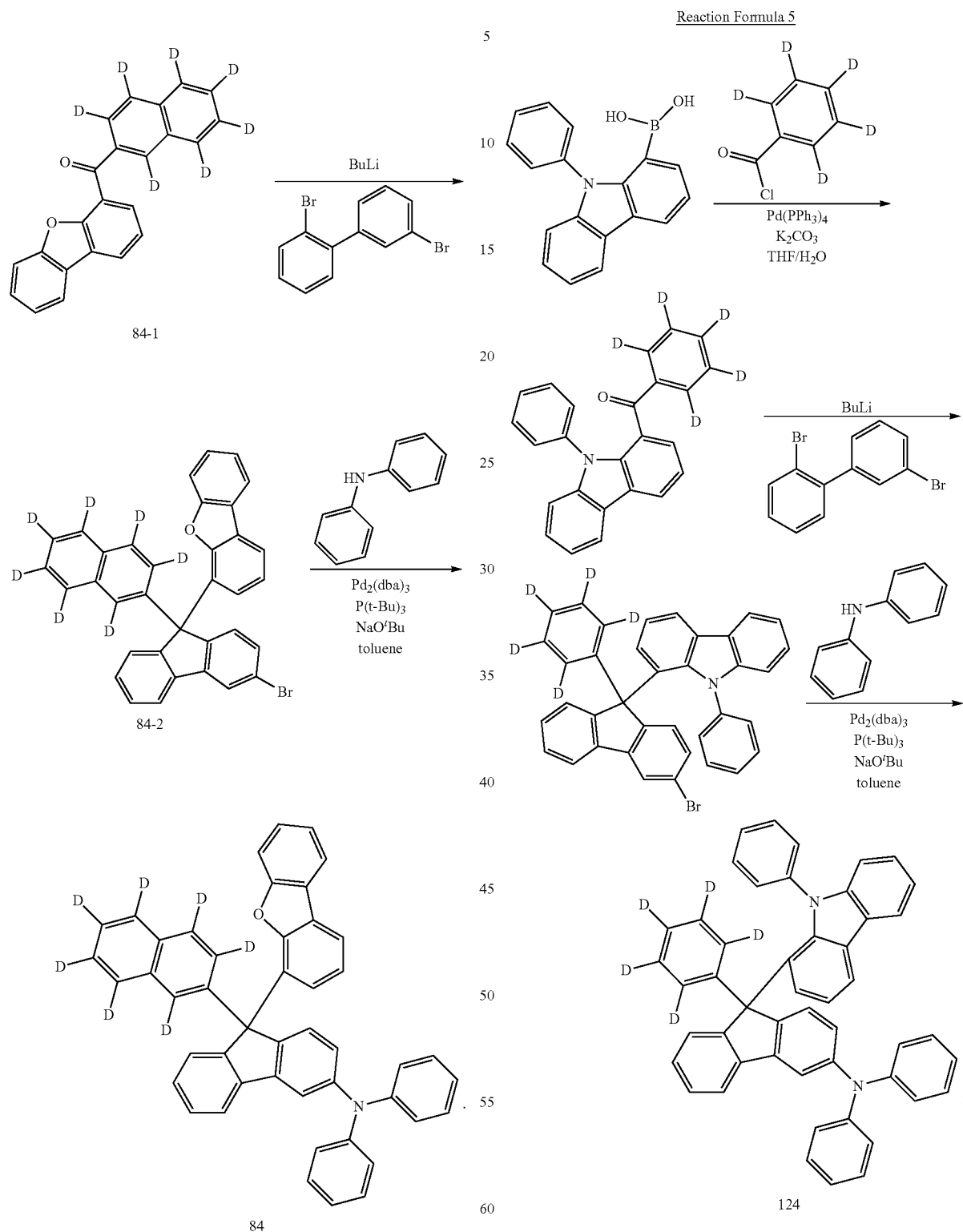

Compound 84 was obtained by performing substantially the same method as the synthetic method of Compound 64, except that 2-naphthoyl-d[7] chloride (1.97 g) was used instead of benzoyl-d[5] chloride (4.23 g, yield: 67%).

Compound 124 was obtained by performing substantially the same method as the synthetic method of Compound 4, except that (9-phenyl-9H-carbazol-1-yl)boronic acid (2.87 g) was used instead of dibenzo[b,d]thiophen-4-ylboronic acid (4.25 g, yield: 65%).

6. Synthesis of Compound 144

7. Synthesis of Compound 184

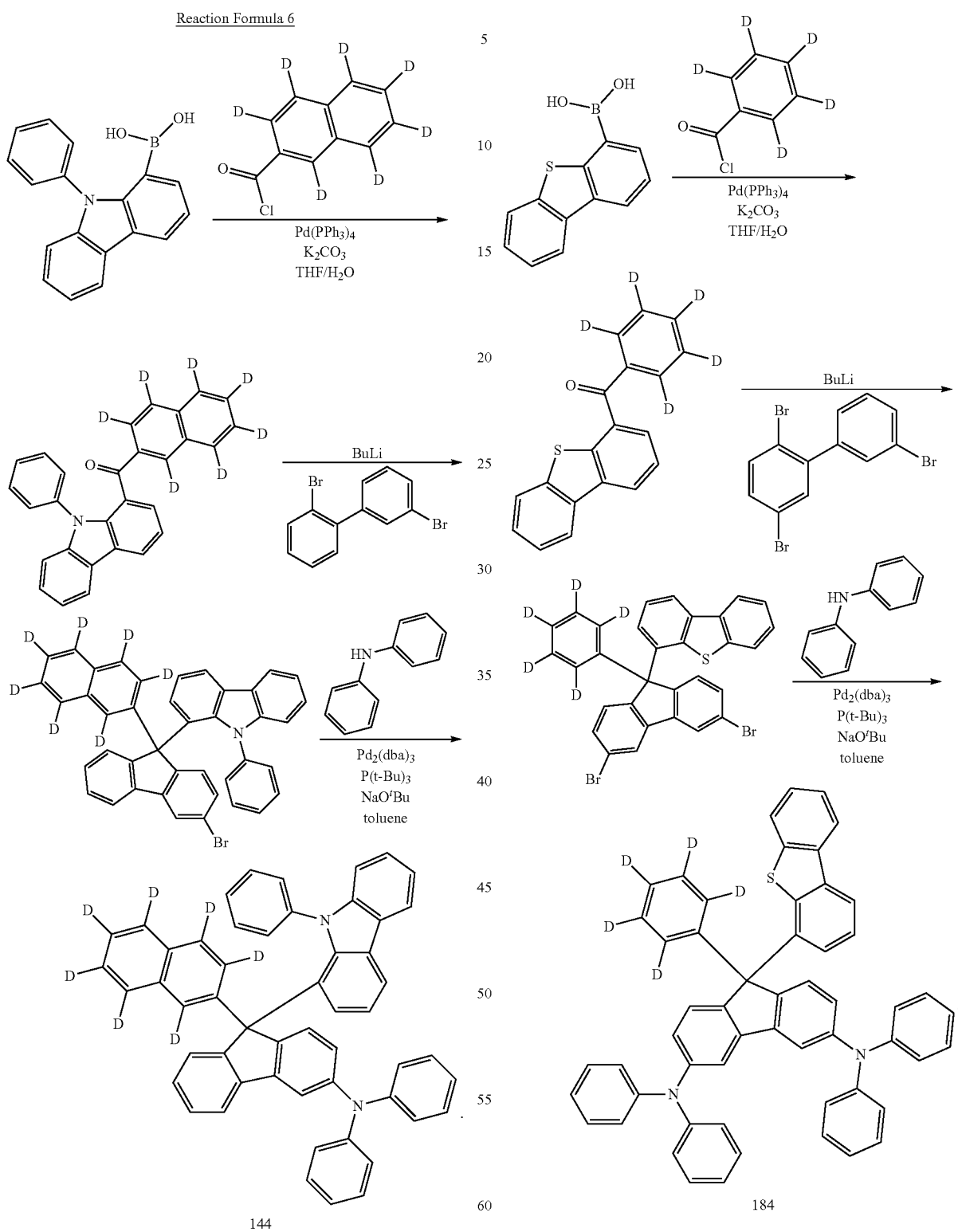

Compound 144 was obtained by performing substantially the same method as the synthetic method of Compound 124, except that 2-naphthoyl-$d^7$ chloride (1.97 g) was used instead of benzoyl-$d^5$ chloride (4.31 g, yield: 61%).

Compound 184 was obtained by performing substantially the same method as the synthetic method of Compound 4, except that 2,5,3'-tribromo-1,1'-biphenyl (3.12 g) was used instead of 2,3'-dibromo-1,1'-biphenyl; and diphenylamine, $Pd_2(dba)_3$, P(t-Bu)$_3$, and NaOtBu were used two times more (5.04 g, yield: 66%).

273
8. Synthesis of Compound 204
274
9. Synthesis of Compound 244
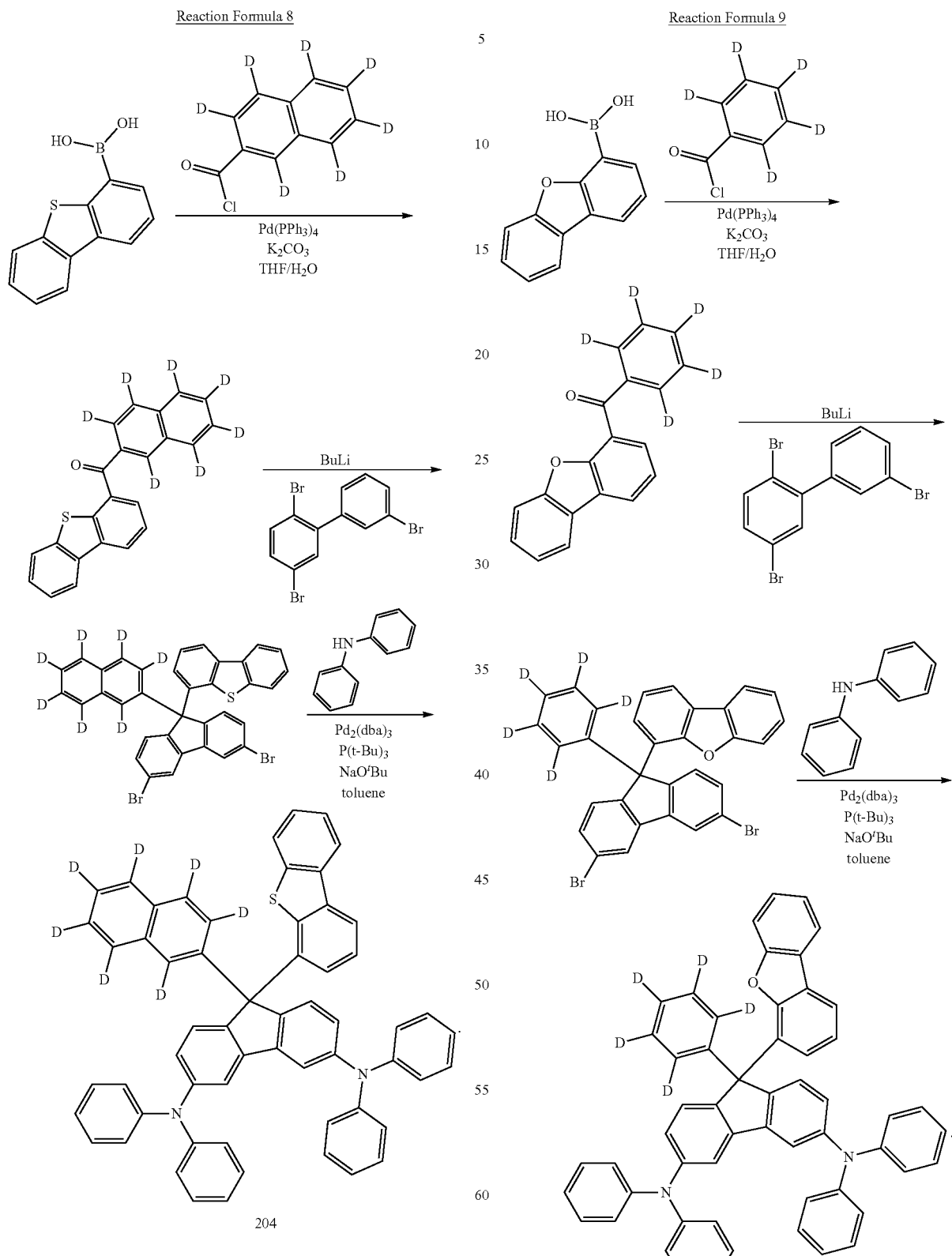
Compound 204 was obtained by performing substantially the same method as the synthetic method of Compound 184, except that 2-naphthoyl-$d^7$ chloride (1.97 g) was used instead of benzoyl-$d^5$ chloride (5.79 g, yield: 71%).

Compound 244 was obtained by performing substantially the same method as the synthetic method of Compound 184, except that dibenzo[b,d]furan-4-ylboronic acid (2.12 g) was used instead of dibenzo[b,d]thiophen-4-ylboronic acid (5.29 g, yield: 69%).

10. Synthesis of Compound 264

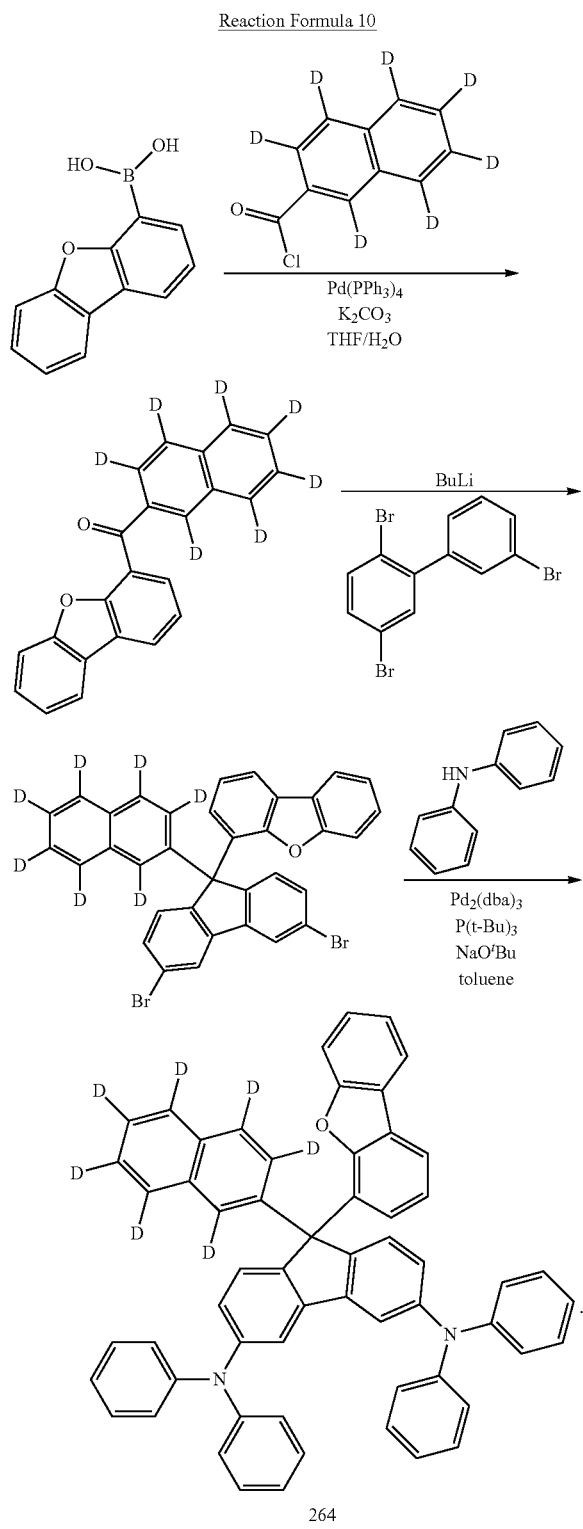

Compound 204 was obtained by performing substantially the same method as the synthetic method of Compound 184, except that 2-naphthoyl-$d^7$ chloride (1.97 g) was used instead of benzoyl-$d^5$ chloride (6.16 g, yield: 77%).

$^1$H NMR and MS/FAB of the Synthesized Compounds are shown in Table 1:

TABLE 1

| Compound number | $^1$H NMR | MS/FAB |
|---|---|---|
| Compound 4 | 8.45 (d, 1H), 8.35 (d, 1H), 7.93-7.90 (dd, 2H), 7.62-7.49 (m, 6H), 7.38 (dd, 1H), 7.28-7.24 (m, 6H), 7.08-7.00 (m, 7H) | 597.23 |
| Compound 24 | 8.45 (d, 1H), 8.35 (d, 1H), 7.93-7.90 (dd, 2H), 7.62-7.49 (m, 6H), 7.38 (dd, 1H), 7.28-7.24 (m, 6H), 7.08-7.00 (m, 7H) | 649.26 |
| Compound 64 | 7.98 (d, 1H), 7.90-7.88 (d, 2H), 7.62 (s, 1H), 7.55-7.50 (m, 3H), 7.38-7.24 (m, 9H), 7.09-7.00 (m, 8H) | 581.26 |
| Compound 84 | 7.98 (d, 1H), 7.90-7.88 (d, 2H), 7.62 (s, 1H), 7.55-7.50 (m, 3H), 7.38-7.24 (m, 9H), 7.09-7.00 (m, 8H) | 633.28 |
| Compound 124 | 8.45 (d, 1H), 8.19 (d, 1H) 7.90 (d, 1H), 7.62-7.50 (m, 10H), 7.38 (dd, 1H), 7.28-7.20 (m, 7H), 7.08-6.98 (m, 8H) | 656.30 |
| Compound 144 | 8.45 (d, 1H), 8.19 (d, 1H) 7.90 (d, 1H), 7.62-7.50 (m, 10H), 7.38 (dd, 1H), 7.28-7.20 (m, 7H), 7.08-6.98 (m, 8H) | 708.33 |
| Compound 184 | 8.45 (d, 1H), 8.35 (d, 1H), 7.93 (s, 1H), 7.62-7.49 (m, 7H), 7.28-7.24 (m, 9H), 7.08-7.00 (m, 14H) | 764.31 |
| Compound 204 | 8.45 (d, 1H), 8.35 (d, 1H), 7.93 (s, 1H), 7.62-7.49 (m, 7H), 7.28-7.24 (m, 9H), 7.08-7.00 (m, 14H) | 816.34 |
| Compound 244 | 7.98 (d, 1H), 7.88 (d, 1H), 7.62 (s, 2H), 7.51 (m, 3H), 7.39-7.24 (m, 11H), 7.09-7.00 (m, 15H) | 748.33 |
| Compound 264 | 7.98 (d, 1H), 7.88 (d, 1H), 7.62 (s, 2H), 7.51 (m, 3H), 7.39-7.24 (m, 11H), 7.09-7.00 (m, 15H) | 800.36 |

(Manufacture and Evaluation of Organic Electroluminescence Device Including Amine Compound)

The emission characteristics of organic electroluminescence devices including the amine compound of an embodiment in a hole transport region were evaluated as follows. The method for manufacturing the organic electroluminescence device for the evaluation of the device is described below.

The amine compounds of Compounds 4, 24, 64, 84, 124, 144, 184, 204, 244 and 264 as described above were used as hole transport layer materials to manufacture the organic electroluminescence devices of examples 1 to 10. Comparative Examples 1 to 4 are the organic electroluminescence devices manufactured by using each of Comparative Example Compounds C1, C2, C3, and C4 as a hole transport region material.

Compounds used in Examples 1 to 10 and Comparative Examples 1 to 4 are as follows.
Example Compounds
4
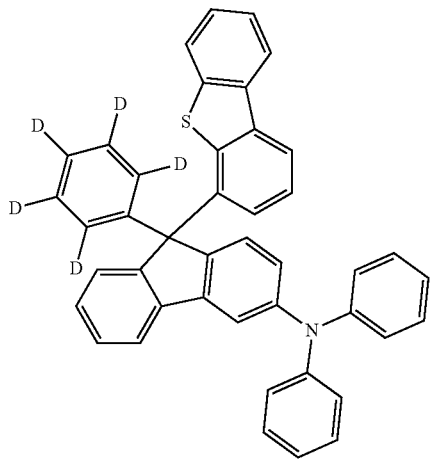
84
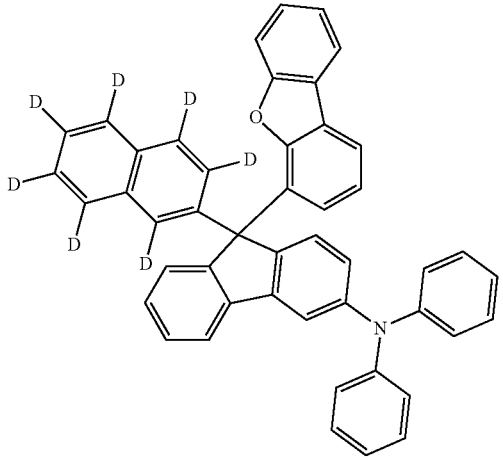
24
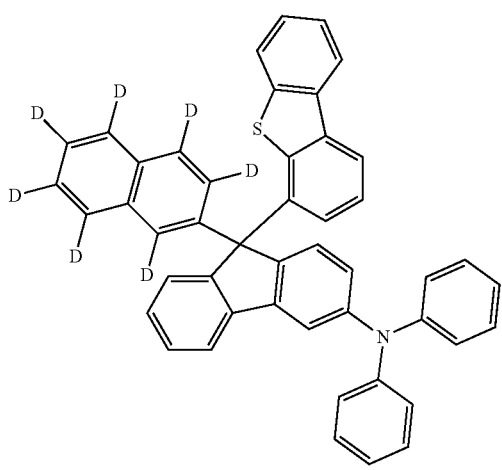
124
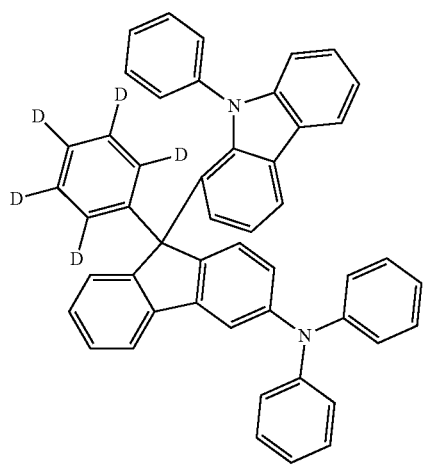
64
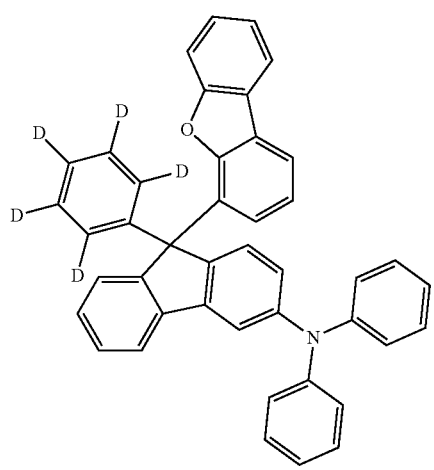
144
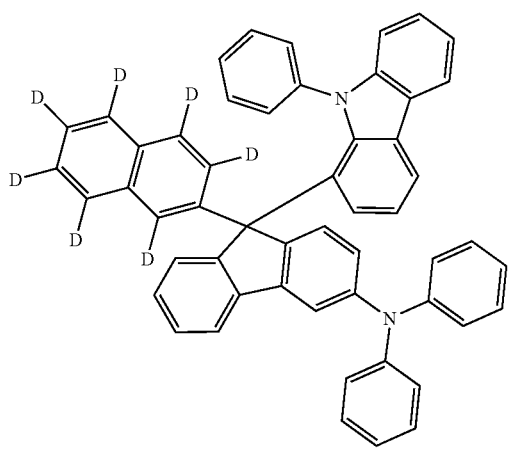

184
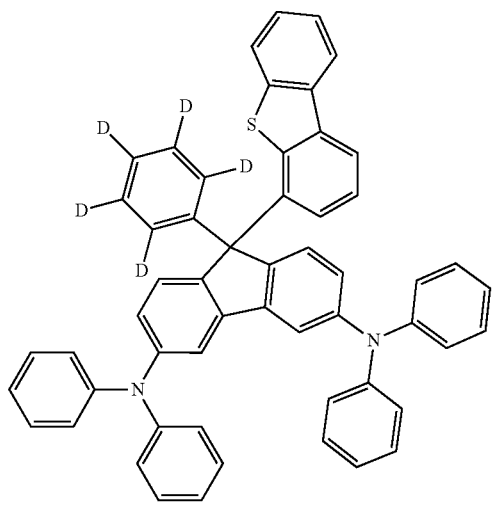
204
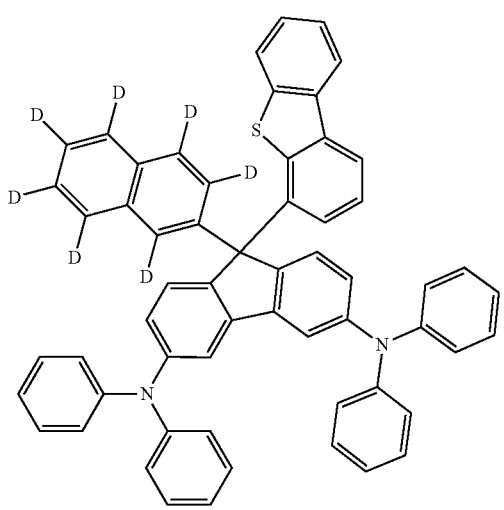
244
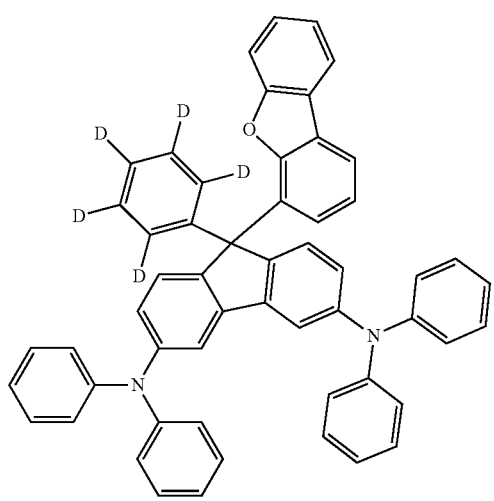
264
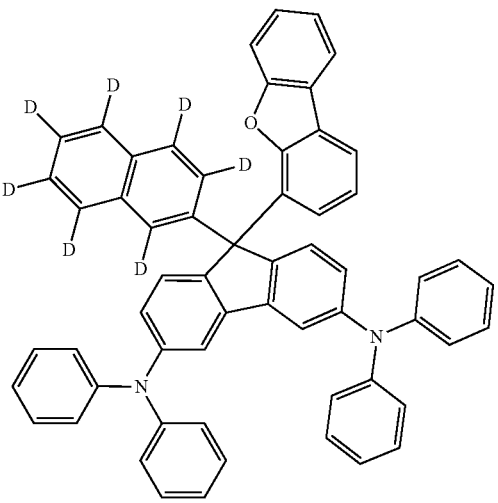
Comparative Example Compounds
C1
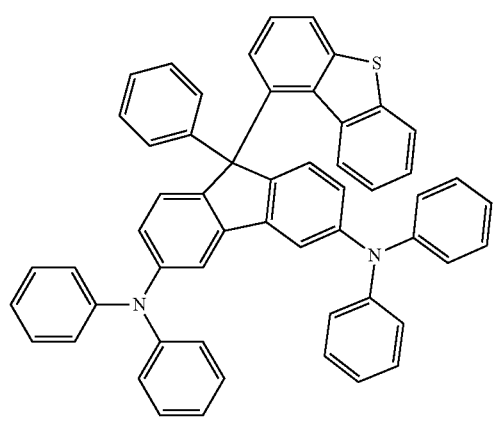
C2
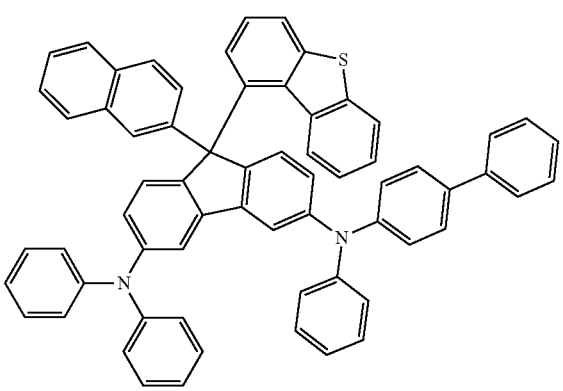

-continued

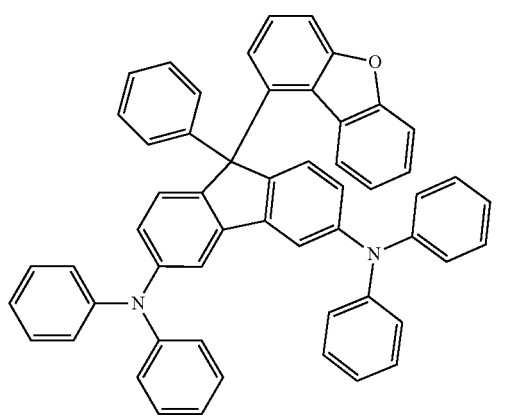

C3

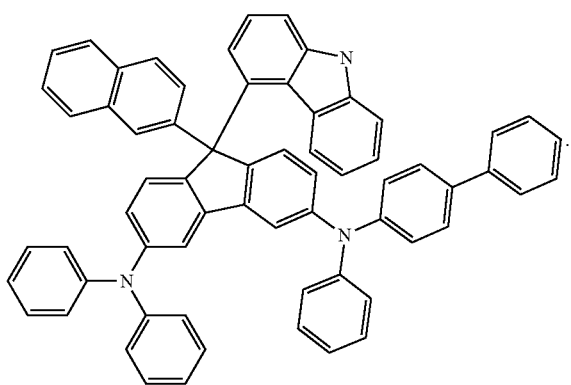

C4

Manufacture of Organic Electroluminescence Device

Organic electroluminescence devices including an amine Example Compound or a Comparative Example Compound in a hole transport region were manufactured via the following method.

For an anode, an ITO glass substrate of about 15 Ω/cm² (about 1,200 Å) made by Corning Co. was cut to a size of 50 mm×50 mm×0.7 mm, cleansed by ultrasonic waves in isopropyl alcohol and pure water for about 5 minutes, and then cleansed by ultraviolet irradiation for about 30 minutes and exposure to ozone. The ITO glass substrate was installed on a vacuum deposition apparatus.

On the ITO glass substrate, 2-TNATA was deposited in vacuum to a thickness of about 600 Å to form a hole injection layer, and on the hole injection layer, the Example Compound or Comparative Compound was deposited in vacuum to a thickness of about 300 Å to form a hole transport layer.

On the hole transport layer, 9,10-di(naphthalen-2-yl)anthracene (hereinafter, DNA) as a blue fluorescent host and 4,4'-bis[2-(4-(N,N-diphenylamino)phenyl)vinyl]biphenyl (hereinafter, DPAVBi) as a blue fluorescent dopant were co-deposited at a weight ratio of 98:2 to form an emission layer having a thickness of about 300 Å.

Then, Alq₃ was deposited on the emission layer to form an electron transport layer having a thickness of about 300 Å, and LiF (which is an alkaline metal halide) was deposited on the electron transport layer to form an electron injection layer having a thickness of about 10 Å. Next, Al was deposited in vacuum to a thickness of about 3,000 Å to form an LiF/Al cathode electrode, thereby manufacturing an organic electroluminescence device.

The materials of each layer used in the manufacture of the organic electroluminescence devices are as follows.

Functional Layer Compound

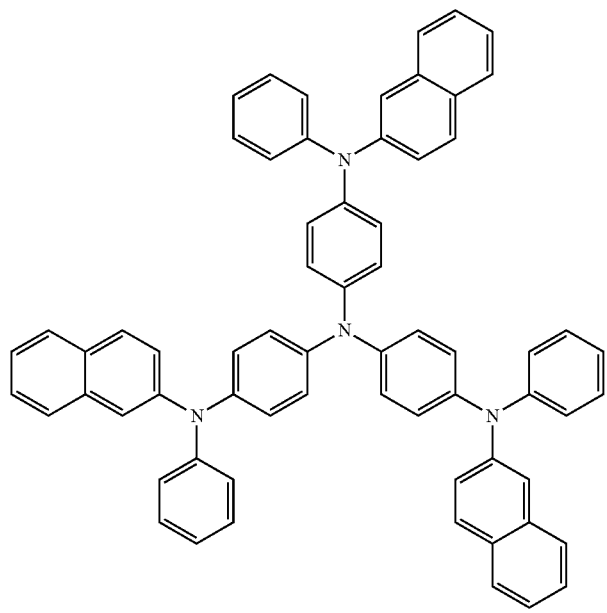

2-TNATA

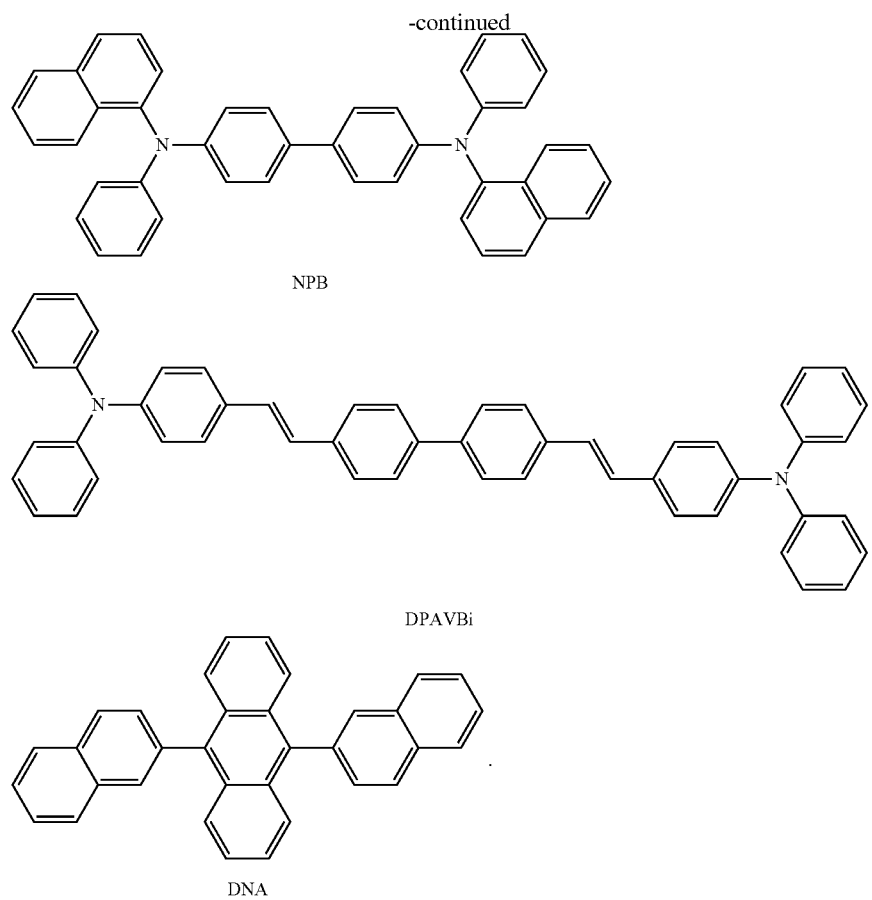

Evaluation of Organic Electroluminescence Device Characteristics

The characteristics of the manufactured organic electroluminescence devices were evaluated using a brightness distribution measurement device. The driving voltage, brightness, efficiency, luminous wavelength, and service life ($T_{80}$, unit: time) of the organic electroluminescence devices according to the Examples and Comparative Examples were measured. The driving voltage (V), current efficiency (cd/A) at a current density of 50 mA/cm$^2$, and brightness (cd/m$^2$) of each of the manufactured organic electroluminescence devices are shown in Table 2. The half service life (which is the time taken to reduce the brightness to 50% with respect to a brightness of 5,000 nit) is also shown in Table 2. The half service life was measured by continuous driving at a current density of 100 mA/cm$^2$. The brightness spectrum of each of the Examples and Comparative Examples was measured with a spectroradiometer. A luminous peak, (e.g., the maximum luminous wavelength) was determined from the measured brightness spectrum.

TABLE 2

| Device manufactured examples | Hole transport material | Drive voltage (V) | Current density (mA/cm$^2$) | Brightness (cd/m$^2$) | Efficiency (cd/A) | Luminous color | Half service life (hr @ 100 mA/cm$^2$) |
|---|---|---|---|---|---|---|---|
| Comparative Example 1 | Comparative Example 1 | 4.71 | 50 | 3145 | 6.29 | Blue | 320 |
| Comparative Example 2 | Comparative Example 2 | 4.63 | 50 | 3150 | 6.30 | Blue | 342 |
| Comparative Example 3 | Comparative Example 3 | 4.86 | 50 | 3270 | 6.54 | Blue | 351 |
| Comparative Example 4 | Comparative Example 4 | 4.82 | 50 | 3105 | 6.21 | Blue | 333 |
| Example 1 | Compound 4 | 4.35 | 50 | 3705 | 7.41 | Blue | 375 |
| Example 2 | Compound 24 | 4.15 | 50 | 3480 | 6.96 | Blue | 374 |
| Example 3 | Compound 64 | 4.36 | 50 | 3740 | 7.48 | Blue | 381 |
| Example 4 | Compound 84 | 4.24 | 50 | 3520 | 7.04 | Blue | 388 |

TABLE 2-continued

| Device manufactured examples | Hole transport material | Drive voltage (V) | Current density (mA/cm$^2$) | Brightness (cd/m$^2$) | Efficiency (cd/A) | Luminous color | Half service life (hr @ 100 mA/cm$^2$) |
|---|---|---|---|---|---|---|---|
| Example 5 | Compound 124 | 4.15 | 50 | 3640 | 7.28 | Blue | 369 |
| Example 6 | Compound 144 | 4.13 | 50 | 3900 | 7.80 | Blue | 394 |
| Example 7 | Compound 184 | 4.00 | 50 | 3610 | 7.22 | Blue | 379 |
| Example 8 | Compound 204 | 4.21 | 50 | 3430 | 6.86 | Blue | 398 |
| Example 9 | Compound 244 | 4.36 | 50 | 3455 | 6.91 | Blue | 378 |
| Example 10 | Compound 264 | 4.45 | 50 | 3280 | 6.56 | Blue | 380 |

Referring to the results of Table 2, when the amine compound according to an embodiment of the present disclosure is applied to the hole transport layer HTL of the organic electroluminescence device 10, it is confirmed that high efficiency, high brightness, low driving voltage, and a long service life of the device may be achieved. Referring to the results of Examples 1 to 10 and Comparative Examples 1 to 4, it is confirmed that the Examples (each including the amine compound containing a fluorene group, an deuterated aryl group substituted to the fluorene group, a heteroaryl group substituted to the fluorene group, and at least one amine group substituted to the fluorene group) each show high efficiency, high brightness, low driving voltage, and long service life characteristics compared to Comparative Examples each including the amine compound not containing the fluorene group and the aryl group which is substituted with deuterium.

In comparison, Comparative Examples 1 to 4 emit light in a blue wavelength region, but have low luminous efficiency and service life characteristics compared to the Examples. In addition, Comparative Examples 1 to 4 show higher driving voltages than the Examples.

The amine compound of an embodiment includes an aryl group substituted to the fluorene group, where all the carbons of the aryl group are substituted with deuterium, and thus provides excellent service life characteristics when applied to a device, compared to Comparative Example Compounds that do not include the aryl group substituted with deuterium. In addition, the amine compound of an embodiment may include a fused polycyclic compound (such as a fluorene group, a dibenzofuran group, a dibenzothiophene group, and/or a carbazole group) to thus improve heat resistance and durability against a high temperature environment. The organic electroluminescence device including the amine compound of an embodiment is capable of achieving high efficiency, high brightness, low driving voltage, and a long service life due to having a stable structure in which heat resistance and durability are improved.

The organic electroluminescence device of an embodiment may have high efficiency and increased service life characteristics.

The amine compound of an embodiment may be applied to an emission layer of the organic electroluminescence device to contribute to efficiency and a long service life of the organic electroluminescence device.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although described with reference to embodiments of the present disclosure, it will be understood that various changes and modifications of the present disclosure may be made by having ordinary skill in the art without departing from the spirit and technical field of the present disclosure as set forth in the following claims and their equivalents.

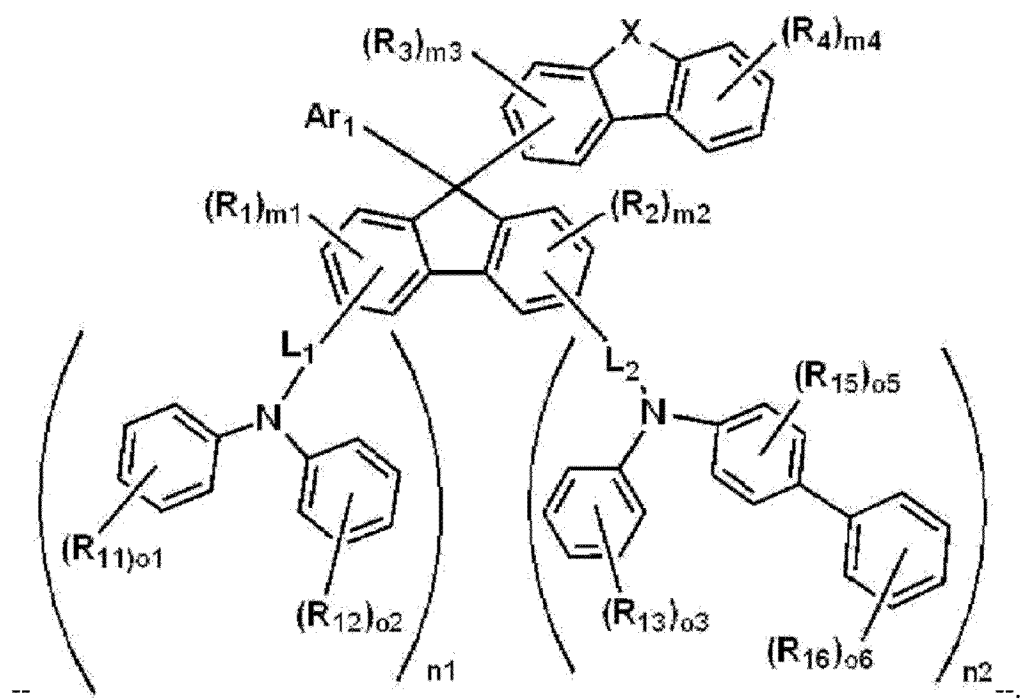

What is claimed is:
1. An organic electroluminescence device comprising:
a first electrode;
a second electrode facing the first electrode; and
a plurality of organic layers between the first electrode and the second electrode,
wherein at least one of the organic layers comprises an amine compound;
wherein the amine compound comprises: a fluorene group; an aryl group having 6 to 60 ring-forming carbon atoms, which is substituted to the fluorene group; a heteroaryl group having 2 to 60 ring-forming carbon atoms, which is substituted to the fluorene group; and at least one amine group, which is substituted to the fluorene group;

wherein only the aryl group is substituted with deuterium, and
wherein all substitutable carbons of the aryl group are substituted with deuterium.

2. The organic electroluminescence device of claim 1, wherein the heteroaryl group is a substituted or unsubstituted dibenzofuran group, a substituted or unsubstituted dibenzothiophene group, or a substituted or unsubstituted carbazole group.

3. The organic electroluminescence device of claim 1, wherein the organic layers comprise a hole transport region, an emission layer, and an electron transport region, and the hole transport region comprises the amine compound.

4. The organic electroluminescence device of claim 3, wherein the hole transport region comprises a hole transport layer and a hole injection layer, and the hole transport layer or the hole injection layer comprises the amine compound.

5. The organic electroluminescence device of claim 1, wherein the amine compound is represented by Formula 1:

Formula 1 wherein, in Formula 1,
X is O, S, or $NAr_6$;
$L_1$ and $L_2$ are each independently a direct linkage, a substituted or unsubstituted arylene group having 6 to 60 ring-forming carbon atoms, or a substituted or unsubstituted heteroarylene group having 2 to 60 ring-forming carbon atoms;
$R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;
$m_1$, $m_2$, and $m_4$ are each independently an integer of 0 to 4;
$m_3$ is an integer of 0 to 3;
$Ar_1$ is a phenyl group substituted with deuterium, a naphthyl group substituted with deuterium, or a biphenyl group substituted with deuterium;
$Ar_2$ to $Ar_6$ are each independently a substituted or unsubstituted aryl group having 6 to 60 ring-forming carbon atoms, or a substituted or unsubstituted heteroaryl group having 3 to 60 ring-forming carbon atoms;
$n_1$ and $n_2$ are each independently 0 or 1; and
at least one of $n_1$ or $n_2$ is 1.

6. The organic electroluminescence device of claim 5, wherein the amine compound represented by Formula 1 is represented by at least one of Formula 1-1 to Formula 1-3:

Formula 1-1

Formula 1-2

Formula 1-3 wherein, in Formula 1-1 to Formula 1-3,
$L_1$, $L_2$, $R_1$ to $R_4$, $m_1$ to $m_4$, $Ar_1$ to $Ar_6$, $n_1$ and $n_2$ are each independently the same as defined in Formula 1.

7. The organic electroluminescence device of claim 5, wherein the amine compound represented by Formula 1 is represented by at least one of Formula 2-1 to Formula 2-5:

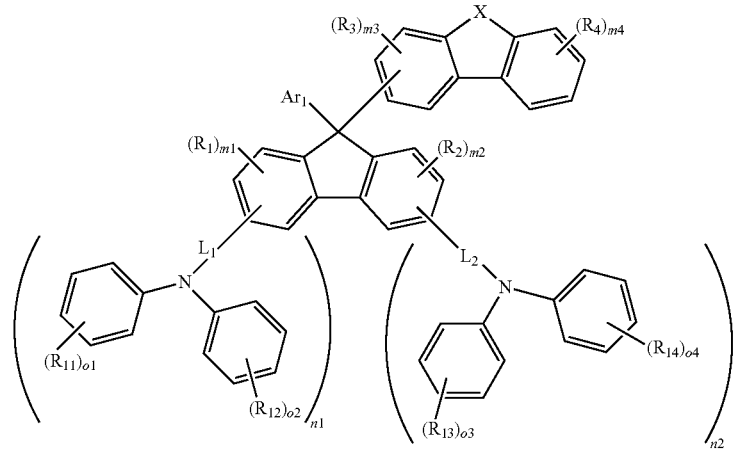
Formula 2-1
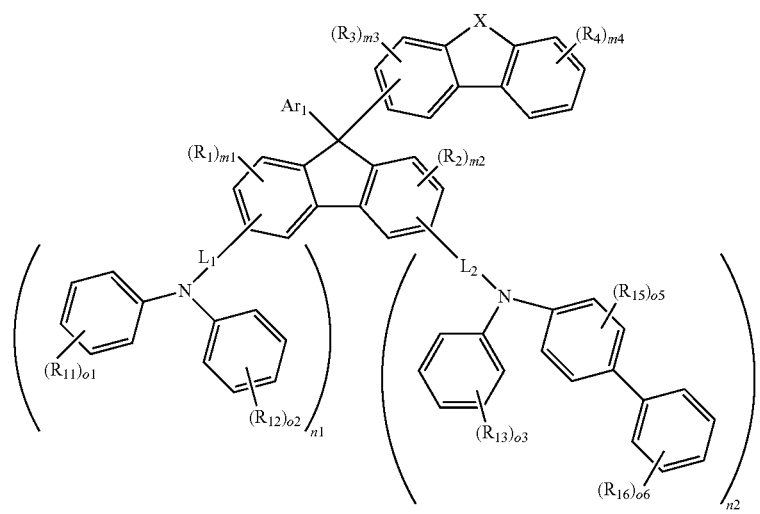
Formula 2-2
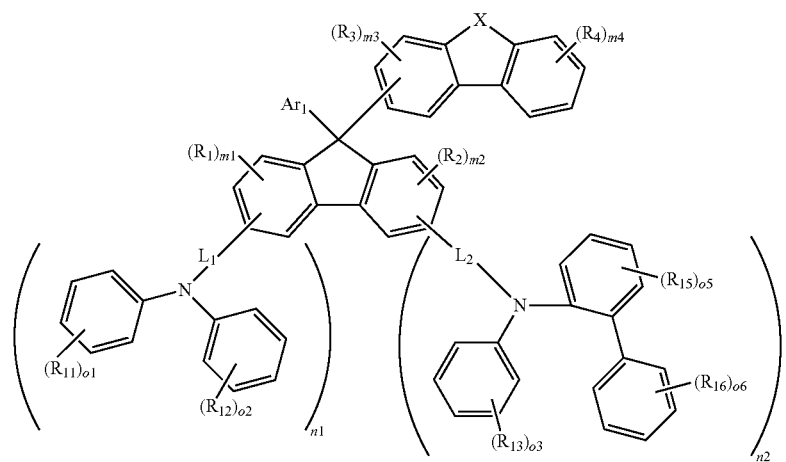
Formula 2-3

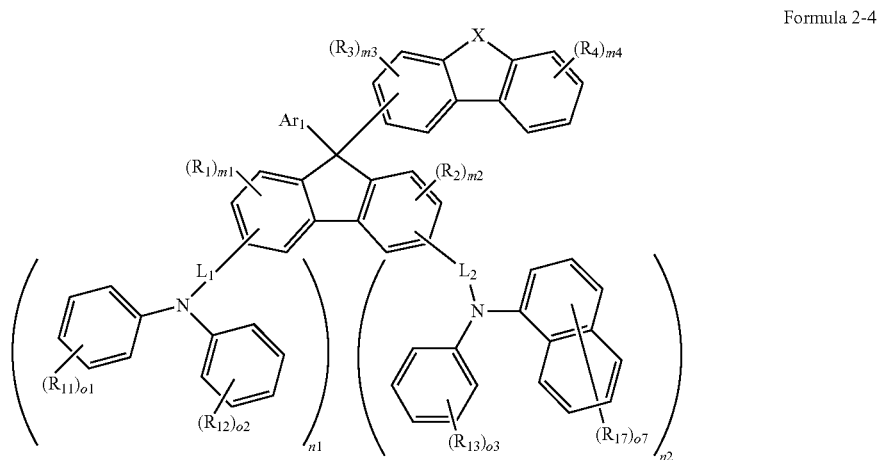

Formula 2-4

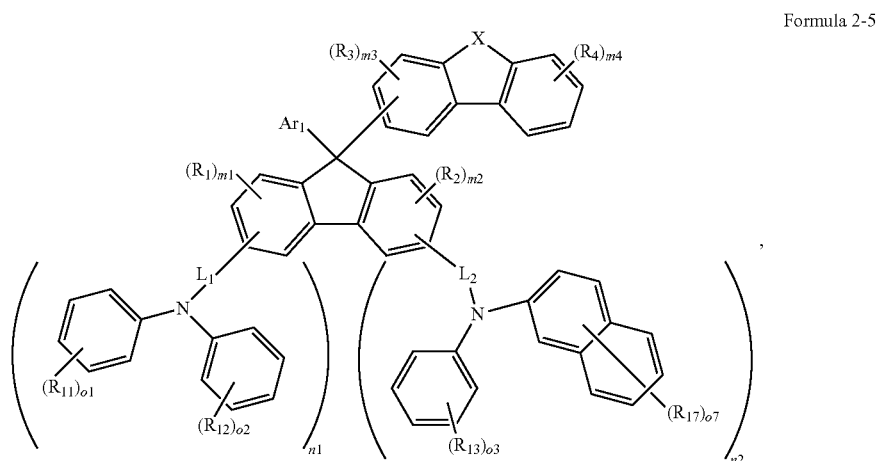

Formula 2-5 wherein, in Formula 2-1 to Formula 2-5, $R_{11}$ to $R_{17}$ are each independently a hydrogen atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

8. The organic electroluminescence device of claim 5, wherein the amine compound represented by Formula 1 is represented by Formula 3-1:

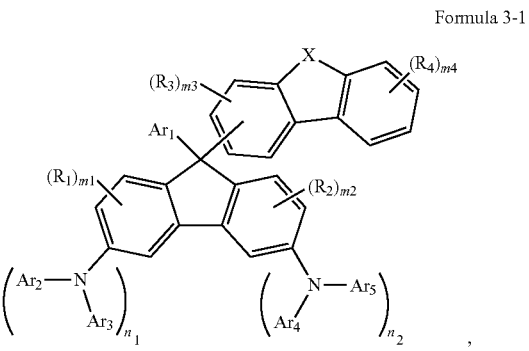

Formula 3-1 wherein, in Formula 3-1,

X, $Ar_1$ to $Ar_5$, $R_1$ to $R_4$, $n_1$, $n_2$, and $m_1$ to $m_4$ are each independently the same as defined in Formula 1.

9. The organic electroluminescence device of claim 5, wherein the amine compound represented by Formula 1 is represented by at least one of Formula 4-1 and Formula 4-2:

Formula 4-1

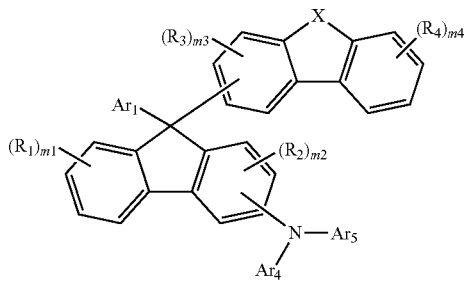

Formula 4-2

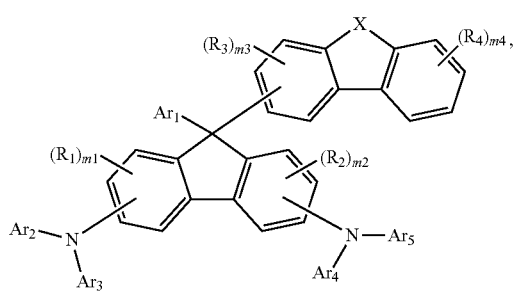

wherein, in Formula 4-1 and Formula 4-2,

X, $Ar_1$ to $Ar_5$, $R_1$ to $R_4$, and $m_1$ to $m_4$ are each independently the same as defined in Formula 1.

10. The organic electroluminescence device of claim 5, wherein X is $NAr_6$, and $Ar_6$ is a substituted or unsubstituted phenyl group.

11. The organic electroluminescence device of claim 5, wherein the amine compound represented by Formula 1 is at least one of the compounds represented by Compound Group 1:

Compound Group 1

1

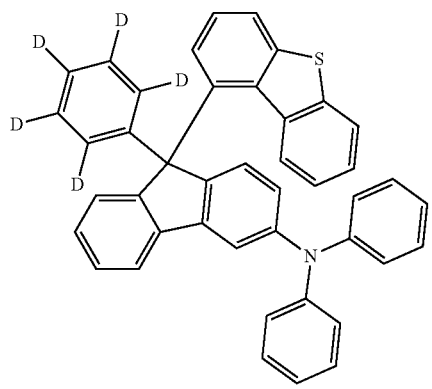

2

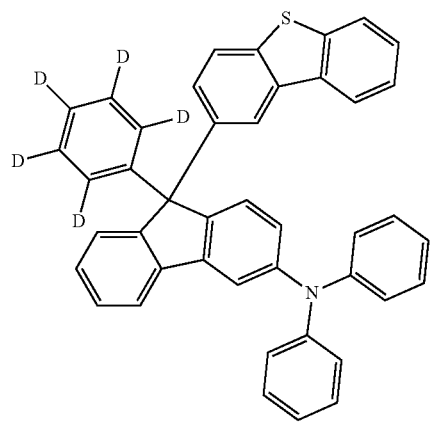

3

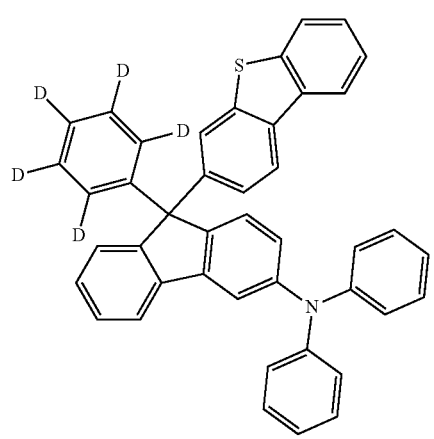

4

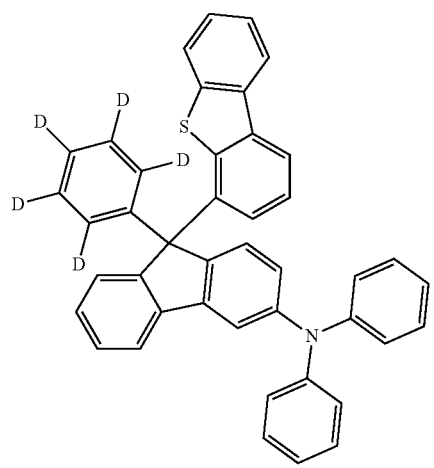

295
-continued
5
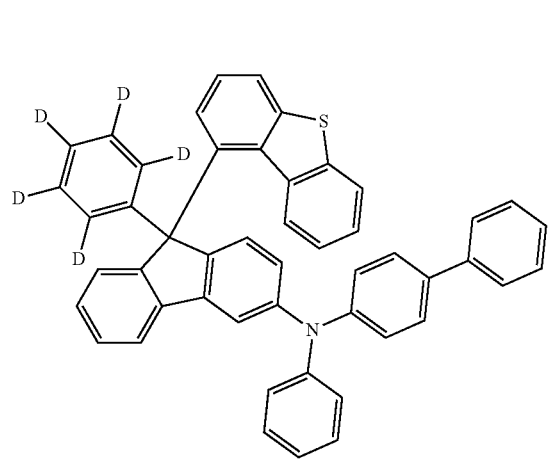
6
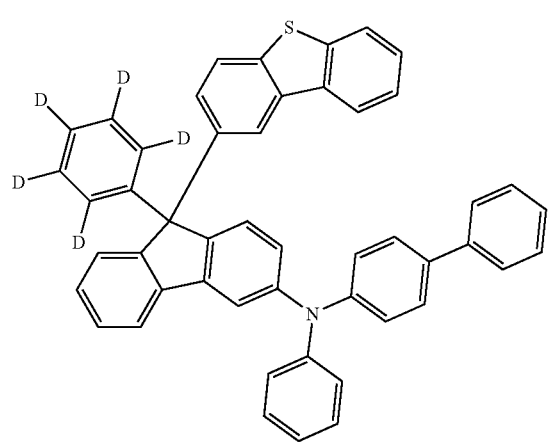
7
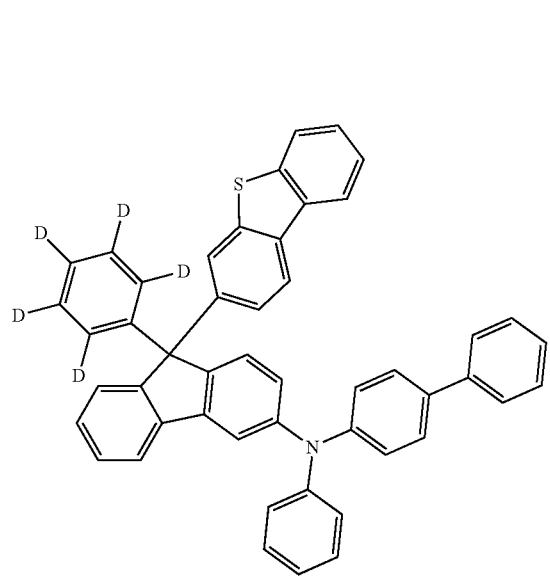
296
-continued
5
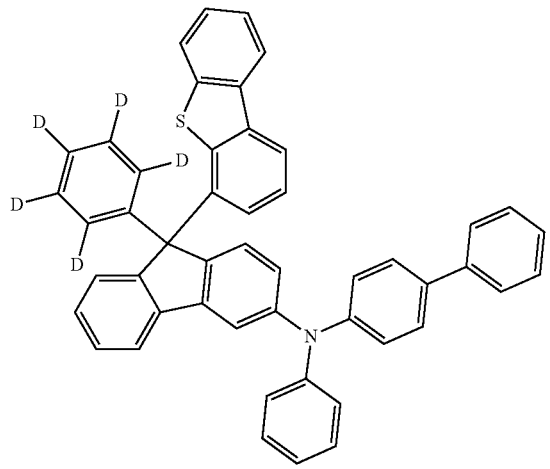
8
6
9
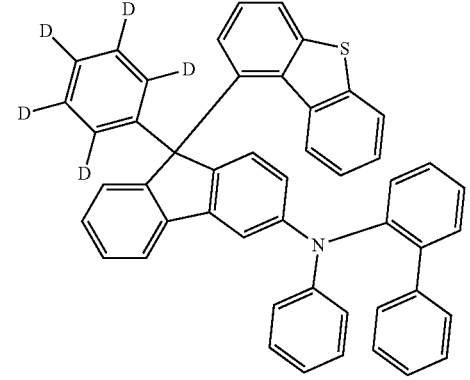
10
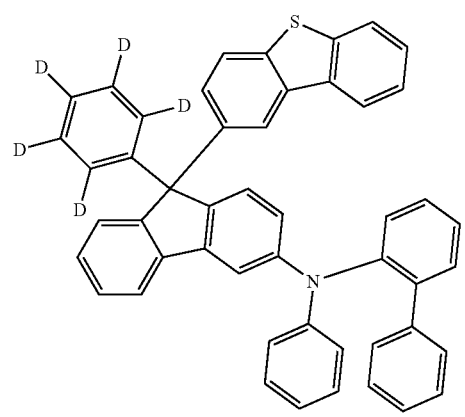

-continued
11
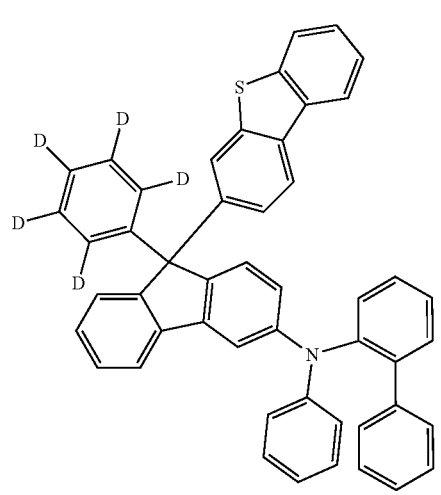
12
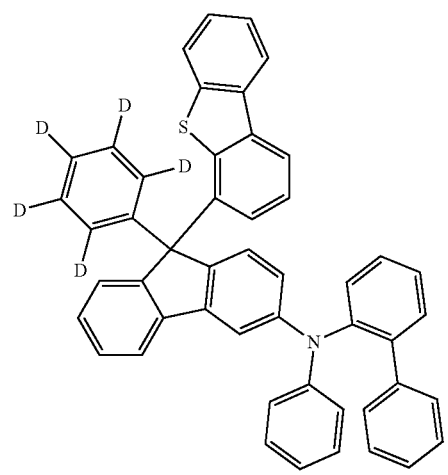
13
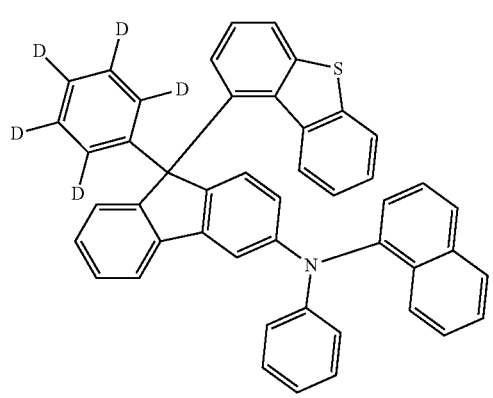
-continued
14
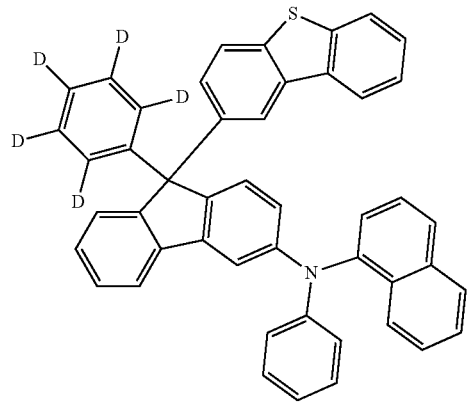
15
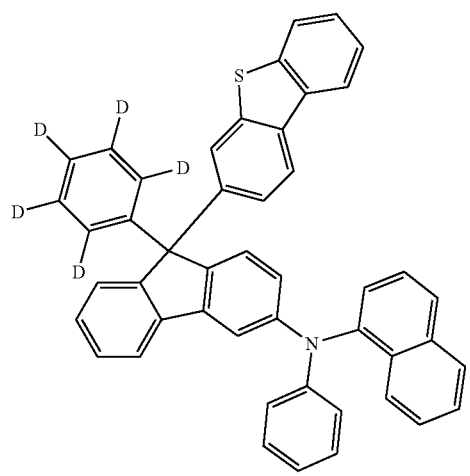
16
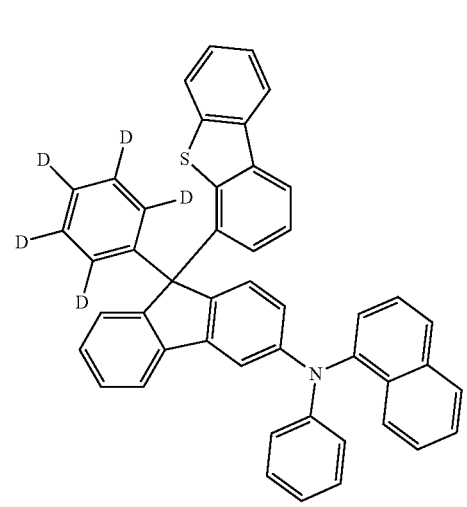

17
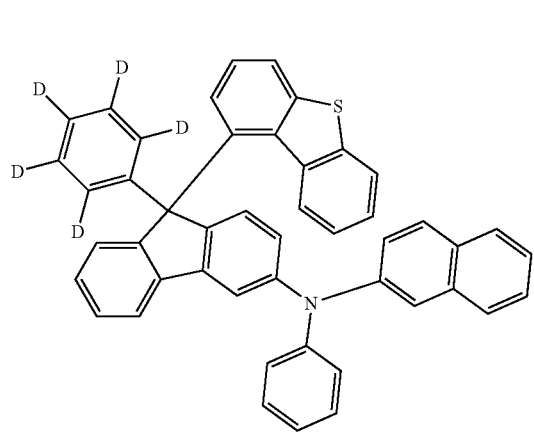
18
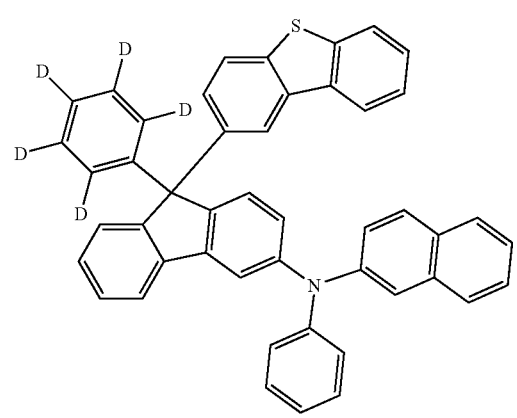
19
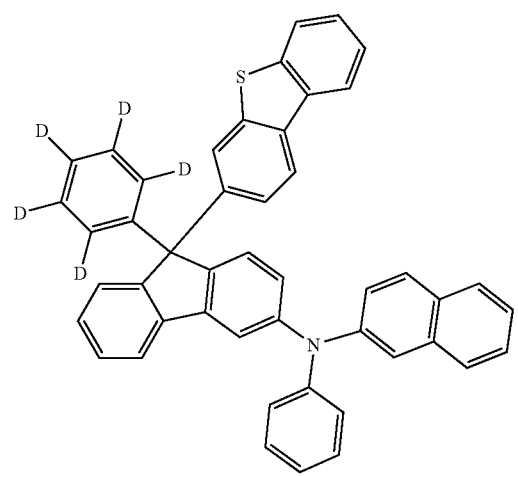
20
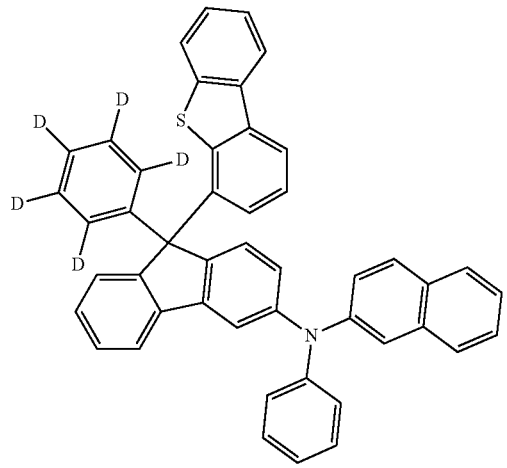
21
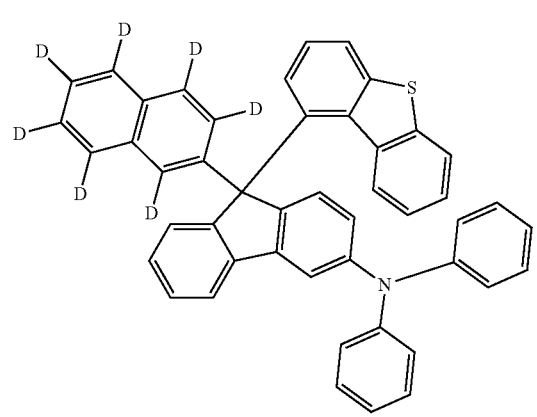
22
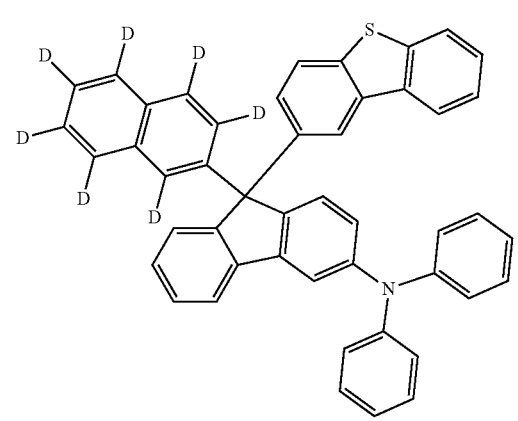

23
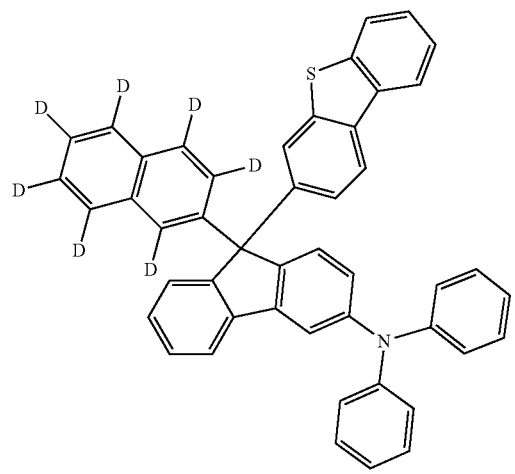
24
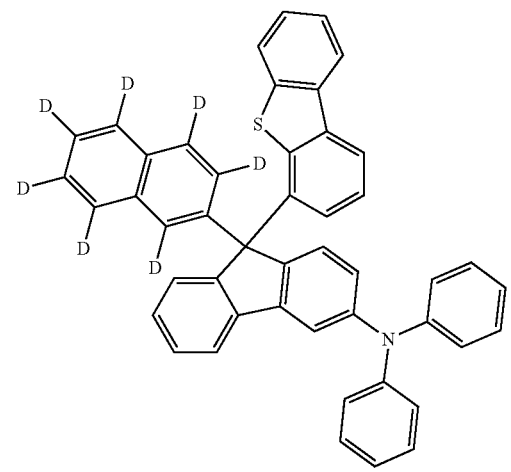
25
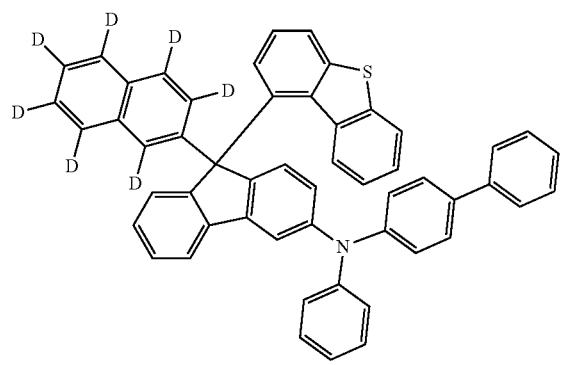
26
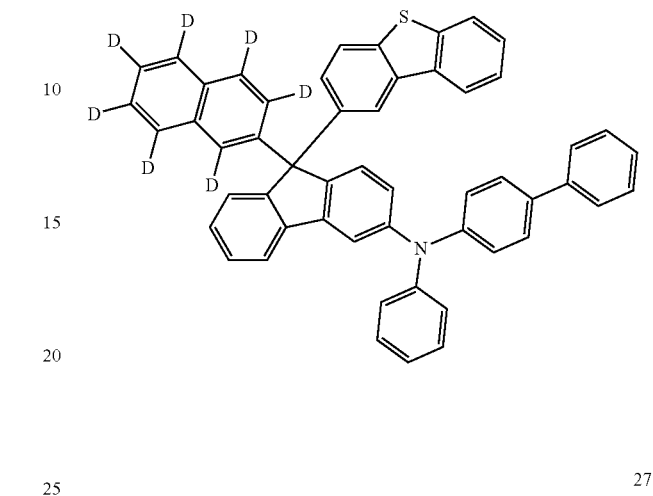
27
28
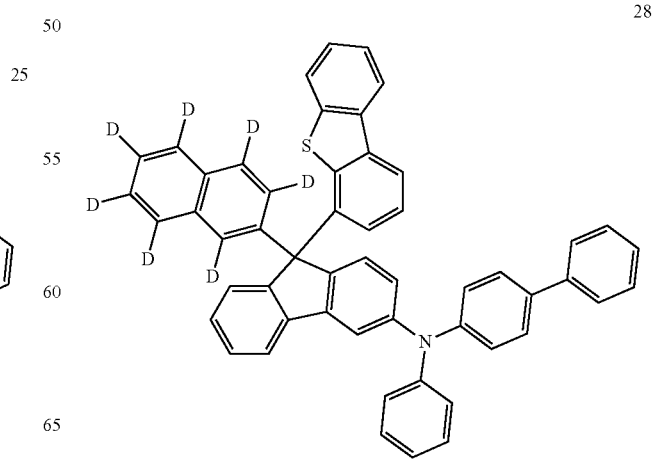

29
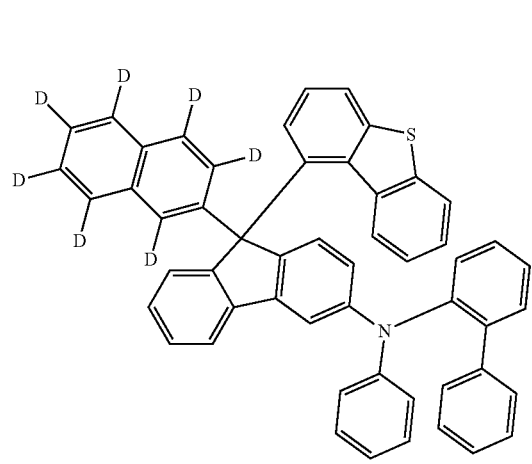
30
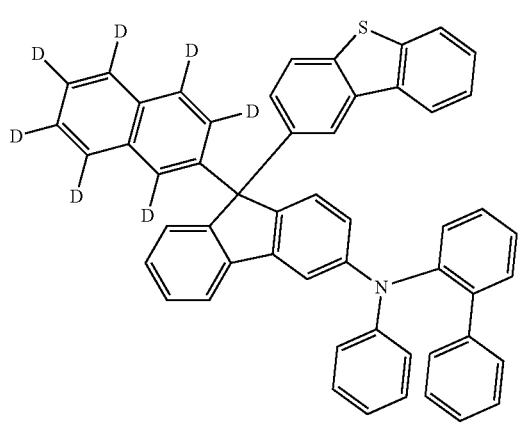
31
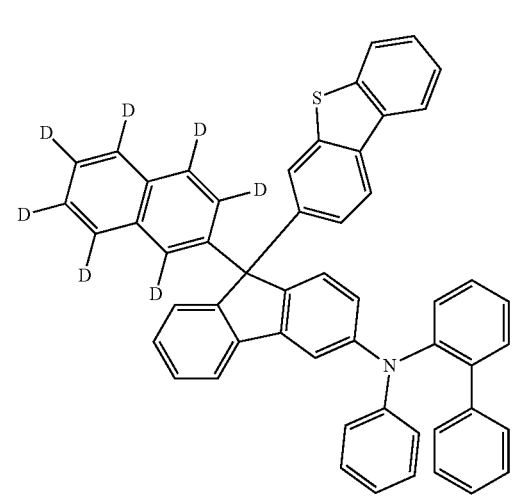
32
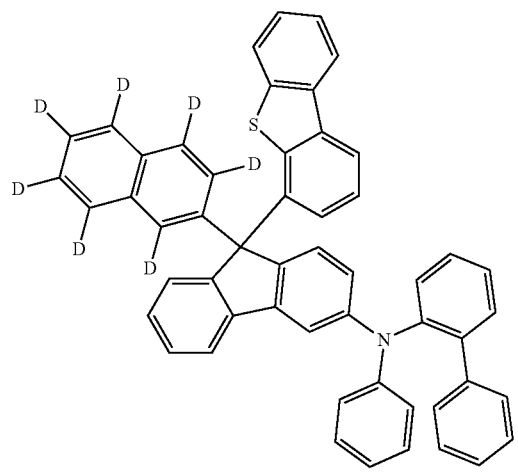
33
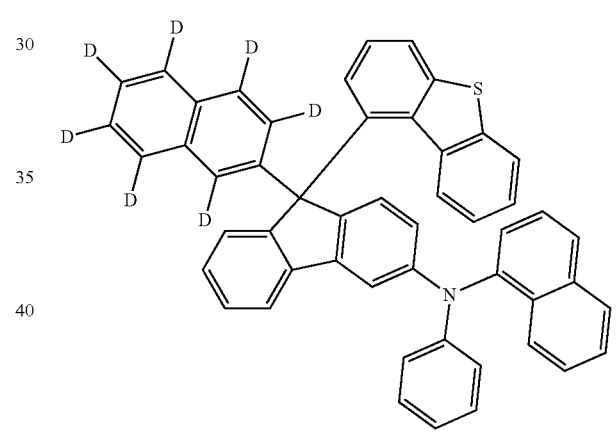
34
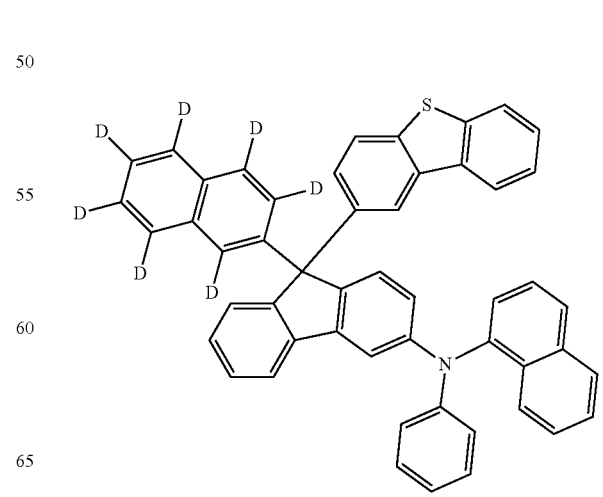

35
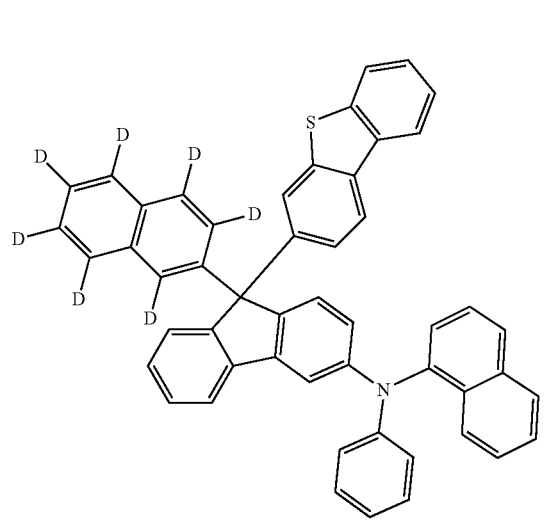
36
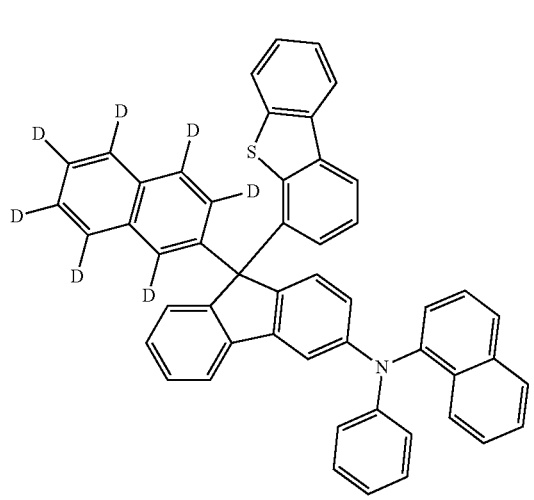
37
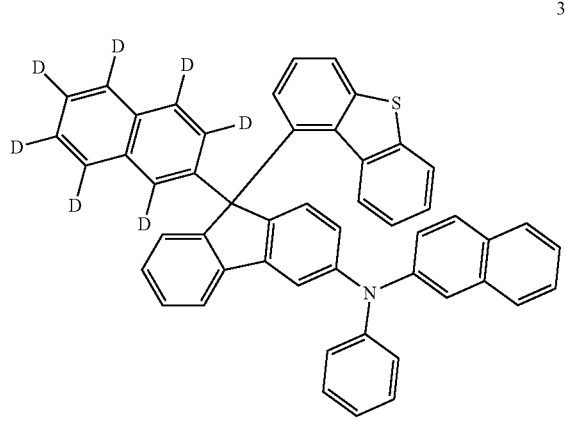
38
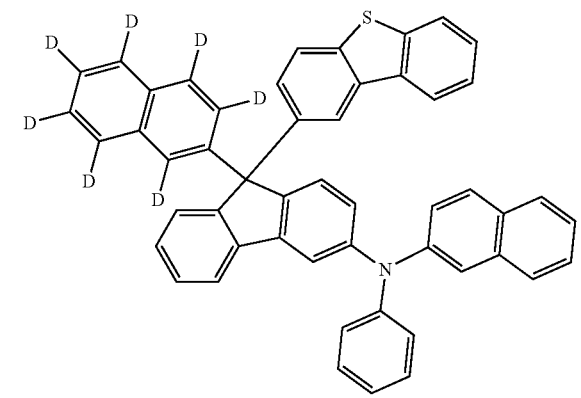
41
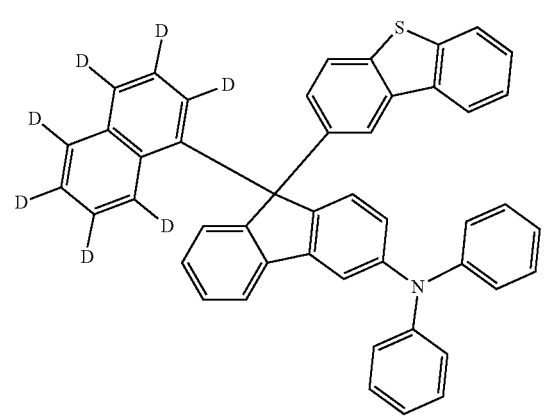
42

307
-continued
43
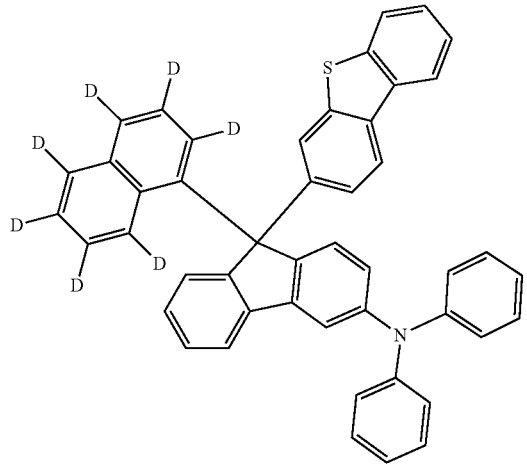
43
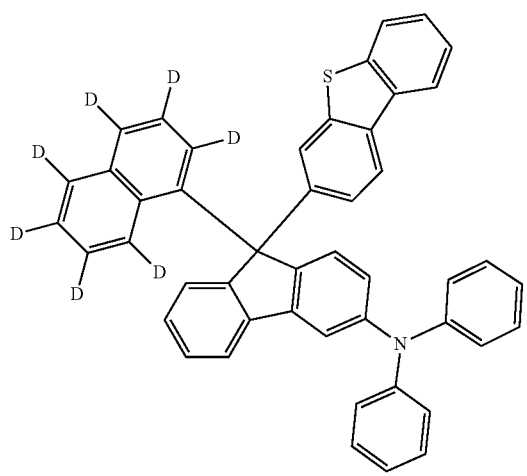
44
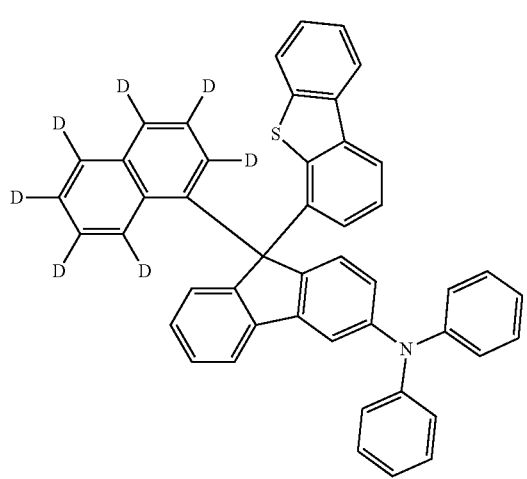
308
-continued
45
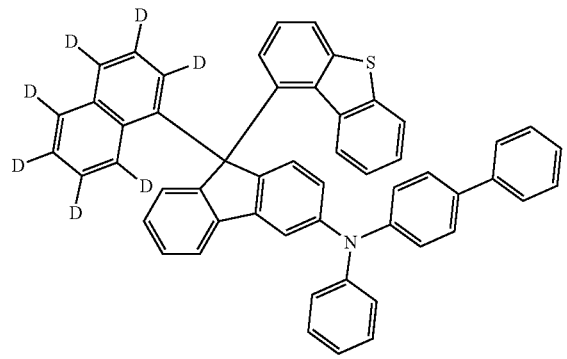
46
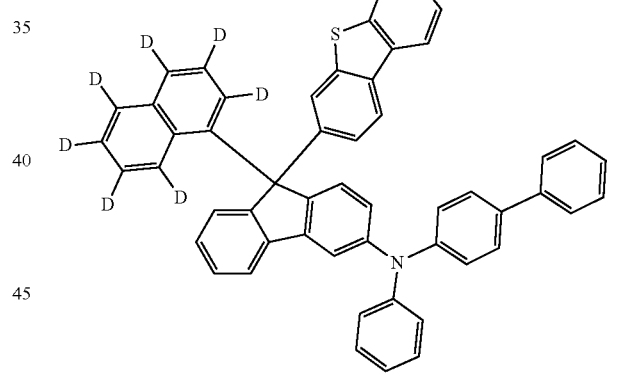
47
48
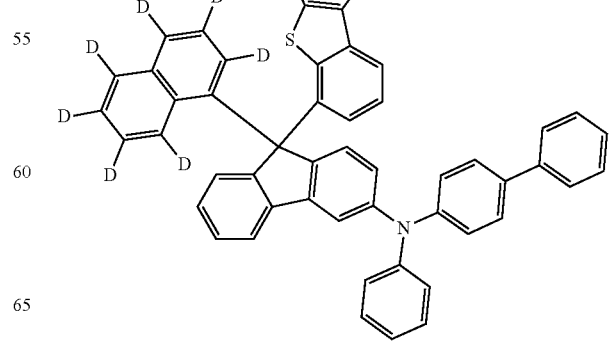

309
-continued
49
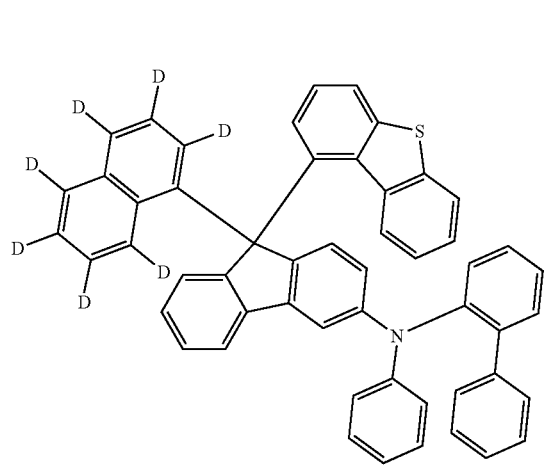
50
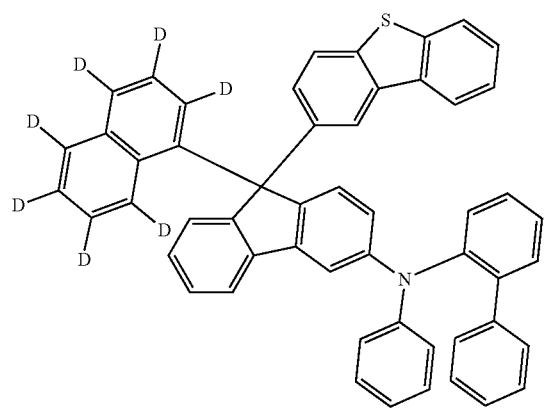
51
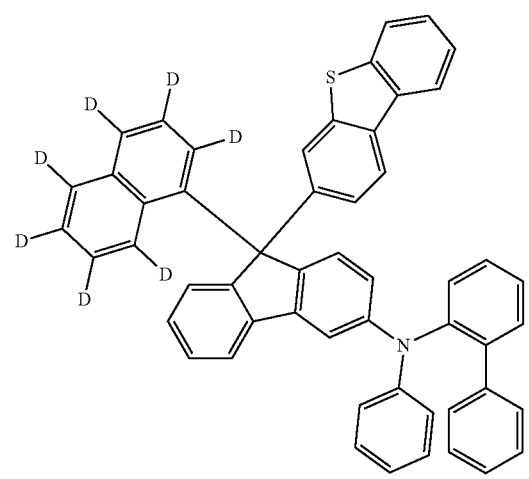
310
-continued
52
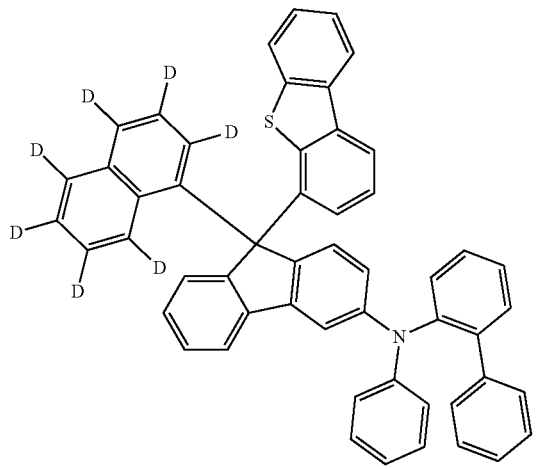
53
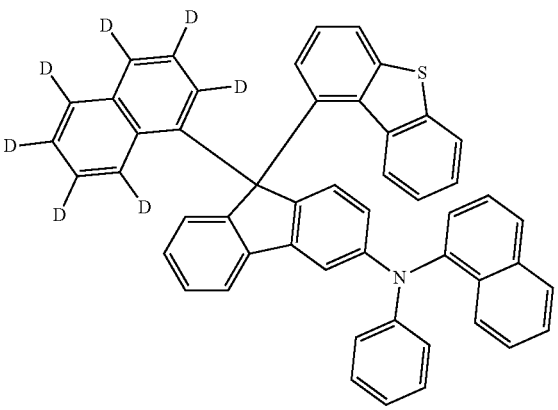
54
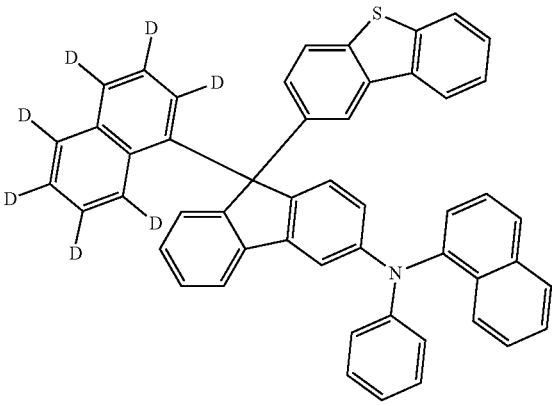

55
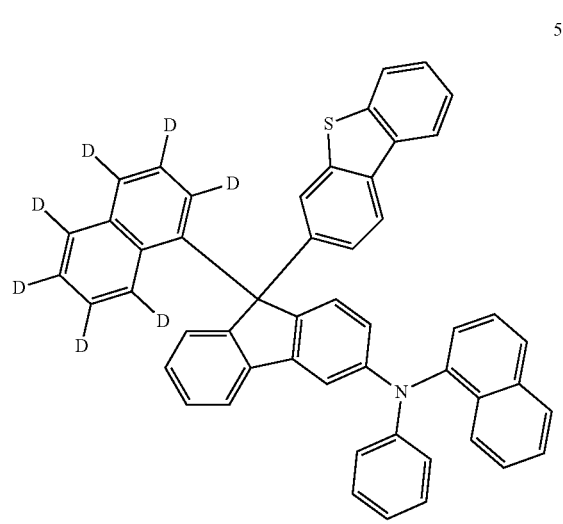
56
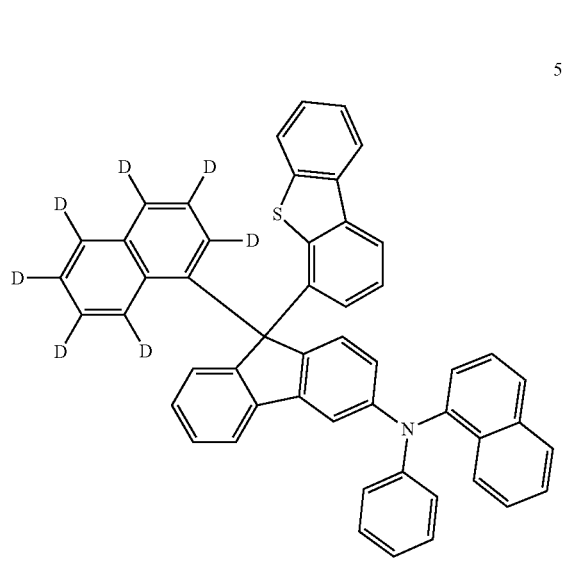
57
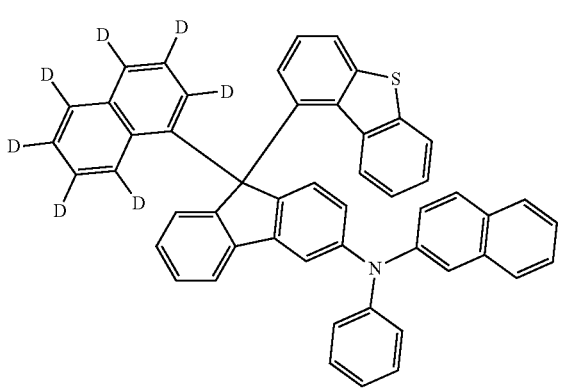
58
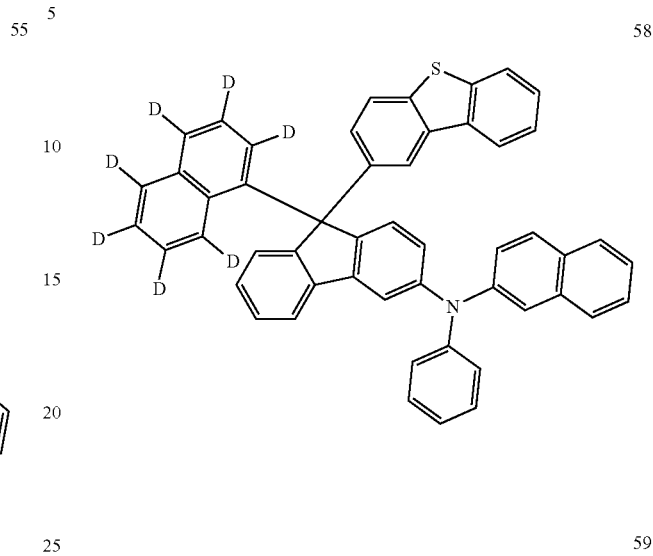
59
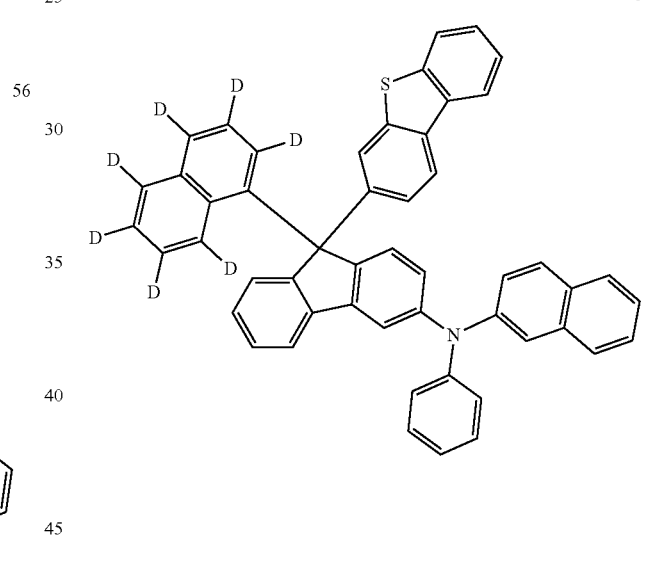
60
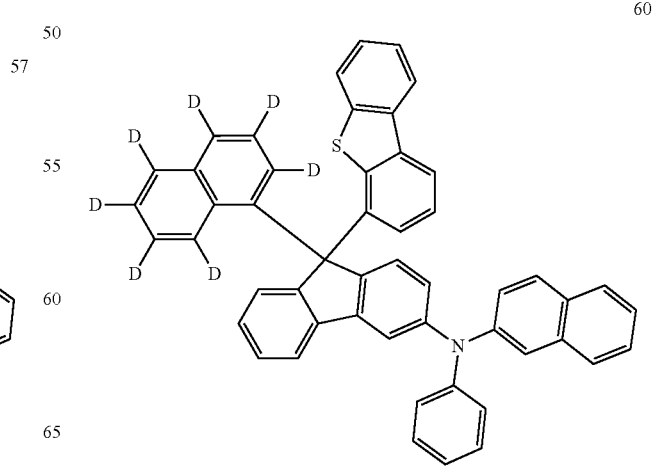

61
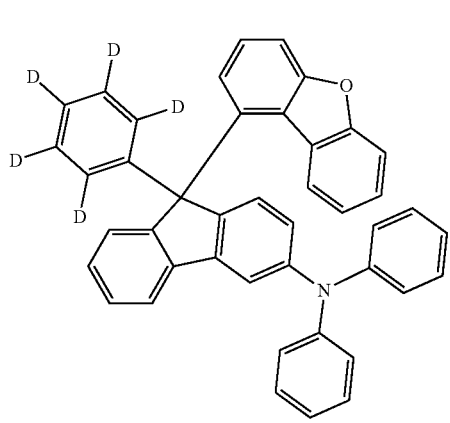
62
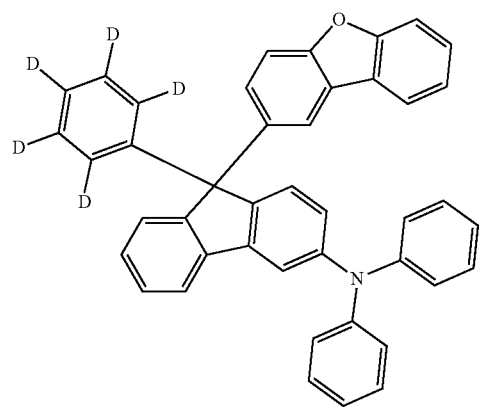
63
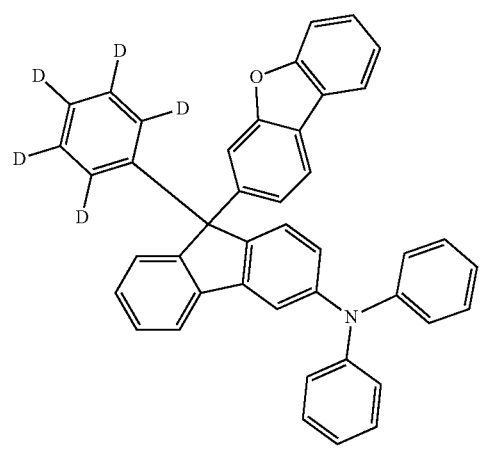
64
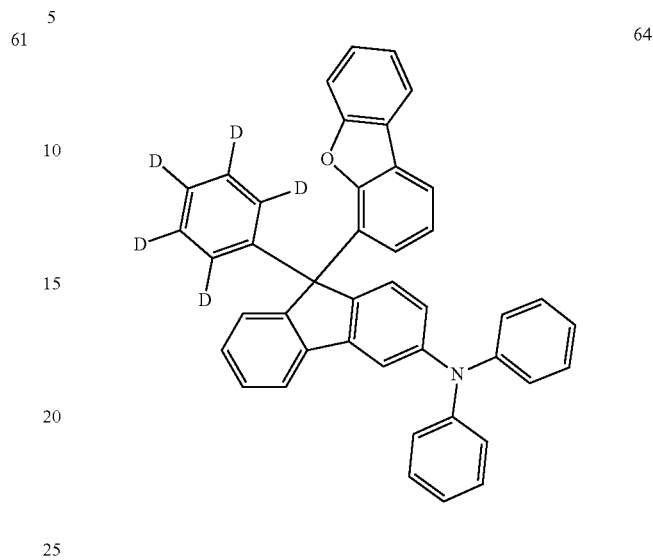
65
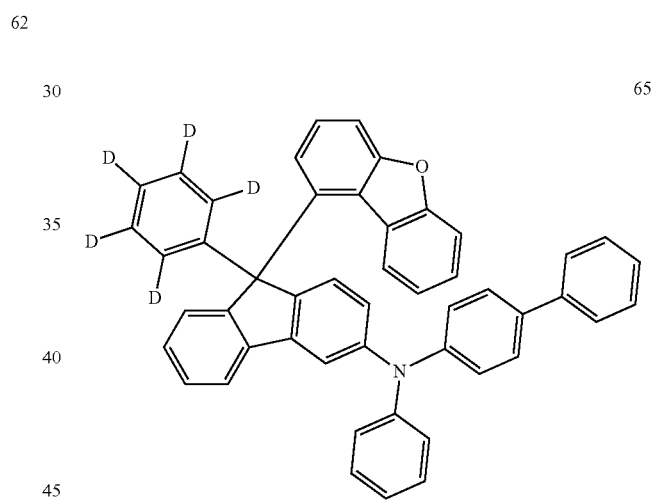
66
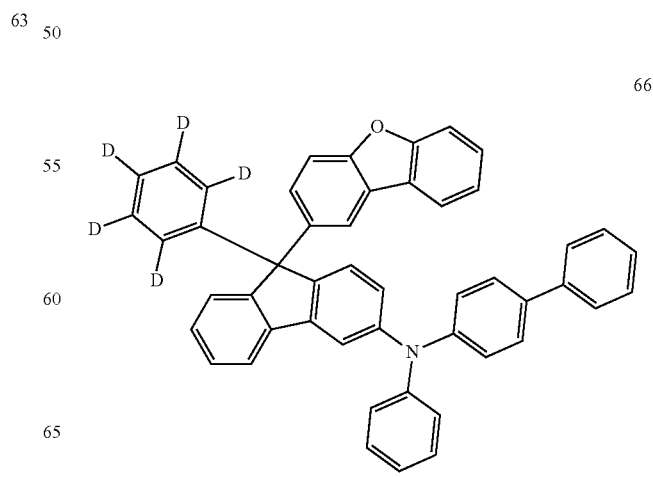

67
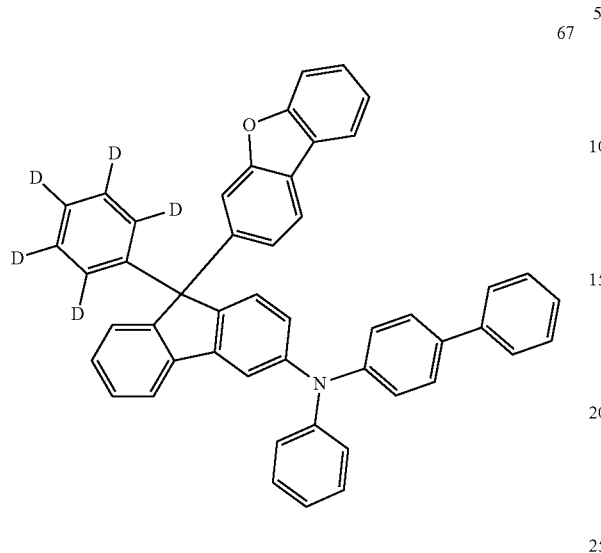
68
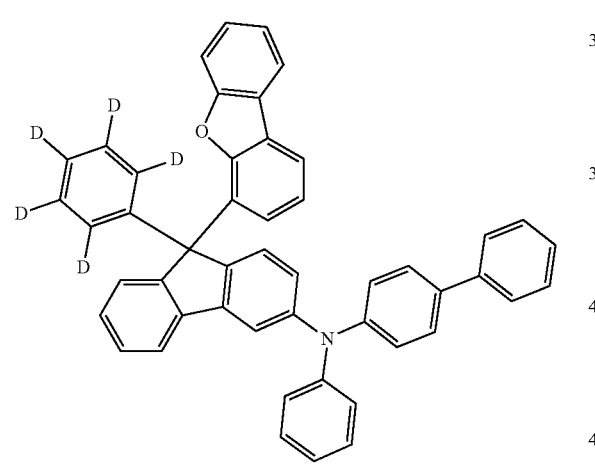
69
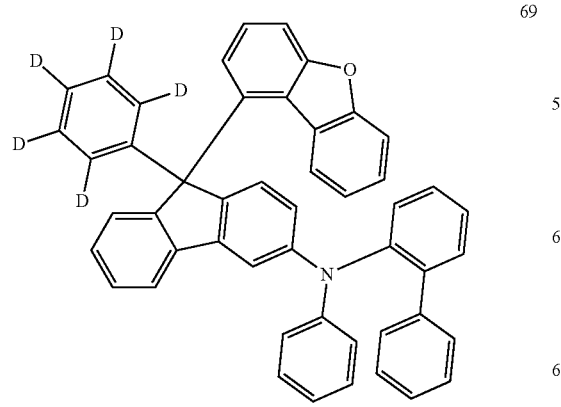
70
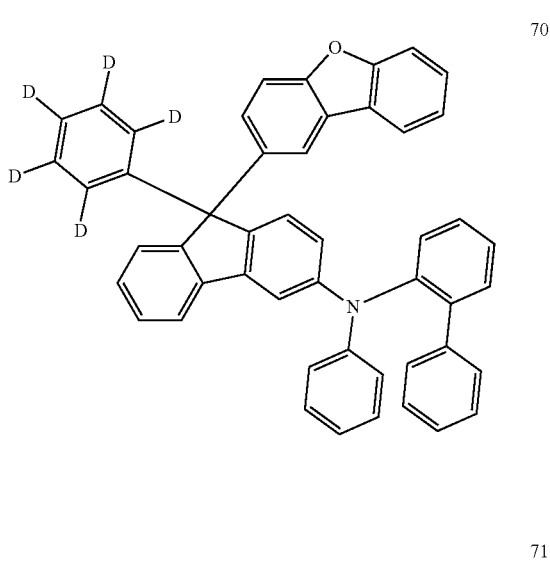
71
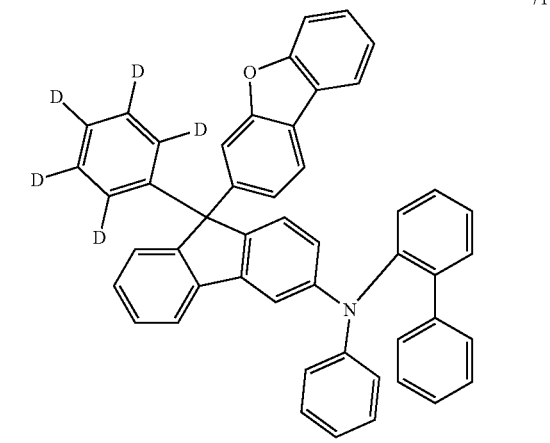
72
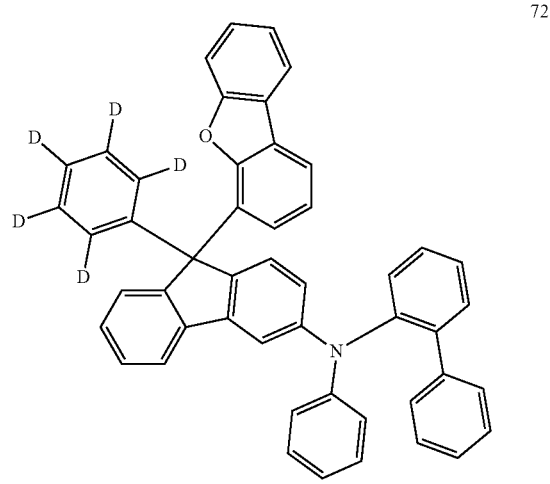

73
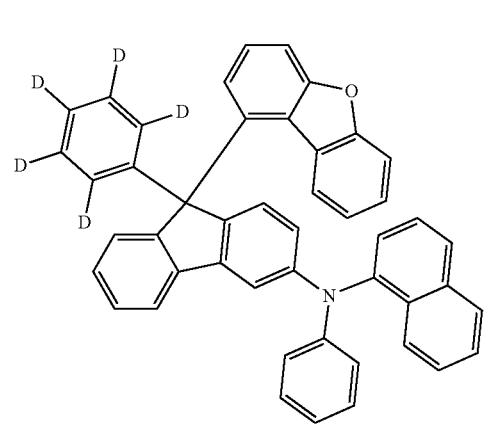
74
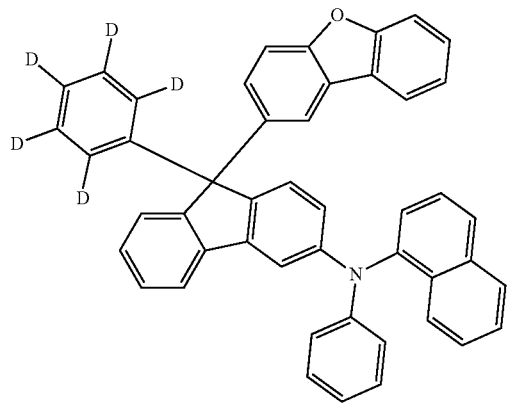
75
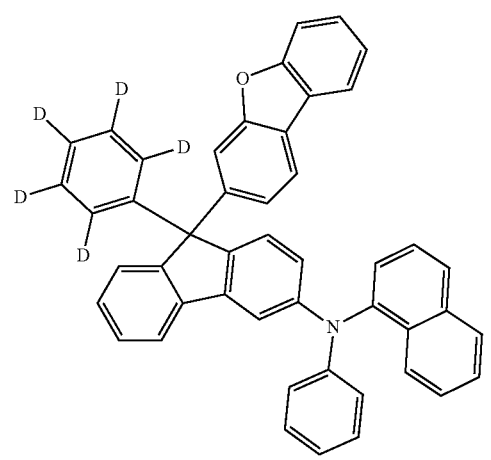
76
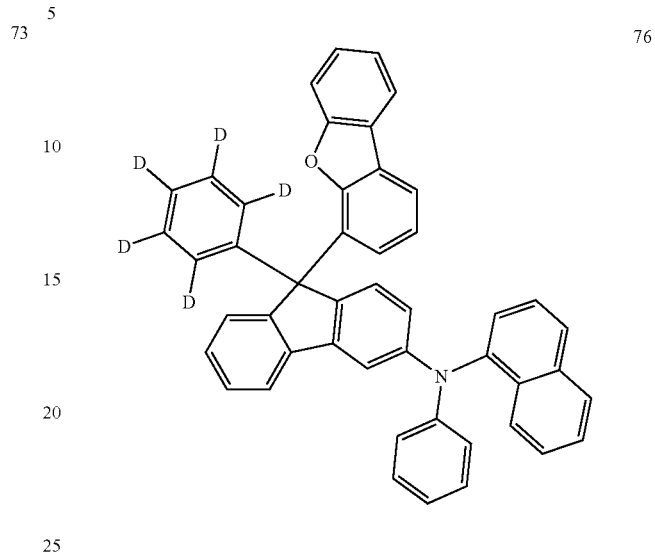
77
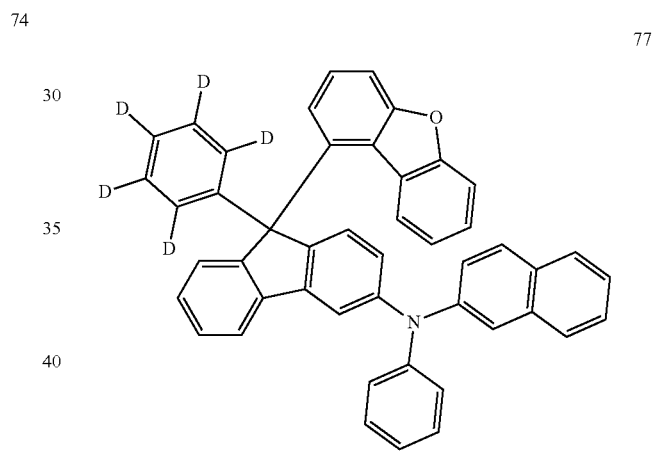
78
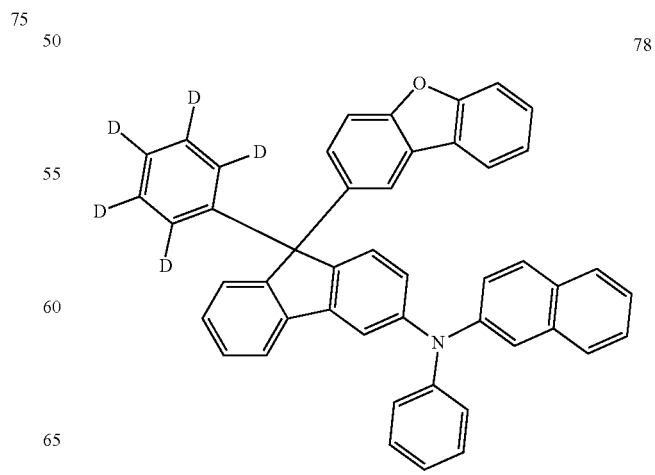

79
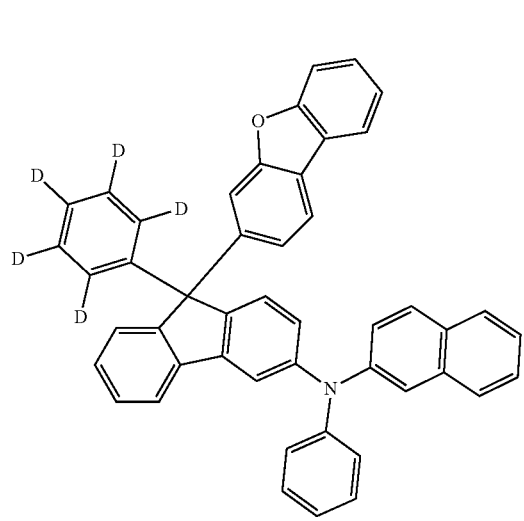
80
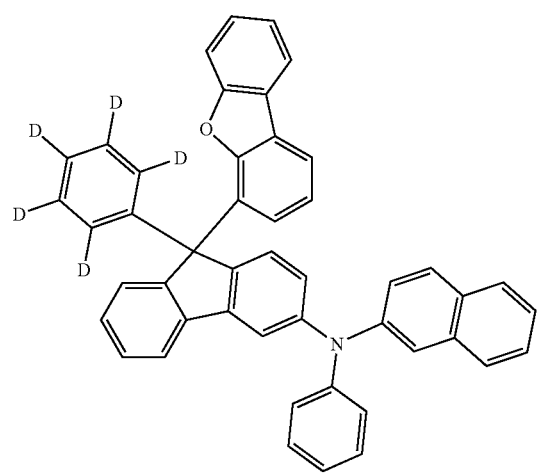
81
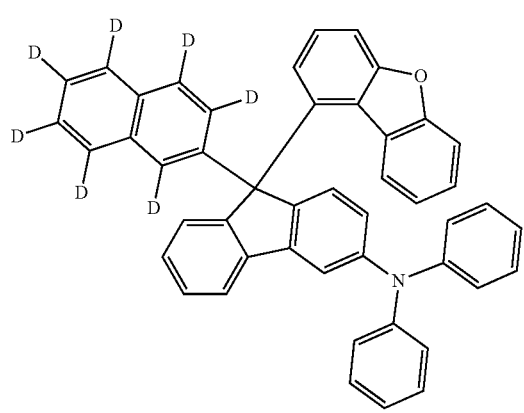
82
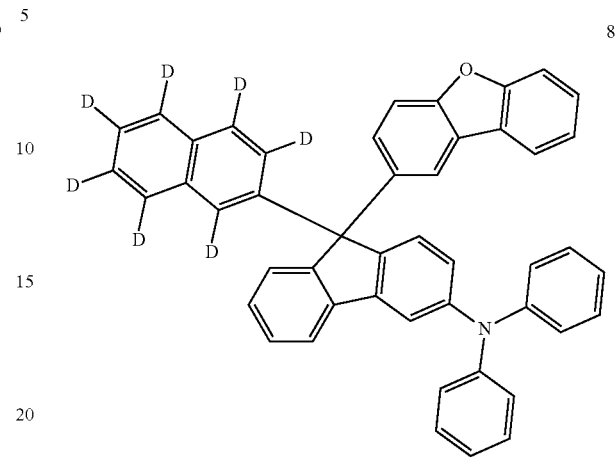
83
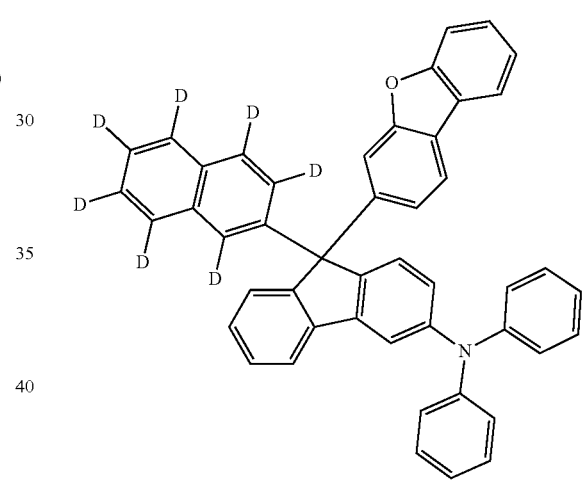
84
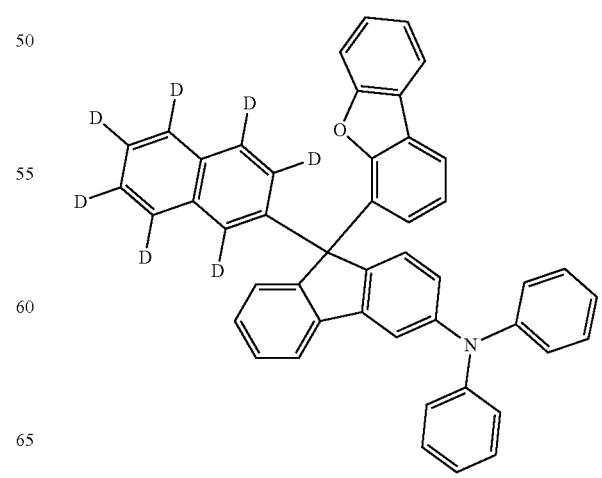

321
-continued
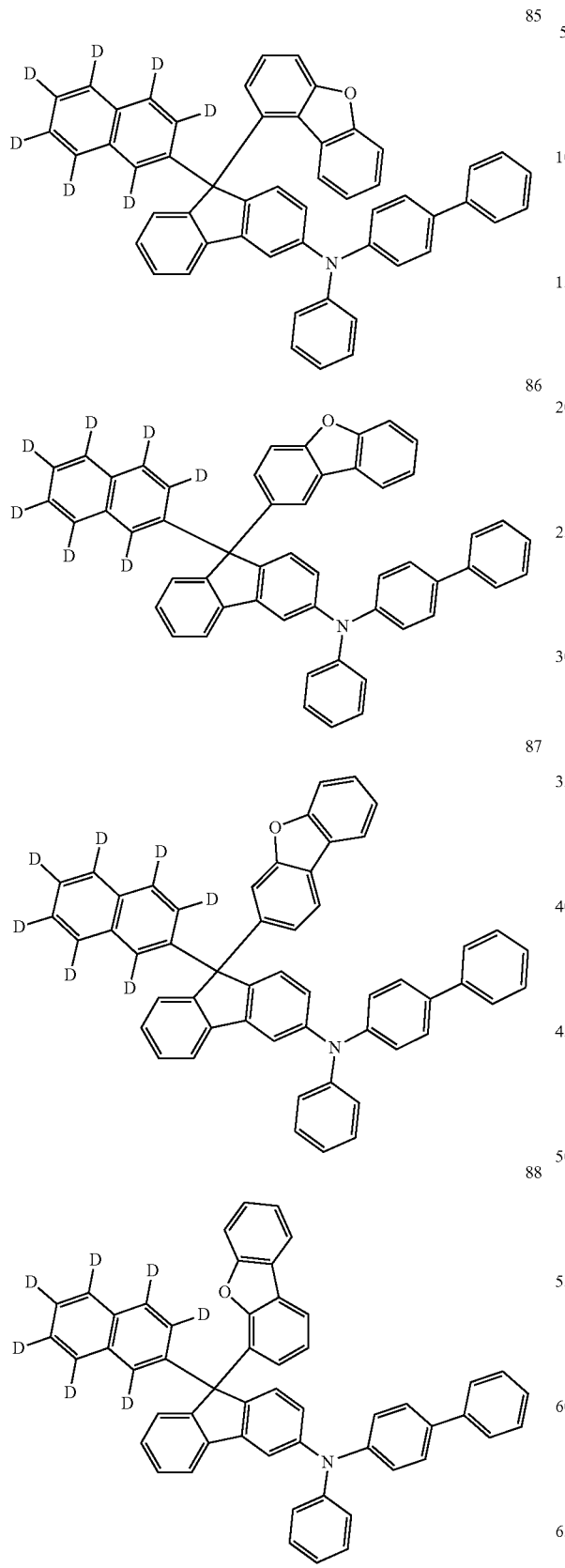
322
-continued
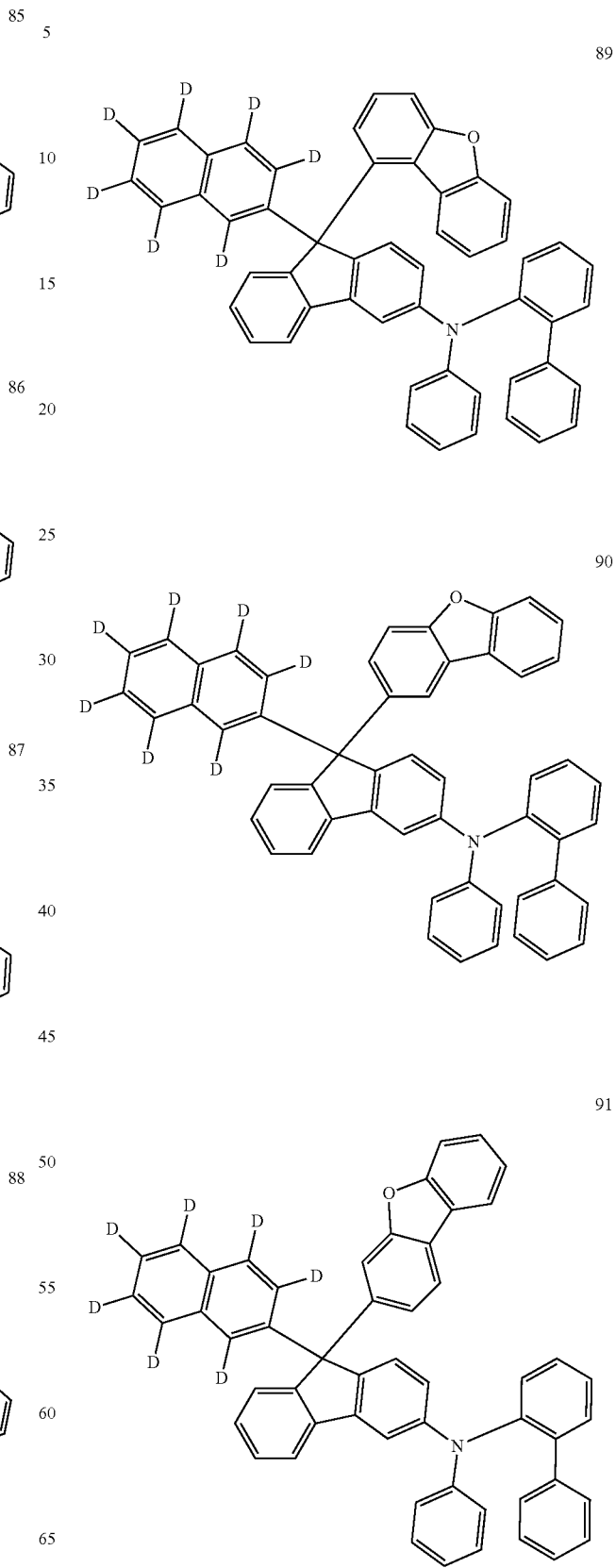

92
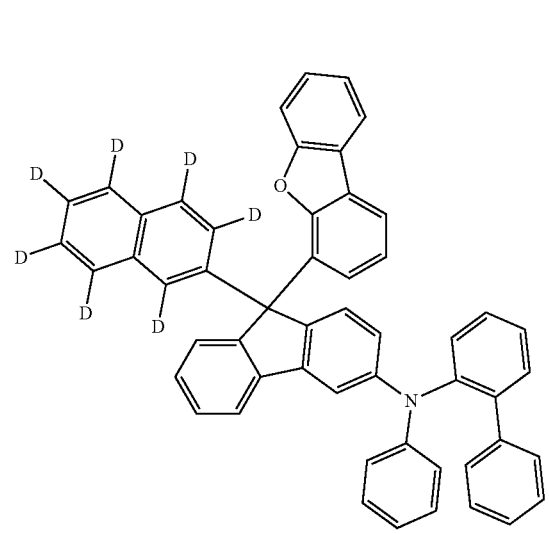
93
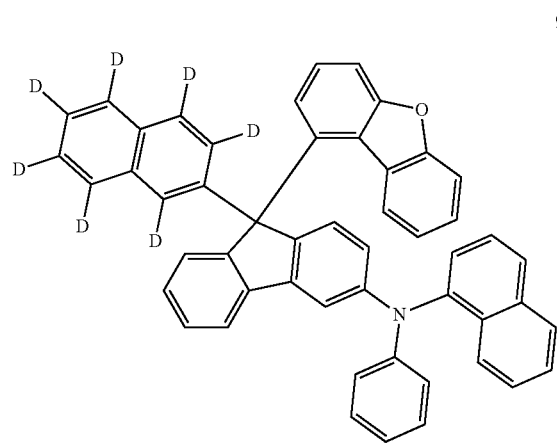
94
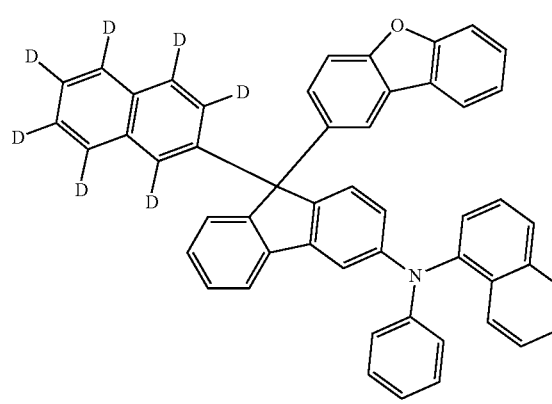
95
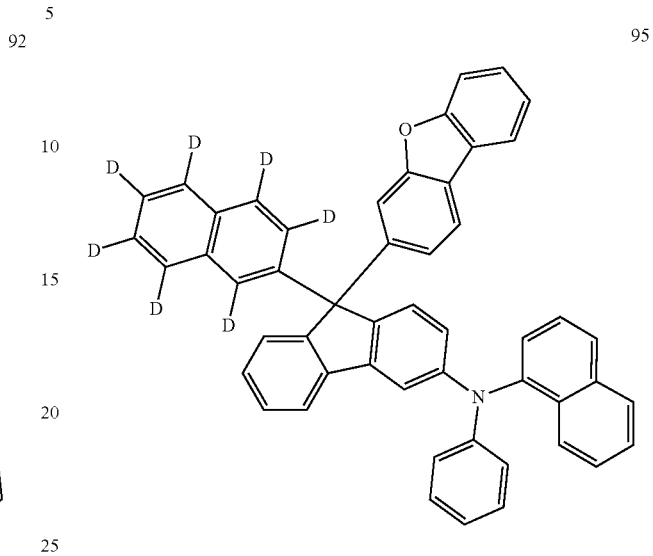
96
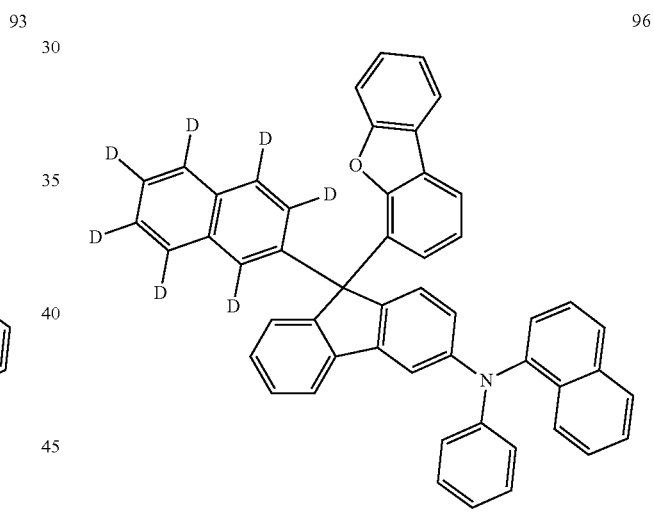
97
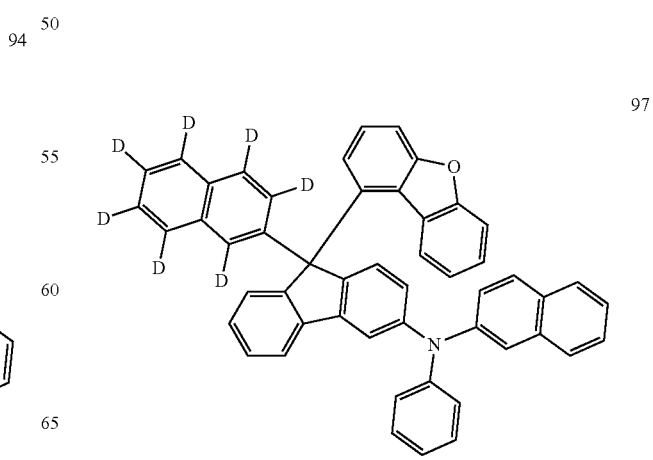

325
-continued
98
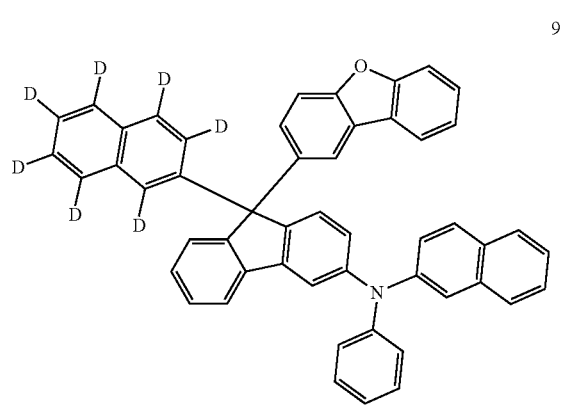
99
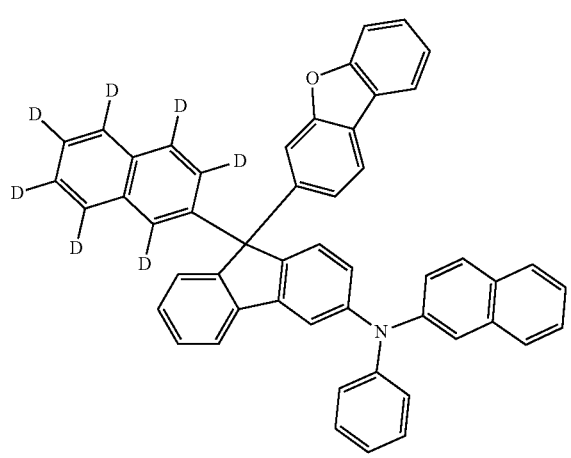
100
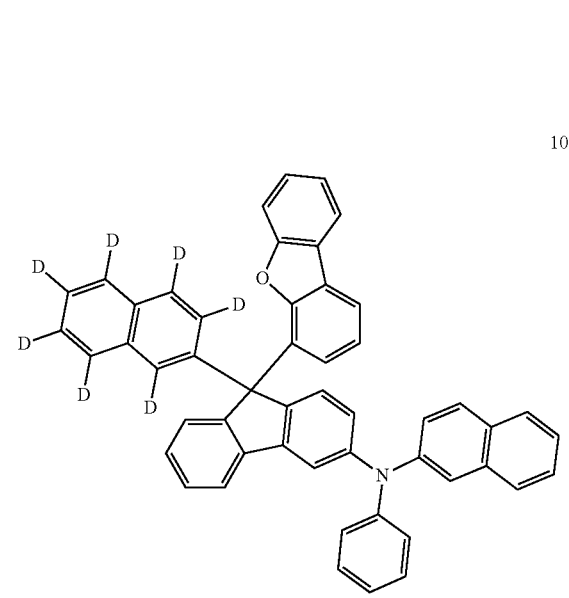
326
-continued
101
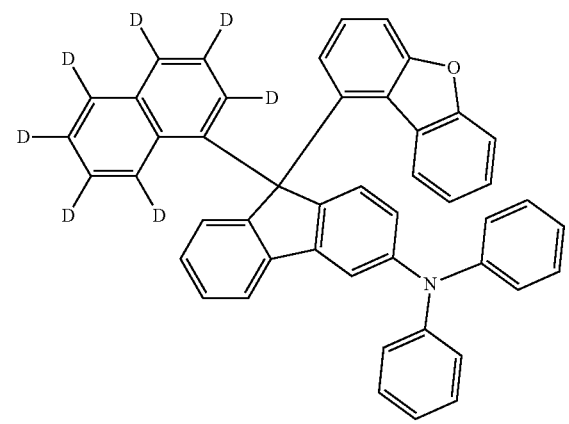
102
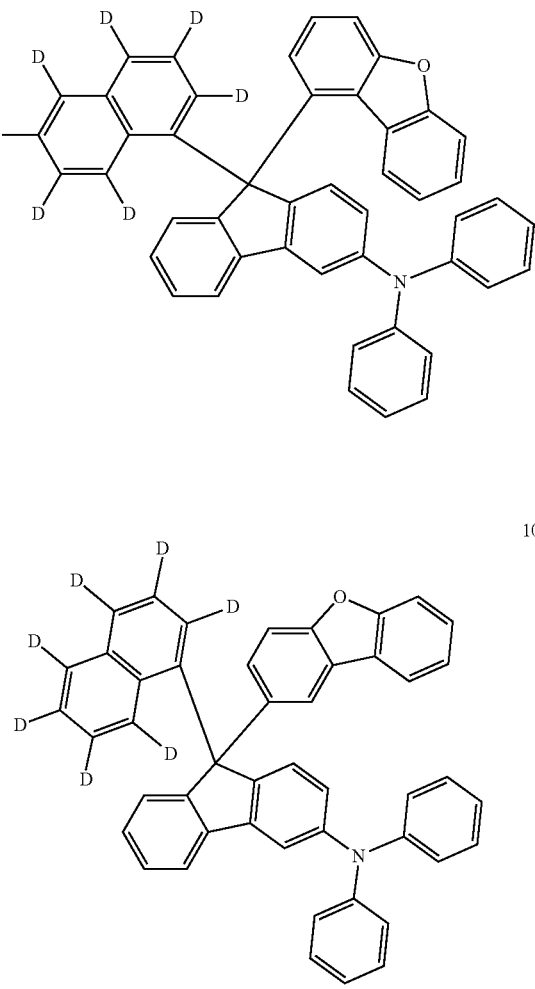
103
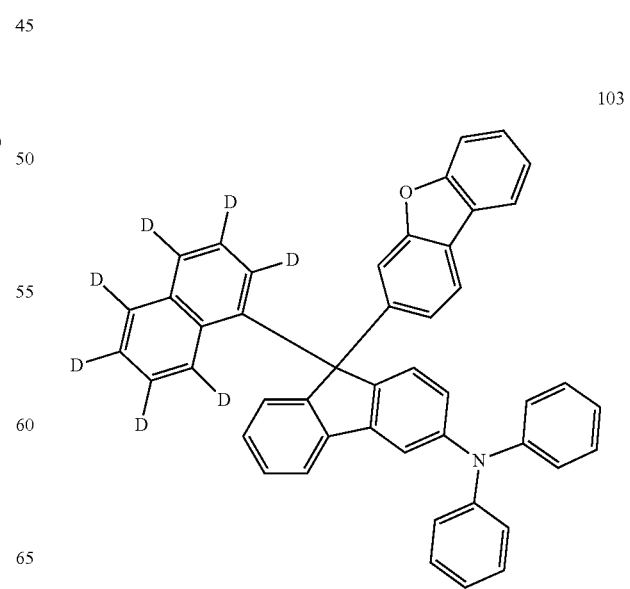

327
-continued
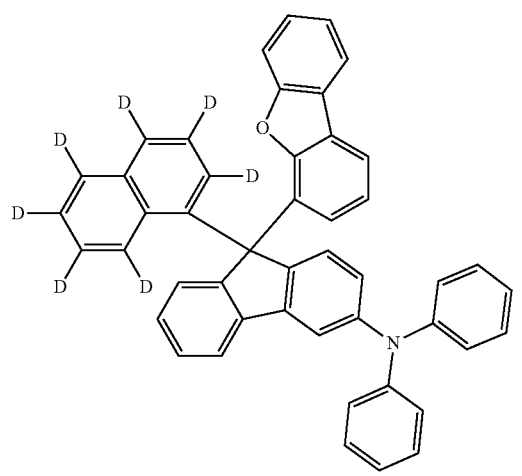
328
-continued
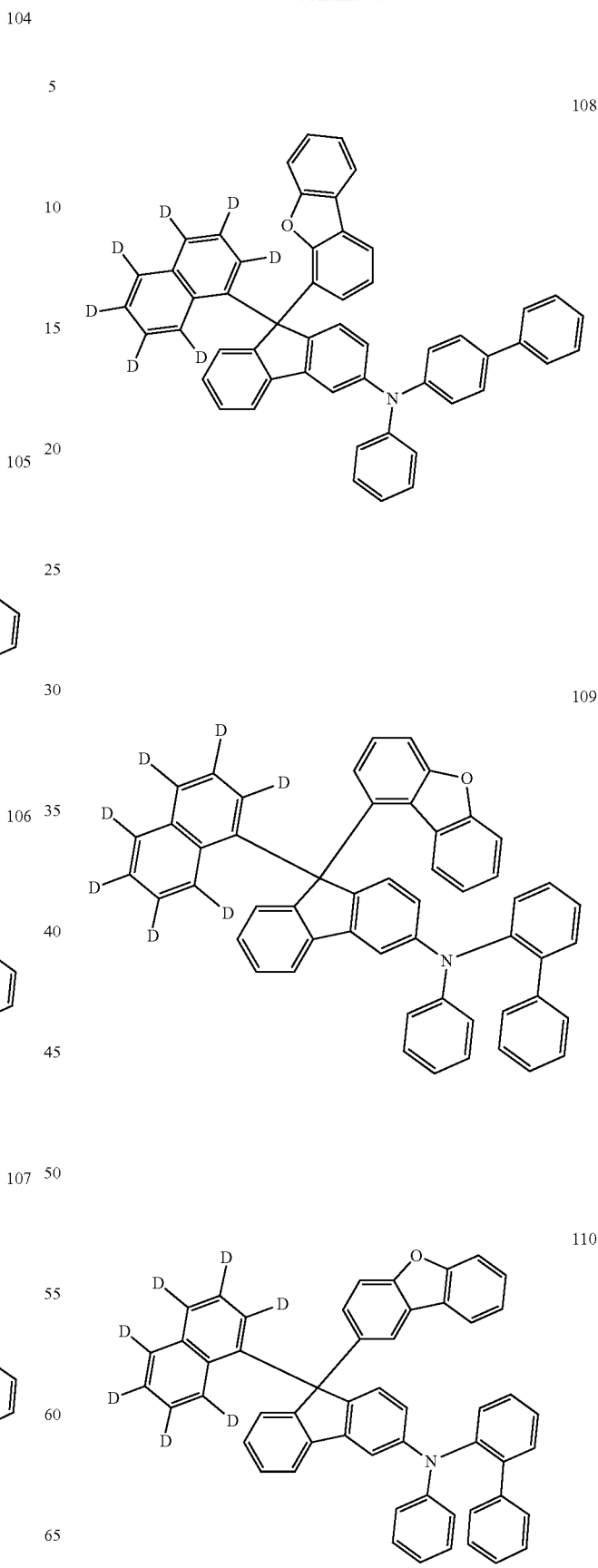

111
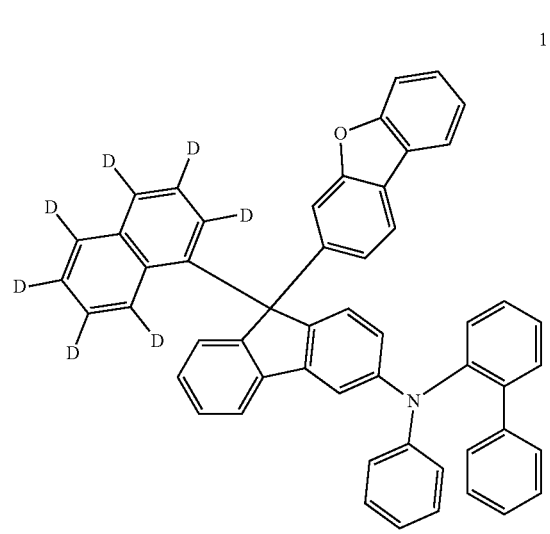
112
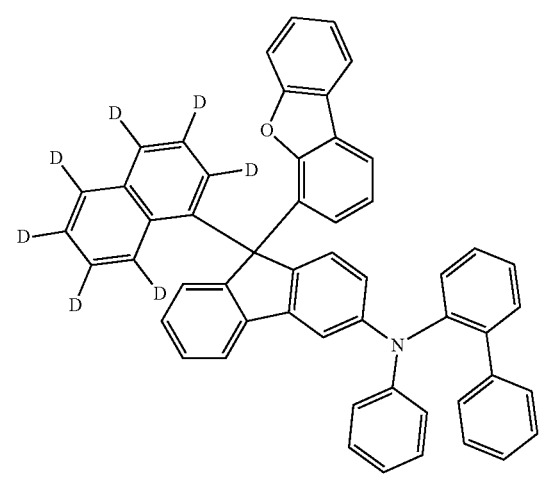
113
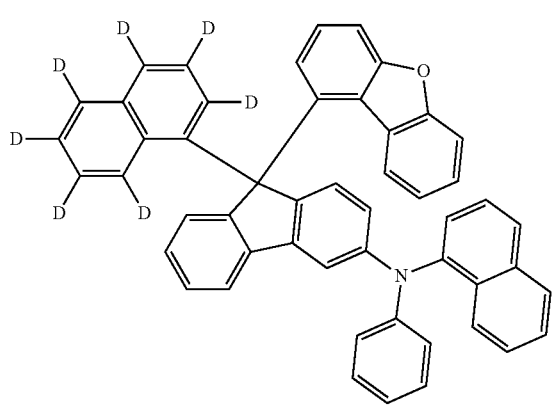
114
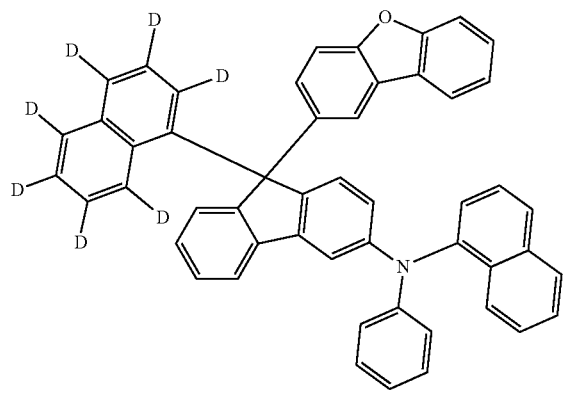
115
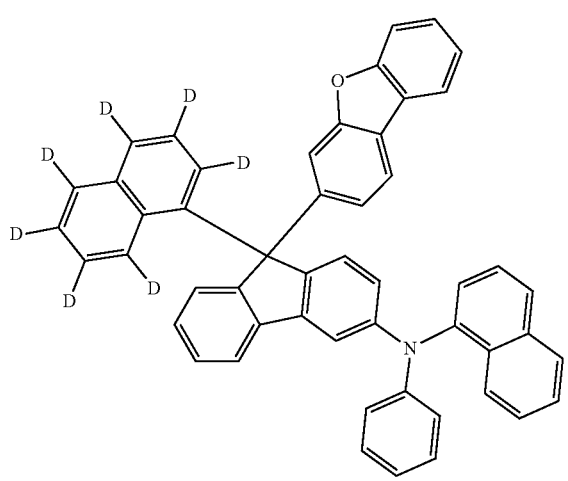
116
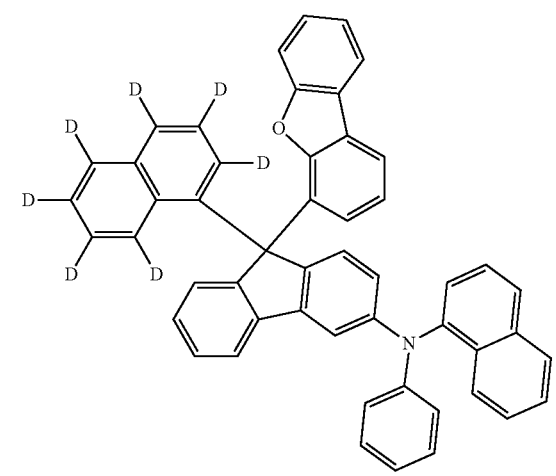

331
-continued
117
118
119
120
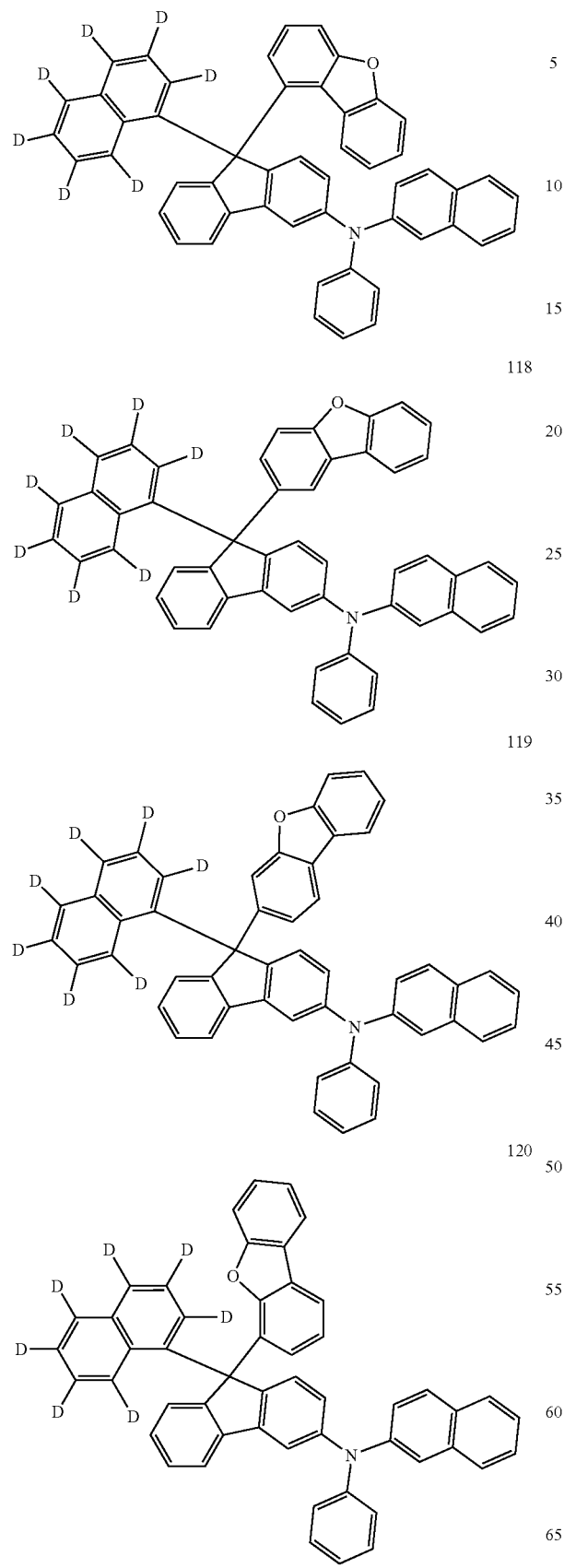
332
-continued
121
122
123
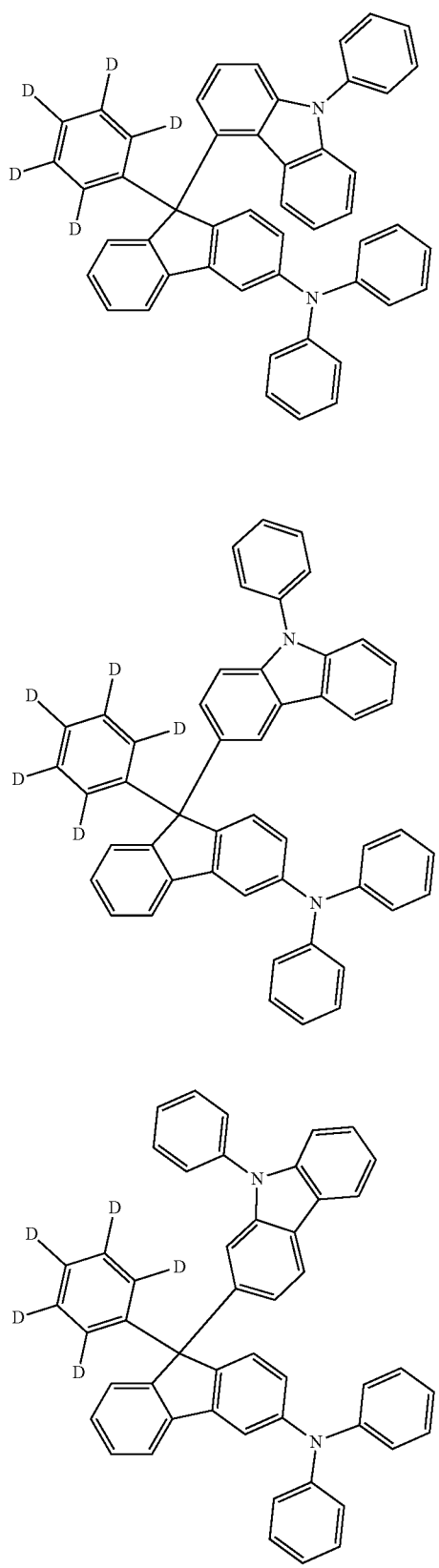

-continued
124
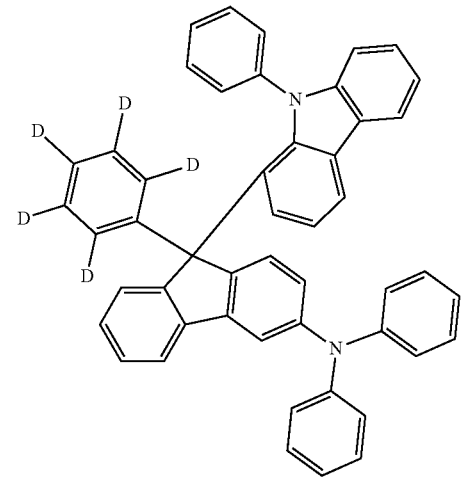
125
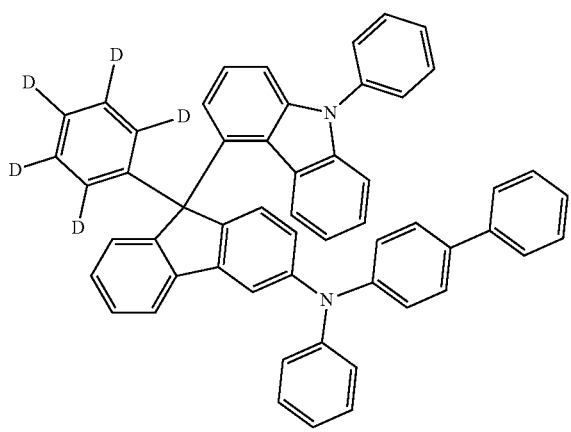
126
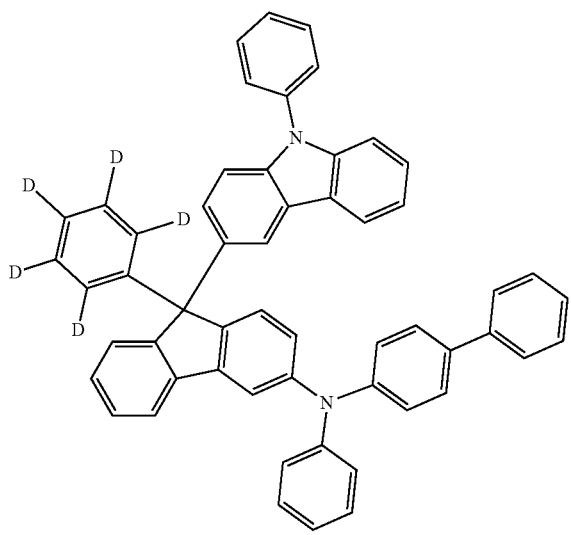
-continued
127
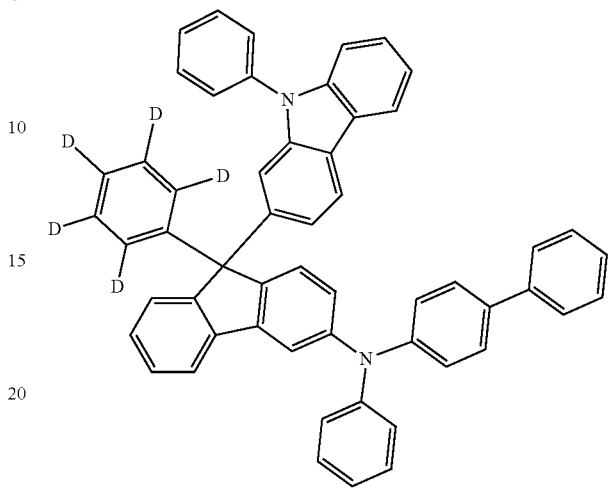
128
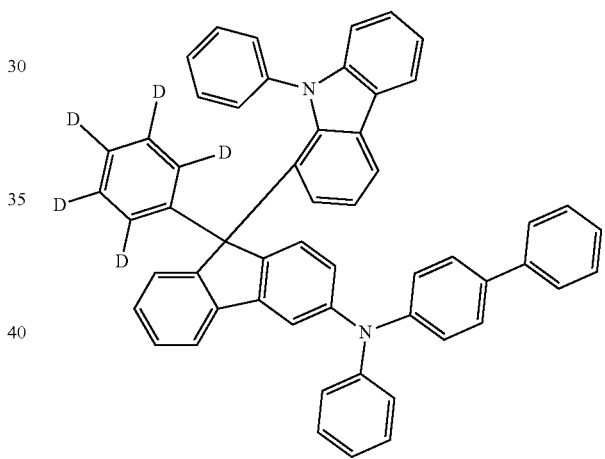
129
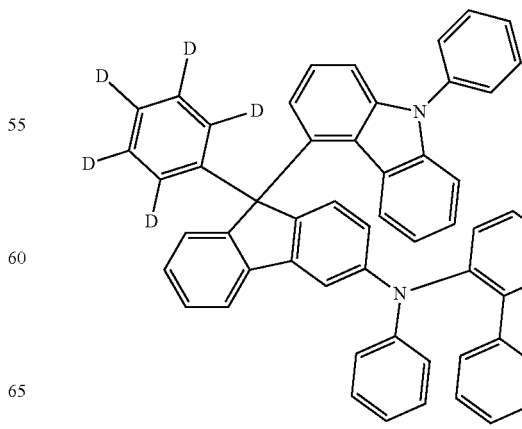

130
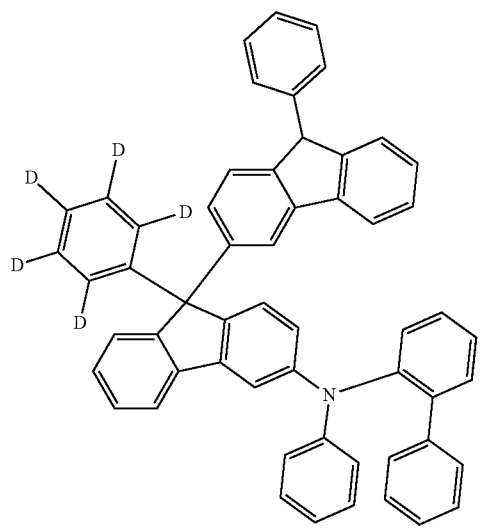
131
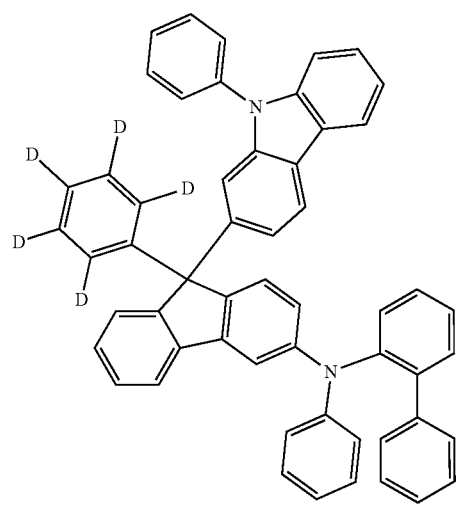
132
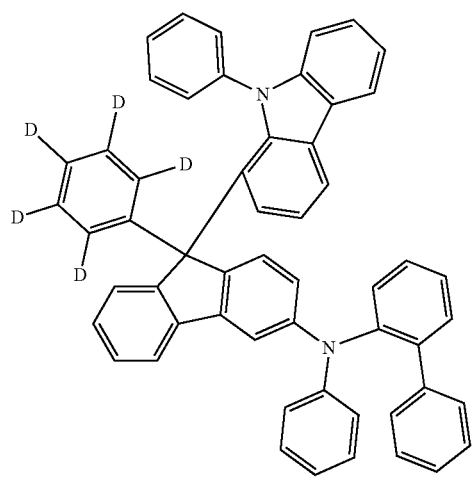
133
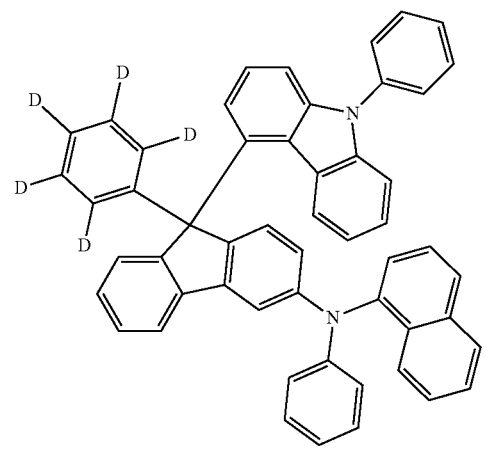
134
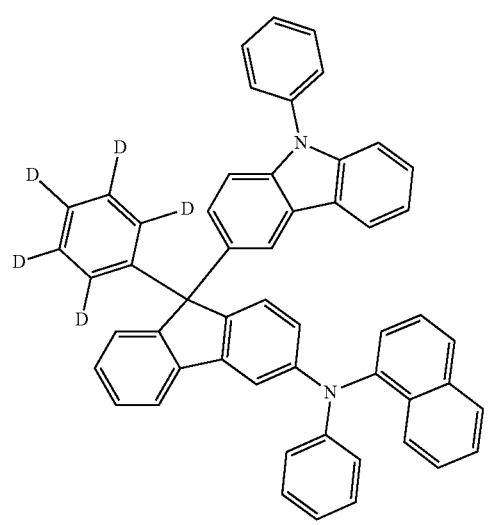
135
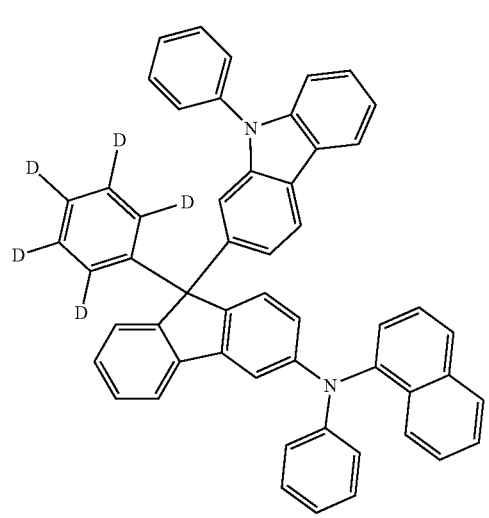

136
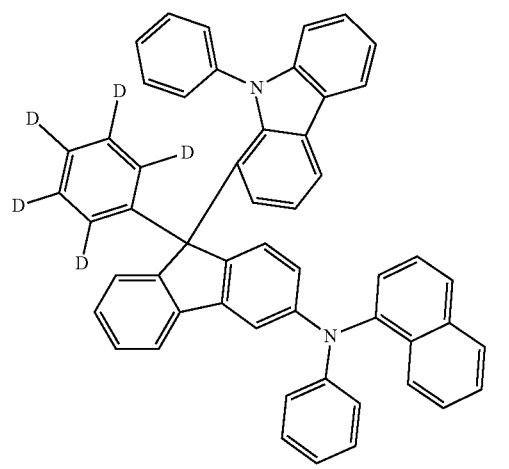
137
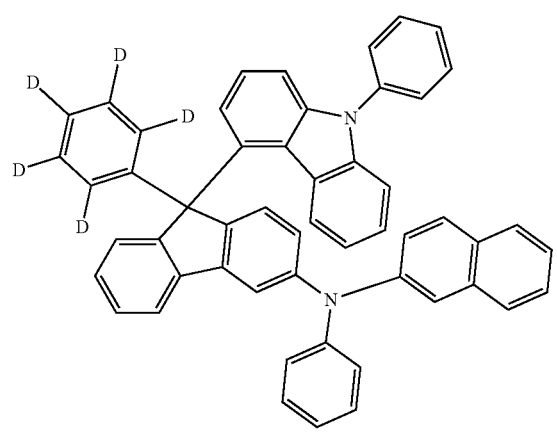
138
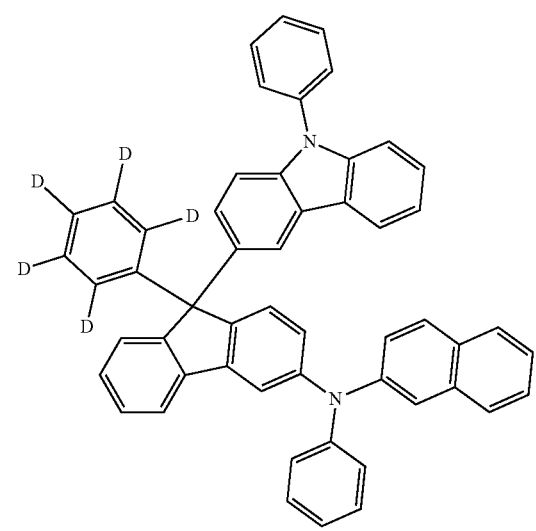
139
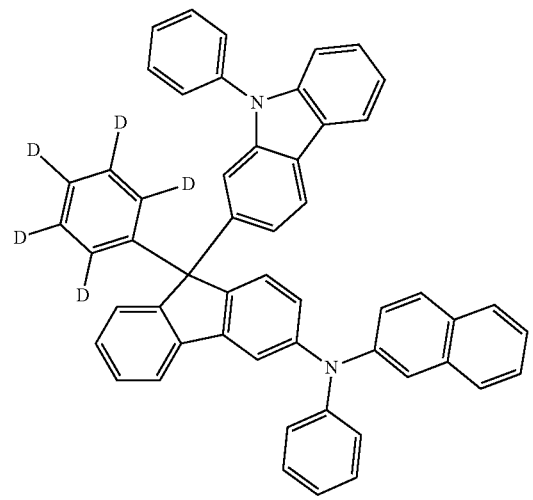
140
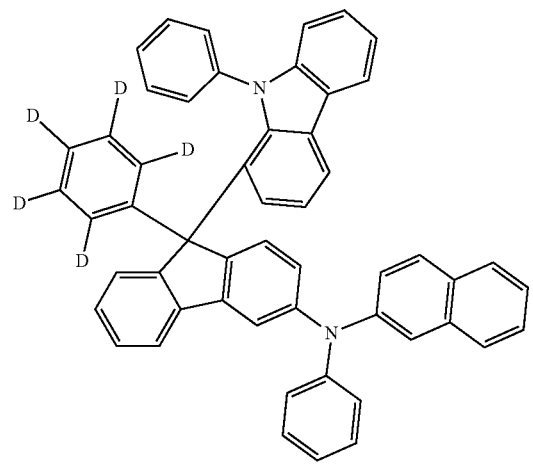
141
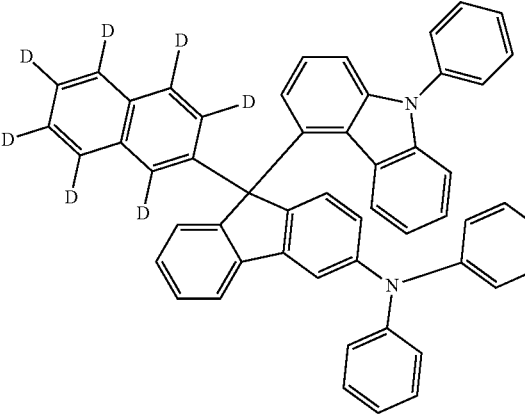

339
-continued
142
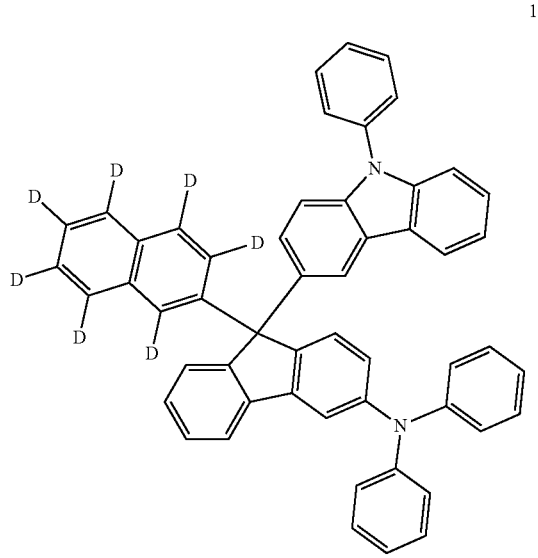
143
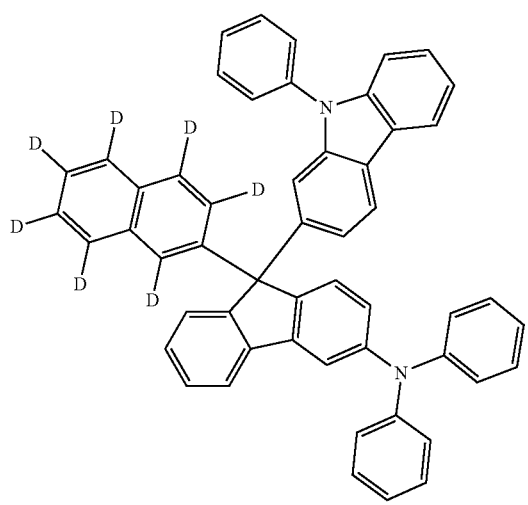
144
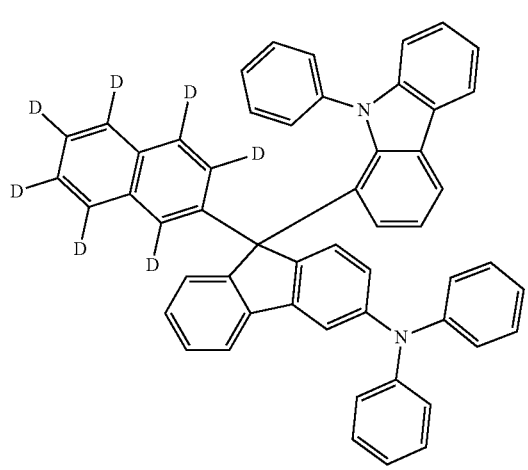
340
-continued
145
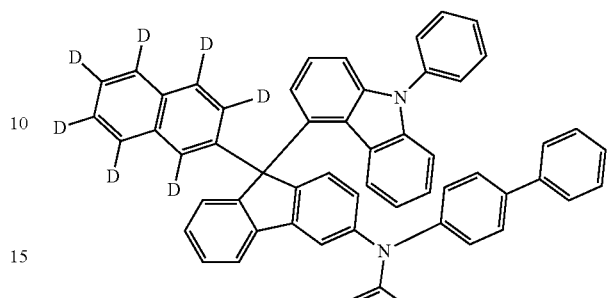
146
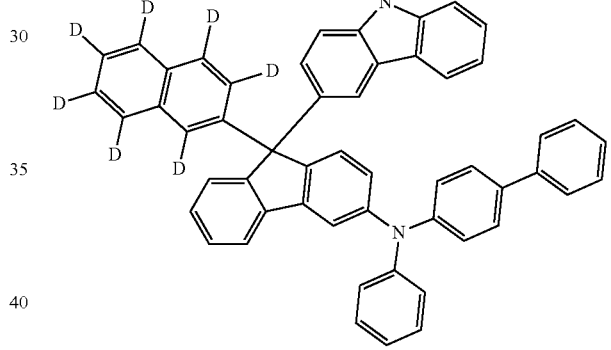
147
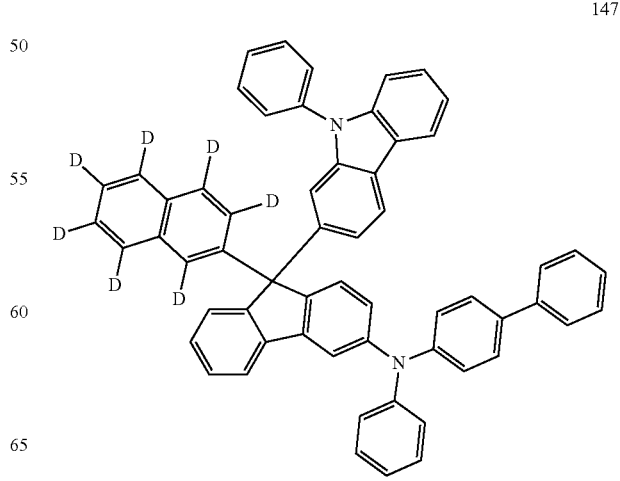

148
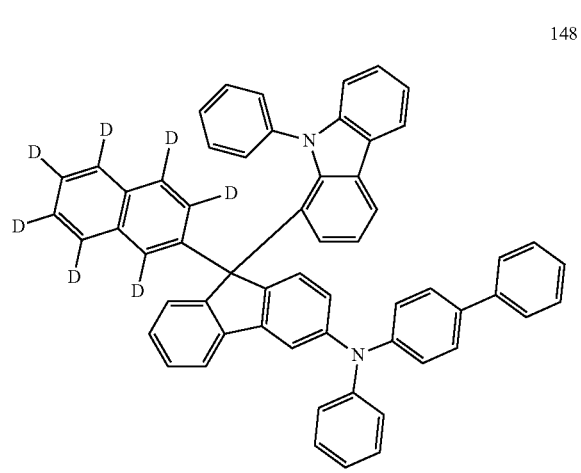
149
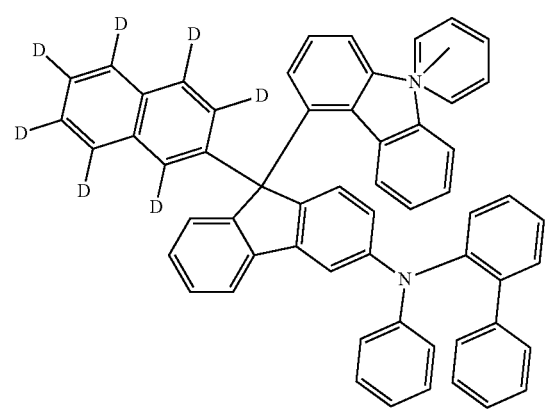
150
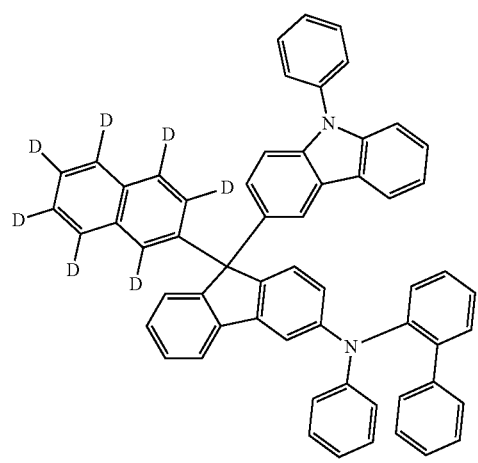
151
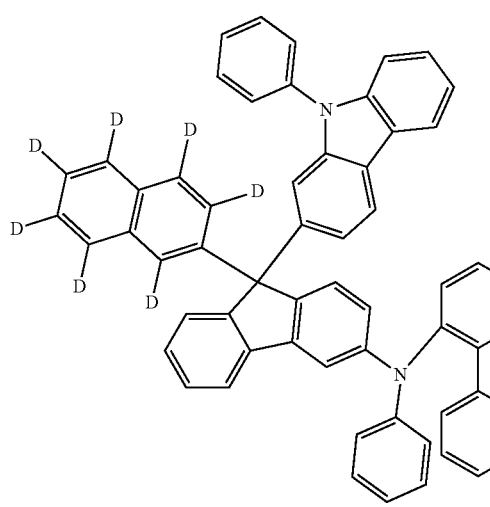
152
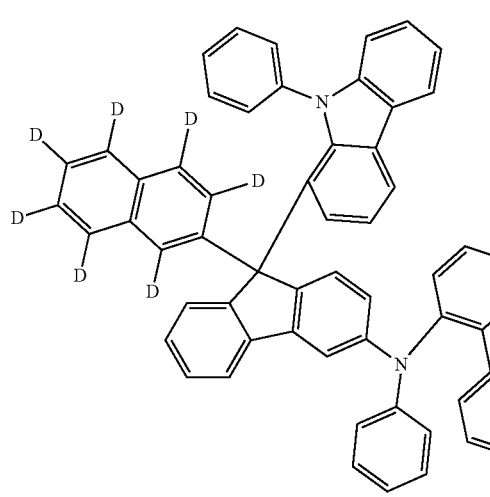
153
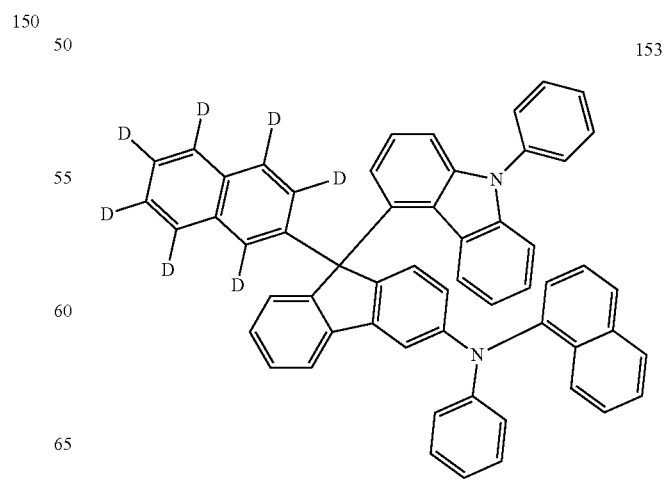

343
-continued
154
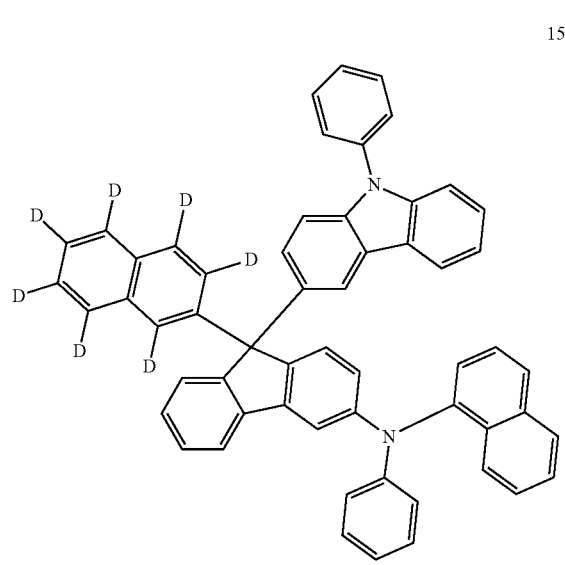
155
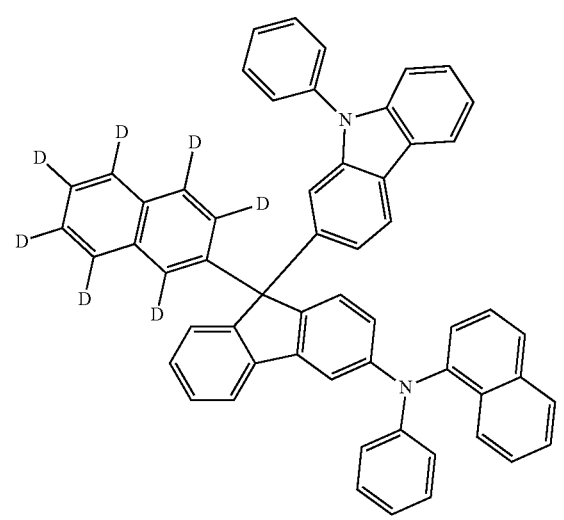
156
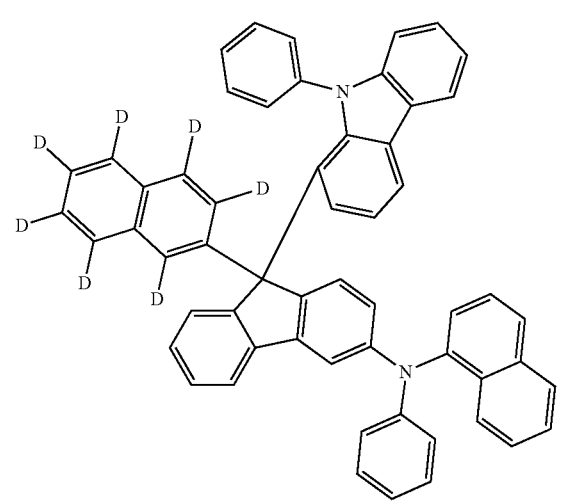
344
-continued
157
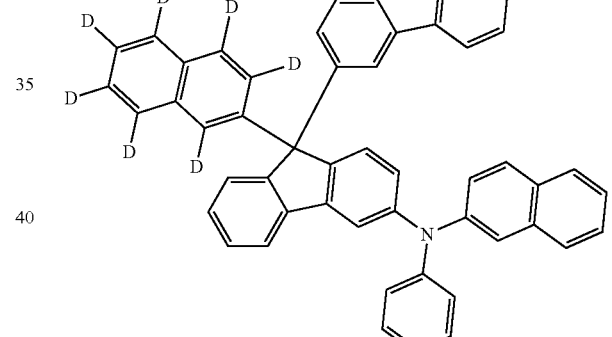
158
159
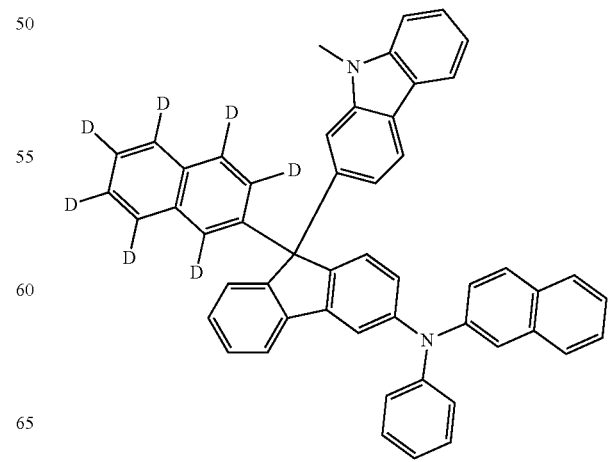

345
-continued
160
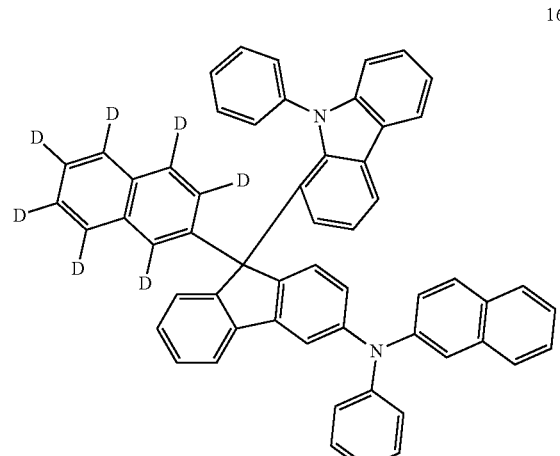
161
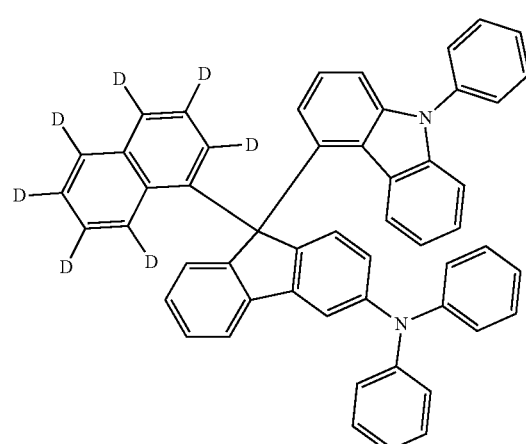
162
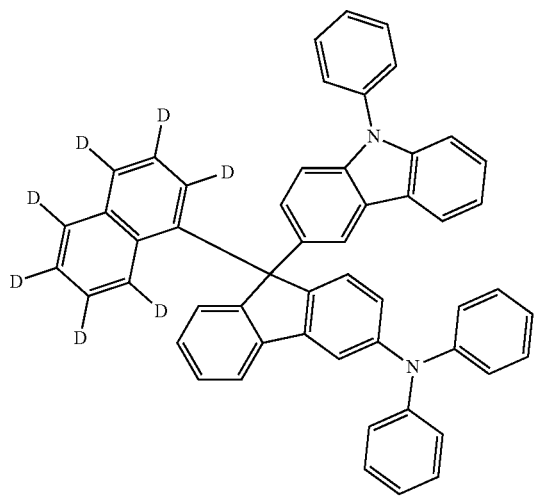
346
-continued
163
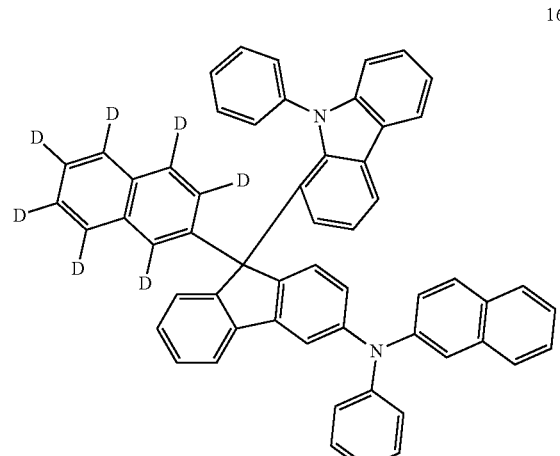
164
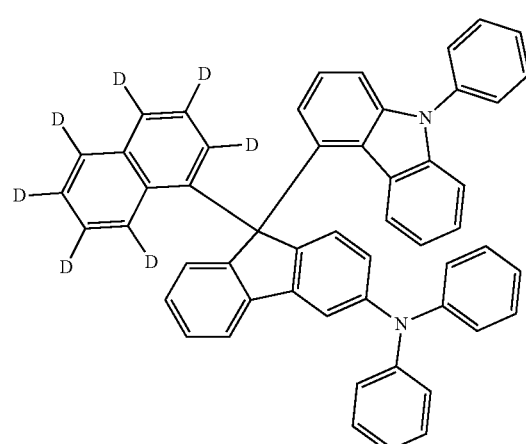
165
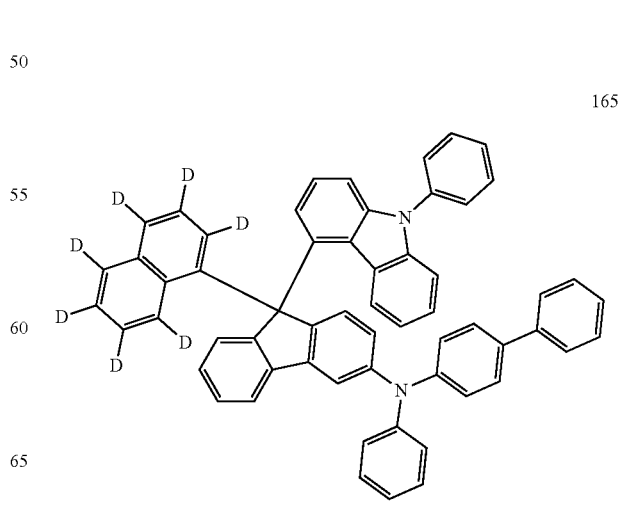

347
-continued
166
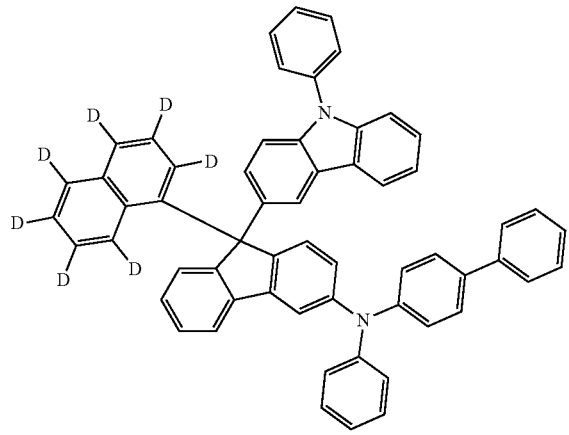
167
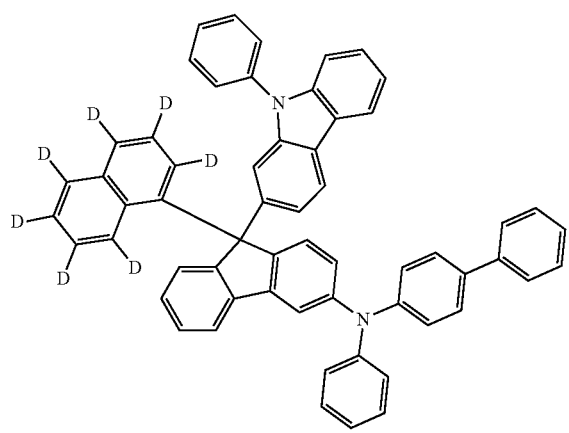
168
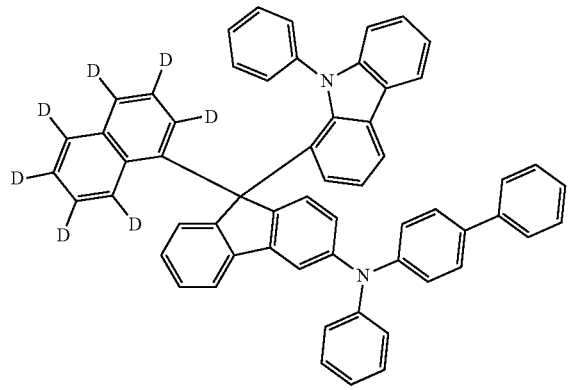
348
-continued
169
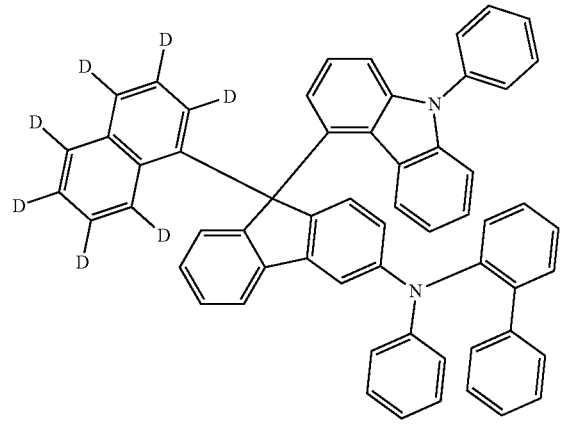
170
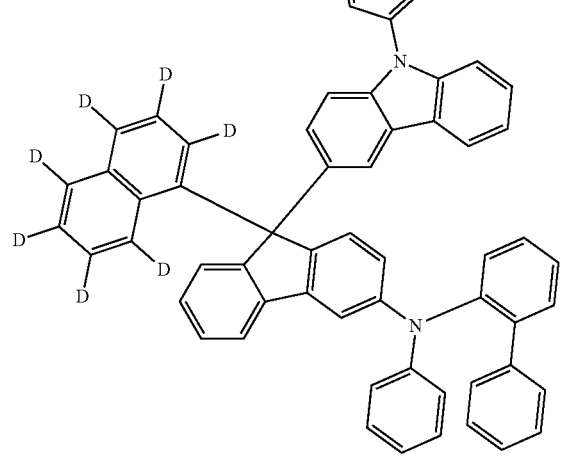
171
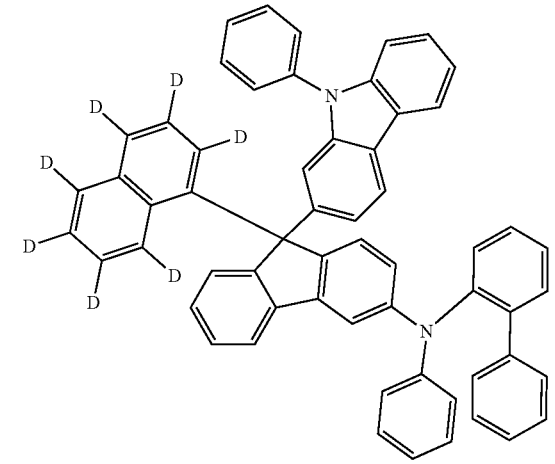

172
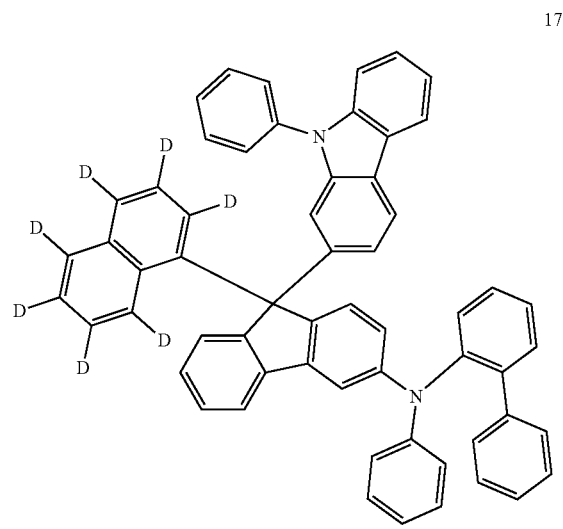
173
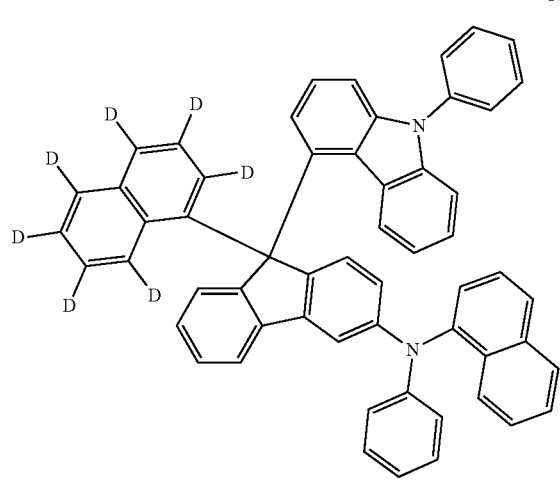
174
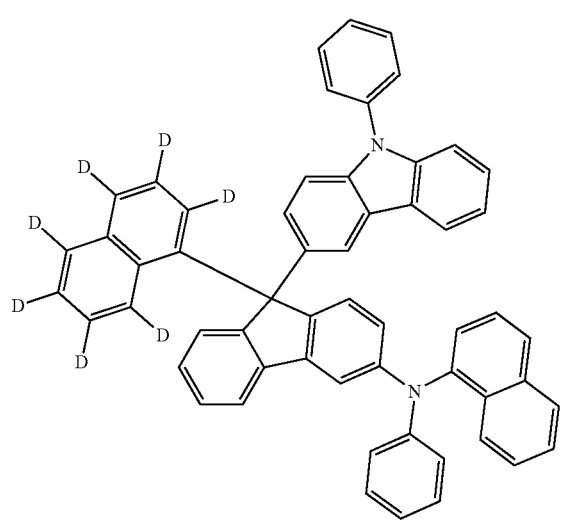
177
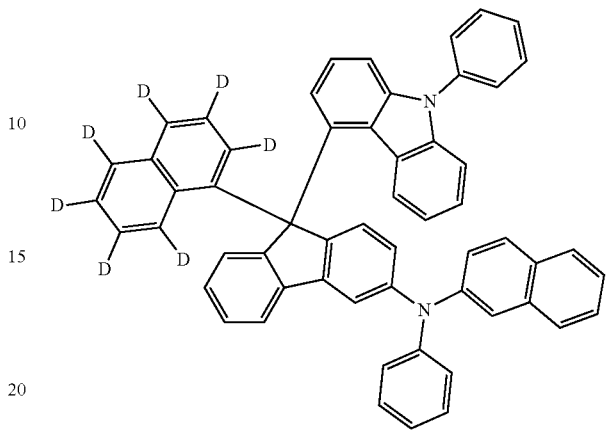
178
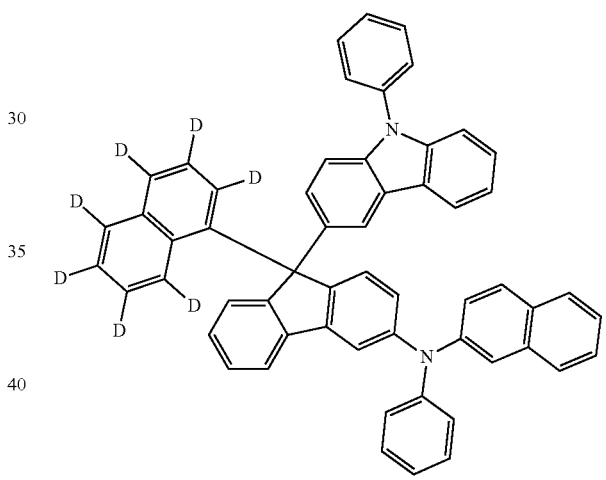
179
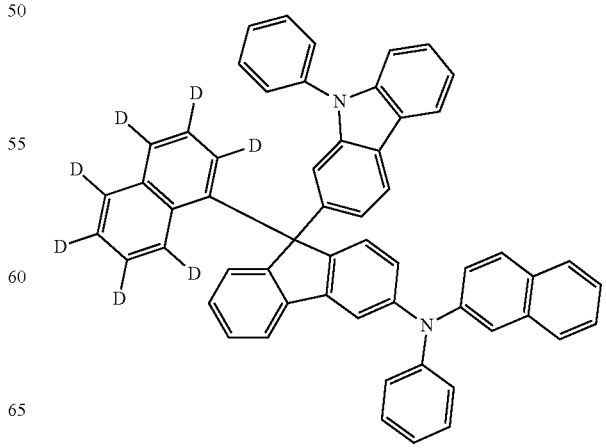

180
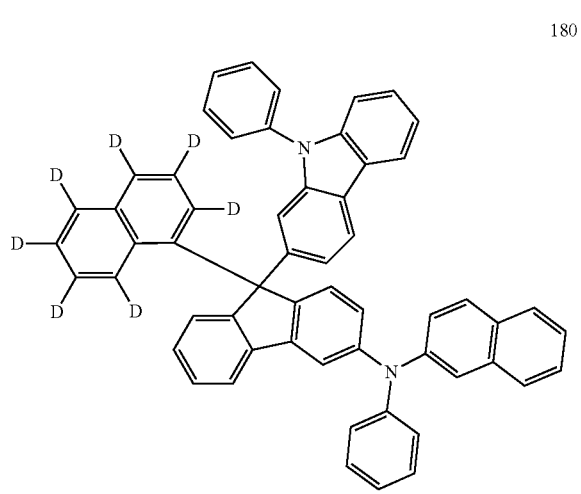
181
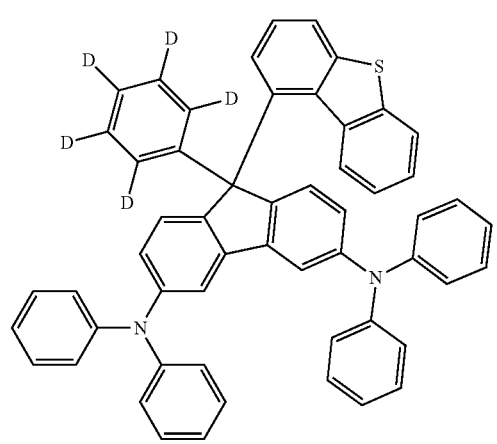
182
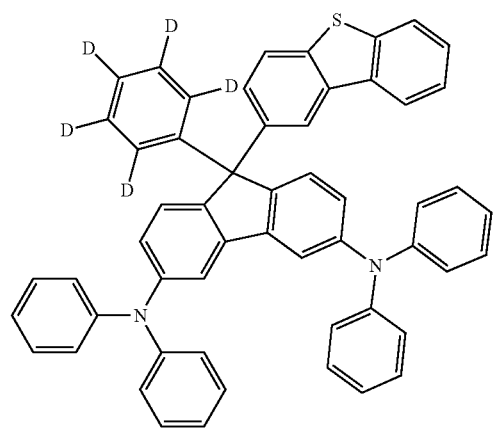
183
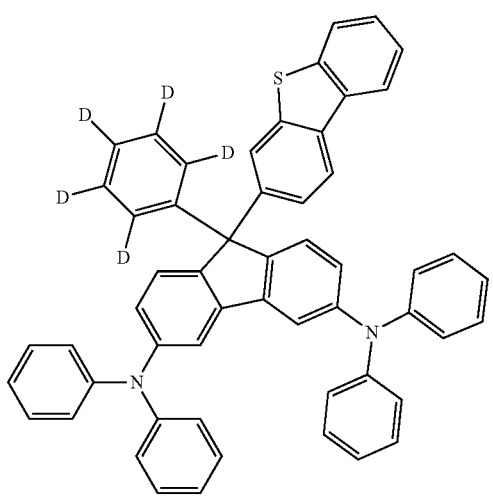
184
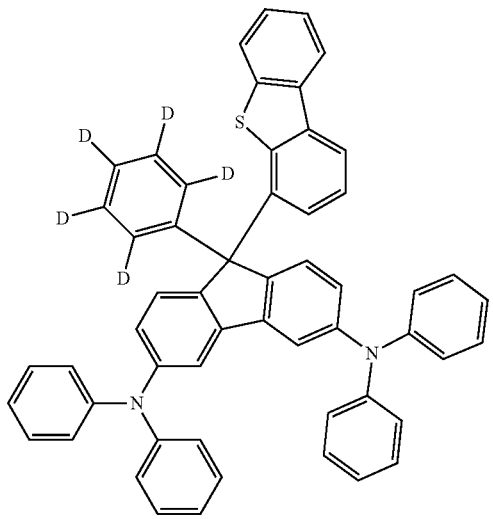
185
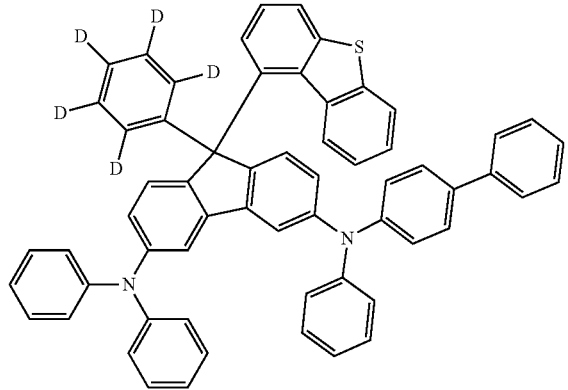

| 186 | 189 |
|---|---|
| 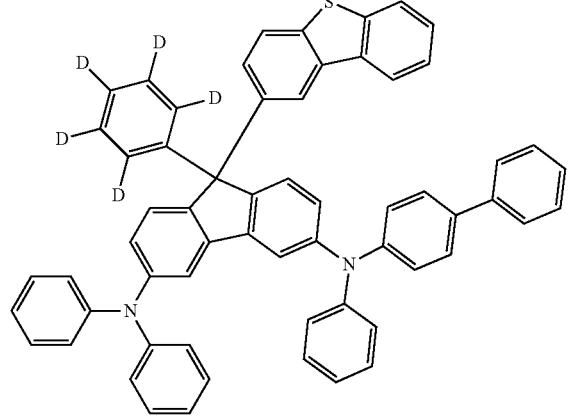 | 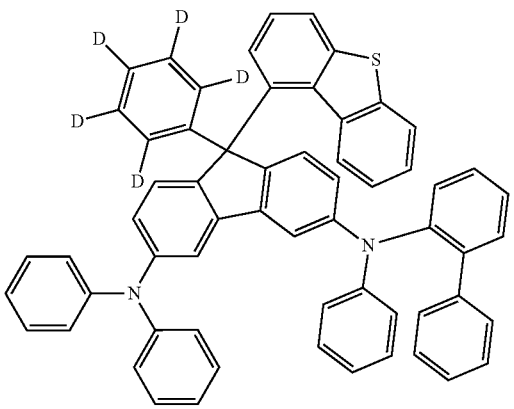 |
| 187 | 190 |
| 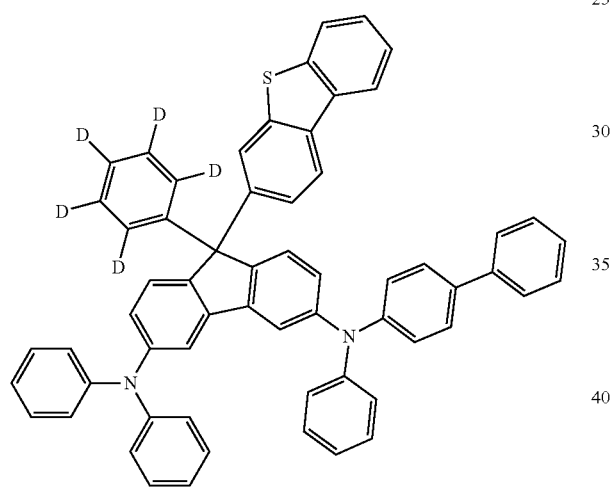 | 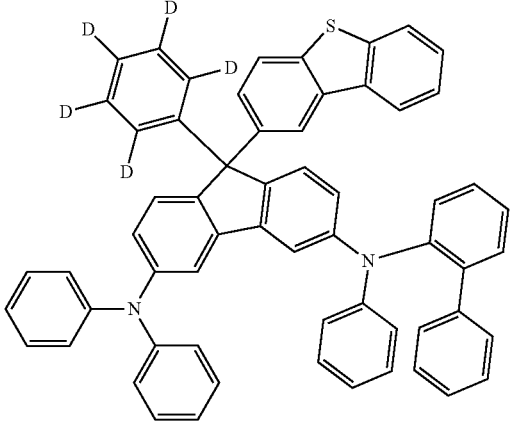 |
| 188 | 191 |
| 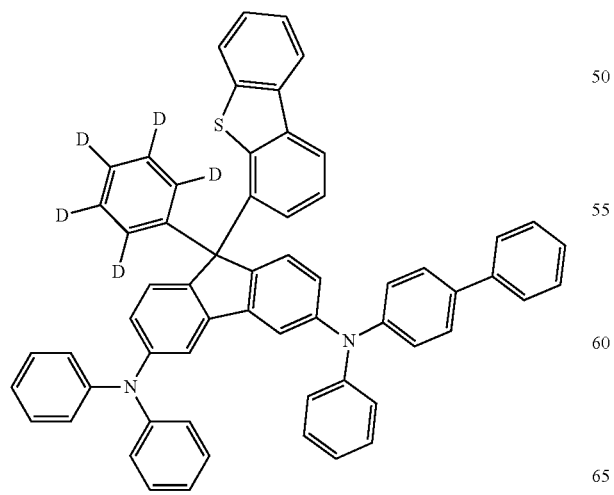 | 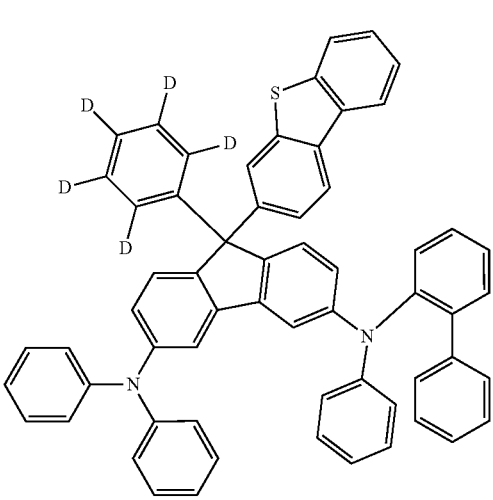 |

-continued
192
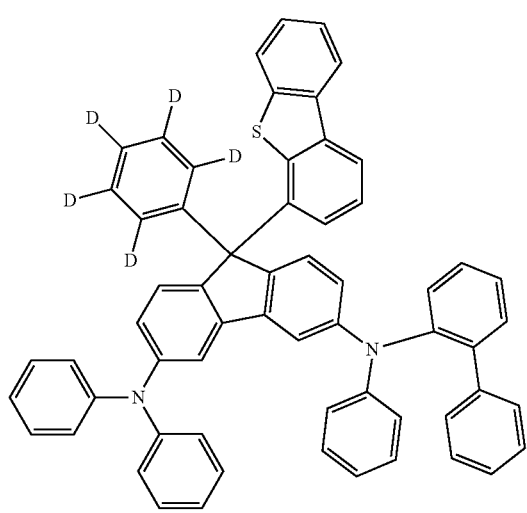
193
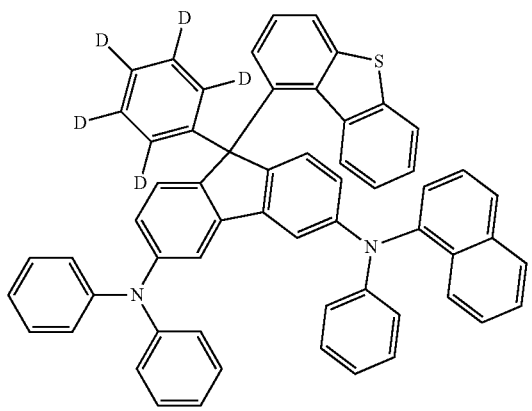
194
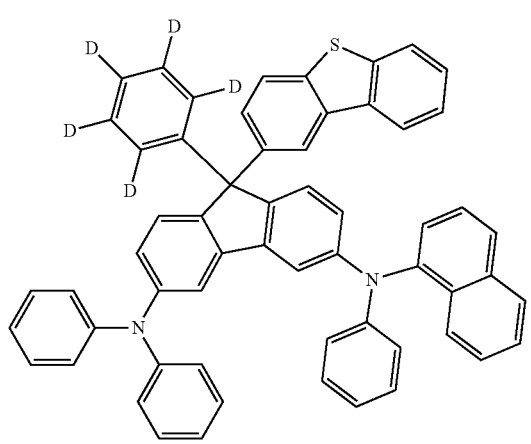
-continued
195
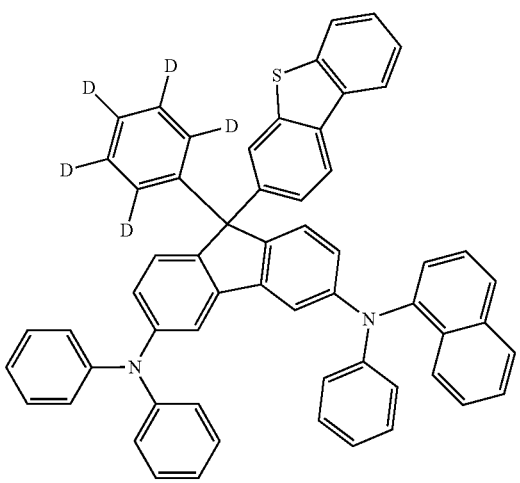
196
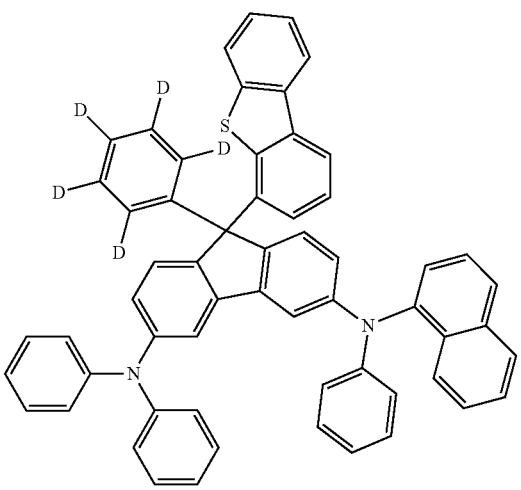
197
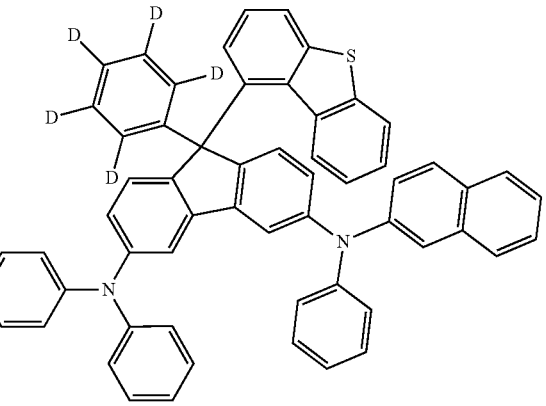

198
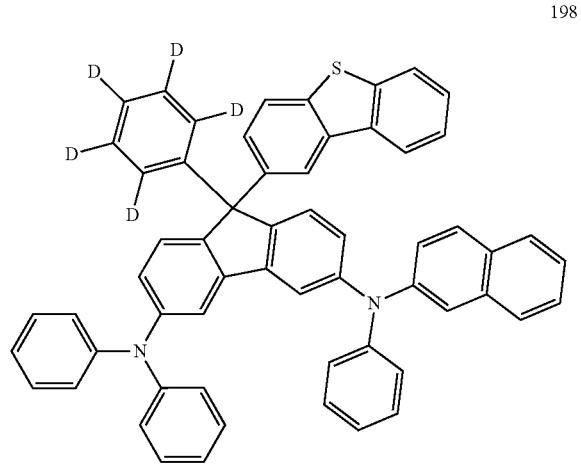
199
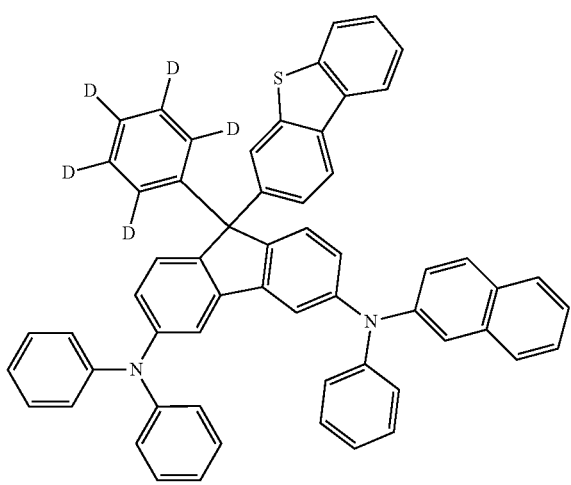
200
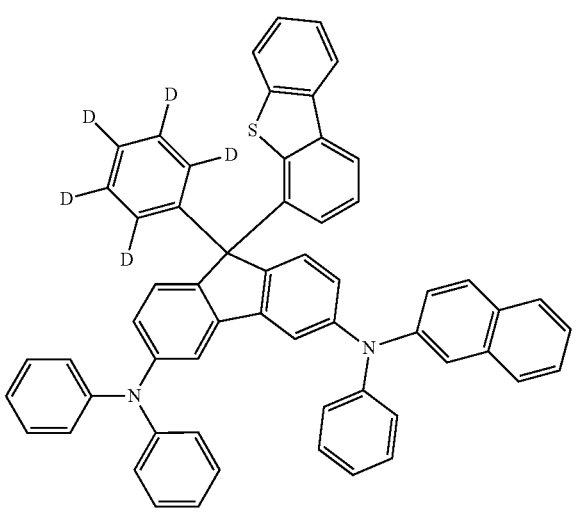
201
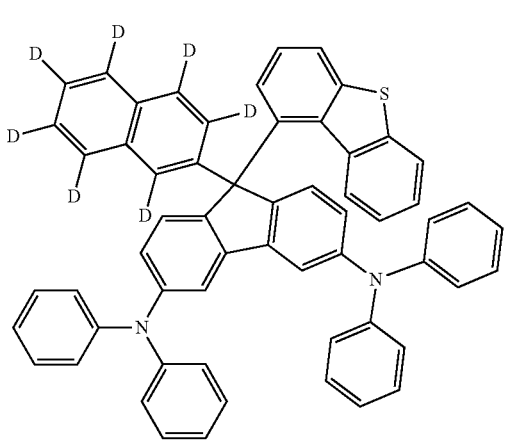
202
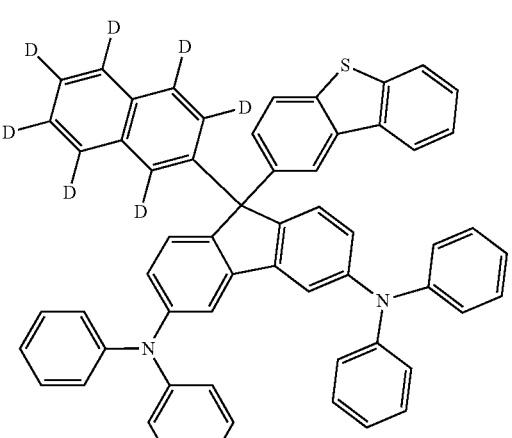
203
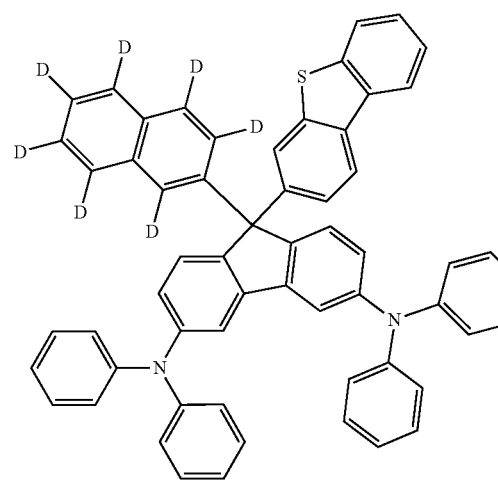

359
-continued
204
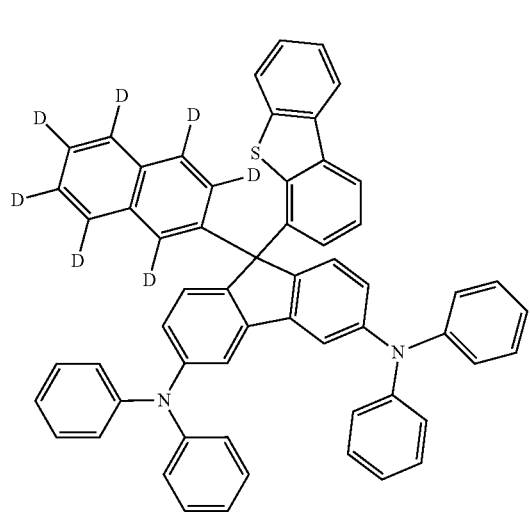
205
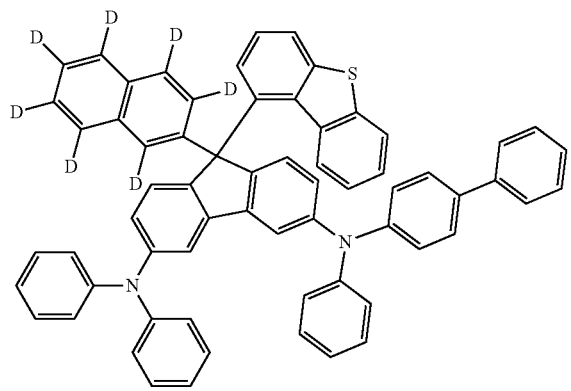
206
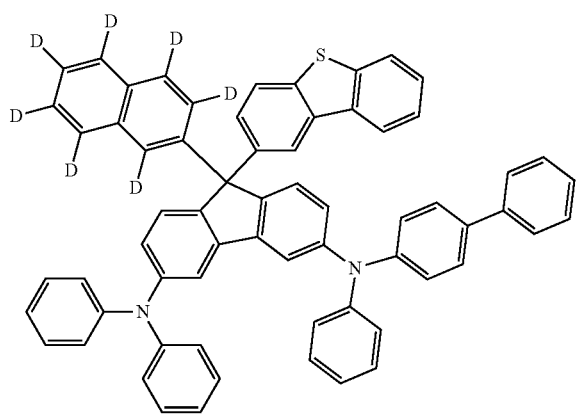
360
-continued
207
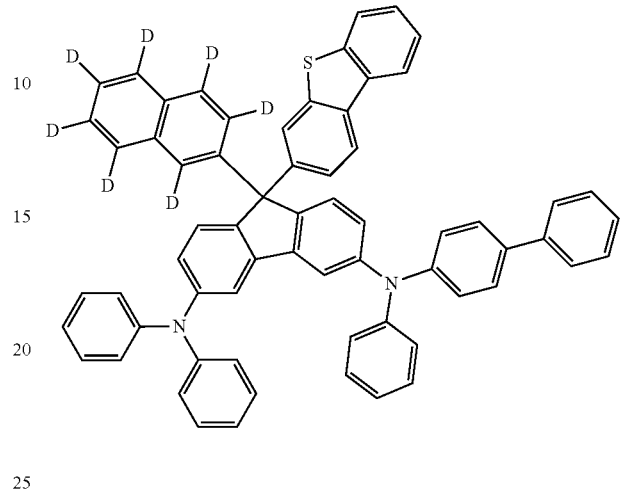
208
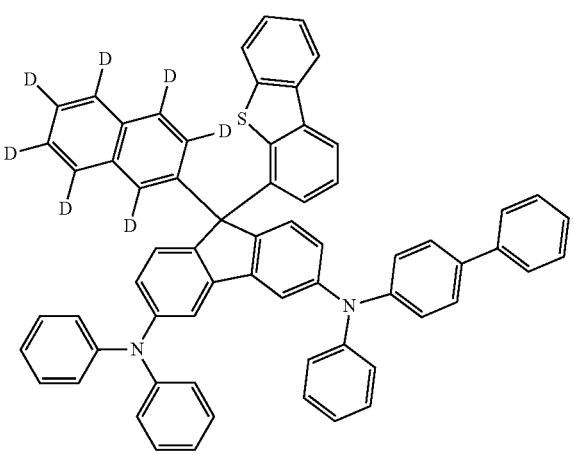
209
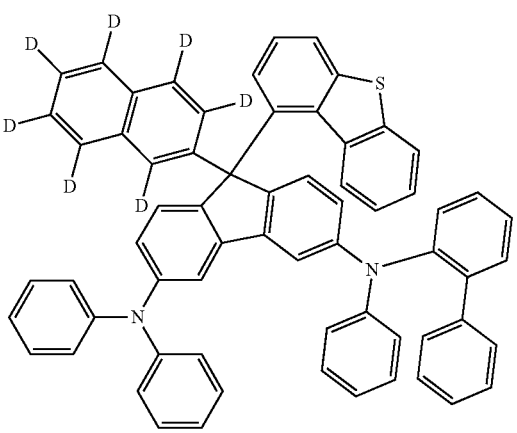

361
-continued
210
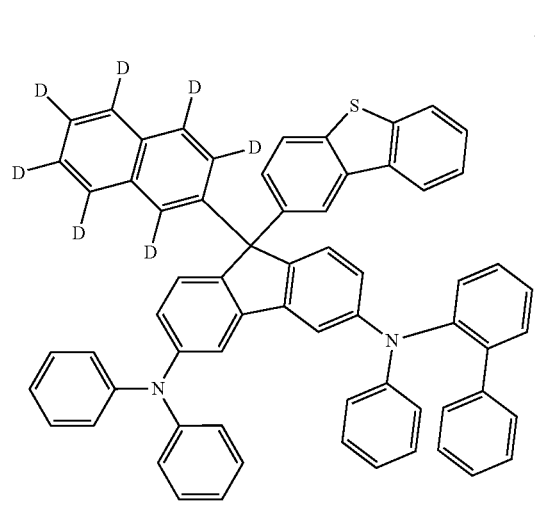
211
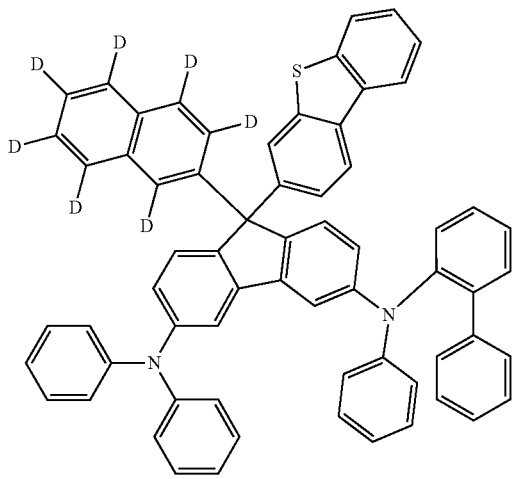
212
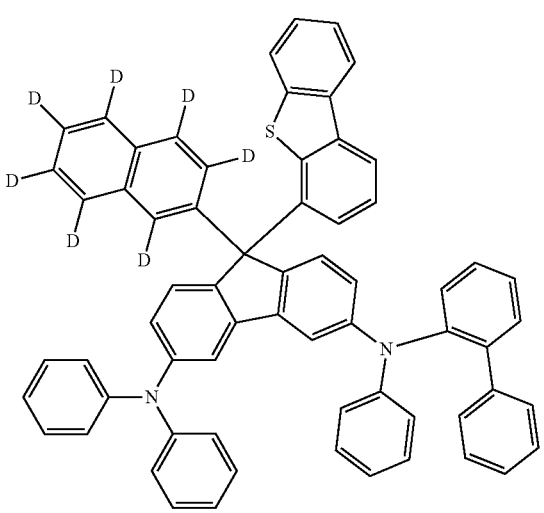
362
-continued
213
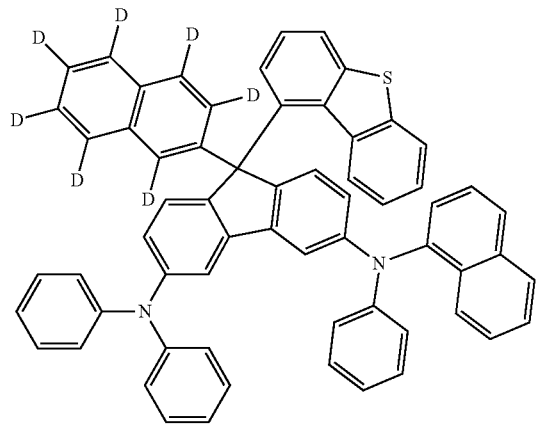
214
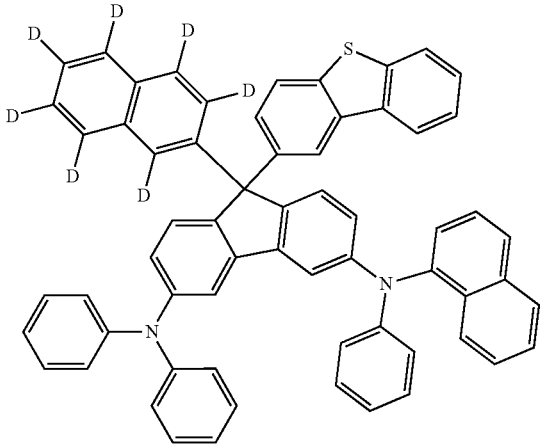
215
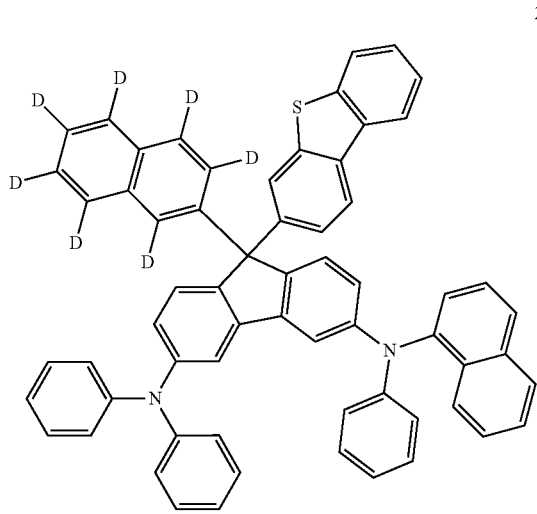

216 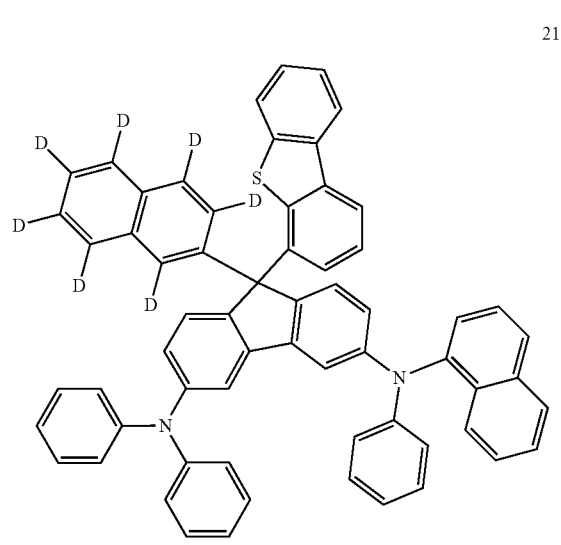
217 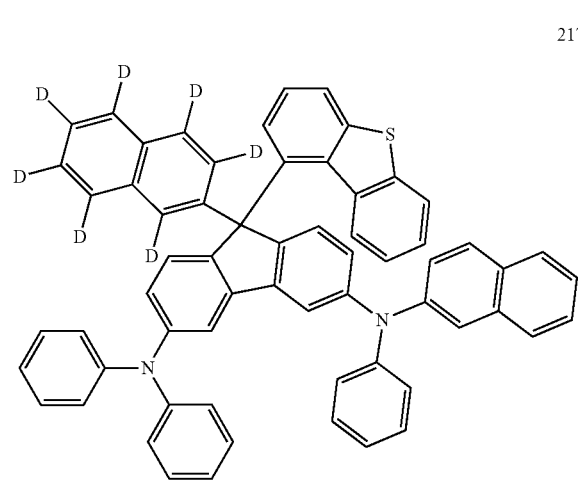
218 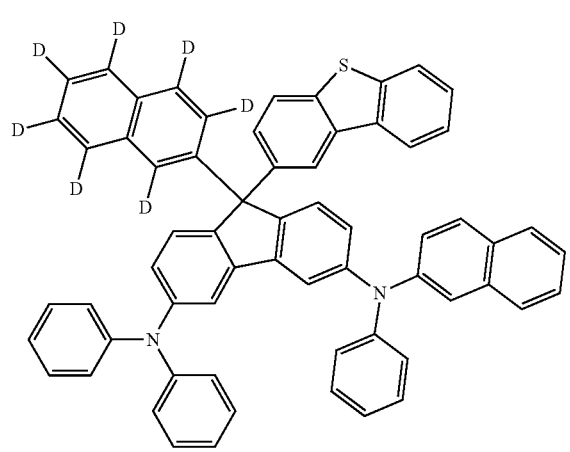
219 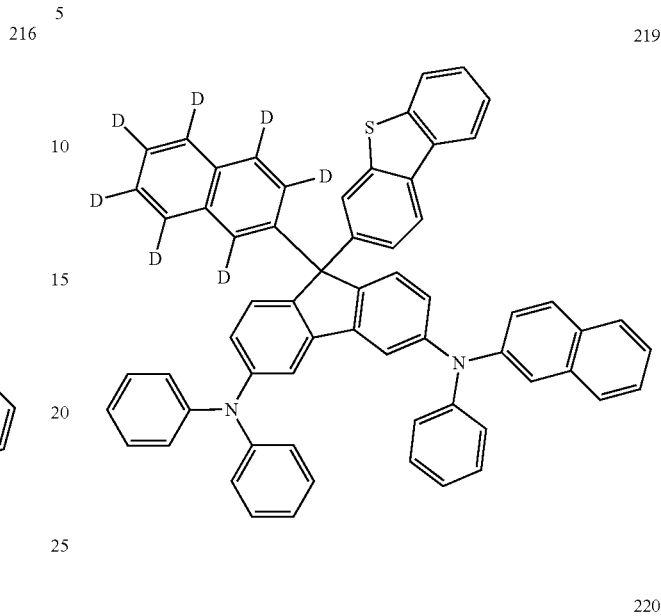
220 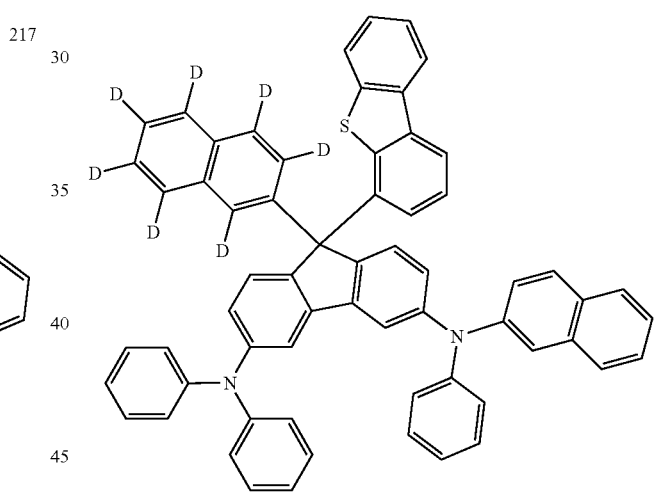
221 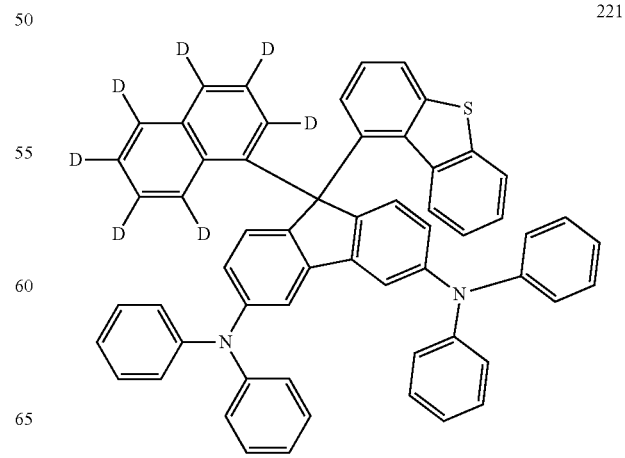

222
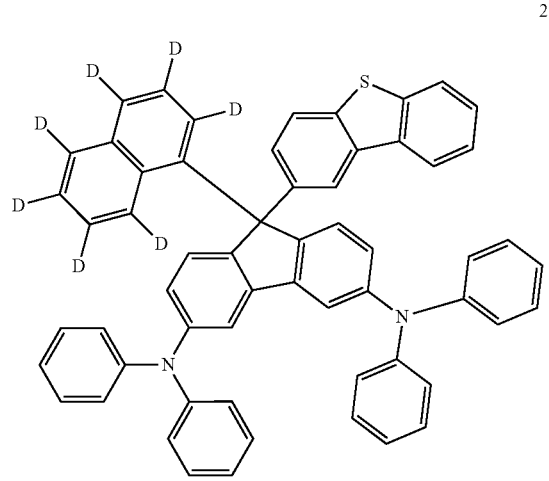
223
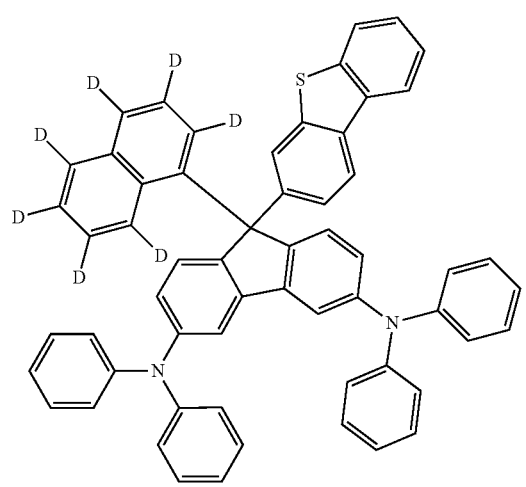
224
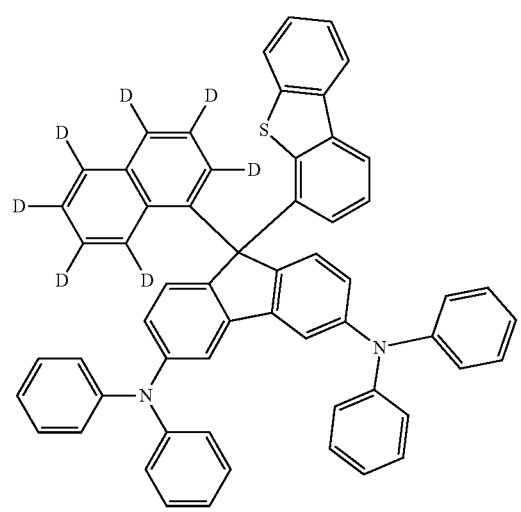
225
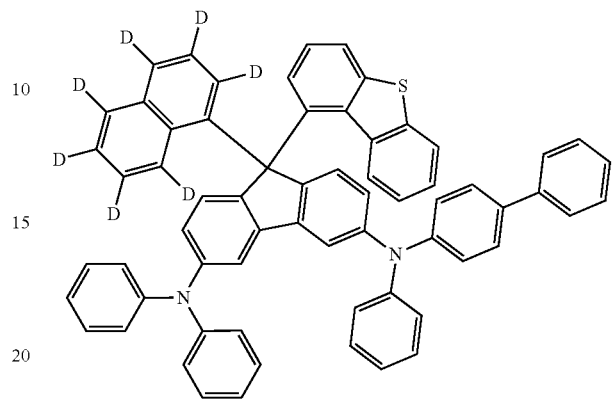
226
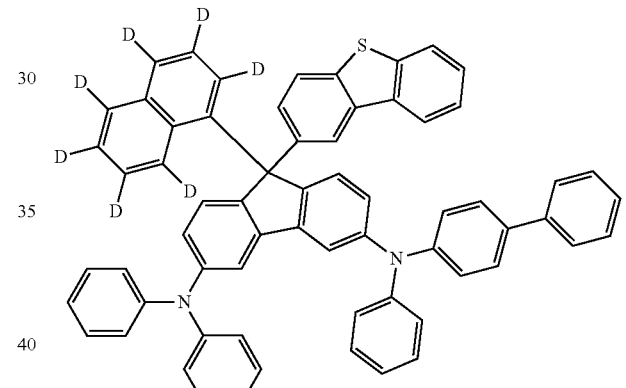
227
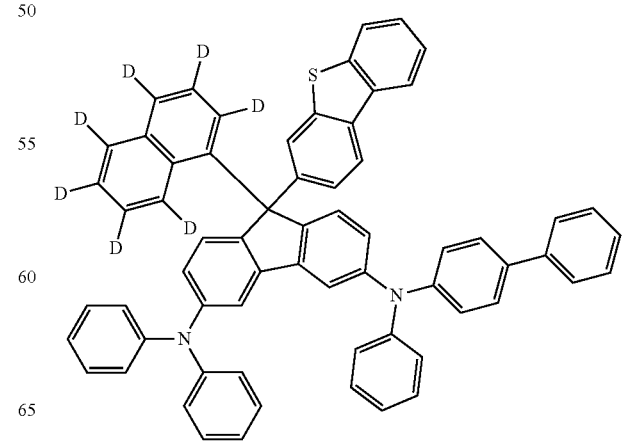

228
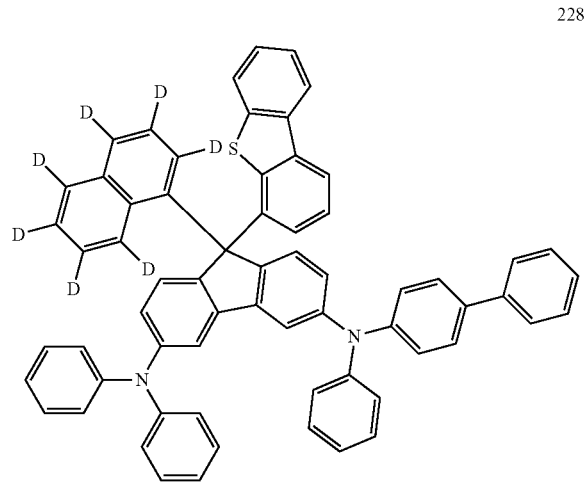
229
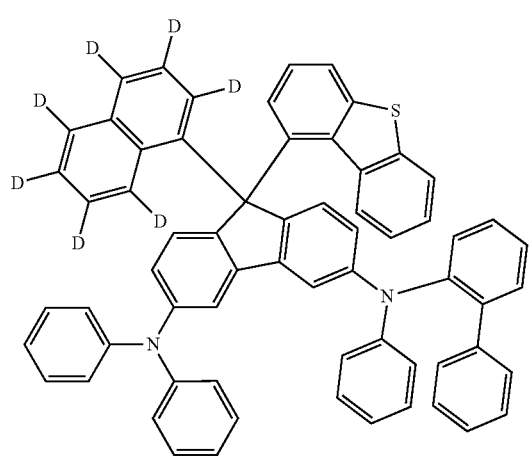
230
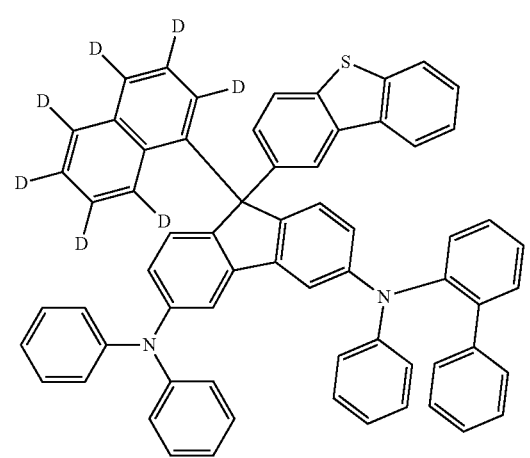
231
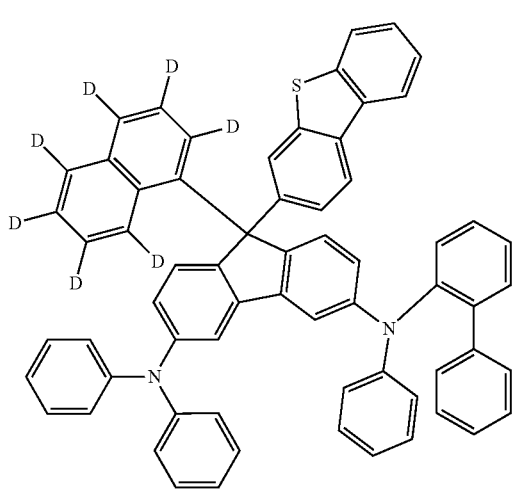
232
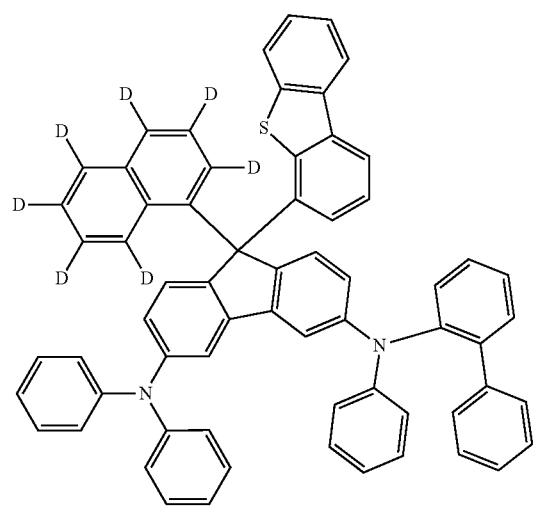
233
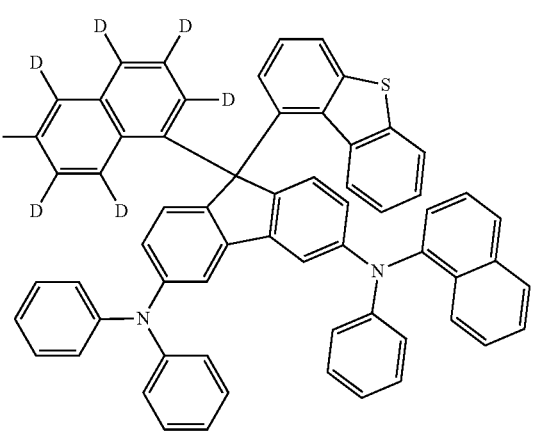

234
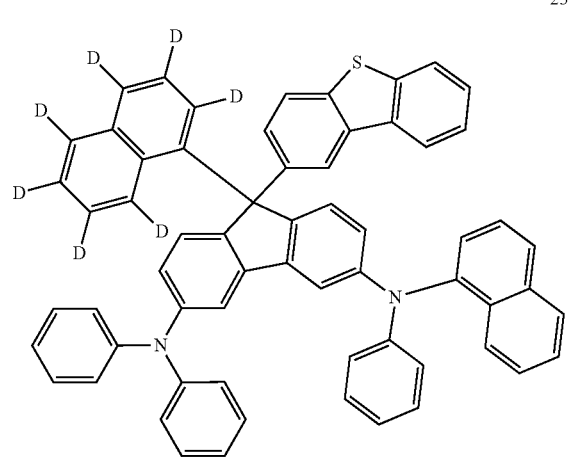
235
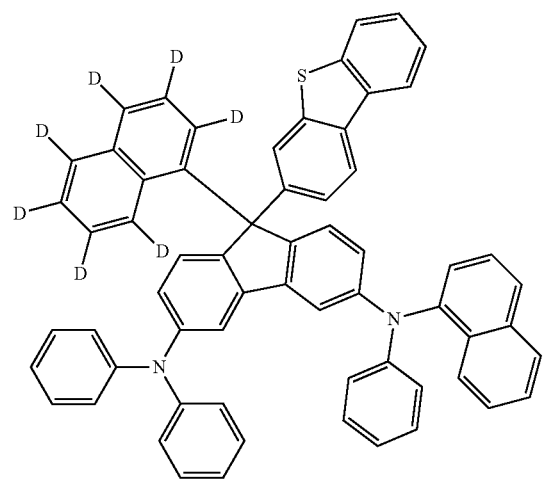
236
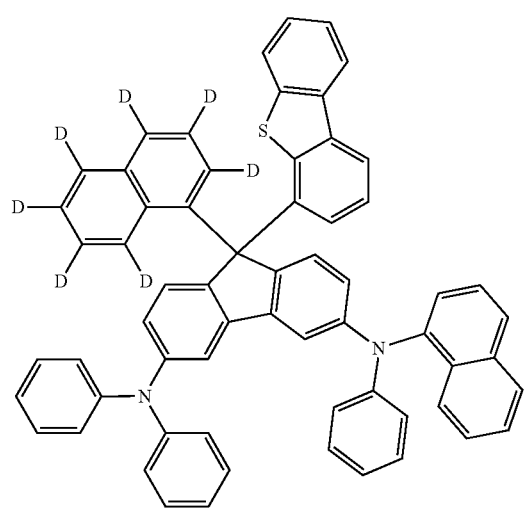
237
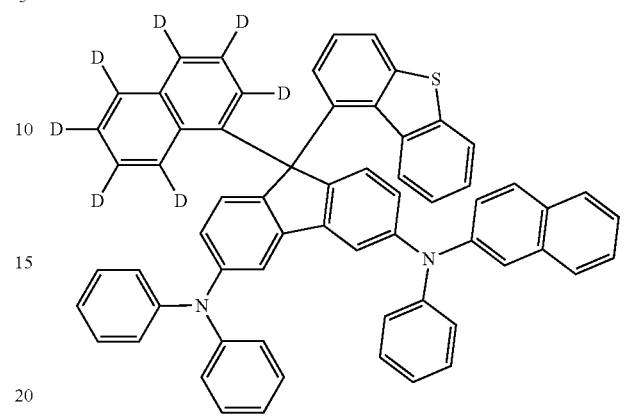
238
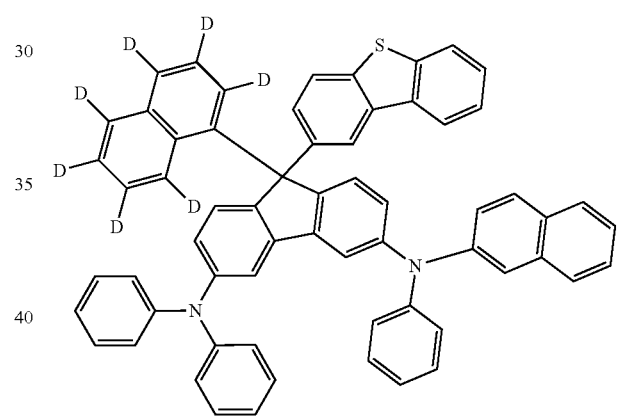
239
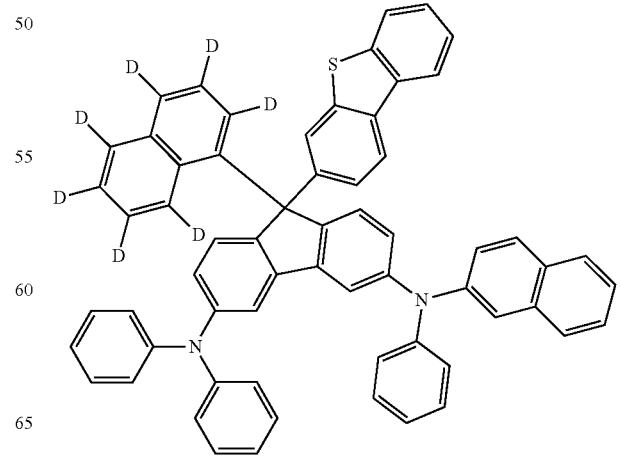

240
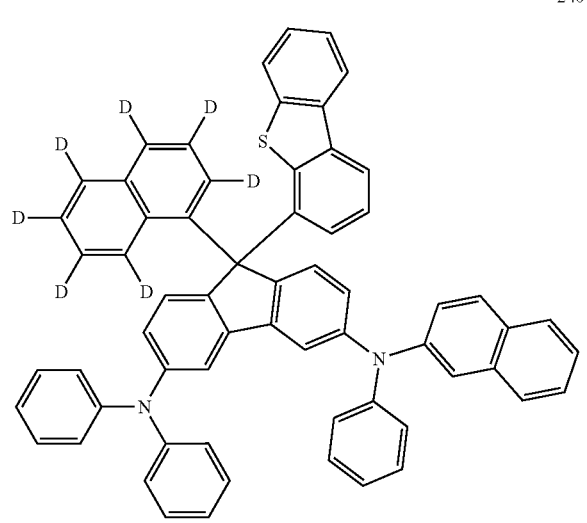
241
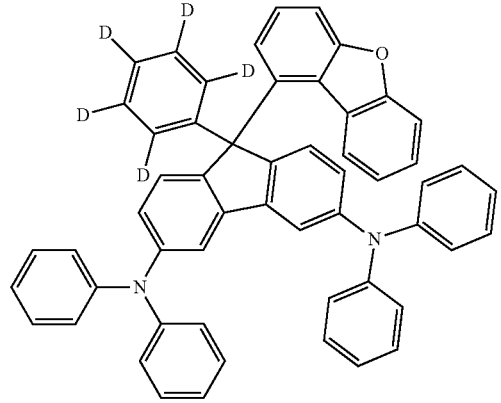
242
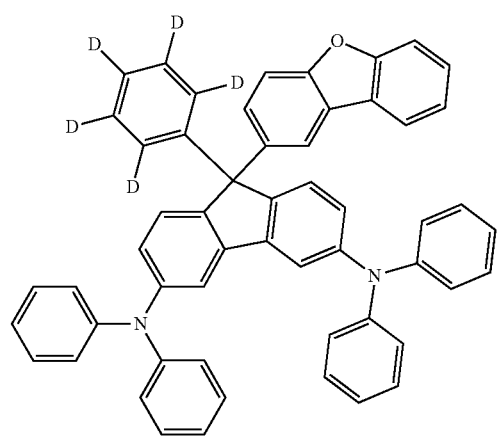
243
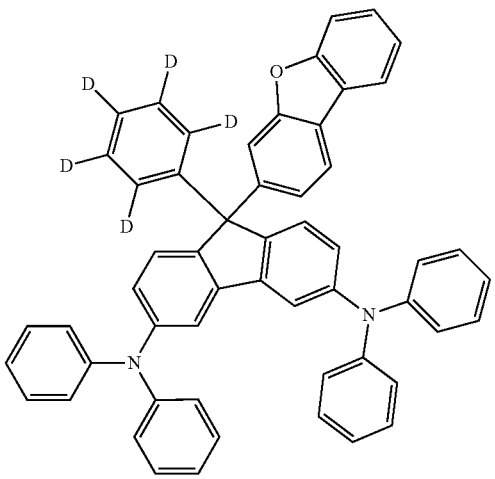
244
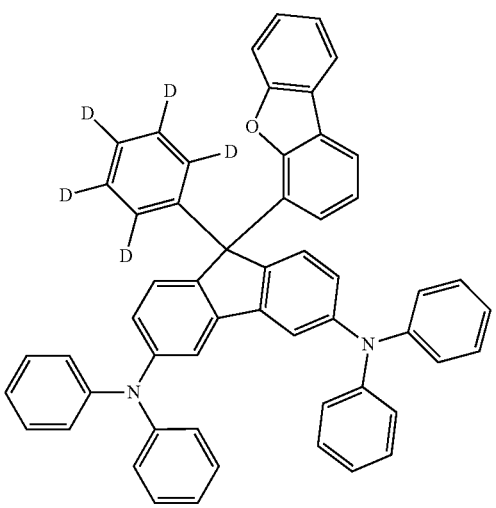
245
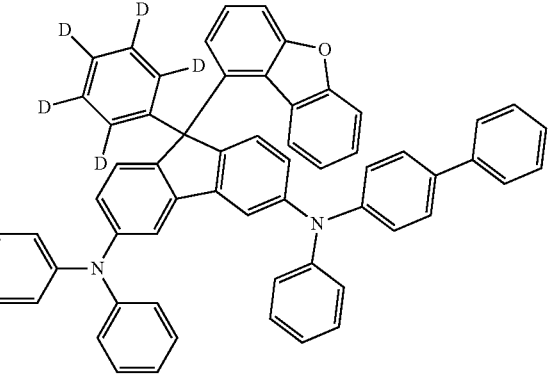

246 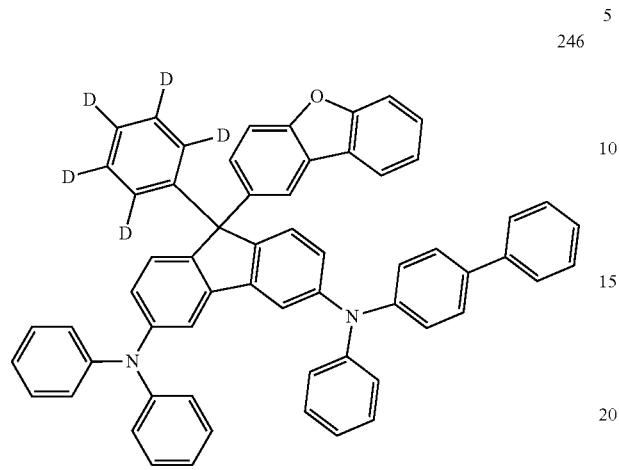
247 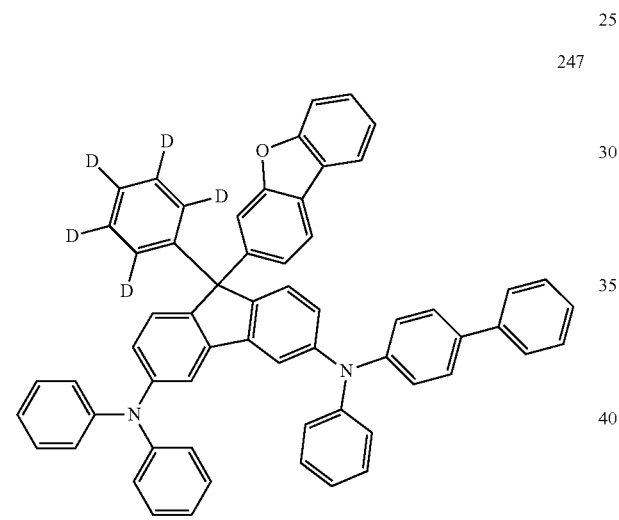
248 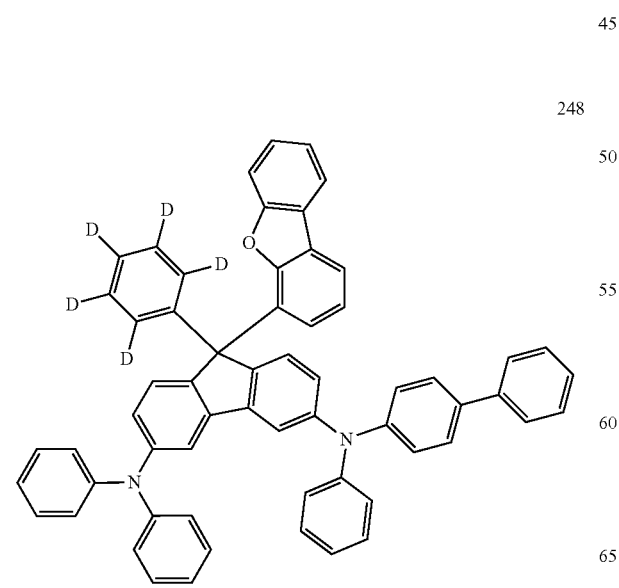
249 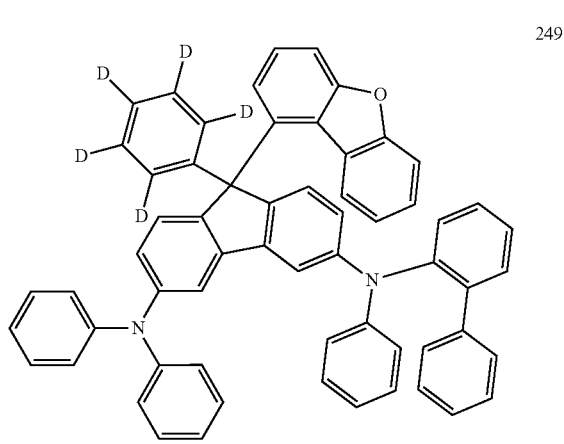
250 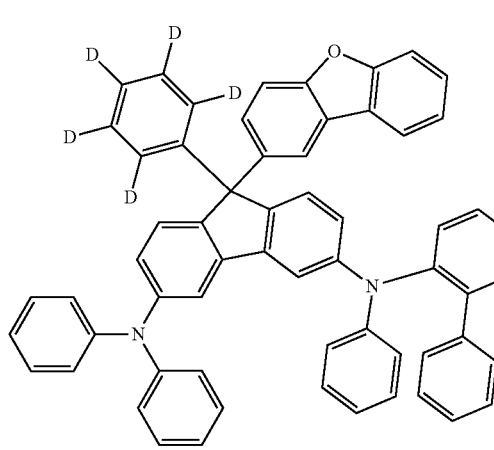
251 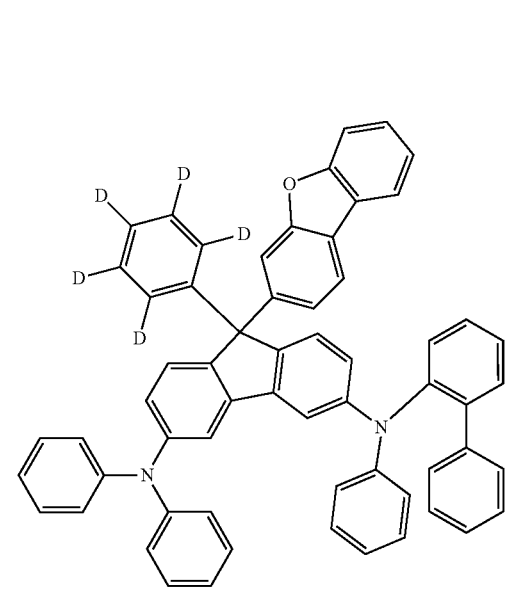

375
-continued
252
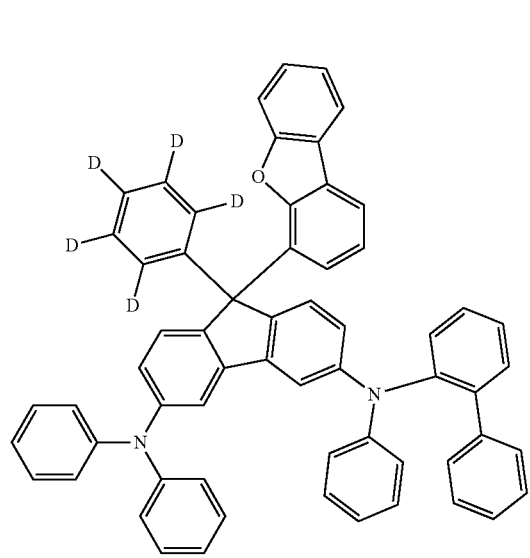
253
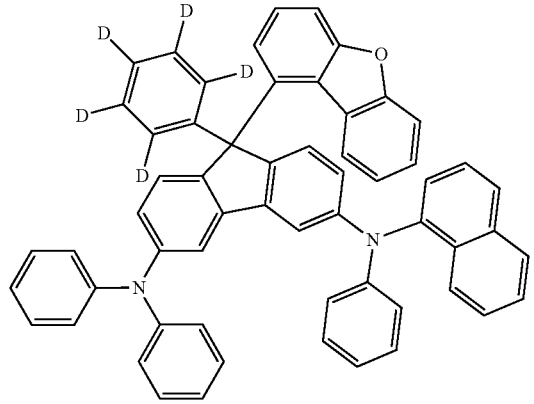
254
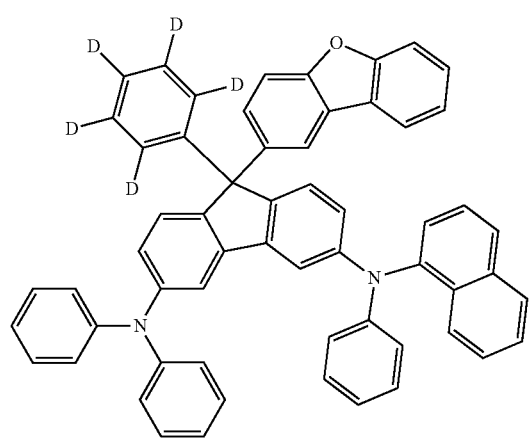
376
-continued
255
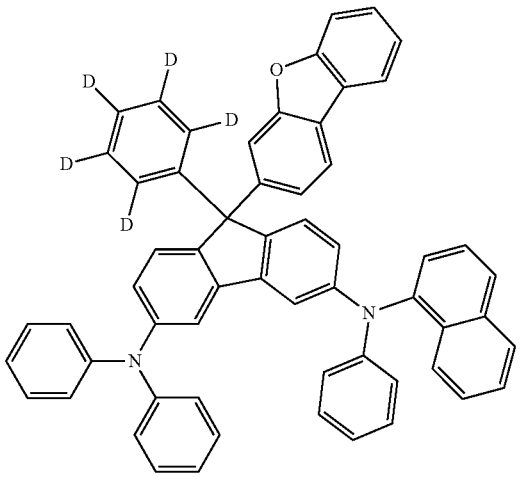
256
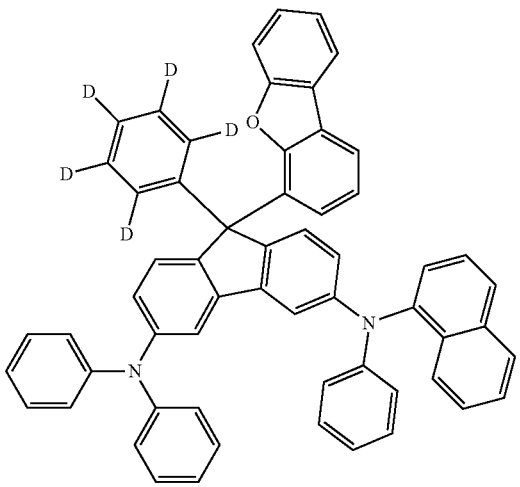
257
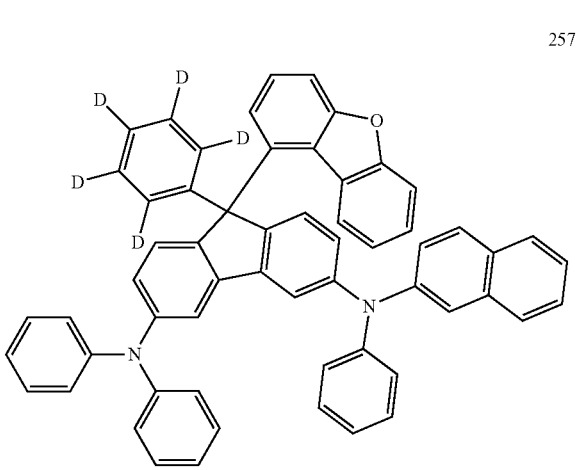

258
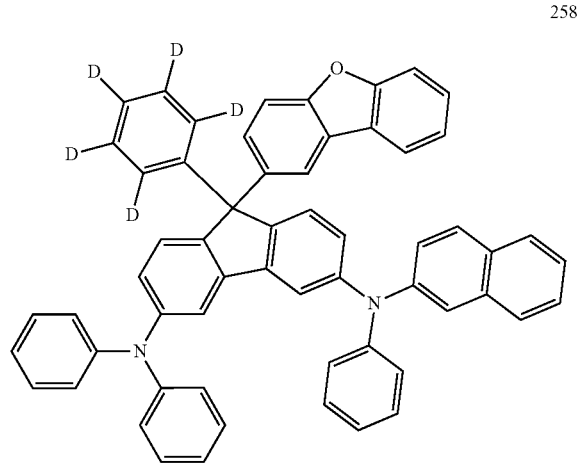
259
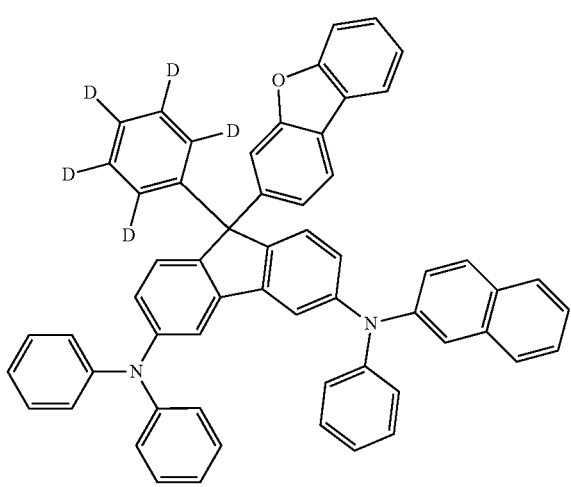
260
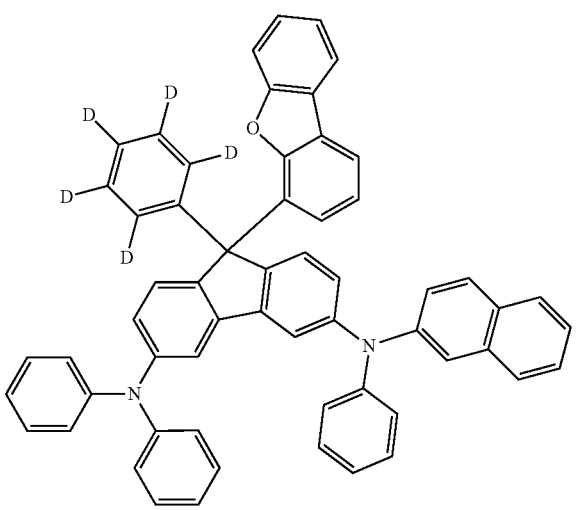
261
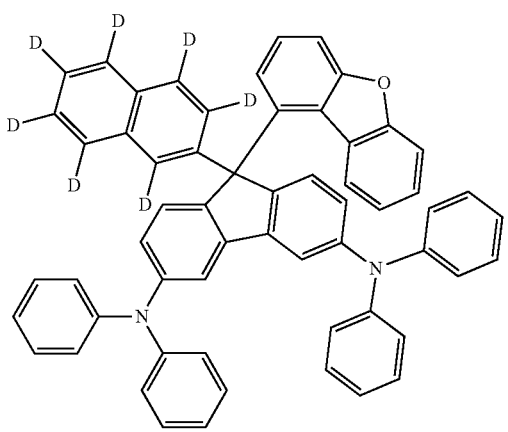
262
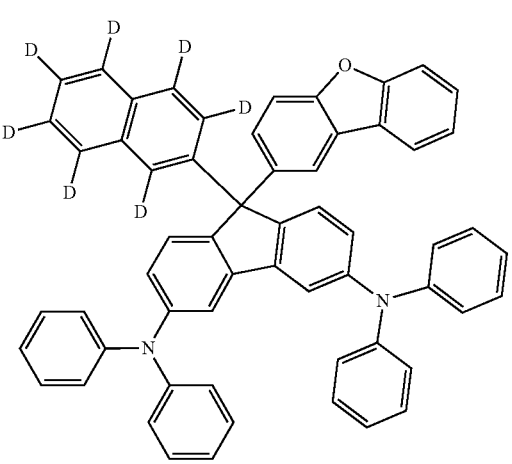
263
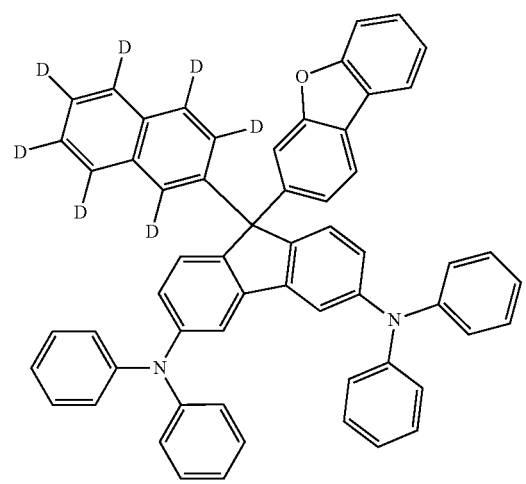

264
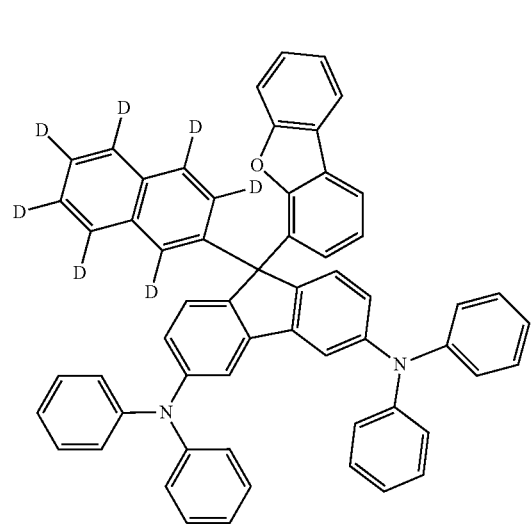
265
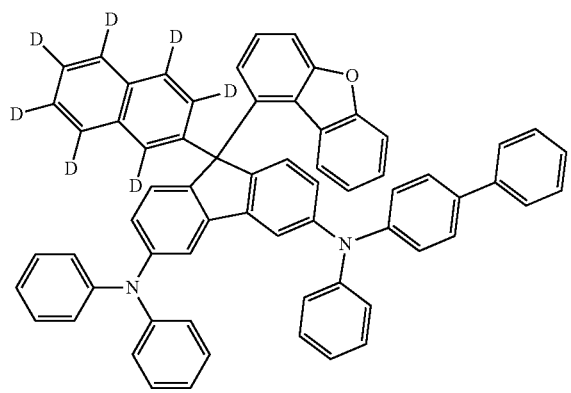
266
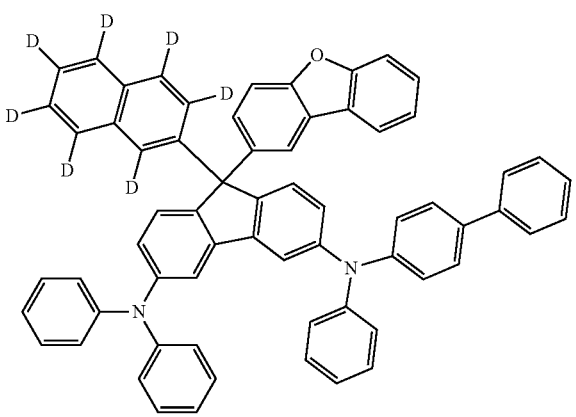
267
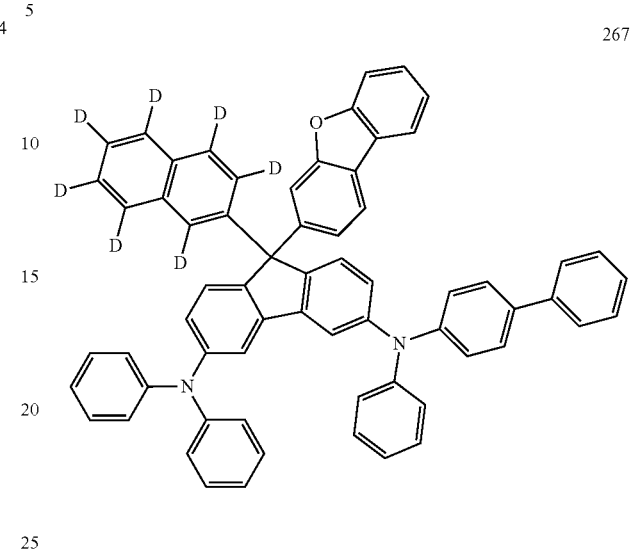
268
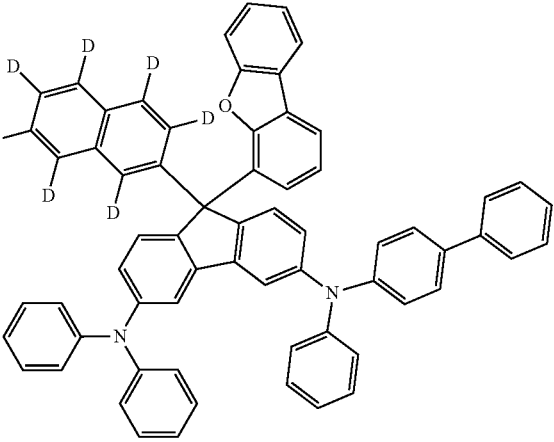
269
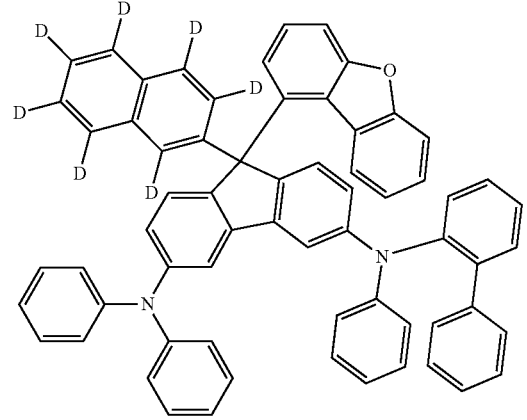

270
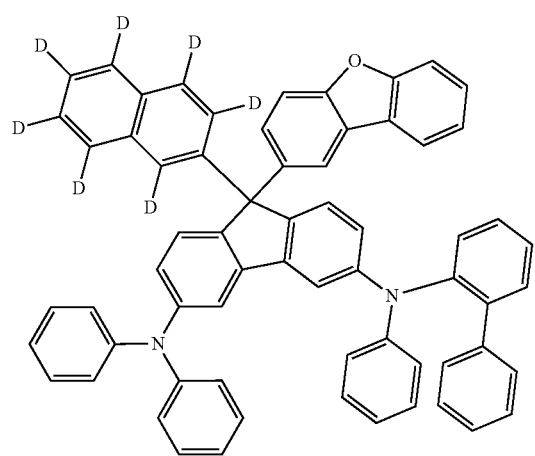
271
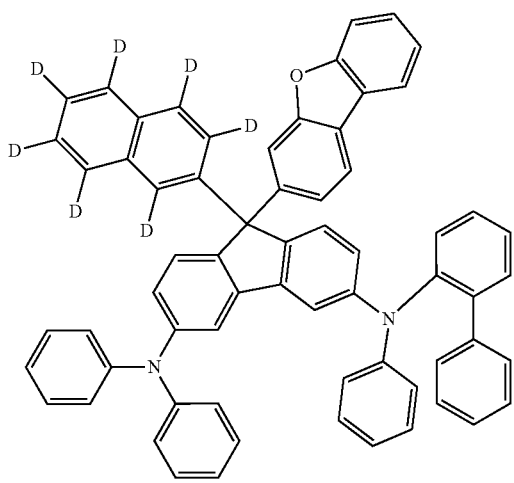
272
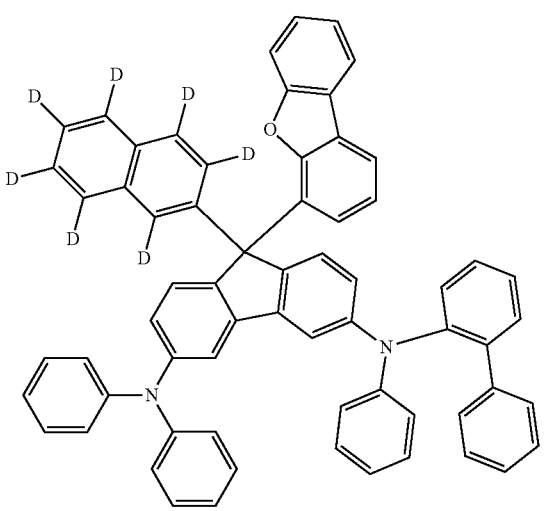
273
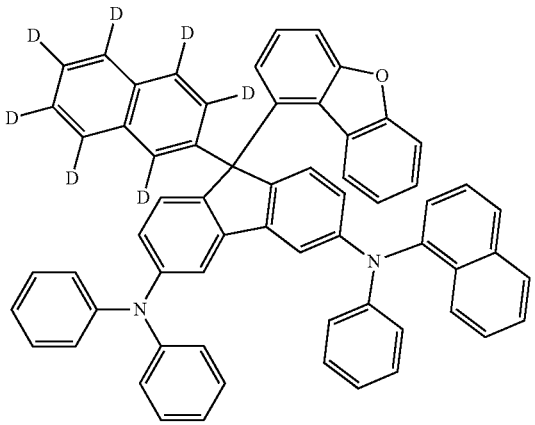
274
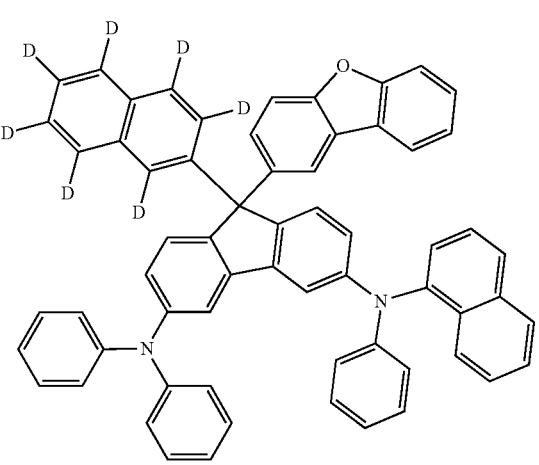
275
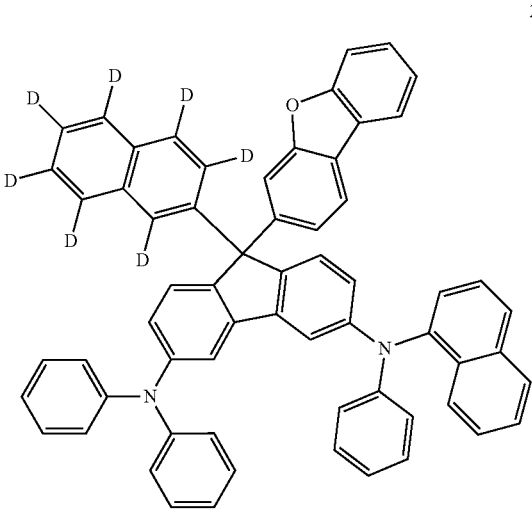

383
-continued
276
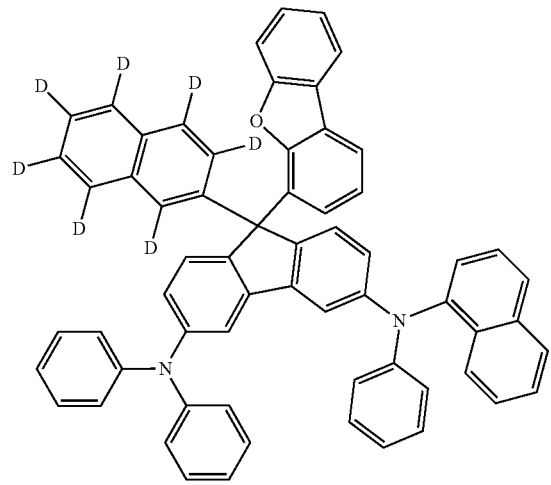
277
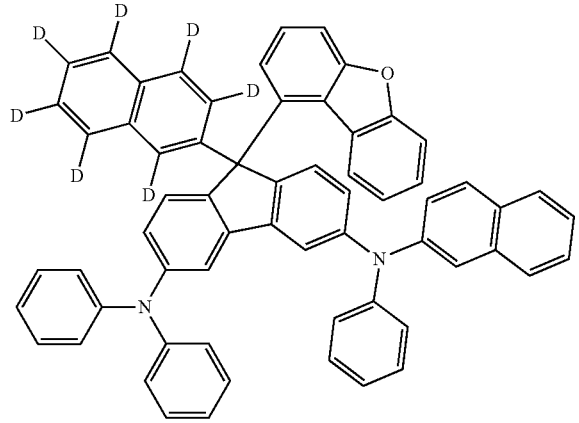
278
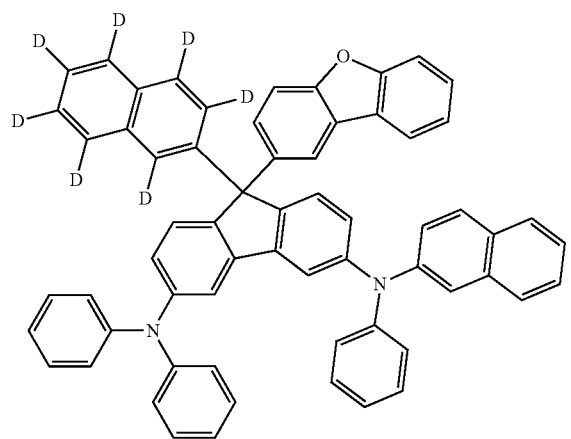
384
-continued
279
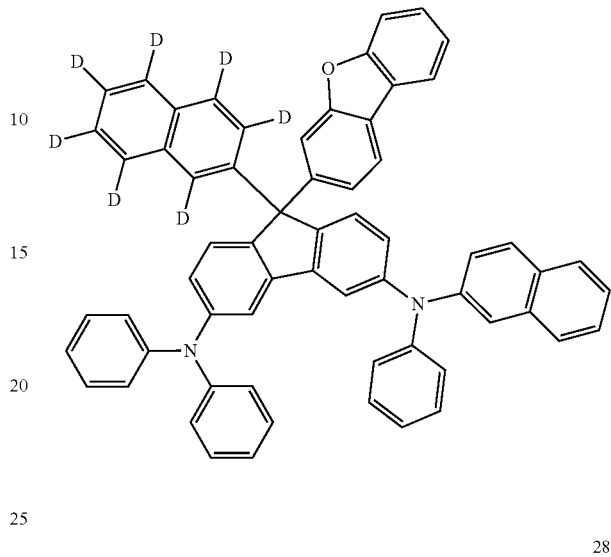
280
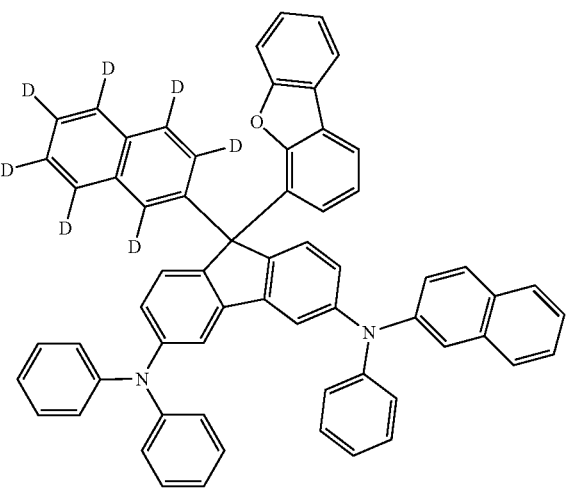
281
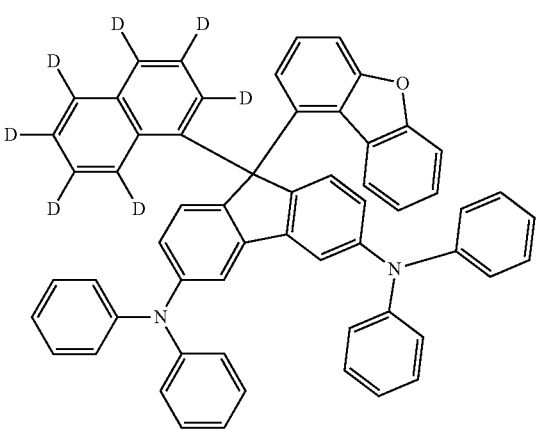

282
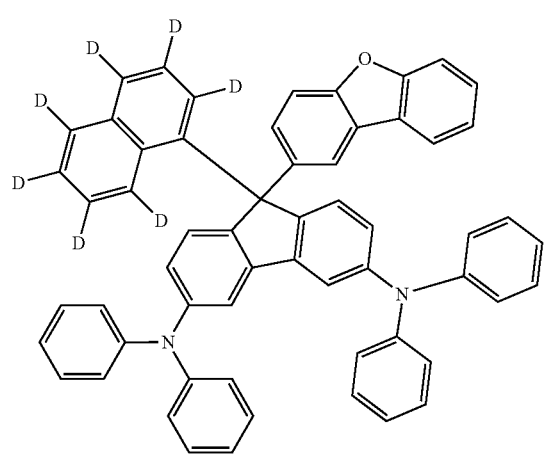
283
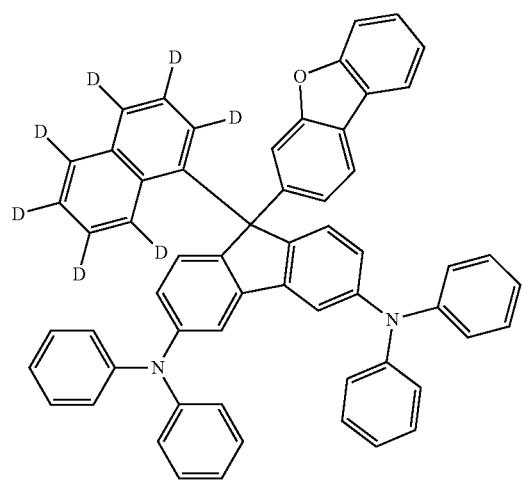
284
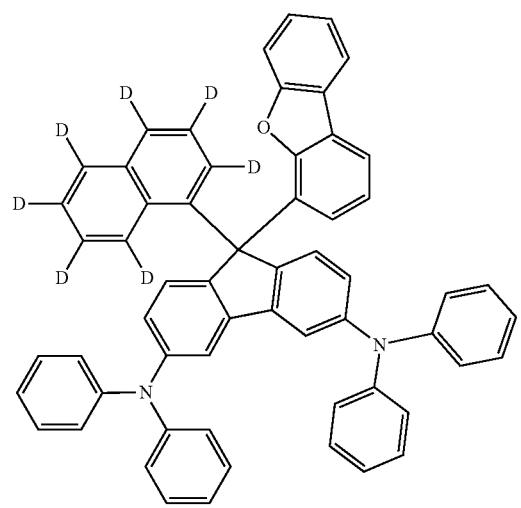
285
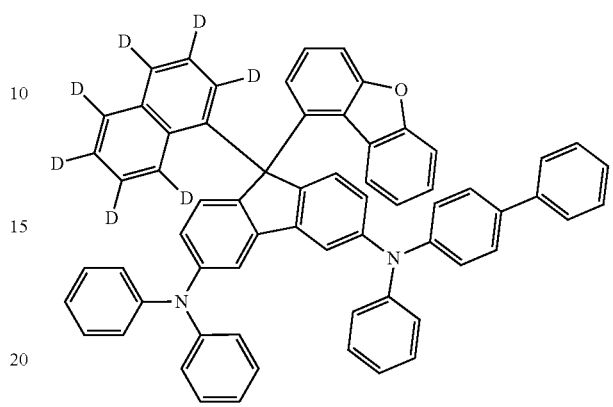
286
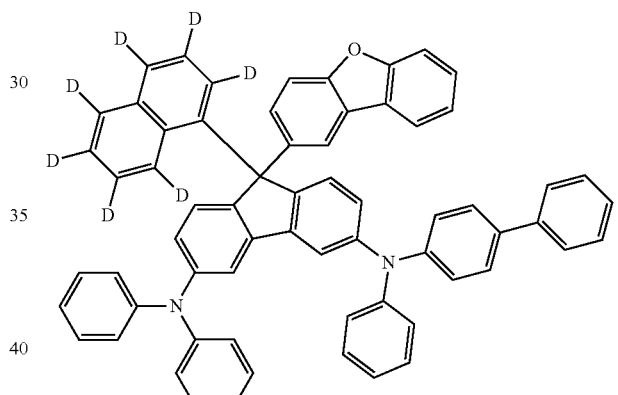
287
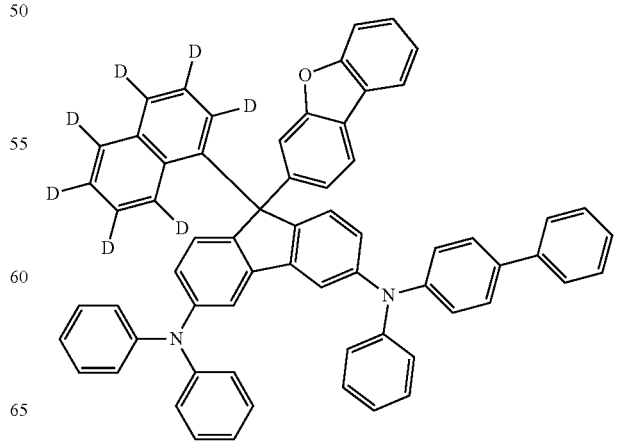

387
-continued
288
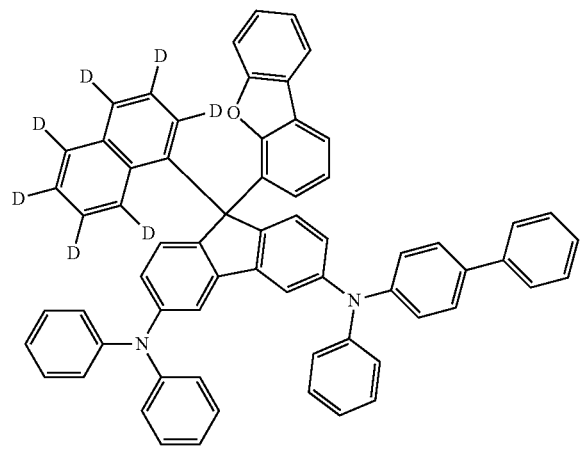
289
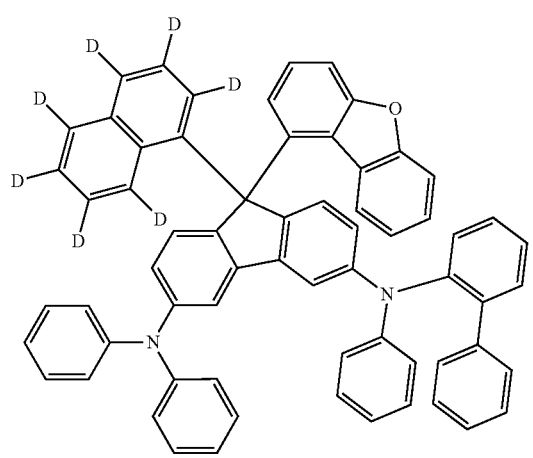
290
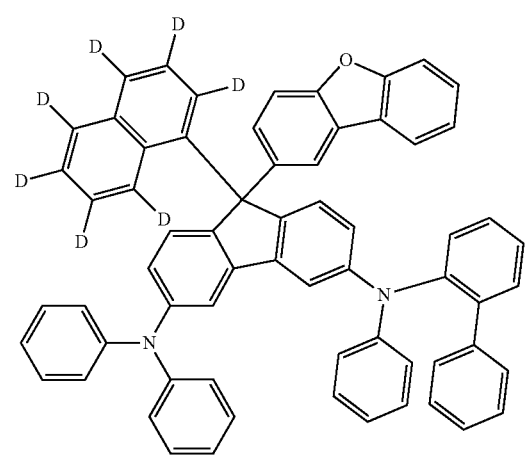
388
-continued
291
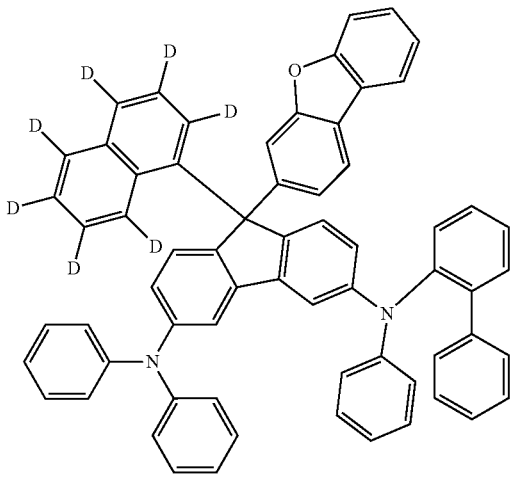
292
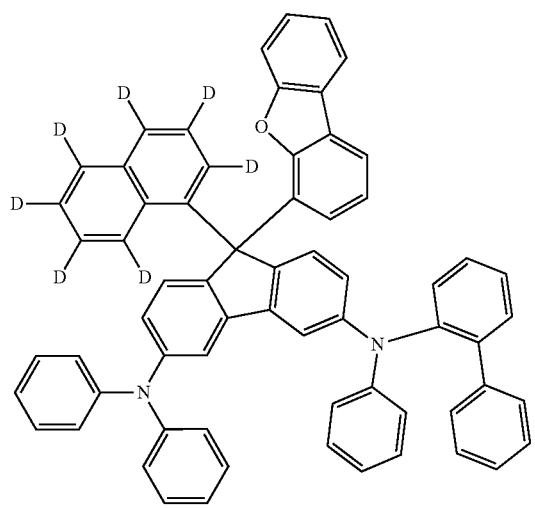
293
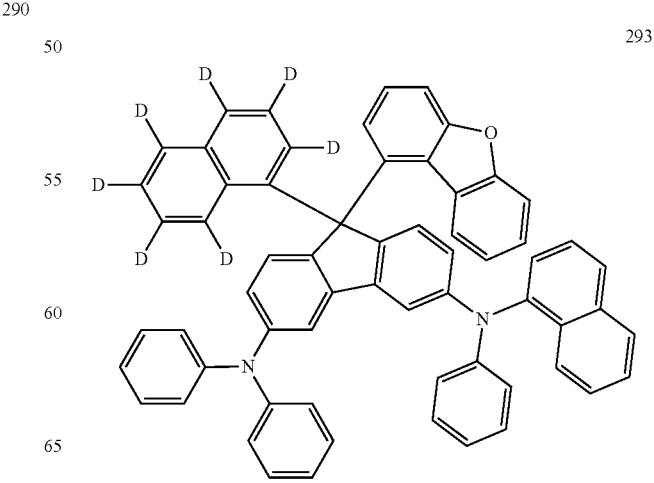

-continued
294
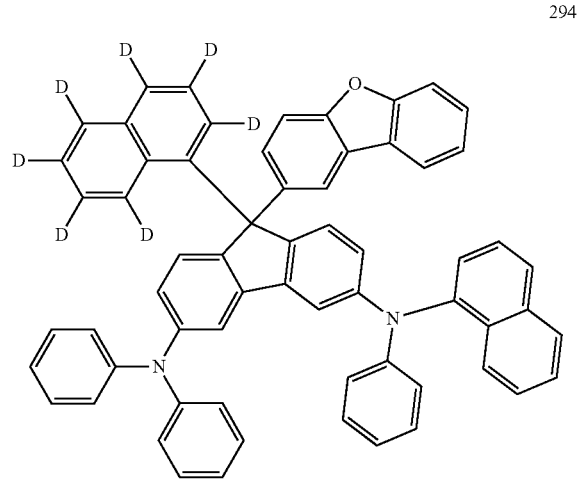
295
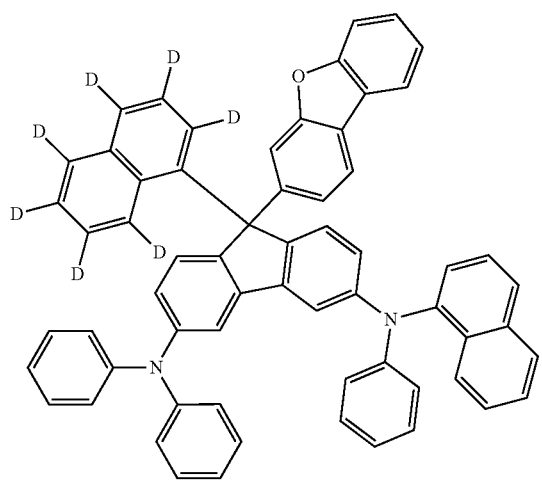
296
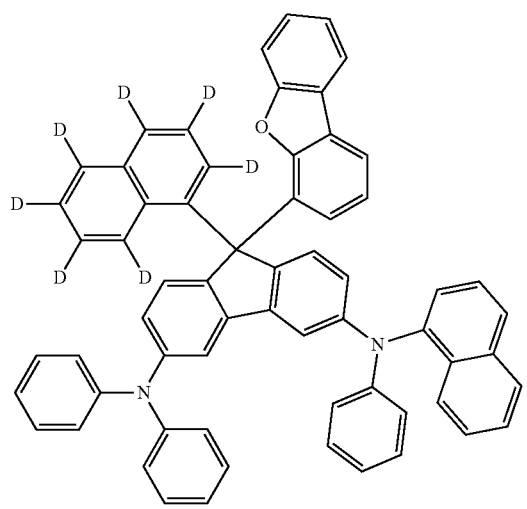
-continued
297
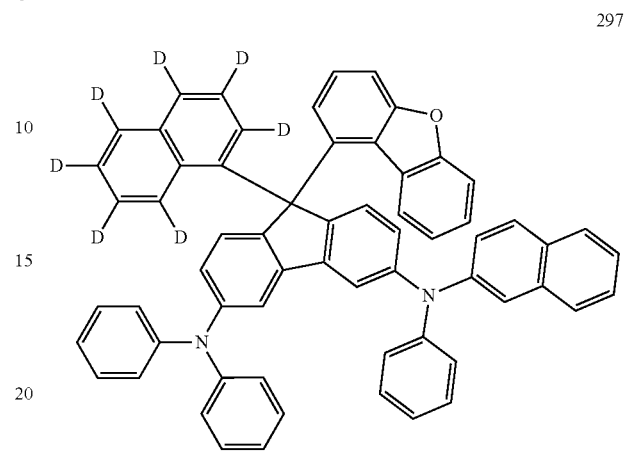
298
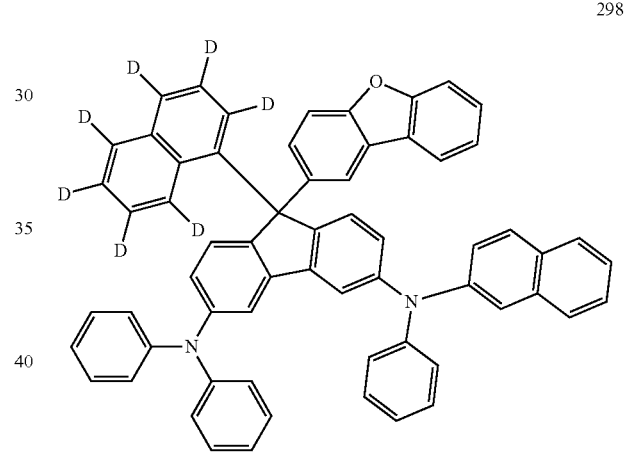
299
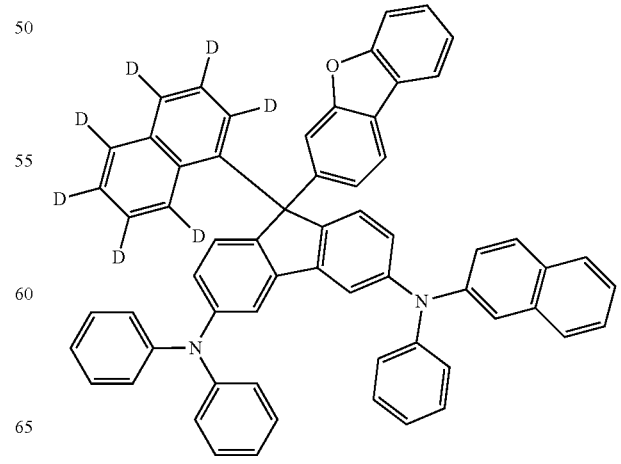

391
-continued
300
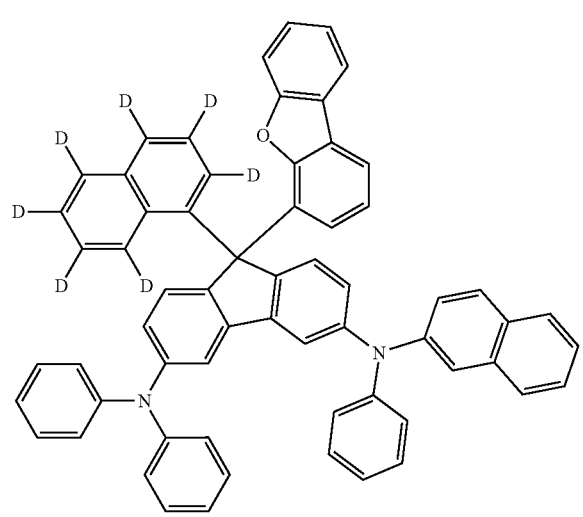
301
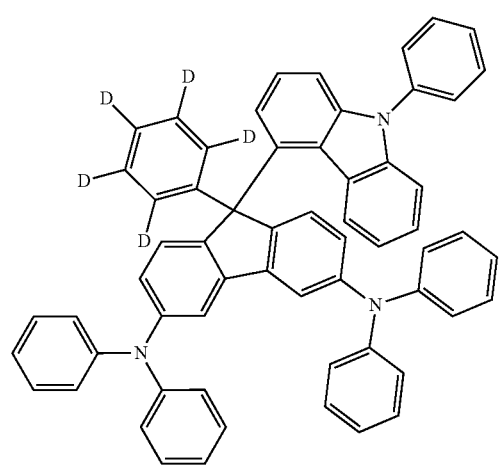
302
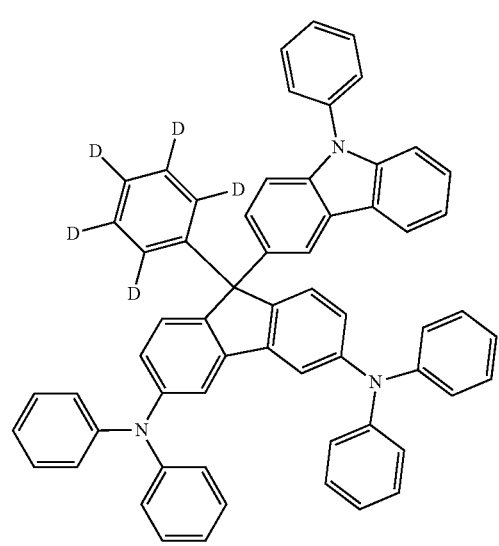
392
-continued
303
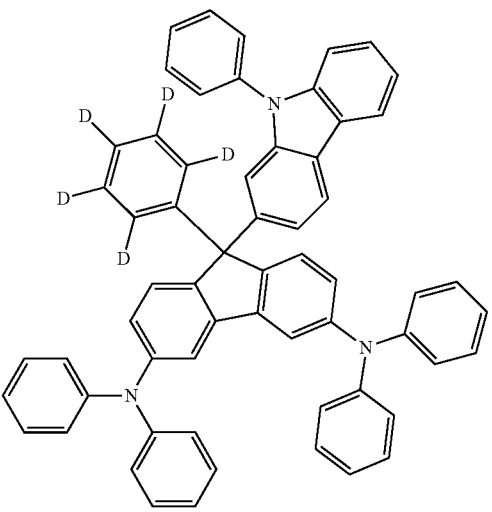
304
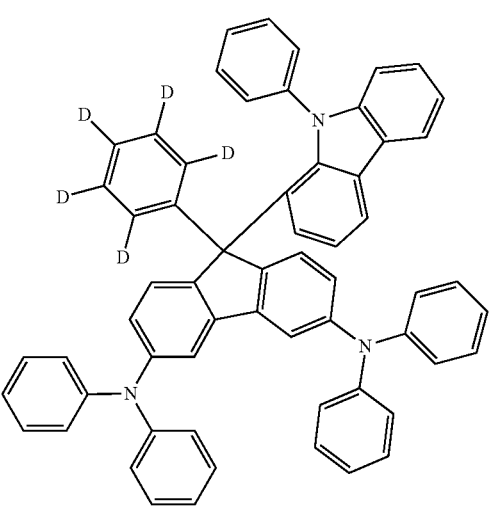
305
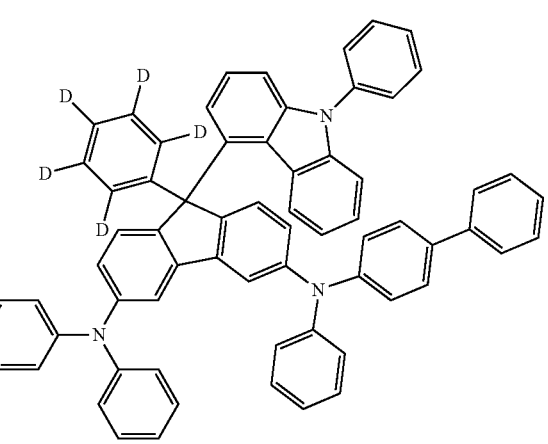

306
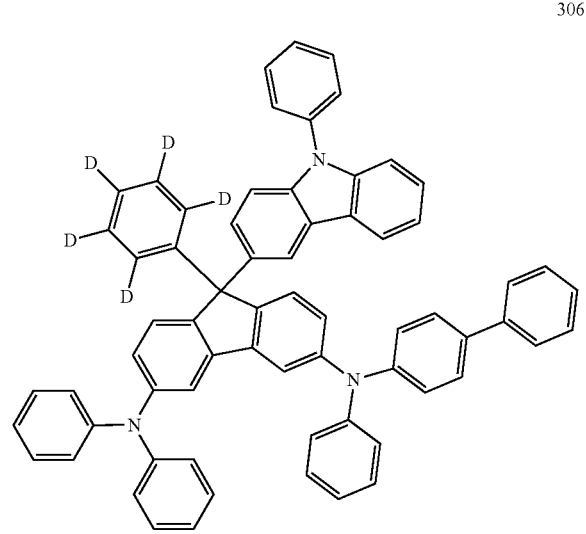
307
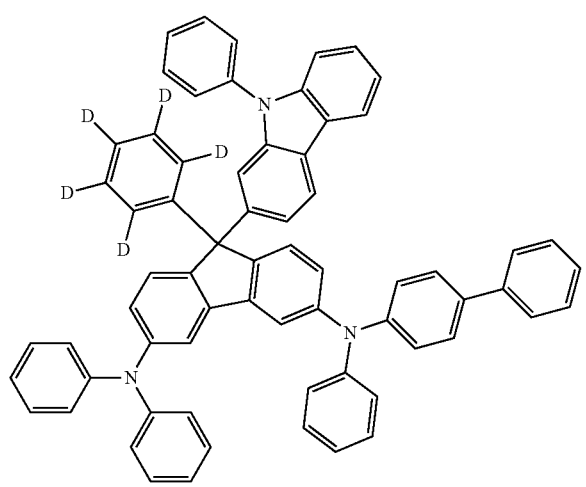
308
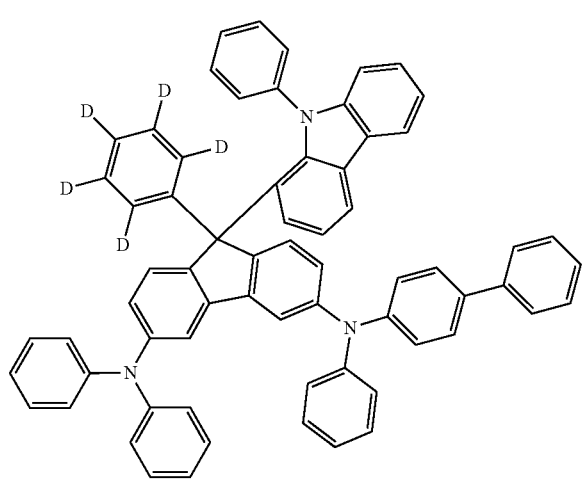
309
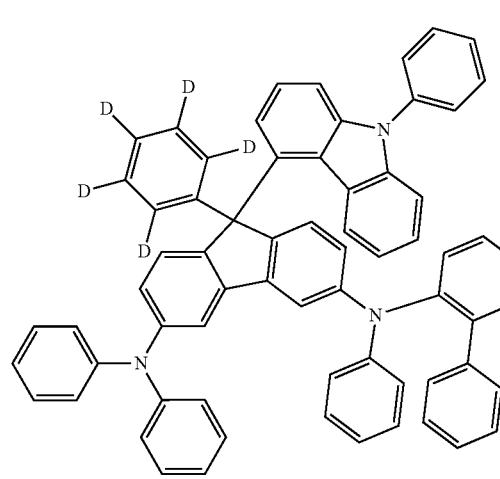
310
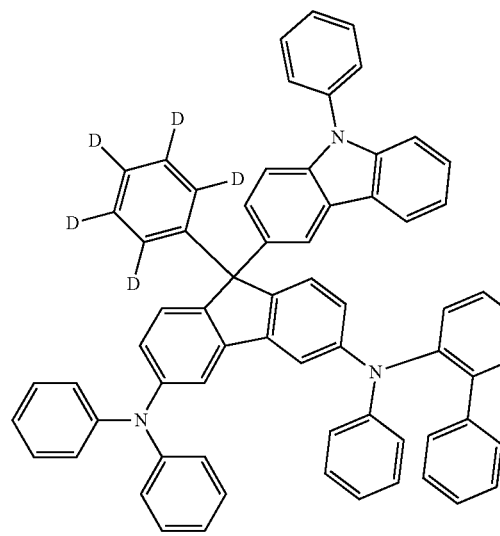
311
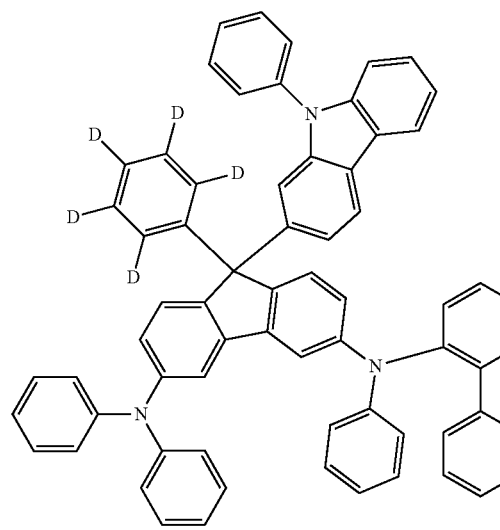

-continued
312
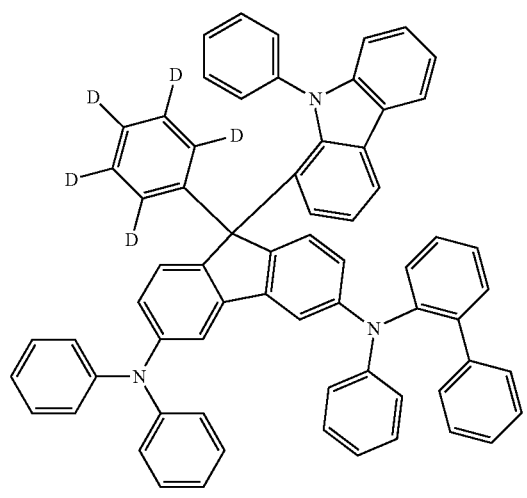
313
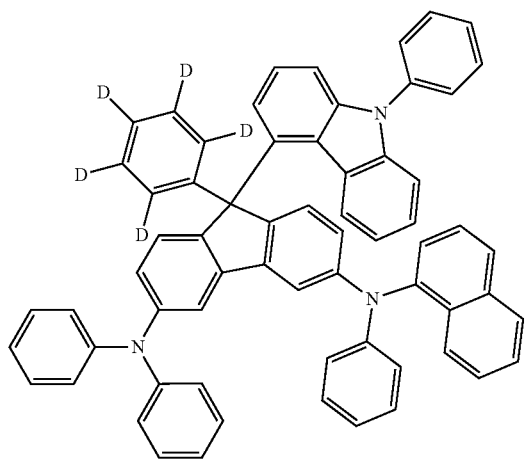
314
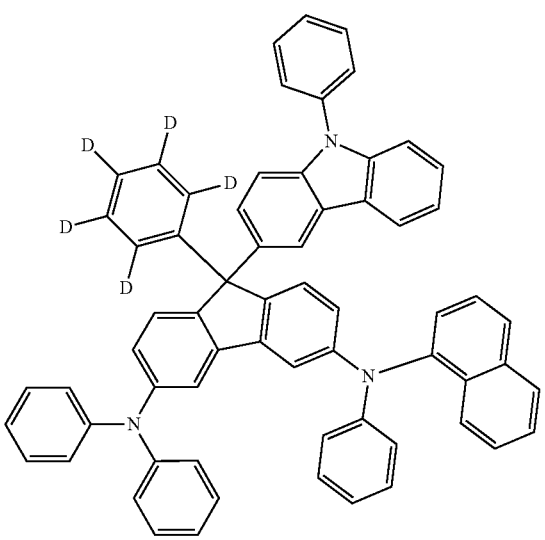
-continued
315
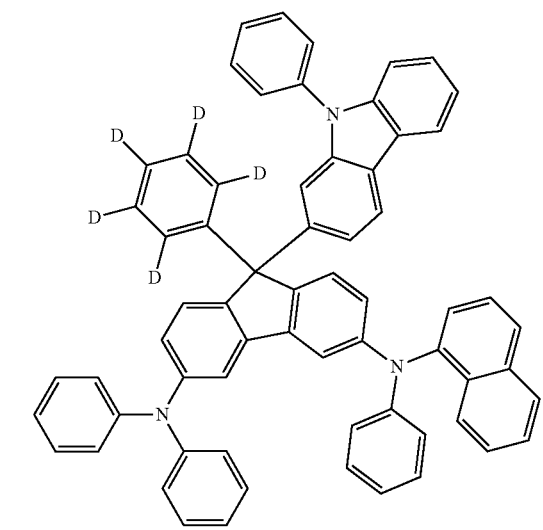
316
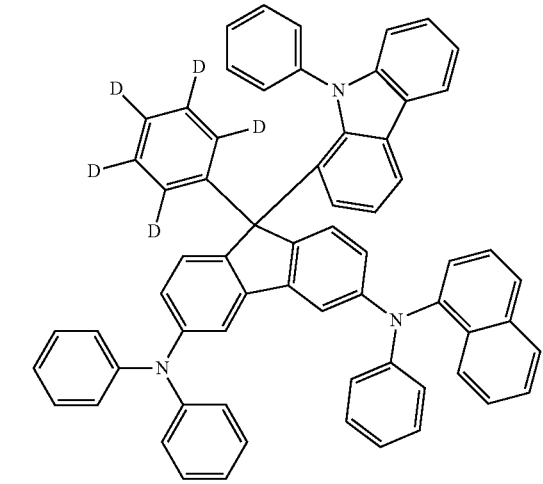
317
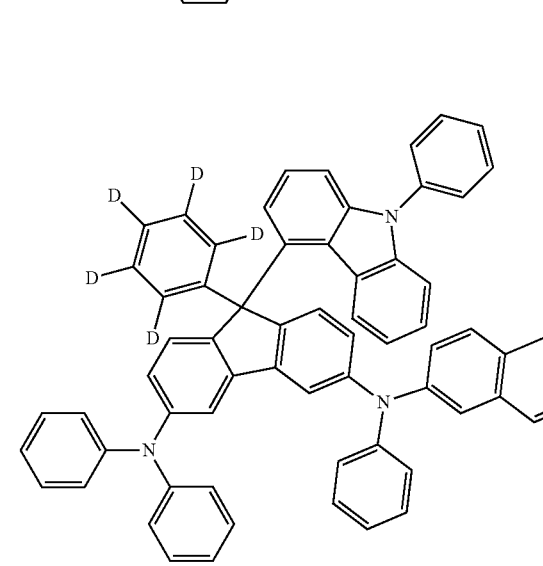

318
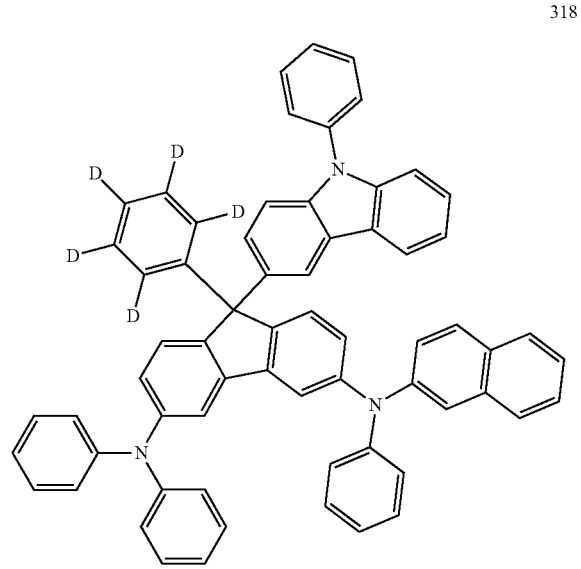
319
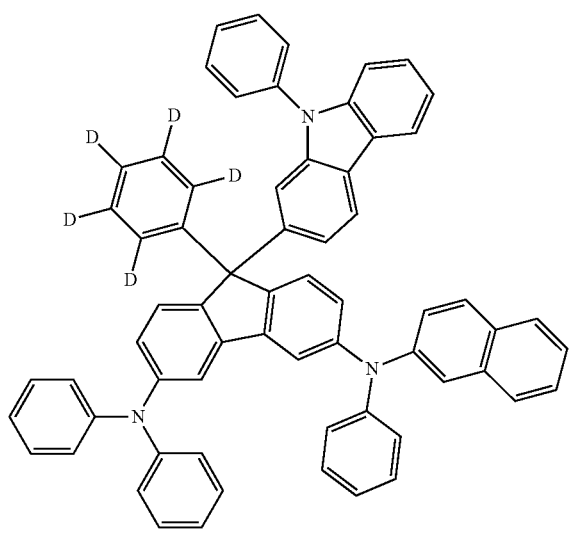
320
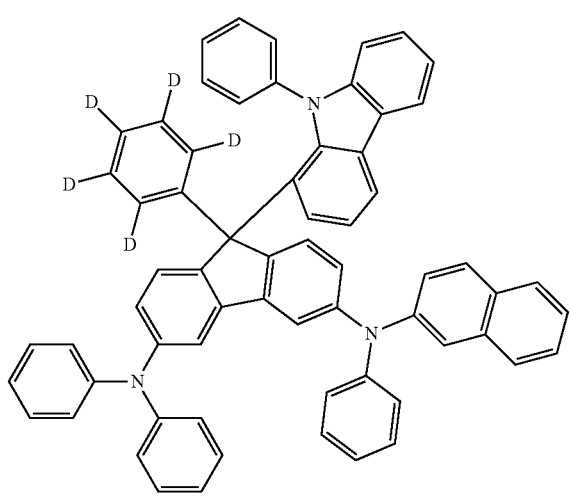
321
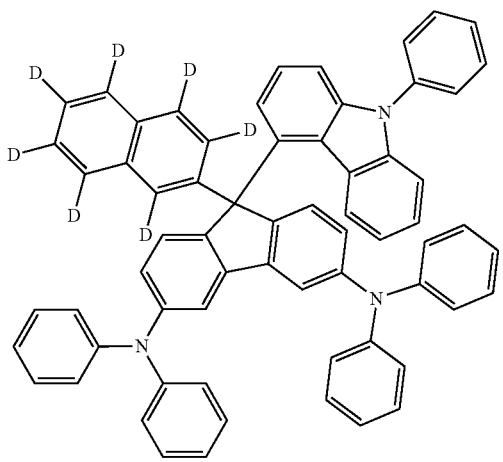
322
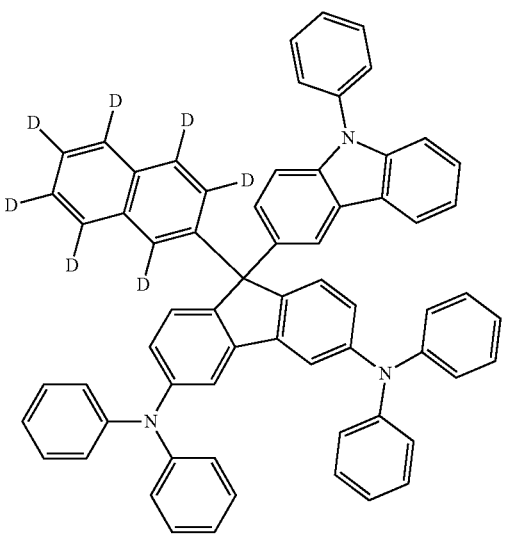
323
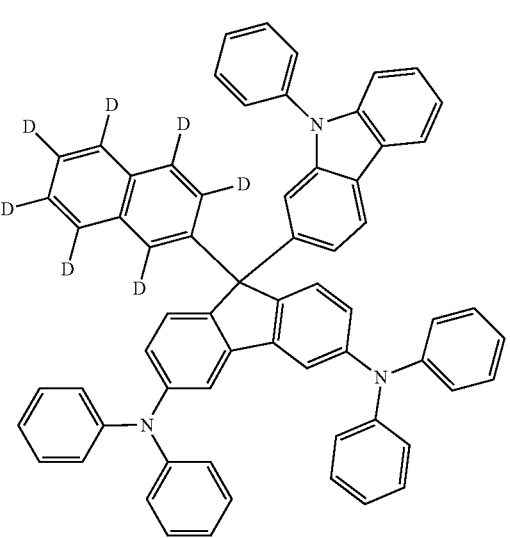

399
-continued
324
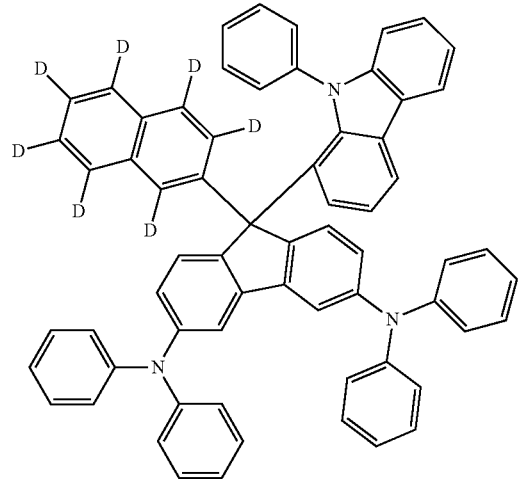
325
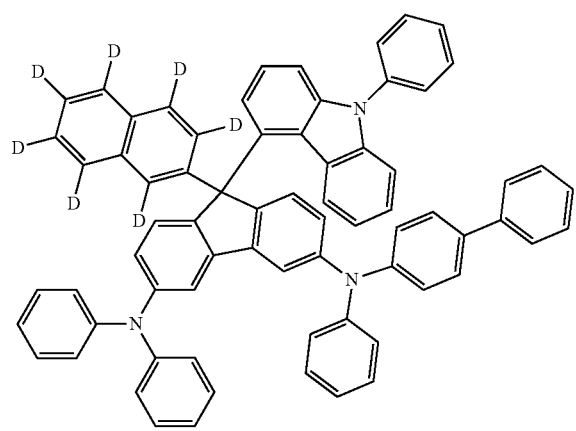
326
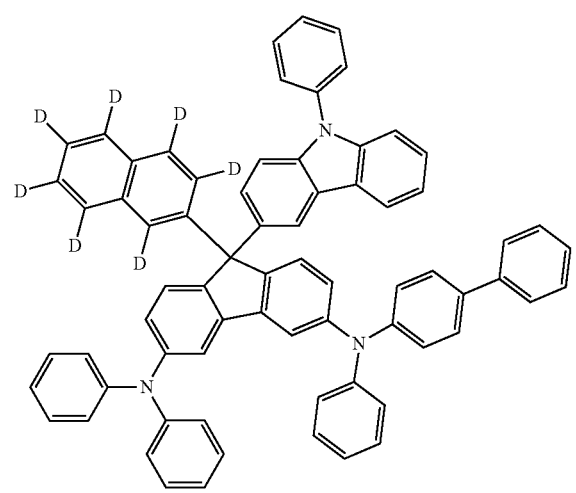
400
-continued
327
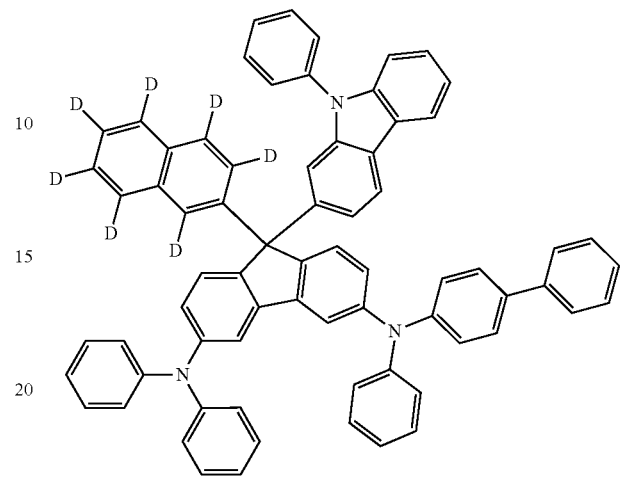
328
329
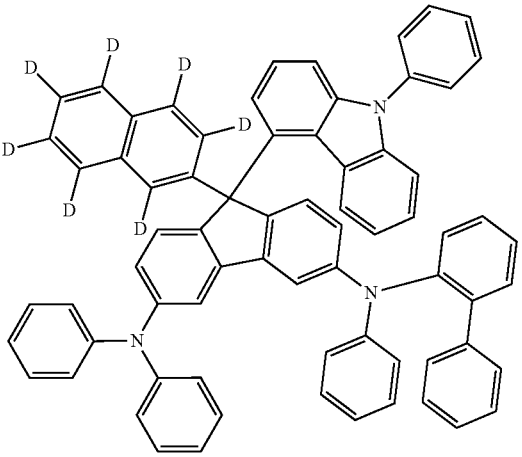

401
-continued
330
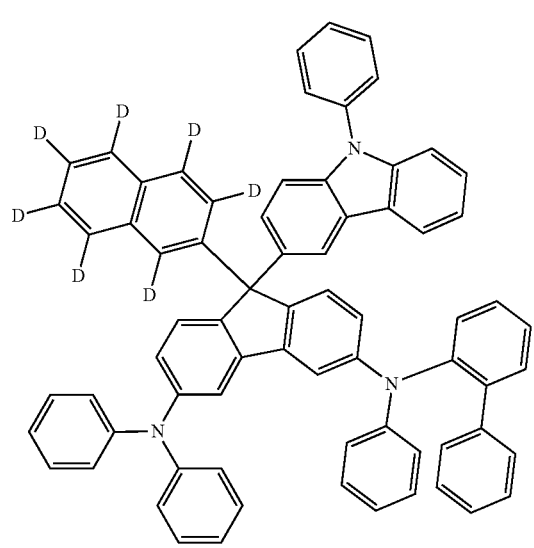
331
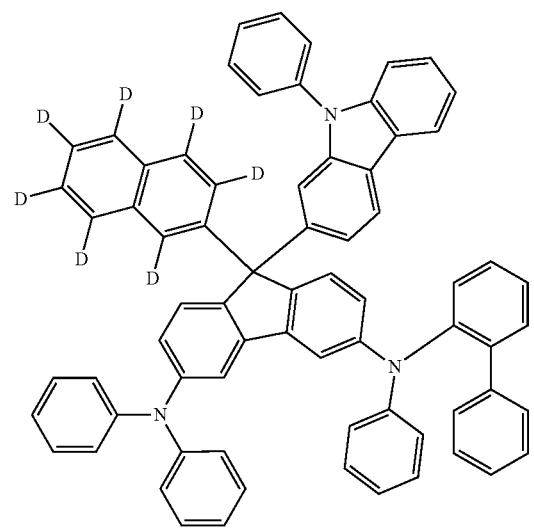
332
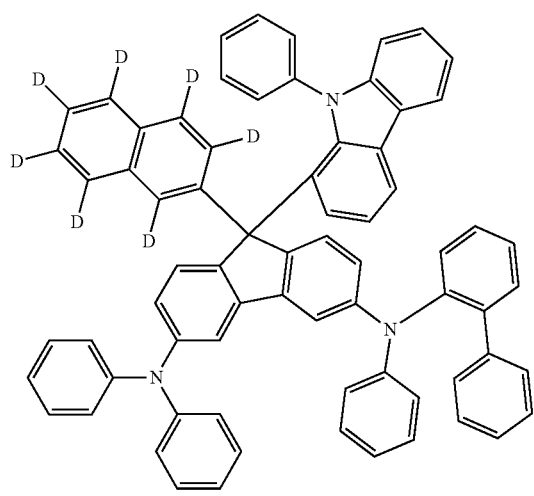
402
-continued
333
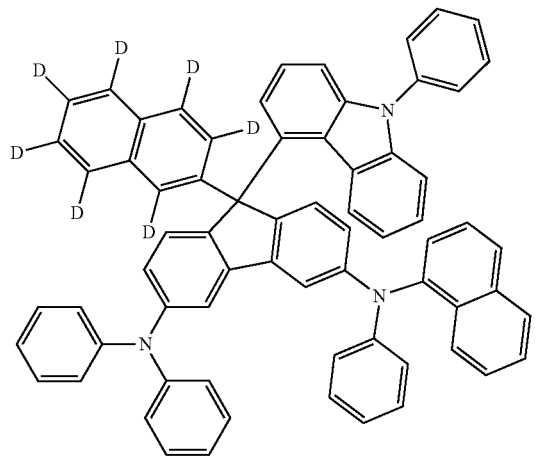
334
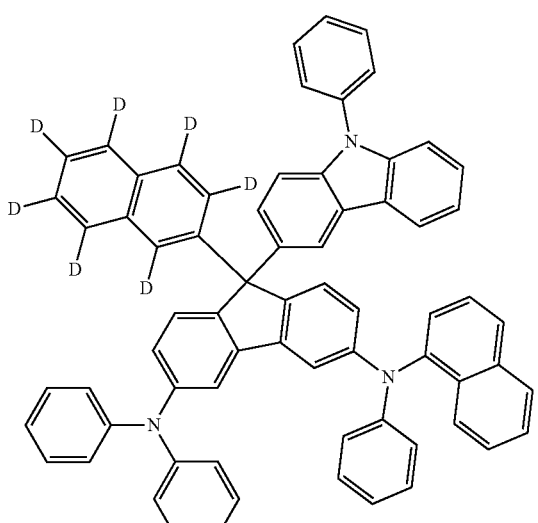
335
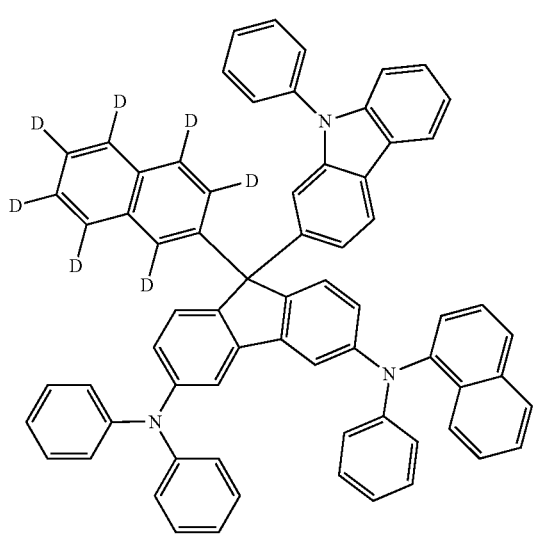

336
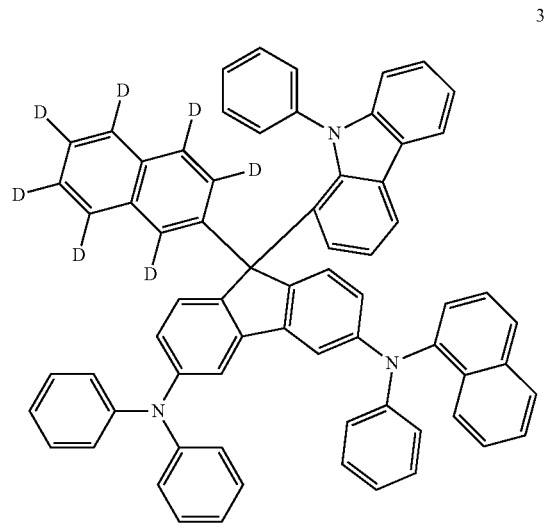
339
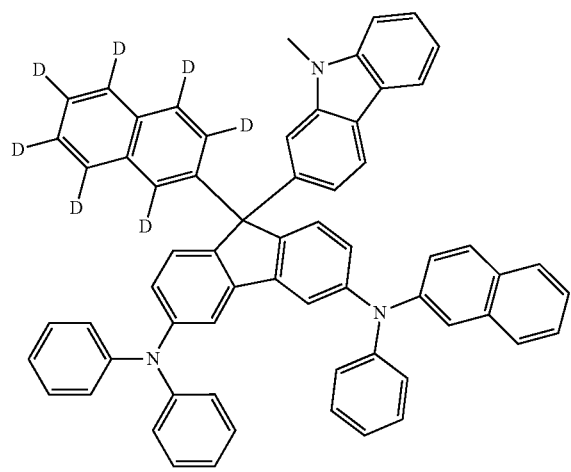
340
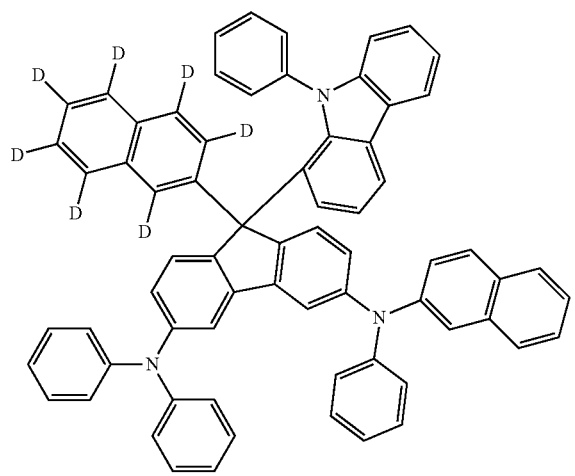
341
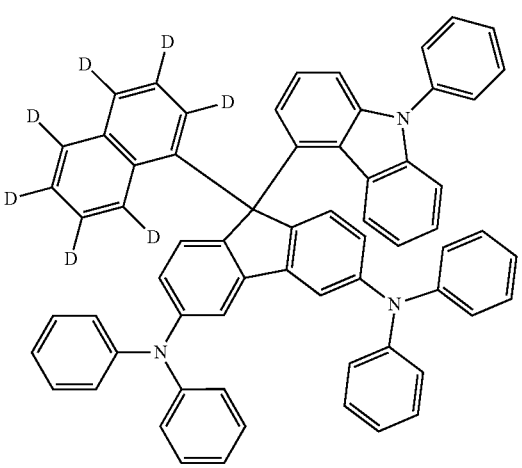
342
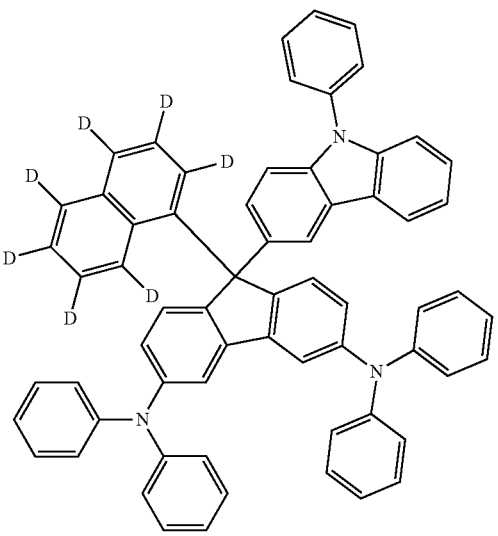
343
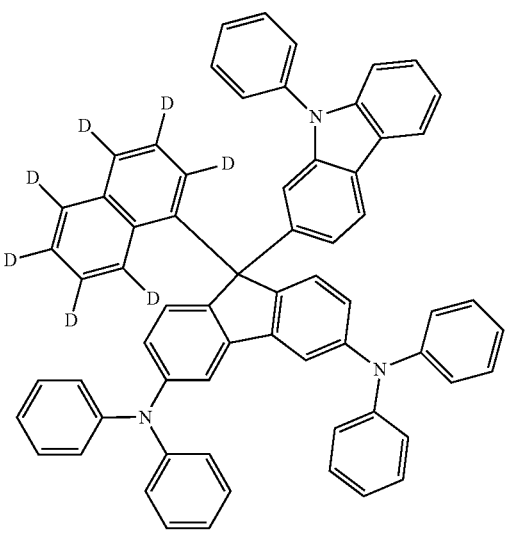

344
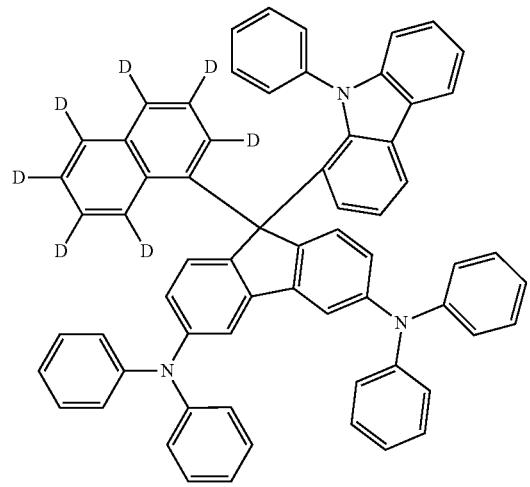
345
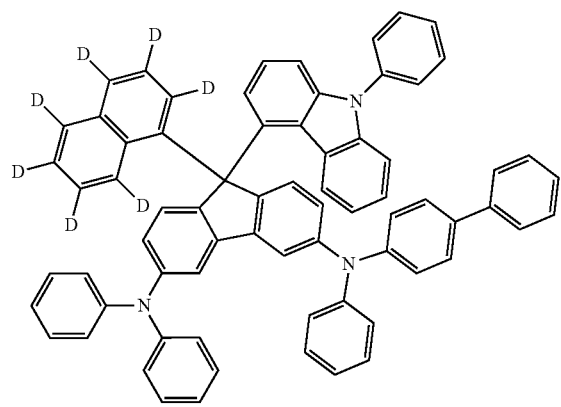
346
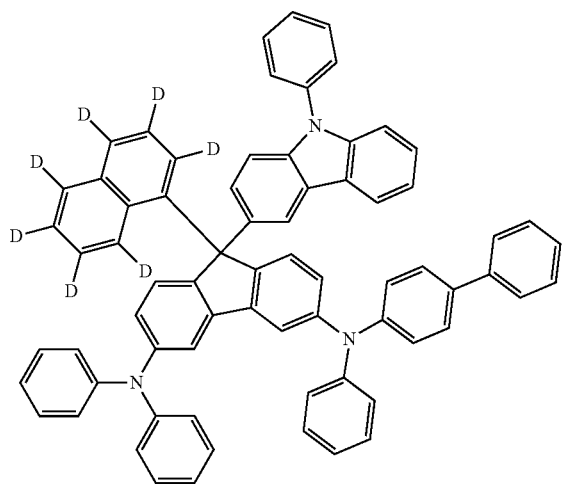
347
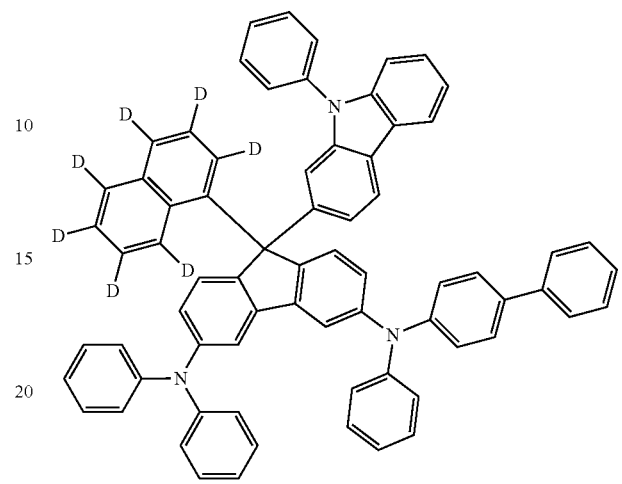
348
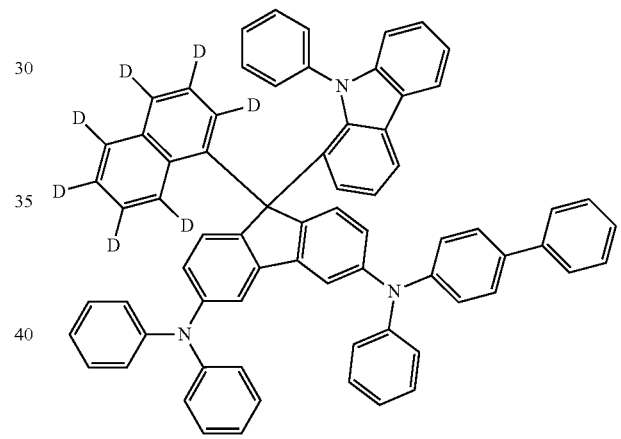
349
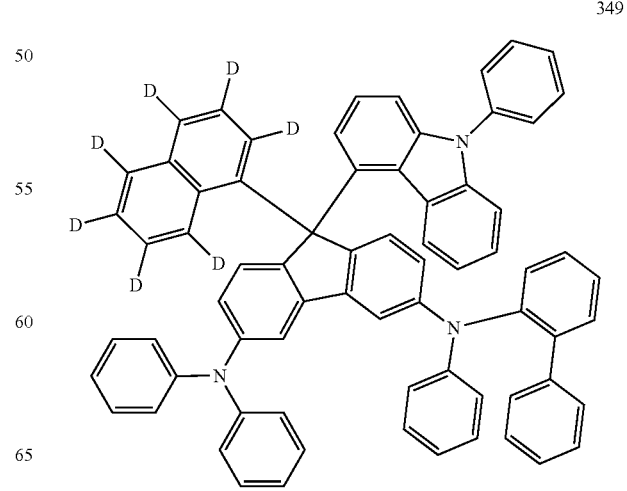

350
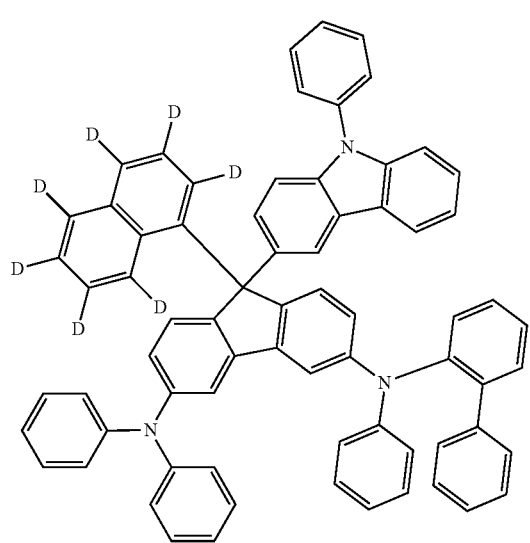
351
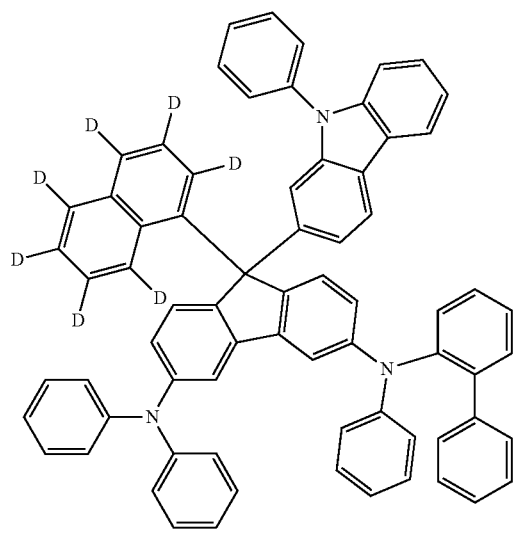
352
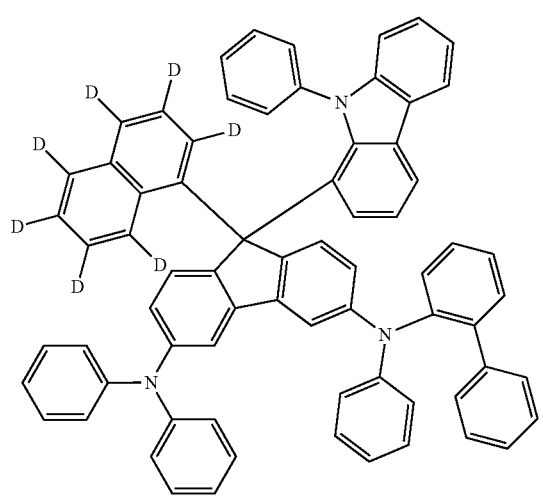
353
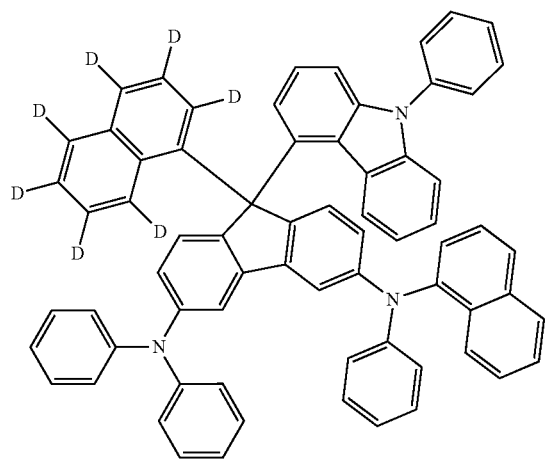
354
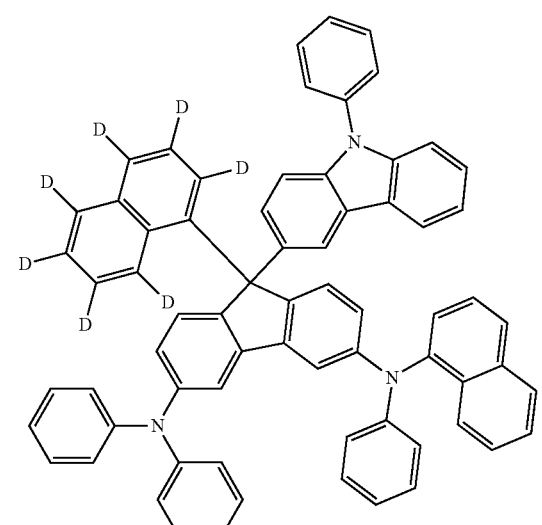
355
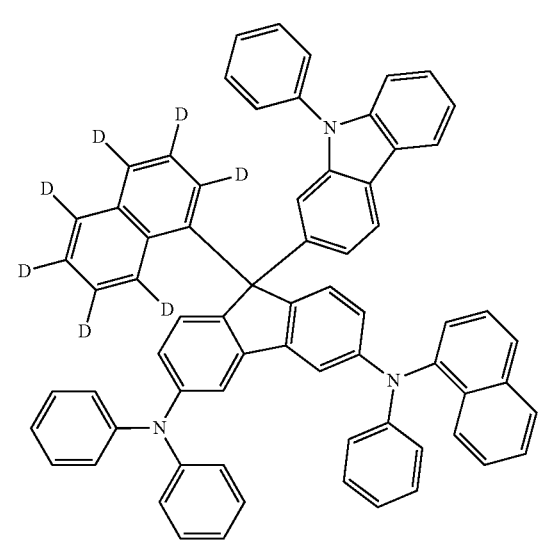

409
-continued
356
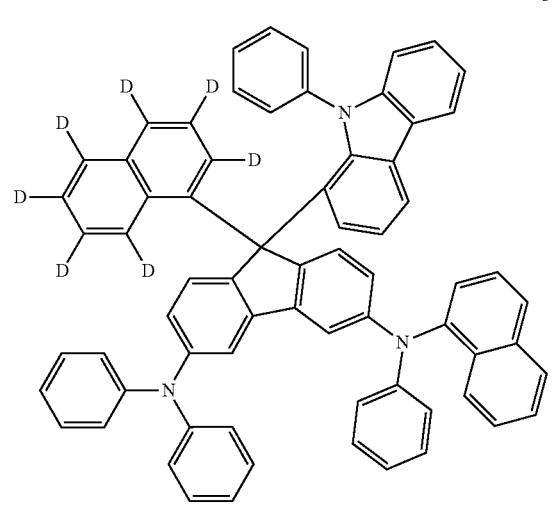
357
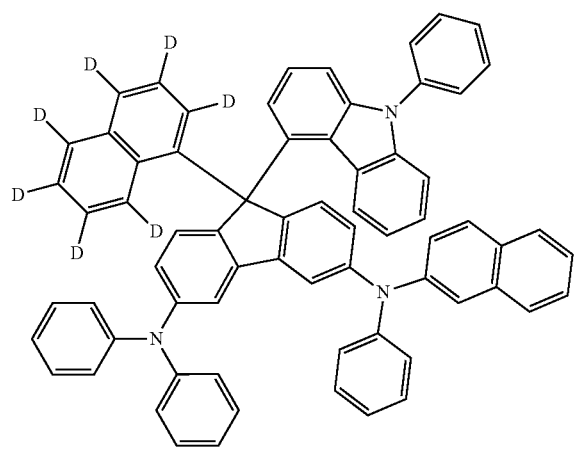
358
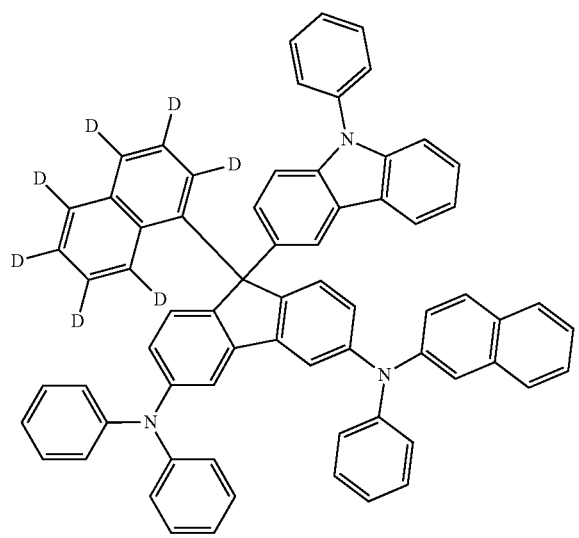
410
-continued
359
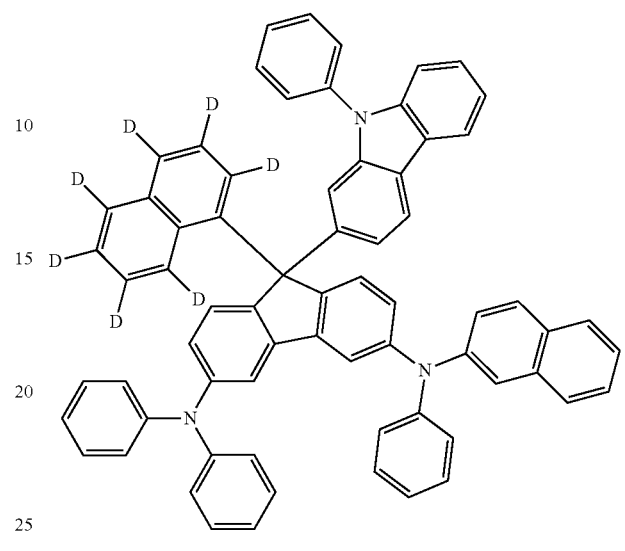
360
175
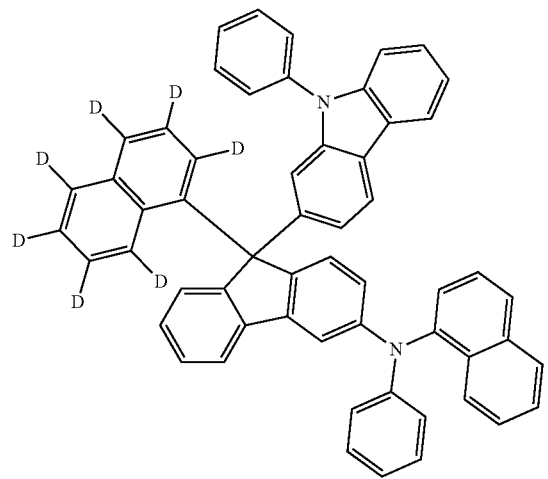

-continued

176

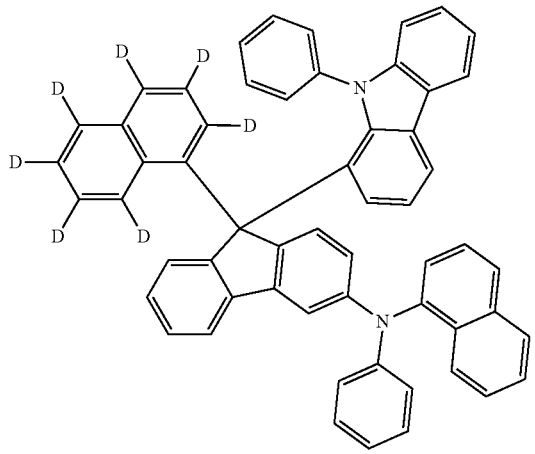

337

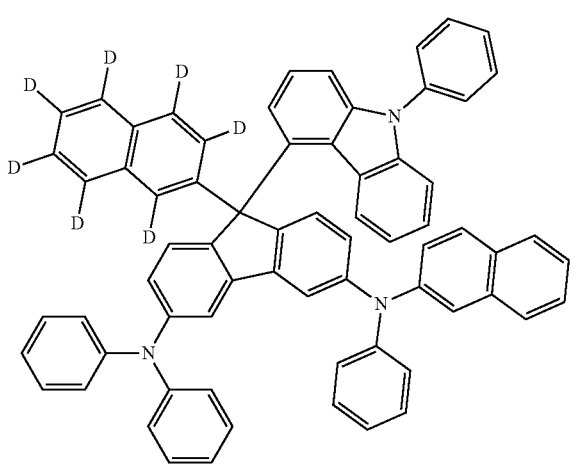

338

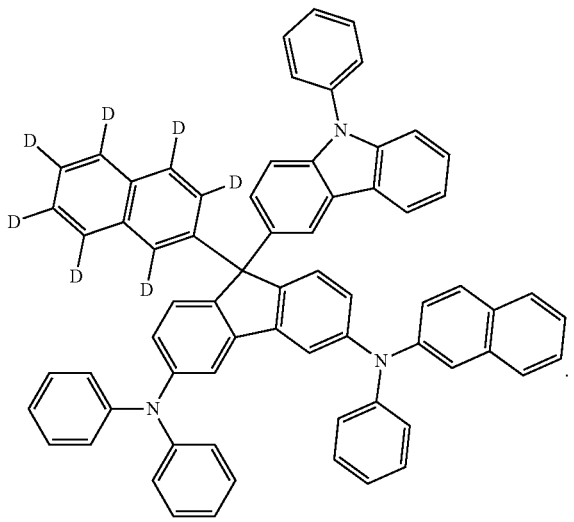

12. An organic electroluminescence device comprising:
a first electrode;
a second electrode facing the first electrode; and
a plurality of organic layers between the first electrode and the second electrode, wherein at least one organic layer of the organic layers comprises an amine compound represented by Formula 1:

Formula 1

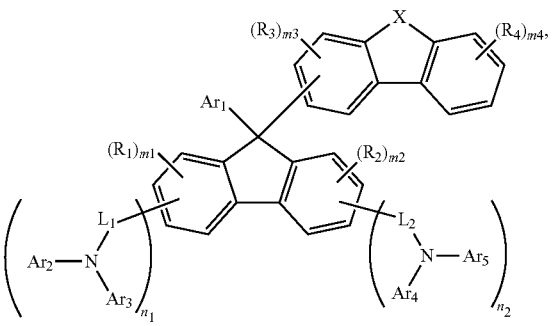

wherein, in Formula 1,

X is O, S, or $NAr_6$;

$L_1$ and $L_2$ are each independently a direct linkage, a substituted or unsubstituted arylene group having 6 to 60 ring-forming carbon atoms, or a substituted or unsubstituted heteroarylene group having 2 to 60 ring-forming carbon atoms;

$R_1$ to $R_4$ are each independently a hydrogen atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$m_1$, $m_2$, and $m_4$ are each independently an integer of 0 to 4;

$m_3$ is an integer of 0 to 3;

$Ar_1$ is a phenyl group substituted with deuterium, a naphthyl group substituted with deuterium, or a biphenyl group substituted with deuterium;

$Ar_2$ to $Ar_6$ are each independently a substituted or unsubstituted aryl group having 6 to 60 ring-forming carbon atoms, or a substituted or unsubstituted heteroaryl group having 3 to 60 ring-forming carbon atoms;

$n_1$ and $n_2$ are each independently 0 or 1;

at least one of $n_1$ or $n_2$ is 1 and only $Ar_1$ is substituted with deuterium.

13. The organic electroluminescence device of claim 12, wherein the amine compound represented by Formula 1 is represented by at least one of Formula 1-1 to Formula 1-3:

Formula 1-1

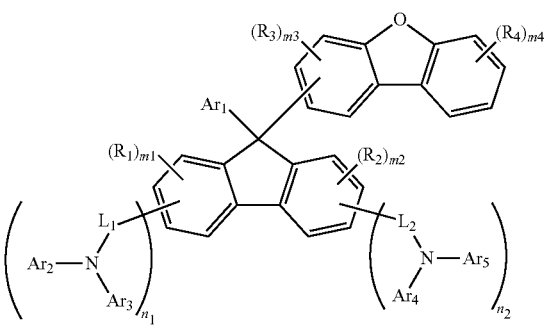

413
-continued
Formula 1-2
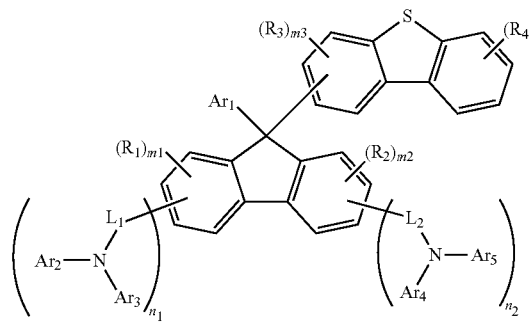
414
-continued
Formula 1-3
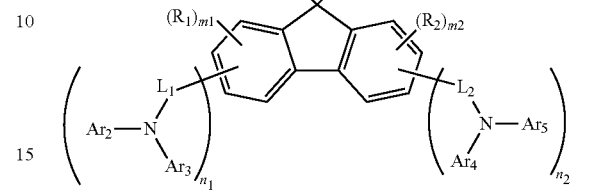
wherein, in Formula 1-1 to Formula 1-3,
$L_1$, $L_2$, $R_1$ to $R_4$, $m_1$ to $m_4$, $Ar_1$ to $Ar_6$, $n_1$ and $n_2$ are each independently the same as defined in Formula 1.
14. The organic electroluminescence device of claim 12, wherein the amine compound represented by Formula 1 is represented by at least one of Formula 2-1 to Formula 2-5:
Formula 2-1
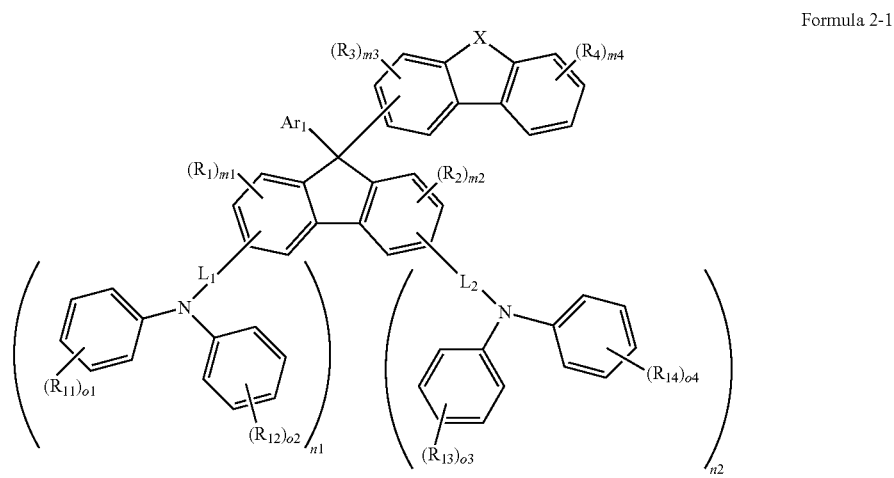
Formula 2-2
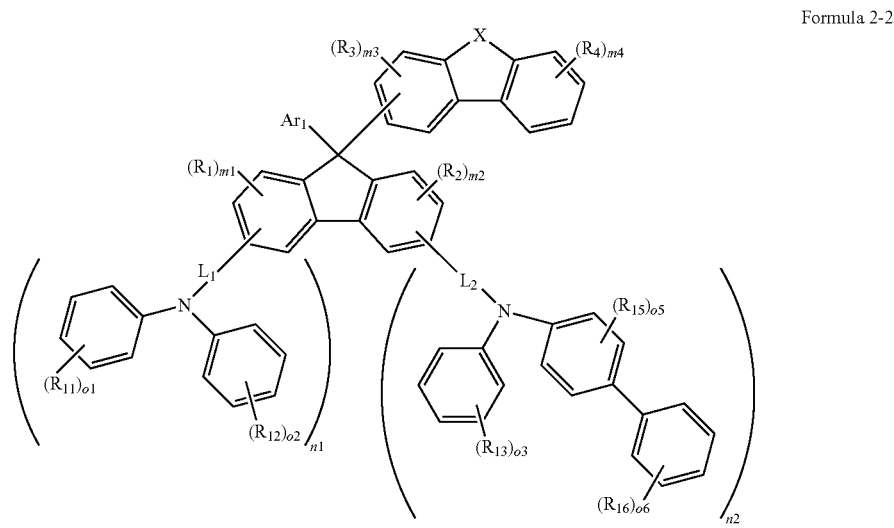

Formula 2-3

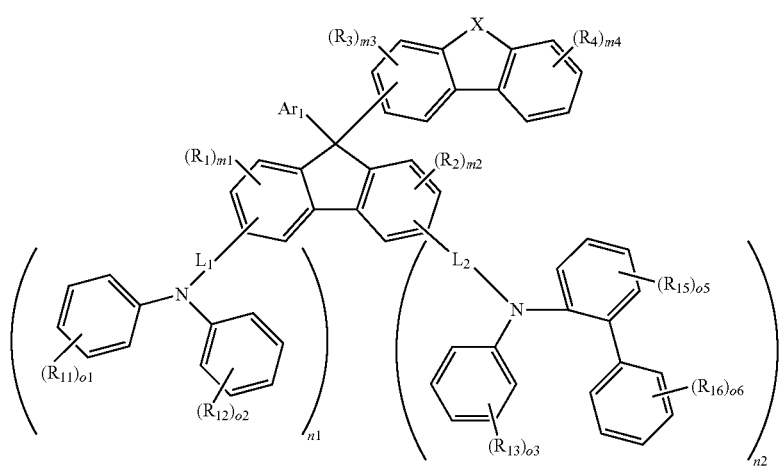

Formula 2-4

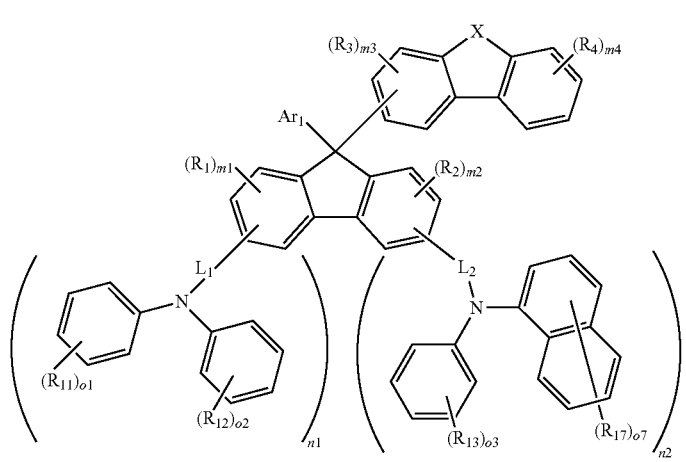

Formula 2-5

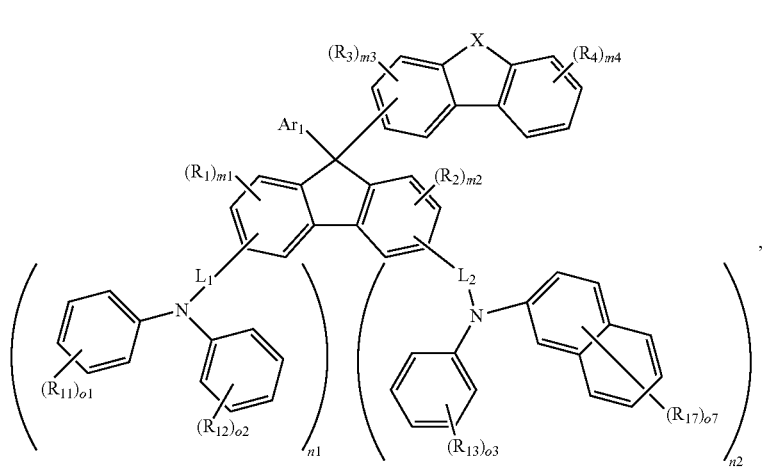

wherein, in Formula 2-1 to Formula 2-5, $R_{11}$ to $R_{17}$ are each independently a hydrogen atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

15. The organic electroluminescence device of claim 12, wherein the amine compound represented by Formula 1 is represented by Formula 3-1:

Formula 3-1

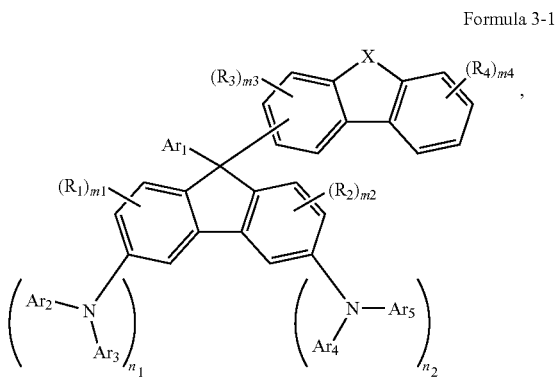

wherein, in Formula 3-1,

X, Ar₁ to Ar₅, R₁ to R₄, n₁, n₂, and m₁ to m₄ are each independently the same as defined in Formula 1.

16. An amine compound represented by Formula 1:

Formula 1

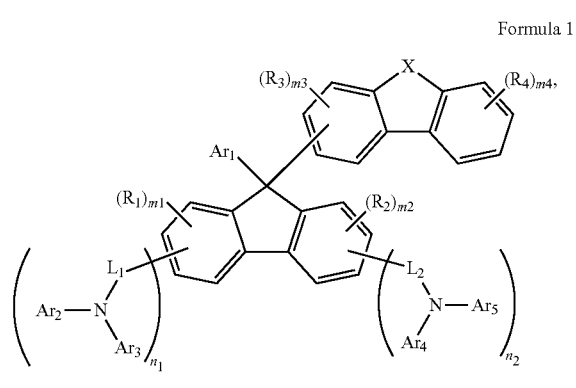

wherein, in Formula 1,

X is O, S, or NAr₆;

L₁ and L₂ are each independently a direct linkage, a substituted or unsubstituted arylene group having 6 to 60 ring-forming carbon atoms, or a substituted or unsubstituted heteroarylene group having 2 to 60 ring-forming carbon atoms;

R₁ to R₄ are each independently a hydrogen atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

m₁, m₂, and m₄ are each independently an integer of 0 to 4;

m₃ is an integer of 0 to 3;

Ar₁ is a phenyl group substituted with deuterium, a naphthyl group substituted with deuterium, or a biphenyl group substituted with deuterium;

Ar₂ to Ar₆ are each independently a substituted or unsubstituted aryl group having 6 to 60 ring-forming carbon atoms, or a substituted or unsubstituted heteroaryl group having 3 to 60 ring-forming carbon atoms;

n₁ and n₂ are each independently 0 or 1;

at least one of n₁ or n₂ is 1 and only Ar₁ is substituted with deuterium.

17. The amine compound of claim 16, wherein the amine compound represented by Formula 1 is represented by at least one of Formula 1-1 to Formula 1-3:

Formula 1-1

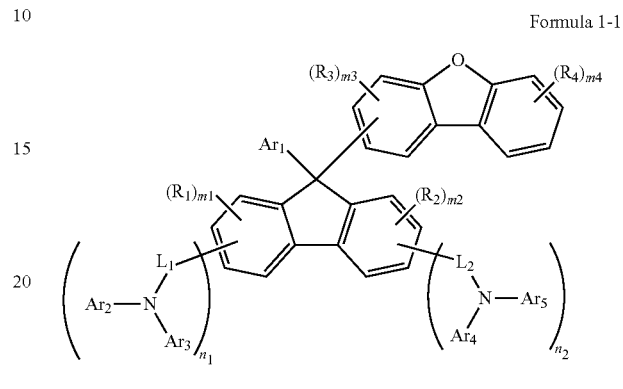

Formula 1-2

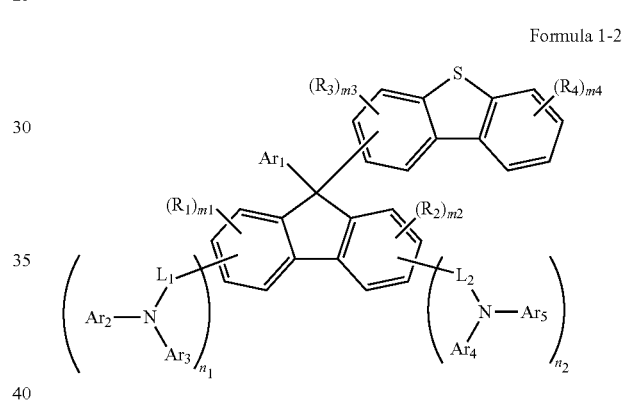

Formula 1-3

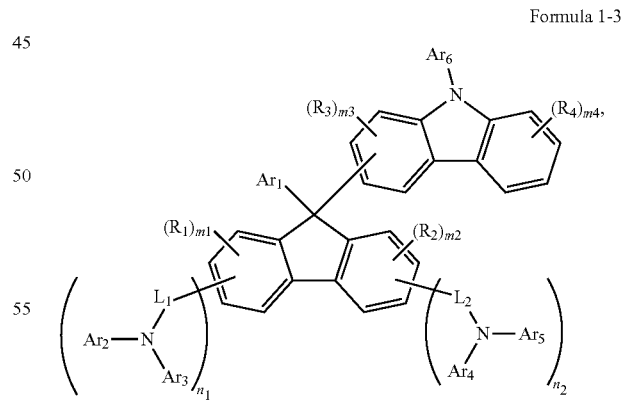

wherein, in Formula 1-1 to Formula 1-3,

L₁, L₂, R₁ to R₄, m₁ to m₄, Ar₁ to Ar₆, n₁ and n₂ are each independently the same as defined in Formula 1.

18. The amine compound of claim 16, wherein the amine compound represented by Formula 1 is represented by at least one of Formula 2-1 to Formula 2-5:

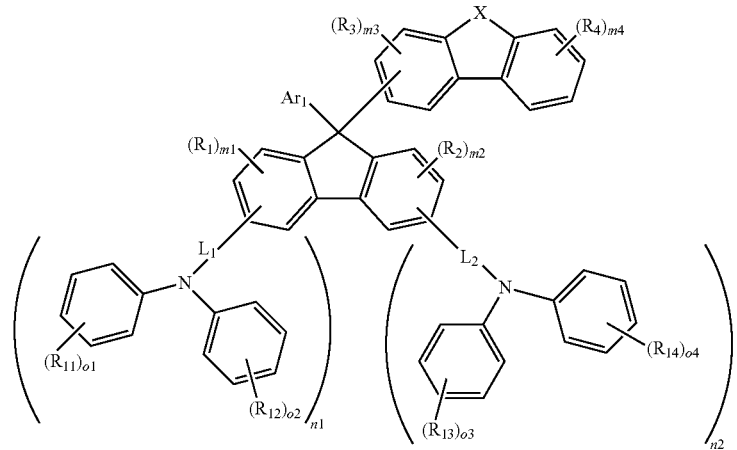
Formula 2-1
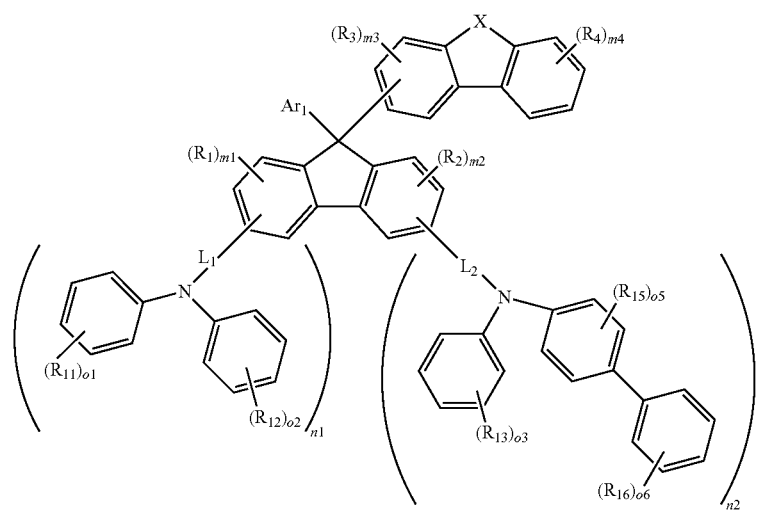
Formula 2-2
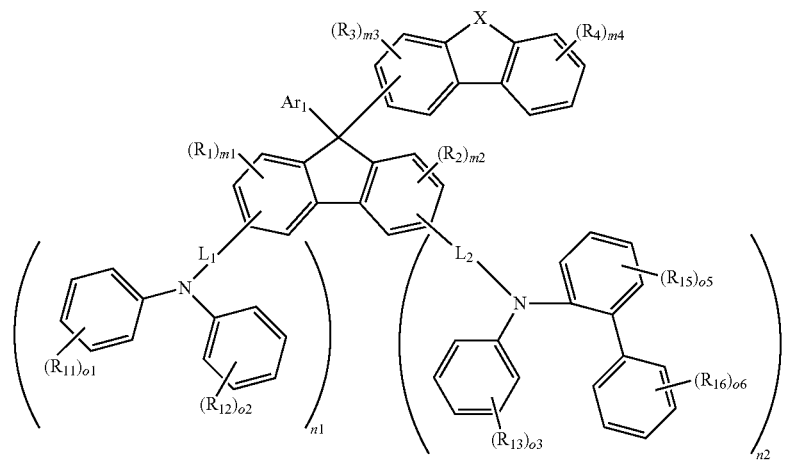
Formula 2-3

Formula 2-4

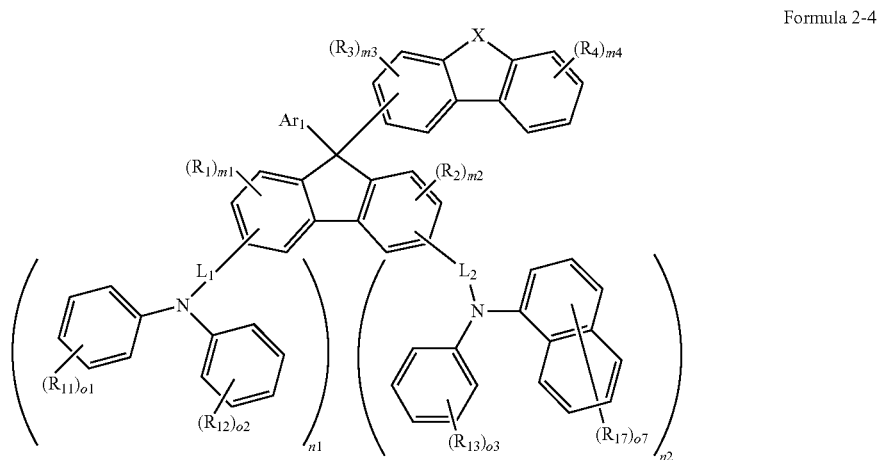

Formula 2-5

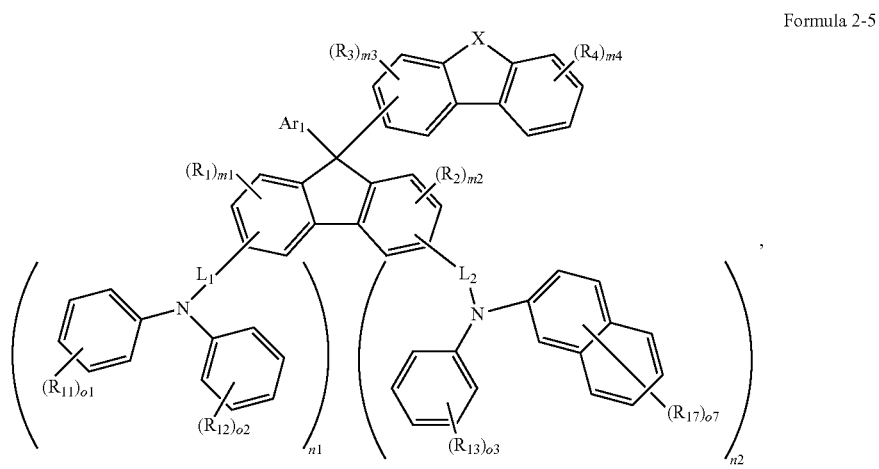

wherein, in Formula 2-1 to Formula 2-5, $R_{11}$ to $R_{17}$ are each independently a hydrogen atom, a halogen atom, a substituted or unsubstituted alkyl group having 1 to 20 carbon atoms, a substituted or unsubstituted aryl group having 6 to 60 ring-forming carbon atoms, or a substituted or unsubstituted heteroaryl group having 2 to 60 ring-forming carbon atoms, and/or are optionally bonded to an adjacent group to form a ring;

$o_1$ to $o_4$ and $o_6$ are each independently an integer of 0 to 5;

$o_5$ is an integer of 0 to 4;

$o_7$ is an integer of 0 to 7; and

X, $R_1$ to $R_4$, $L_1$, $L_2$, $n_1$, $n_2$, $m_1$ to $m_4$ and $Ar_1$ are each independently the same as defined in Formula 1.

19. The amine compound of claim 16, wherein the amine compound represented by Formula 1 is represented by Formula 3-1:

Formula 3-1

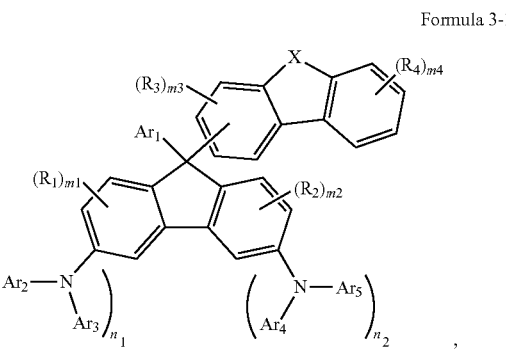

wherein, in Formula 3-1,

X, $Ar_1$ to $Ar_5$, $R_1$ to $R_4$, $n_1$, $n_2$, and $m_1$ to $m_4$ are each independently the same as defined in Formula 1.

20. The amine compound of claim 16, wherein the amine compound represented by Formula 1 comprises at least one of the compounds represented by Compound Group 1:

Compound Group 1
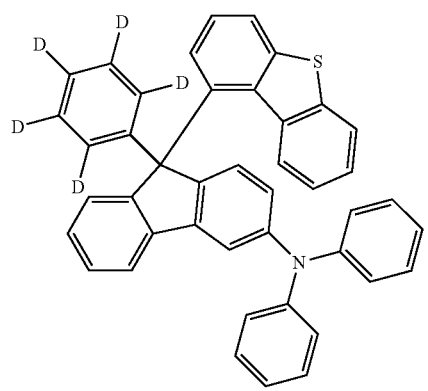
1
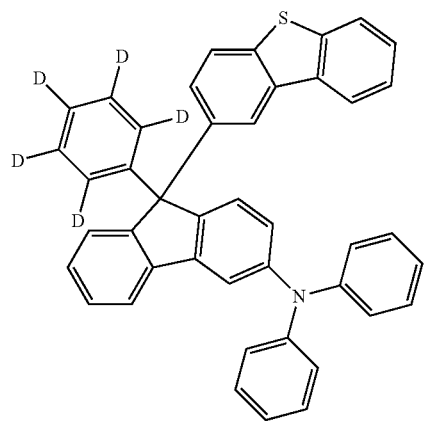
2
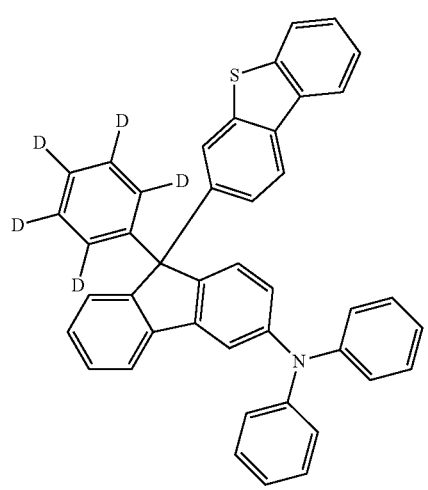
3
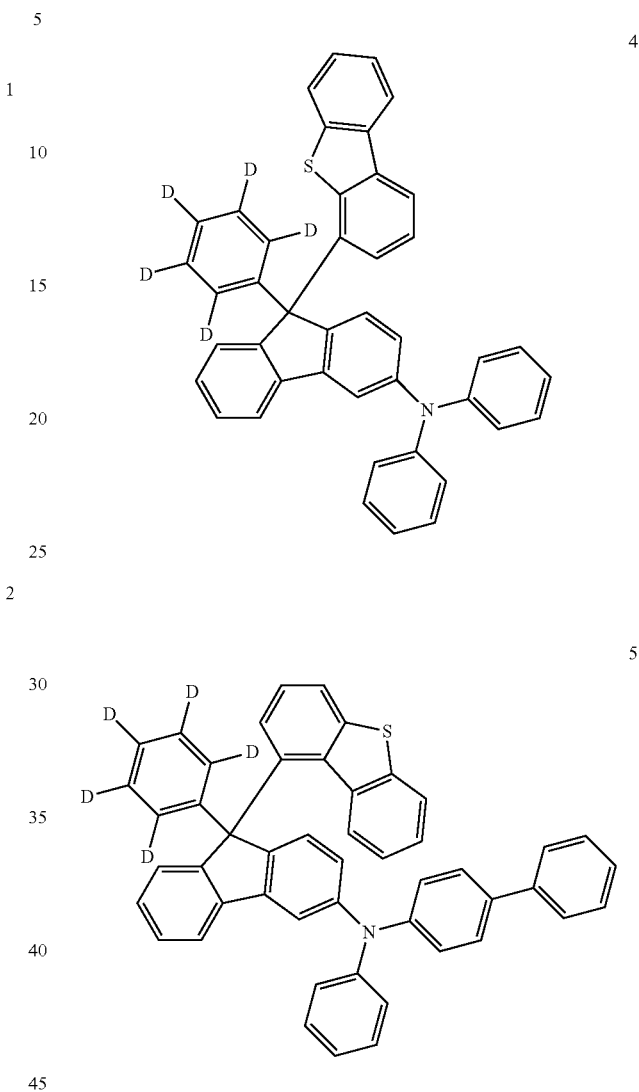

7
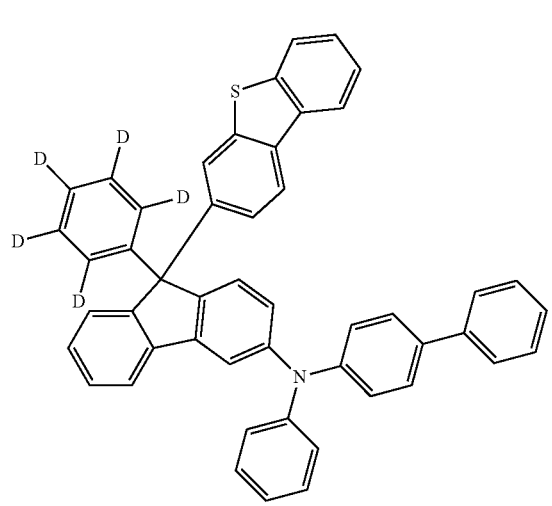
8
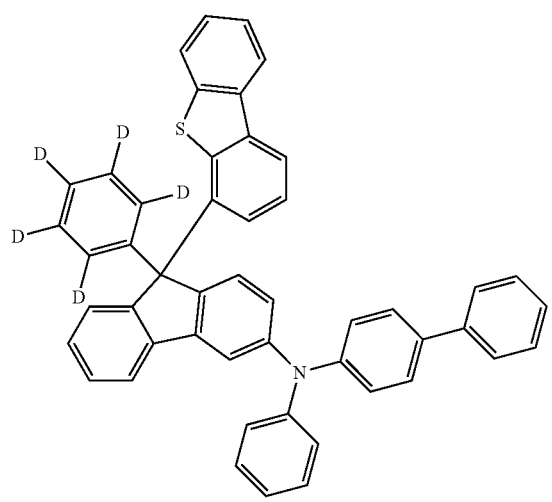
9
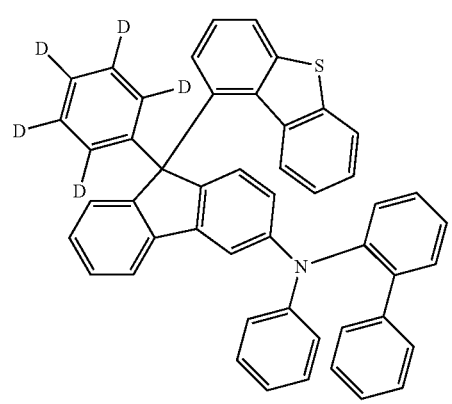
10
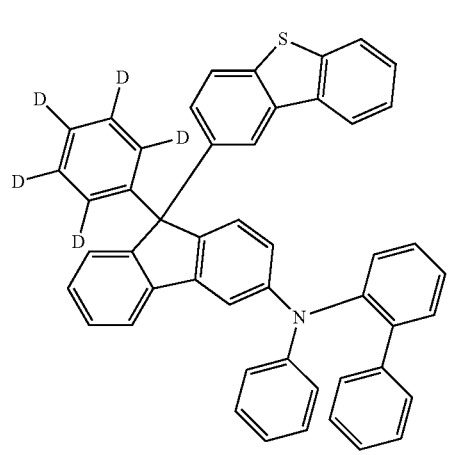
11
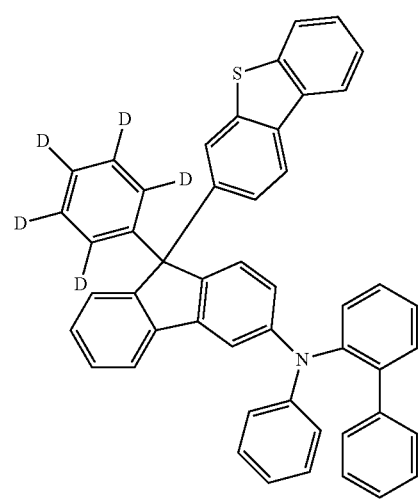
12
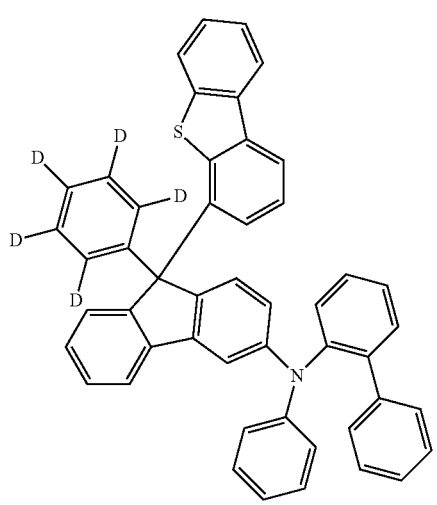

13
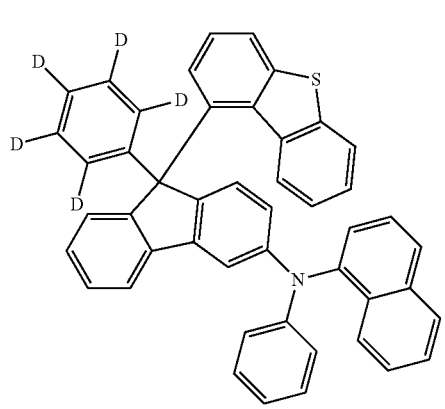
14
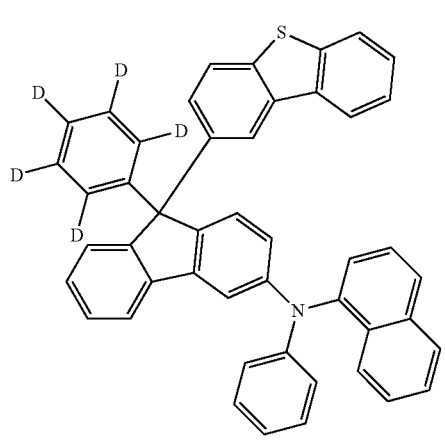
15
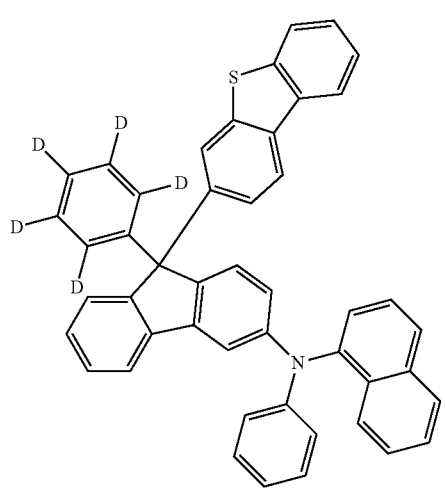
16
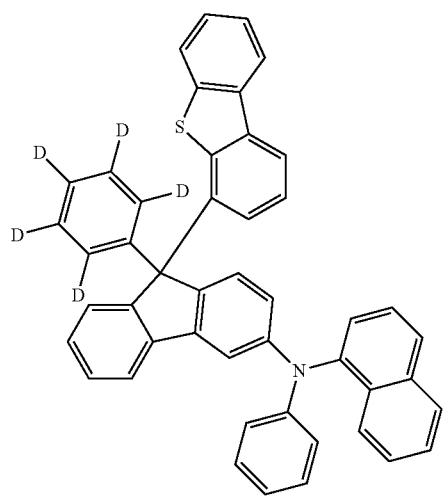
17
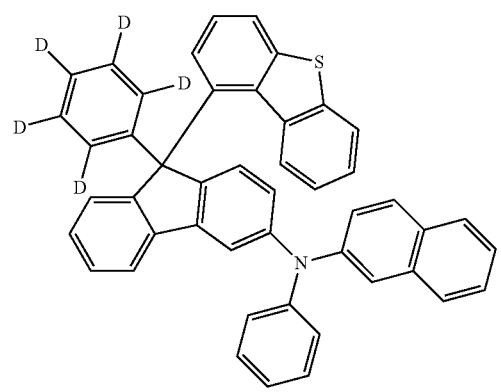
18
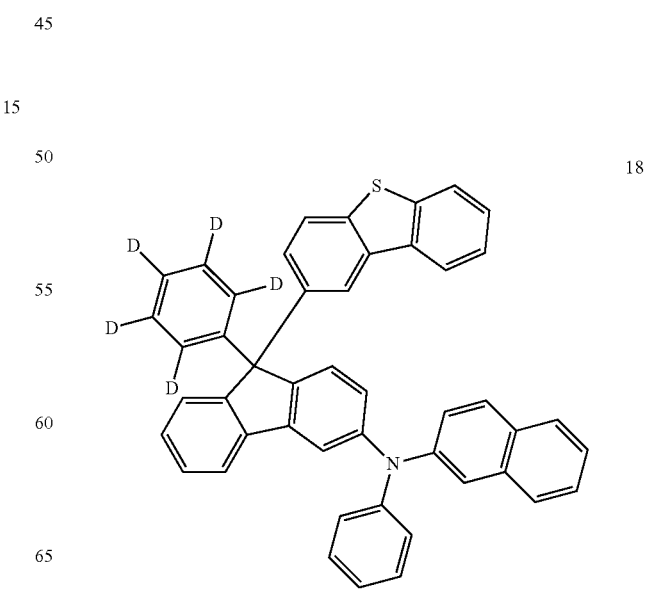

19
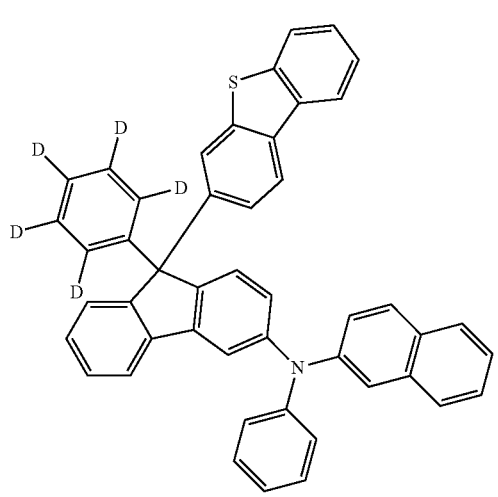
20
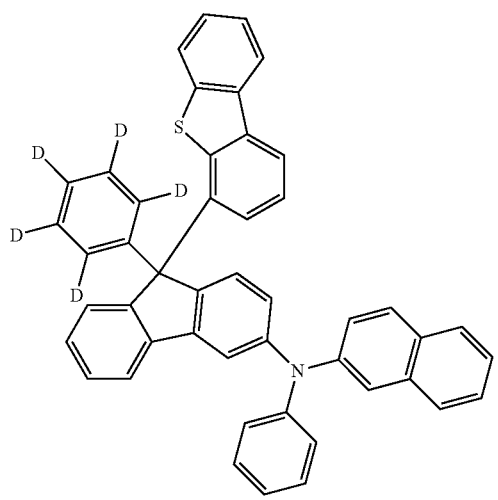
21
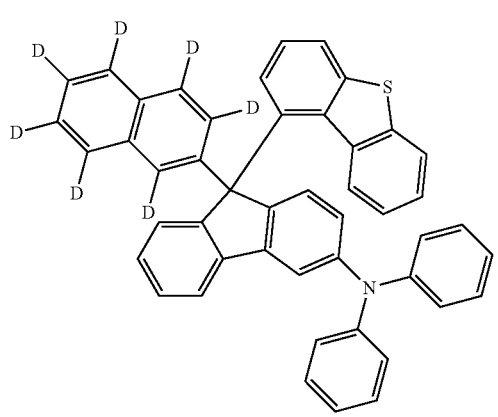
22
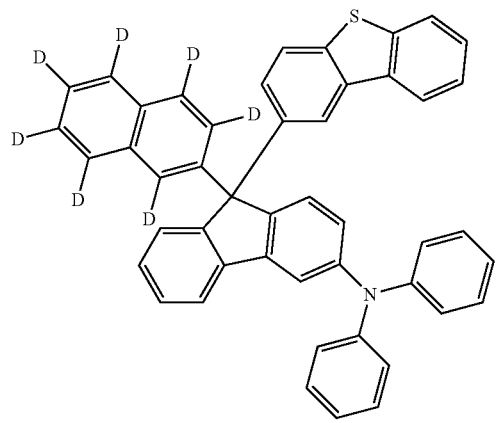
23
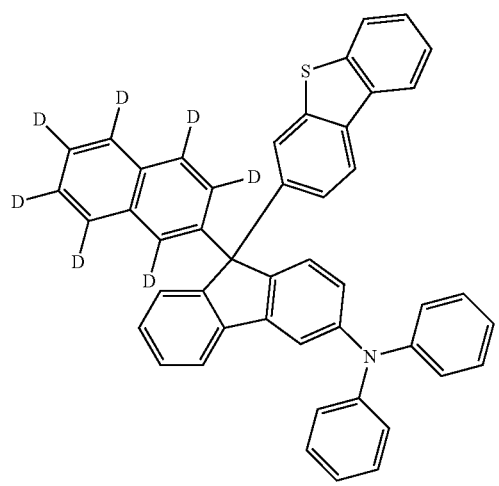
24
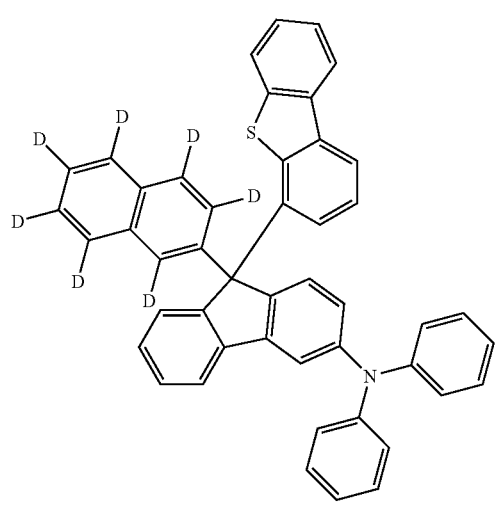

431
-continued
25
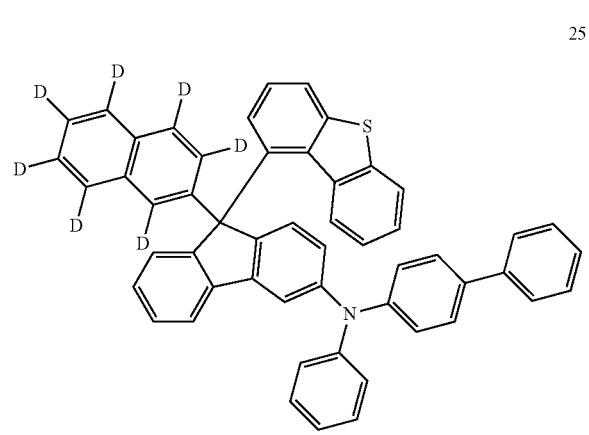
26
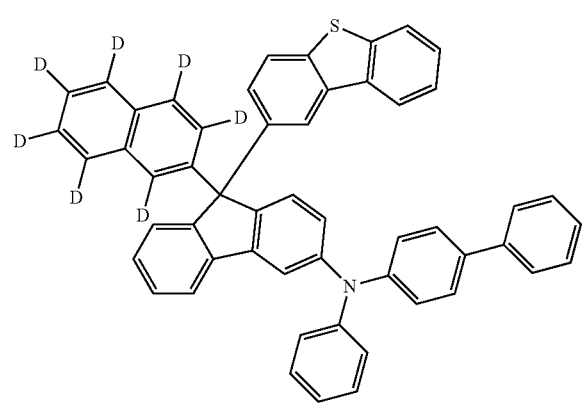
27
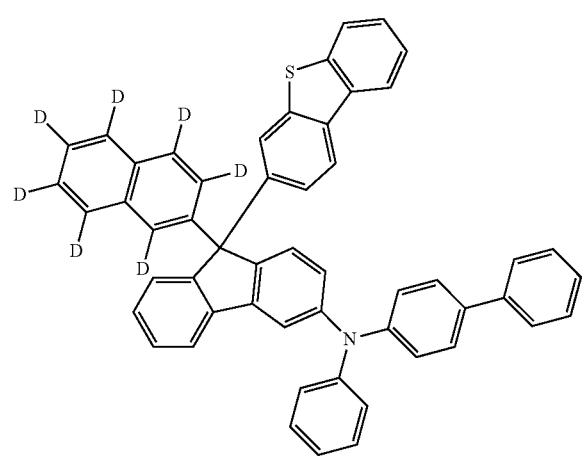
432
-continued
28
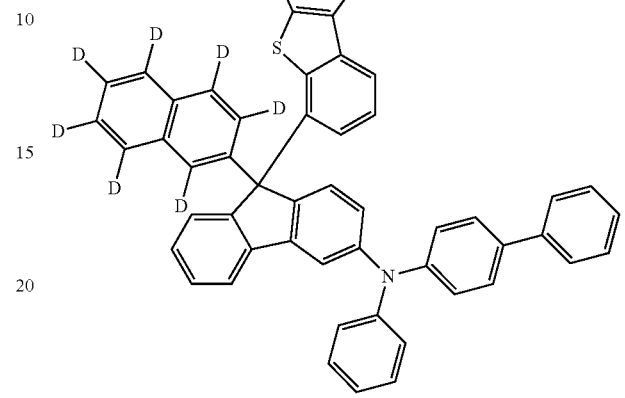
29
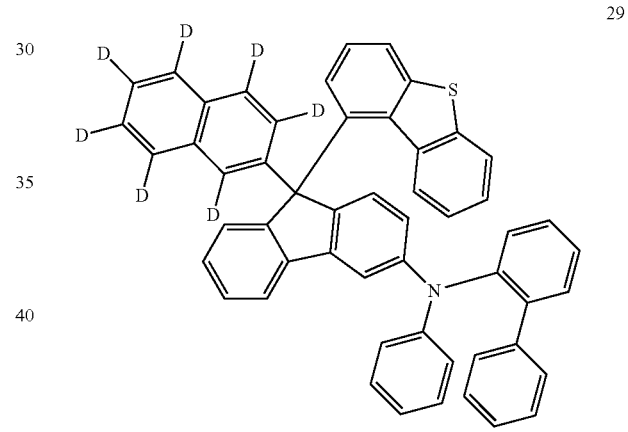
30
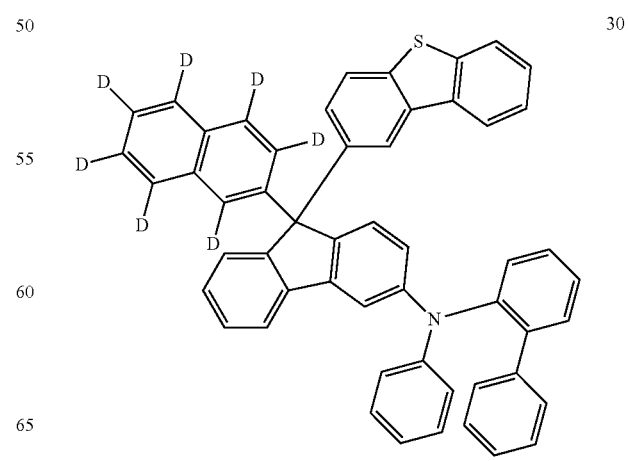

433
31
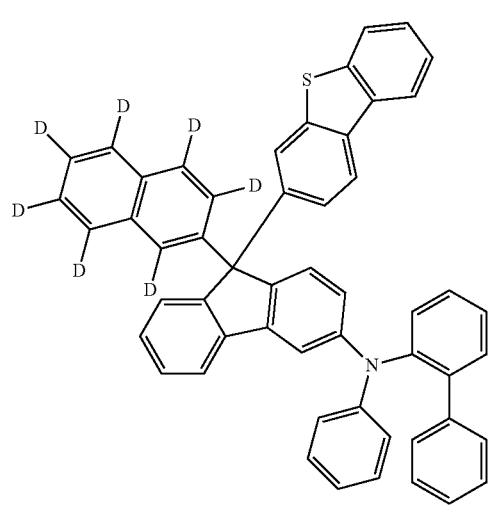
32
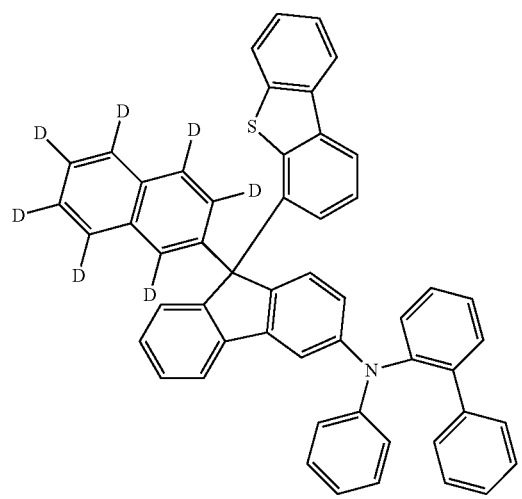
33
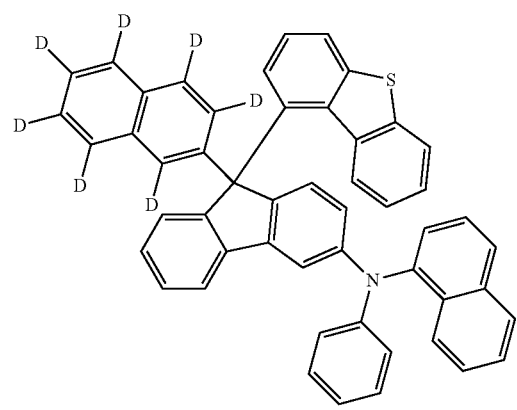
434
34
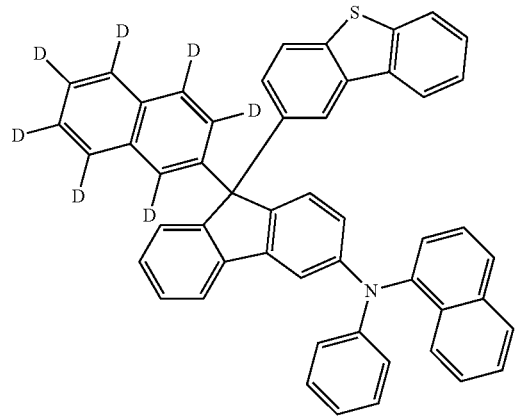
35
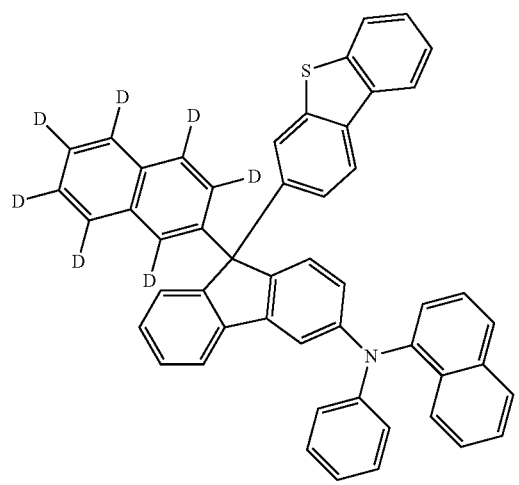
36
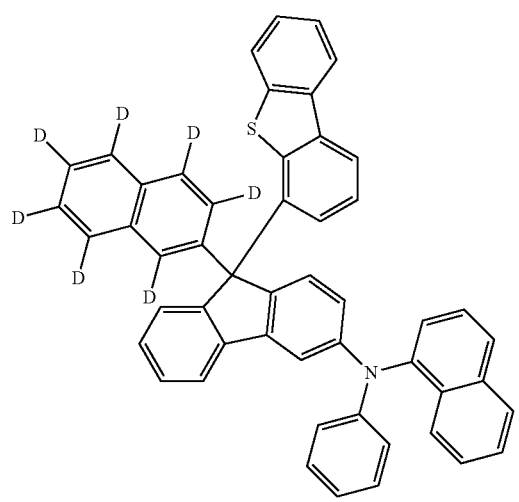

37
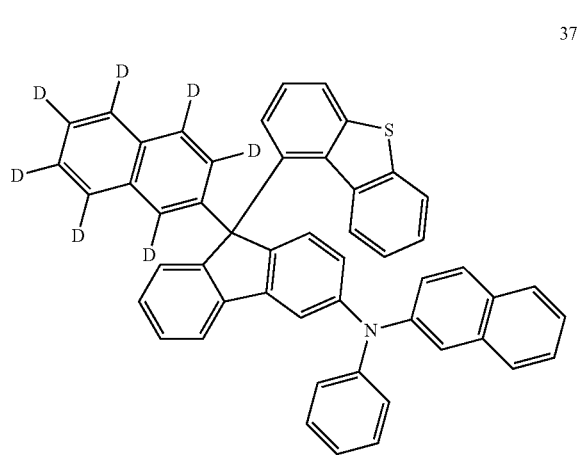
38
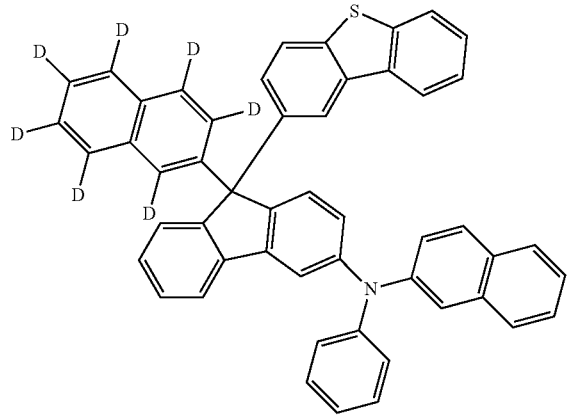
41
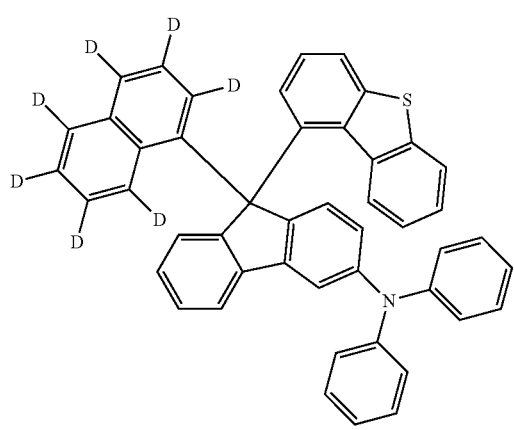
42
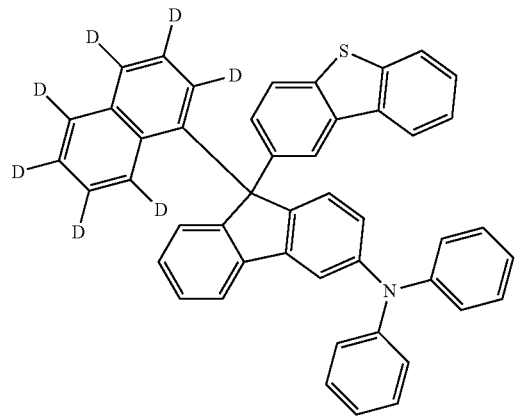
43
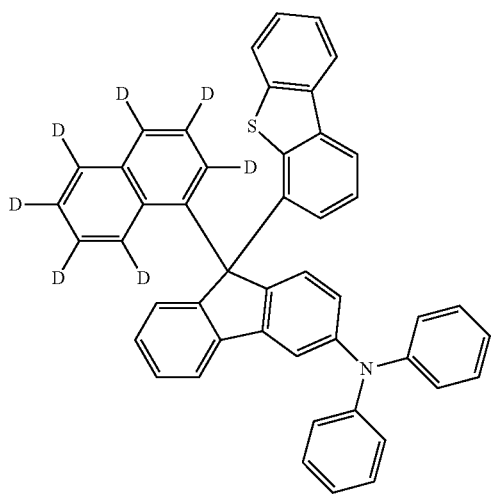
44

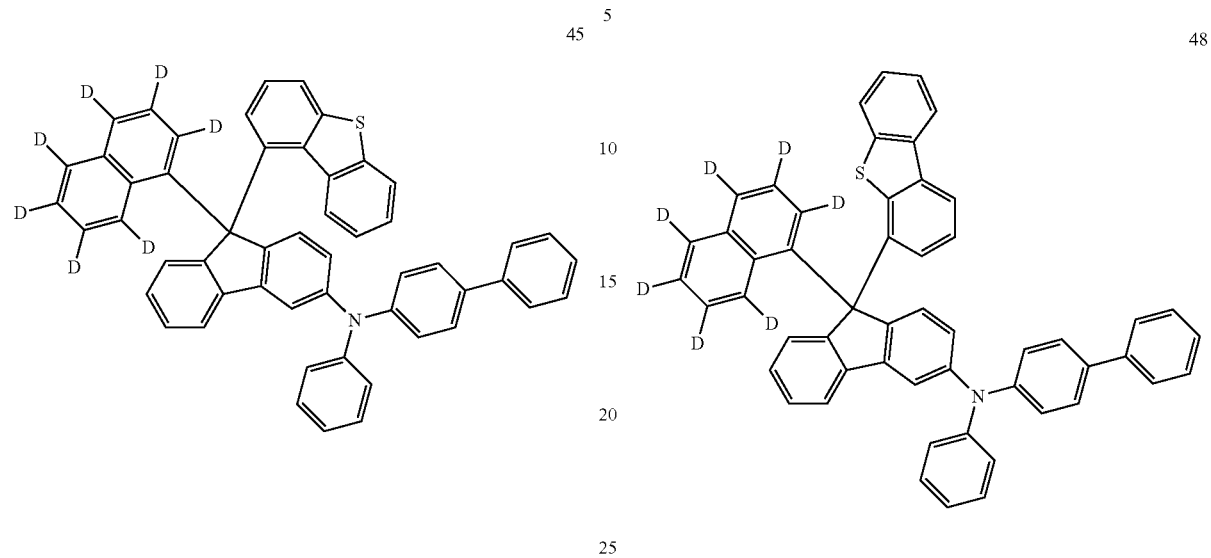
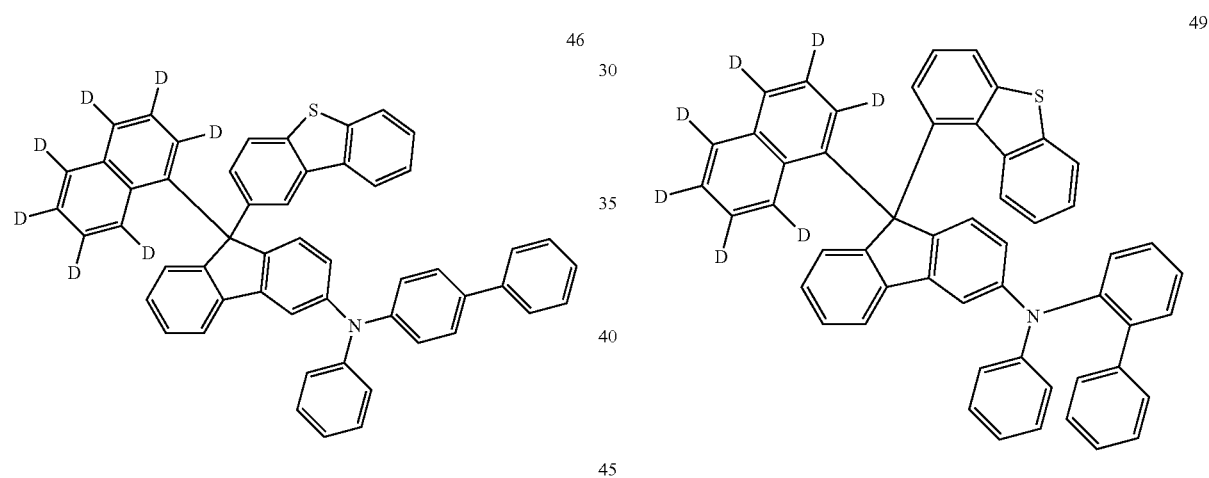
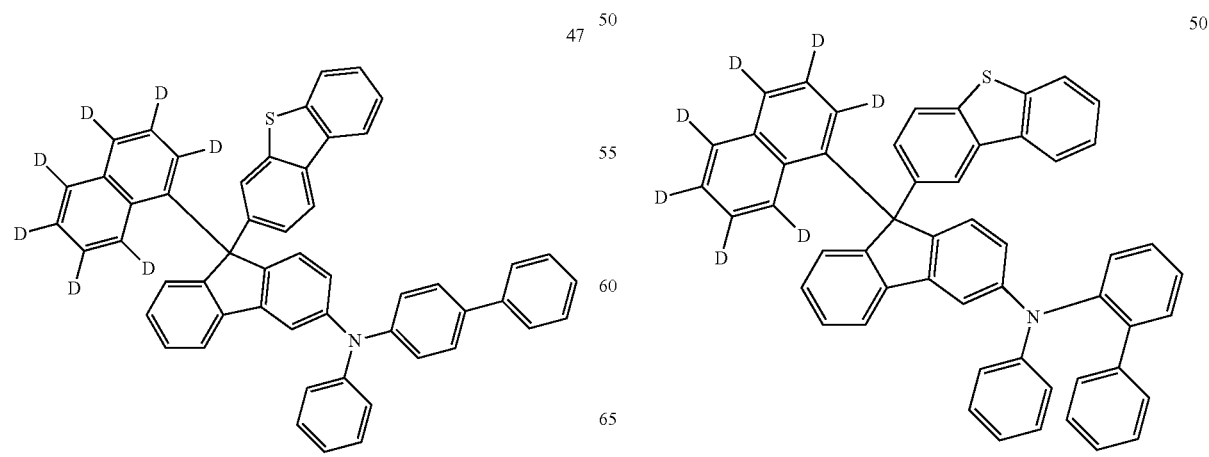

51
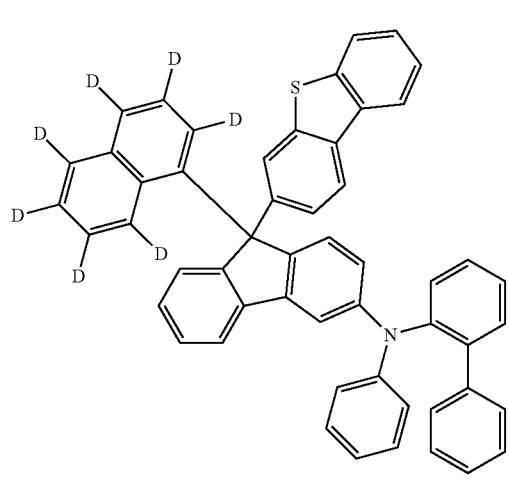
52
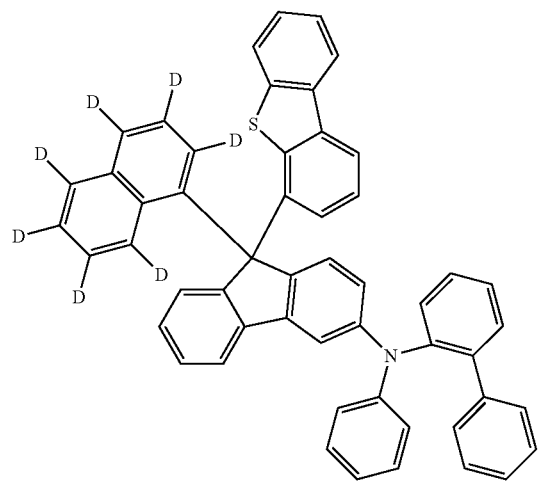
53
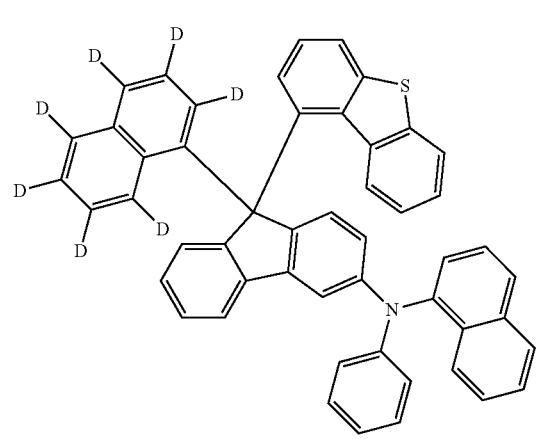
54
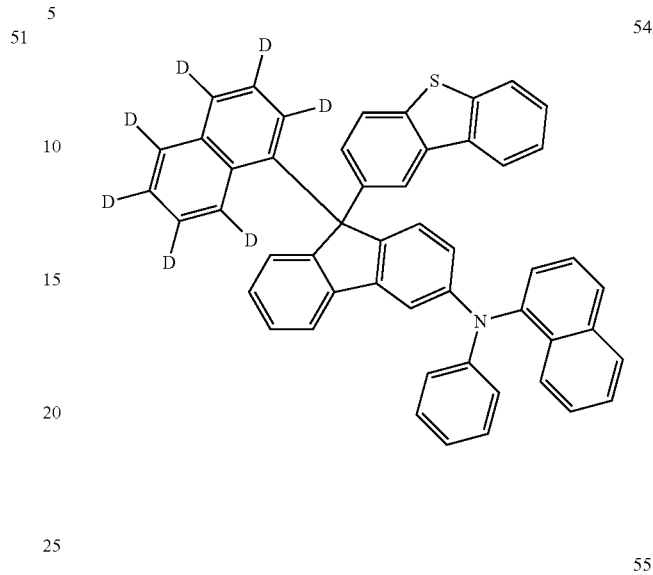
55
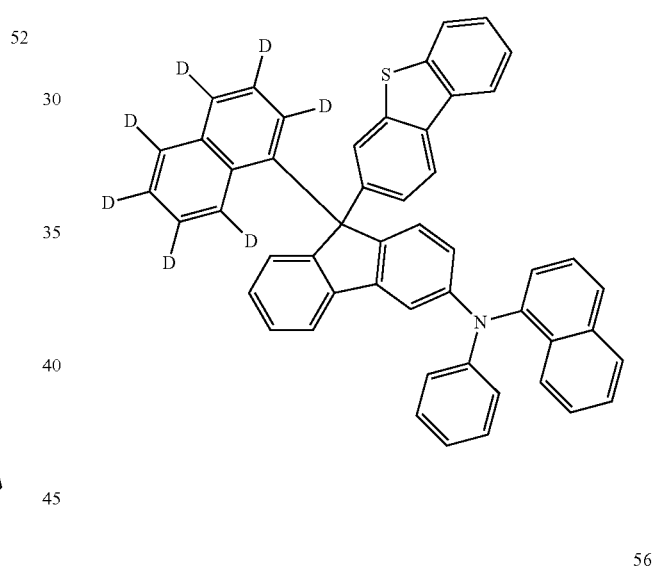
56
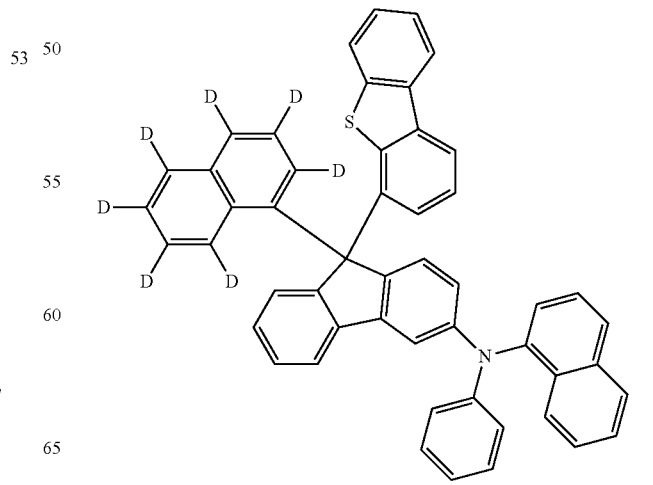

57
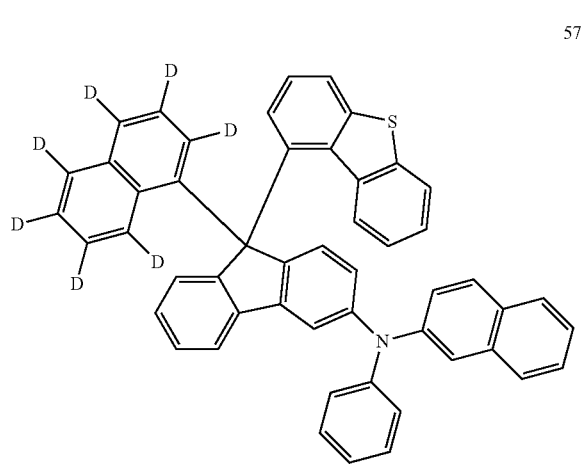
58
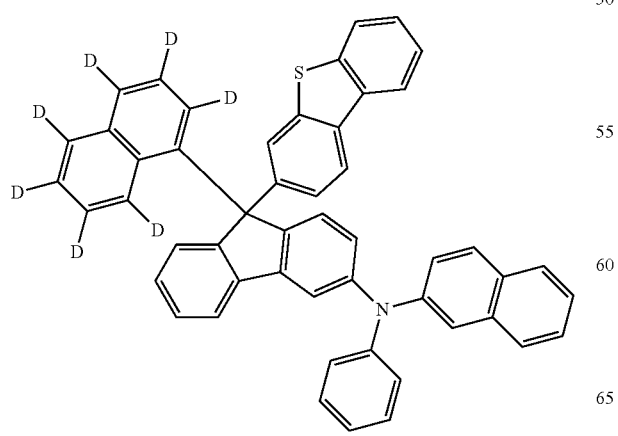
59
60
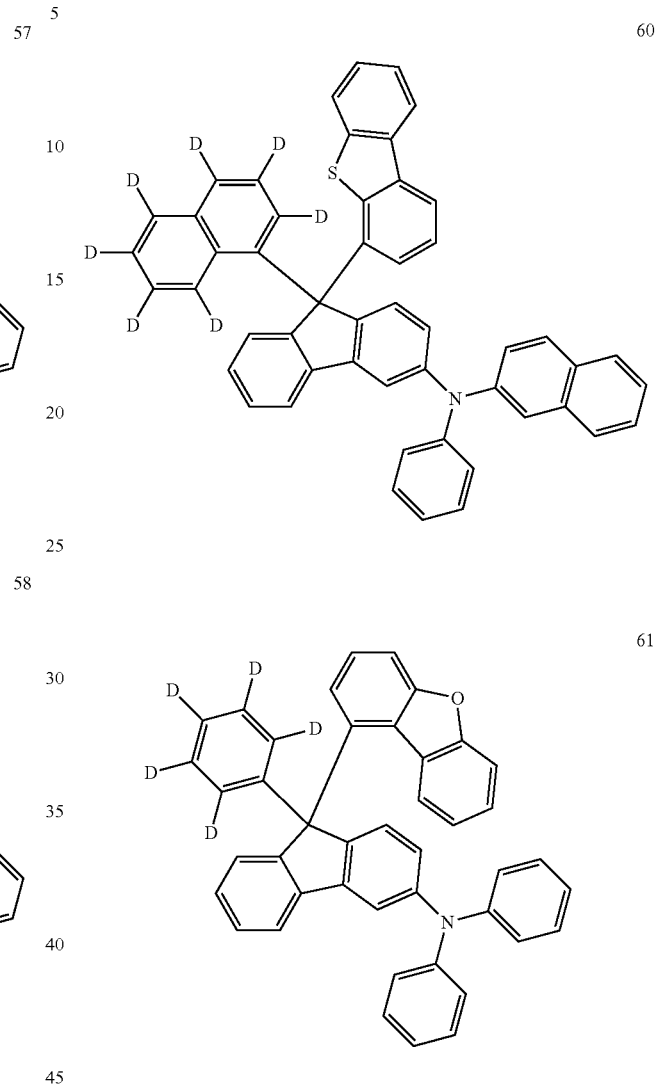
61
62
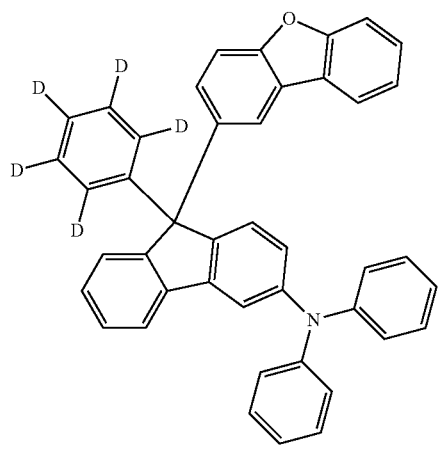

63
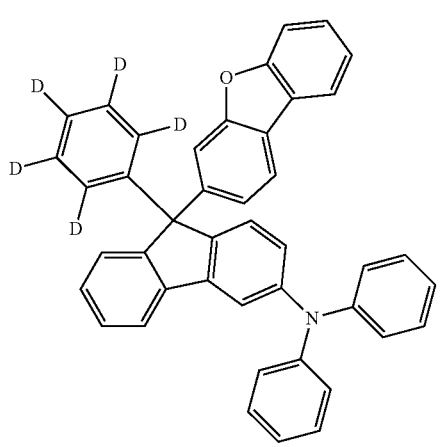
64
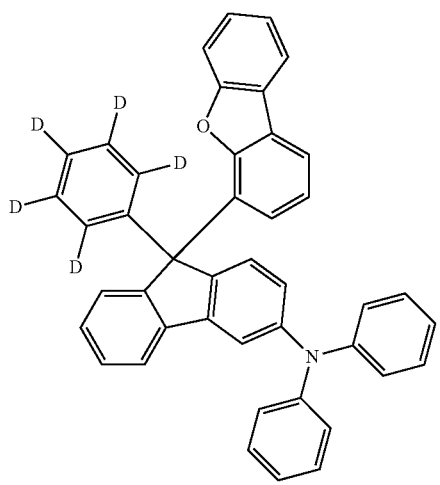
65
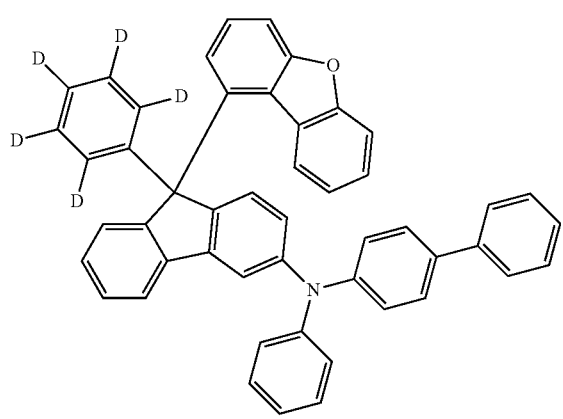
66
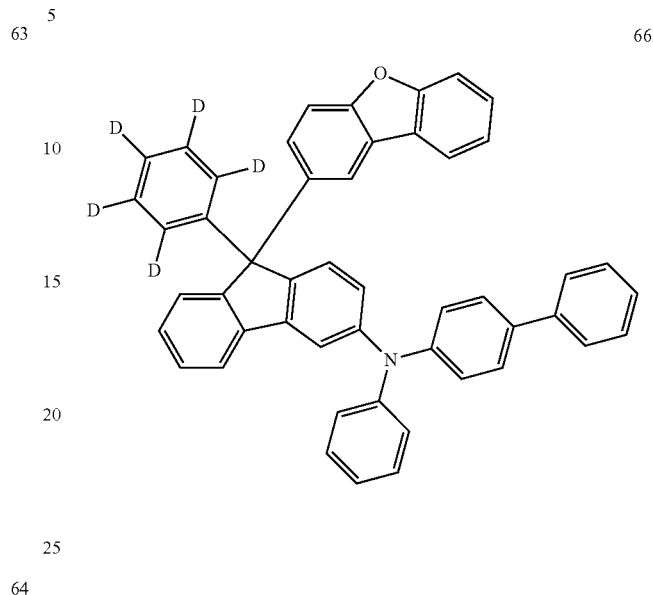
67
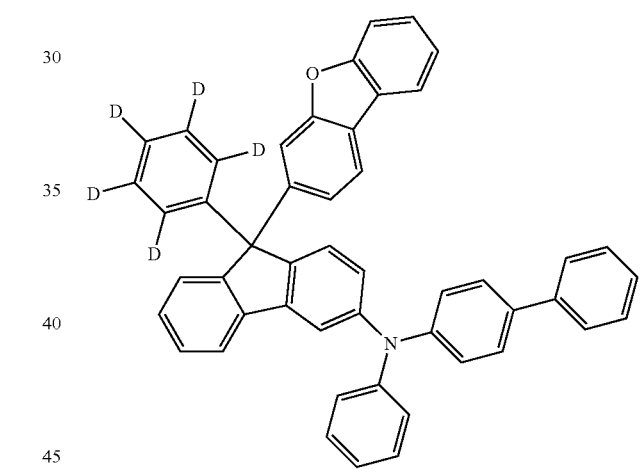
68
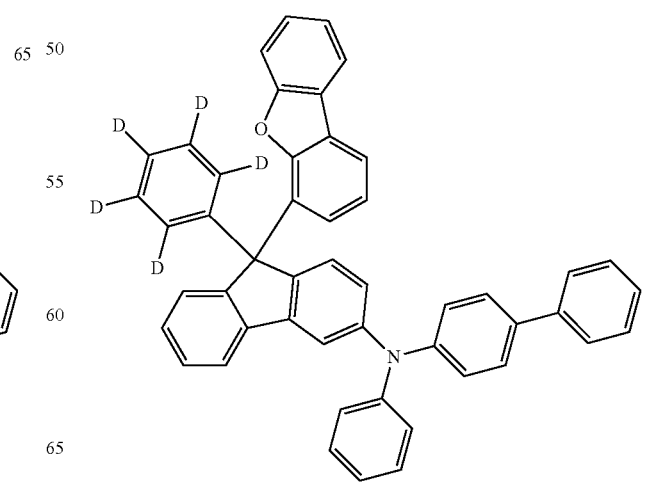

69
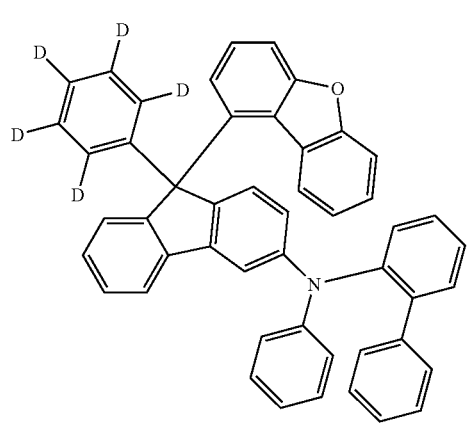
70
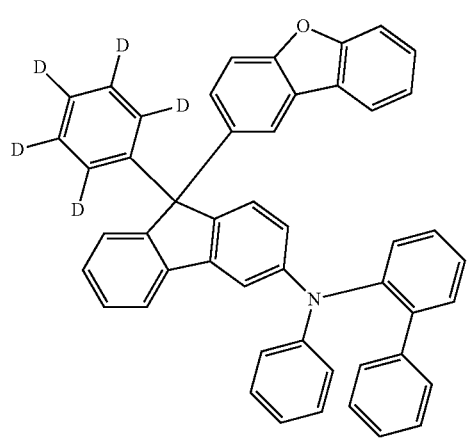
71
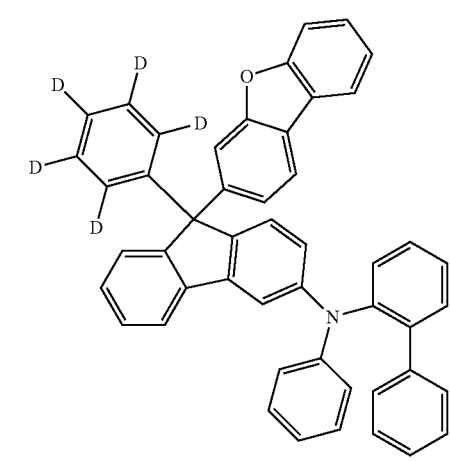
72
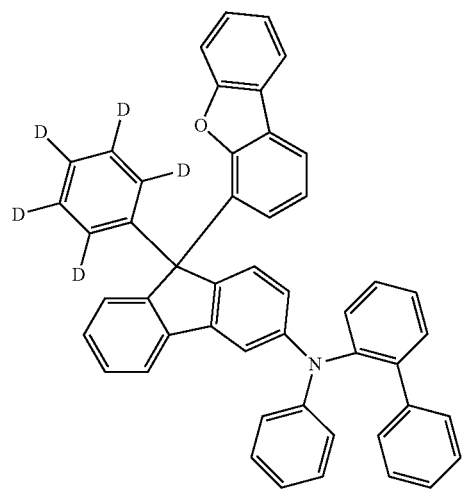
73
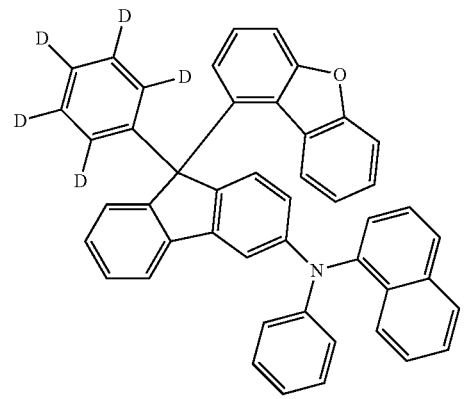
74
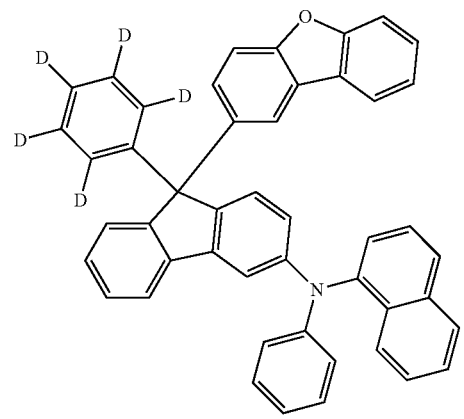

75
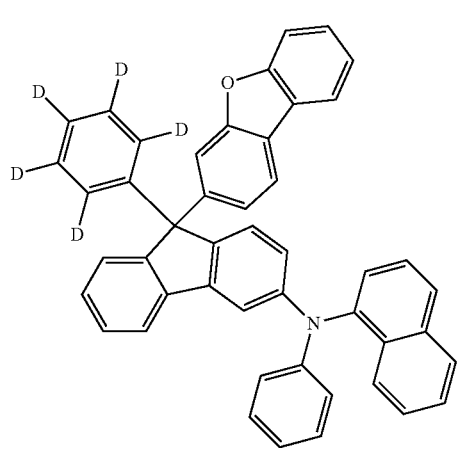
76
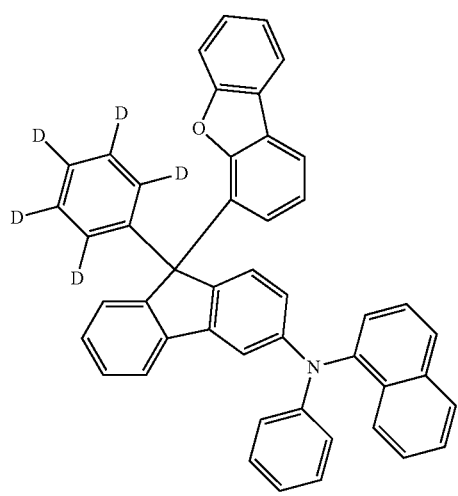
77
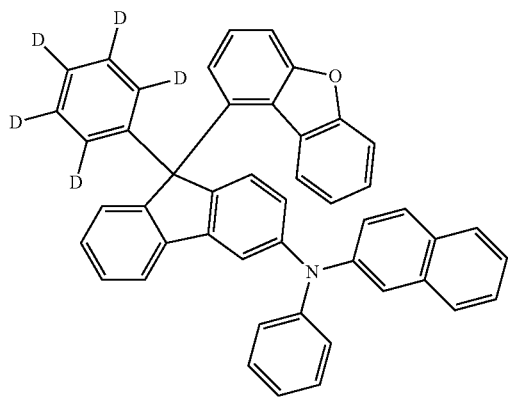
78
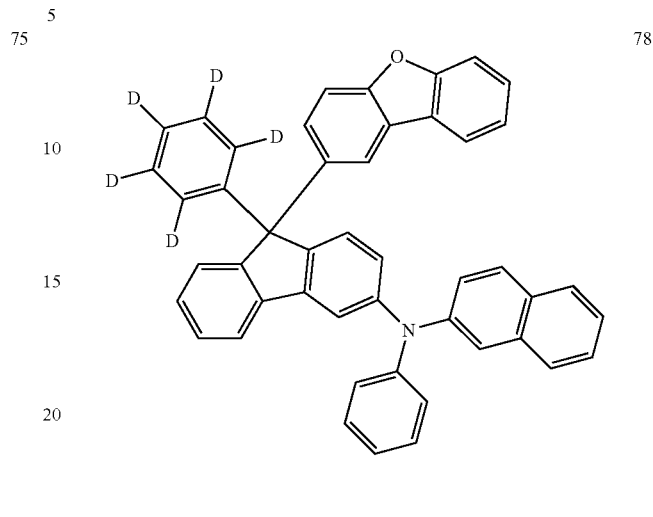
79
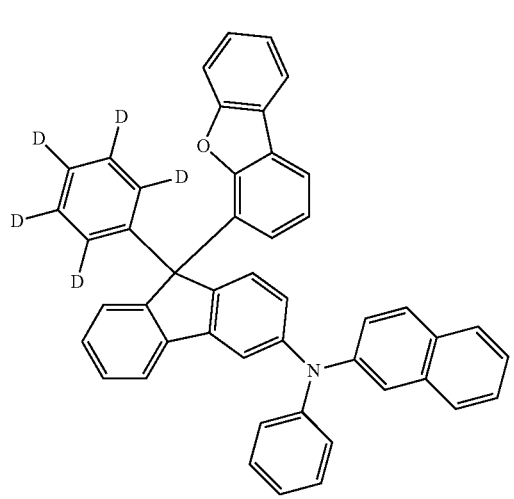
80

81
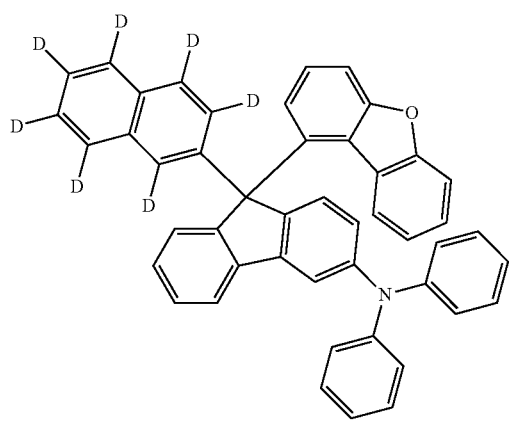
82
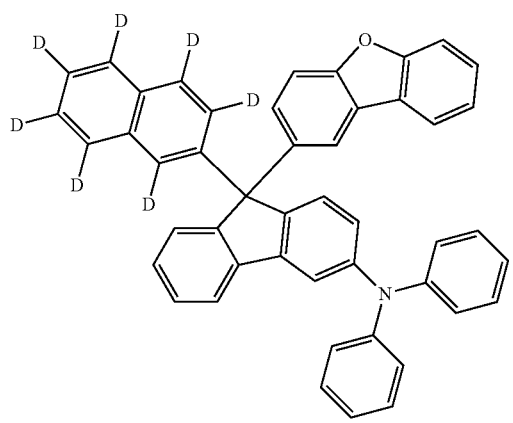
83
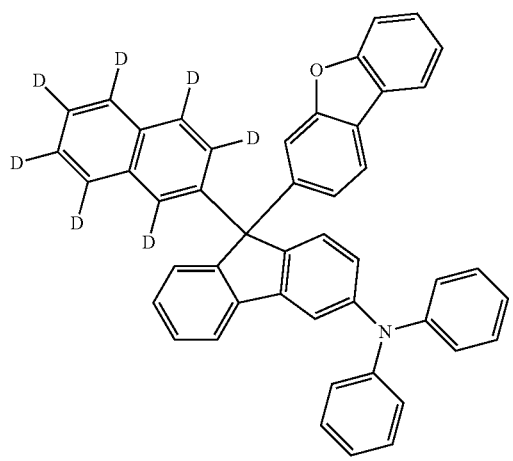
84
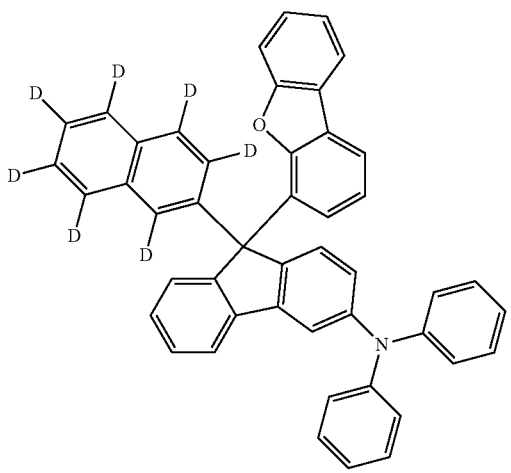
85
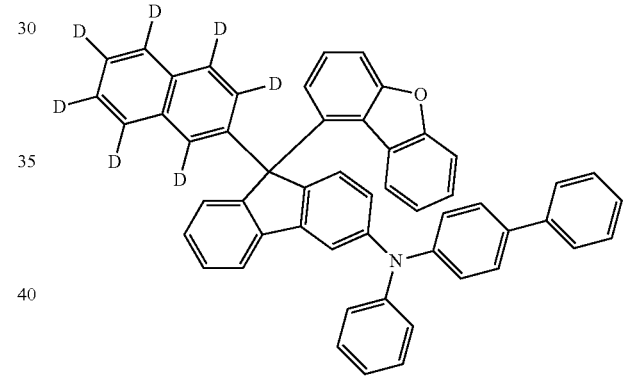
86
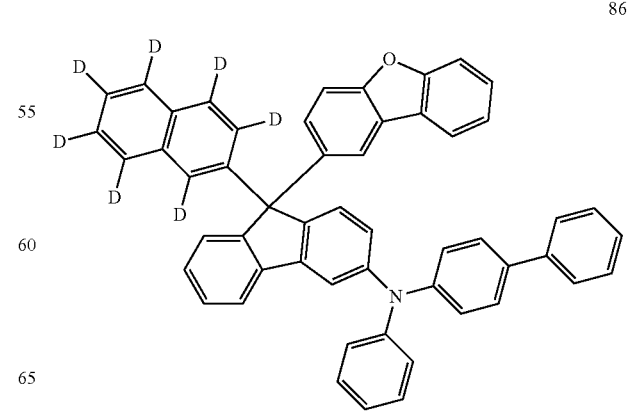

451
-continued
87
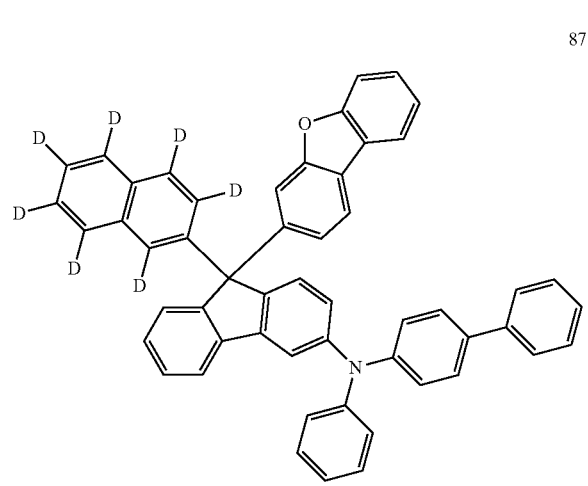
88
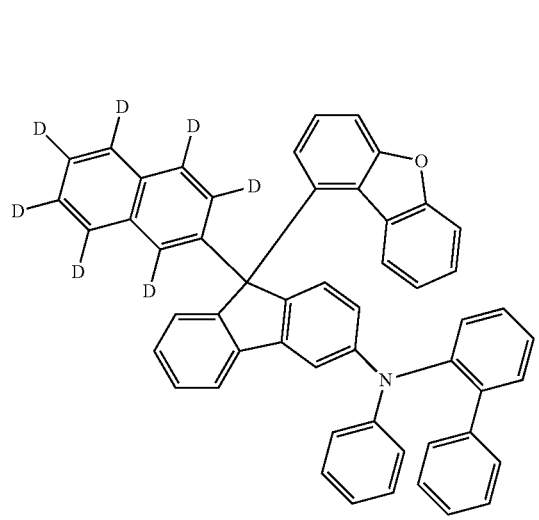
452
-continued
90
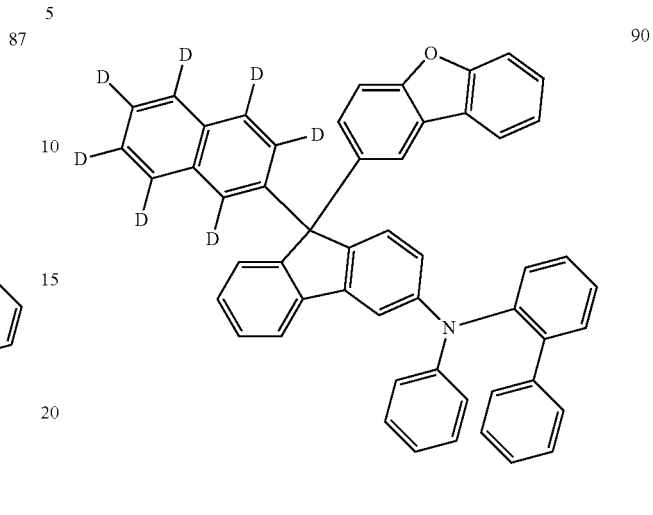
91
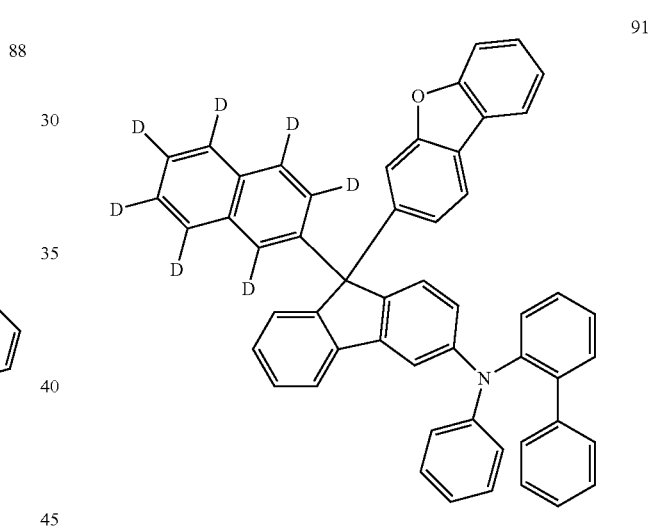
92
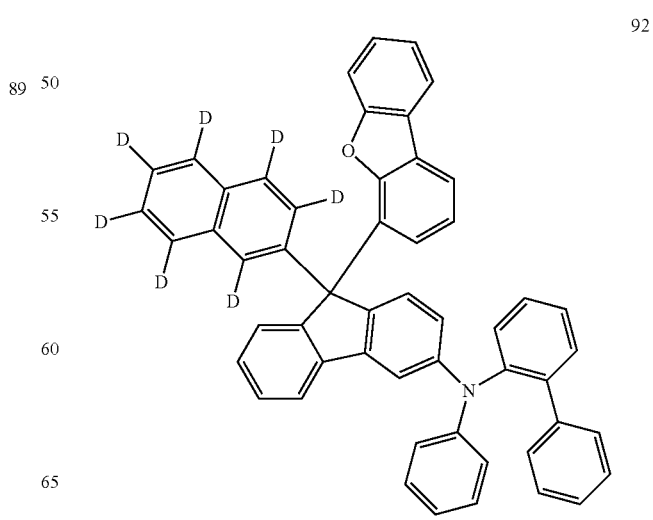

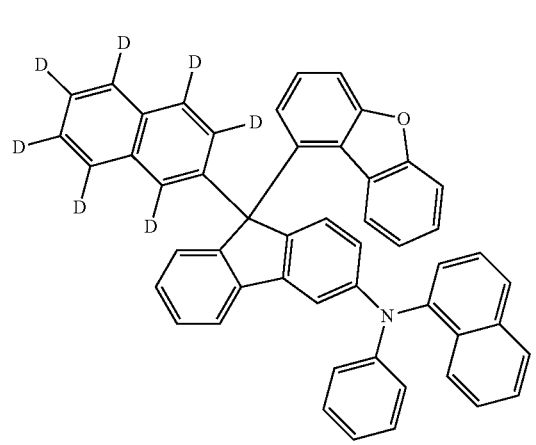
93
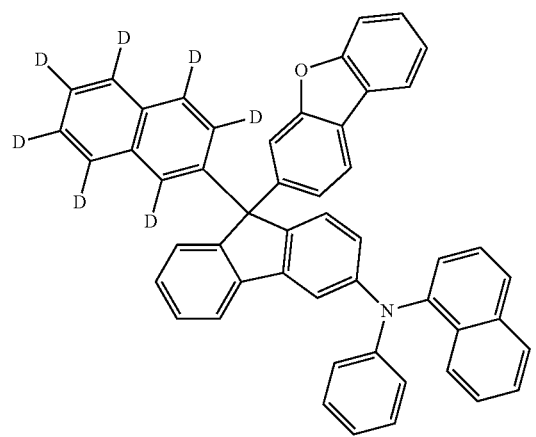
94
95
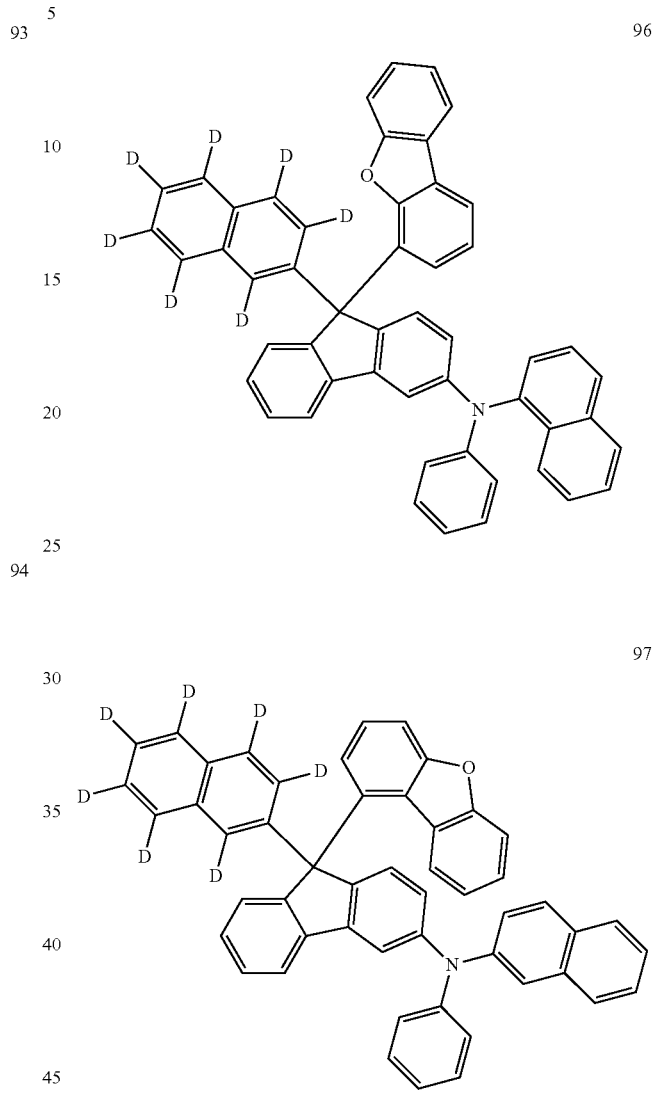
96
97
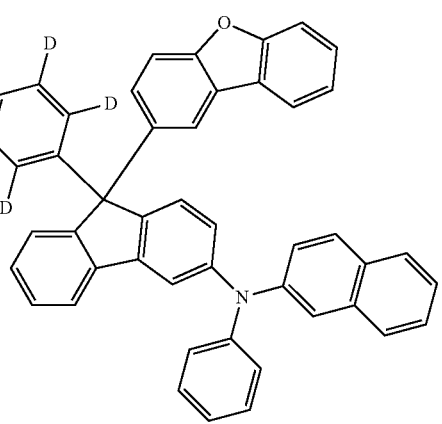
98

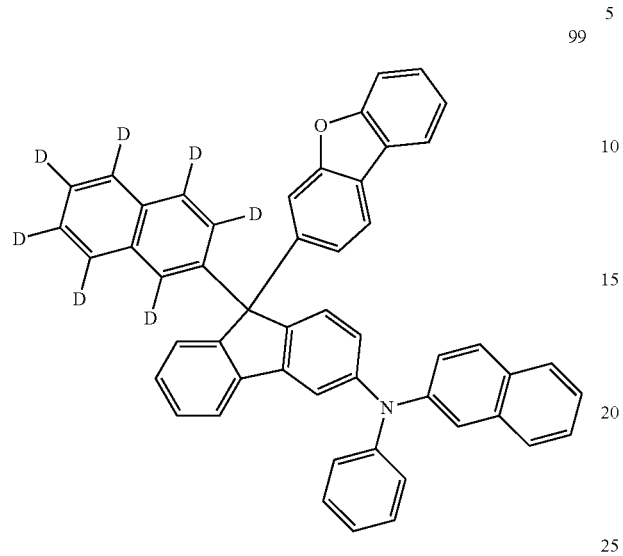
99
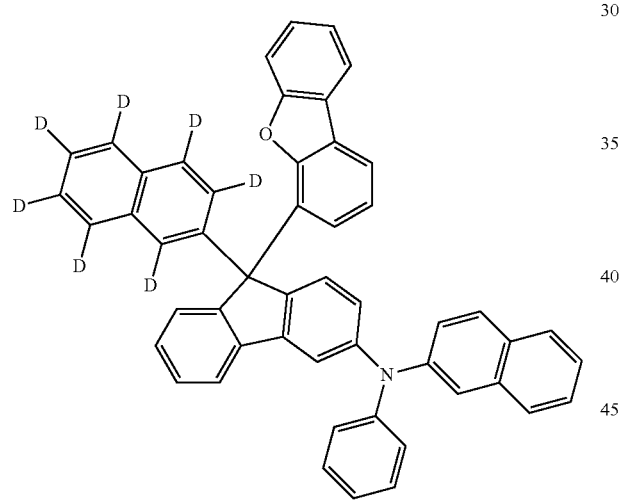
100
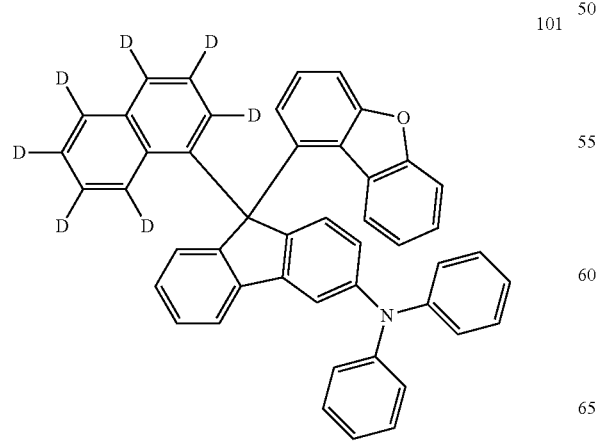
101
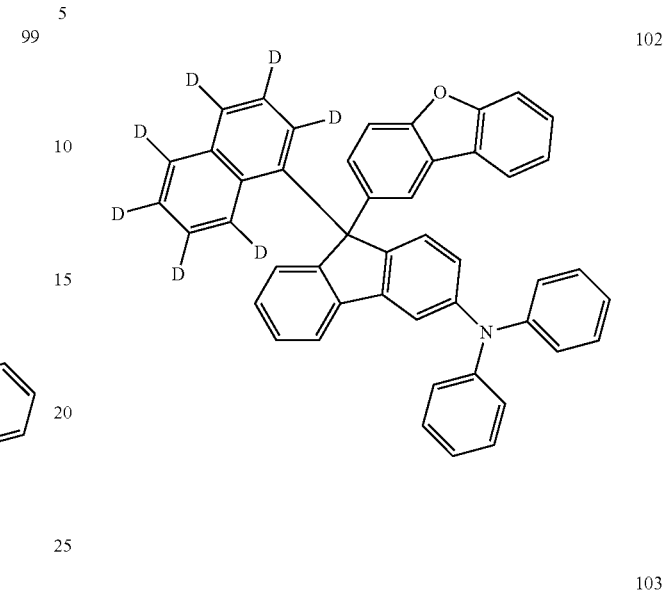
102
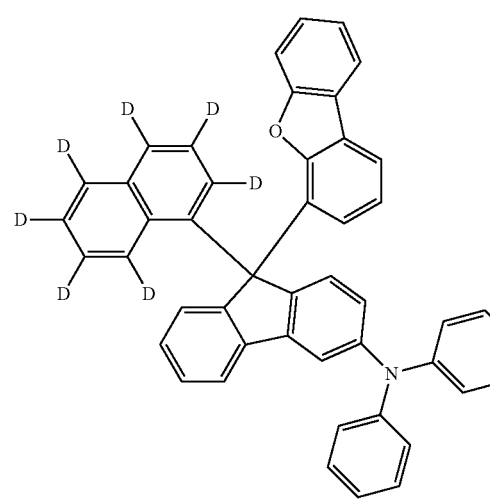
103
104

105 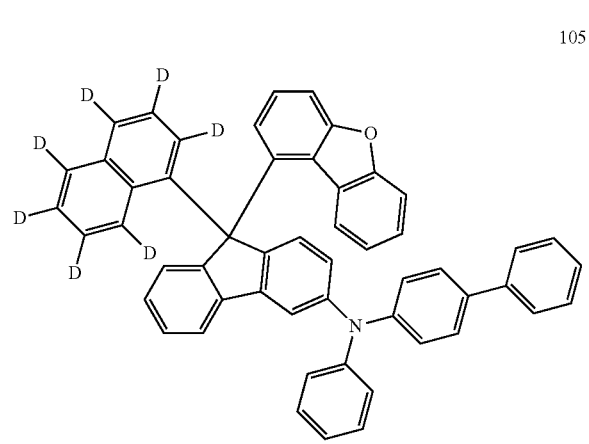
106 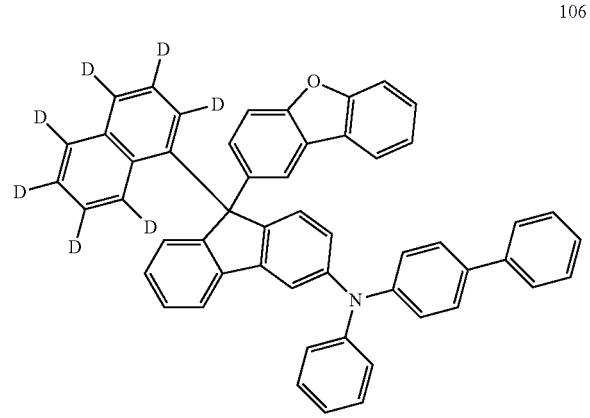
107 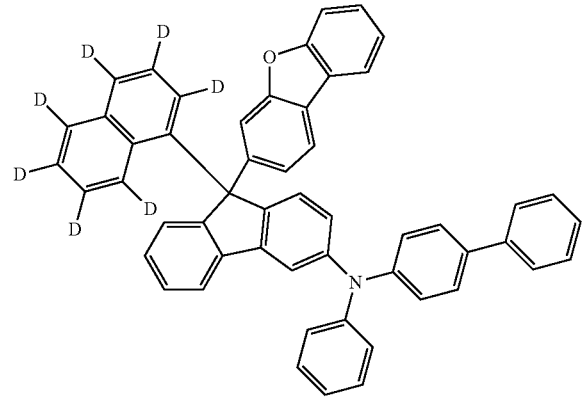
108 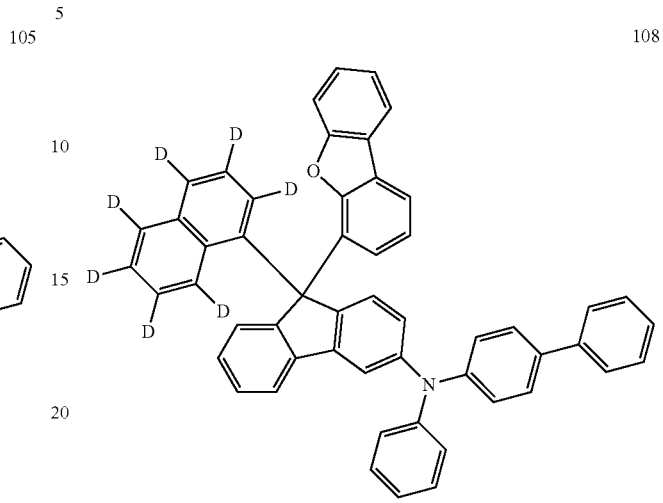
109 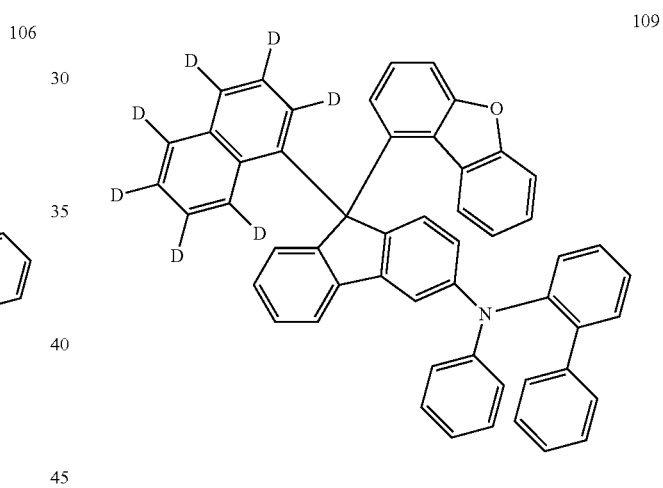
110 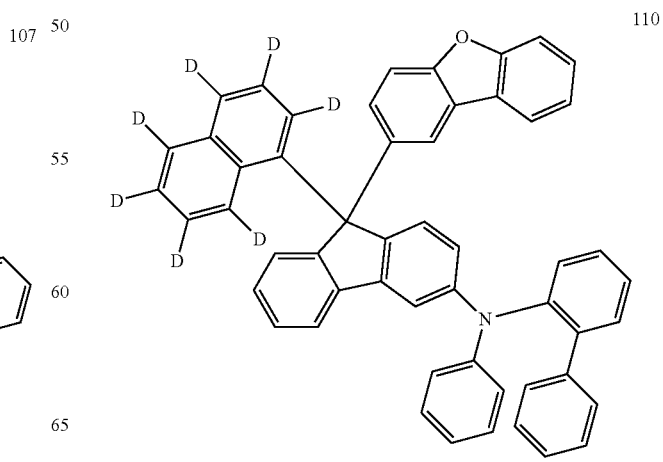

111 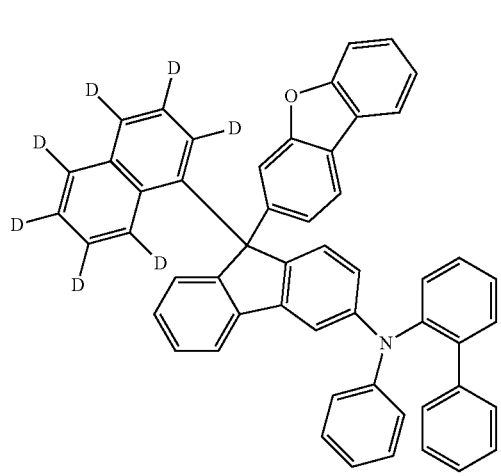
112 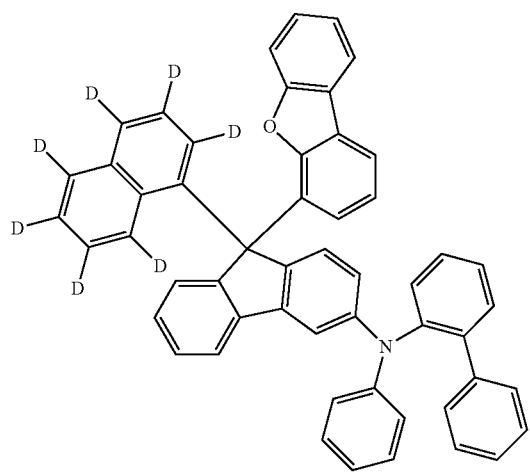
113 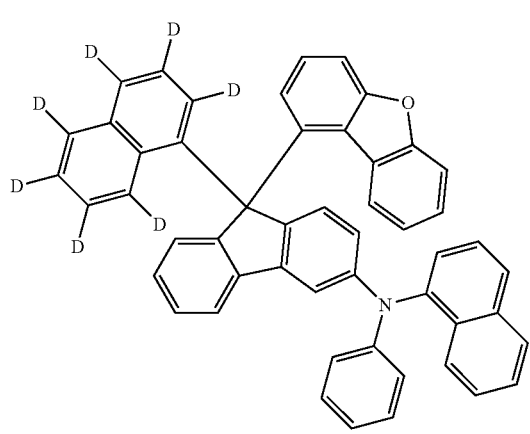
114 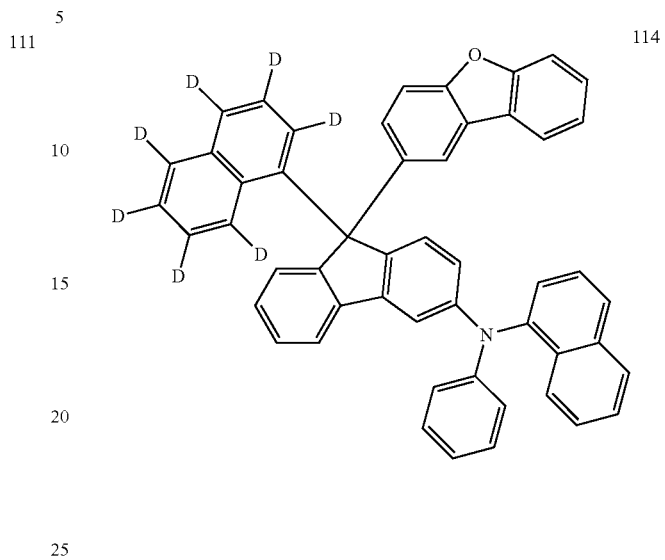
115 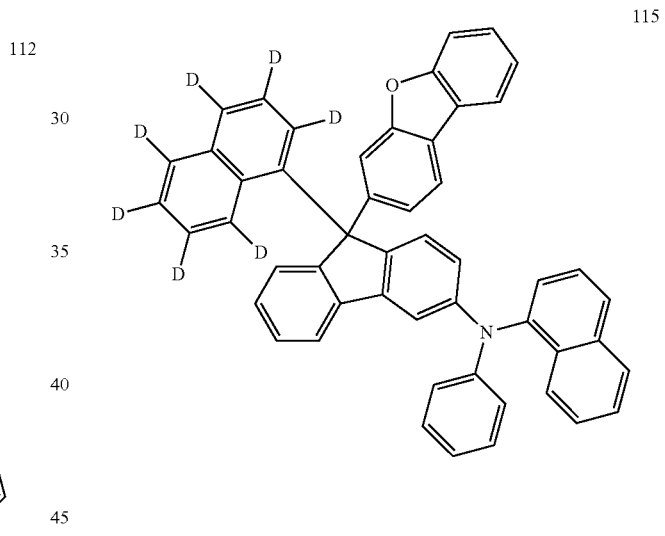
116 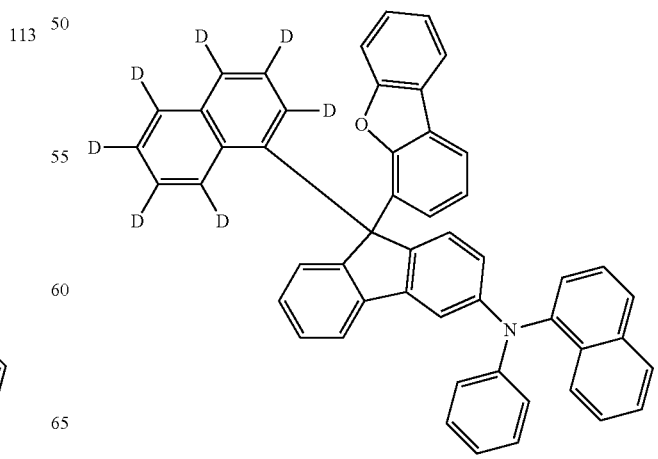

117
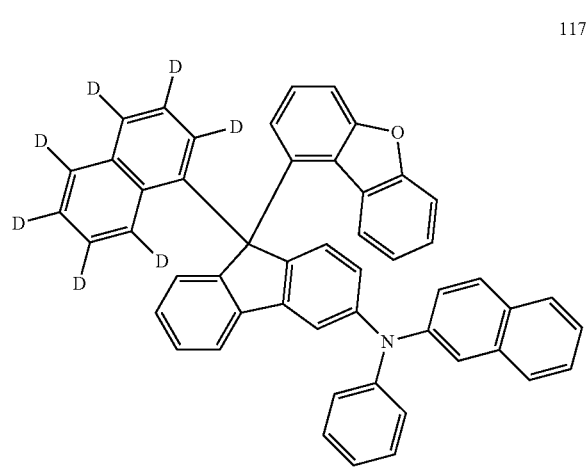
118
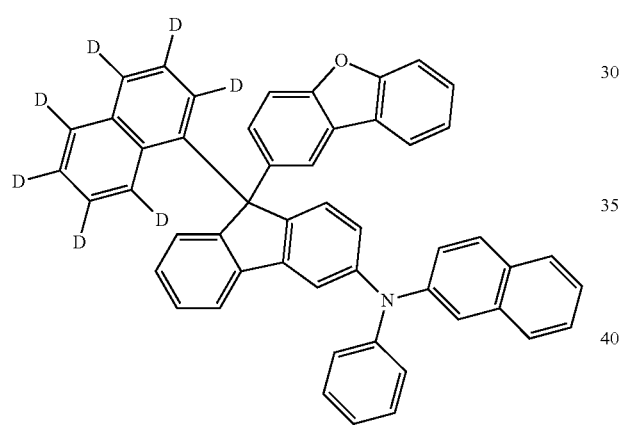
119
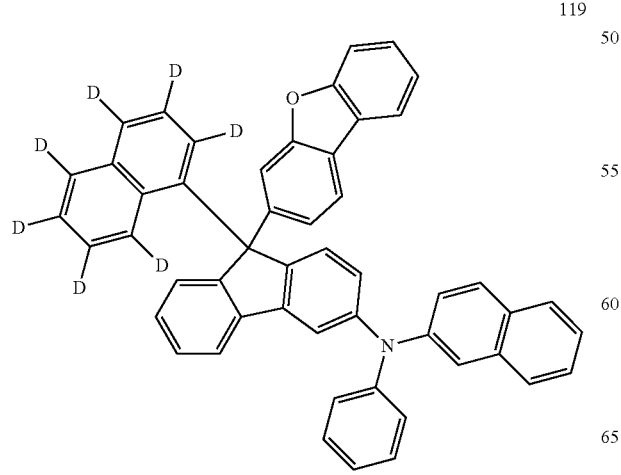
120
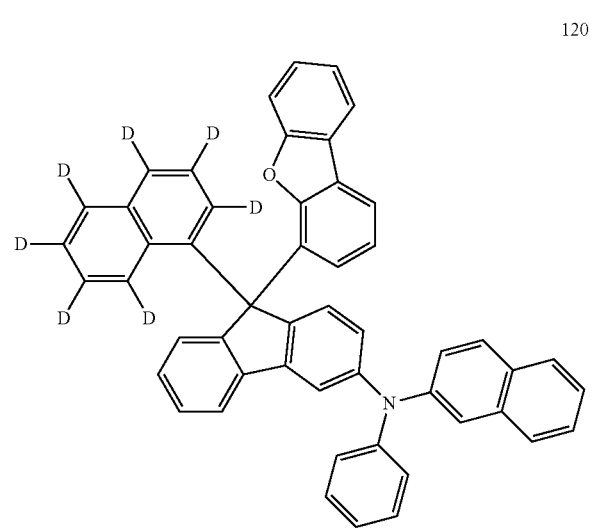
121
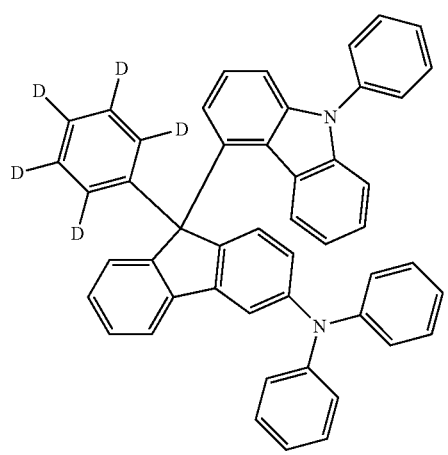
122
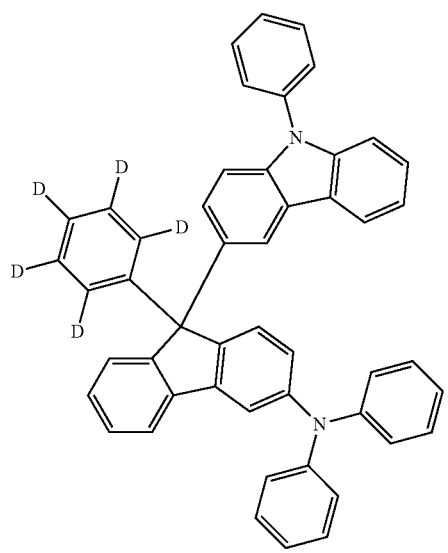

463
-continued
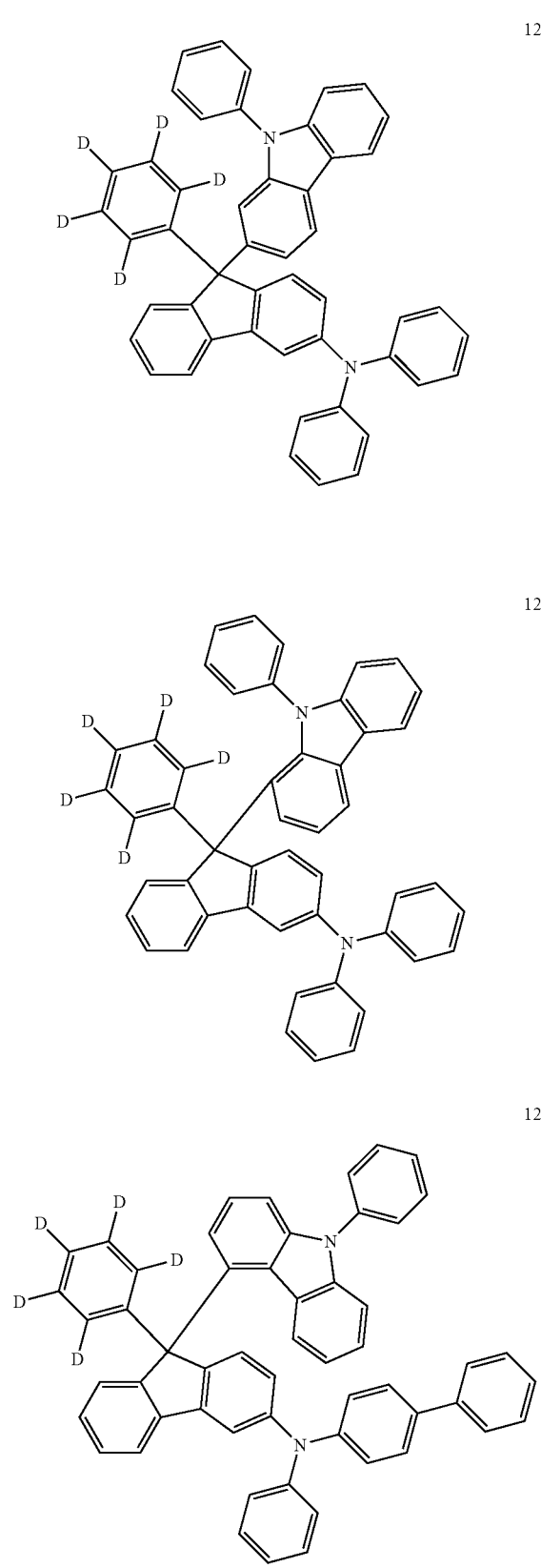
464
-continued
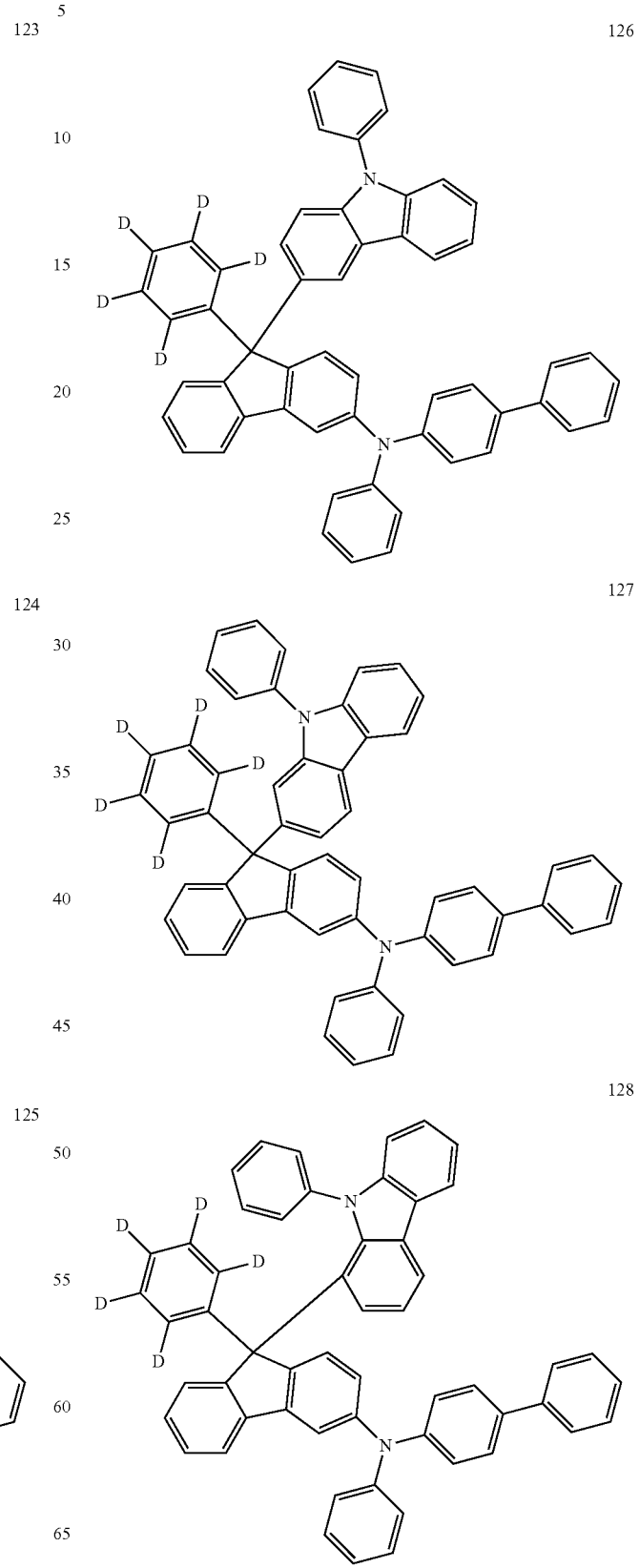

129
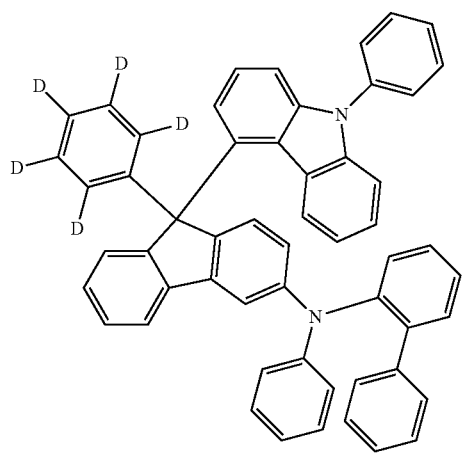
132
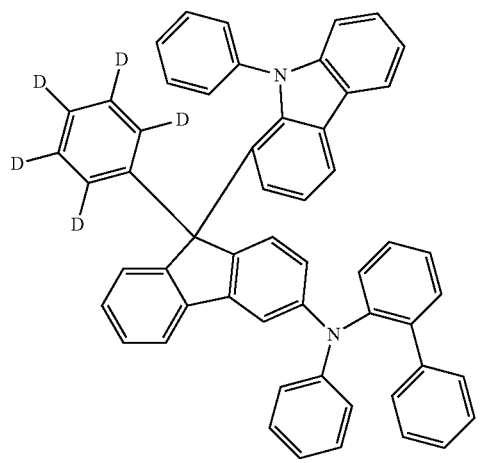
130
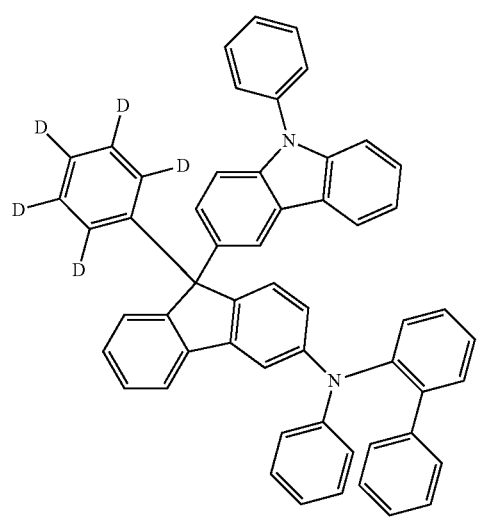
133
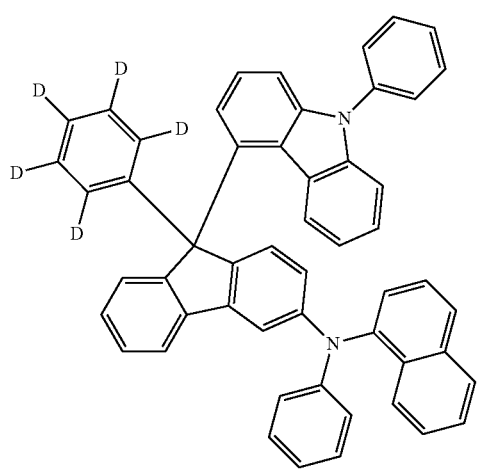
131
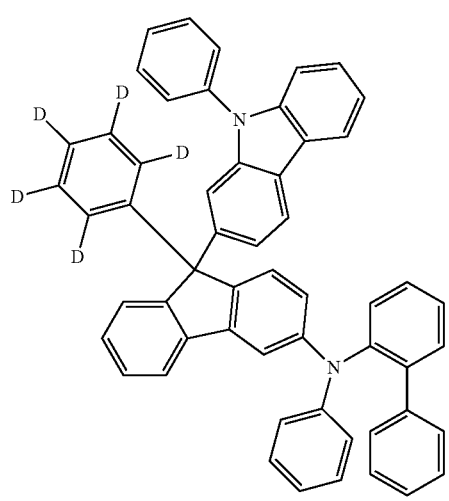
134
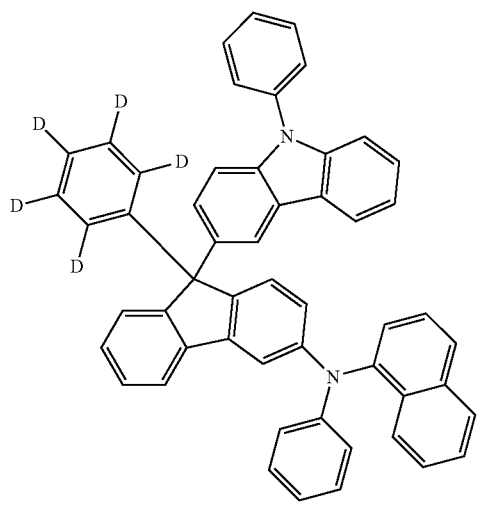

467
-continued
135
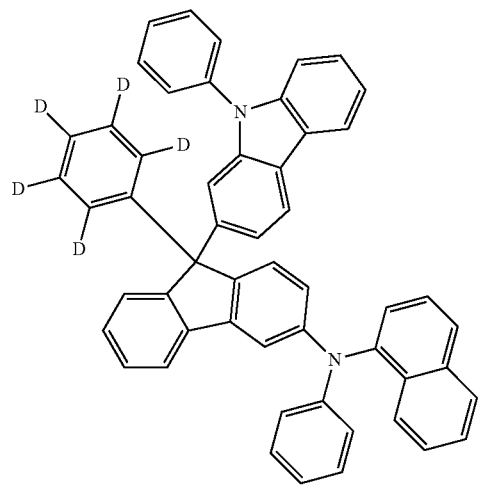
136
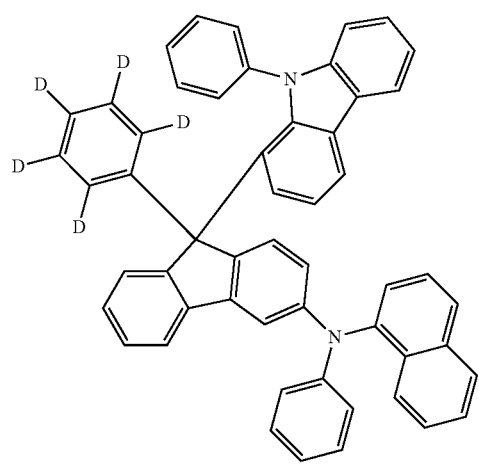
137
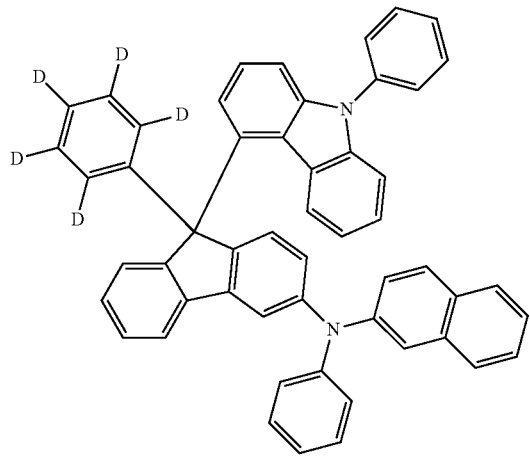
468
-continued
138
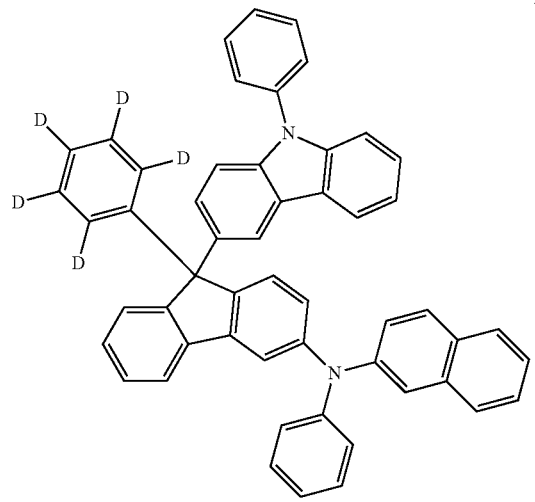
139
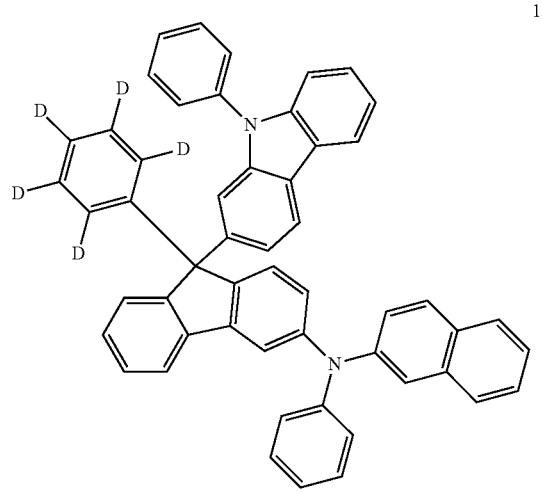
140
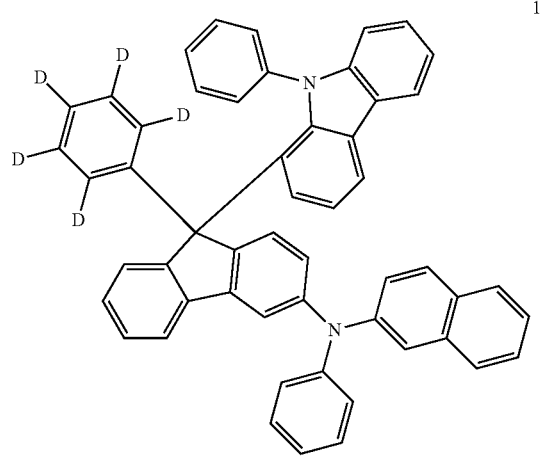

141
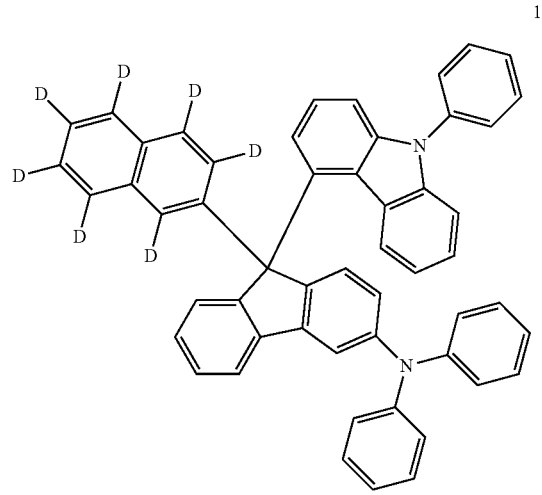
142
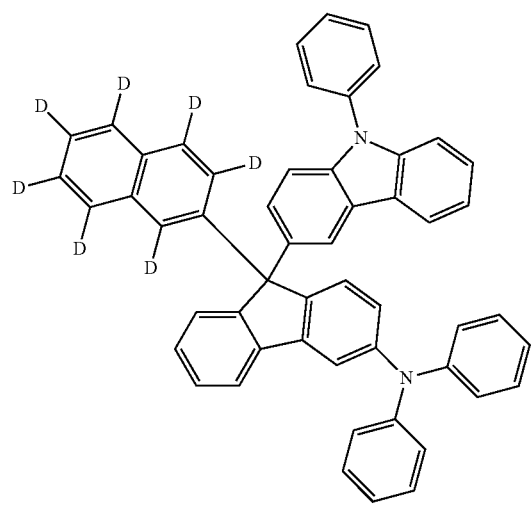
143
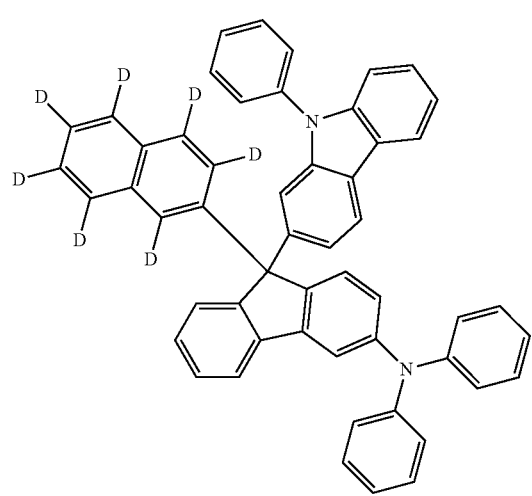
144
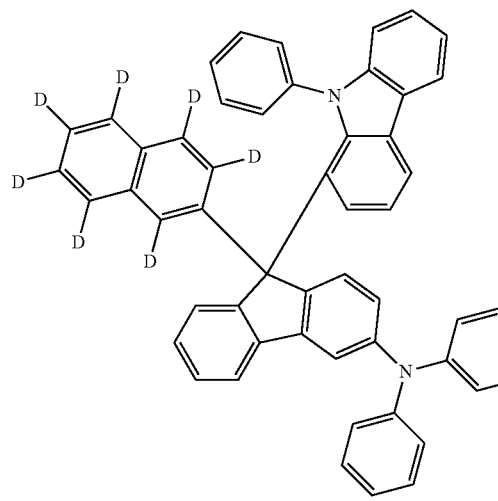
145
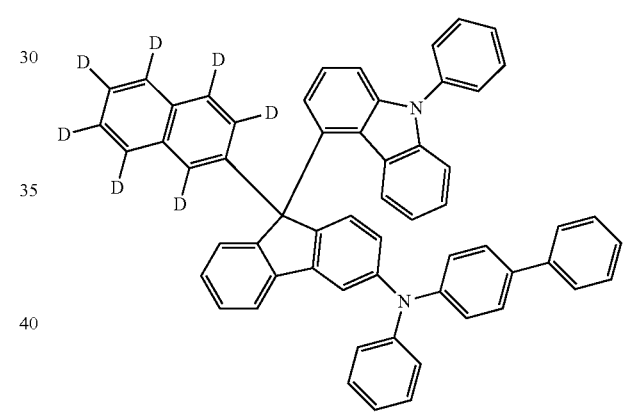
146
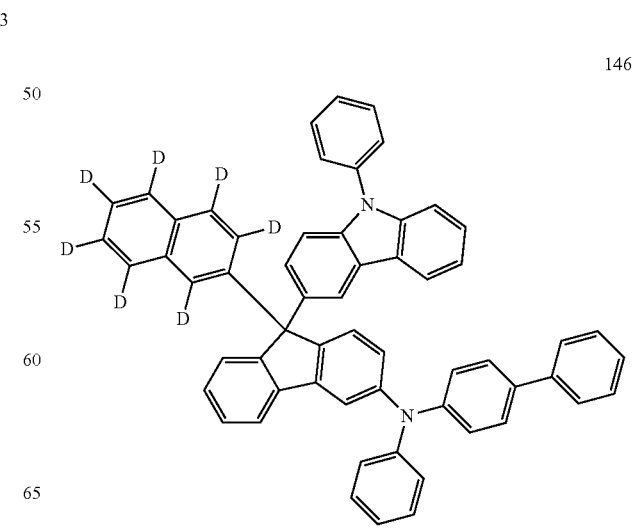

147
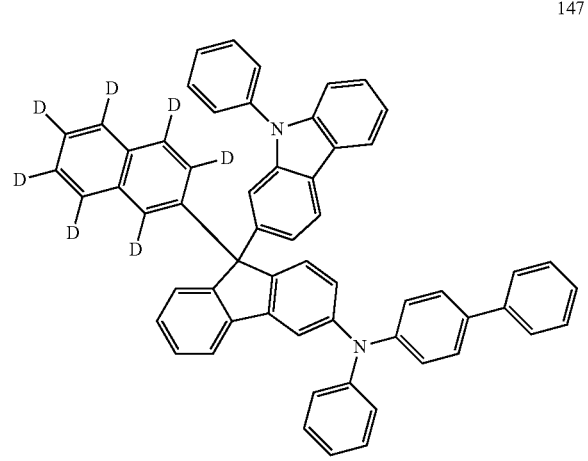
148
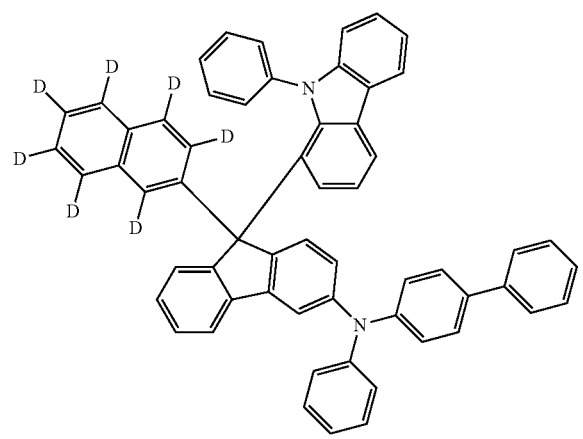
149
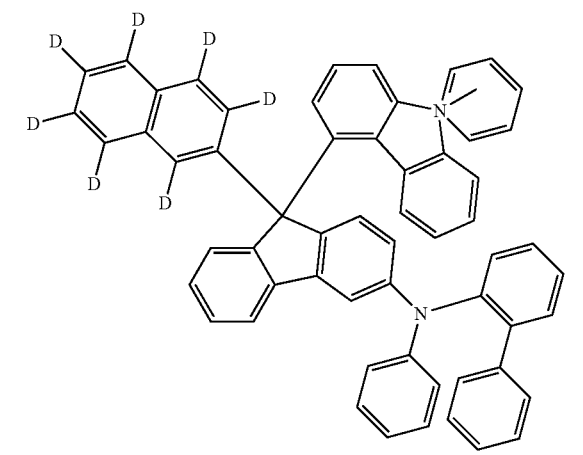
150
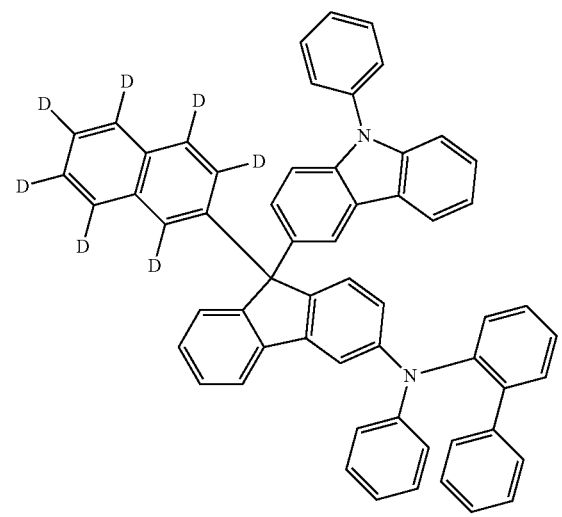
151
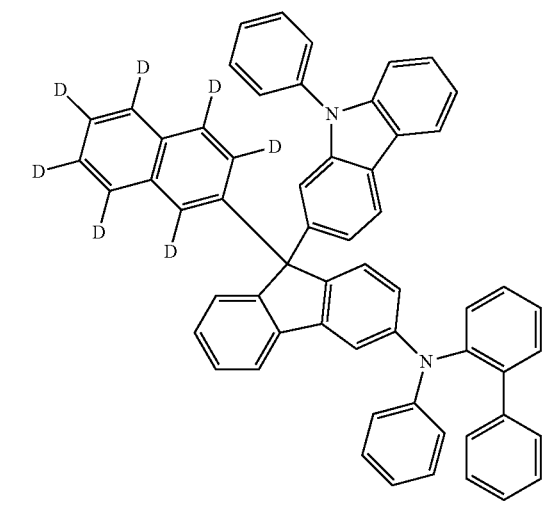
152
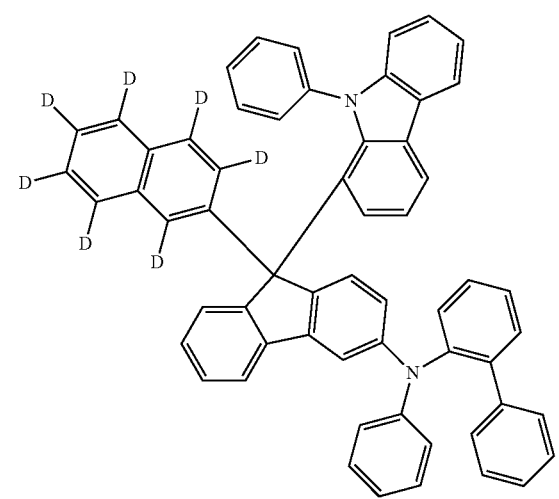

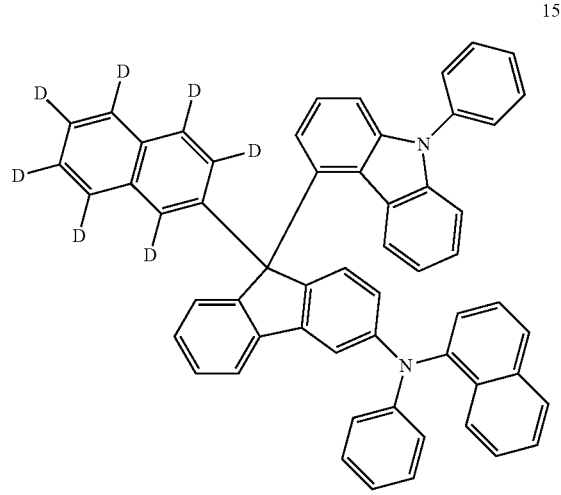

159
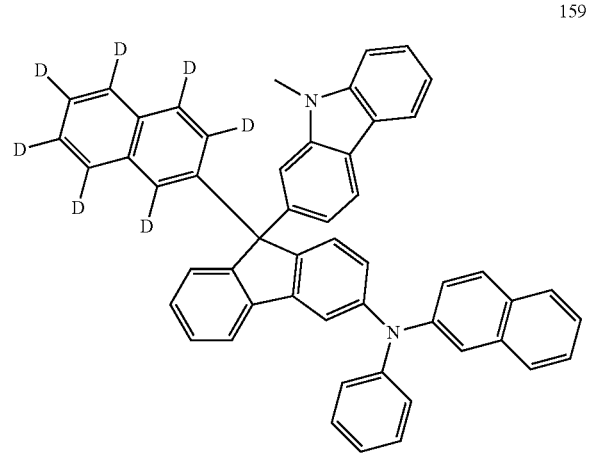
160
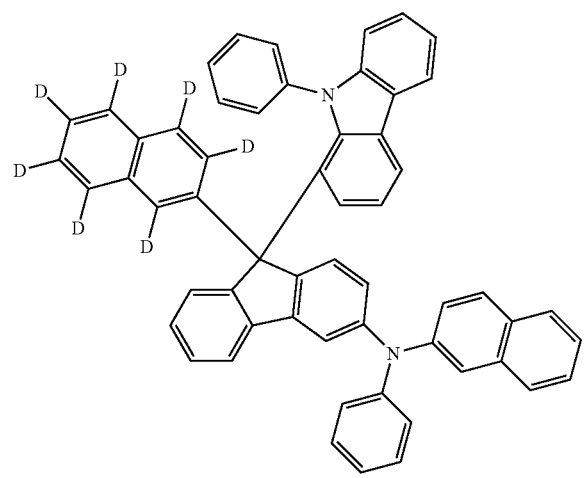
161
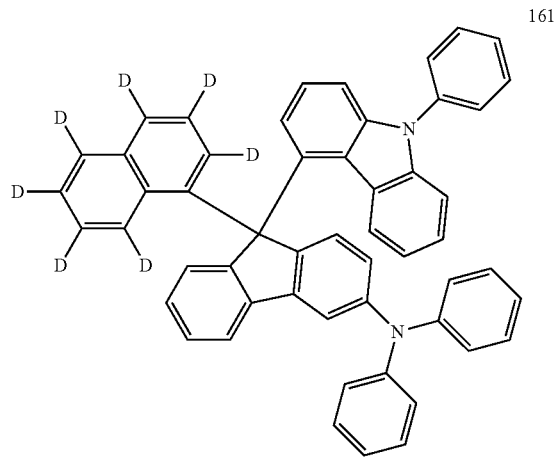
162
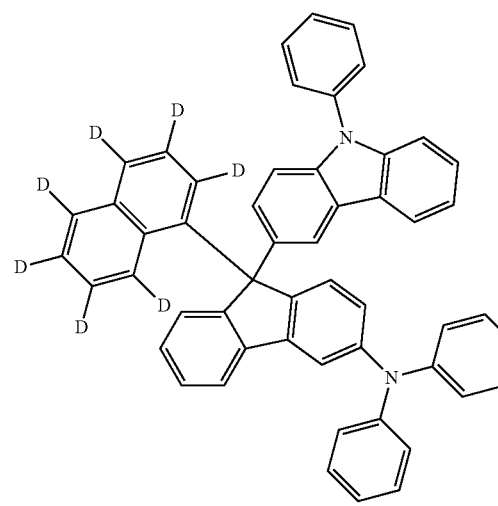
163
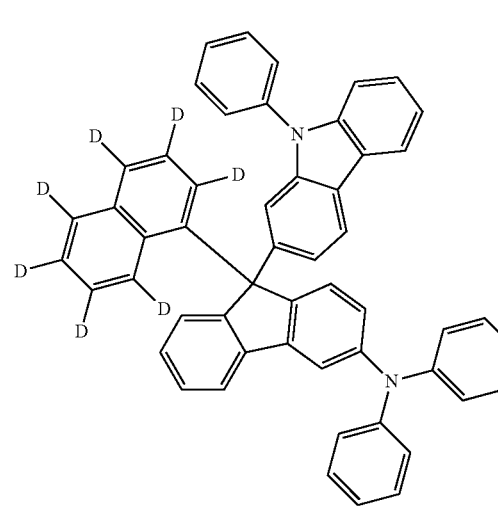
164
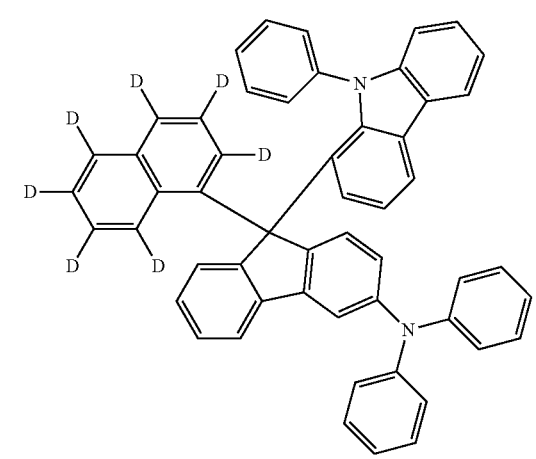

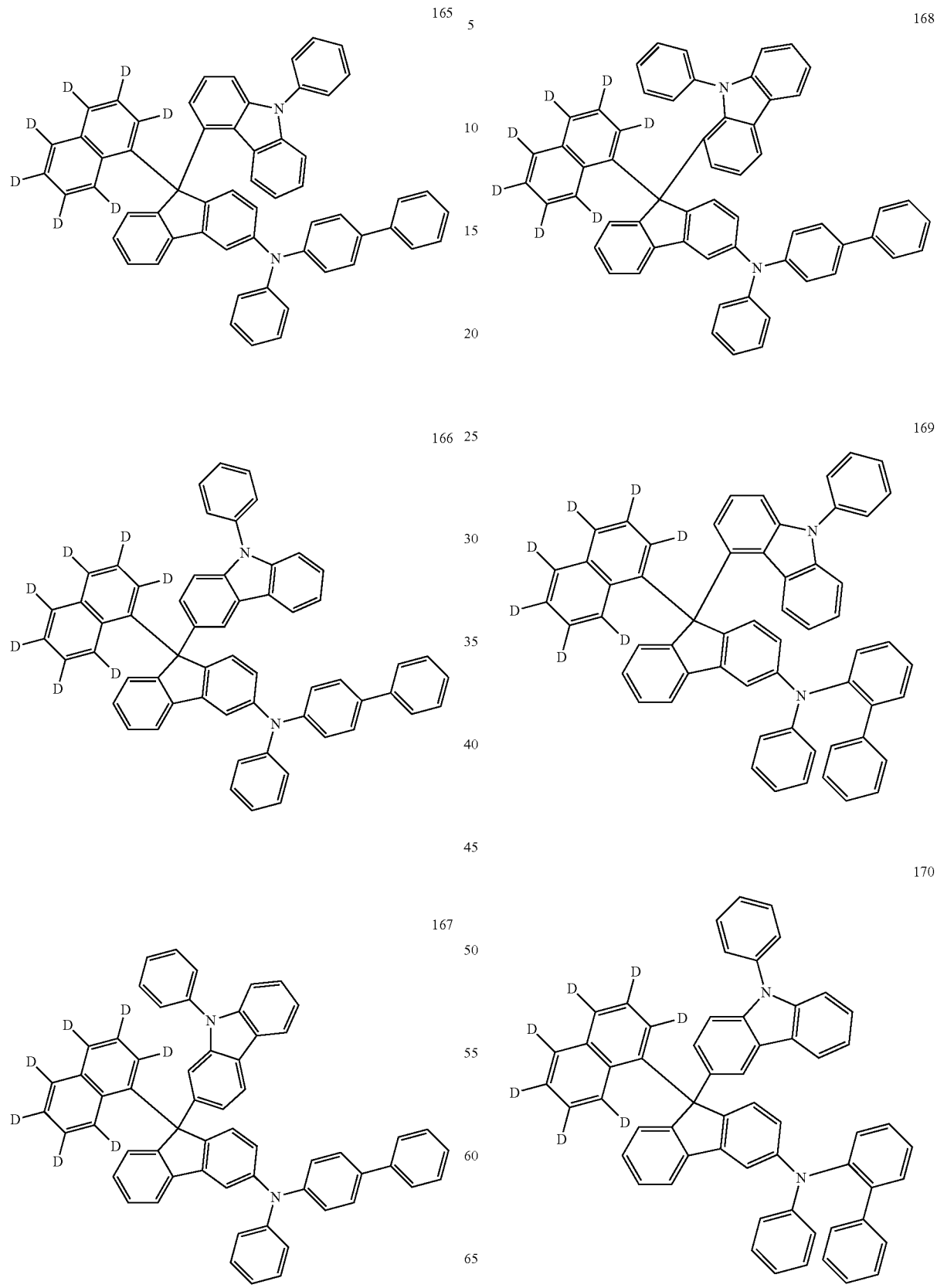

-continued
171
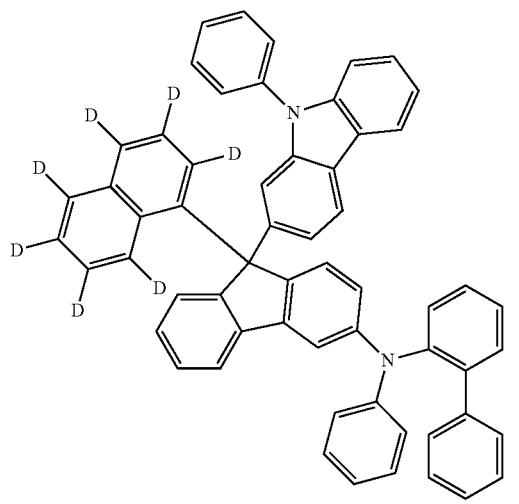
172
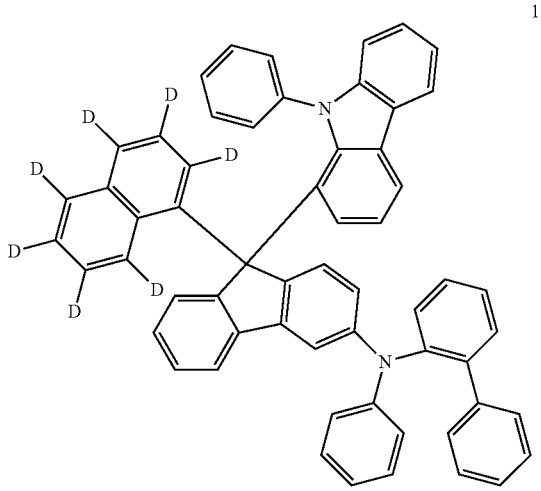
173
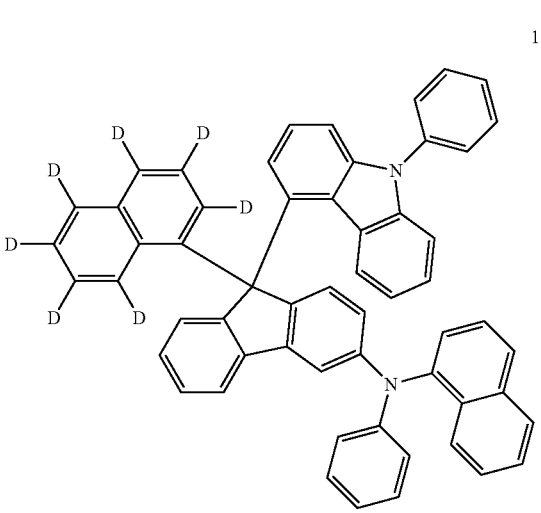
-continued
174
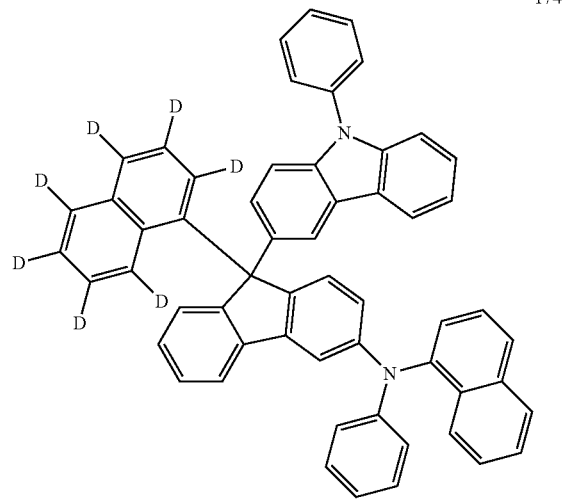
177
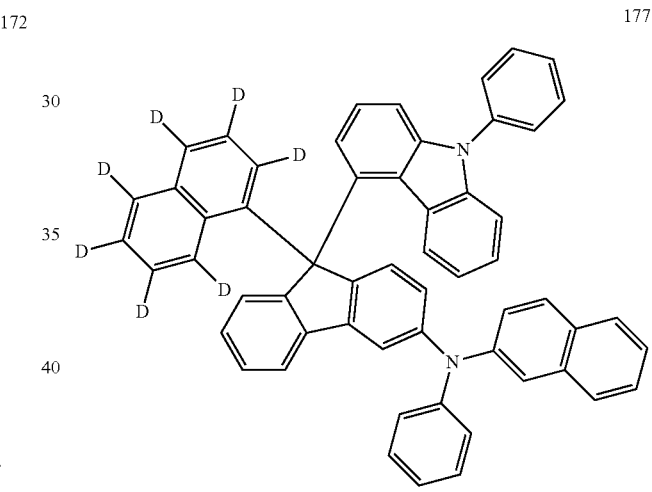
178
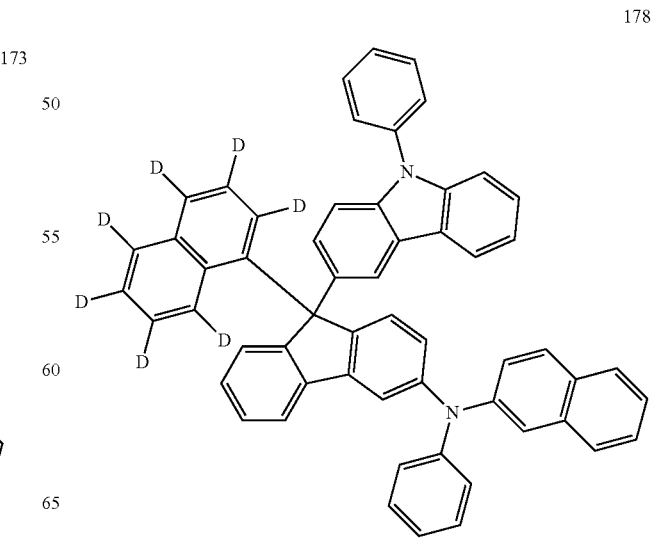

481
-continued
179
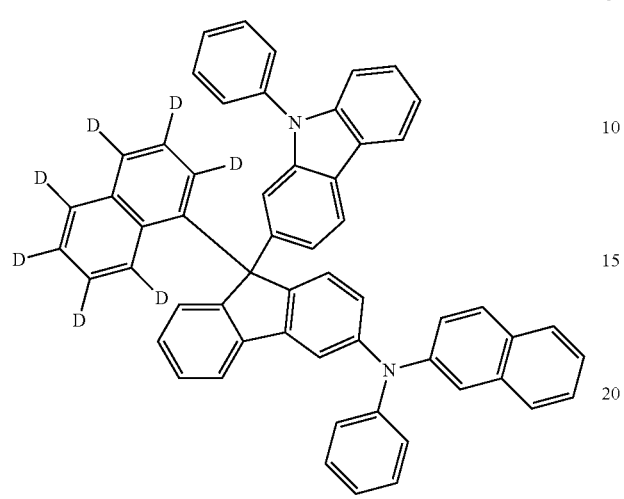
180
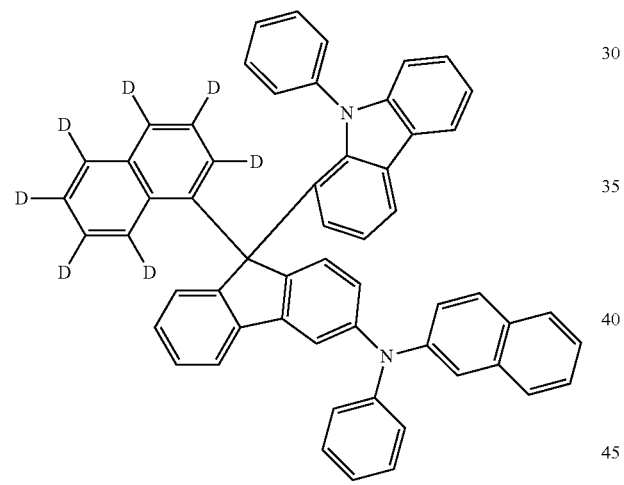
181
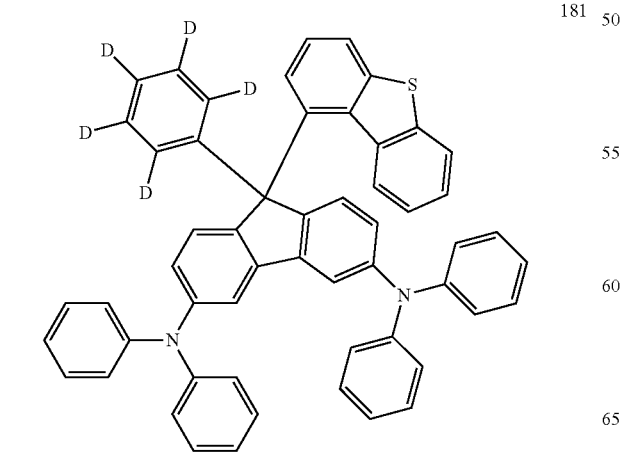
482
-continued
182
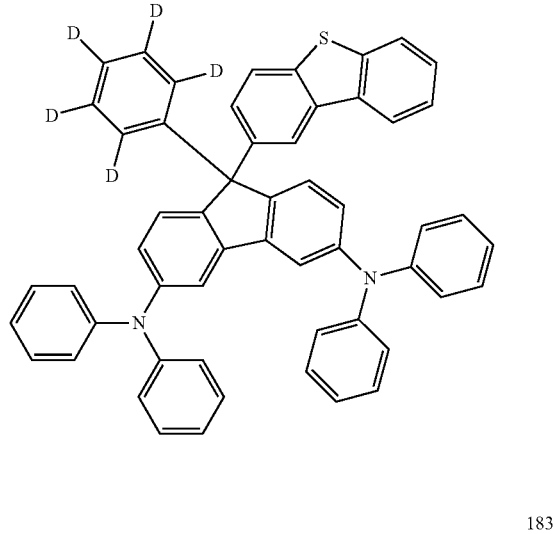
183
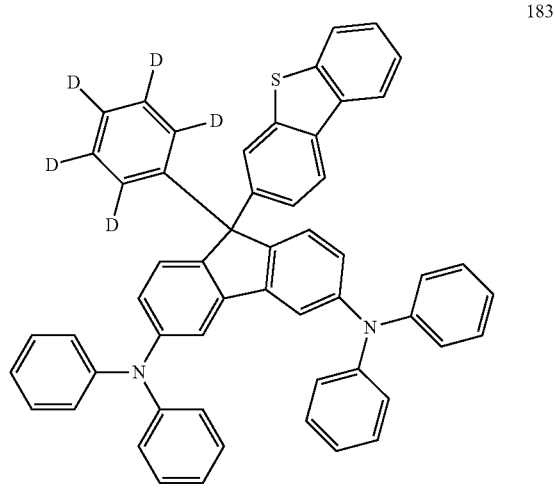
184
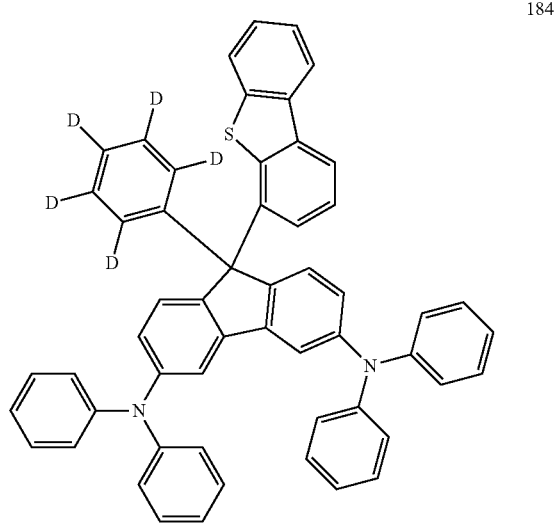

185
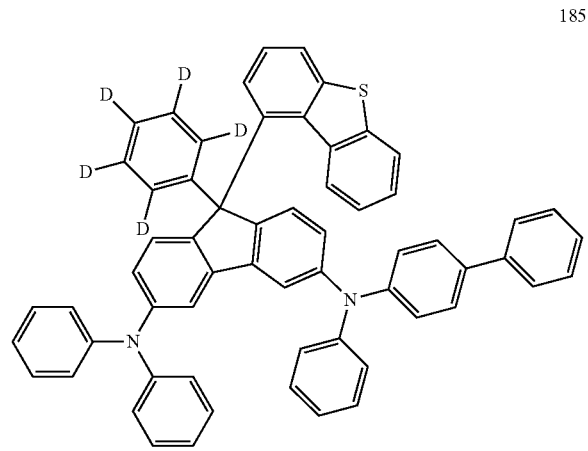
186
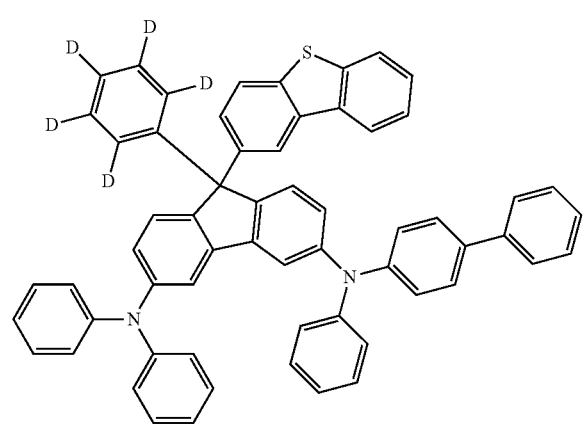
187
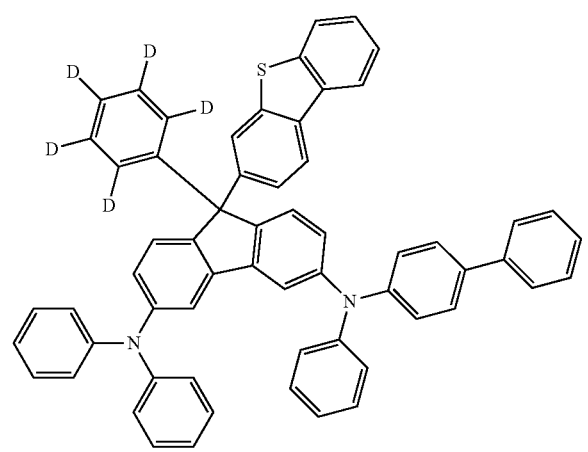
188
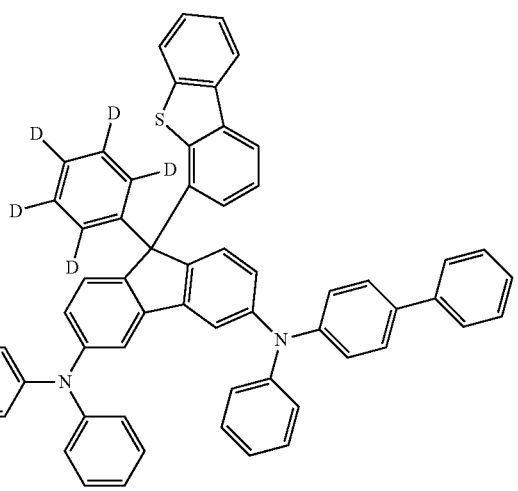
189
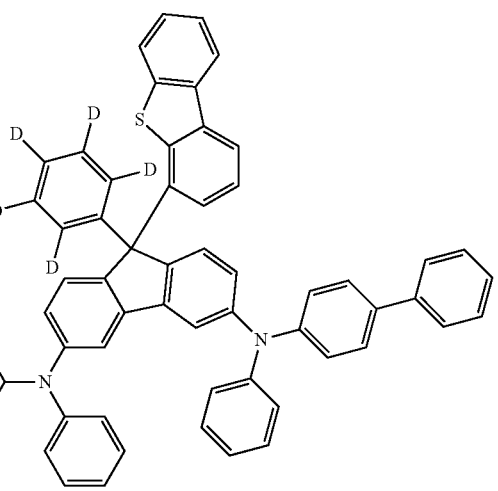
190
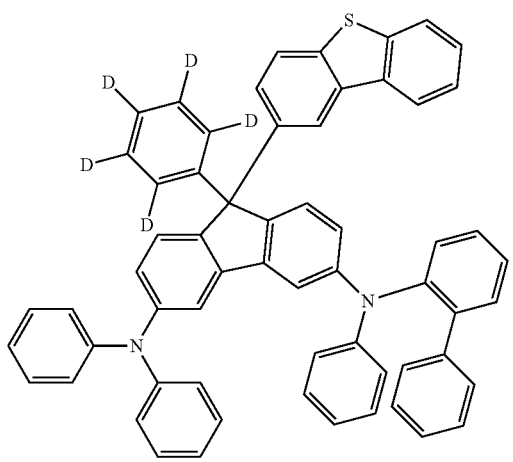

485
-continued
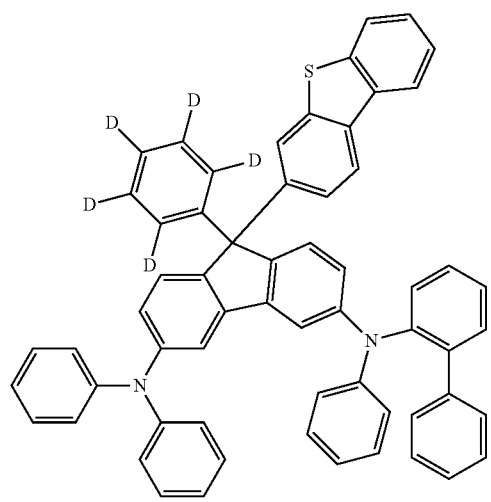
191
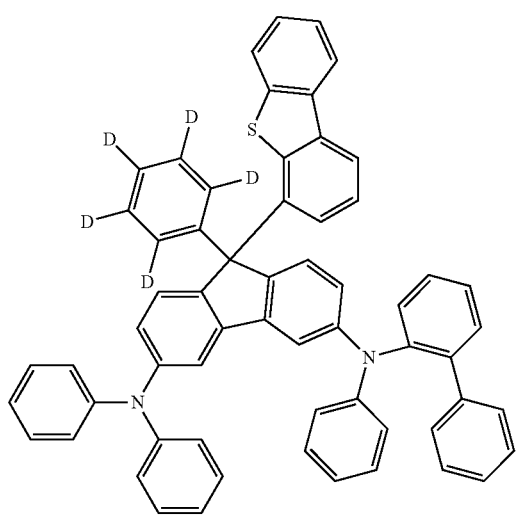
192
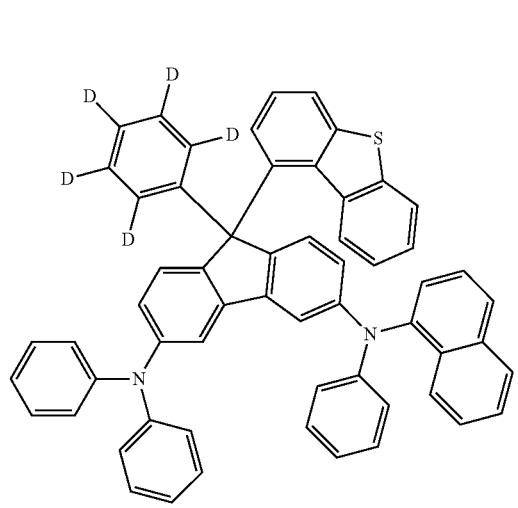
193
486
-continued
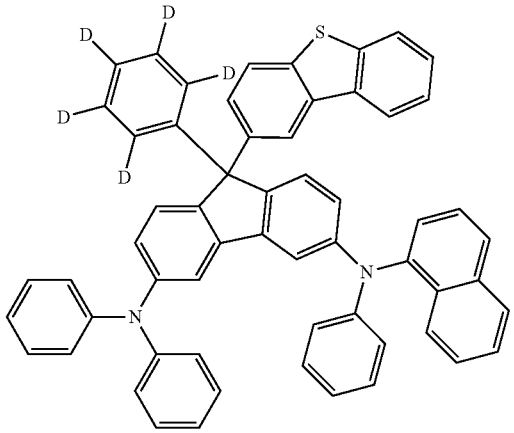
194
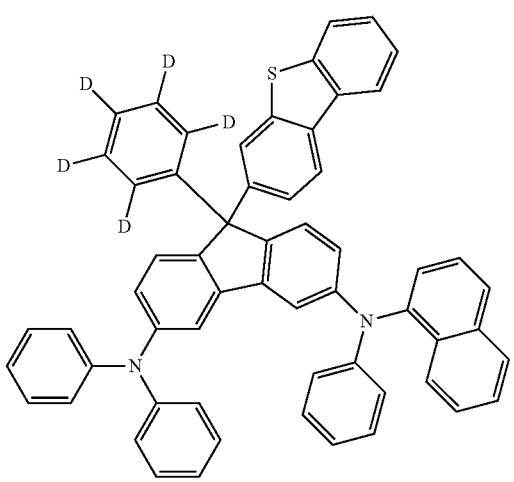
195
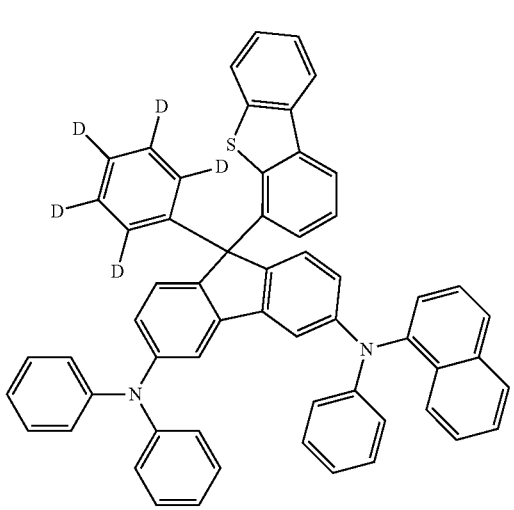
196

487
-continued
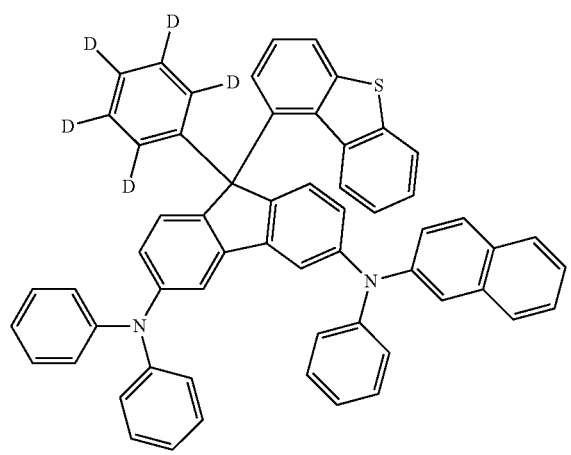
197
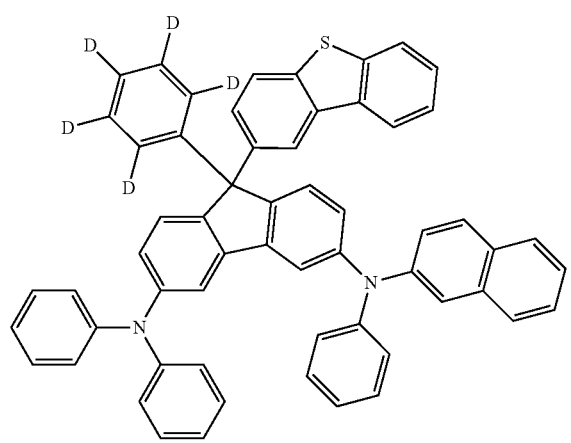
198
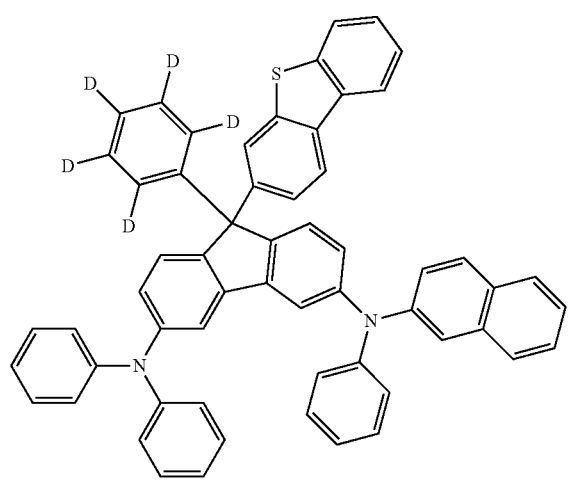
199
488
-continued
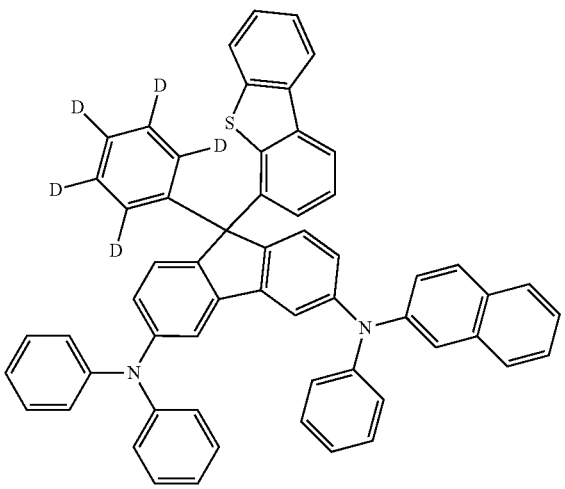
200
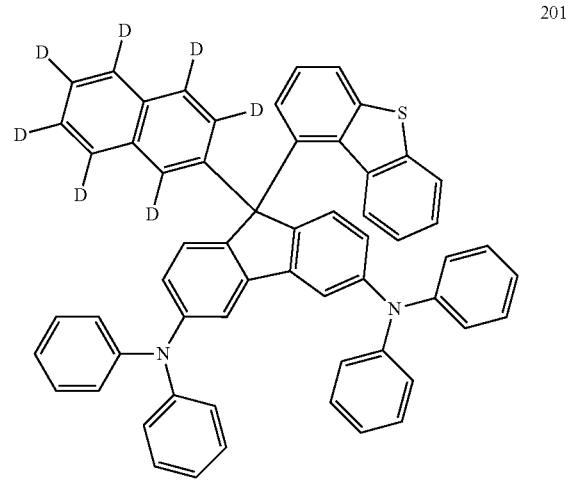
201
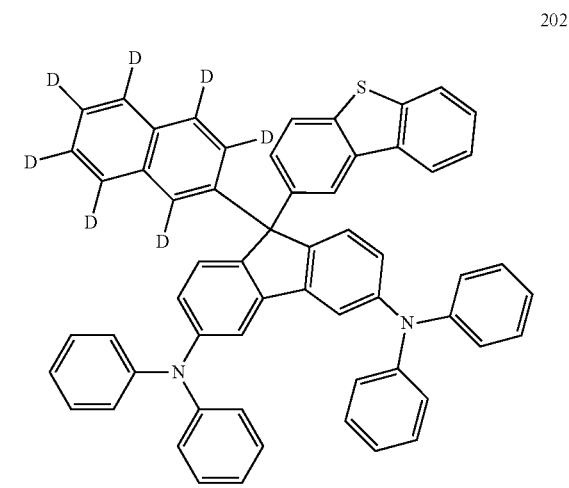
202

489
-continued
203
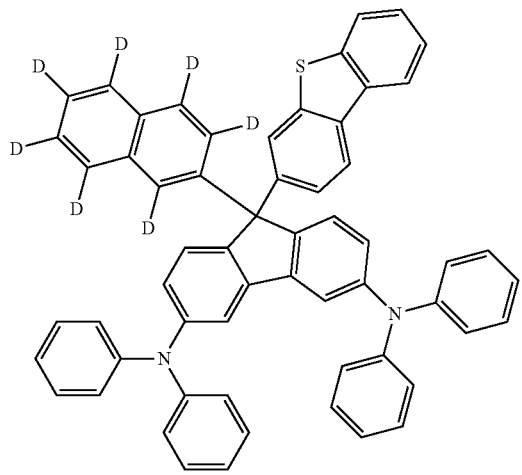
204
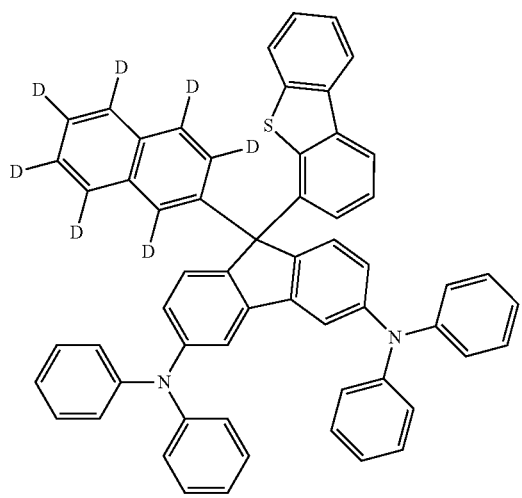
205
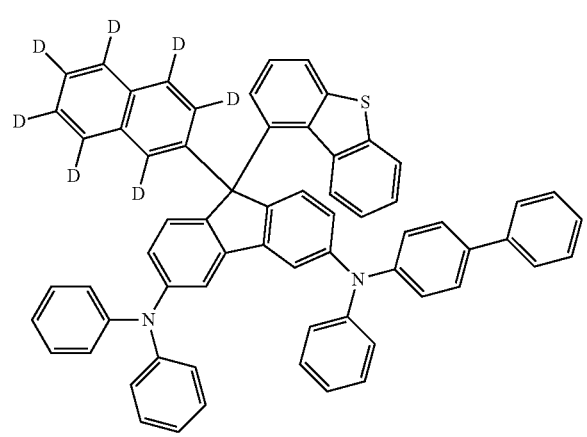
490
-continued
206
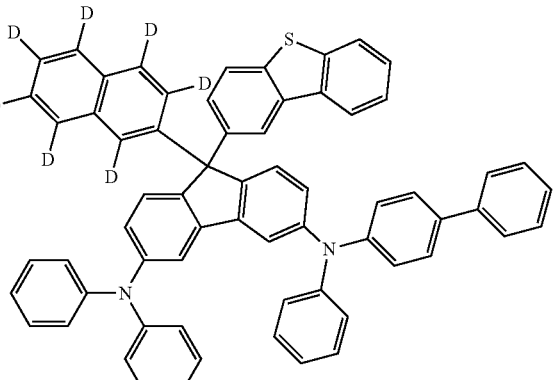
207
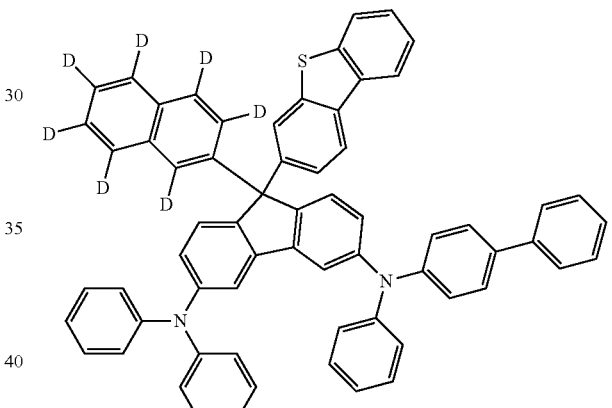
208
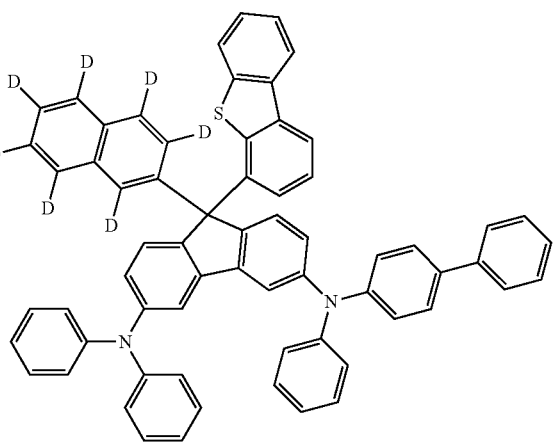

209
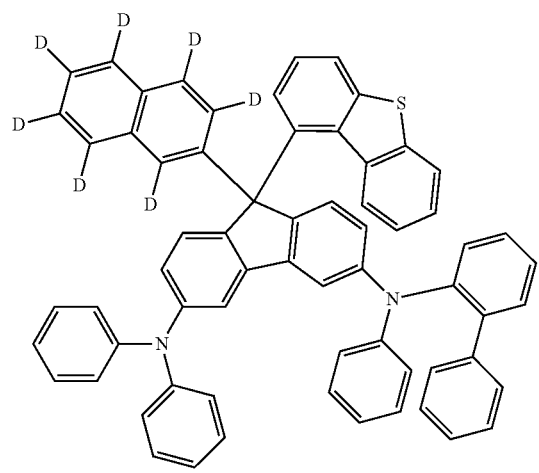
210
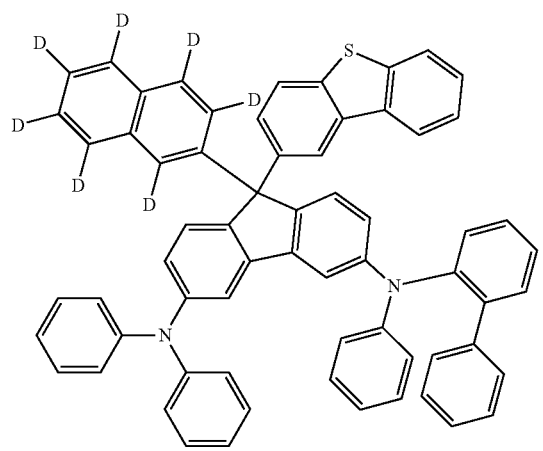
211
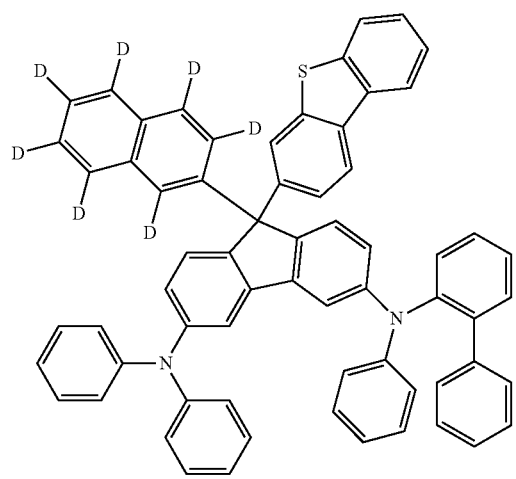
212
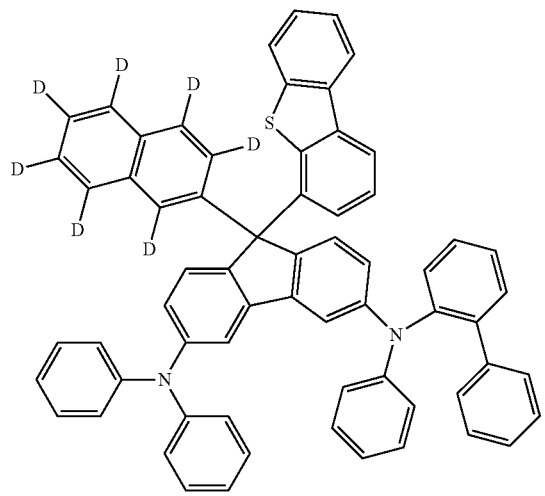
213
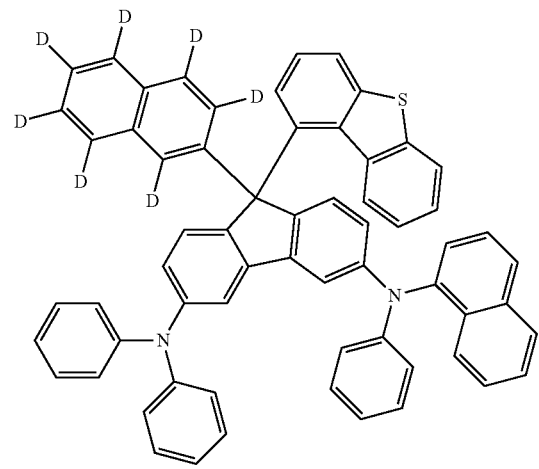
214
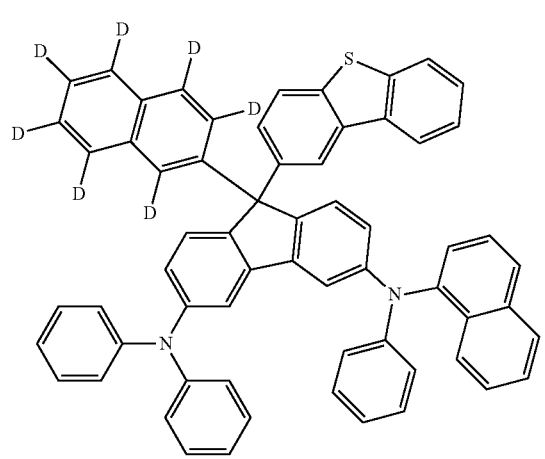

493
-continued
215
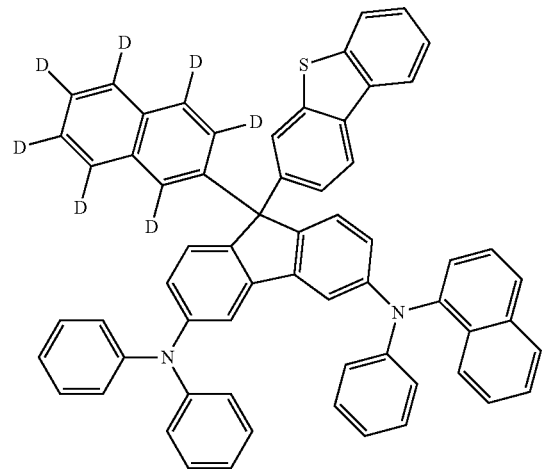
216
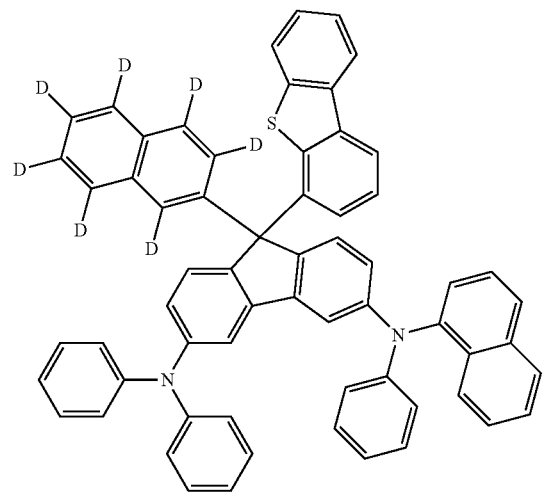
217
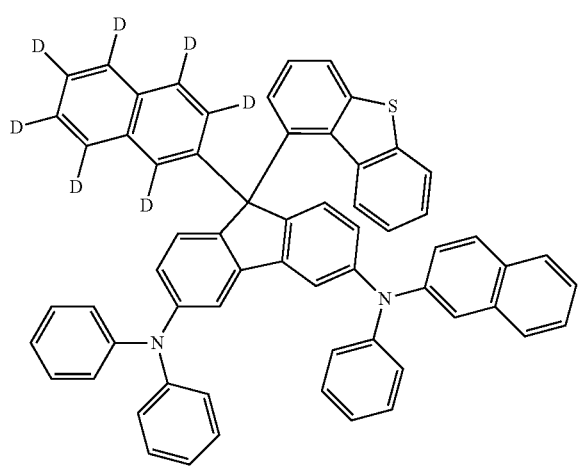
494
-continued
218
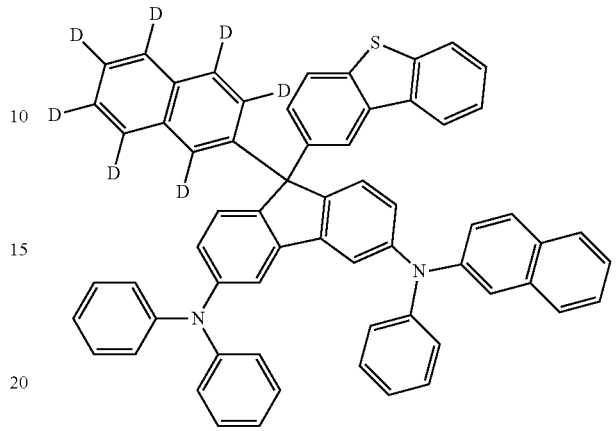
219
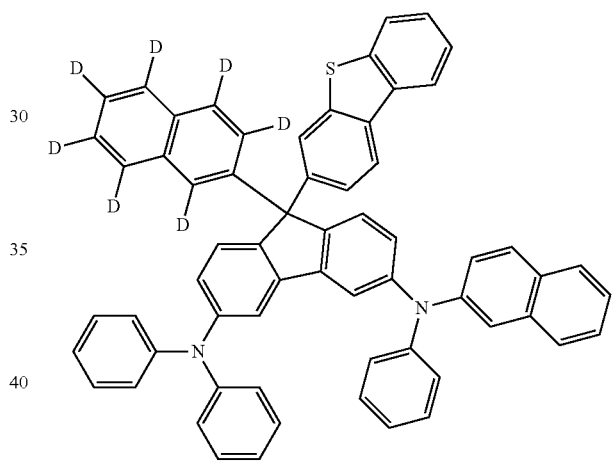
220
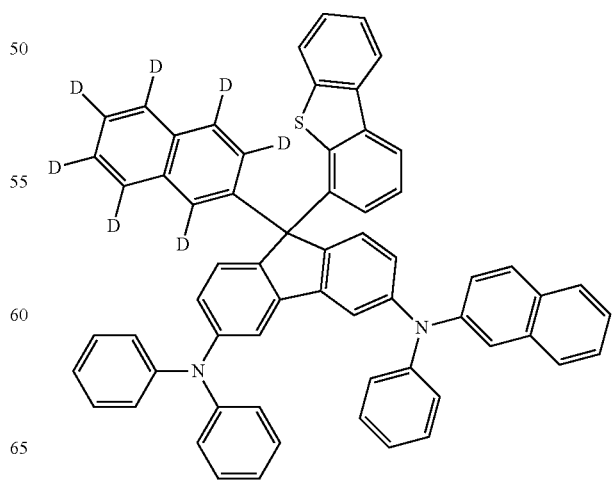

221
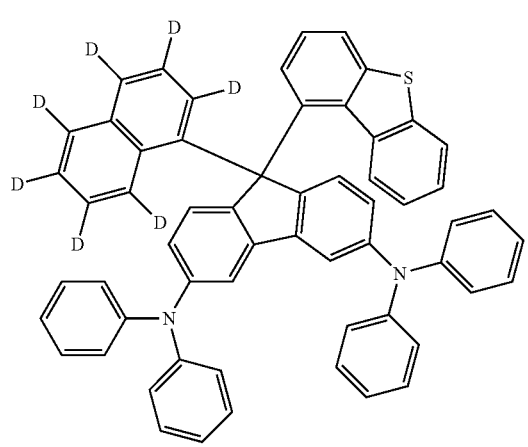
222
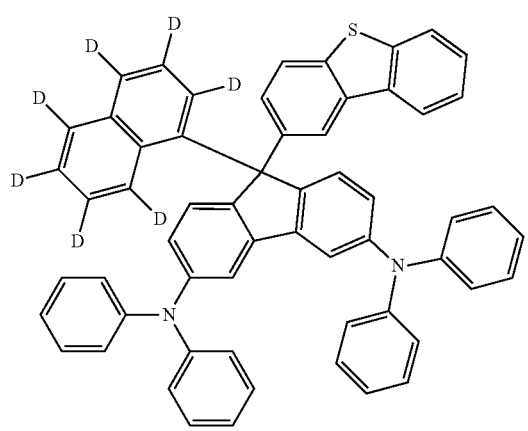
223
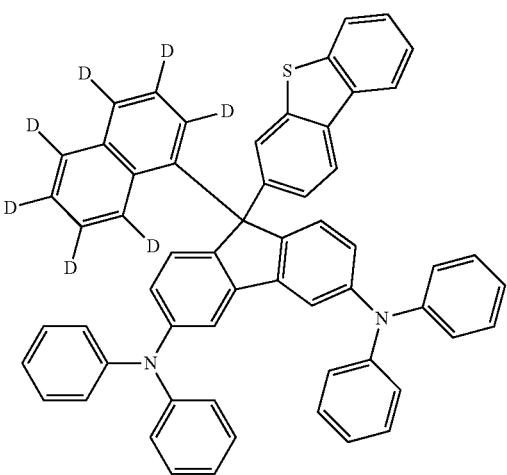
224
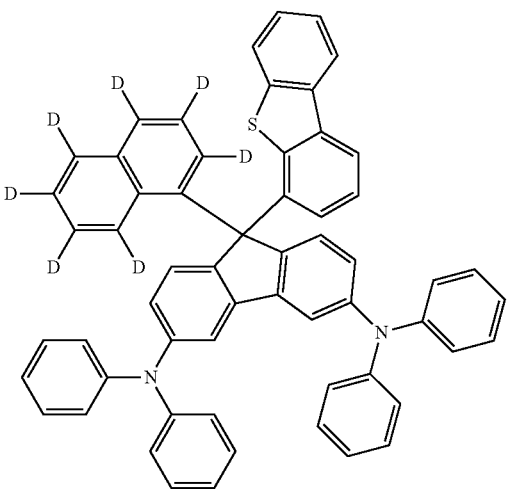
225
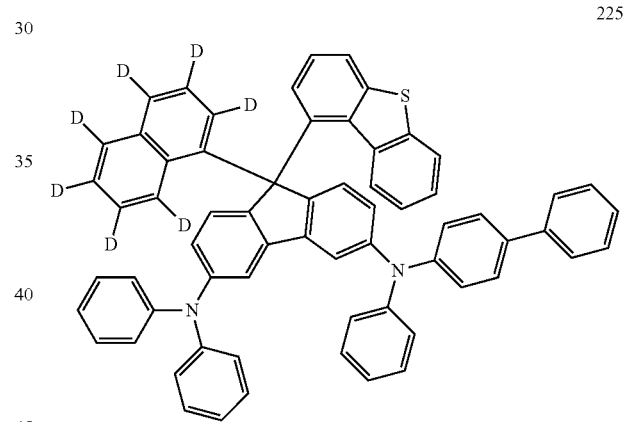
226
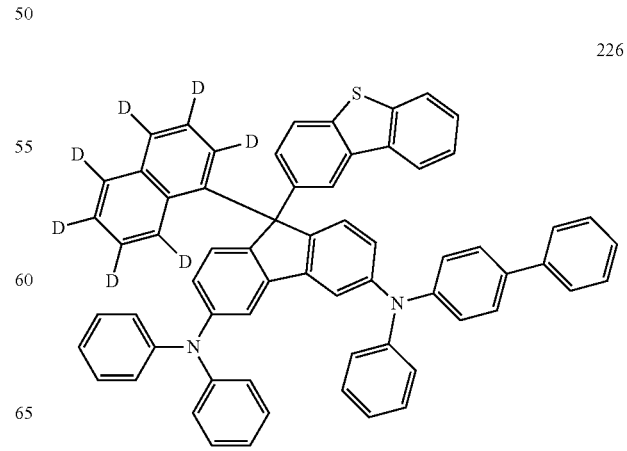

497
-continued
498
-continued
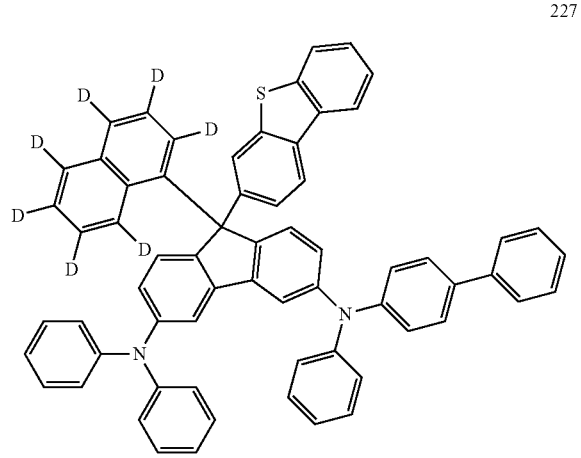
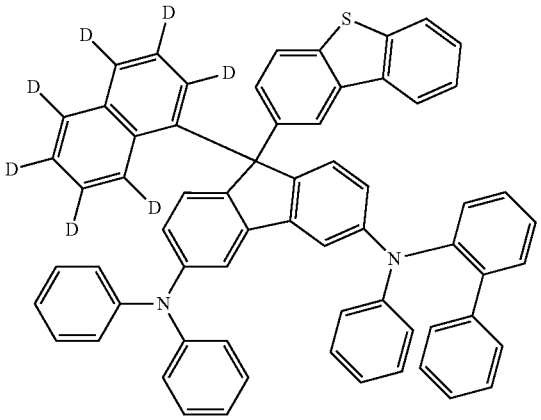

233
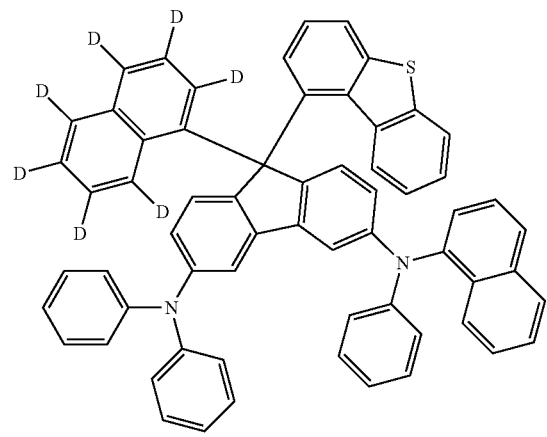
234
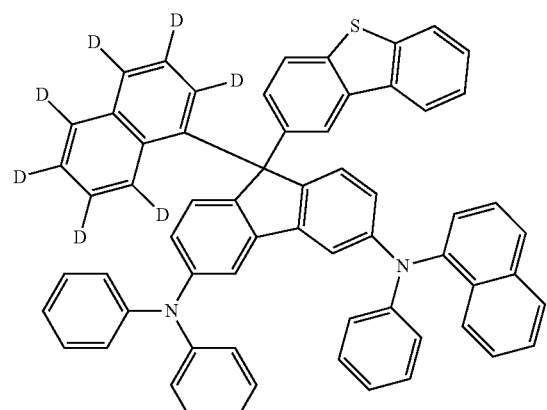
235
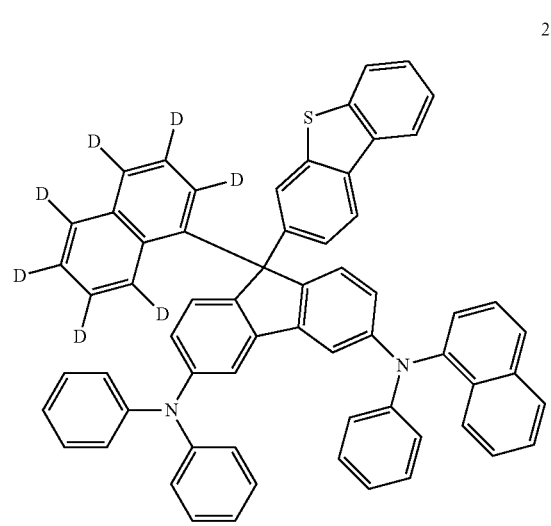
236
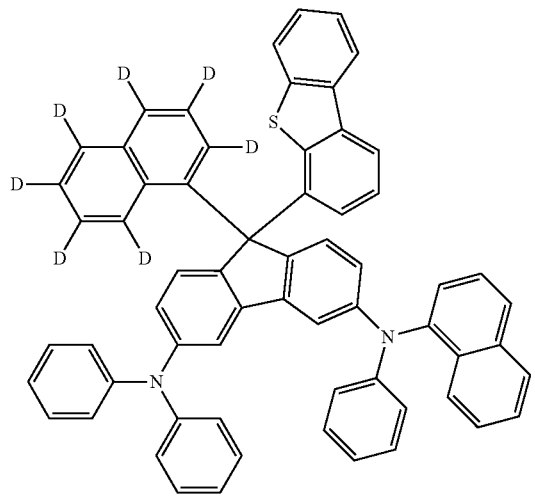
237
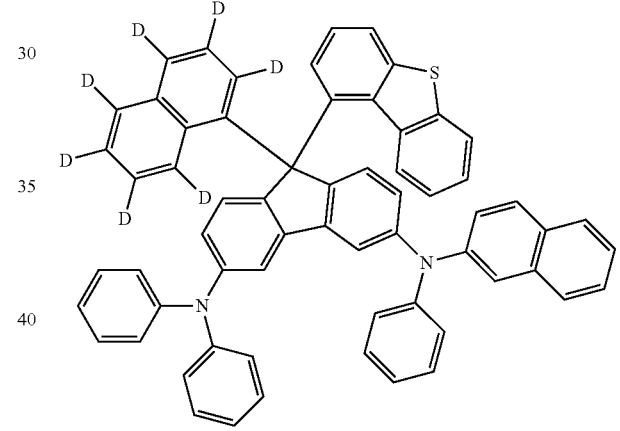
238
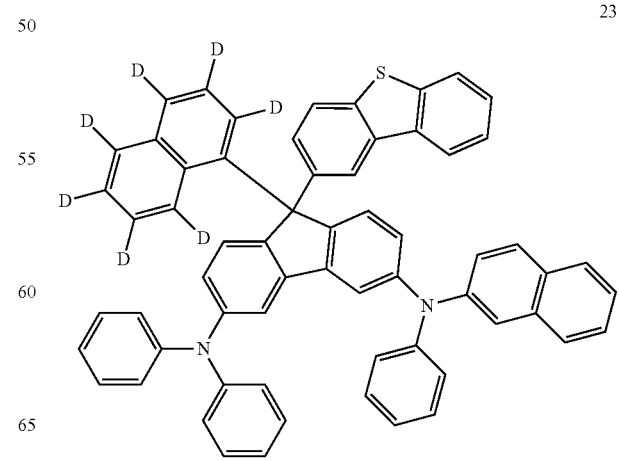

501
-continued
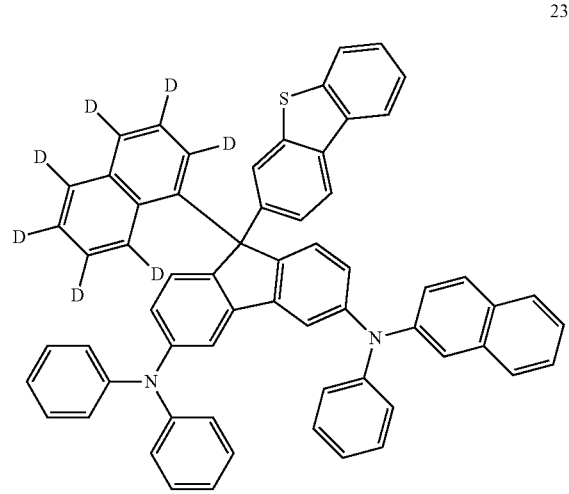
239
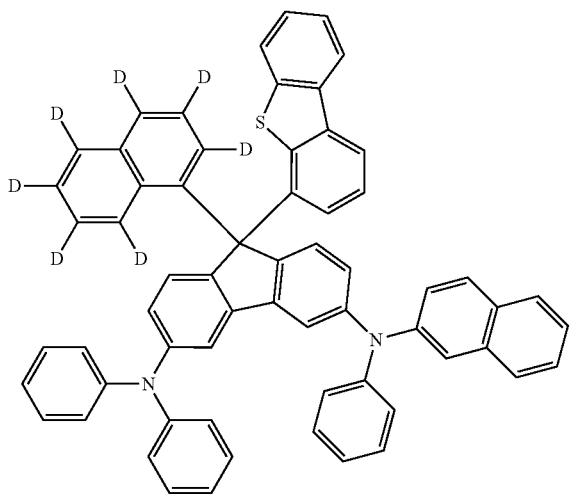
240
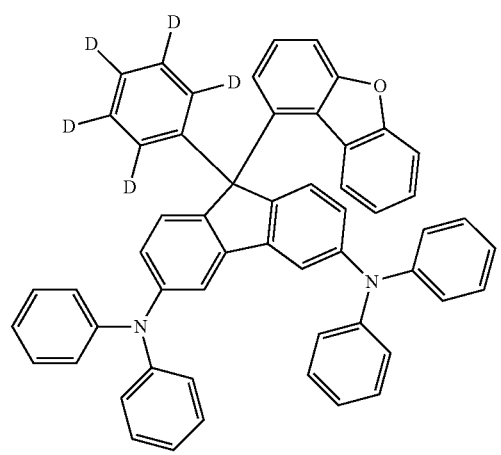
241
502
-continued
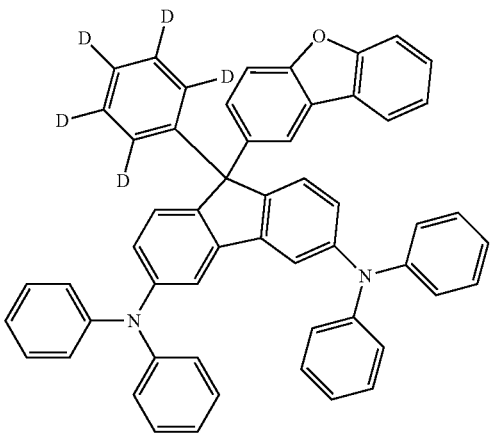
242
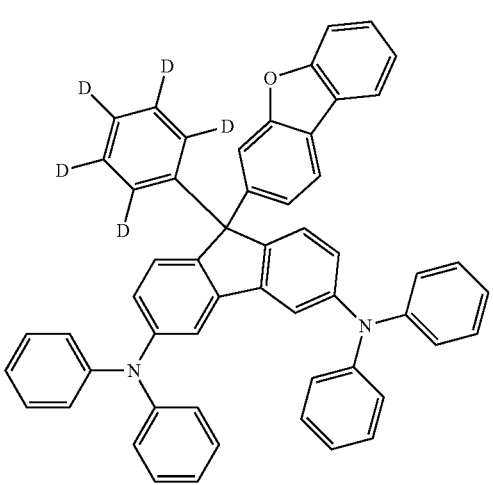
243
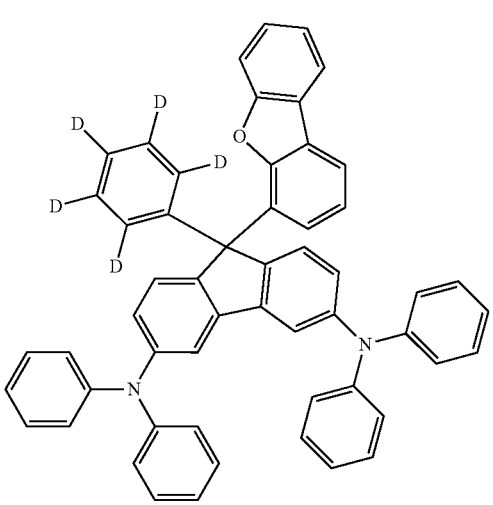
244

245
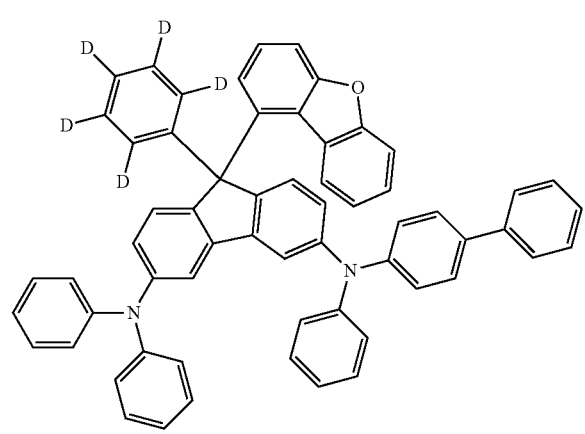
246
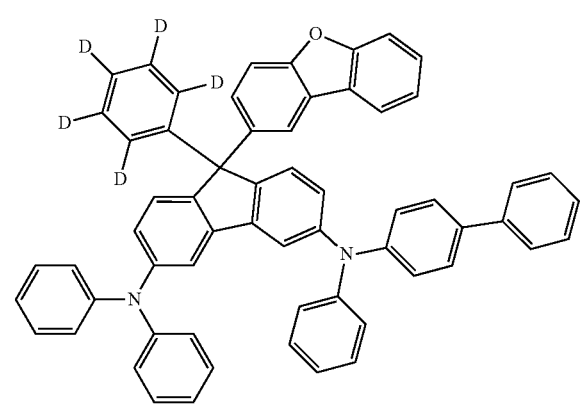
247
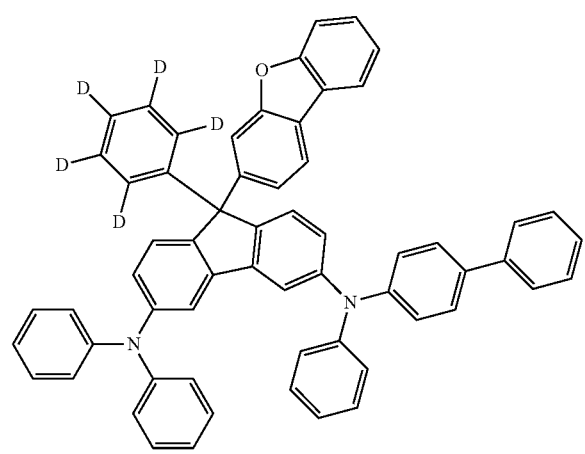
248
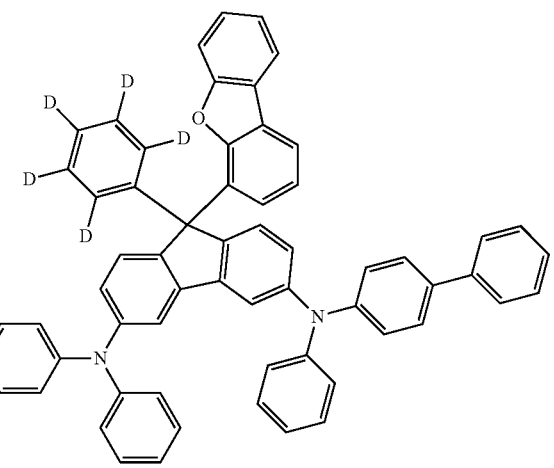
249
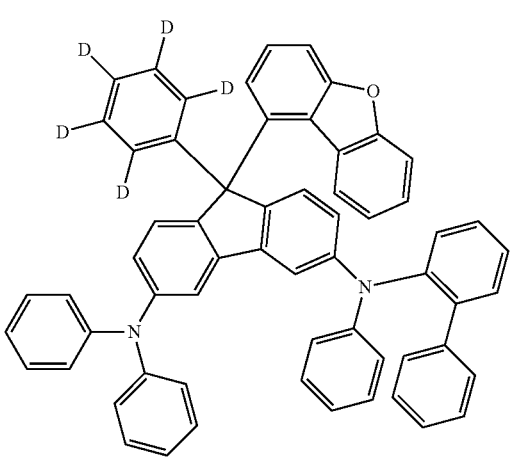
250
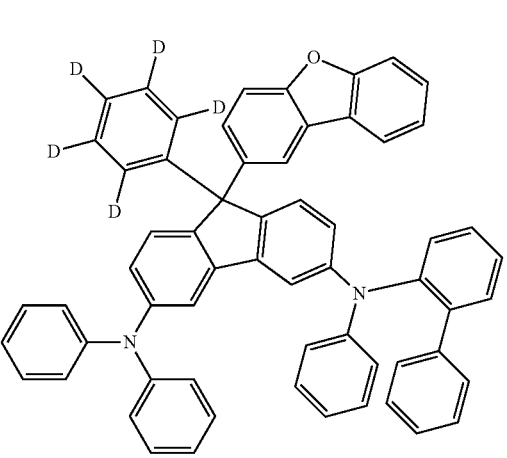

505
-continued
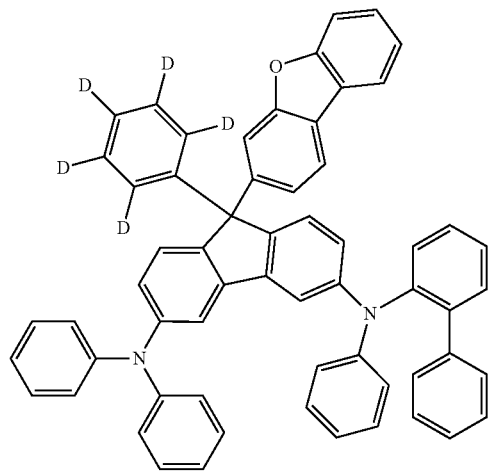
251
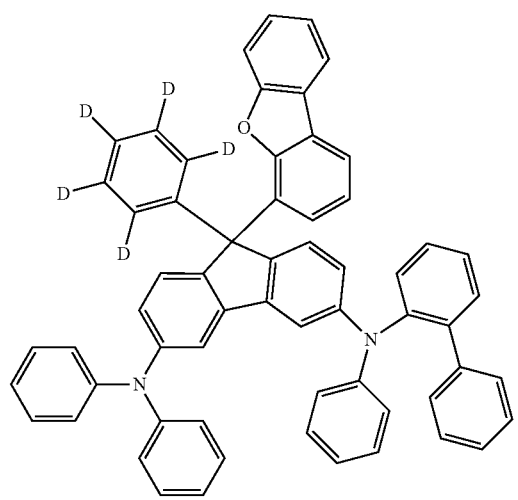
252
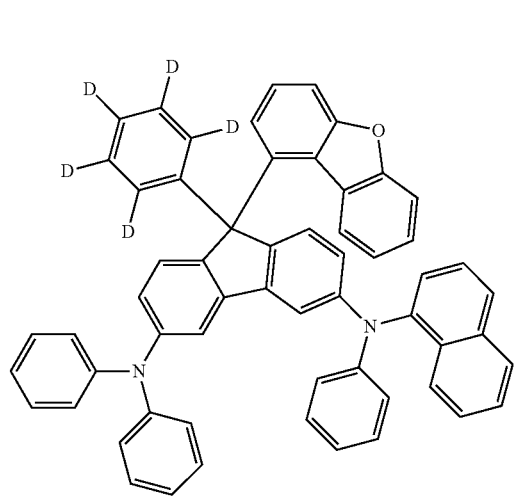
253
506
-continued
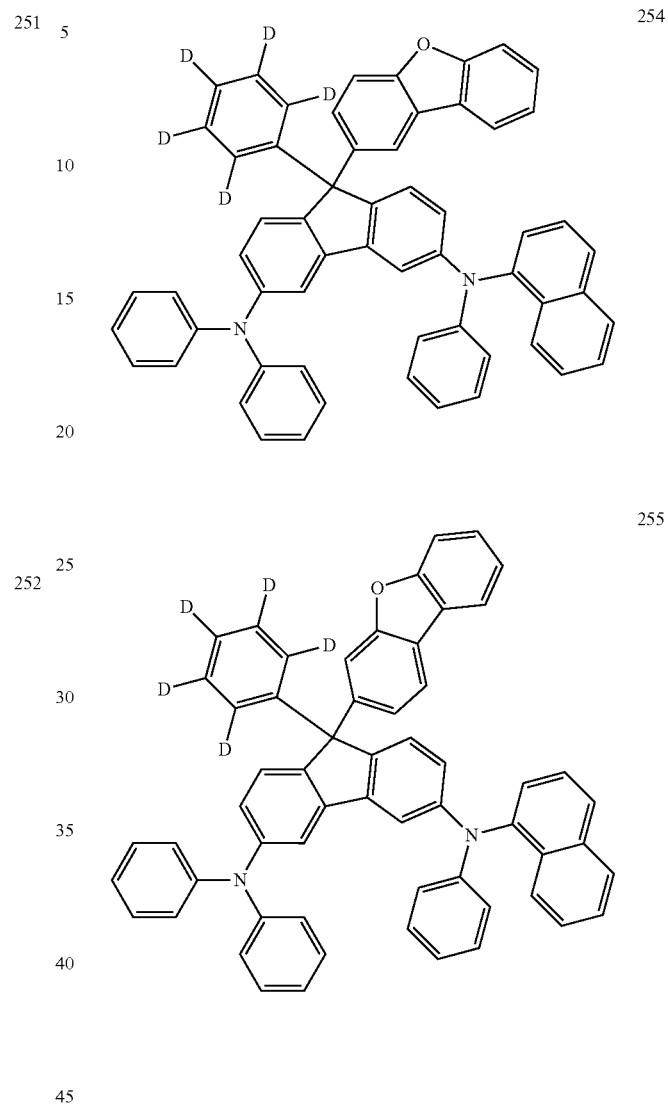
254
255
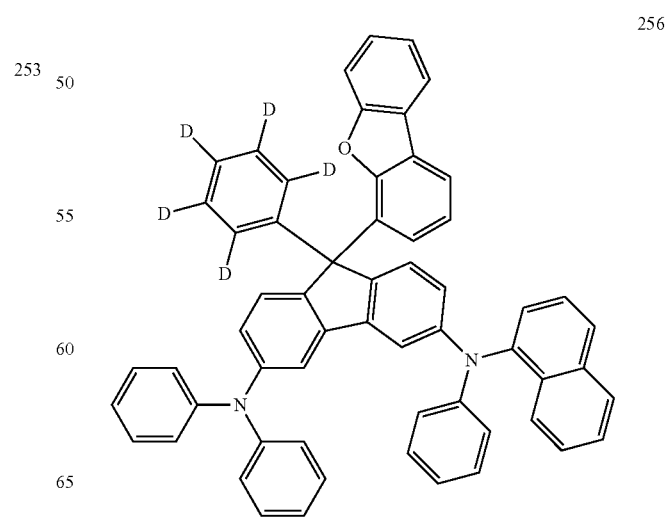
256

507
-continued
257
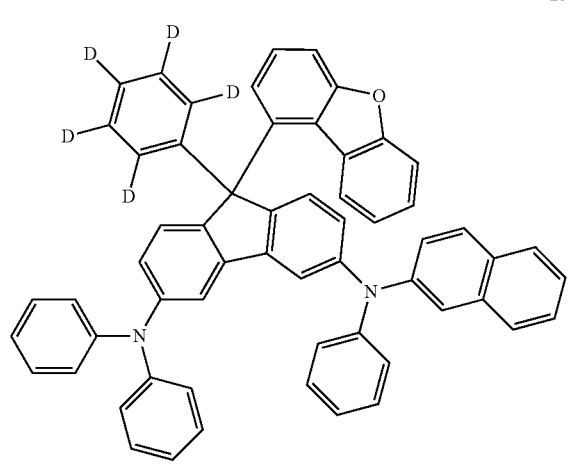
258
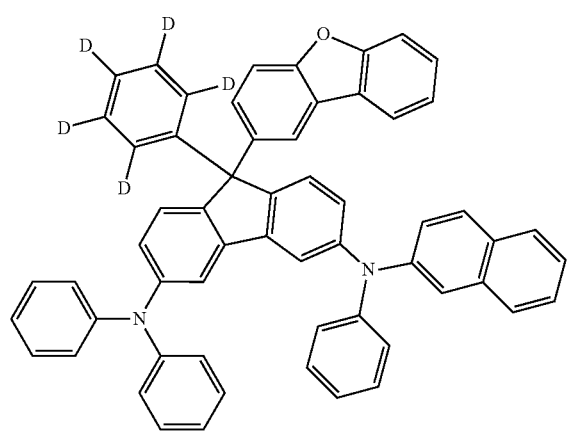
259
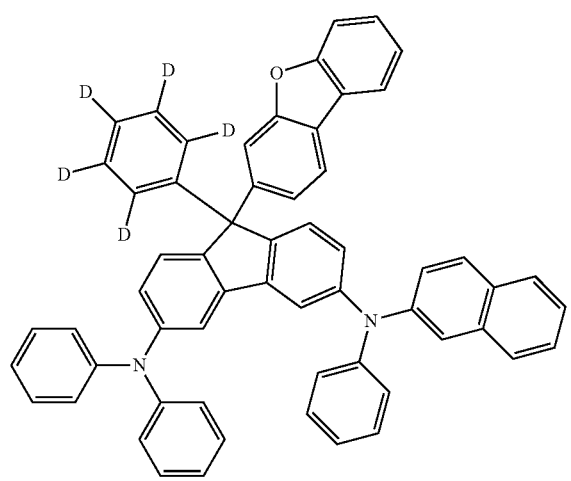
508
-continued
260
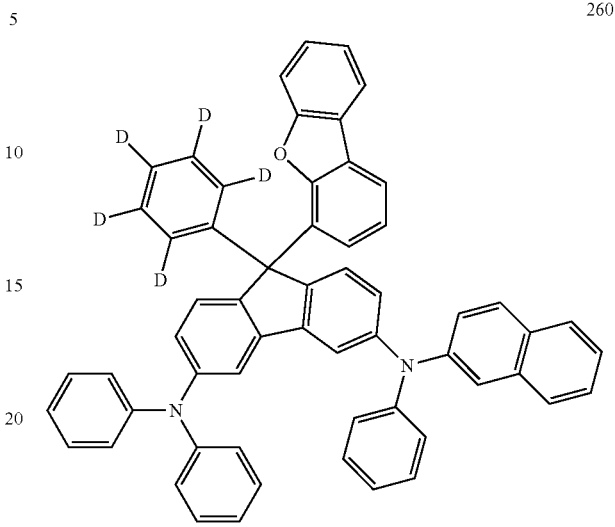
261
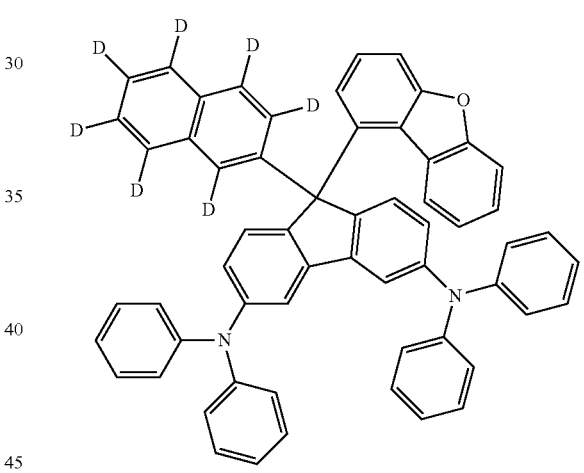
262
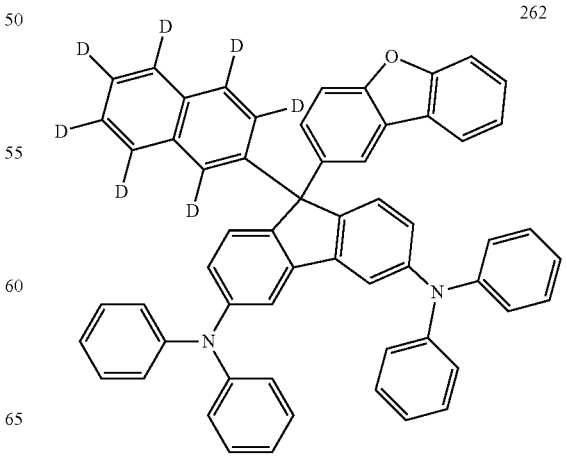

509
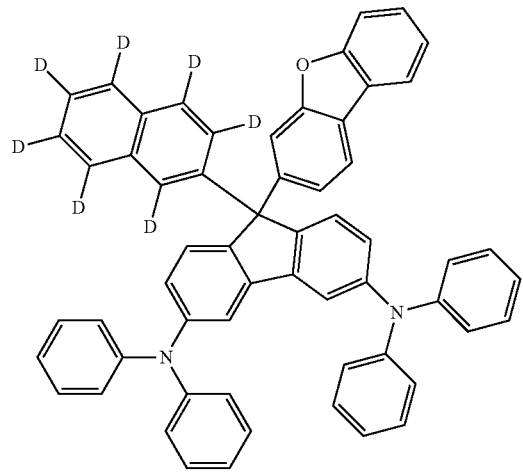
263
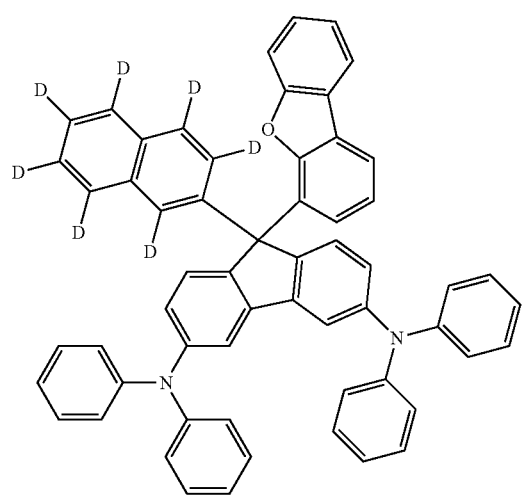
264
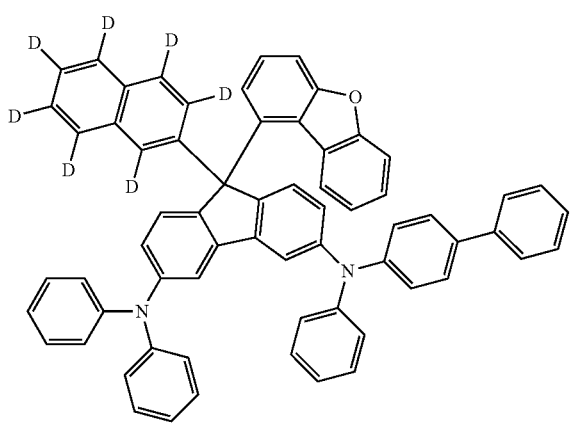
265
510
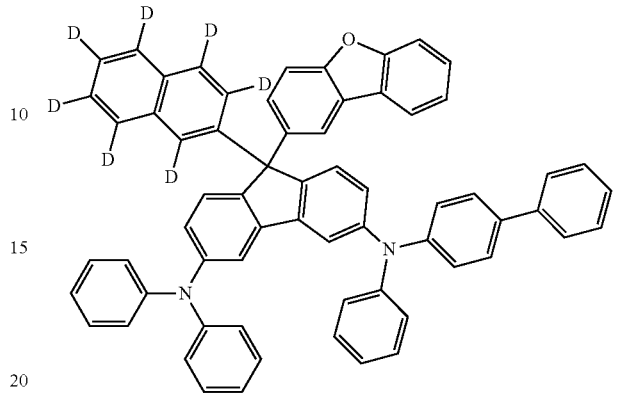
266
267
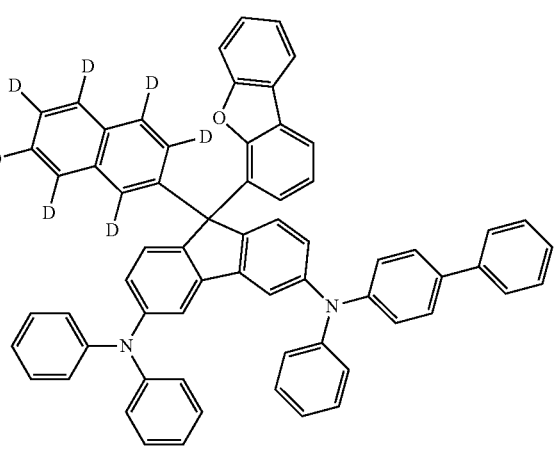
268

511
-continued
269
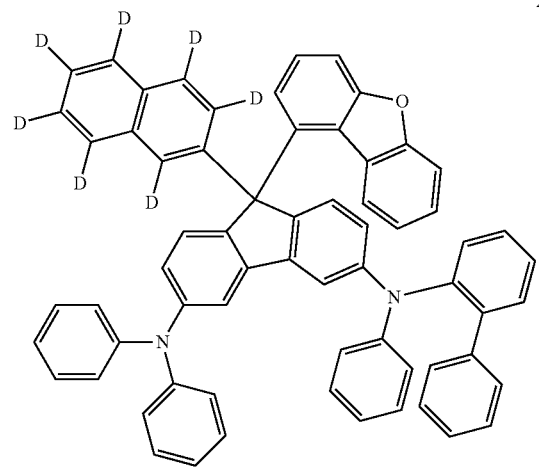
270
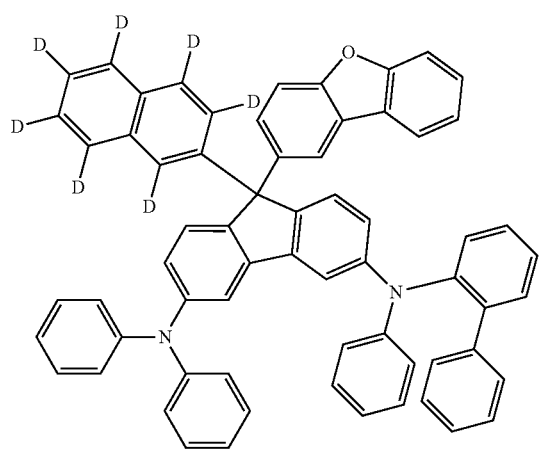
271
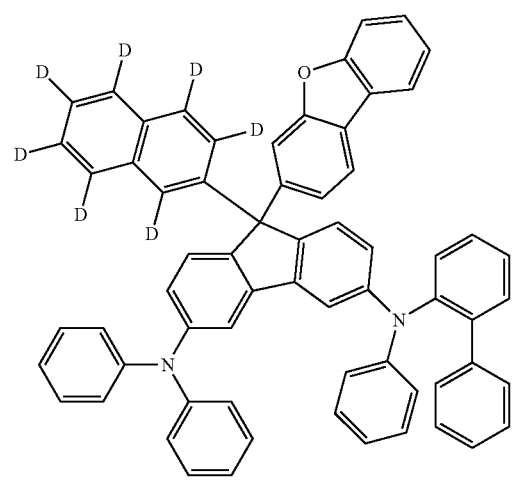
512
-continued
272
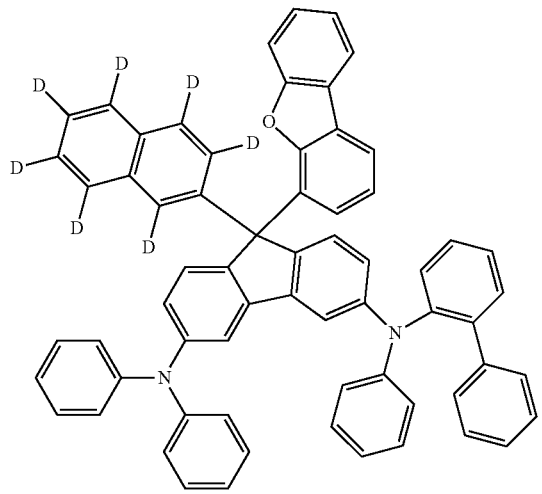
273
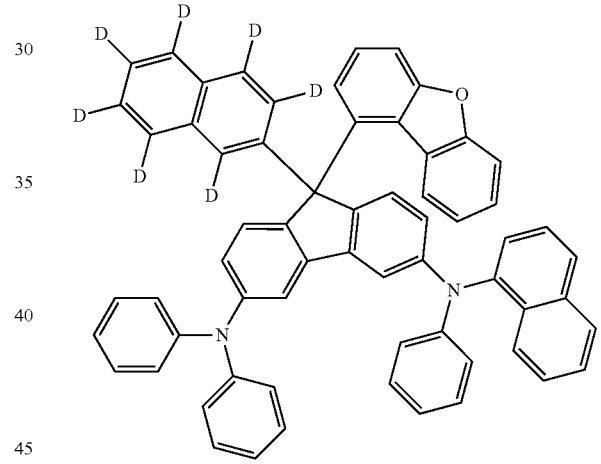
274
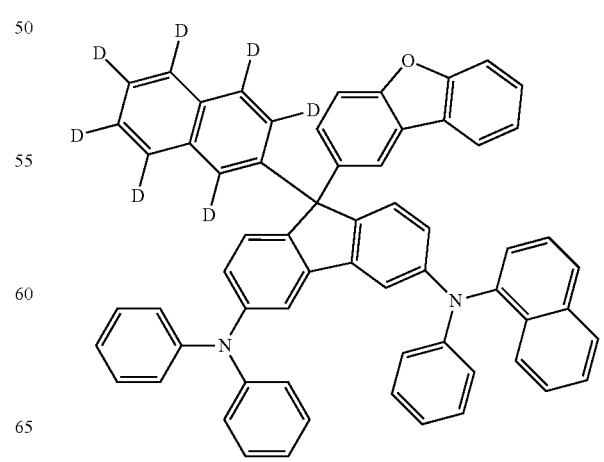

513
-continued
514
-continued
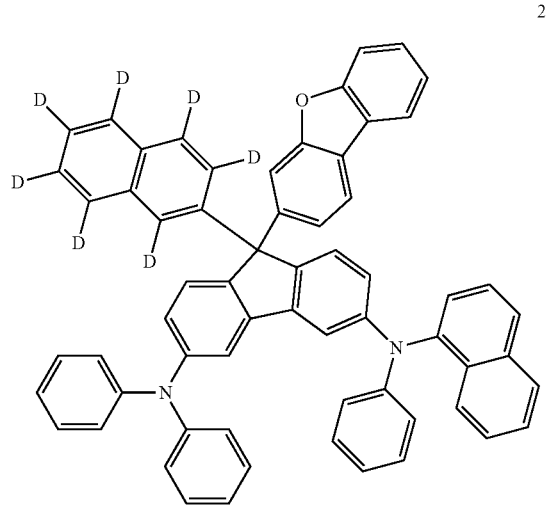
275
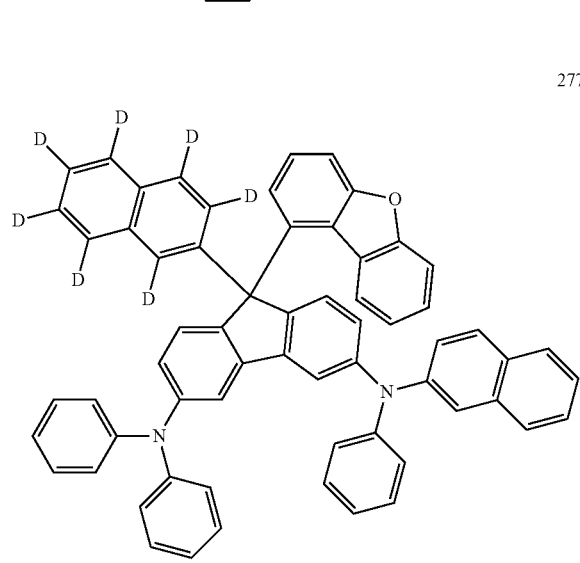
276
277
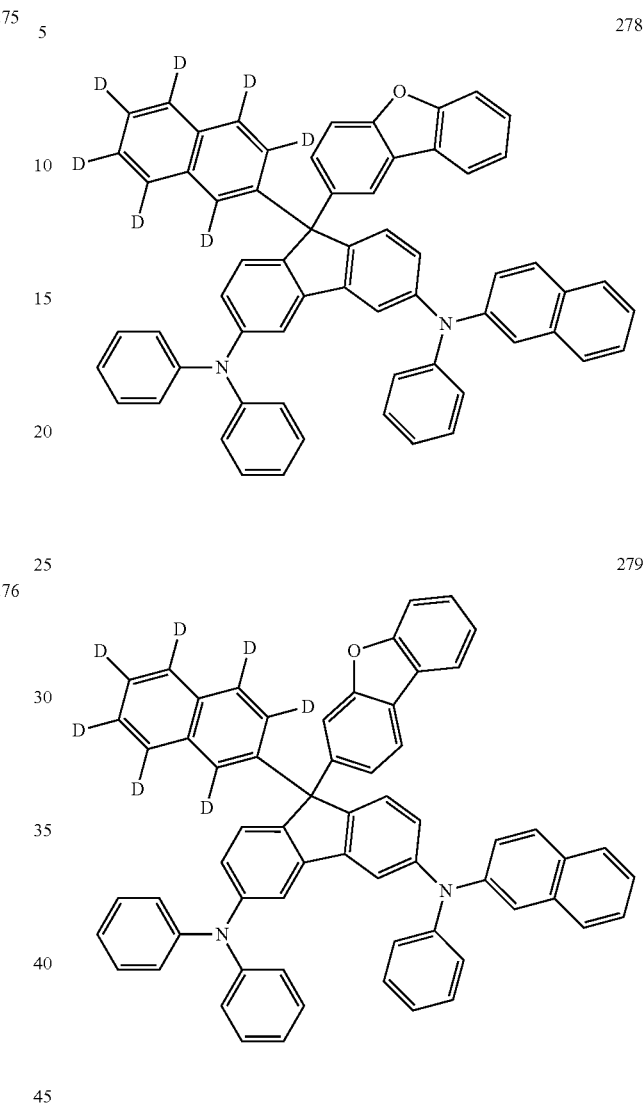
278
279
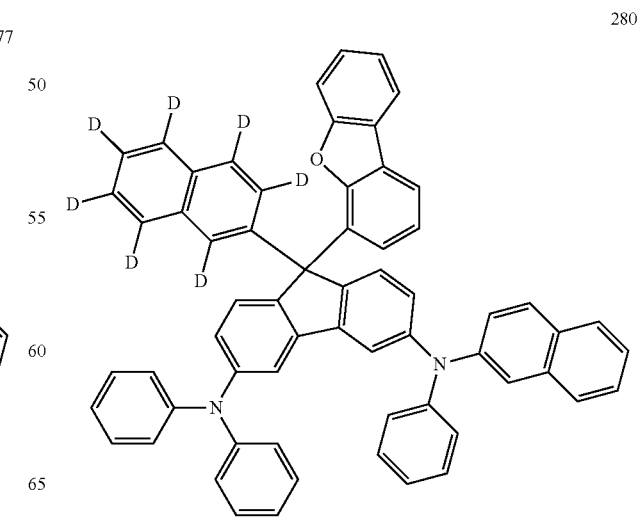
280

281 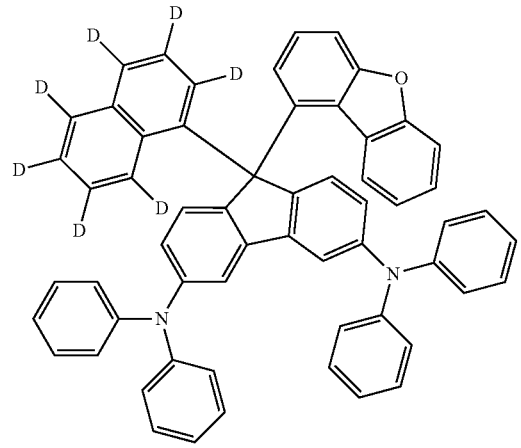
282 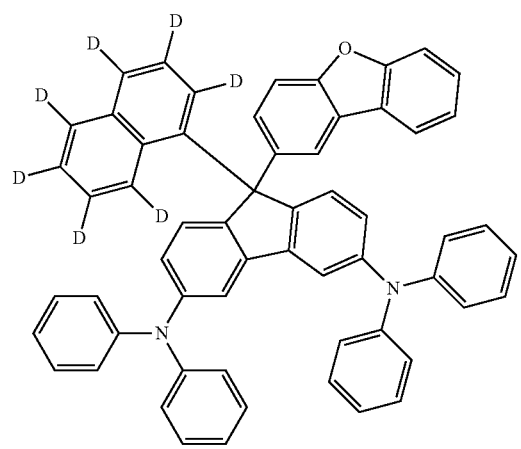
283 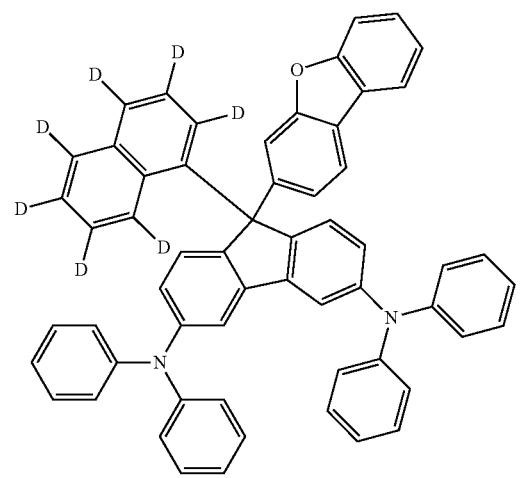
284 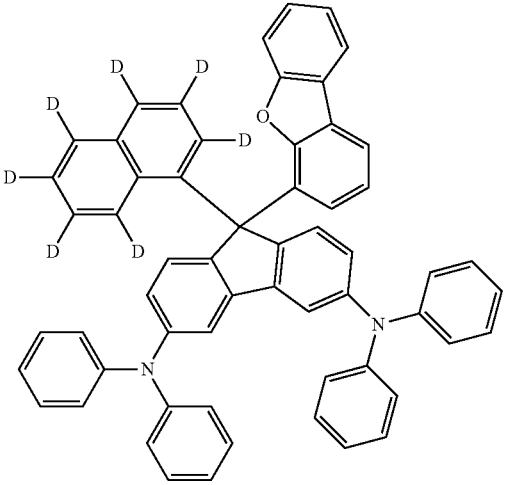
285 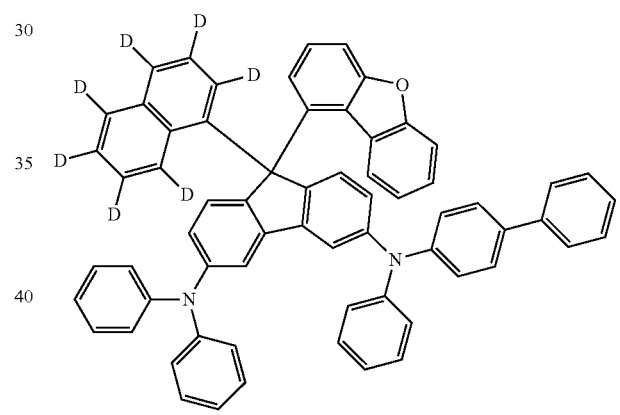
286 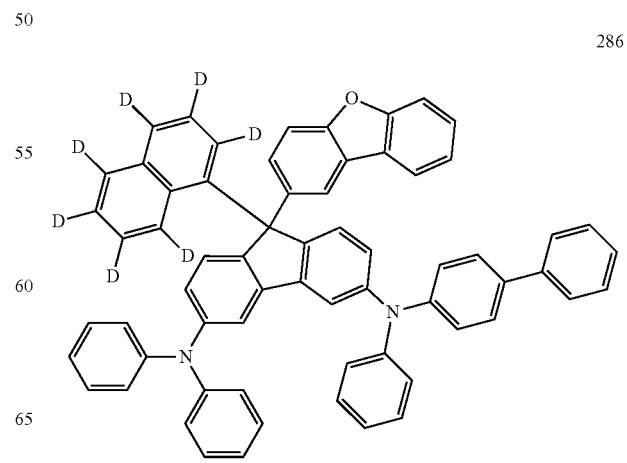

517
-continued
287
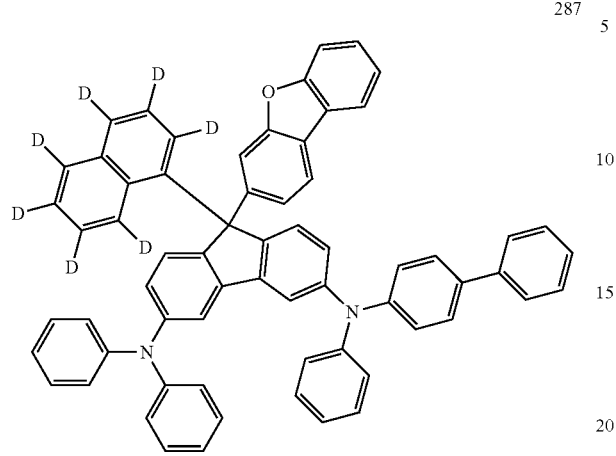
288
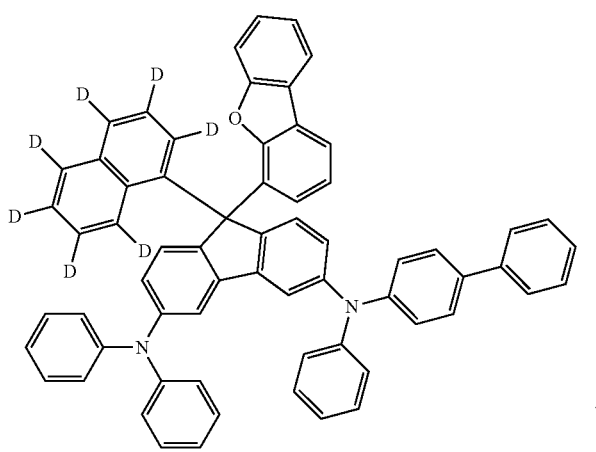
289
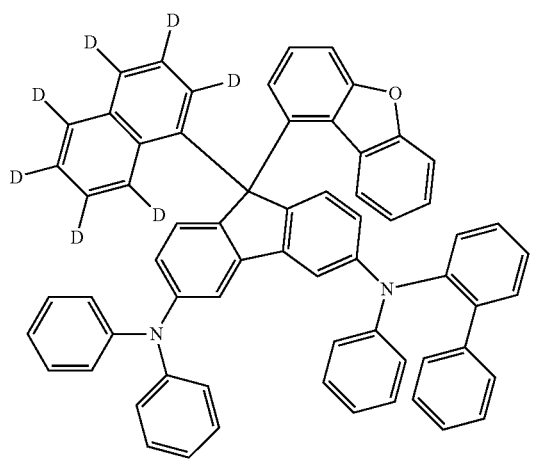
518
-continued
290
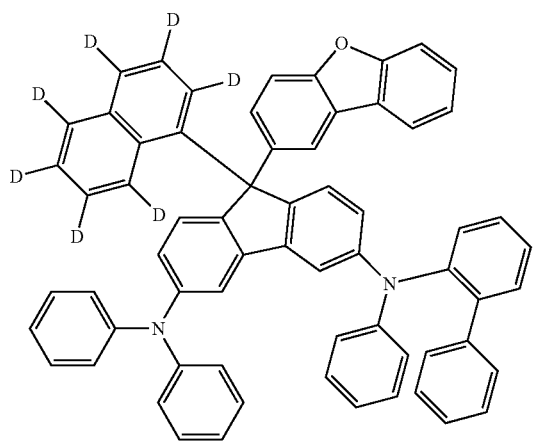
291
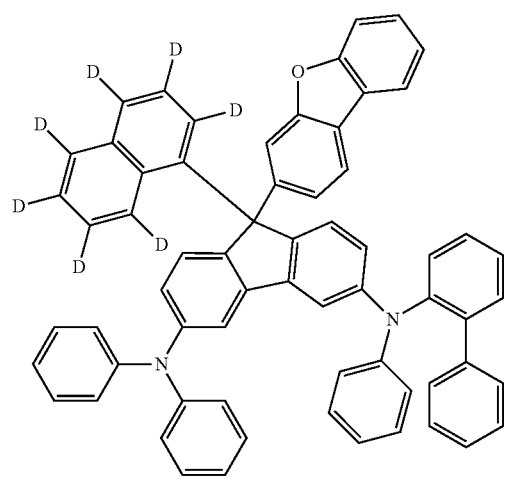
292
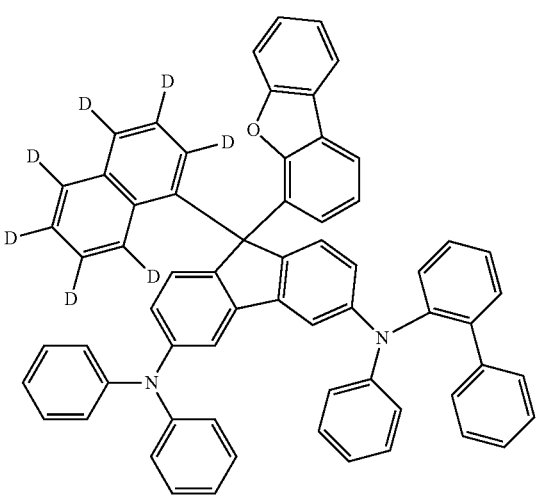

519
-continued
293
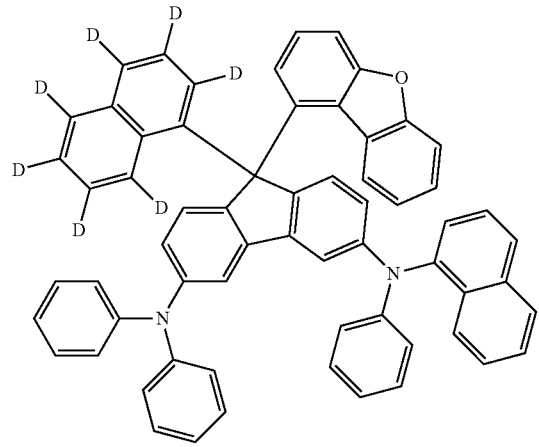
294
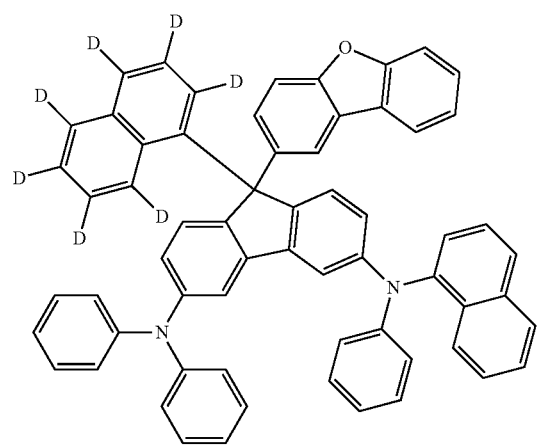
295
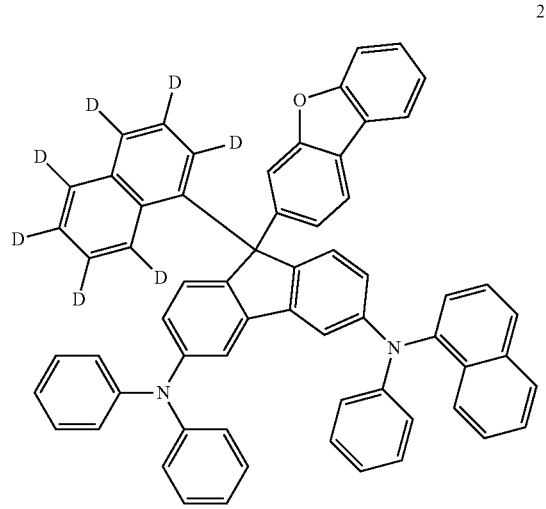
520
-continued
296
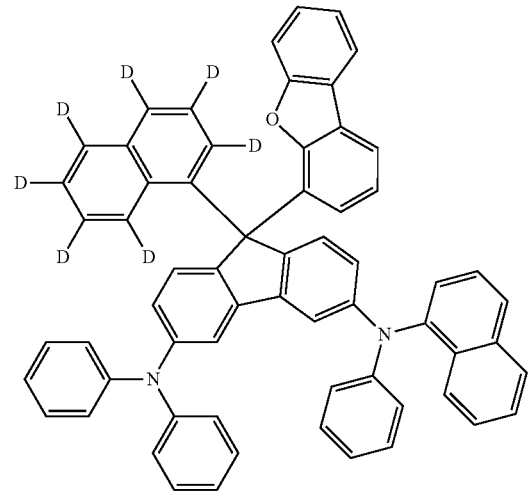
297
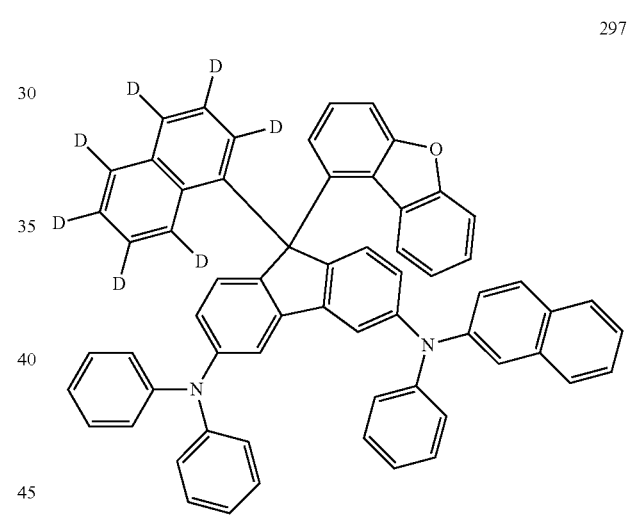
298
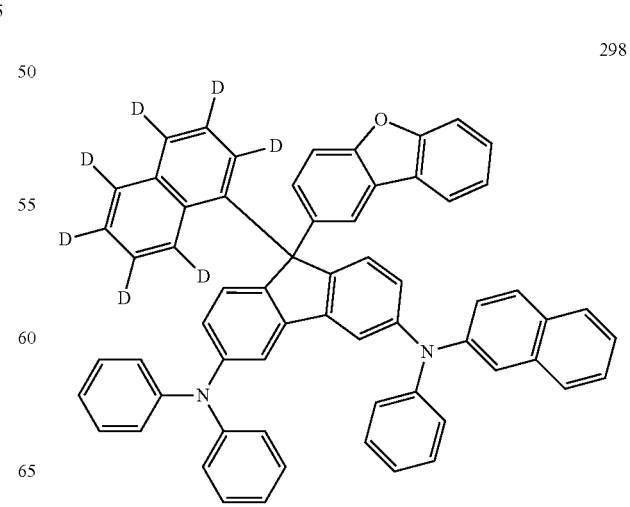

521
-continued
522
-continued
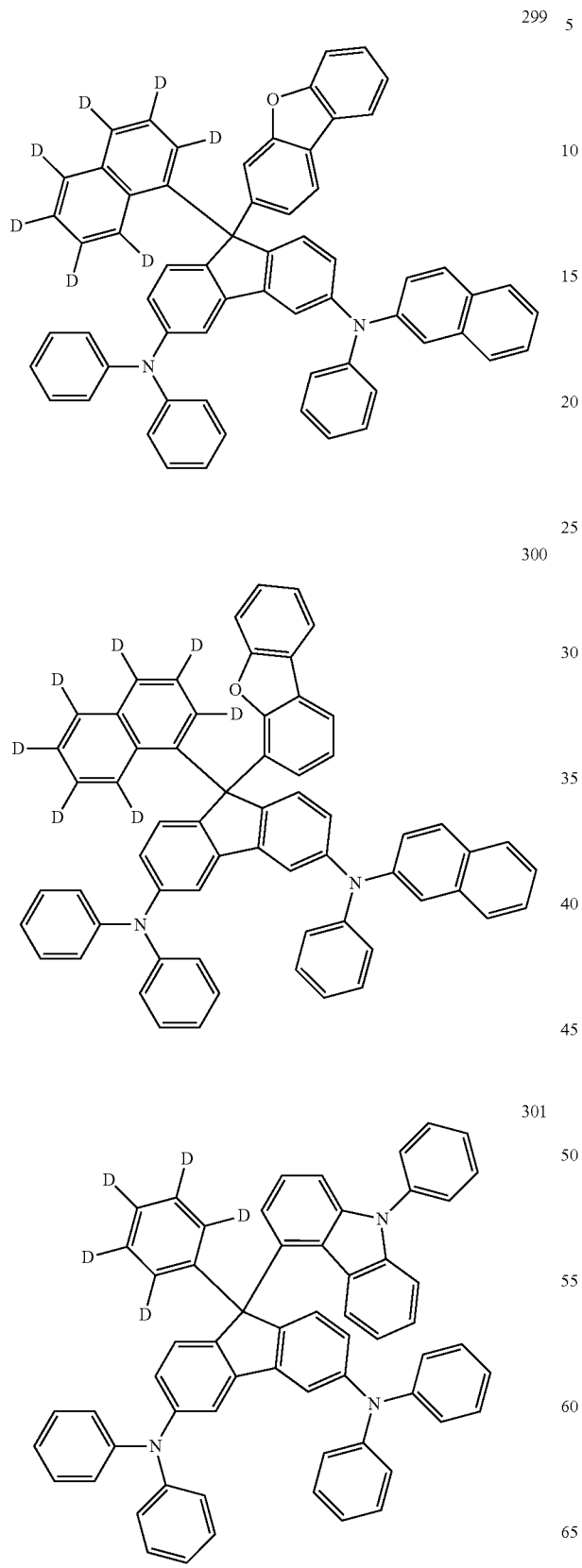
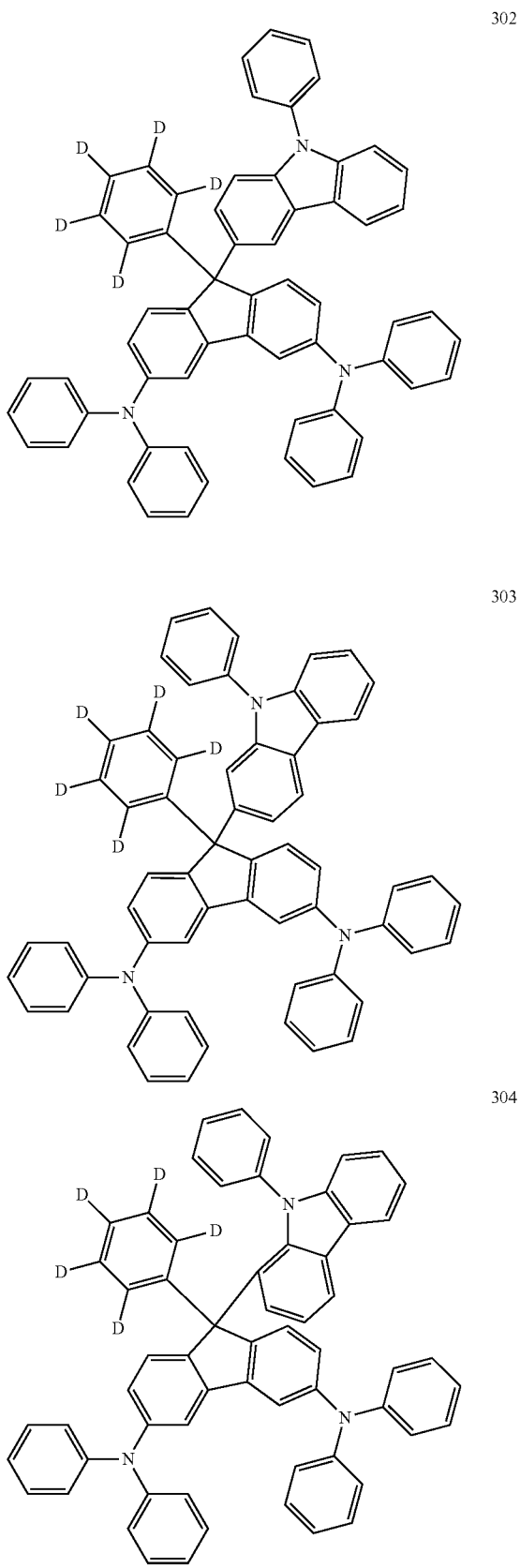

| 523 -continued | 524 -continued |
|---|---|
| 305 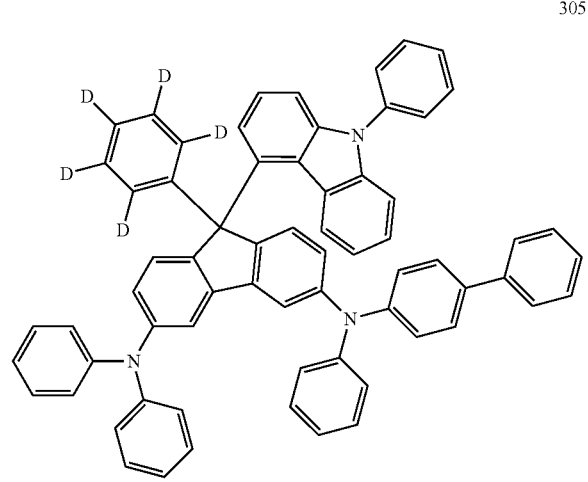 | 308 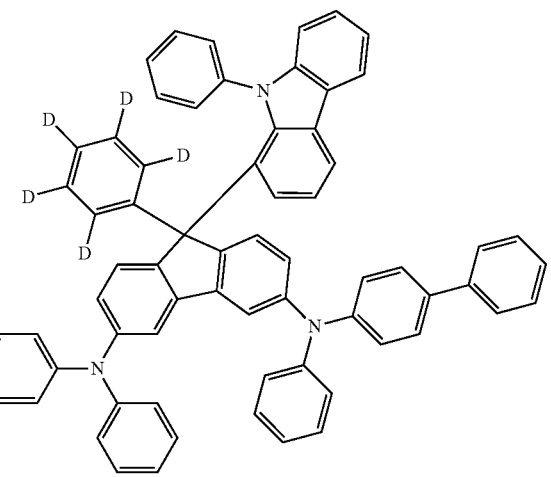 |
| 306 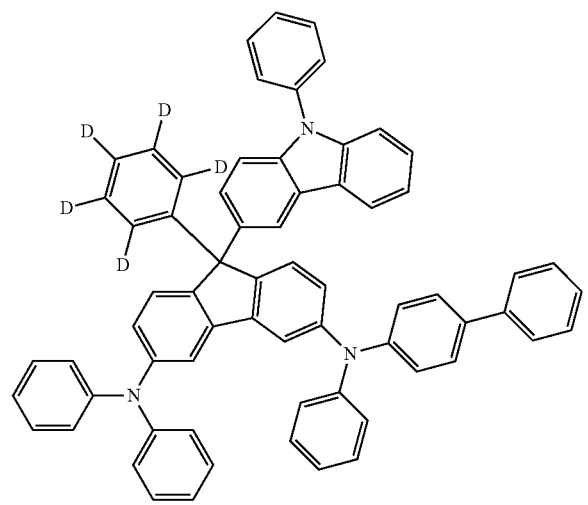 | 309 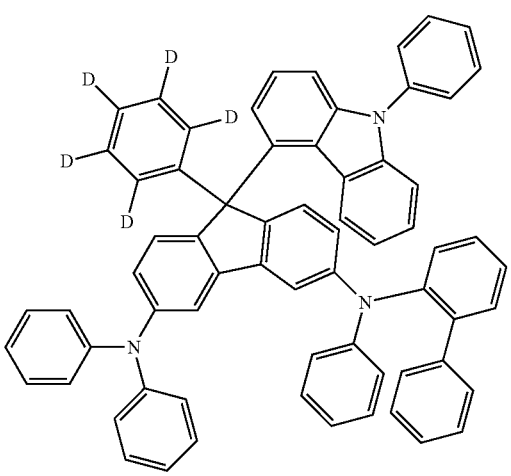 |
| 307 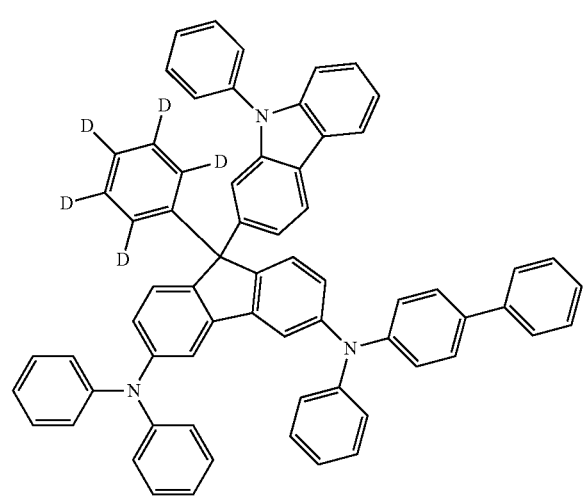 | 310 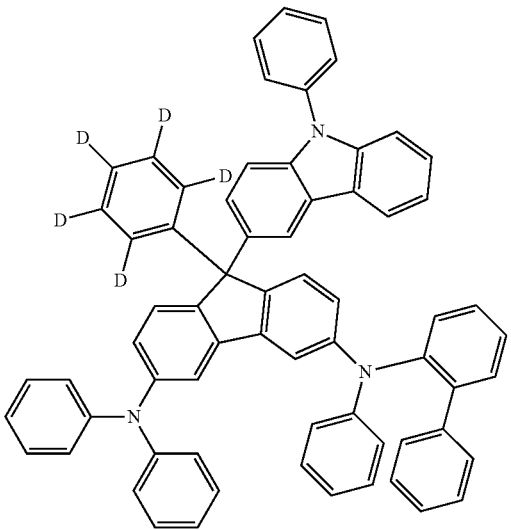 |

525
-continued
311
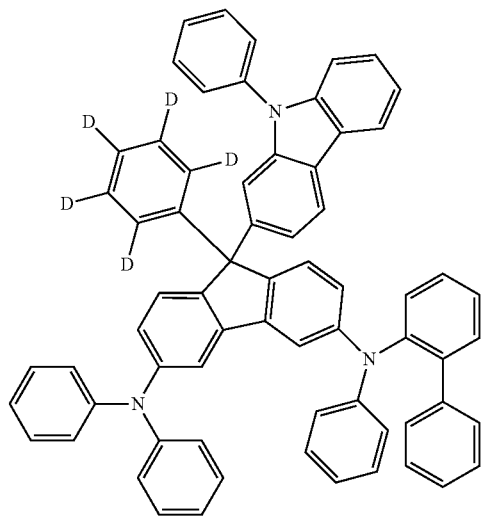
312
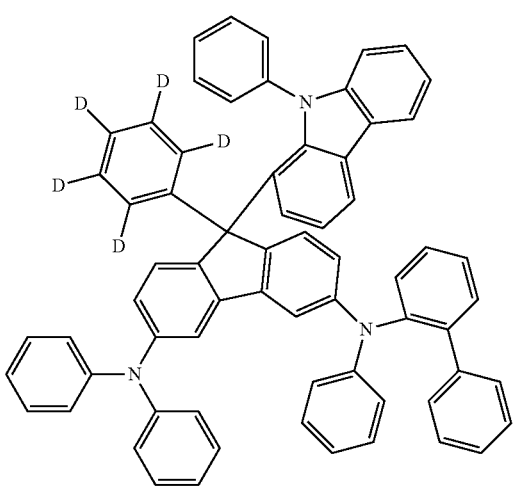
313
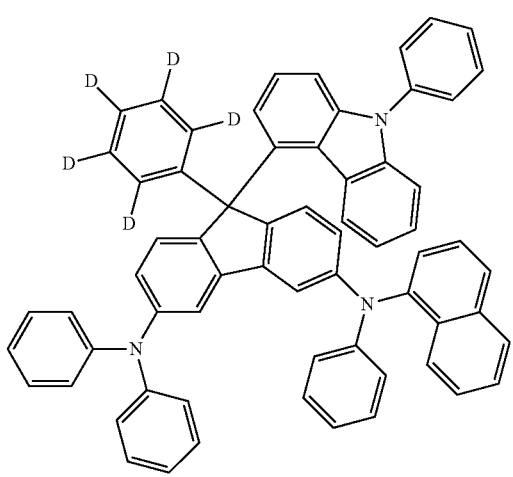
526
-continued
314
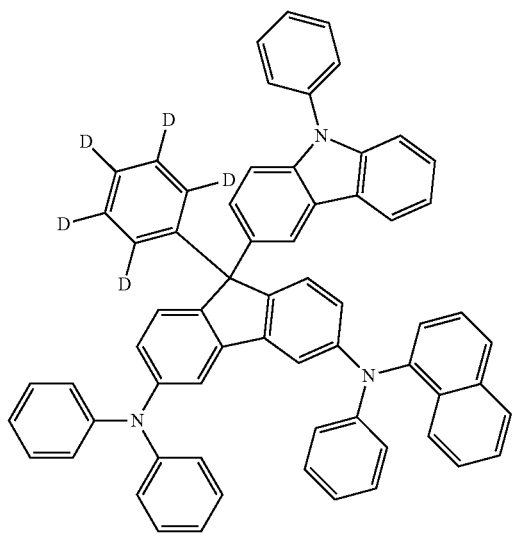
315
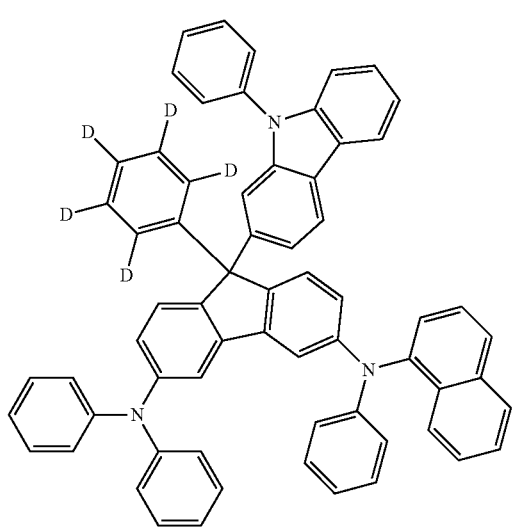
316
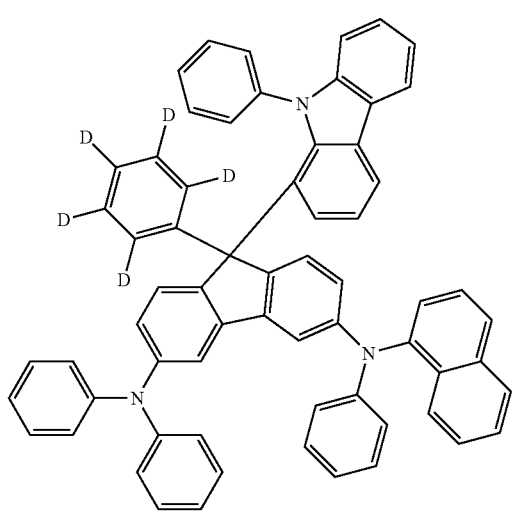

527
-continued
317
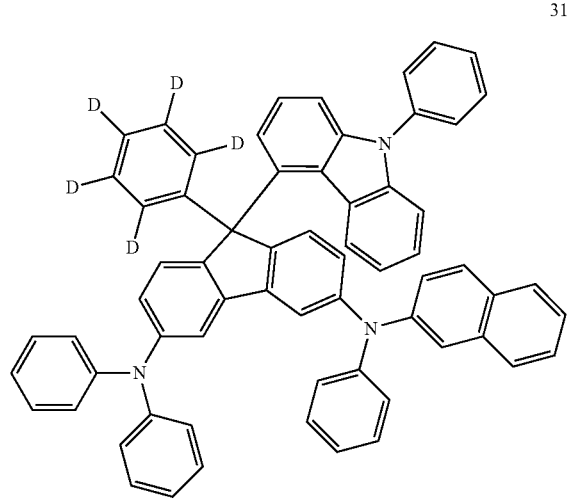
318
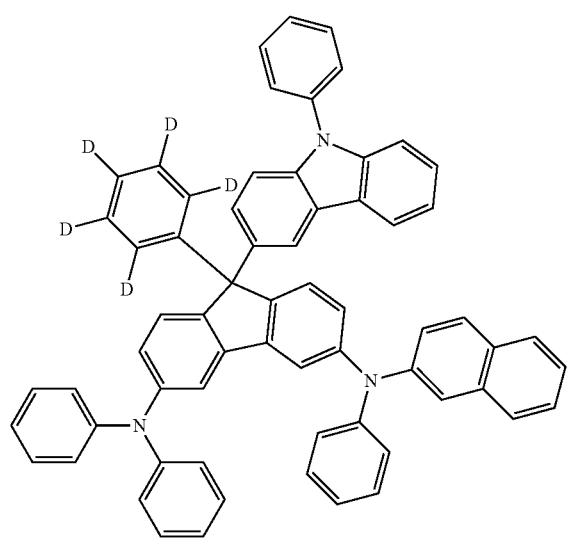
319
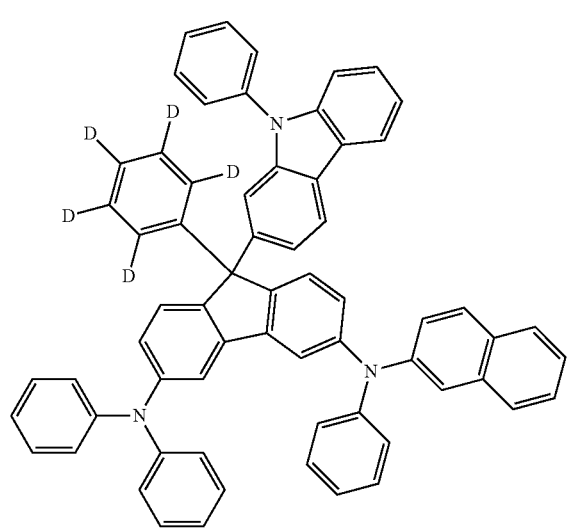
528
-continued
320
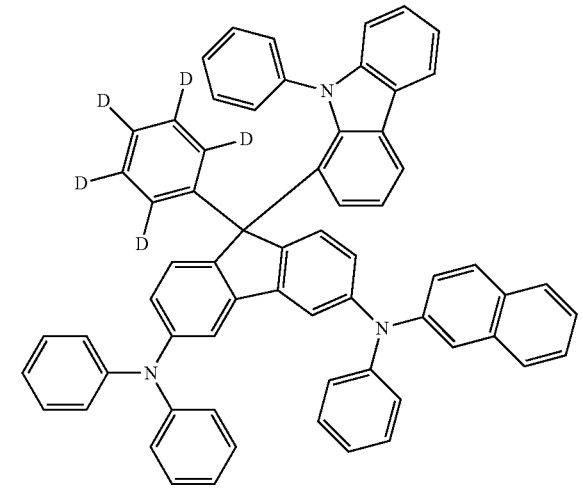
321
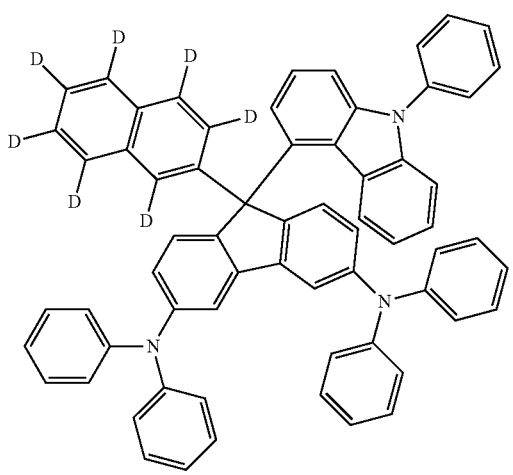
322
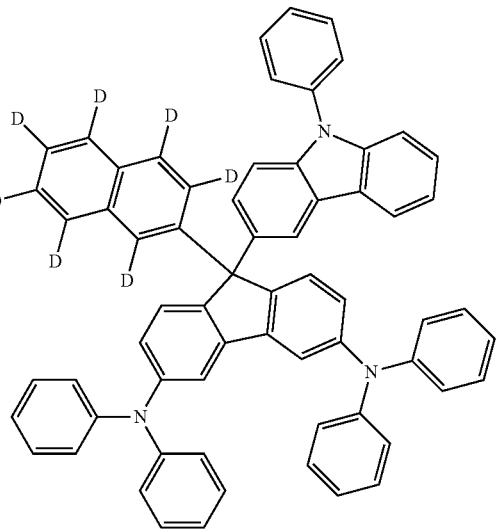

529
-continued
323
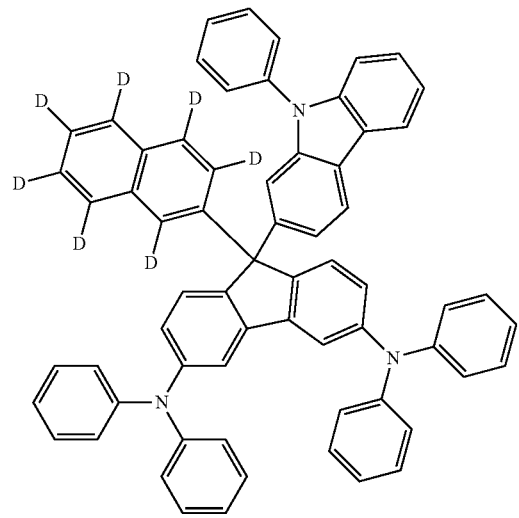
324
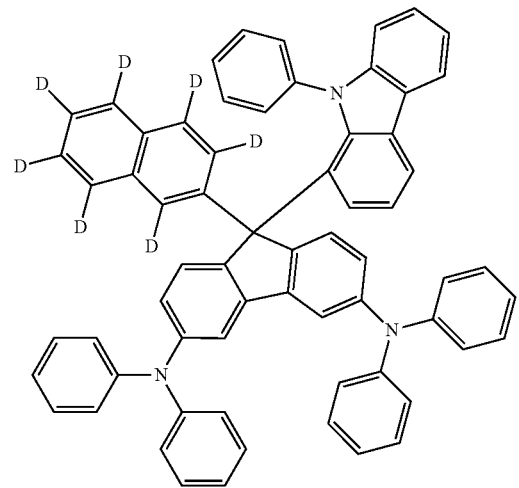
325
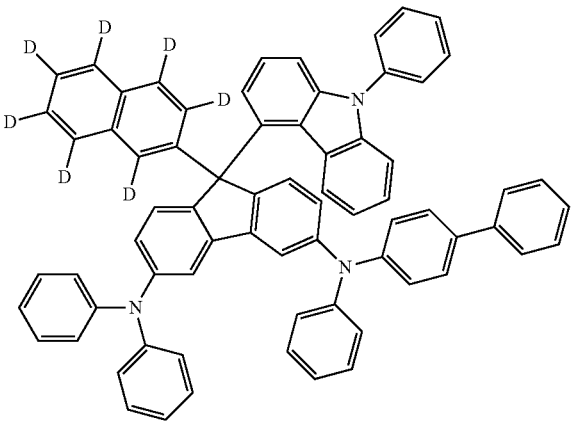
530
-continued
326
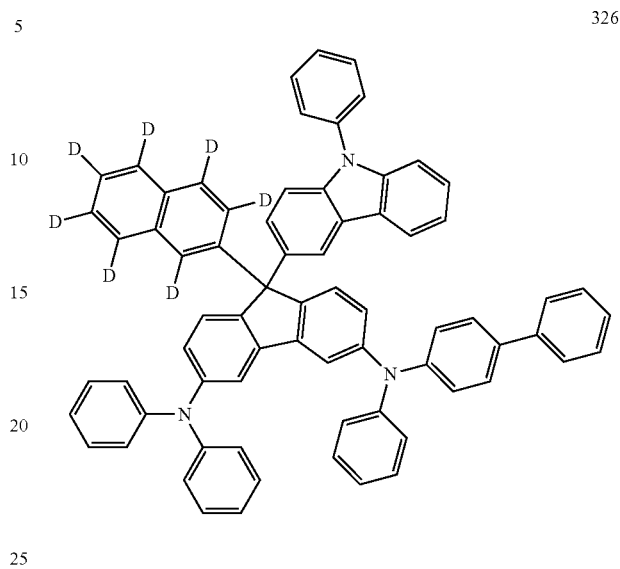
327
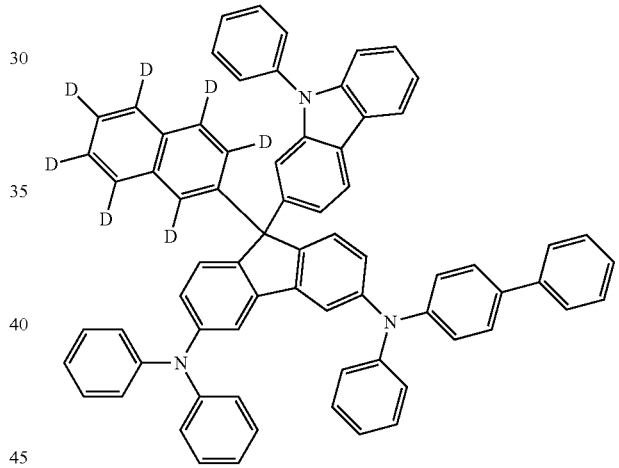
328
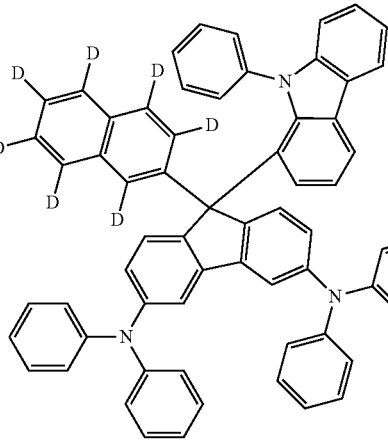

531
-continued
329
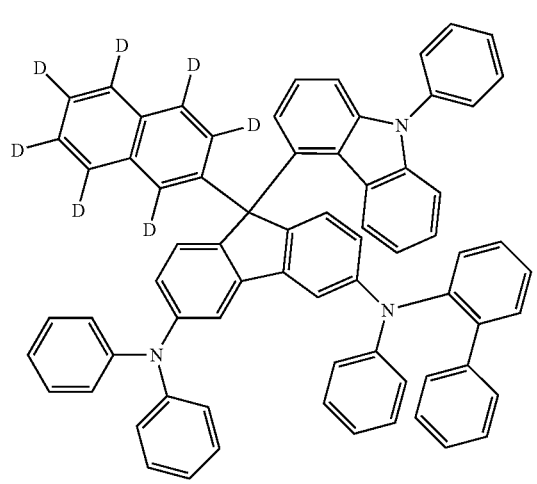
330
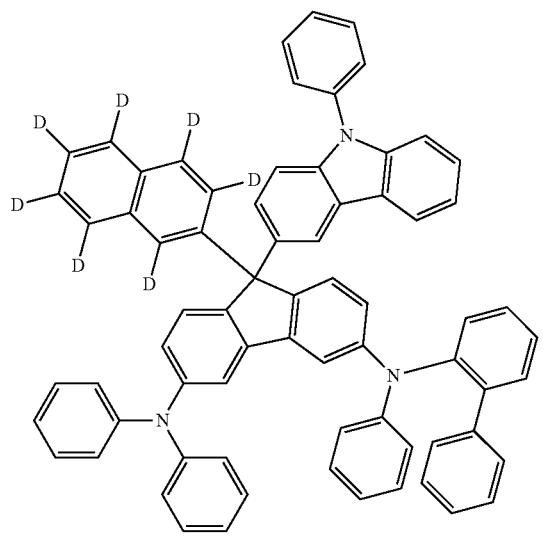
331
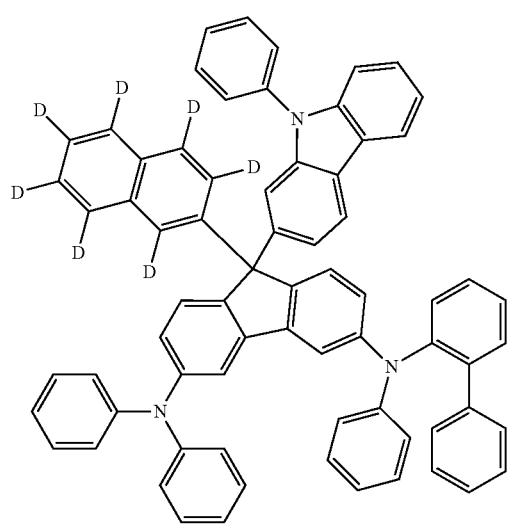
532
-continued
332
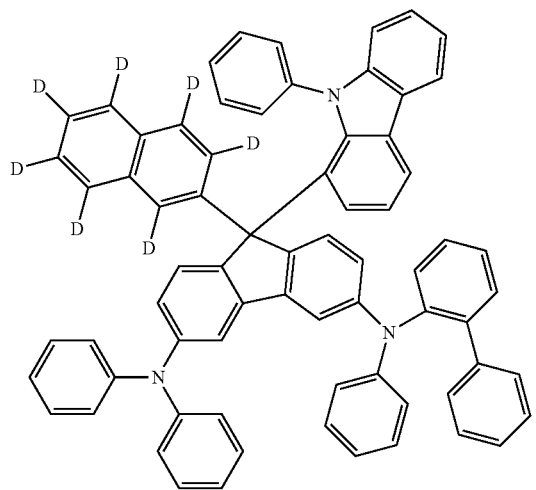
333
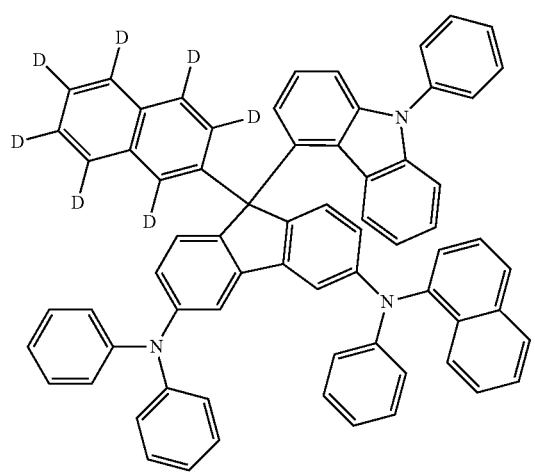
334
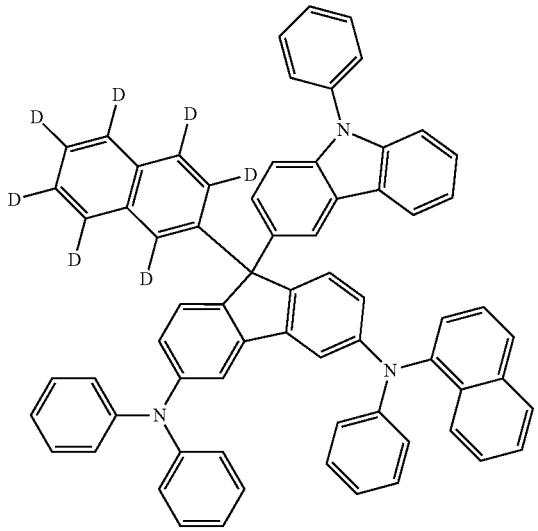

533
-continued
335
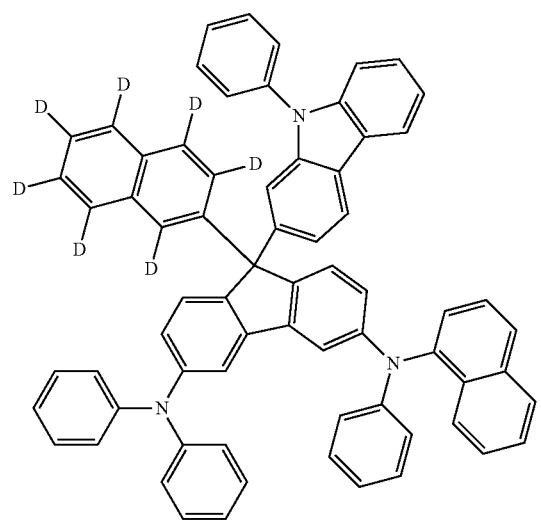
336
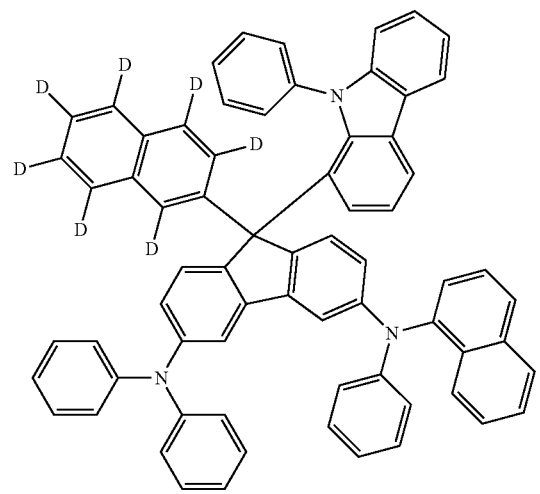
339
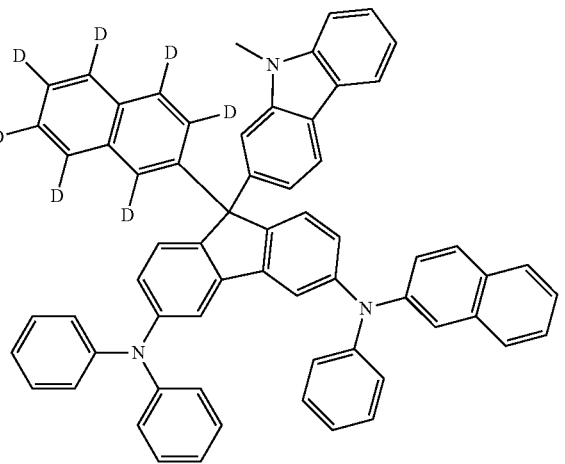
534
-continued
340
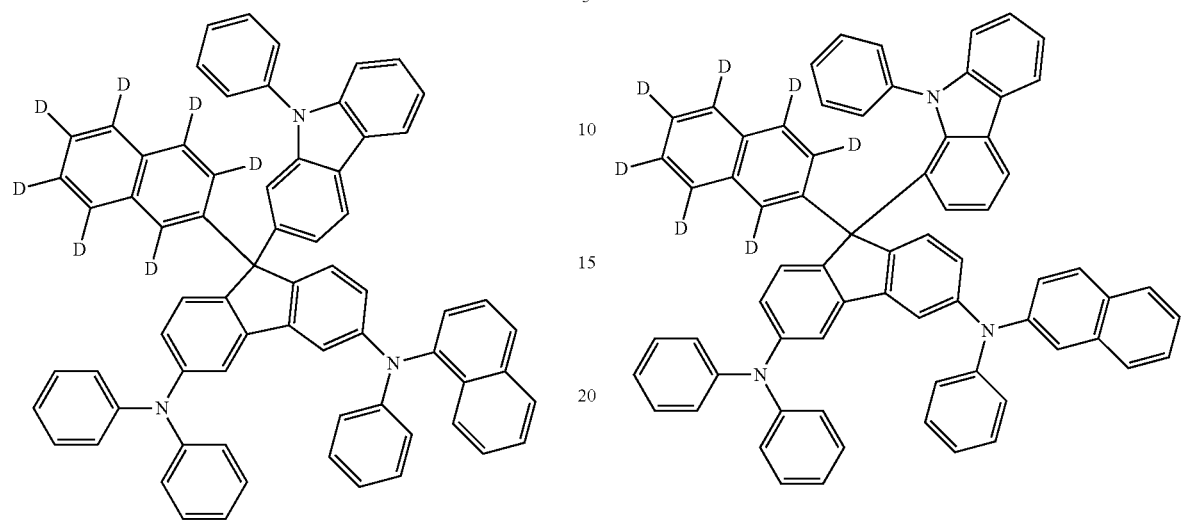
341
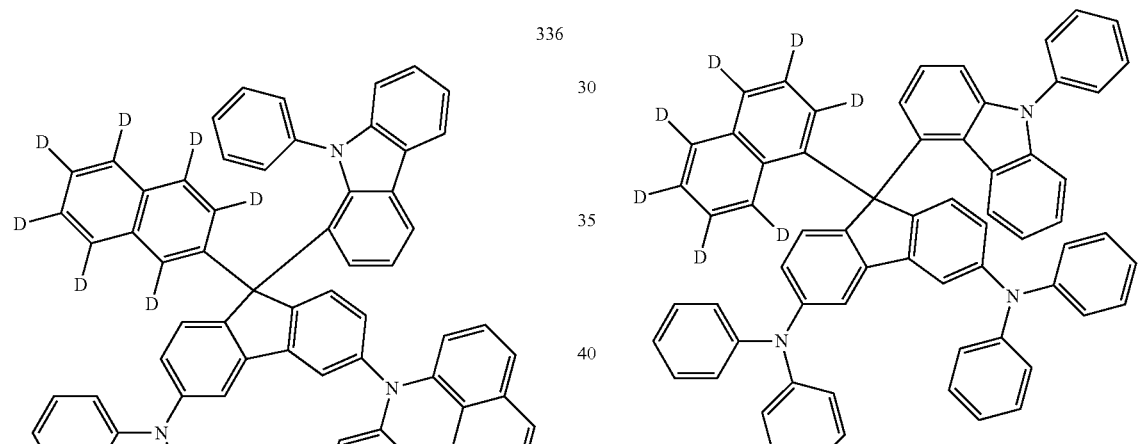
342
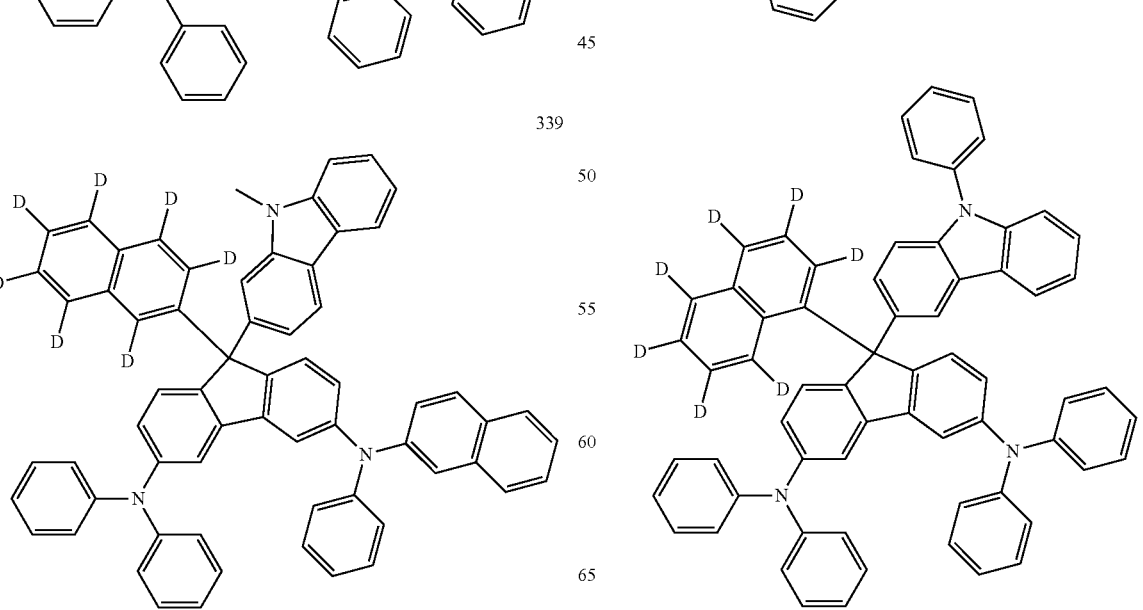

343
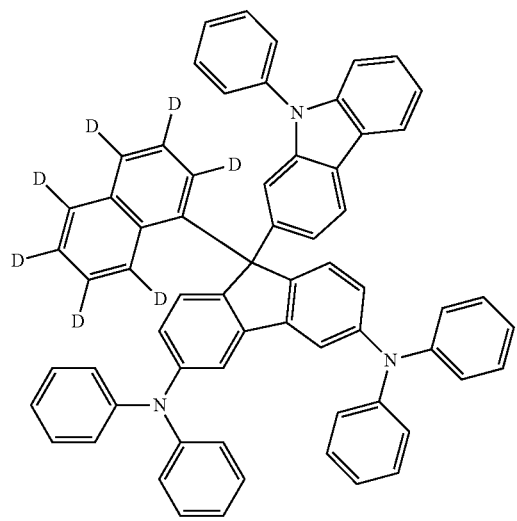
344
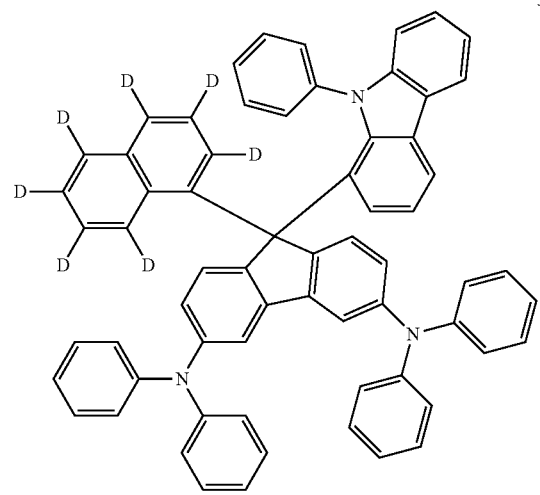
345
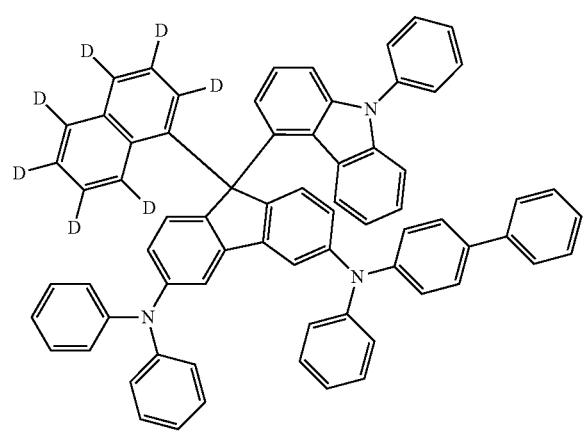
346
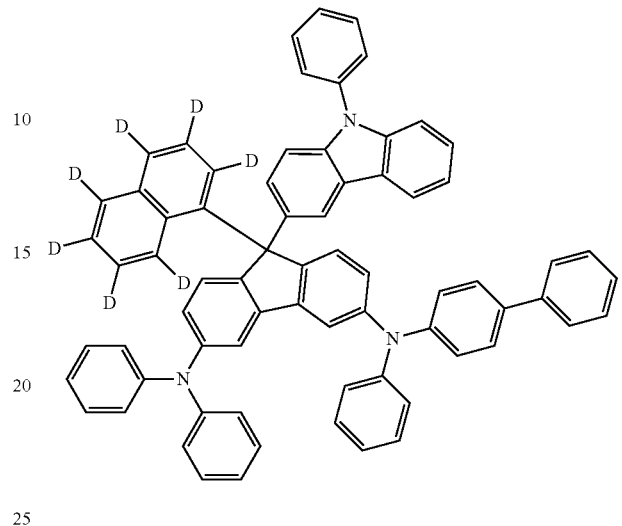
347
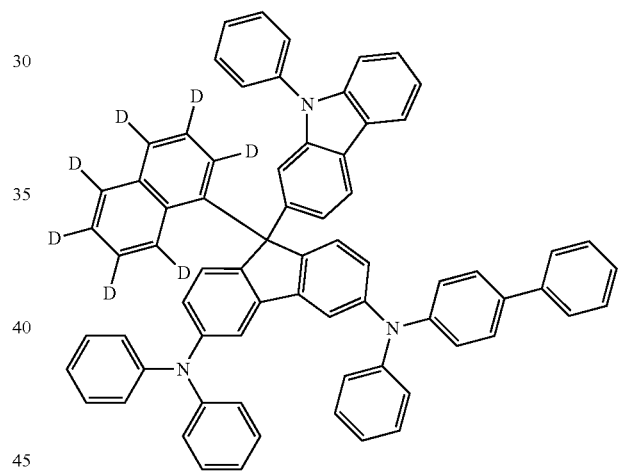
348
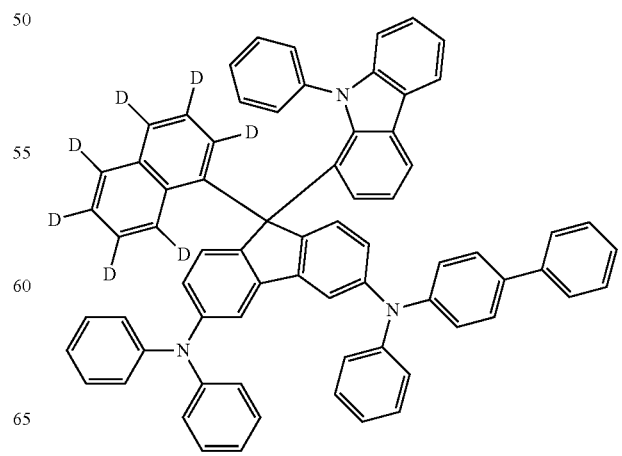

349
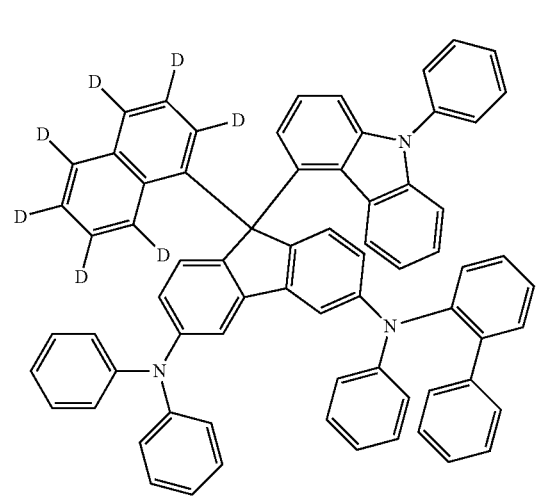
350
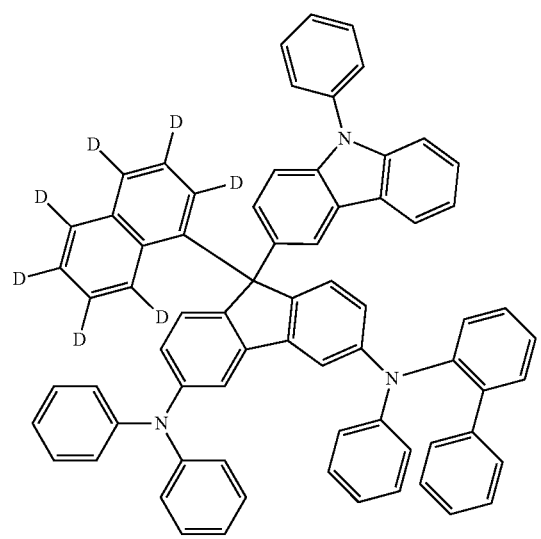
351
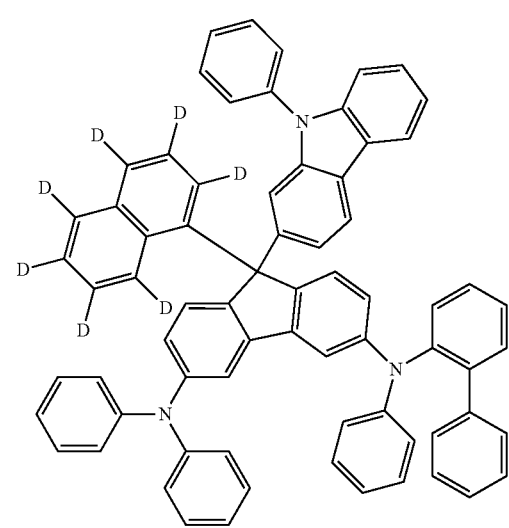
352
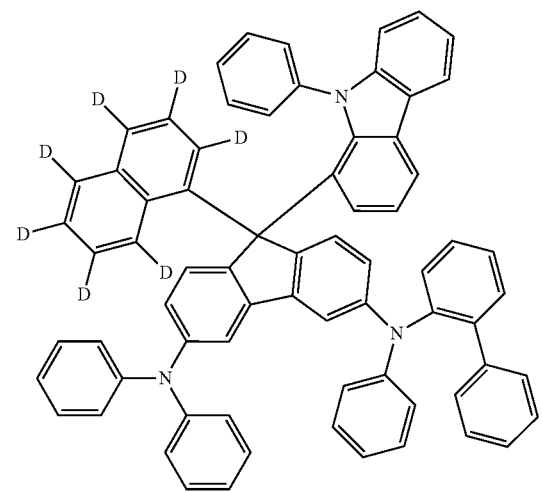
353
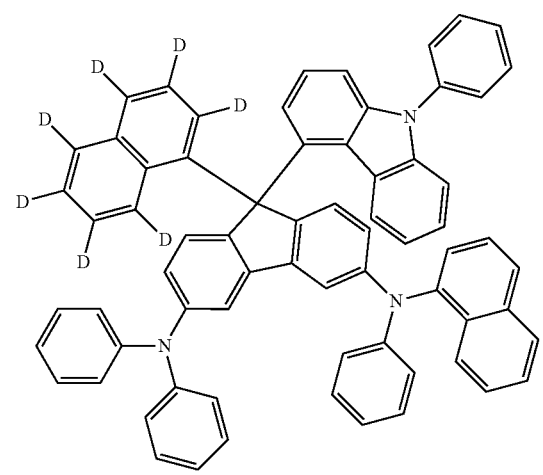
354
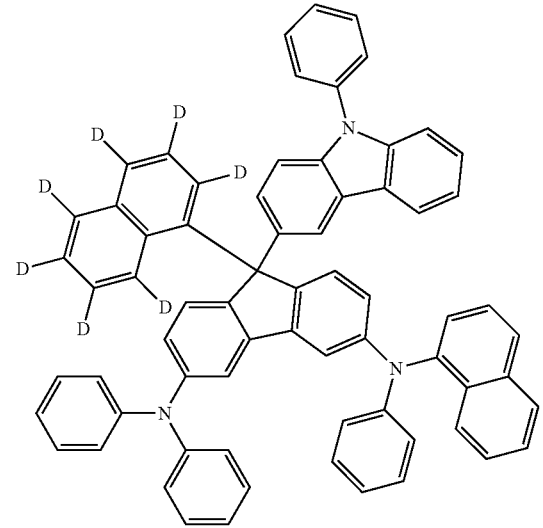

355
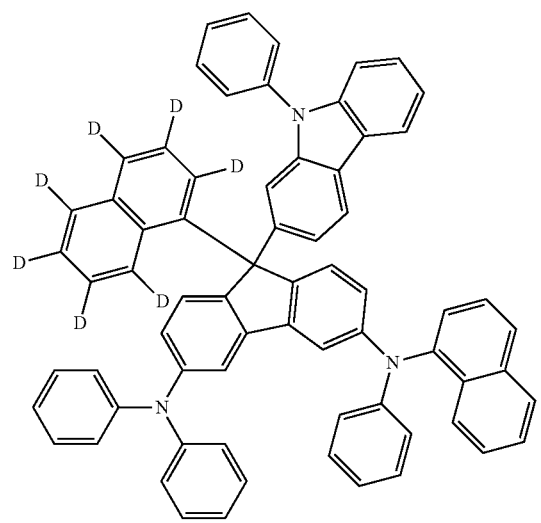
356
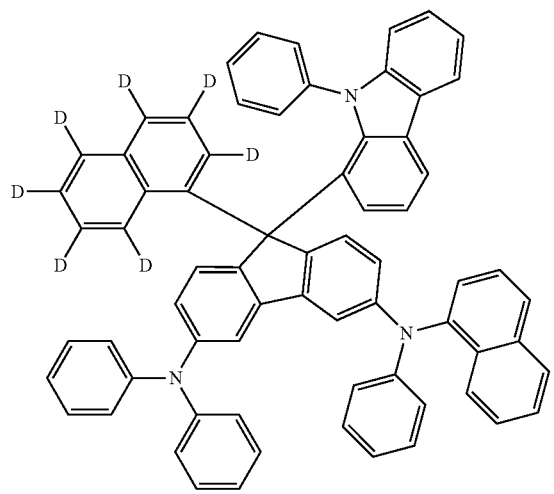
357
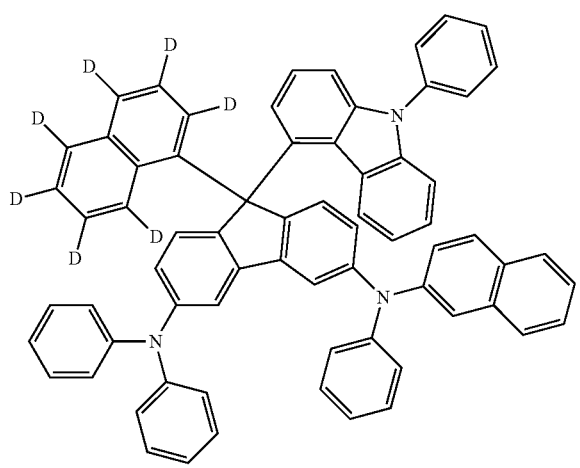
358
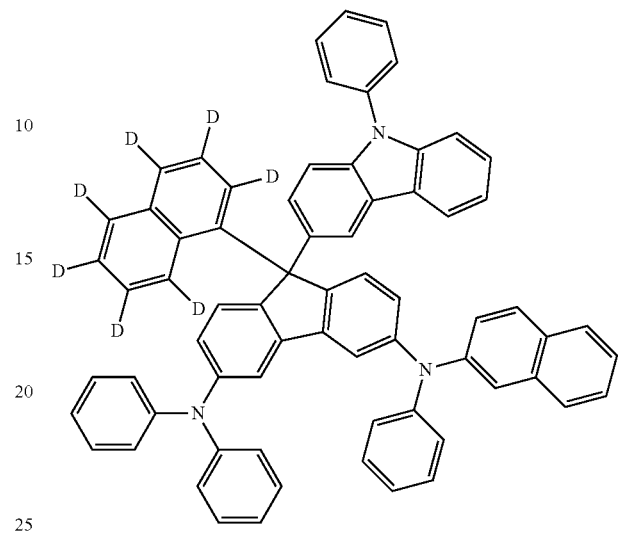
359
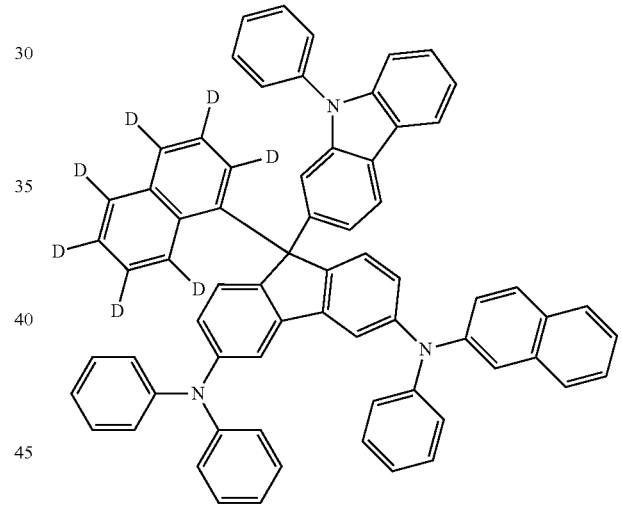
360
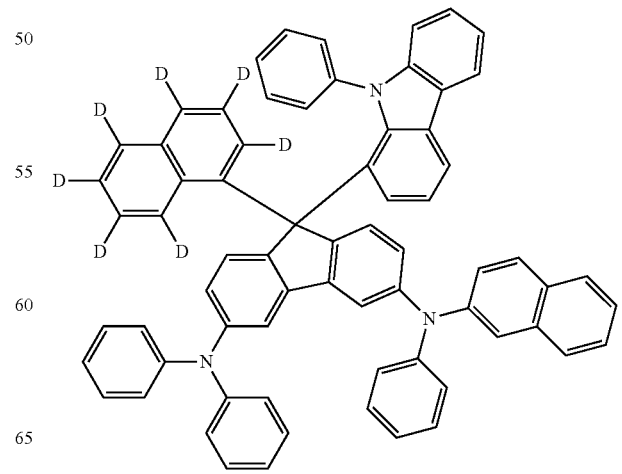

175
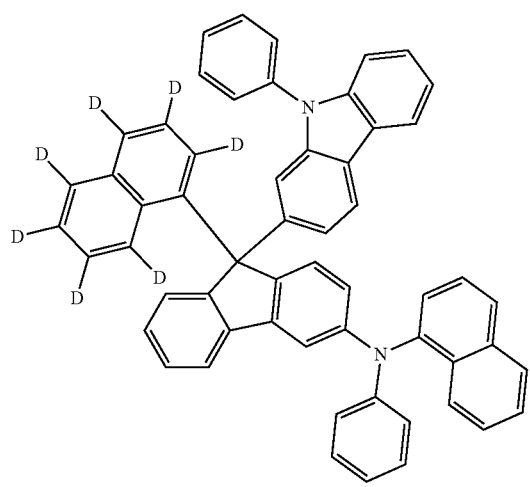
176
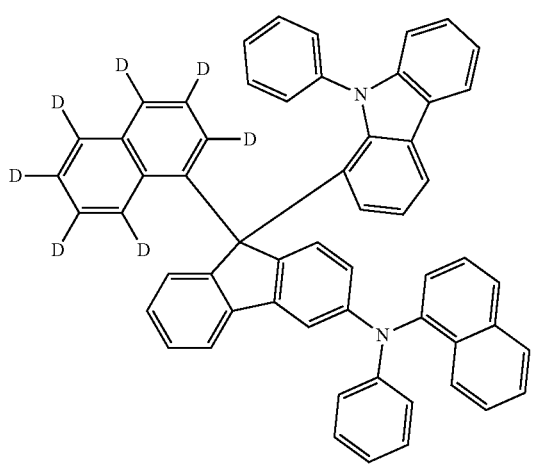
337
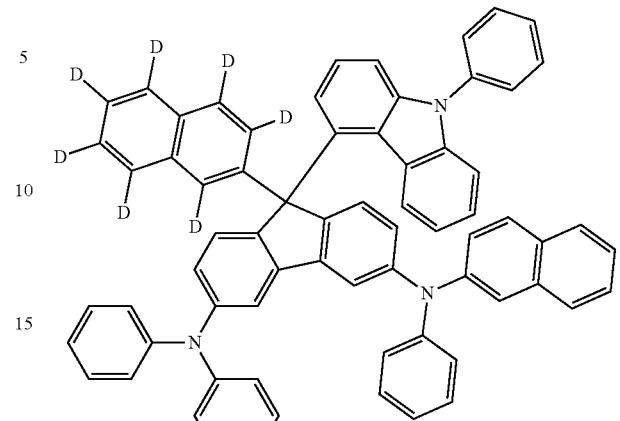
338
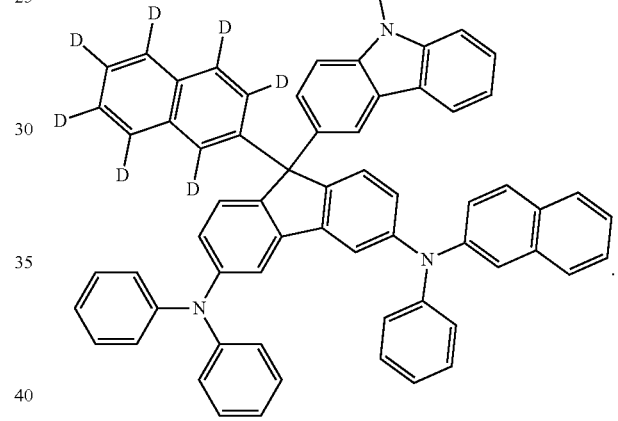
* * * * *

UNITED STATES PATENT AND TRADEMARK OFFICE
CERTIFICATE OF CORRECTION

PATENT NO. : 11,856,844 B2  
APPLICATION NO. : 17/080732  
DATED : December 26, 2023  
INVENTOR(S) : Dongjun Kim et al.

Page 1 of 5

It is certified that error appears in the above-identified patent and that said Letters Patent is hereby corrected as shown below:

In the Claims

Column 289-290, Lines 10-15, Claim 7, Formula 2-2, delete

"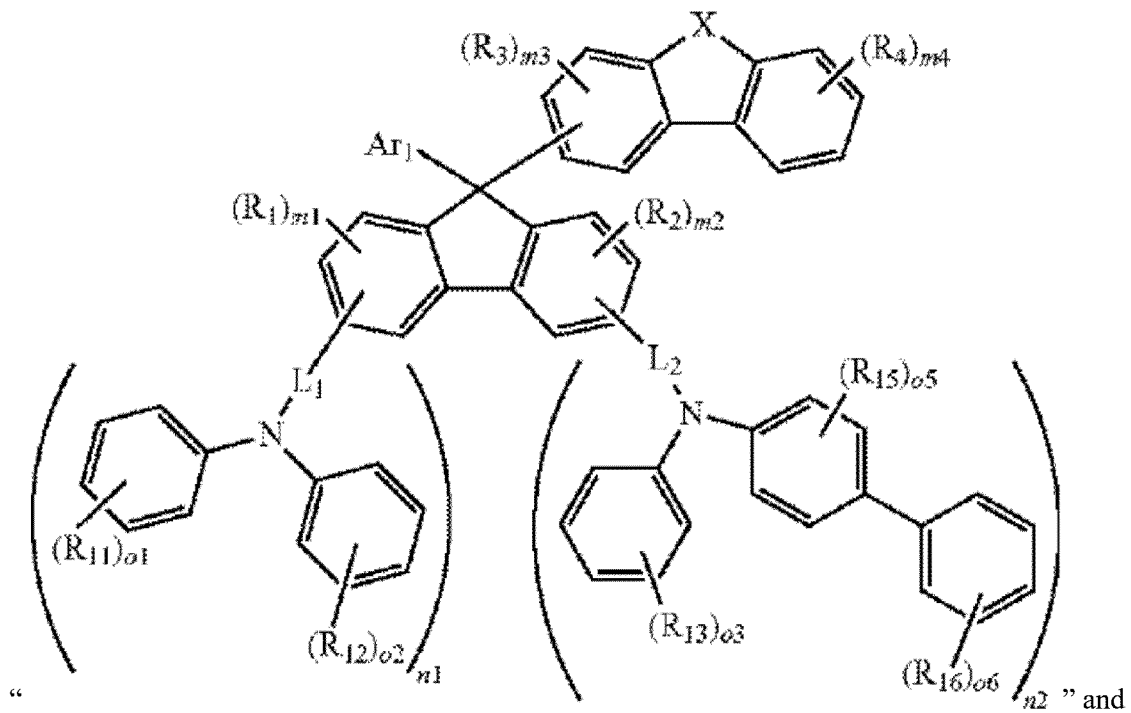 " and

Signed and Sealed this  
Twenty-first Day of January, 2025

Coke Morgan Stewart  
*Acting Director of the United States Patent and Trademark Office*

CERTIFICATE OF CORRECTION (continued)
U.S. Pat. No. 11,856,844 B2

Column 307, Lines 25-45, Claim 11, Formula 43, after

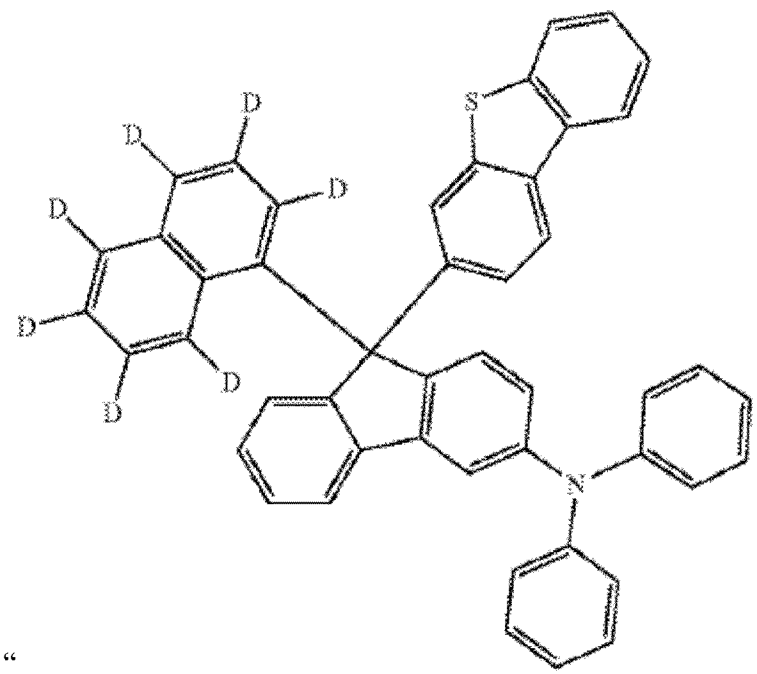

", delete duplicate insert --

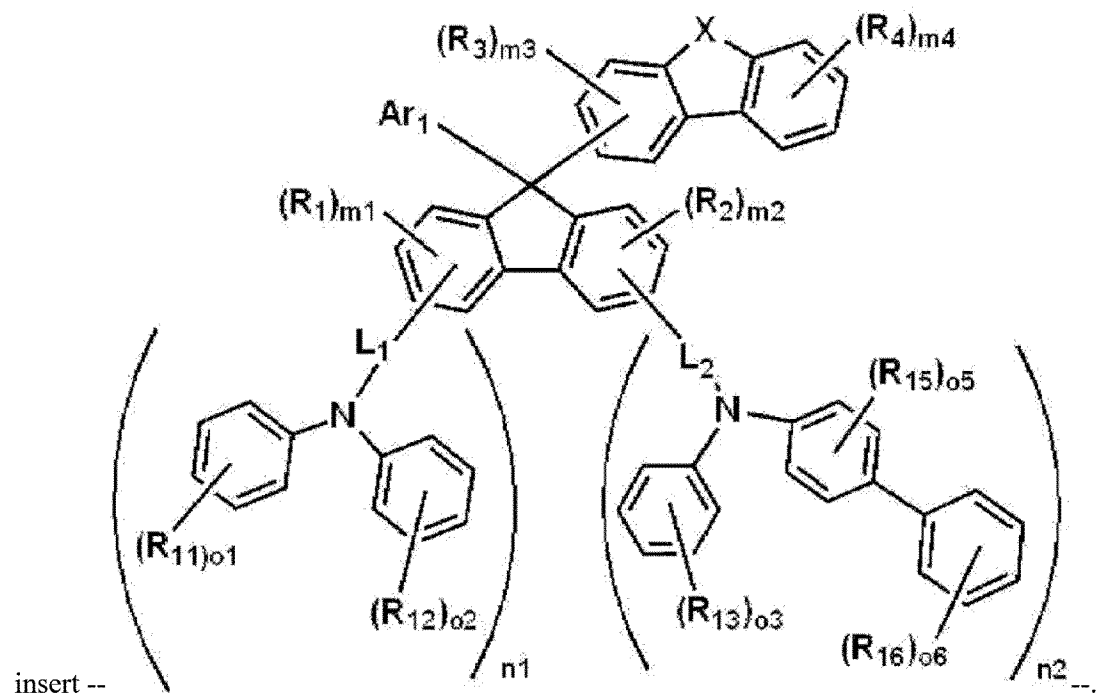

--.

CERTIFICATE OF CORRECTION (continued)
U.S. Pat. No. 11,856,844 B2

"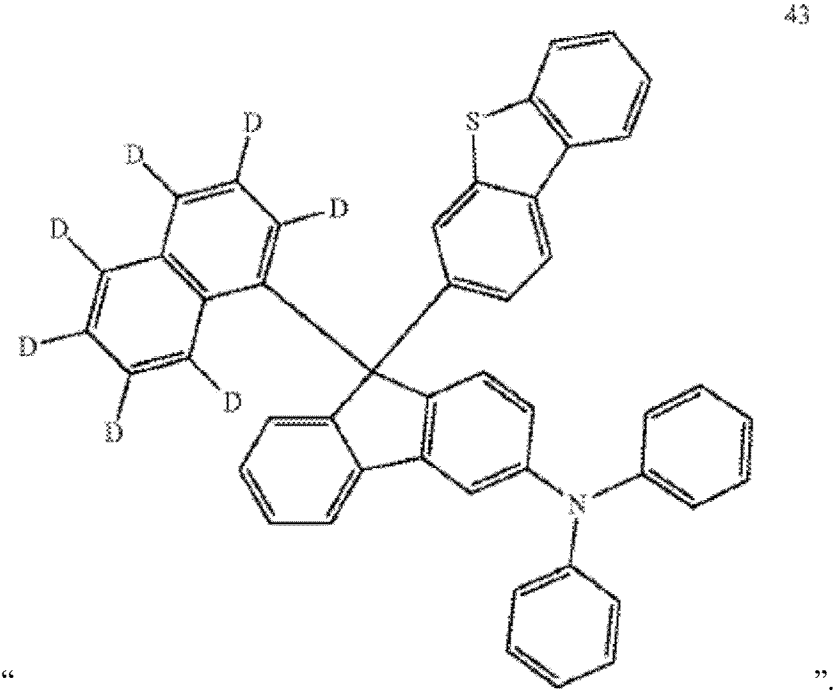".

Column 412, Line 46, Claim 12, after "1", insert -- , --.

Columns 413-414, Lines 30-35, Claim 14, in Formula 2-2, delete

"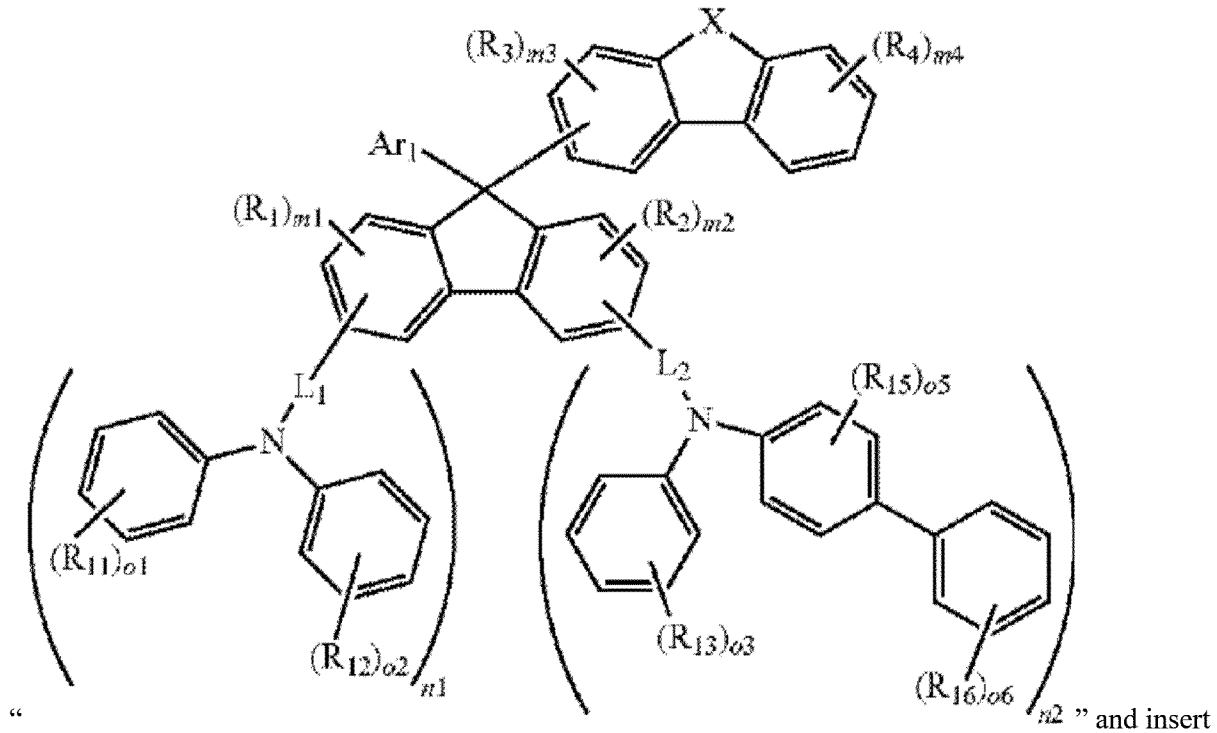" and insert

CERTIFICATE OF CORRECTION (continued)
U.S. Pat. No. 11,856,844 B2

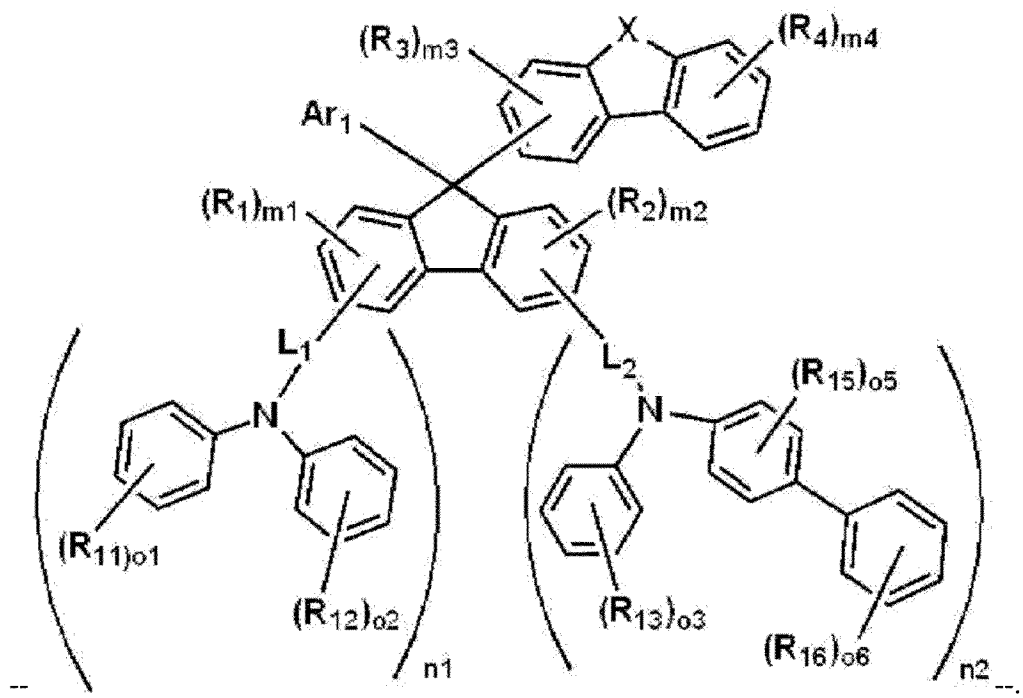

Column 418, Line 2, Claim 16, after "1", insert -- , --.

Columns 419-420, Lines 10-20, Claim 18, Formula 2-2, delete

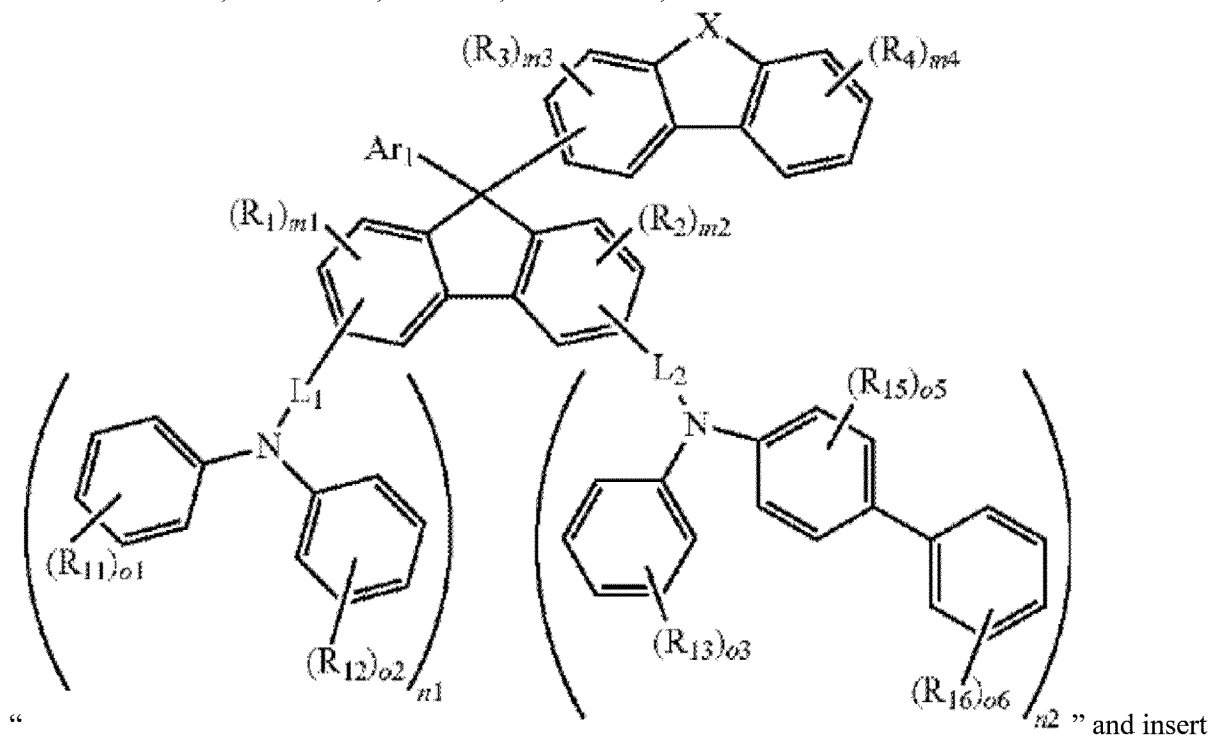

" and insert